(12) United States Patent
Markwalder et al.

(10) Patent No.: US 9,758,492 B2
(45) Date of Patent: Sep. 12, 2017

(54) IDO INHIBITORS

(71) Applicant: Bristol-Myers Squibb Company, Princeton, NJ (US)

(72) Inventors: Jay A. Markwalder, Lahaska, PA (US); Steven P. Seitz, Swarthmore, PA (US); James Aaron Balog, Lambertville, NJ (US); Audris Huang, New Hope, PA (US); Sunil Kumar Mandal, Bangalore (IN); Shefali Srivastava, Jaipur (IN); David K. Williams, Delran, NJ (US); Libing Chen, Newtown, PA (US)

(73) Assignees: Bristol-Myers Squibb Company, Princeton, NJ (US); Syngene International Limited, Bommasandra, Bangalore (IN); Syngene International Limited, Princeton, NJ (US)

( * ) Notice: Subject to any disclaimer, the term of this patent is extended or adjusted under 35 U.S.C. 154(b) by 0 days.

(21) Appl. No.: 14/914,184

(22) PCT Filed: Aug. 26, 2014

(86) PCT No.: PCT/US2014/052600
§ 371 (c)(1),
(2) Date: Feb. 24, 2016

(87) PCT Pub. No.: WO2015/031295
PCT Pub. Date: Mar. 5, 2015

(65) Prior Publication Data
US 2016/0200674 A1 Jul. 14, 2016

Related U.S. Application Data

(60) Provisional application No. 61/870,371, filed on Aug. 27, 2013.

(51) Int. Cl.
| | | |
|---|---|---|
| *C07D 257/04* | (2006.01) |
| *A61K 31/17* | (2006.01) |
| *A61K 31/18* | (2006.01) |
| *A61K 31/381* | (2006.01) |
| *A61K 31/41* | (2006.01) |
| *A61K 31/422* | (2006.01) |
| *A61K 31/427* | (2006.01) |
| *A61K 31/4439* | (2006.01) |
| *A61K 31/451* | (2006.01) |
| *A61K 31/4709* | (2006.01) |
| *A61K 31/497* | (2006.01) |
| *A61K 31/50* | (2006.01) |
| *A61K 31/506* | (2006.01) |
| *A61K 31/5375* | (2006.01) |
| *A61K 45/06* | (2006.01) |
| *C07D 211/14* | (2006.01) |
| *C07D 237/20* | (2006.01) |
| *C07D 333/38* | (2006.01) |
| *C07D 401/10* | (2006.01) |
| *C07D 407/12* | (2006.01) |

(Continued)

(52) U.S. Cl.
CPC ............ *C07D 257/04* (2013.01); *A61K 31/17* (2013.01); *A61K 31/18* (2013.01); *A61K 31/381* (2013.01); *A61K 31/41* (2013.01); *A61K 31/422* (2013.01); *A61K 31/427* (2013.01); *A61K 31/4439* (2013.01); *A61K 31/451* (2013.01); *A61K 31/4709* (2013.01); *A61K 31/497* (2013.01); *A61K 31/50* (2013.01); *A61K 31/506* (2013.01); *A61K 31/5375* (2013.01); *A61K 45/06* (2013.01); *C07B 59/002* (2013.01); *C07C 275/42* (2013.01); *C07C 311/05* (2013.01); *C07C 311/09* (2013.01); *C07C 317/44* (2013.01); *C07D 211/14* (2013.01); *C07D 215/06* (2013.01); *C07D 231/12* (2013.01); *C07D 237/20* (2013.01); *C07D 277/22* (2013.01); *C07D 309/14* (2013.01); *C07D 333/10* (2013.01); *C07D 333/38* (2013.01); *C07D 401/10* (2013.01); *C07D 401/12* (2013.01); *C07D 403/12* (2013.01); *C07D 407/12* (2013.01); *C07D 409/12* (2013.01); *C07D 411/12* (2013.01); *C07D 413/12* (2013.01); *C07D 417/12* (2013.01); *C07C 2101/02* (2013.01); *C07C 2101/04* (2013.01); *C07C 2101/08* (2013.01); *C07C 2101/14* (2013.01); *C07C 2101/16* (2013.01); *C07C 2101/18* (2013.01)

(58) Field of Classification Search
CPC .................................................... C07D 257/04
See application file for complete search history.

(56) References Cited

FOREIGN PATENT DOCUMENTS

| EP | 1 619 184 A2 * | 1/2006 |
| WO | WO2007/075598 A2 | 7/2007 |

(Continued)

OTHER PUBLICATIONS

Dolusic, Eduard et al., Indoleamine 2,3-dioxygenase inhibitors: a patent review (2008-2012), Expert Opinion on Therapeutic Patents, vol. 23(10), 1367-1381 (2013).

*Primary Examiner* — Yong Chong
(74) *Attorney, Agent, or Firm* — Serena Farquharson-Torres; Maureen S. Gibbons

(57) ABSTRACT

There are disclosed compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

11 Claims, No Drawings

(51) Int. Cl.
*C07D 417/12* (2006.01)
*C07D 403/12* (2006.01)
*C07D 309/14* (2006.01)
*C07D 215/06* (2006.01)
*C07D 231/12* (2006.01)
*C07D 333/10* (2006.01)
*C07D 401/12* (2006.01)
*C07D 409/12* (2006.01)
*C07D 411/12* (2006.01)
*C07D 413/12* (2006.01)
*C07D 277/22* (2006.01)
*C07C 275/42* (2006.01)
*C07C 311/05* (2006.01)
*C07C 311/09* (2006.01)
*C07C 317/44* (2006.01)
*C07B 59/00* (2006.01)

(56) References Cited

FOREIGN PATENT DOCUMENTS

WO    WO2008/058178 A1    5/2008
WO    WO 2012/149540 A1    11/2012

\* cited by examiner

IDO INHIBITORS

CROSS-REFERENCE TO RELATED APPLICATIONS

This application claims the benefit of U.S. Provisional Application No. 61/870,371, filed Aug. 27, 2013, the disclosure of which is incorporated herein by reference in its entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Tryptophan is an amino acid which is essential for cell proliferation and survival. It is required for the biosynthesis of the neurotransmitter serotonin, the synthesis of the cofactor nicotinamide adenine dinucleotide (NAD), and is an important component in the immune system response ("immune escape") to tumors. Depletion of levels of tryptophan is associated with adverse effects on the proliferation and function of lymphocytes and diminished immune system response.

The enzyme indoleamine-2,3-deoxygenase (IDO) is overexpressed in many human tumors. IDO catalyzes the initial, rate-limiting step in the conversion of tryptophan to N-formylkynurenime. Moreover, IDO has been implicated in neurologic and psychiatric disorders including mood disorders as well as other chronic diseases characterized by IDO activation and tryptophan degradation such as viral infections, for example, AIDS, Alzheimer's disease, cancers including T-cell leukemia and colon cancer, autoimmune diseases, diseases of the eye such as cataracts, bacterial infections such as Lyme disease, and streptococcal infections.

Accordingly, an agent which is safe and effective in inhibiting the function of IDO would be an important addition for the treatment of patients with diseases or conditions affected by the activity of the enzyme.

SUMMARY OF THE INVENTION

The present invention provides compounds and/or pharmaceutically acceptable salts thereof, stereoisomers thereof or tautomers thereof, methods of modulating or inhibiting the enzymatic activity of IDO, and methods for treating various medical conditions using said compounds.

The present invention also provides processes and intermediates for making the compounds of the present invention and/or pharmaceutically acceptable salts thereof or stereoisomers thereof or tautomers thereof. The present invention also provides pharmaceutical compositions comprising a pharmaceutically acceptable carrier and one or more of the compounds of the present invention and/or pharmaceutically acceptable salts thereof or stereoisomers thereof or tautomers thereof.

The compounds of the invention and/or pharmaceutically acceptable salts thereof or stereoisomers thereof or tautomers thereof may be used in the treatment and/or prophylaxis of multiple diseases or disorders associated with enzymatic activity of IDO inhibition, such as cancer, viral infections, autoimmune diseases, and other maladies.

The compounds of the invention and/or pharmaceutically acceptable salts thereof or stereoisomers thereof or tautomers thereof may be used in therapy.

The compounds of the invention and/or pharmaceutically acceptable salts thereof or stereoisomers thereof or tautomers thereof may be used for the manufacture of a medicament for the treatment and/or prophylaxis of multiple diseases or disorders associated with enzymatic activity of IDO.

The compounds of the invention and/or pharmaceutically acceptable salts thereof or stereoisomers thereof or tautomers thereof can be used alone, in combination with other compounds of the present invention and/or pharmaceutically acceptable salts thereof or stereoisomers thereof or tautomers thereof, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides compounds of Formula (I)

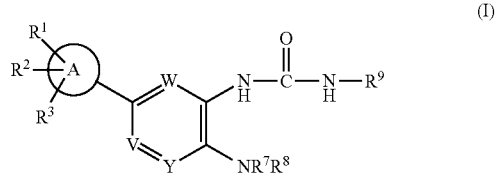

wherein:
W is $CR^4$ or N,
V is $CR^5$ or N, and
Y is $CR^6$ or N;

is optionally substituted aryl or optionally substituted 5- to 7-membered monocyclic heteroaryl;

$R^1$ is COOH, optionally substituted heterocyclyl, $-NHSO_2R^{20}$,

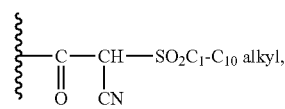

$-CONHSO_2R^{21}$, $-CONHCOOR^{22}$ or $-SO_2NHCOR^{23}$;

$R^2$ and $R^3$ are independently H, halogen, optionally substituted $C_1$-$C_6$ alkyl, optionally substituted $C_1$-$C_6$ alkoxy or optionally substituted $N(C_1$-$C_6$ alkyl$)_2$;

$R^4$, $R^5$ and $R^6$ are independently H, halogen, CN, OH, optionally substituted $C_1$-$C_6$ alkyl or optionally substituted $C_1$-$C_6$ alkoxy;

$R^7$ and $R^8$ are independently H, optionally substituted $C_1$-$C_6$ alkyl, optionally substituted aryl, optionally substituted $C_1$-$C_6$ alkoxy, optionally substituted $C_3$-$C_8$ cycloalkyl, optionally substituted di-deutero-$C_1$-$C_{10}$-alkyl, optionally substituted $C_2$-$C_{10}$ alkynyl, optionally substituted 5- to 7-membered monocyclic heteroaryl, optionally substituted 8- to 10-membered bicyclic heteroaryl, optionally substituted aryl $C_1$-$C_6$ alkyl, arylsulfonyl, optionally substituted $C_2$-$C_6$ alkenyl, or optionally substituted $C_5$-$C_8$ cycloalkenyl,
provided that only one of $R^7$ and $R^8$ is H,
or $R^7$ and $R^8$ are taken together with the nitrogen to which they are attached to form an optionally substituted 5- to 10-membered monocyclic or bicyclic heterocyclic ring, or an optionally substituted 5- to 7-membered monocyclic heteroaryl ring;

$R^9$ is optionally substituted aryl; optionally substituted $C_3$-$C_8$ cycloalkyl, optionally substituted $C_1$-$C_6$ alkyl, optionally substituted 5- to 7-membered monocyclic heterocyclo, optionally substituted 7- to 10-membered bicyclic heterocyclo, optionally substituted 5- to 7-membered monocyclic heteroaryl, optionally substituted 8- to 10-membered bicyclic heteroaryl, optionally substituted $C_1$-$C_6$ alkanoyloxy 5- to 7-membered monocyclic heteroaryl, $R^{24}CO—$, optionally substituted $C_1$-$C_6$ alkoxy, optionally substituted aryloxy, optionally substituted $C_2$-$C_6$ alkenyl, optionally substituted $C_2$-$C_6$ alkynyl, or optionally substituted $C_5$-$C_8$ cycloalkenyl;

$R^{20}$ is optionally substituted $C_1$-$C_6$ alkyl, $CH_2CF_3$, $CF_3$ or $CF_2CF_3$;

$R^{21}$ is optionally substituted $C_1$-$C_6$ alkyl or optionally substituted $C_3$-$C_8$ cycloalkyl;

$R^{22}$ is optionally substituted $C_1$-$C_6$ alkyl, optionally substituted $C_3$-$C_8$ cycloalkyl, optionally substituted $C_2$-$C_6$ alkenyl, or optionally substituted $C_2$-$C_6$ alkynyl;

$R^{23}$ is optionally substituted $C_1$-$C_6$ alkyl, optionally substituted $C_3$-$C_8$ cycloalkyl, optionally substituted $C_2$-$C_6$ alkenyl, or optionally substituted $C_2$-$C_6$ alkynyl;

$R^{24}$ is optionally substituted aryl-$C_1$-$C_6$-alkyl, optionally substituted $C_1$-$C_6$ alkylaryl, aryl-$C_1$-$C_6$-alkyl(hydroxy), or optionally substituted $C_1$-$C_6$ alkyl;

and/or a stereoisomer, a tautomer or a pharmaceutically acceptable salt thereof. thereof.

In a second aspect, the invention provides a compound of Formula (I) within the scope of the first aspect wherein:
W is $CR^4$;
V is $CR^5$;
Y is $CR^6$ or N;
$R^4$ is H or halo;
$R^5$ is H or halo; and
$R^6$ is H or halo;
and/or a stereoisomer, a tautomer or a pharmaceutically acceptable salt thereof.

In a third aspect, the invention provides a compound of Formula (I) within the scope of the first or second aspect wherein

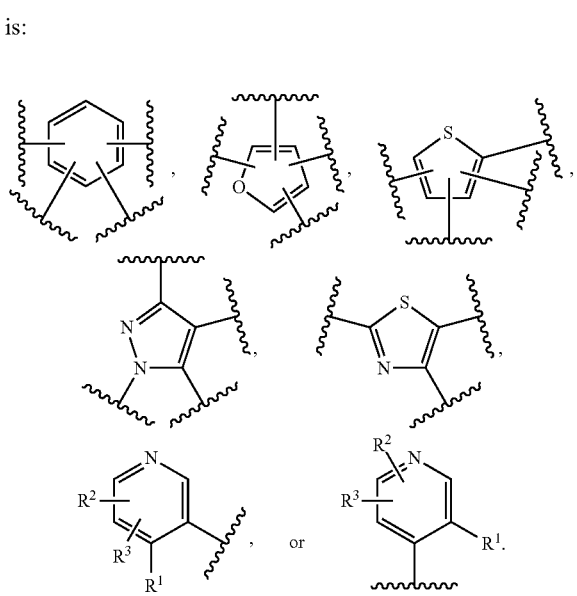

A is:

and/or a stereoisomer, a tautomer or a pharmaceutically acceptable salt thereof.

In a fifth aspect, the invention provides a compound of Formula (I) within the scope of the first, second, third or fourth aspects wherein:
$R^1$ is COOH, optionally substituted heterocyclyl, $—NHSO_2R^{20}$,

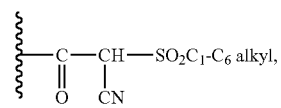

$—CONHSO_2R^{21}$ or $—CONHCOOR^{22}$;
$R^2$ is H, halogen, optionally substituted $C_1$-$C_6$ alkyl or optionally substituted $C_1$-$C_6$ alkoxy; and
$R^3$ is H or $C_1$-$C_6$ alkyl;
and/or a stereoisomer, a tautomer or a pharmaceutically acceptable salt thereof.

In a sixth aspect, the invention provides a compound of Formula (I) within the scope of any of the first to fifth aspects set out above wherein:
$R^1$ is COOH, optionally substituted heterocyclyl, $—NHSO_2CH_3$,

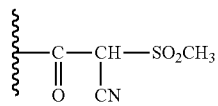

or $—CONHSO_2R^{21}$;
where $R^{21}$ is $C_1$-$C_6$ alkyl, $C_3$-$C_8$ cycloalkyl or $CF_3$;
$R^2$ is H, $CH_3$, $C_2H_5$, $CH_3O$, $CF_3O$, F, or Cl; and
$R^3$ is H, $CH_3$, or $C_2H_5$;
and/or a stereoisomer, a tautomer or a pharmaceutically acceptable salt thereof.

A is phenyl or a 5- to 6-membered monocyclic heteroaryl, and/or a stereoisomer, a tautomer or a pharmaceutically acceptable salt thereof.

In a fourth aspect, the invention provides a compound of Formula (I) within the scope of the first, second or third aspect wherein In another aspect, the invention provides a compound of Formula (I) within the scope of any of the first to sixth aspects set out above wherein:

$R^7$ and $R^8$ are independently optionally substituted $C_1$-$C_6$ alkyl, optionally substituted aryl, optionally substituted $C_1$-$C_6$ alkoxy, optionally substituted $C_3$-$C_8$ cycloalkyl, optionally substituted di-deutero-$C_1$-$C_6$-alkyl, optionally substituted $C_1$-$C_6$-alkylphenyl-$C_1$-$C_6$-alkyl, optionally substituted $C_2$-$C_6$ alkynyl, optionally substituted $C_3$-$C_8$-cycloalkyl-$C_1$-$C_6$-alkyl, optionally substituted $C_1$-$C_6$-alkoxy-$C_1$-$C_6$-alkyl, optionally substituted 5- to 6-membered monocyclic heteroaryl, optionally substituted 7- to 10-membered bicyclic heteroaryl, optionally substituted aryl $C_1$-$C_6$ alkyl, phenylsulfonyl, optionally substituted $C_2$-$C_6$ alkenyl, or 5- to 6-membered monocyclic heteroaryl-$C_1$-$C_6$-alkyl, or $R^7$ and $R^8$ are taken together with the nitrogen to which they are attached to form (a) a 7- to 10-membered bicyclic heterocyclic ring which is optionally substituted with a phenyl-$C_1$-$C_6$-alkyl group, or (b) a 5- to 7-membered monocyclic heterocyclic ring which is optionally substituted with 1 or 2 $C_1$-$C_6$ alkyl groups, phenyl, a $C_1$-$C_6$-alkyl-substituted 5- to 7-membered monocyclic heteroaryl, and/or 1 or 2 halo groups; or (c) a 5- to 7-membered monocyclic heteroaryl which is optionally substituted with a $C_1$-$C_6$ alkyl;

$R^9$ is optionally substituted aryl; optionally substituted $C_3$-$C_8$ cycloalkyl, optionally substituted $C_1$-$C_6$ alkyl, optionally substituted $C_1$-$C_6$ alkoxy, optionally substituted $C_1$-$C_6$ alkylaryl, optionally substituted $C_1$-$C_6$ alkoxyaryl, optionally substituted $C_3$-$C_8$ cycloalkyl $C_1$-$C_6$ alkyl, optionally substituted 5- to 7-membered monocyclic heterocyclo, optionally substituted 7- to 10-membered bicyclic heterocyclo, optionally substituted 5- to 6-membered monocyclic heteroaryl, optionally substituted 8- to 10-membered bicyclic heteroaryl, optionally substituted $C_1$-$C_6$ alkanoyloxy 5- to 7-membered monocyclic heteroaryl, optionally substituted aryloxy, optionally substituted $C_2$-$C_6$ alkenyl, optionally substituted $C_2$-$C_6$ alkynyl, or optionally substituted $C_5$-$C_8$ cycloalkenyl, $C_2$-$C_6$ alkynylaryl, $C_2$-$C_6$ alkynyloxyaryl, 5- to 6-membered heteroarylaryl, 5- or 6-membered heterocycloaryl, $C_3$-$C_8$ cycloalkylaryl or $C_1$-$C_6$ alkanoyl.

and/or a pharmaceutically acceptable salt thereof, tautomer thereof or stereoisomer thereof.

In another aspect, the invention provides a compound of Formula (II)

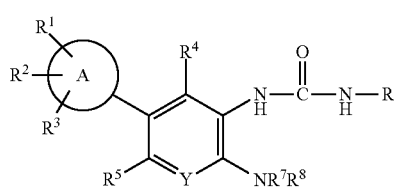

(II)

wherein:
Y is $CR^6$ or N;

is phenyl substituted with $R^1$, and optionally substituted with $R^2$ and/or $R^3$ or

is a 5- to 7-membered monocyclic heteroaryl substituted with $R^1$, and optionally substituted with $R^2$ and/or $R^3$;

$R^1$ is COOH, optional substituted tetrazol-5-yl, —NHSO$_2$R$^{20}$,

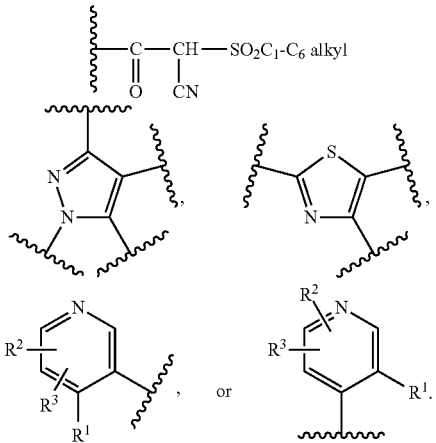

or —CONHSO$_2$R$^{21}$;

$R^{20}$ is $C_6$ alkyl or $CF_3$;
$R^{21}$ is $C_1$-$C_6$ alkyl, $C_3$-$C_8$ cycloalkyl or $CF_3$;
$R^2$ is H, $C_1$-$C_6$ alkyl, halo, optionally substituted $C_1$-$C_6$-alkoxy or N($C_1$-$C_6$ alkyl)$_2$;
$R^3$ is H, $C_1$-$C_6$ alkyl, $C_1$-$C_6$ alkoxy, or halo;
$R^4$ is H, halo or $C_1$-$C_6$ alkyl;
$R^5$ is H, halo or $C_1$-$C_6$ alkyl;
$R^6$ is H or halo;
$R^7$ and $R^8$ are independently H, optionally substituted $C_1$-$C_6$ alkyl, optionally substituted aryl, optionally substituted $C_3$-$C_8$ cycloalkyl, phenylsulfonyl, dideutero-$C_1$-$C_6$-alkyl, optionally substituted $C_3$-$C_8$-cycloalkyl-$C_1$-$C_6$-alkyl, optionally substituted aryl-$C_1$-$C_6$-alkyl, optionally substituted $C_2$-$C_6$ alkynyl, optionally substituted 5- to 7-membered monocyclic heterocyclo, optionally substituted 7- to 10-membered bicyclic heterocyclo, optionally substituted $C_1$-$C_6$-alkoxy-$C_1$-$C_6$-alkyl, 5- to 7-membered monocyclic heteroaryl-$C_1$-$C_6$-alkyl, $C_2$-$C_6$ alkenyl, or $C_5$-$C_8$ cycloalkenyl, provided that only one of $R^7$ and $R^8$ is H, and wherein the optional substituents on $R^7$ and $R^8$, where possible, are 1 or 2 groups independently selected from hydroxy, optionally substituted $C_1$-$C_6$ alkyl, optionally substituted $C_1$-$C_6$ alkoxy, halo, optionally substituted aryl, optionally substituted $C_3$-$C_8$ cycloalkyl, 5- to 7-membered monocyclic heteroaryl or 5- to 7-membered monocyclic heterocyclic;

or $R^7$ and $R^8$ are taken together with the nitrogen to which they are attached to form an optionally substituted 5- to 7-membered monocyclic heterocyclo ring, an optionally substituted 7- to 10-membered bicyclic heterocyclo ring, an optionally substituted 5- to 7-membered monocyclic heteroaryl ring, an optionally substituted 5- to 7-membered monocyclic heteroaryl-substituted 5- to 7-membered monocyclic heterocyclo ring, or a $C_3$-$C_8$-cycloalkyl-$C_1$-$C_6$-alkyl-substituted 7- to 10-membered bicyclic heterocyclo ring;

$R^9$ is H, $C_1$-$C_{10}$ alkyl, aryl, optionally substituted phenyl, $C_1$-$C_6$ alkylphenyl, optionally substituted $C_1$-$C_6$ alkoxyphenyl, di-$C_1$-$C_6$-alkylphenyl, dihalo($C_1$-$C_6$-alkyl)phenyl, $C_2$-$C_6$ alkynylphenyl, optionally substituted 5- to 7-membered monocyclic heteroaryl, 7- to 10-membered bicyclic heteroaryl, $C_3$-$C_8$ cycloalkyl, $C_3$-$C_8$-cycloalkyl-$C_1$-$C_6$-alkyl, $C_2$-$C_6$ alkynyloxyphenyl, $C_2$-$C_6$-alkynyl-$C_1$-$C_6$-alkoxyphenyl, 5- to 7-membered monocyclic heteroarylphenyl, di-$C_1$-$C_6$-alkylaminophenyl, $C_1$-$C_6$ alkylsulfonylaminophenyl, 5- to 7-membered monocyclic heterocyclophenyl, $C_3$-$C_8$ cycloalkyl optionally substituted phenyl, optionally substituted phenyl-$C_1$-$C_6$-alkylcarbonyl, phenyl-$C_1$-$C_6$-alkyl or $C_1$-$C_6$ alkylcarbonyl;

and/or a pharmaceutically acceptable salt thereof, a tautomer thereof or stereoisomer thereof.

In a further aspect, the invention provides a compound of Formula (II) within the scope of the eighth aspect wherein:

Y is $CR^6$;
$R^4$ and $R^5$ are independently H or F;
$R^6$ is H, F, or Cl;

Ⓐ is phenyl;
$R^1$ is COOH,

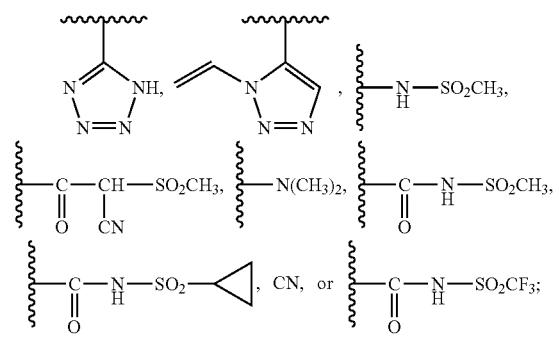

$R^2$ is H, $CH_3$, $CH_3O$, $CF_3O$, $C_2H_5$, Cl, or F;
$R^3$ is H or F;
$R^7$ and $R^8$ are independently H, $CH_3$, $C_2H_5$, $C_3H_7$, n-$C_4H_9$, i-$C_3H_7$, i-$C_4H_9$, t-$C_4H_9$, t-$C_4H_9CH_2$,

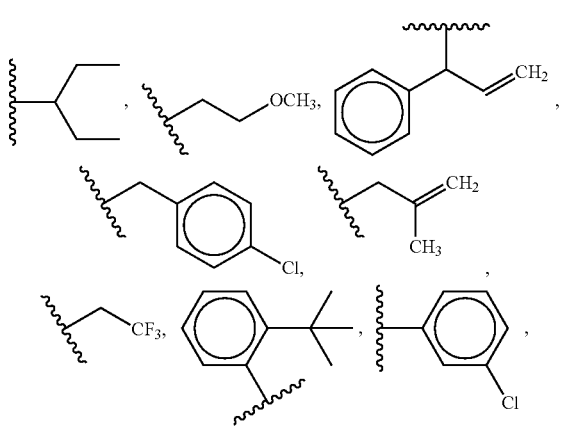

-continued

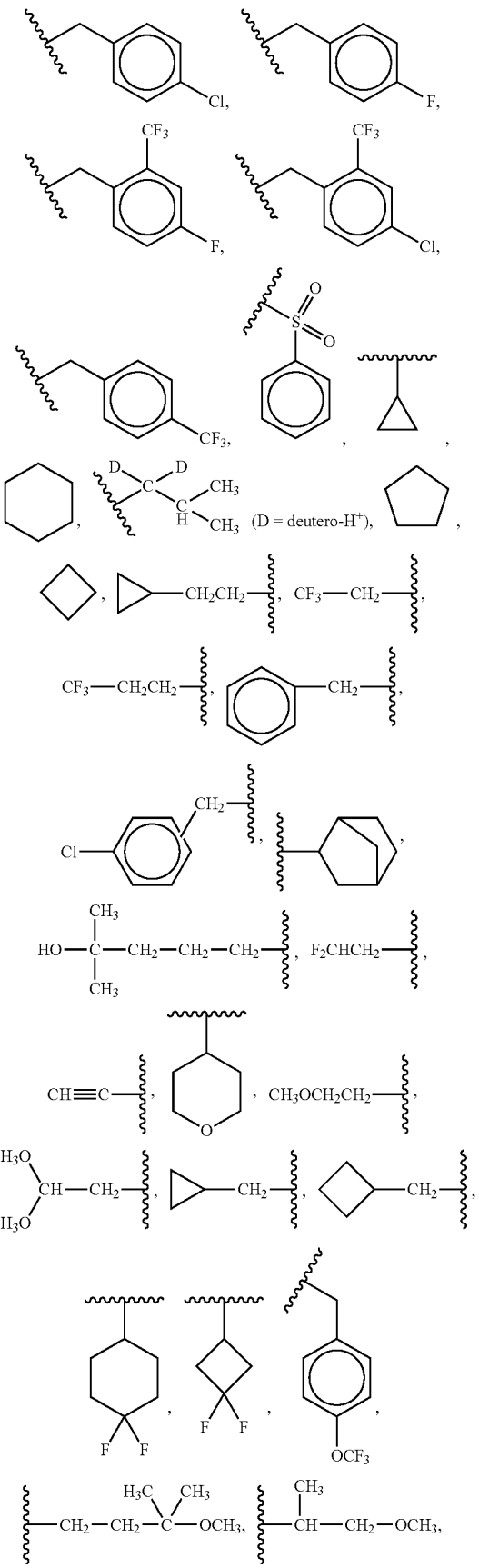

-continued
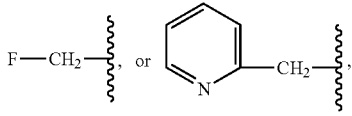
or R[7] and R[8] are taken together with the nitrogen to which they are attached to form
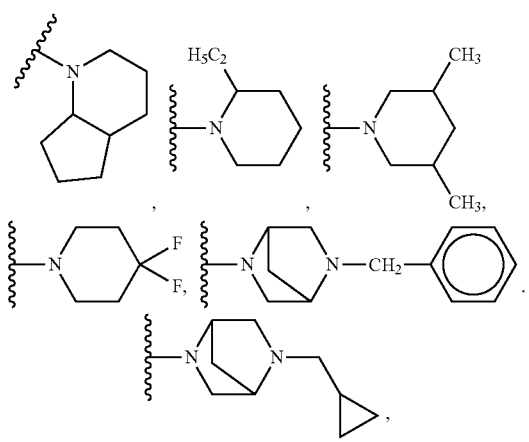
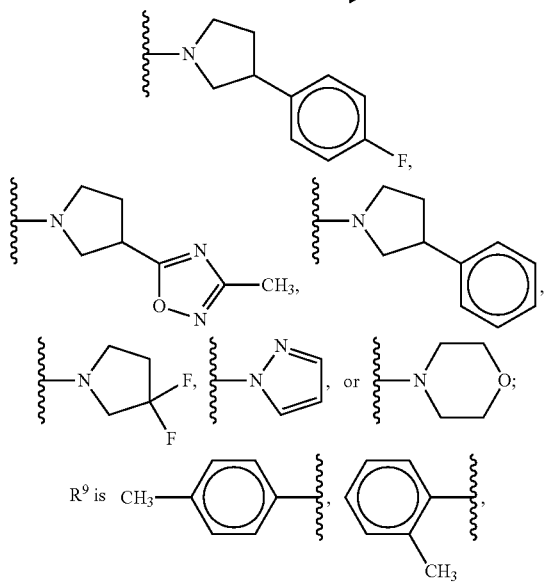
R[9] is
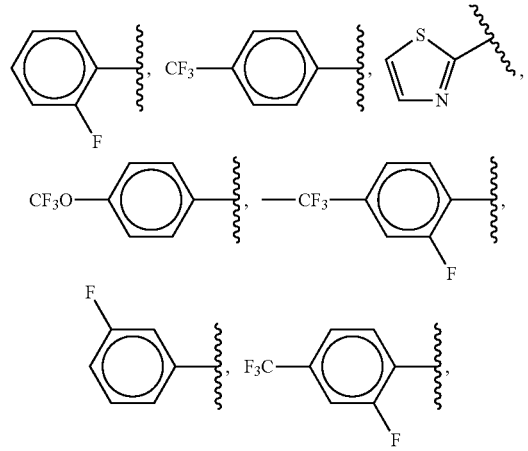
-continued
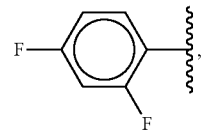
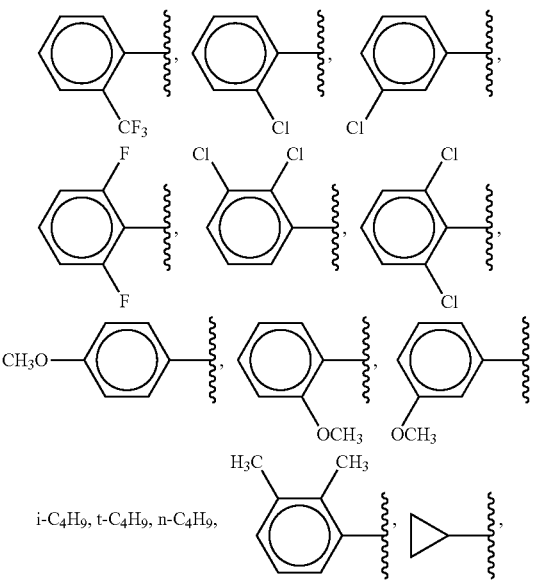
i-C$_4$H$_9$, t-C$_4$H$_9$, n-C$_4$H$_9$,
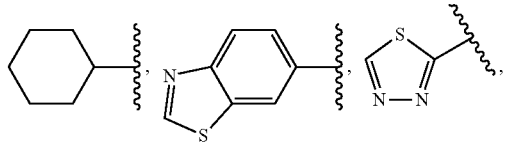
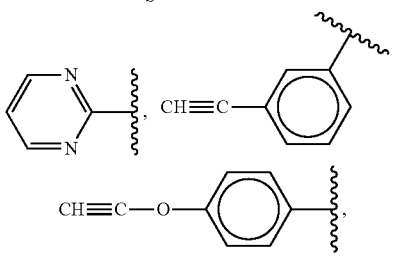
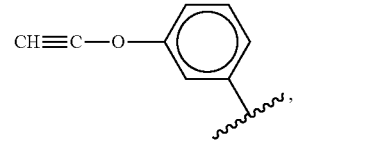
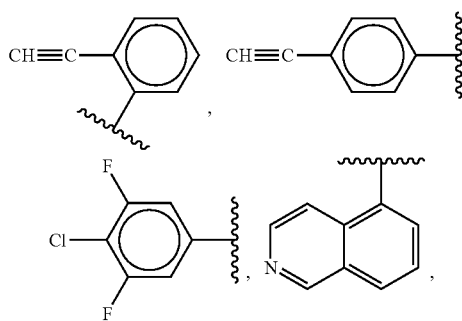

-continued
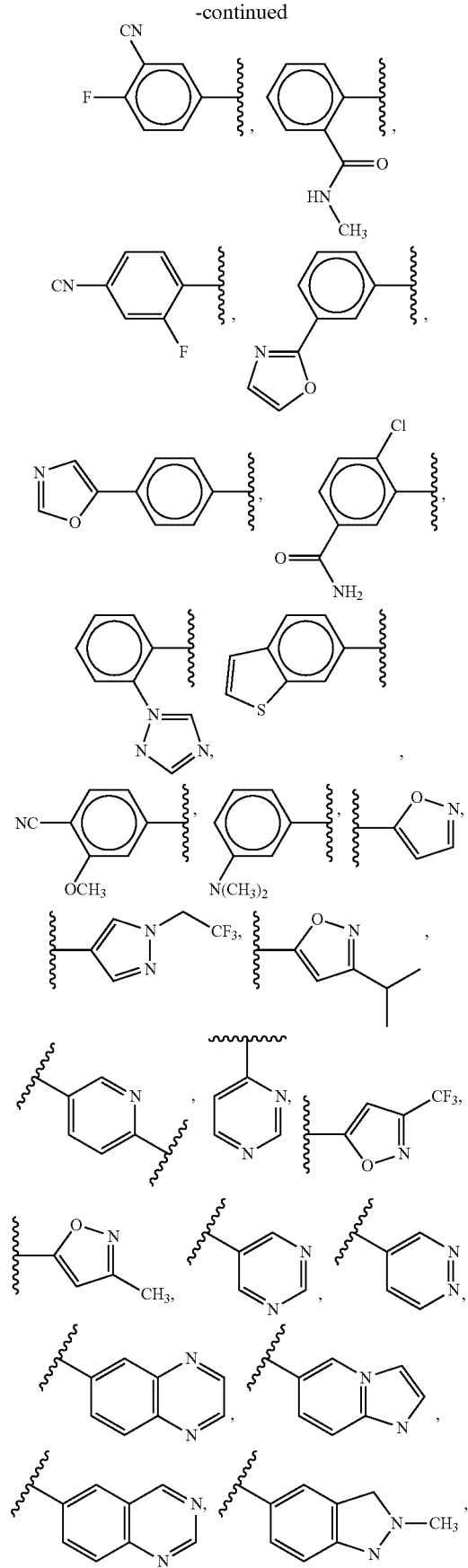
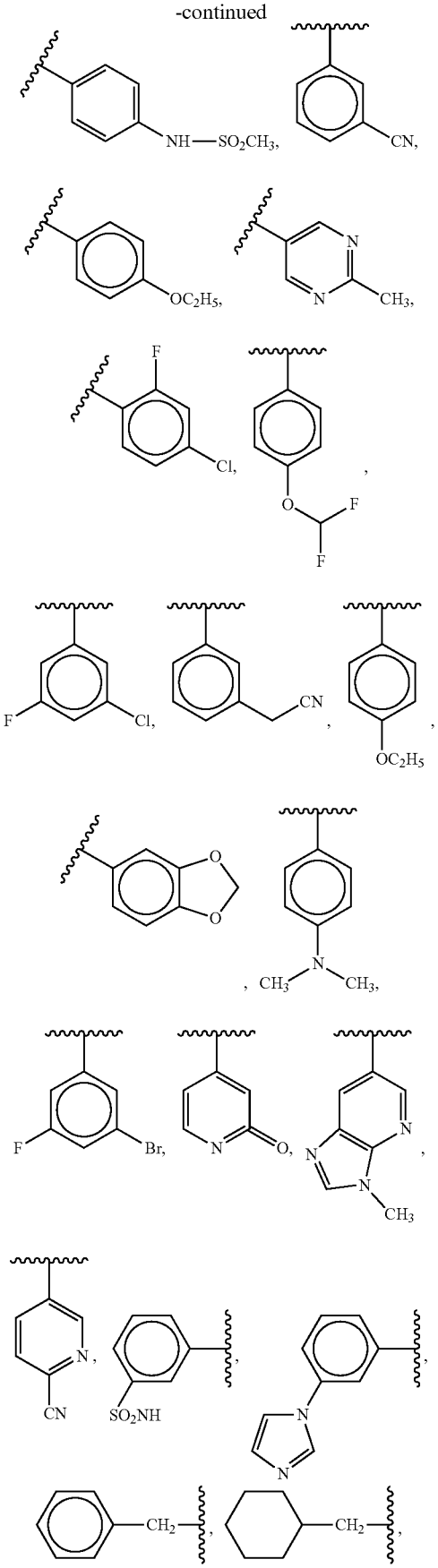

-continued

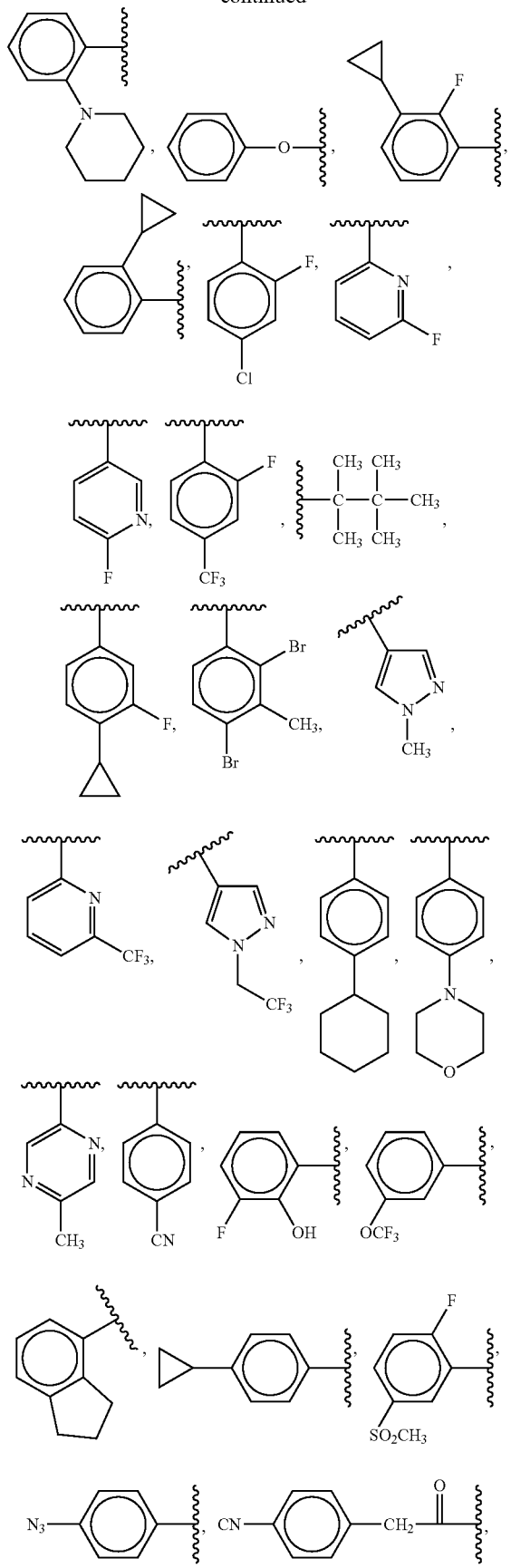

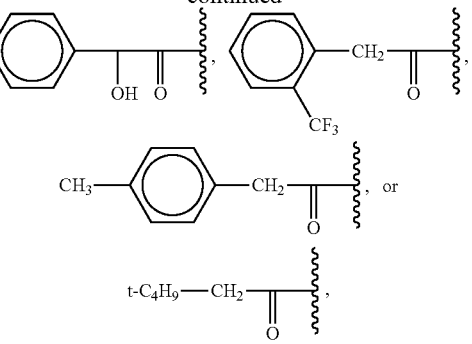

and/or a pharmaceutically acceptable salt thereof, a tautomer thereof or stereoisomer thereof.

In another aspect, the invention provides a compound selected from the exemplified examples within the scope of the previous aspects, or a pharmaceutically acceptable salt, tautomer or stereoisomer thereof.

In another aspect, the invention provides a compound selected from any subset list of compounds within the scope of any of the above aspects.

In another embodiment, the compounds of the invention have human IDO $IC_{50}$ values ≤1500 nM.

In another embodiment, the compounds of the invention have human IDO $IC_{50}$ values ≤250 nM.

In another embodiment, the compounds of the invention have human IDO $IC_{50}$ values ≤50 nM.

In another embodiment, the compounds of the invention have human IDO $IC_{50}$ values ≤20 nM.

In another embodiment, the compounds of the invention have human IDO $IC_{50}$ values ≤10 nM.

II. Other Embodiments of the Invention

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising: a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

III. Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity by forming a covalent bond with the enzyme.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-10 or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-O1 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas (I) and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

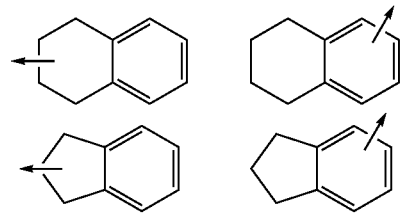

Arrowed lines drawn from the ring system indicate that the bond may be attached to any of the suitable ring atoms.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (NO) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., Design of Prodrugs, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). Prodrugs and Targeted Delivery (*Methods and Principles in Medicinal Chemistry*), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

Referring to Scheme 1 set out below, treatment of compounds (i) where X is a halogen, such as Cl, Br or I, and Q is a halogen with amines $HNR^7R^8$ and a suitable base in a solvent such as THF, DMF, NMP, dioxane or the like affords intermediates (ii). Generally heating is required. Suitable bases include, but are not limited to aliphatic tertiary amines, sodium or potassium carbonate, or an excess of the reacting primary or secondary amine HNR$^7$R$^8$. Reduction of the nitro group in compounds (ii) to afford anilines (iii) can be effected by various means including catalytic hydrogenation and dissolving metal reductions both in their various forms. See House, H. O., *Modern Synthetic Reactions*, Second Edition, W. A. Benjamin, Inc., Menlo Park, Calif., publ. (1972). A preferred method for effecting this reduction without removal of the halogen substituent X involves stirring a solution of (ii) in a wet alcoholic solvent with an acid such as ammonium chloride and finely divided zinc. Treatment of anilines (iii) with an isocyanate R$^9$N=C=O (iva), affords urea compounds (iv). Typically, this reaction is performed in a solvent such as THF at a temperature between ambient and the boiling point of the solvent. Coupling of (iv) with arylboronic acids or esters (ivb), preferably under the conditions of Suzuki (see Kotha, S. et al., *Tetrahedron*, 58:9633-9695 (2002)) affords compounds of the invention I. Typically, this reaction is performed by heating the halide and the boronic acid or ester to from about 90 to about 98° C. with a base such as aqueous tribasic sodium or potassium phosphate or sodium or potassium carbonate in a solvent such as dioxane, DMF, THF, or NMP using a catalyst such as tetrakis(triphenylphosphine)palladium or Cl$_2$Pd(dppf). Many variations on this reaction involving the use of different temperatures, solvents, bases, anhydrous conditions, catalysts, boronate derivatives, and halide surrogates such as triflates are known to those skilled in the art of organic/medicinal chemistry. Mild conditions have been reported for the coupling of sensitive boronic acid derivatives. See Kinzel, T. et al., *J. Am. Chem. Soc.*, 132 (40):14073-14075 (2010). Related coupling reactions for the conversion of (iv) and other aryl halide intermediates described in later Schemes into compounds of the invention include the Heck (olefin) (*J. Am. Chem. Soc.*, 96(4):1133-1136 (1974)), Stille (organostannane) (*Synthesis*, 803-815 (1992)), Sonogashira (acetylene) (Sonogashira, K. et al., *Tetrahedron Lett.*, 16(50):4467-4470 (1975)), and Negishi (organozinc) (*Aldrichimica Acta*, 38(3):71-78 (2005)) coupling reactions.

Scheme 1

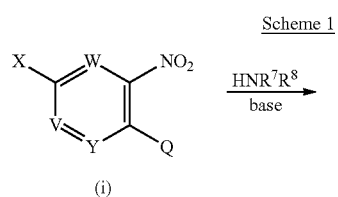

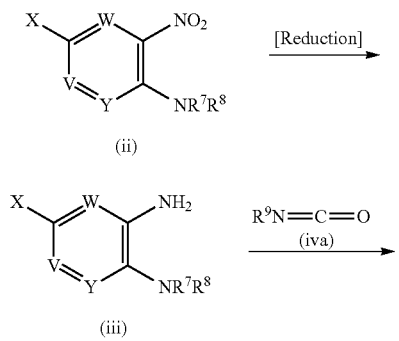

Scheme 2 describes a preparation of compounds of the invention I similar to that of Scheme 1 but with the transformations performed in a different order. In this Scheme the Suzuki or related coupling is performed on intermediate (iii) to afford aniline (v) which is derivatized by reaction with an isocyanate (iva) to afford compounds of the invention I.

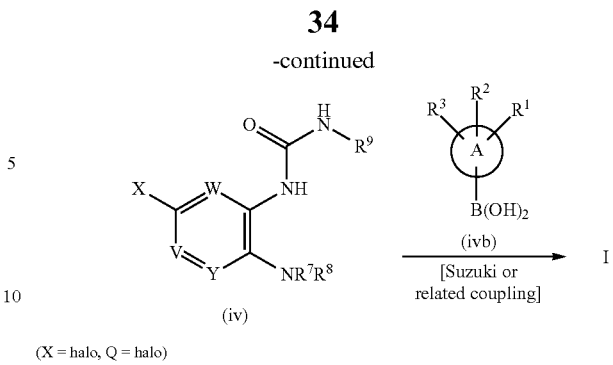

(X = halo, Q = halo)

Scheme 2

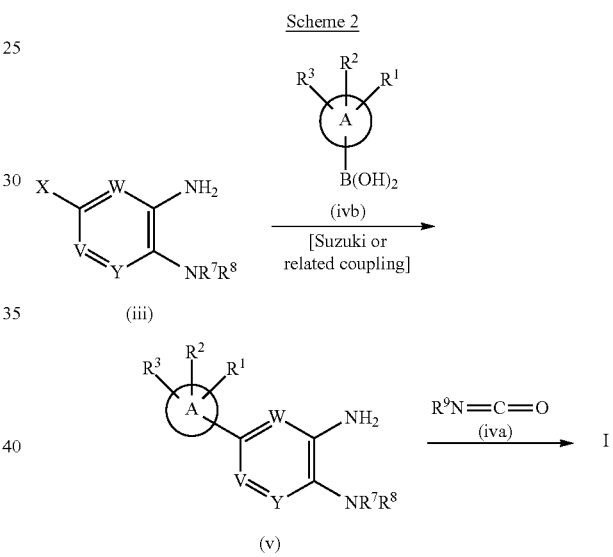

Scheme 3 illustrates a route to compounds of the invention I in which the Suzuki or related coupling is performed on intermediates (ii) to afford intermediates (vi). Reduction under the conditions described above provides anilines (v) which react with isocyanates to afford compounds of the invention I.

Scheme 3

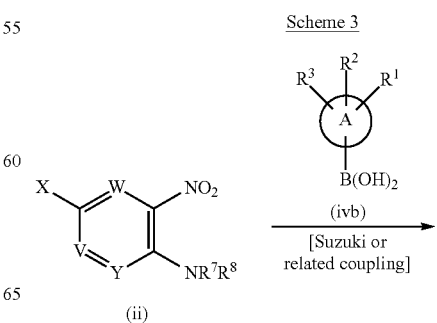

-continued

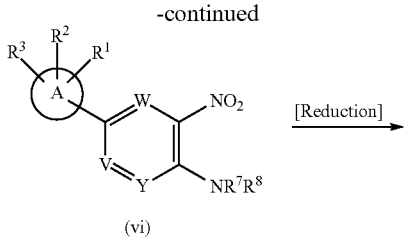

(vi)

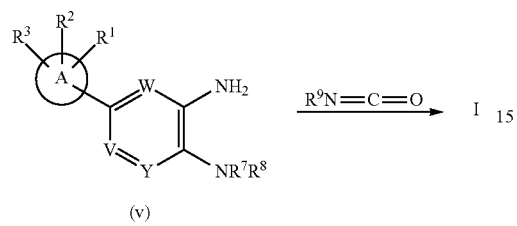

(v)

Scheme 4 illustrates a method suitable for preparation of compounds of the invention I for which the boronic acid/ester or related derivatives of the

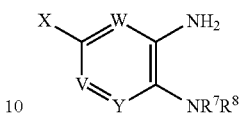

group do not readily undergo coupling reactions or are not commercially available or readily accessible. Derivative (iii) can be coupled with boronate ester dimers such as bis(neopentylglycolato)diboron (vii) by heating in a solvent such as DMSO, dioxane, toluene or DMF in the presence of a base such as potassium acetate and a catalyst such as $Cl_2Pd(dppf)$ to give aryl boronate esters (viii). These esters can undergo Suzuki or related couplings as described above, to afford intermediates (v). Functionalization of (v) as above by treatment with $R^9N=C=O$ (iva) affords compounds of the invention I.

Scheme 4

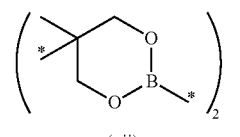

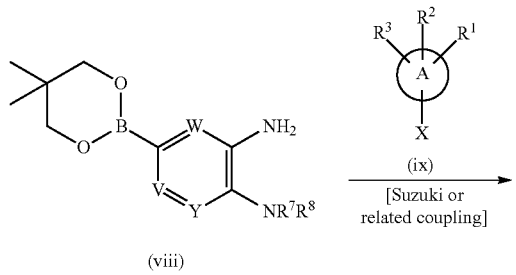

In Scheme 5 the order of synthetic steps is changed from that shown in Scheme 4. Accordingly, aryl boronate esters (viii) are functionalized by coupling with $R^9N=C=O$ to give amides or ureas-ureas (x). Alternatively, (x) may be prepared by the conditions shown in Scheme 4 on (iii). These derivatives undergo Suzuki or related coupling reactions to afford compounds of the invention I.

Scheme 5

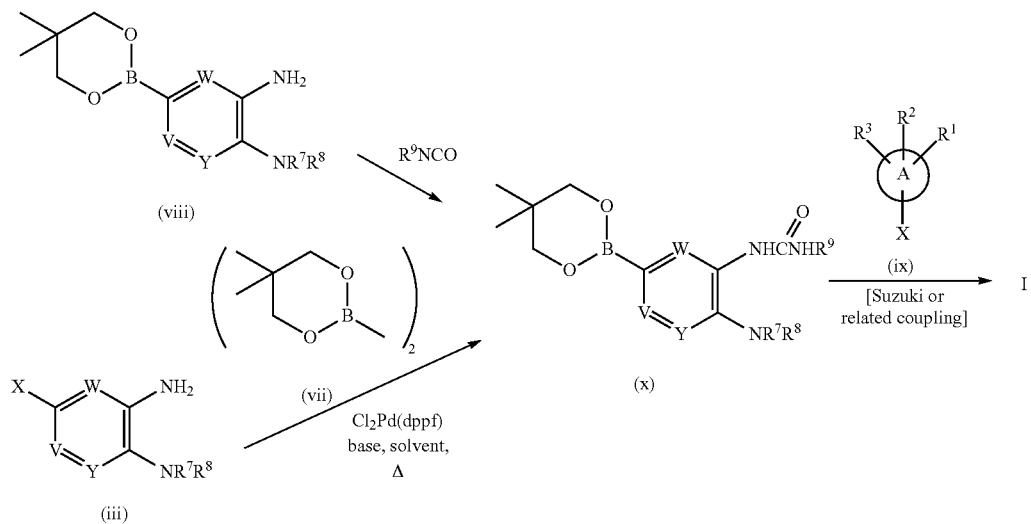

Scheme 6 describes an additional method for the preparation of compounds of the invention I. Treatment of acid or ester (xi) with primary or secondary amines $HNR^7R^8$, either in excess or in the presence of a suitable base such as an aliphatic tertiary amine, optionally in the presence of a solvent such as DMF or NMP, at elevated temperature provides adducts (xii). Esters (xii) may be saponified to the corresponding carboxylic acids (xiii) under various conditions familiar to those of ordinary skill in the art. Generally this is effected using an alkali metal hydroxide (MOH) in aqueous solution, preferably with an organic co-solvent such as methanol or THF. Carboxylic acids (xiii) can be converted (by treatment with DPPA and a tertiary amine base) to acyl azides which rearrange (Curtius rearrangement) upon heating to form isocyanates which can be trapped by alcohols R'OH to furnish carbamates (xiv). Many variations on the Curtius rearrangement are familiar to those skilled in the art of organic/medicinal chemistry which have utility for the transformation of carboxylic acids such as (xiii) into carbamates (xiv) or the related amines (iii). Transformation of carbamates (xiv) into the corresponding anilines (xii) is effected in a manner which depends upon the nature of the R' group. Typically, acidic conditions (~4M HCl in dioxane or ~1:1 $TFA-CH_2Cl_2$) are used for acid-labile carbamates (R'=t-Bu). Benzylic carbamates are generally cleaved to the corresponding anilines by exposure to hydrogen gas in the presence of a noble metal catalyst such as Pd or Pt or by phase transfer hydrogenolysis. (*Synthesis*, 685 (1976).) Methods for transformation of anilines (iii) into compounds of the invention I are described in the other Schemes.

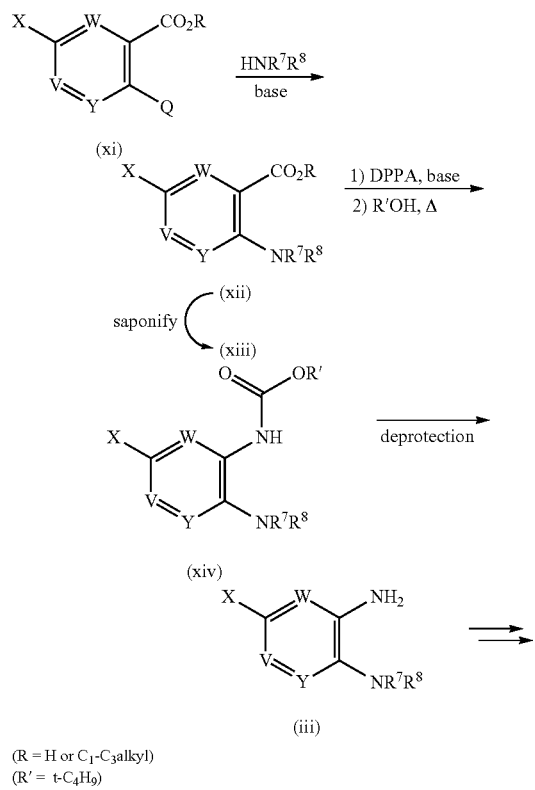

Scheme 7 describes a preparation of compounds of the invention I similar to that of Scheme 6 in which the intermediate isocyanate formed in the Curtius rearrangement is intercepted by an amine $R^9NH_2$ to generate urea intermediate (iv). Intermediate (xv) is further transformed using the Suzuki or related coupling into compounds of the invention I.

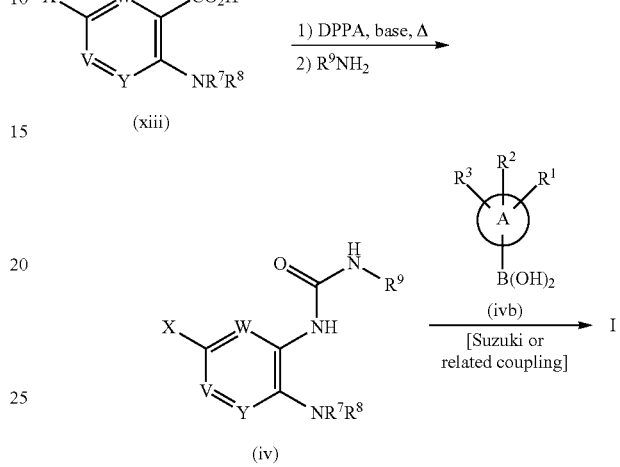

In Scheme 8 an earlier aniline intermediate (iii) is converted into the corresponding urea derivative (iv) as shown. Suzuki or related coupling reactions serve to transform this intermediate into compounds of the invention I.

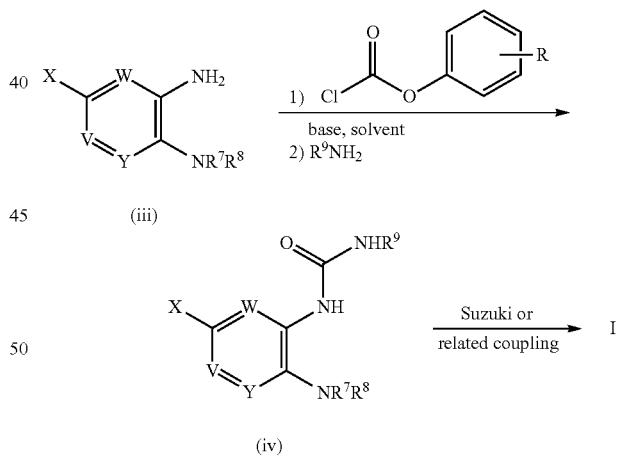

Scheme 9 describes a preparation of compounds of the invention starting from dibromoaniline or related dihaloheterocycles (xx) where X and Q are each halo. Introduction of the $NHCONHR^9$ group is accomplished as in the above Schemes to provide dibromourea (xxi). This intermediate can undergo Suzuki or related coupling at the less hindered bromide to afford intermediate (xxii). Finally, treatment with amines $HNR^7R^8$ and an appropriate catalyst, preferably using the conditions of Buchwald affords compounds of the invention I.

Scheme 9

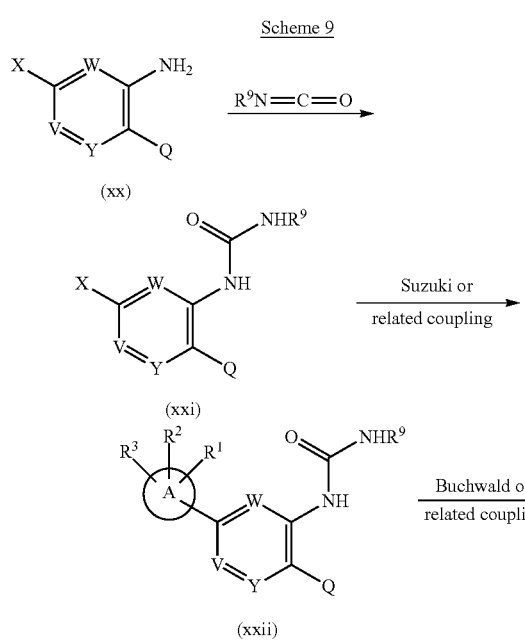

Intermediates prepared in the above Schemes may require further elaboration in order to be converted into compounds of the invention. Examples of this are provided in the following Schemes.

Scheme 10 illustrates the conversion of nitriles (xxiii) into tetrazole intermediates (xxiv) which can be converted to compounds of the invention as described herein. Typically, the nitrile (xxiii) is prepared by chemistry described above (often Suzuki coupling on an intermediate such as (iii)) and heated with an azide such as tributyltinazide in a solvent such as toluene at or near the boiling point. Compounds (xxiv) may be converted to compounds of the invention I or may be intermediates which are transformed into compounds of the invention I by methods taught in the previous schemes. This methodology could be used to prepare heteroaromatic tetrazole derivatives in addition to the phenyl derivatives shown.

Scheme 10

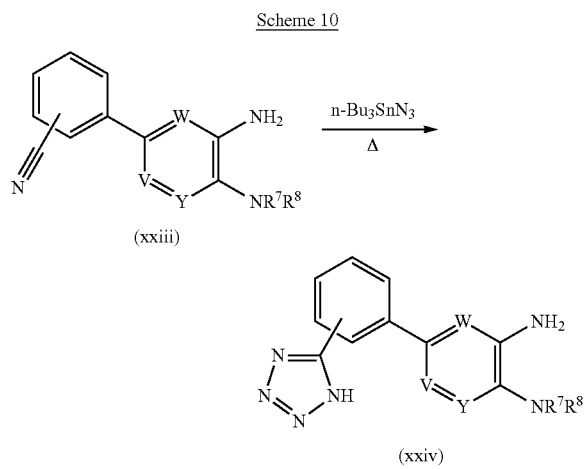

Scheme 11 illustrates the transformation of intermediates or compounds of the invention into further intermediates or compounds of the invention by functional group interconversions. Accordingly, alkyl ethers (xxix) can be converted to phenols by treatment with Lewis acids such as BBr3, preferably in a solvent such as $CH_2Cl_2$ or $CH_2ClCH_2Cl$. Re-alkylation affords new ether derivatives (xxx) in which the carboxylic acid has also been alkylated. Alternatively, phenols may be alkylated using the Mitsunobu reaction. (Reviewed in: Kumara Swamy, K. C. et al., "Mitsunobu and Related Reactions: Advances and Applications", Chem. Rev., 109:2551-2651 (2009).) Further transformation affords carboxylic acids derivatives (xxxi) or protected intermediates which could be further transformed into compounds of the invention I. The saponification reaction is generally accomplished by the use of an alkali metal hydroxide in aqueous or mixed aqueous/organic solvents. This methodology could be used to prepare heteroaromatic carboxylate derivatives in addition to the phenyl derivatives shown.

Scheme 11

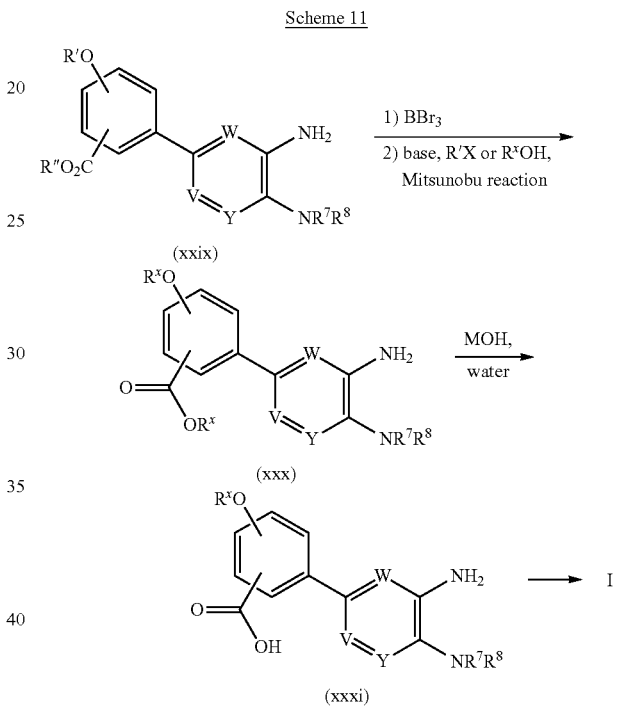

The carboxylic acids prepared in Scheme 11 can be derivatized (Scheme 12) to provide acylsulfonamides (xxxii) which may be transformed into compounds of the invention I using chemistry described in the schemes above. Generally, the conversion of carboxylic acids to acylsulfonamides is accomplished using a coupling reagent such as CDI and a base such as DBU in a solvent such as DMF or THF. This methodology could be used to prepare heteroaromatic acylsulfonamide derivatives in addition to the phenyl derivatives shown.

Scheme 12

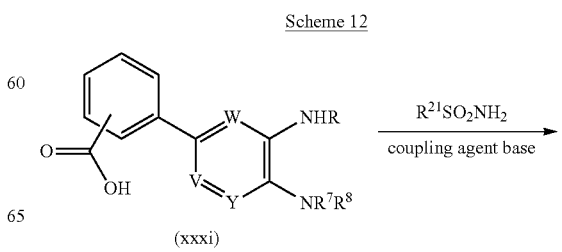

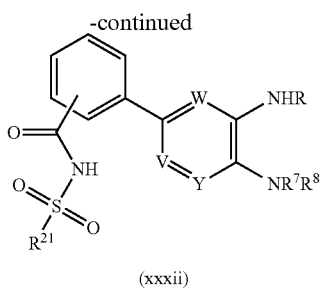

(xxxii)

The methods described in the Schemes above can be used to prepare amine derivatives (xxxiii) which may be further elaborated by treatment with a base and an electrophile such as an acyl or sulfonyl chloride or a carboxylic or sulfonic acid anhydride or activated esters or the like to prepare carboxamide or sulfonamide compounds of the invention I (Scheme 13). Alternatively, this derivatization may be performed on an earlier intermediate which may be transformed into compounds of the invention I using reactions described in the Schemes above. This methodology may be used to prepare heteroaromatic amine derivatives in addition to the aniline derivatives shown.

Scheme 13

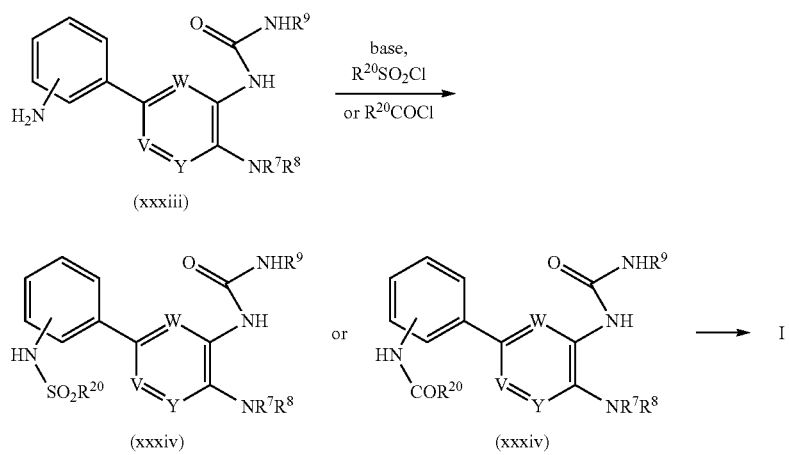

General Experimental

Air- or moisture-sensitive reactions were generally performed under an atmosphere of nitrogen or argon in anhydrous solvents (EMD DRISOLV®). Zinc (–325 mesh) for nitro group reduction was obtained from Alfa Aesar. Reaction concentrations indicated in the tables and procedures are given in units of molar and are approximate. Temperatures are given in degrees Celsius. Reactions were monitored for completeness by thin layer chromatography (TLC) or tandem liquid chromatography-mass spectroscopy (LCMS). For TLC, 0.25 mm plates coated with Silica60/F254 were used with visualization by UV light at ~254 nM, exposure to iodine vapor, or heating with PMA (phosphomolybdic acid solution), ninhydrin in ethanol, anisaldehyde solution, or ceric ammonium molybdate solution.

Unless otherwise specified, "dried" refers to the addition of anhydrous $MgSO_4$ followed by filtration and rinsing the residual solids with an appropriate organic solvent. "Stripped" means concentration under reduced pressure, generally on a rotary evaporator. "Silica gel chromatography", "flash chromatography", or "chromatographed on silica gel" refers to glass column chromatography performed in a manner similar to that described by Still (J. Org. Chem., 43:2923 (1978)). Typically silica gel 60 (EMD, 230-400 mesh ASTM) is used with solvents from JT Baker or Mallinckrodt. HPLC refers to purification by reverse-phase high-performance liquid chromatography generally on C18 columns using the stated mobile phases. Analytical HPLC runs were performed using the columns, flow rates, and mobile phases indicated. It is understood that analytical HPLC retention times ($T_r$) are reported in minutes, and may be dependent on temperature, pH, and other factors. ISCO refers to chromatography on pre-packed silica gel cartridges using automated systems marketed by Teledyne Isco. For all chromatographic purifications the isolation of product by concentration of the appropriate fractions by evaporation at or below ambient pressure is implied. Melting points were determined on a Thomas-Hoover Uni-Melt apparatus and are uncorrected. Generally, mass spectral results are reported as the $(M+H)^+$ value. For halogenated compounds where two or more peaks are significant, m/z for one peak in the cluster, generally the most intense, is reported. $^1H$ NMR spectra were recorded on dilute solutions at 400 or 500 MHz on VARIAN® or JEOL® instruments in the solvents indicated. Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities.

Unless otherwise specified, the various substituents of the compounds as employed herein are defined in the same manner as compounds of the invention of Formula (I).

For ease of reference, the following abbreviations are used herein.

Abbreviations

| | |
|---|---|
| AcOH, HOAc | acetic acid |
| ACN | acetonitrile |
| Ac$_2$O | acetic anhydride |
| ADDP | 1,1'-(azodicarbonyl)dipiperidine |
| aq. | aqueous |
| Bn | benzyl |
| Boc | t-butyl carbamate |
| Boc$_2$O | di-t-butyl dicarbonate |
| BOP | Benzotriazol-1-yloxytris(dimethylamino)phosphonium hexafluorophosphate |
| Bu | butyl |
| Cbz | benzyl carbamate |
| conc. | concentrated |
| DCE | dichloroethane |
| DCM | dichloromethane |
| DIAD | diisopropyl azodicarboxylate |
| DIEA | N,N-diisopropylethylamine |
| DMAP | 4-N,N-dimethylaminopyridine |
| DMF | dimethylformamide |
| DMSO | dimethylsulfoxide |
| DMT-MM | 4-(4,6-dimethoxy-1,3,5-triazin-2-yl)-4-methylmorpholinium chloride |
| EDC | 1-(3-(dimethylamino)propyl)-3-ethylcarbodiimide hydrochloride |
| Et | ethyl |
| EtOAc | ethyl acetate |
| EtOH | ethanol |
| Et$_2$O | diethyl ether |
| Et$_3$N | triethylamine |
| Fmoc | 9-fluorenylmethyl carbamate |
| h | hour(s) |
| HATU | O-(7-azabenzotriazol-1-yl)-N,N,N',N'-tetramethyluronium hexafluorophosphate |
| HOAt | 1-hydroxy-7-azabenzotriazole |
| HPLC | high performance liquid chromatography |
| i-PrOH | isopropanol |
| KOAc | potassium acetate |
| LAH | Lithium aluminum hydride |
| min | minute(s) |
| Me | methyl |
| MeCN | acetonitrile |
| MeOH | methanol |
| Me$_2$NH | dimethylamine |
| NaHMDS | sodium bis(trimethylsilyl)amide |
| Na(OAc)$_3$BH | sodium triacetoxyborohydride |
| n-BuLi | n-butyllithium |
| NCS | N-chlorosuccinimide |
| NMM | N-methylmorpholine |
| NMP | n-methylpyrrolidinone |
| NMR | nuclear magnetic resonance |
| OTf | trifluoromethylsulfonyloxy |
| Pd/C | palladium on carbon |
| Pd(dppf)$_2$Cl$_2$ | [1,1'-bis(diphenylphosphino)ferrocene]dichloropalladium(II) |
| Pd(OAc)$_2$ | palladium acetate |
| Pd(PPh$_3$)$_4$ | tetrakis(triphenylphosphine)palladium |
| Pd$_2$(dba)$_3$ | tris(dibenzylideneacetone)dipalladium(0) |
| PE | Petroleum ether |
| Ph | phenyl |
| PhMe | toluene |
| Ph$_2$TfN | 1,1,1-trifluoro-N-phenyl-N-(trifluoromethyl)sulfonyl methanesulfonamide |
| PPh$_3$ | triphenyl phosphine |
| RB | Round-bottom flask |
| rt | room temperature |
| sat. | saturated |
| t-Bu | tertiary butyl |
| t-BuOH | tertiary butanol |
| TFA | trifluoroacetic acid |
| Tf$_2$O | trifluoromethylsulfonic anhydride |
| THF | tetrahydrofuran |
| TMS | trimethylsilyl |
| TsO | p-toluenesulfonyl |

Analytical HPLC Conditions:

[a] Waters Sunfire C18 4.6×150 mm 3.5μ. 1 mL/min, 10-90% methanol-water 0.2% H$_3$PO$_4$, gradient over 15 min.

[b] Waters Sunfire C18 4.6×150 mm 3.5μ. 1 mL/min, 10-90% methanol-water 0.2% H$_3$PO$_4$, gradient over 10 min.

[c] YMC S5 ODS, 4.6×50 mm. 4 mL/min, 10-90% methanol-water 0.2% H$_3$PO$_4$, gradient over 12 min.

[d] Waters X-Bridge Phenyl 4.6×150 mm 3.5μ, 1 mL/min, 10-90% methanol-water 0.2% H$_3$PO$_4$, gradient over 10 min.

[e] YMC S5 ODS, 4.6×50 mm. 4 mL/min, 10-90% methanol-water 0.2% H$_3$PO$_4$, gradient over 4 min.

[f] YMC S5 ODS, 4.6×50 mm. 1 mL/min, 10-90% methanol-water 0.2% H$_3$PO$_4$, gradient over 15 min.

[g] Sunfire C18 3.0×150 mm 3.5μ. 0.5 mL/min, 14-95% acetonitrile-water, 0.05% TFA, gradient over 12 min.

[h] YMC pro c18 S5 ODS, 4.6×50 mm. 4 mL/min, 10-90% methanol-water 0.2% H$_3$PO$_4$, gradient over 12 min.

[i] SUPELCO® Ascentis 4.6×50 mm, 2.7 n C18, 4 mL/min, 5-95% acetonitrile-water, 10 mM NH$_4$OAc, gradient over 4 min. (Column temp.=35° C.)

[j] Waters Acquity UPLC BEH C18, 2.1×50 mm, 1.7-μm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

[k] Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

[l] Luna C18, 4.6×30 mm, 3-μm particles; 10-90% MeOH-water (0.1% TFA in both phases) gradient over 5 min. Flow: 4 mL/min.

[m] ZORBAX® SB C18, 4.6×75 mm, 50-90% MeOH-water (0.1% TFA in both phases) gradient over 8 min. Flow: 2.5 mL/min.

[n] YMC S5 ODS, 4.6×50 mm. 4 mL/min, 10-90% methanol-water 0.05% TFA, gradient over 4 mM.

[o] Luna C18, 4.6×30 mm, 3-μm particles; 10-86% CH$_3$CN-water (10 mM NH$_4$OAc in both phases) gradient over 2 min. Flow: 4 mL/min.

[p] Luna C18, 4.6×30 mm, 3-μm particles; 10-85.5% MeOH-water (0.1% TFA in both phases) gradient over 2 min. Flow: 4 mL/min.

[q] Luna C18, 4.6×30 mm, 3-μm particles; 10-90% MeOH-water (0.1% TFA in both phases) gradient over 3.5 min. Flow: 4 mL/min.

[r] PHENOMENEX®, 2.0×30 mm, 2.5-μm particles; 26-90% MeOH-water (0.1% TFA in both phases) gradient over 3 min. Flow: 1 mL/min.

[s] Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

[t] Column: Xbridge (150×4.6 mm), 3.5μ; Method: 0.05% TFA in water pH2.5; Mobile Phase A: Buffer: acetonitrile (95:5) Mobile Phase B: acetonitrile: Buffer (95:5) Flow: 1.0 ml/min.

[u] Column: Sunfire (150×4.6 mm), Method: 0.05% TFA in water pH2.5 Mobile Phase A: Buffer: acetonitrile (95:5) Mobile Phase B: acetonitrile: Buffer (95:5) Flow: 1.0 ml/min.

[v] Column: Ascentis Express C8 (5×2.1 mm) 2.7 μM particles, 10 mM in ammonium formate. 98:2 to 2:98 water-acetonitrile gradient over 1.5 min. Flow: 1.0 ml/min.

[w] Phenomenex-Luna C18 3 um 4.6×30 mm, 0% B-95% B with flow rate 4 mL/min and 2 min gradient time; Solvent A: 10% water/90% acetonitrile with 10 mM NH₄OAc; Solvent B: 10% water/90% acetonitrile with 10 mM NH₄OAc, wavelength 220 nM.

[x] Phenomenex Luna C18, 2.0×30 mm, 5-μm particles; Mobile Phase A: 10:90 water:MeOH 0.1% TFA; Mobile Phase B: 10:90 water:MeOH 0.1% TFA; Temperature: RT; Gradient: 0% B for a 0.2 min hold, then 0-100% B over 2.5 minutes, then a 3-minute hold at 100% B; Flow: 1.5 mL/min.

[y] Waters Acquity UPLC BEH C18, 2.1×50 mm, 1.7-μm particles; Mobile Phase A: water with 0.05% TFA; Mobile Phase B: acetonitrile with 0.05% TFA; Temperature: 50° C.; Gradient: 2-98% B over 1 minutes, then a 0.5-minute hold at 100% B; Flow: 0.8 mL/min.

Example 1

1-(4-(Diisobutylamino)-2'-(1H-tetrazol-5-yl)biphenyl-3-yl)-3-p-tolylurea

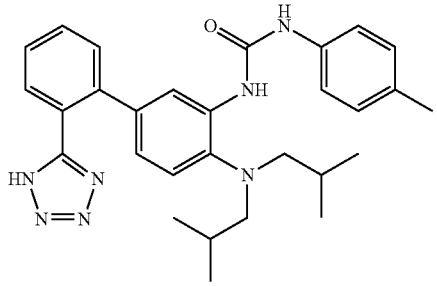

1A. 4-Bromo-N,N-diisobutyl-2-nitroaniline

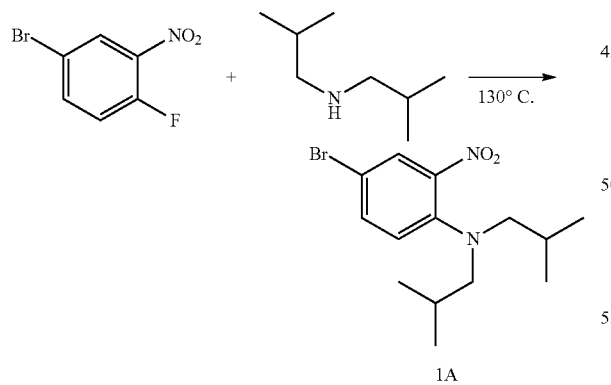

A solution of diisobutylamine (0.284 g, 2.200 mmol) and 4-bromo-1-fluoro-2-nitrobenzene (0.220 g, 1 mmol) was heated at 130° C. for 6 h. The reaction was cooled and diluted with ethyl acetate. This solution was washed with aq. HCl then brine, dried, and stripped to afford 0.3 g (87%) of 4-bromo-N,N-diisobutyl-2-nitroaniline (1A) as an orange oil. ¹H NMR (400 MHz, DMSO-d₆) δ ppm 7.90 (d, 1H, J=2.6 Hz); 7.60 (dd, 1H, J=9.0, 2.4 Hz); 7.32 (d, 1H, J=9.0 Hz); 2.89 (d, 4H, J=7.3 Hz); 1.76-1.86 (m, 2H); 0.77 (d, 12H, J=6.4 Hz). MS(ES): m/z=331 [M+H]⁺.

1B. 4-Bromo-N1,N1-diisobutylbenzene-1,2-diamine

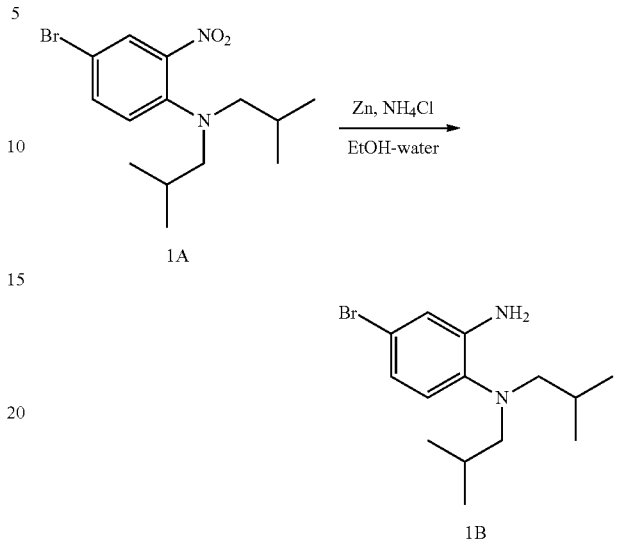

To a stirred solution of 4-bromo-N,N-diisobutyl-2-nitroaniline (1A) (0.9 g, 2.7 mmol) in ethanol (Volume: 10 mL) was added 2 mL of water followed by ammonium chloride (1.46 g, 27.3 mmol) then zinc (1.79 g, 27.3 mmol). The mixture was stirred 1 h, cooling to RT then diluted with dichloromethane and filtered. The filtrate was washed with water, dried, and stripped to afford an oil. Chromatography on silica gel (gradient elution with ether-hexanes) afforded, after removal of solvent, 0.66 g (77%) of 4-bromo-N1,N1-diisobutylbenzene-1,2-diamine (1B) as a pale purple oil. MS(ES): m/z=301 [M+H]⁺. ¹H NMR (400 MHz, DMSO-d₆) δ ppm 6.92 (d, 1H, J=8.4 Hz); 6.81 (d, 1H, J=2.2 Hz); 6.63 (dd, 1H, J=8.1, 2.2 Hz); 2.53 (d, 4H, J=7.0 Hz); 1.59-1.69 (m, 2H); 0.84 (d, 12H, J=6.6 Hz).

1C. 1-(5-Bromo-2-(diisobutylamino)phenyl)-3-p-tolylurea

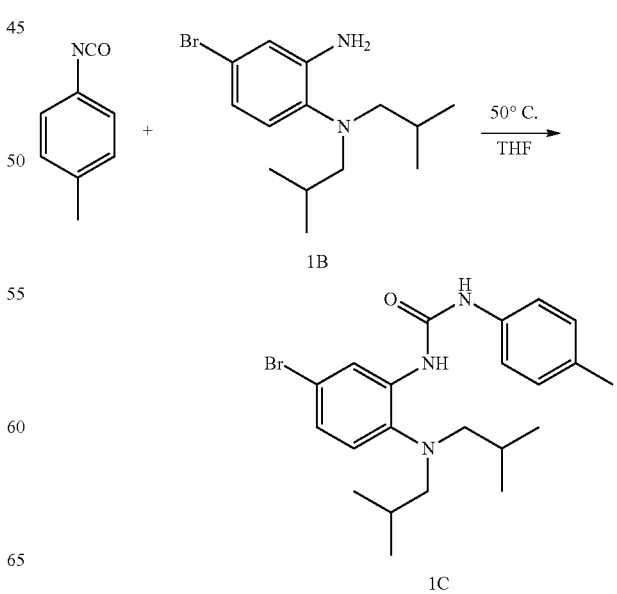

To a stirred solution of 4-bromo-N1,N1-diisobutylbenzene-1,2-diamine (1B) (0.1 g, 0.33 mmol) in THF (Volume: 1 mL) was added 1-isocyanato-4-methylbenzene (0.067 g, 0.50 mmol). The solution was stirred 1 h at 50° C. then purified by silica gel chromatography (gradient elution with EtOAc-hexanes). Concentration of the appropriate fractions afforded 0.12 g (79%) of 1-(5-bromo-2-(diisobutylamino)phenyl)-3-p-tolylurea (1C) as a white solid. $^1$H NMR (400 MHz, DMSO-$d_6$) δ ppm 9.48 (1H, s), 8.20 (1H, d, J=2.4 Hz), 7.95 (1H, s), 7.35 (2H, d, J=8.4 Hz), 7.18 (d, 1H, J=8.6 Hz), 7.07-7.13 (3H, m), 2.68 (4H, d, J=6.6 Hz), 2.24 (3H, s), 1.58-1.68 (2H, m), 0.82 (12H, d, J=6.6 Hz). MS(ES): m/z=434 [M+H]$^+$.

1. 1-(4-(Diisobutylamino)-2'-(1H-tetrazol-5-yl)biphenyl-3-yl)-3-p-tolylurea

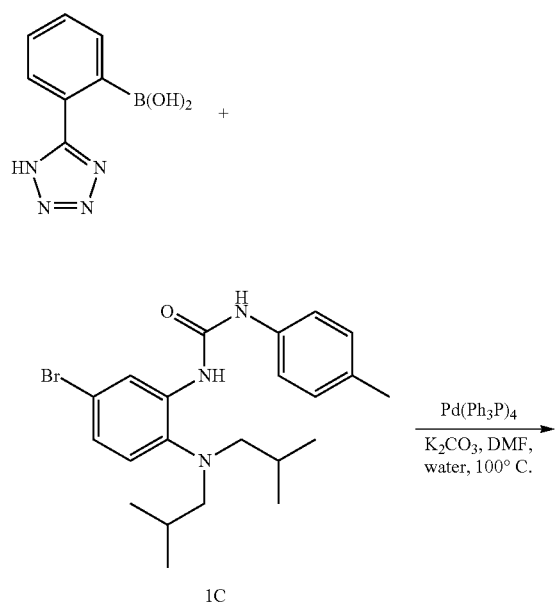

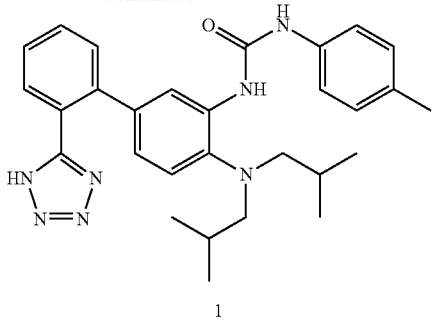

To a suspension of 2-(1H-tetrazol-5-yl)phenylboronic acid (0.062 g, 0.32 mmol) and 1-(5-bromo-2-(diisobutylamino)phenyl)-3-p-tolylurea (1C) (0.07 g, 0.162 mmol) and tetrakis(triphenylphosphine)palladium(0) (0.019 g, 0.016 mmol) in degassed DMF (Volume: 2 mL) was added aq. potassium carbonate (0.540 mL, 0.809 mmol). The mixture was placed under nitrogen and heated at 100° C. for 2 h. The reaction was cooled, diluted with aq. HCl, and extracted twice with dichloromethane. The organic extracts were combined, dried, stripped, and purified by prep. HPLC (Axia 30×100 mm column, MeOH-water-TFA gradient). Concentration of the appropriate fraction afforded 0.061 g (74%) of 1-(4-(diisobutylamino)-2'-(1H-tetrazol-5-yl)biphenyl-3-yl)-3-p-tolylurea (1) as a white powder. $^1$H NMR (400 MHz, DMSO-$d_6$) δ ppm 9.32 (1H, s), 7.90 (1H, d, J=2.2 Hz), 7.83 (1H, s), 7.65-7.70 (1H, m), 7.60 (1H, d, J=7.7 Hz), 7.50-7.57 (2H, m), 7.33 (2H, d, J=8.4 Hz), 7.05-7.10 (3H, m), 6.52 (1H, dd, J=8.1, 2.1 Hz), 2.66 (4H, d, J=6.8 Hz), 1.59-1.69 (2H, m), 0.83 (12H, d, J=6.6 Hz). MS(ES): m/z=498 [M+H]$^+$.

Using the method described (Examples 1A and 3A are representative), the appropriate amines HNR$^7$R$^8$ were reacted with 2-fluoro-5-bromonitrobenzene in the indicated (Table 1A) solvents at the indicated temperatures. Any additional tertiary amine base utilized in these transformations is indicated in the table. This afforded nitroanilines which were processed by the procedure for the conversion of 1A into 1B to afford intermediates.

TABLE 1A

Preparation of Intermediates (iii) from a Commercially-Available Fluoro nitrobenzene

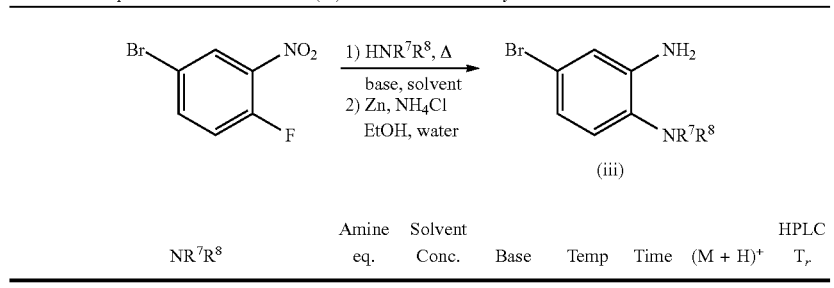

| | NR$^7$R$^8$ | Amine eq. | Solvent Conc. | Base | Temp | Time | (M + H)$^+$ | HPLC T$_r$ |
|---|---|---|---|---|---|---|---|---|
| iiia | (2-tert-butylphenyl)NH– | 3 | None | None | 140 | 20 h | 319 | 4.48$^l$ |

TABLE 1A-continued

Preparation of Intermediates (iii) from a Commercially-Available Fluoro nitrobenzene $$\text{Br}\underset{F}{\overset{NO_2}{\bigcirc}} \xrightarrow[\substack{\text{2) Zn, NH}_4\text{Cl} \\ \text{EtOH, water}}]{\substack{\text{1) HNR}^7\text{R}^8, \Delta \\ \text{base, solvent}}} \text{Br}\underset{NR^7R^8}{\overset{NH_2}{\bigcirc}}$$

(iii)

| NR⁷R⁸ | | Amine eq. | Solvent Conc. | Base | Temp | Time | (M + H)⁺ | HPLC T$_r$ |
|---|---|---|---|---|---|---|---|---|
| iiib | [N-methyl-N-cyclohexyl] | 2 | THF 0.4 M | None | 50 | 3 h | 285 | 2.40[l] |
| iiic | [N-ethyl-N-cyclohexyl] | 2 | THF 0.1 M | None | 50 | 3 h | 299 | 2.20[c] |
| iiid | [decahydroquinoline] | 2 | THF 0.4 M | None | 50 | 3 h | 311 | 3.17[l] |
| iiif | [N-H-N-cyclohexyl] | 2.2 | THF 0.8 M | None | 60 | 1 h | 269 | 2.92[l] |
| iiig | [N-methyl-N-tetrahydropyranyl] | 1.3 HCl salt | DMF 1 M | Et₃N 2.5 eq. | 100 | 2 h | 269 | 2.92[l] |
| iiih | [N-methyl-N-(2,2-dimethoxyethyl)] | 3 | NMP 1 M | None | 100 | 0.5 h | 224 (M + H − 2 MeOH)⁺ | 2.48[l] |

TABLE 1A-continued

Preparation of Intermediates (iii) from a Commercially-Available Fluoro nitrobenzene

[Reaction scheme: 4-bromo-2-nitro-1-fluorobenzene + 1) HNR⁷R⁸, Δ, base, solvent; 2) Zn, NH₄Cl, EtOH, water → 4-bromo-2-amino-1-(NR⁷R⁸)benzene (iii)]

| | NR⁷R⁸ | Amine eq. | Solvent Conc. | Base | Temp | Time | (M + H)⁺ | HPLC $T_r$ |
|---|---|---|---|---|---|---|---|---|
| iiii | N(CH₂CH₂OCH₃)₂ | 3 | NMP 1 M | None | 100 | 0.5 h | 303 | 1.68$^o$ |
| iiij | N(propyl)(CH₂-cyclopropyl) | 3 | NMP 1 M | None | 60 | 1.5 h | 285 | 2.32$^l$ |
| iiik | NH-CH₂-CHF₂ | 1.5 | NMP 2 M | Et₃N 1.4 eq. | 55 | 2 h | 251 | 2.15$^l$ |
| iiil | N(CH₂-CHF₂)(CH₂-cyclopropyl) | 1.2 HCl salt | NMP 0.6 M | Et₃N 2.2 eq. | 130 | 1.5 h | 325 | 3.14$^l$ |
| iiim | N(CH₂CH₂CF₃)(CH₂-cyclopropyl) | 1.1 HCl salt | NMP 1 M | DIEA 2 eq. | 135 | 4 h | 339 | 4.25$^l$ |
| iiin | N(CH₂-cyclopropyl)₂ | 1.2 HCl salt | NMP 1 M | DIEA 2.2 eq. | 130 | 2 h | 297 | 3.66$^l$ |
| iiio | N(ethyl)(CH₂CH₂OCH₃) | 3 | NMP 1 M | None | 100 | 17 h | 275 | 2.06$^l$ |

TABLE 1A-continued

Preparation of Intermediates (iii) from a Commercially-Available Fluoro nitrobenzene 1) HNR⁷R⁸, Δ, base, solvent
2) Zn, NH₄Cl, EtOH, water → (iii)

| | NR⁷R⁸ | Amine eq. | Solvent Conc. | Base | Temp | Time | (M + H)⁺ | HPLC $T_r$ |
|---|---|---|---|---|---|---|---|---|
| iiip | N-ethyl-N-cyclopentyl | 1.1 HCl salt | NMP 1 M | Et₃N 2.3 eq. | 100 | 3 h | 285 | 2.59$^l$ |
| iiiq | N-methyl-N-cycloheptyl | 1.2 HCl salt | NMP 1 M | DIEA 3 eq. | 110 | 3 h | 299 | 3.10$^l$ |
| iiir | N-(cyclopropylmethyl)-N-cyclohexyl | 1.2 HCl salt | NMP 1 M | DIEA 3 eq. | 120 | 3 h | 325 | 1.71$^p$ |
| iiis | N-propyl-N-cyclohexyl | 1.2 HCl salt | NMP 1 M | DIEA 2.5 eq. | 120 | 3 h | 313 | 1.72$^p$ |
| iiit | N,N-dibutyl | 3 | NMP 1 M | None | 100 | 1 h | 301 | 1.79$^p$ |
| iiiu | N-isobutyl-N-(cyclopropylmethyl) | 1.3 HCl salt | NMP 1 M | DIEA 2.8 eq. | 120 | 20 | 299 | 1.81$^p$ |

TABLE 1A-continued

Preparation of Intermediates (iii) from a Commercially-Available Fluoro nitrobenzene Br-C6H3(NO2)(F) + 1) HNR⁷R⁸, Δ, base, solvent; 2) Zn, NH₄Cl, EtOH, water → Br-C6H3(NH2)(NR⁷R⁸) (iii)

| | NR⁷R⁸ | Amine eq. | Solvent Conc. | Base | Temp | Time | (M + H)⁺ | HPLC $T_r$ |
|---|---|---|---|---|---|---|---|---|
| iiiv | N(isobutyl)(cyclobutylmethyl) | 1 HCl salt | NMP 0.5 M | DIEA 3 eq. | 135 | 5 h | 313 | 2.05$^p$ |
| iiiw | N(methyl)(4,4-difluorocyclohexyl) | 1.4 HCl salt | NMP 0.5 M | DIEA 3 eq. | 110 | 3 h | 321 | 2.43$^p$ |
| iiix | N(ethyl)(neopentyl) | 1.4 HCl salt | NMP 0.6 M | DIEA 3 eq. | 110 | 3 h | 287 | 2.54$^p$ |
| iiiy | 2-ethylpiperidin-1-yl | 2.5 | NMP 1 M | None | 110 | 3 h | 285 | 2.06$^p$ |
| iiiz | N(isobutyl)(cyclohexyl) | 1.7 | NMP 1 M | DIEA 1.3 eq. | 140 | 24 h | 327 | 2.88$^q$ |
| iiiab | N(2-cyclopropylethyl)(isobutyl) | 1.2 HCl salt | NMP 1 M | DIEA 2.5 eq. | 125 | 4 h | 313 | 2.61$^l$ |
| iiiac | N(C(CD3)(CH3))(cyclohexyl) | 1.7 | NMP 1 M | DIEA 1.3 eq. | 140 | 24 h | 329 | 2.86$^q$ |

TABLE 1A-continued

Preparation of Intermediates (iii) from a Commercially-Available Fluoro nitrobenzene

| | NR⁷R⁸ | Amine eq. | Solvent Conc. | Base | Temp | Time | (M + H)⁺ | HPLC $T_r$ |
|---|---|---|---|---|---|---|---|---|
| iiiad | N-isobutyl-isopropyl | 1.7 HCl salt | NMP 1 M | DIEA 3 eq. | 140 | 24 h | 287 | 2.32$^l$ |
| iiiag | N-propyl-cyclopentyl | 1.4 | NMP 1 M | DIEA 1.3 eq. | 140 | 18 h | 299 | 2.34$^q$ |
| iiiah | N-isobutyl-cyclopentyl | 1.4 | NMP 1 M | DIEA 1.2 eq. | 140 | 4 h | 313 | 2.64$^q$ |
| iiiaj | N-butyl-cyclohexyl | 1.4 HCl salt | NMP 0.6 M | DIEA 3 eq. | 140 | 18 h | 327 | 2.01$^q$ |
| iiiak | N-methyl-isobutyl | 4 | NMP 1 M | None | 140 | 4 h | 259 | 1.73$^q$ |
| iiial | N-isobutyl-cyclobutyl | 0.8 | NMP 1 M | DIEA 1.4 eq. | 130 | 5 h | 299 | 2.08$^q$ |
| iiiam | N-propyl-benzyl | 1.4 | NMP 1.5 M | Et₃N 1.1 eq. | 100 | 2 h | 321 | 3.90$^q$ |

TABLE 1A-continued

Preparation of Intermediates (iii) from a Commercially-Available Fluoro nitrobenzene Br-[benzene ring with NO₂ and F] → 1) HNR⁷R⁸, Δ base, solvent; 2) Zn, NH₄Cl EtOH, water → Br-[benzene ring with NH₂ and NR⁷R⁸] (iii)

| | NR⁷R⁸ | Amine eq. | Solvent Conc. | Base | Temp | Time | (M + H)⁺ | HPLC $T_r$ |
|---|---|---|---|---|---|---|---|---|
| iiian | N(CH₂CH(CH₃)CF₃)(CH₂CH(CH₃)₂) | 1.4 | NMP 1 M | DIEA 1.2 eq. | 130 | 19 h | 369 | 2.76$^q$ |
| iiiao | N(cyclohexyl)(CH₂CH(CH₃)CH₂CF₃) | 1 | NMP 1 M | Et₃N 1.2 eq. | 140 | 6 h | 395 | 2.84$^r$ |
| iiiap | N(CH₂CH₂OCH₃)(CH₂-4-ClC₆H₄) | 1.4 HCl salt | NMP 1 M | DIEA 1.2 eq. | 130 | 19 h | 371 | 2.39$^q$ |
| iiiaq | N(cyclohexyl)(CH₂CHF₂) | 1.1 HCl salt | NMP 1 M | DIEA 2.4 eq. | 150 | 18 h | 335 | 2.51$^q$ |
| iiiar | N(CH₂CF₃)(CH₂CH(CH₃)₂) | 1.3 | NMP 1.3 M | DIEA 1.5 eq. | 130 | 20 h | 339 | 2.63$^q$ |
| iiias | NH(CH₂CH(CH₃)₂) | 3 | DMF 0.6 M | None | 80 | 1 h | 273 | 4.59$^l$ |

TABLE 1A-continued
Preparation of Intermediates (iii) from a Commercially-Available Fluoro nitrobenzene
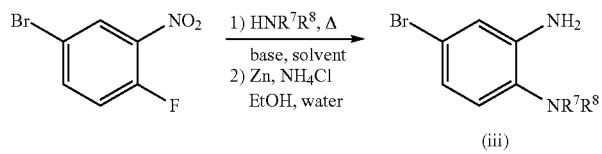
| | NR⁷R⁸ | Amine eq. | Solvent Conc. | Base | Temp | Time | (M + H)⁺ | HPLC T$_r$ |
|---|---|---|---|---|---|---|---|---|
| iiiat | | 2 | NMP 1.5 M | DIEA 1.2 eq. | 110-115 | 7 h | 351 | 1.23$^k$ |
| iiiau | | 1.1 | NMP 1.5 M | DIEA 1.1 eq. | 110-120 | 6 h | 369 | 3.35$^l$ |
| iiiav | | 1.1 | NMP 1.5 M | DIEA 1.2 eq. | 120 | 4 h | 397 | 3.97$^l$ |
| iiiaw | | 1.3 | NMP 1.5 M | DIEA 2 eq. | 140 | 30 | 369 | 2.06$^p$ |
| iiiax | | 4 | NMP 1.5 M | None | 120 | 72 | 313 | 4.64$^l$ |
| iiiay | | 2 | NMP 1.5 M | DIEA 1 eq. | 130 | 16 | 327 | 1.63$^p$ |

TABLE 1A-continued

Preparation of Intermediates (iii) from a Commercially-Available Fluoro nitrobenzene

| NR⁷R⁸ | | Amine eq. | Solvent Conc. | Base | Temp | Time | (M + H)⁺ | HPLC $T_r$ |
|---|---|---|---|---|---|---|---|---|
| iiiaz | (N-isobutyl, N-(2-isopropoxyethyl)) | 1.5 | NMP 1.5 M | DIEA 1 eq. | 100 | 1 | 331 | 3.40$^l$ |
| iiibc | (NH-tert-butyl) | 10 | None | None | 46 | 3 h | (M − H)⁻ 271 | 2.24$^v$ |
| iiibd | (pyrazol-1-yl) | 1.2 | DMF 0.5 M | K₂CO₃ 3 eq | 80 | 18 h | (M − H)⁻ 266 | 1.84$^v$ |

Using the methods described (Example 1A and 3A are representative), the appropriate amines HNR⁷R⁸ were reacted with 2,4-difluoro-5-bromonitrobenzene in the indicated (Table 1B) solvents at the indicated temperatures. Any additional tertiary amine base utilized in these transformations is indicated in the table. This afforded nitroanilines which were processed by the procedure for the conversion of 1A into 1B to afford the intermediates (iii).

Certain aniline derivatives iii may be made by alkylation of nitroanilines followed by reduction as described above. The procedure below is illustrative.

4-bromo-N-cyclohexyl-N-(2-methylallyl)-2-nitroaniline

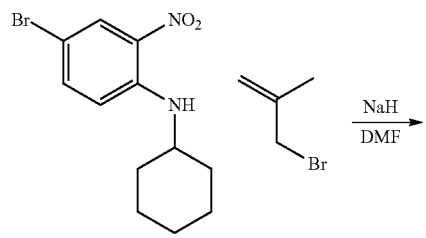

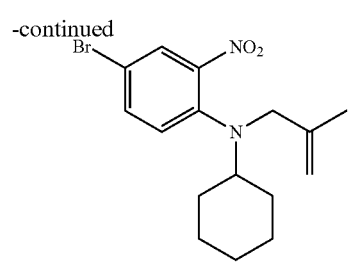

A solution of 4-bromo-N-cyclohexyl-2-nitroaniline (0.598 g, 1.999 mmol) in DMF (4 mL) was treated with 3-bromo-2-methylprop-1-ene (0.403 mL, 4.00 mmol) followed by sodium hydride (0.137 g, 4.00 mmol). The reaction was stirred at RT for 15 min. and then treated with an additional 0.3 g of sodium hydride and 0.4 mL of alkylating agent. The reaction was stirred an additional 4 h at RT then carefully quenched with glacial HOAc then diluted with water. This dark mixture was ext. with ether, and the org. ext. was dried, stripped, and submitted purified by ISCO. Concentration of the appropriate fractions afforded 0.32 g (43%) of 4-bromo-N-cyclohexyl-N-(2-methylallyl)-2-nitroaniline as an oil. LCMS: 353 (M+H)⁺. HPLC Tr: 2.48 g.

4-bromo-N-(4-chlorobenzyl)-N-cyclohexyl-2-nitroaniline

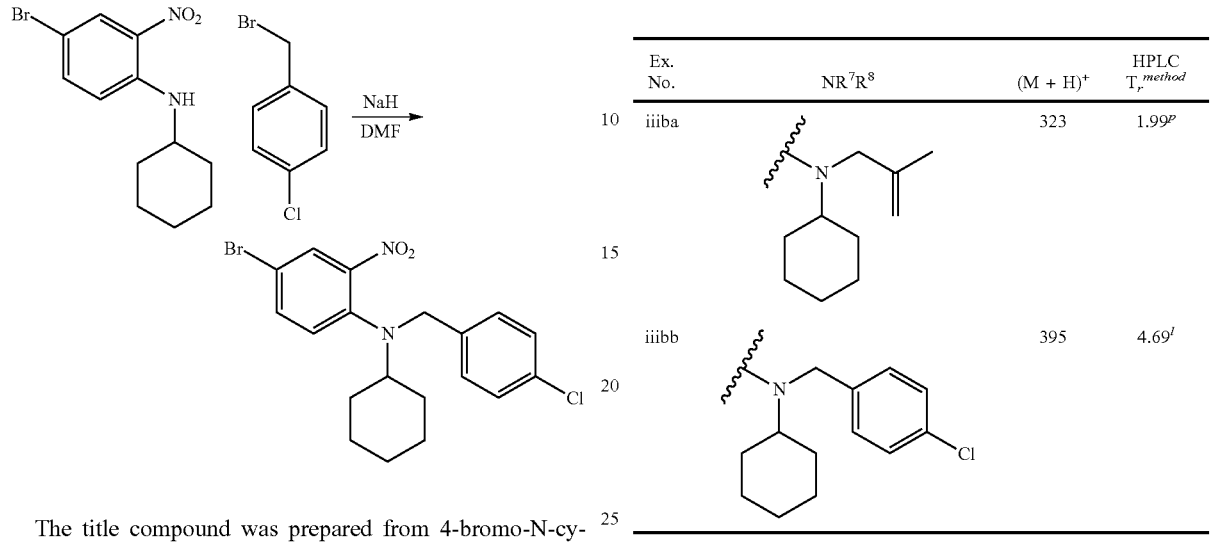

The title compound was prepared from 4-bromo-N-cyclohexyl-2-nitroaniline and 4-chlorobenzylbromide using the procedure for preparation of 4-bromo-N-cyclohexyl-N-(2-methylallyl)-2-nitroaniline. LCMS: 425 (M+H)+. HPLC Tr: 5.48$^t$.

Reduction of the nitro groups as described above affords anilines iii:

| Ex. No. | NR$^7$R$^8$ | (M + H)+ | HPLC T$_r^{method}$ |
|---|---|---|---|
| iiiba | N-cyclohexyl-N-(2-methylallyl) | 323 | 1.99$^p$ |
| iiibb | N-cyclohexyl-N-(4-chlorobenzyl) | 395 | 4.69$^t$ |

TABLE 1B

Preparation of Intermediates from a Commercially-Available Difluoronitrobenzene

| Ex. No. | NR$^7$R$^8$ | Amine eq. | Solvent conc. | Base | Temp | Time | (M + H)+ | HPLC T$_r^{method}$ |
|---|---|---|---|---|---|---|---|---|
| iiica | N-methyl-N-cyclohexyl | 1.3 | THF 0.3 M | Et$_3$N 1.3 eq. | 60 | 1.5 h | 285 | 3.43$^l$ |
| iiicb | N-isobutyl-N-cyclohexyl | 1.2 | NMP 0.7 M | DIEA 1.3 eq. | 140 | 24 h | 345 | 2.39$^r$ |
| iiicc | N-(2,2-difluoroethyl)-N-cyclopropylmethyl, HCl salt | 1.2 | NMP 0.5 M | Et$_3$N 2.2 eq. | 130 | 1.5 h | 325 | 3.14$^l$ |

TABLE 1B-continued

Preparation of Intermediates from a Commercially-Available Difluoronitrobenzene

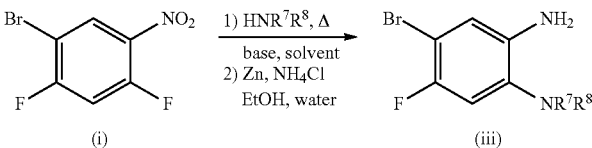

| Ex. No. | NR⁷R⁸ | Amine eq. | Solvent conc. | Base | Temp | Time | (M + H)⁺ | HPLC $T_r^{method}$ |
|---|---|---|---|---|---|---|---|---|
| iiicd | (diisobutylamino-cyclohexyl structure) | 1.1 | DMF 1 M | Et₃N 1.5 eq. | 60 | 1.5 h | 317 | 2.25$^P$ |

Preparation of Intermediates from a Commercially-Available Difluoronitrobenzene

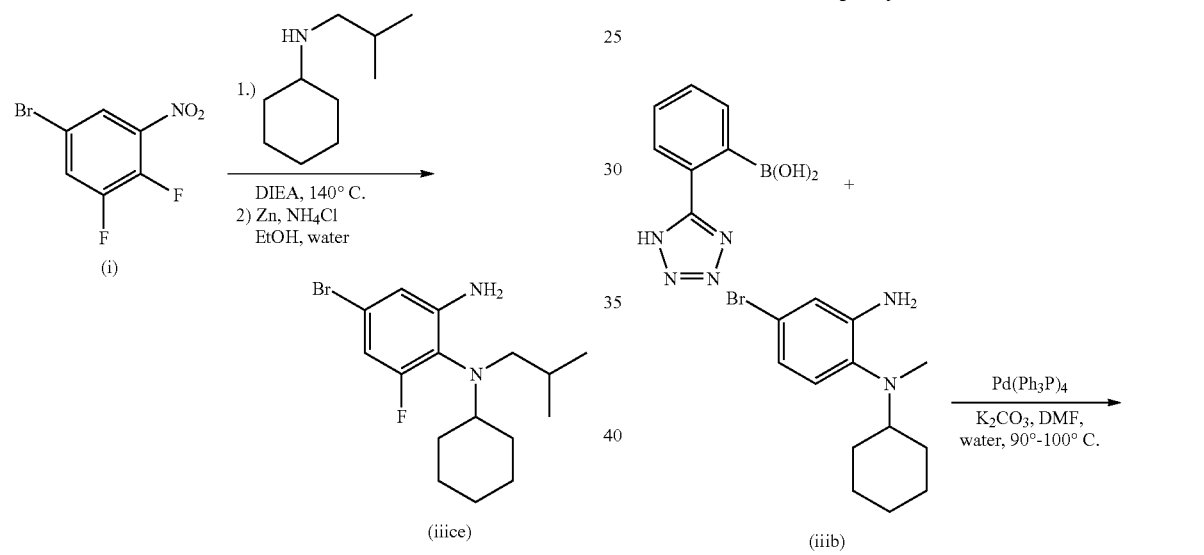

4-bromo-N1-cyclohexyl-6-fluoro-N1-isobutylbenzene-1,2-diamine was prepared from 5-bromo-1,2-difluoro-3-nitrobenzene and N-isobutylcyclohexanamine by the procedures outlined in the examples above.

Example 2

1-(4-(Cyclohexyl(methyl)amino)-2'-(1H-tetrazol-5-yl)biphenyl-3-yl)-3-(4-(trifluoromethyl)phenyl)urea

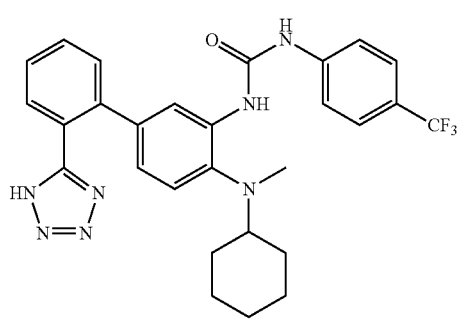 [SMILES: CN(c1ccc(-c2ccccc2-c2nnn[nH]2)cc1NC(=O)Nc1ccc(C(F)(F)F)cc1)C1CCCCC1]

2A. N4-Cyclohexyl-N4-methyl-2'-(1H-tetrazol-5-yl)biphenyl-3,4-diamine

To a suspension of 2-(1H-tetrazol-5-yl)phenyl-boronic acid (0.68 g, 3.6 mmol) and 4-bromo-N1-cyclohexyl-N1-methylbenzene-1,2-diamine (iiib) (0.57 g, 2 mmol) and tetrakis(triphenylphosphine)palladium(0) (0.12 g, 0.100 mmol) in DMF (Volume: 8 mL) was added aq. potassium carbonate (5.00 mL, 10.0 mmol). The mixture was placed under nitrogen and heated at 100° C. for 3 h. LCMS indicated reaction is ~50% complete, so it was treated with an additional 0.15 g of boronic acid and 0.04 g of catalyst and heated at 90° C. overnight. The reaction was cooled and poured into diluted aq. HOAc. The resulting mixture was extracted twice with chloroform. The combined organic extracts were dried, stripped, and chromatographed on silica gel (gradient elution with EtOAc-hexanes, 1% HOAc) to afford, after removal of solvent, N4-cyclohexyl-N4-methyl-2'-(1H-tetrazol-5-yl)biphenyl-3,4-diamine (2A) (0.17 g, 23% yield) as a beige foam. $^1$H NMR (400 MHz, DMSO-d$_6$) δ ppm 11.93 (br. s, 1H); 7.48-7.66 (m, 4H); 6.79 (d, 1H, J=7.9 Hz); 6.52 (d, 1H, J=2.2 Hz); 6.12 (dd, 1H, J=7.9, 1.8 Hz); 4.6-4.8 (br. s, 2H); 2.68-2.76 (m, 1H); 1.90 (s, 3H); 1.64-1.76 (m, 4H); 1.50-1.58 (m, 1H); 1.26-1.39 (m, 2H); 1.02-1.19 (m, 3H). MS(ES): m/z=349 [M+H]$^+$.

2. 1-(4-(Cyclohexyl(methyl)amino)-2'-(1H-tetrazol-5-yl)biphenyl-3-yl)-3-(4-(trifluoromethyl)phenyl)urea

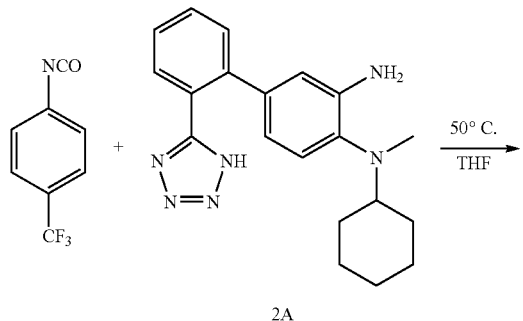

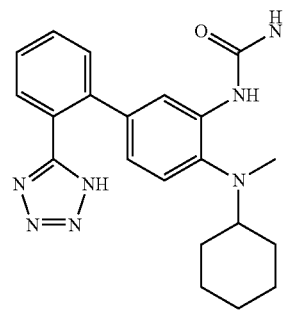

To a stirred solution of N4-cyclohexyl-N4-methyl-2'-(1H-tetrazol-5-yl)biphenyl-3,4-diamine (2A) (0.015 g, 0.043 mmol) in THF (Volume: 0.2 mL) was added 1-isocyanato-4-(trifluoromethyl)benzene (0.014 g, 0.073 mmol). The solution was stirred 2 h at 50° C. then cooled and purified by prep. HPLC (Axia 21×100 mm column, MeOH-water-TFA gradient). Concentration of the appropriate fraction afforded 1-(4-(cyclohexyl(methyl)amino)-2'-(1H-tetrazol-5-yl)biphenyl-3-yl)-3-(4-(trifluoromethyl)phenyl)urea (2) (0.012 g, 49% yield) as a white powder. $^1$H NMR (400 MHz, DMSO-d$_6$) δ ppm 9.92 (s, 1H); 8.44 (s, 1H); 8.02 (s, 1H); 7.60-7.71 (m, 6H); 7.52-7.56 (m, 2H); 7.12 (d, 1H, J=8.1 Hz); 6.58 (d, 1H, J=7.7 Hz); 2.60-2.66 (m, 1H); 2.58 (s, 3H); 1.81-1.88 (m, 2H); 1.66-1.74 (m, 2H); 1.50-1.57 (m, 1H); 1.01-1.29 (m, 5H). MS(ES): m/z=536 [M+H]$^+$.

Example 3

1-(4-(Cyclopentyl(methyl)amino)-2'-(1H-tetrazol-5-yl)biphenyl-3-yl)-3-p-tolylurea

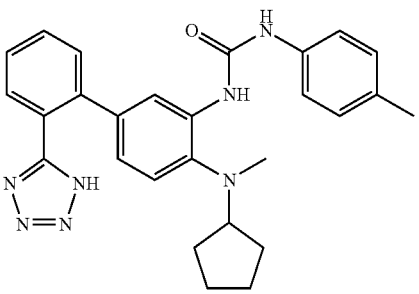 [SMILES: Cc1ccc(NC(=O)Nc2cc(-c3ccccc3-c3nnn[nH]3)ccc2N(C)C2CCCC2)cc1]

3A. 4-Bromo-N-cyclopentyl-N-methyl-2-nitroaniline

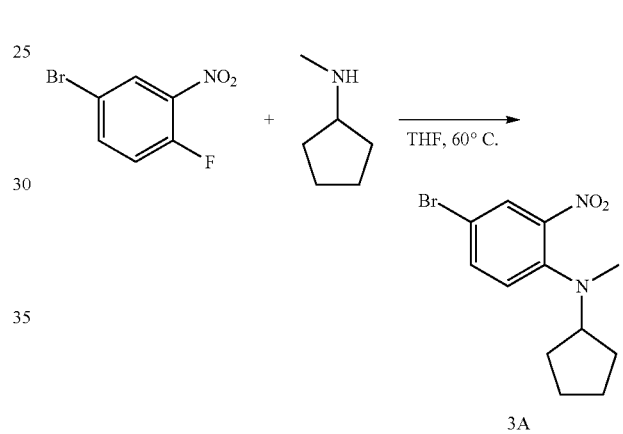

To a stirred solution of 4-bromo-1-fluoro-2-nitrobenzene (0.440 g, 2 mmol) in THF (Volume: 2 mL) was added N-methylcyclopentanamine (0.595 g, 6.00 mmol). The solution was stirred 1 h at 60° C. then cooled and stirred at RT. The solution was diluted with ether and washed with dilute aq. HOAc then aq. sodium bicarbonate then brine. The organic phase was dried and stripped to afford 4-bromo-N-cyclopentyl-N-methyl-2-nitroaniline (3A) (0.57 g, 91% yield) as an orange oil. $^1$H NMR (400 MHz, DMSO-d$_6$) δ ppm 7.94 (d, 1H, J=2.4 Hz); 7.64 (dd, 1H, J=9.0, 2.4 Hz); 7.30 (d, J=9.0 Hz); 3.70-3.79 (m, 1H); 2.58 (s, 3H); 1.44-1.83 (m, 10H). MS(ES): m/z=301 [M+H]$^+$.

3B. N-Cyclopentyl-N-methyl-3-nitro-2'-(1H-tetrazol-5-yl)biphenyl-4-amine

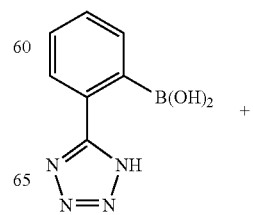

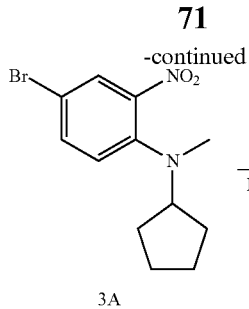

3A

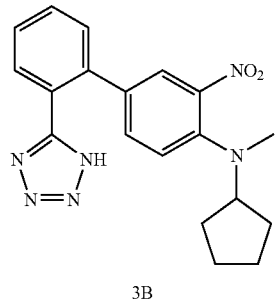

3B

A suspension of 2-(1H-tetrazol-5-yl)phenylboronic acid (0.190 g, 1.000 mmol) and 4-bromo-N-cyclopentyl-N-methyl-2-nitroaniline (3A) (0.150 g, 0.5 mmol) and tetrakis(triphenylphosphine)palladium(0) (0.035 g, 0.03 mmol) in degassed DMF (Volume: 4 mL) was treated with aq. potassium carbonate (1.667 mL, 2.500 mmol). The mixture was placed under nitrogen and heated at 95° C. for 2.5 h. The reaction was diluted with ~4 mL of water and filtered hot. The filtrate was diluted to 40 mL with water, brought to pH 3 with conc. HCl, and stirred vigorously to induce precipitation of product. The resulting red solid was filtered, rinsed with water, and air-dried to afford N-cyclopentyl-N-methyl-3-nitro-2'-(1H-tetrazol-5-yl)biphenyl-4-amine (3B) (0.175 g, 91% yield). $^1$H NMR (400 MHz, DMSO-$d_6$) δ ppm 7.65-7.69 (m, 2H); 7.55-7.62 (m, 2H); 7.53 (d, 1H, J=2.2 Hz); 7.20 (d, 1H, J=8.6 Hz); 7.09 (dd, 1H, J=8.6, 2.2 Hz); 3.77-3.86 (m, 1H); 2.58 (s, 3H); 1.76-1.89 (m, 2H); 1.46-1.69 (m, 8H). MS(ES): m/z=365 [M+H]$^+$.

3C. N4-Cyclopentyl-N4-methyl-2'-(1H-tetrazol-5-yl)biphenyl-3,4-diamine

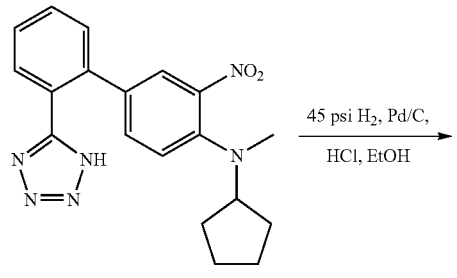

A suspension of N-cyclopentyl-N-methyl-3-nitro-2'-(1H-tetrazol-5-yl)biphenyl-4-amine (0.16 g, 0.439 mmol) and palladium on carbon (0.05 g, 0.047 mmol) in ethanol (Volume: 5 mL) was treated with HCl in dioxane (0.132 mL, 0.527 mmol) and hydrogenated at 45 psi for 30 min. Catalyst was removed by filtration, and the organic solution was stripped and purified by prep. HPLC (Axia 30×100 mm column, MeOH-water-TFA gradient). Concentration of the appropriate fractions afforded N4-cyclopentyl-N4-methyl-2'-(1H-tetrazol-5-yl)biphenyl-3,4-diamine (3C) (0.05 g, 34% yield) as a glass. HPLC T$_r$: 2.76$^l$. MS(ES): m/z=335 [M+H]$^+$.

3. 1-(4-(Cyclopentyl(methyl)amino)-2'-(1H-tetrazol-5-yl)biphenyl-3-yl)-3-p-tolylurea

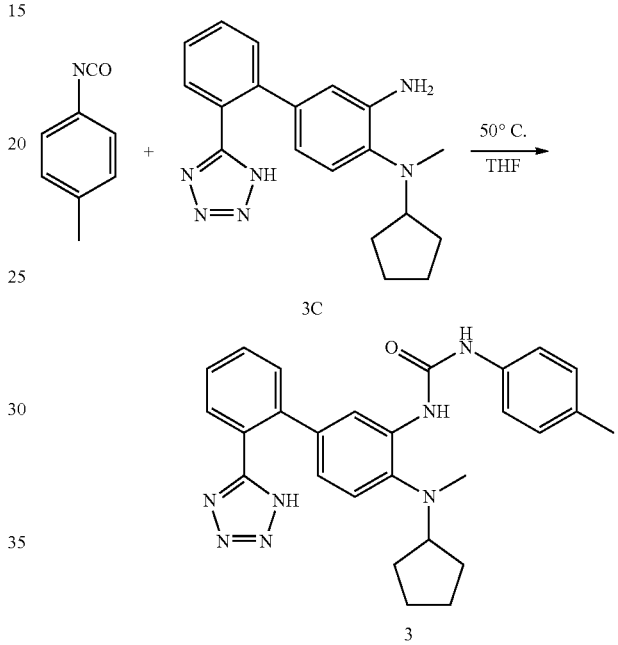

To a solution of N4-cyclopentyl-N4-methyl-2'-(1H-tetrazol-5-yl)biphenyl-3,4-diamine (0.02 g, 0.060 mmol) in THF (Volume: 0.5 mL) was added 1-isocyanato-4-methylbenzene (0.012 g, 0.090 mmol). The solution was stirred 2 h at 50° C. then purified by prep. HPLC (Axia 21×100 mm column, MeOH-water-TFA gradient). Concentration of the appropriate fraction afforded 1-(4-(cyclopentyl(methyl)amino)-2'-(1H-tetrazol-5-yl)biphenyl-3-yl)-3-p-tolylurea (3) (0.009 g, 30.6% yield) as a white powder. MS(ES): m/z=468 [M+H]$^+$. HPLC T$_r$: 12.28$^d$.

Example 4

N-(4'-(Diisobutylamino)-3'-(3-p-tolylureido)biphenyl-2-yl)-1,1,1-trifluoromethanesulfonamide

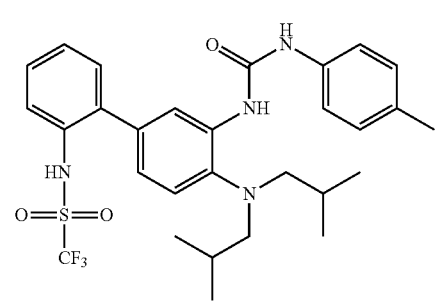 [SMILES: Cc1ccc(NC(=O)Nc2cc(-c3ccccc3NS(=O)(=O)C(F)(F)F)ccc2N(CC(C)C)CC(C)C)cc1]

4A. N-(2-Bromophenyl)-1,1,1-trifluoromethanesulfonamide

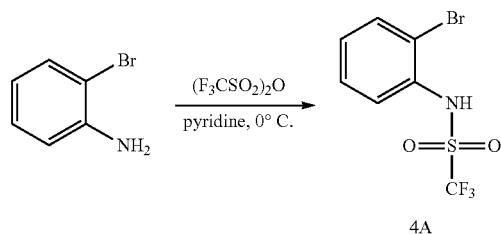

2-Bromoaniline (300 mg, 1.744 mmol) was taken up in DCM (Volume: 5 mL) and cooled to 0° C. Pyridine (2.82 mL, 34.9 mmol) was added, followed by dropwise addition of trifluoromethanesulfonic anhydride (0.440 mL, 2.62 mmol). The reaction was stirred at 0° C. and slowly warmed to rt overnight. The reaction was diluted with DCM, washed with 1N HCl, then brine, dried over $Na_2SO_4$, filtered, and concentrated and purified by ISCO Companion (0-40% EtOAc/hexane; 80 g column). N-(2-bromophenyl)-1,1,1-trifluoromethanesulfonamide (4A) (189 mg, 0.622 mmol, 36% yield) was obtained as a brown oil. $^1$H NMR (400 MHz, $CDCl_3$) δ ppm 7.61-7.65 (2H, m), 7.37 (1H, td, J=7.9, 1.4 Hz), 7.17 (1H, td, J=7.8, 1.4 Hz). MS(ES): m/z=304 [M–H]$^-$.

4B. 4-(5,5-Dimethyl-1,3,2-dioxaborinan-2-yl)-N1,N1-diisobutylbenzene-1,2-diamine

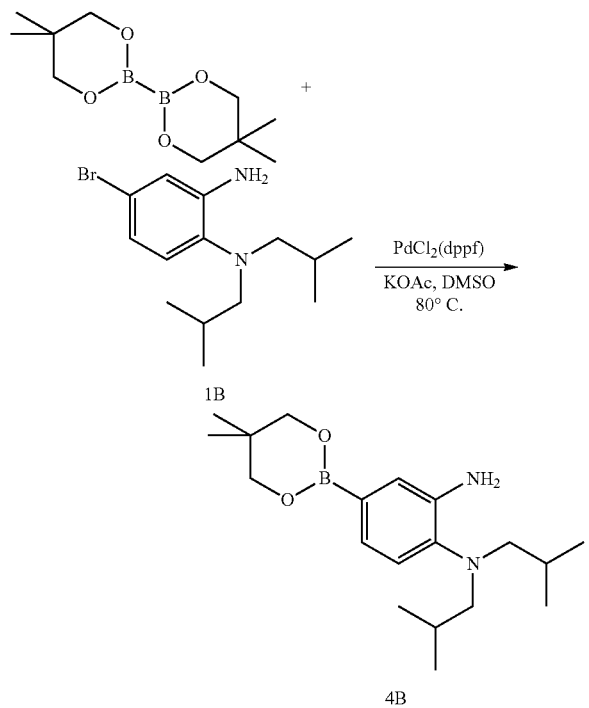

4-Bromo-N1,N1-diisobutylbenzene-1,2-diamine (560 mg, 1.87 mmol), 5,5,5',5'-tetramethyl-2,2'-bi(1,3,2-dioxaborinane) (550 mg, 2.43 mmol), $PdCl_2$(dppf)-$CH_2Cl_2$Adduct (46 mg, 0.056 mmol), and potassium acetate (551 mg, 5.61 mmol) were combined in a 2 dram vial, and DMSO (Volume: 3 mL) was added. The vial was evacuated and filled with argon 3×, then heated at 80° C. for 3 h, cooled to RT and the contents purified by ISCO Companion (0-20% EtOAc/hexane; 80 g column) 4-(5,5-dimethyl-1,3,2-dioxaborinan-2-yl)-N1,N1-diisobutylbenzene-1,2-diamine (355 mg, 1.068 mmol, 57% yield) was obtained as a white solid. $^1$H NMR (400 MHz, chloroform-d) δ ppm 7.12-7.22 (2H, m), 7.01-7.08 (1H, m), 3.74 (4H, s), 2.64 (4H, d, J=7.3 Hz), 1.69-1.85 (2H, m), 1.02 (6H, s), 0.89 (12H, d, J=6.6 Hz). MS(ES): m/z=265 [M+H—$C_5H_8$]$^+$.

4C. N-(3'-Amino-4'-(diisobutylamino)biphenyl-2-yl)-1,1,1-trifluoromethanesulfonamide

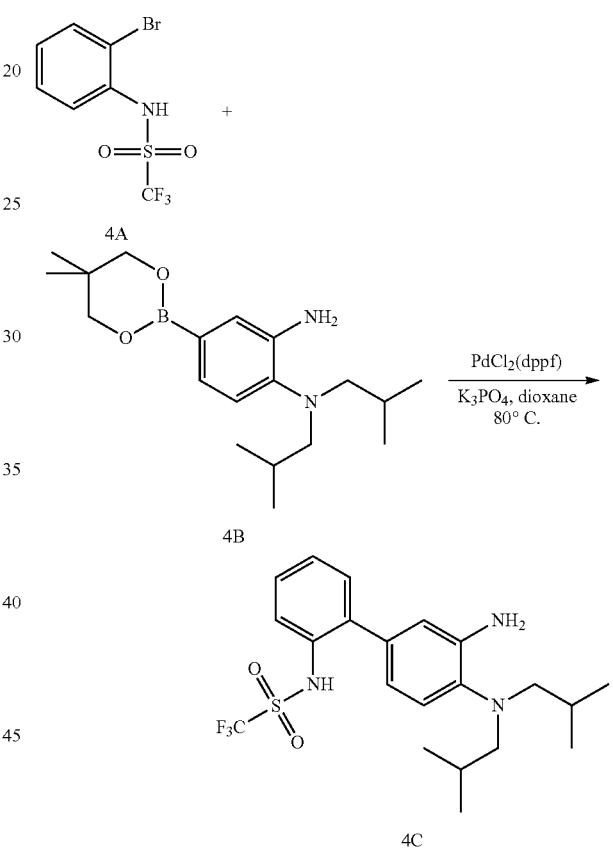

4-(5,5-Dimethyl-1,3,2-dioxaborinan-2-yl)-N1,N1-diisobutylbenzene-1,2-diamine (71 mg, 0.21 mmol), N-(2-bromophenyl)-1,1,1-trifluoromethanesulfonamide (50 mg, 0.16 mmol), $PdCl_2$(dppf)-$CH_2Cl_2$Adduct (13.43 mg, 0.016 mmol), and potassium phosphate, tribasic (0.247 mL, 0.493 mmol) were added to a 2 dram vial and evacuated and filled with argon 3×. The mixture was suspended in 1 mL of dioxane and heated at 80° C. for 3 h, cooled to rt and purified via ISCO Companion (0-20% EtOAc/hexane; 25 g column) N-(3'-Amino-4'-(diisobutylamino)biphenyl-2-yl)-1,1,1-trifluoromethanesulfonamide (30 mg, 0.068 mmol, 41% yield) was obtained as a purple gum. $^1$H NMR (400 MHz, $CDCl_3$) δ ppm 7.64 (d, 1H, J=8.8 Hz); 7.26-7.41 (m, 3H); 7.18 (d, 1H, J=7.9 Hz); 6.62-6.69 (m, 2H); 2.69 (d, 4H, J=7.3 Hz); 1.78-1.91 (m, 2H); 0.98 (d, 12H, J=6.6 Hz). MS(ES): m/z=444 [M+H]$^+$.

4. N-(4'-(Diisobutylamino)-3'-(3-p-tolylureido)biphenyl-2-yl)-1,1,1-trifluoromethanesulfonamide 5A. 5-Bromo-2-(diisobutylamine)-3-fluorobenzoic acid

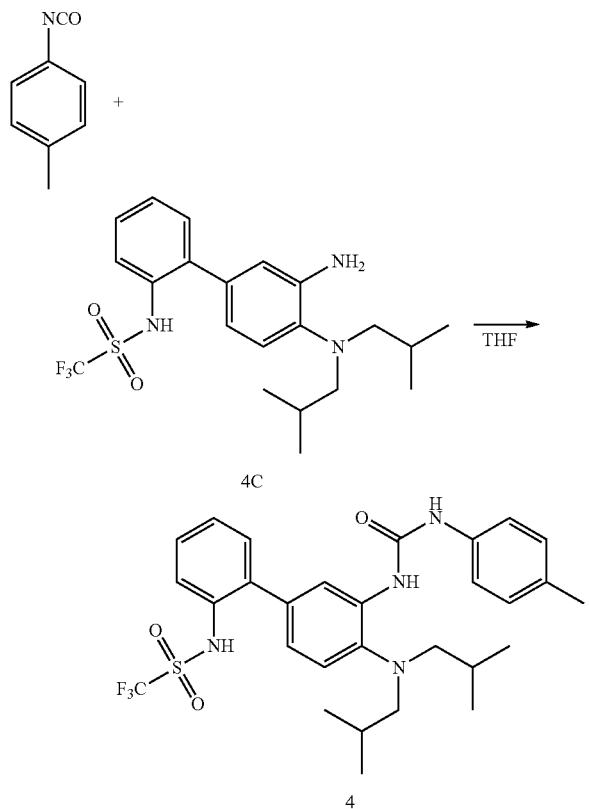

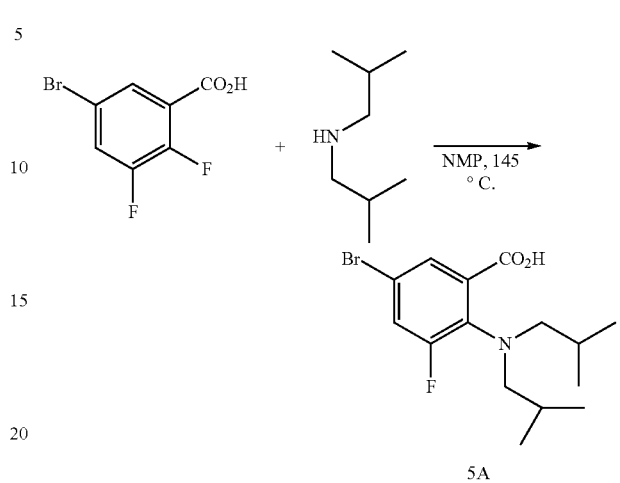

N-(3'-Amino-4'-(diisobutylamino)biphenyl-2-yl)-1,1,1-trifluoromethanesulfonamide (4C) (30 mg, 0.068 mmol) was taken up in THF (Volume: 2 mL) and 1-isocyanato-4-methylbenzene (0.011 mL, 0.088 mmol) was added. The reaction was stirred at rt overnight, and then solvent removed in vacuo. The reaction mixture was purified by prep. HPLC C18 (PHENOMENEX® Luna S5 ODS 21×100 mm, 10 mM NH$_4$OAc in MeOH/H$_2$O gradient) to afford N-(4'-(diisobutylamino)-3'-(3-p-tolylureido)biphenyl-2-yl)-1,1,1-trifluoromethanesulfonamide (23 mg, 58%) as a white solid. $^1$H NMR (400 MHz, MeOD) δ ppm 7.86 (1H, d, J=2.0 Hz), 7.33-7.40 (2H, m), 7.19-7.33 (5H, m), 7.13-7.18 (1H, m), 7.10 (2H, d, J=8.1 Hz), 2.72 (4H, d, J=7.0 Hz), 2.29 (3H, s), 1.69-1.84 (2H, m), 0.91 (12H, d, J=6.8 Hz). MS(ES): m/z=577 [M+H]$^+$.

A solution of 5-bromo-2,3-difluorobenzoic acid (0.75 g, 3.16 mmol) in NMP (Volume: 0.4 mL) was treated with diisobutylamine (1.636 g, 12.66 mmol) and heated to 145° C. for 17 h. Chromatography on silica gel (gradient elution with EtOAc-hexanes-1% HOAc) afforded 0.22 g (20%) of 5-bromo-2-(diisobutylamine)-3-fluorobenzoic acid as an off-white solid plus some mixed fractions. Concentration and silica gel chromatography on the mixed fractions afforded a further 0.3 g of material. MS(ES): m/z=348 [M+H]$^+$. $^1$H NMR (400 MHz, DMSO-d6) δ ppm 14.51 (br.s, 1H); 7.69 (dd, 1H, J=11.9, 2.4 Hz); 7.61 (br. s, 1H); 2.88 (d, 4H, J=6.6 Hz); 1.65-1.77 (m, 2H); 0.82 (d, 12H, J=6.6 Hz).

5B. 4-Bromo-6-fluoro-N1,N1-diisobutylbenzene-1,2-diamine

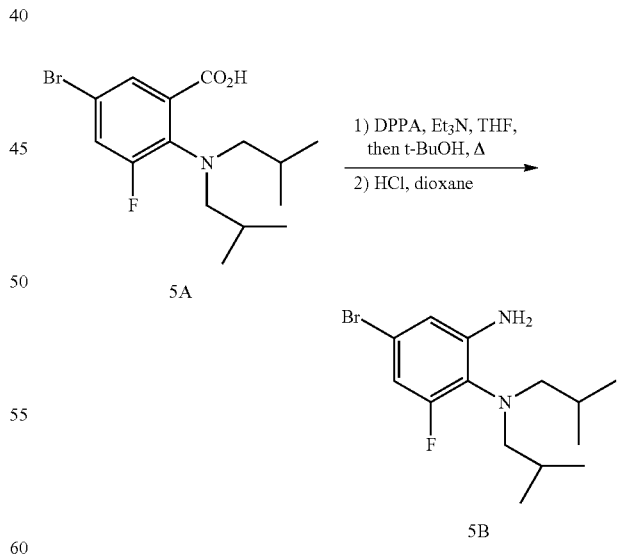

Example 5

1-(4-(Diisobutylamino)-5-fluoro-2'-(1H-tetrazol-5-yl)biphenyl-3-yl)-3-p-tolylurea

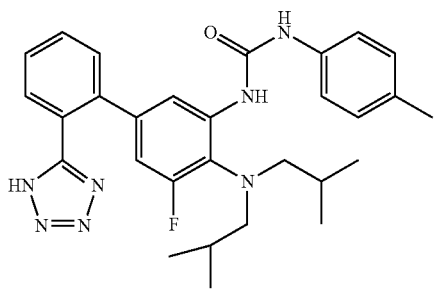

A solution of 5-bromo-2-(diisobutylamino)-3-fluorobenzoic acid (5A) (0.3 g, 0.87 mmol) and triethylamine (0.145 mL, 1.04 mmol) in THF (Volume: 5 mL) was treated with diphenyl phosphorazidate (0.26 g, 0.95 mmol) and stirred 30 min. at RT. The solution was then treated with tert-butanol (2.5 mL, 26 mmol) and heated to reflux. The reaction was stirred overnight at 65° C. then cooled, diluted with ether, and washed with aq. HOAc then aq. sodium bicarbonate. The organic phase was dried, stripped, and redissolved in 4 mL of 4M HCl/dioxane. The resulting solution was stirred 1.5 h at RT then concentrated to afford an oil. LCMS indicated some t-butyl carbamate remained, so the oil was dissolved in 4 mL of HCl/dioxane and stirred 3 h at RT. The reaction was concentrated to near dryness under reduced pressure. Addition of a few drops of methanol afforded a precipitate which was filtered, rinsed with 30% ether-hexanes, and air-dried to afford 0.039 g (14%) of 4-bromo-6-fluoro-N1,N1-diisobutylbenzene-1,2-diamine as a colorless solid. Prep. HPLC (Axia 30×100 mm column, MeOH-water-TFA gradient) on the mother liquor afforded a further 0.04 g of material. MS(ES): m/z=319 [M+H]$^+$. $^1$H NMR (400 MHz, DMSO-d$_6$) δ ppm 6.67 (1H, dd, J=2.2, 1.2 Hz), 6.50 (1H, dd, J=11.4, 2.2 Hz), (NH$_2$ obscured by broad water peak); 2.57-2.72 (4H, m), 1.53-1.63 (2H, m), 0.81-0.87 (12H, m).

5C. 1-(5-Bromo-2-(diisobutylamino)-3-fluorophenyl)-3-p-tolylurea

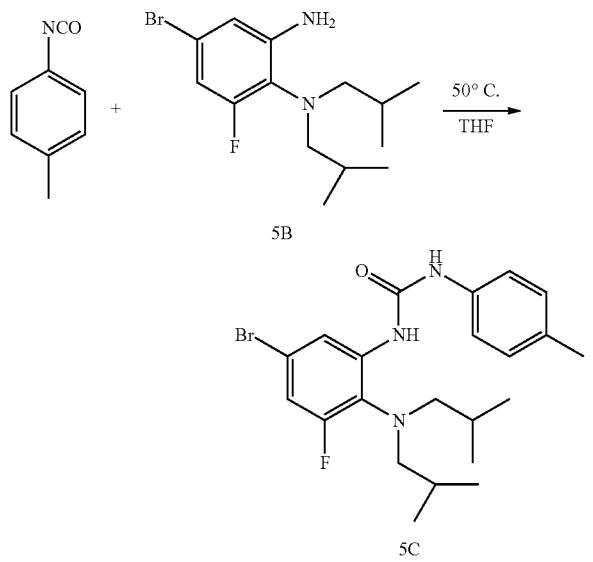

A solution of 4-bromo-6-fluoro-N1,N1-diisobutylbenzene-1,2-diamine (5B) (0.065 g, 0.205 mmol) in THF (Volume: 1 mL) was treated with 1-isocyanato-4-methylbenzene (0.038 g, 0.287 mmol) and placed under nitrogen. The reaction was stirred 30 min. at 50° C. An additional 0.04 g of p-tolylisocyanate was added, and the reaction was stirred 2 h longer at 50° C. The reaction was cooled, treated with 0.03 mL of N,N-dimethylethylenediamine, and chromatographed on silica gel (gradient elution with EtOAc-hexanes). Concentration of the appropriate fractions afforded 0.85 g (92%) of 1-(5-bromo-2-(diisobutylamino)-3-fluorophenyl)-3-p-tolylurea as a colorless solid. $^1$H NMR (400 MHz, DMSO-d$_6$) δ ppm 9.57 (s, 1H); 8.18-8.22 (m, 2H); 7.34 (d, 2H, J=8.6 Hz); 7.10 (d, 2H, J=8.4 Hz); 7.07 (dd, 1H, J=11.4, 2.2 Hz); 2.73-2.84 (br. m, 4H); 2.24 (s, 3H); 1.54-1.64 (2H, m); 0.82 (d, 6H, J=6.6 Hz). MS(ES): m/z=452 [M+H]$^+$.

5. 1-(4-(Diisobutylamino)-5-fluoro-2'-(1H-tetrazol-5-yl)biphenyl-3-yl)-3-p-tolylurea

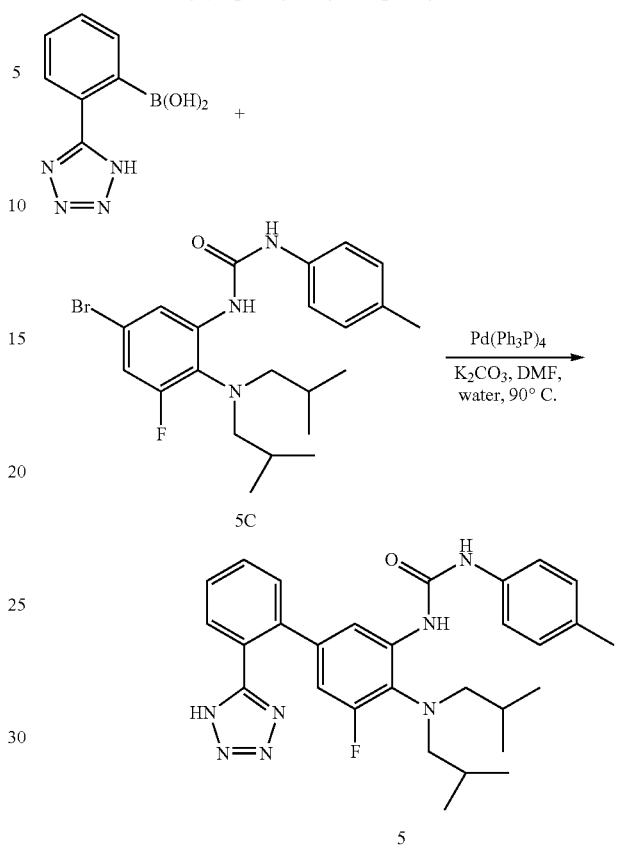

To a mixture of 2-(1H-tetrazol-5-yl)phenylboronic acid (0.025 g, 0.133 mmol) and 1-(5-bromo-2-(diisobutylamino)-3-fluorophenyl)-3-p-tolylurea (5C) (0.03 g, 0.067 mmol) and tetrakis(triphenylphosphine)palladium(0) (7.70 mg, 6.66 µmol) in degassed DMF (Volume: 1 mL) was added aq. potassium carbonate (0.222 mL, 0.333 mmol). The mixture was placed under nitrogen and heated at 90° C. for 1 h. The reaction was cooled, brought to pH 4 with glacial HOAc, filtered, and purified by prep. HPLC (Axia 30×100 mm column, MeOH-water-TFA gradient). Concentration of the appropriate fraction afforded 0.027 g (79%) of 1-(4-(diisobutylamino)-5-fluoro-2'-(1H-tetrazol-5-yl)biphenyl-3-yl)-3-p-tolylurea as a white powder. $^1$H NMR (400 MHz, DMSO-d$_6$) δ ppm 9.47 (s, 1H); 8.14 (s, 1H); 7.82 (d, 1H, J=1.5 Hz); 7.57-7.73 (m, 4H); 7.34 (d, 2H, J=8.4 Hz); 7.11 (d, 2H, J=8.1 Hz); 6.44 (dd, 1H, J=12.8, 2.0 Hz); 2.81 (d, 4H, J=5.7); 2.26 (s, 3H); 1.60-1.70 (m, 2H); 0.86 (d, 12H, J=6.6 Hz). MS(ES): m/z=516 [M+H]$^+$.

Example 6

4'-(Diisobutylamino)-3'-fluoro-5'-(3-p-tolylureido)biphenyl-2-carboxylic acid

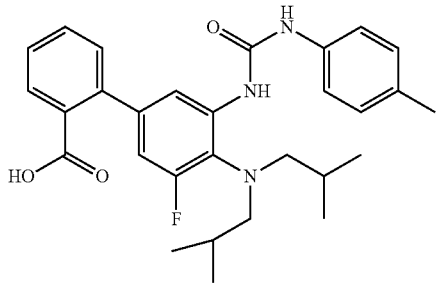 [SMILES: Cc1ccc(NC(=O)Nc2cc(-c3ccccc3C(=O)O)cc(F)c2N(CC(C)C)CC(C)C)cc1]

The title compound was prepared from 5C and 2-carboxyphenylboronic acid by the procedure used to convert 5C into 5. MS(ES): m/z=492 [M+H]+. HPLC T$_r$: 13.02$^d$.

Example 7

4'-(2-tert-Butylphenoxy)-4-ethoxy-3'-(3-p-tolylureido)biphenyl-3-carboxylic acid

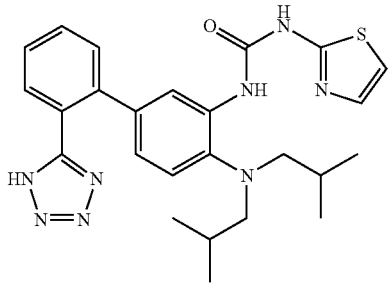 [SMILES: CC(C)CN(CC(C)C)c1ccc(-c2ccccc2-c2nnn[nH]2)cc1NC(=O)Nc1nccs1]

7A. 3'-Amino-4'-(diisobutylamino)biphenyl-2-carbonitrile

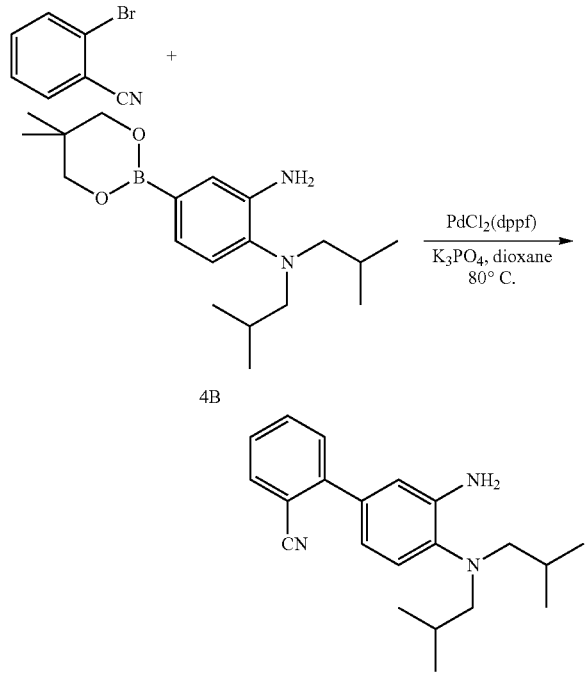

4-(5,5-Dimethyl-1,3,2-dioxaborinan-2-yl)-N1,N1-diisobutylbenzene-1,2-diamine (4B) (356 mg, 1.07 mmol, 2-bromobenzonitrile (150 mg, 0.824 mmol), PdCl$_2$(dppf)-CH$_2$Cl$_2$Adduct (67.3 mg, 0.082 mmol), and potassium phosphate, tribasic (1.24 mL, 2.48 mmol) were added to a 2 dram vial and evacuated and filled with argon 3×. The mixture was heated at 80° C. for 3 h. An additional 0.05 eq. PdCl$_2$(dppf)-CH$_2$Cl$_2$Adduct and 75 mg bromobenzonitrile were added and heating was continued for 3 h. The reaction was cooled to rt and purified via ISCO Companion (EtOAc/hexane gradient) to afford 3'-amino-4'-(diisobutylamino)biphenyl-2-carbonitrile (289 mg, >quantitative yield) as a yellow gum. $^1$H NMR (400 MHz, CDCl$_3$) δ ppm 7.76 (dd, 1H, J=7.0, 1.1 Hz); 7.63 (td, 1H, J=7.6, 1.3 Hz); 7.53 (dd, 1H, J=7.7, 0.9 Hz); 7.41 (td, 1H, J=7.5, 1.1 Hz); 7.18 (d, 1 h, J=8.6 Hz); 6.92-6.97 (m, 2H); 4.2-4.3 (br. s, 2H); 2.69 (d, 4H, J=7.3 Hz); 1.79-1.91 (m, 2H); 0.96 (d, 12H, J=6.8 Hz). MS(ES): m/z=322 [M+H]+.

7B: N4,N4-Diisobutyl-2'-(1H-tetrazol-5-yl)biphenyl-3,4-diamine

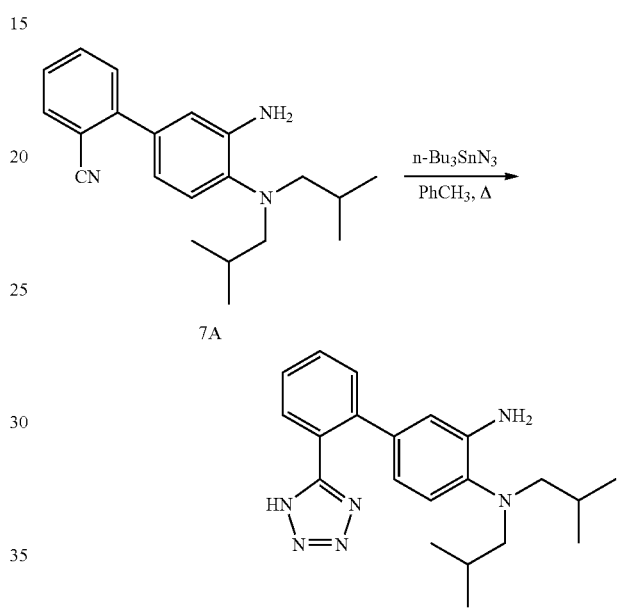

A solution of 3'-amino-4'-(diisobutylamino)biphenyl-2-carbonitrile (7A) (148 mg, 0.460 mmol) and azidotributyltin (0.883 mL, 3.22 mmol) in toluene (Volume: 3 mL) was heated at 110° C. for 5 h. The reaction was cooled to rt and purified via ISCO Companion (EtOAc/hexane gradient with 1% AcOH). N4,N4-Diisobutyl-2'-(1H-tetrazol-5-yl)biphenyl-3,4-diamine (163 mg, 97% yield) was obtained as a yellow solid. $^1$H NMR (400 MHz, CDCl$_3$) δ ppm (all lines are somewhat broad.) 7.96 (d, 1H, J=7.5 Hz); 7.53-7.64 (m, 2H); 7.47 (d, 1H, J=7.3 Hz); 7.08 (d, 1H, J=7.3 Hz); 7.00 (s, 1H); 6.65 (d, 1H, J=7.7 Hz); 2.98-3.10 (br. d, 4H, coupling unresolved); 1.88-1.98 (m, 2H); 0.91 (d, 12H, J=6.6 Hz). MS(ES): m/z=365 [M+H]+.

7. 1-(4-(Diisobutylamino)-2'-(1H-tetrazol-5-yl)biphenyl-3-yl)-3-(thiazol-2-yl)urea

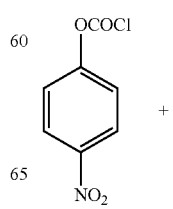

-continued

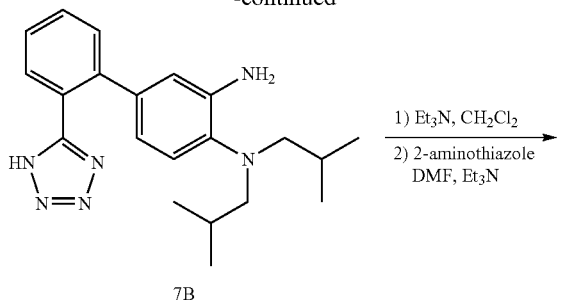

7B

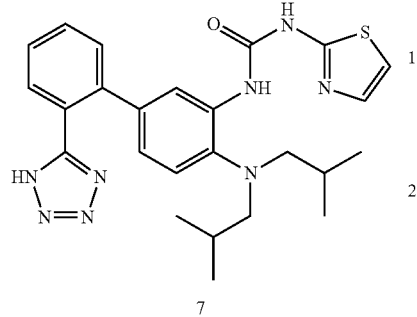

7

N4,N4-Diisobutyl-2'-(1H-tetrazol-5-yl)biphenyl-3,4-diamine (7B) (20 mg, 0.055 mmol) was taken up in DCM (1 mL) and Et₃N (0.038 mL, 0.274 mmol) and 4-nitrophenyl carbonochloridate (13 mg, 0.066 mmol) were added. The reaction was stirred at rt for 1 h, an additional 5 eq. of Et₃N and 1.2 eq. 4-nitrophenyl carbonochloridate were added, and the reaction was stirred overnight. The reaction was diluted with DCM and washed with 0.1M HCl, then brine. The organic phase was dried over Na₂SO₄, filtered and concentrated. The yellow residue was taken up in DMF (1.000 mL) and Et₃N (0.038 mL, 0.274 mmol) and thiazol-2-amine (8.2 mg, 0.082 mmol) were added. The reaction was stirred 3 h at RT then purified by prep. HPLC (C18 PHENOMENEX® Luna S5 ODS 21×100 mm, 10 mM NH₄OAc, MeOH—H₂O gradient). Concentration of the appropriate fractions afforded 1-(4-(diisobutylamino)-2'-(1H-tetrazol-5-yl)biphenyl-3-yl)-3-(thiazol-2-yl)urea (8.4 mg, 31% yield) as an off-white solid. MS(ES): m/z=491 [M+H]⁺. HPLC T$_r$: 2.23$^o$.

Example 8

4'-(Benzyl(3,3,3-trifluoropropyl)amino)-3'-(3-(p-tolyl)ureido)-[1,1'-biphenyl]-2-carboxylic acid

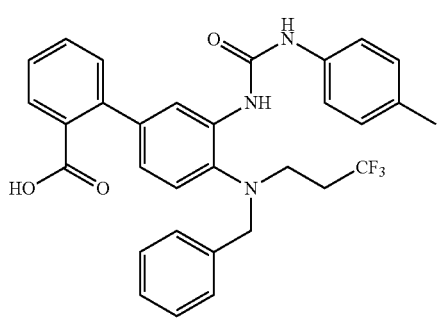 [SMILES: Cc1ccc(NC(=O)Nc2cc(-c3ccccc3C(=O)O)ccc2N(CCC(F)(F)F)Cc2ccccc2)cc1]

8A.
4-Bromo-2-nitro-N-(3,3,3-trifluoropropyl)aniline

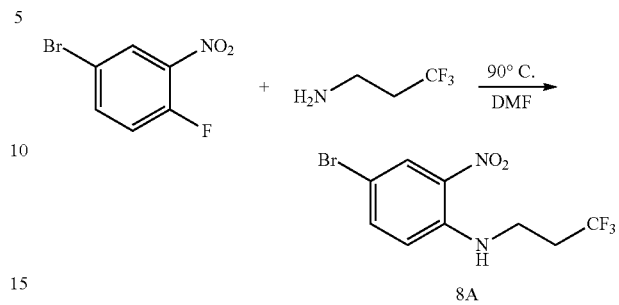

8A

To a solution of 4-bromo-1-fluoro-2-nitrobenzene (0.440 g, 2 mmol) in DMF (1 mL) was added Hunig's base followed by 3,3,3-trifluoropropan-1-amine, HCl (0.419 g, 2.80 mmol). The solution was stirred 1 h at 90° C. then cooled and poured into 40 ml of water. The mixture was rapidly stirred while the pH was adjusted to ~5 with glacial HOAc. Product precipitated and was filtered, rinsed with water, and air-dried to afford 4-bromo-2-nitro-N-(3,3,3-trifluoropropyl)aniline (0.6 g, 91% yield) as an orange powder. Spectra was consistent with the proposed nitroaniline at a purity of >95%. MS(ES): m/z=313 [M+H]⁺, HPLC T$_r$: 2.14$^p$.

8B. N-Benzyl-4-bromo-2-nitro-N-(3,3,3-trifluoropropyl)aniline

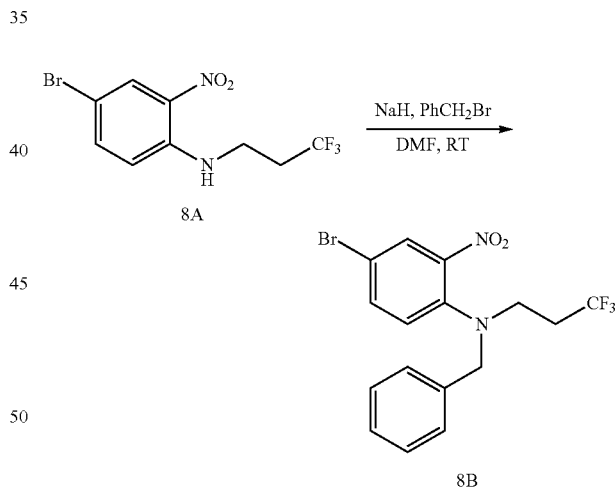

To a solution of 4-bromo-2-nitro-N-(3,3,3-trifluoropropyl)aniline (8A) (0.1 g, 0.319 mmol) in DMF (2 mL) was added sodium hydride (0.038 g, 0.958 mmol). The mixture was stirred 2 min. at RT then treated with (bromomethyl)benzene (0.057 mL, 0.479 mmol). The reaction was stirred 1 h at RT then quenched with aq. HOAc. This mixture was extracted with ether, and the organic extract was dried, stripped and purified by ISCO chromatography (gradient elution with EtOAc-hexanes) to afford N-benzyl-4-bromo-2-nitro-N-(3,3,3-trifluoropropyl)aniline (0.11 g, 81% yield) as an orange oil at a purity of >95%. MS(ES): m/z=405 [M+H]⁺, HPLC T$_r$: 2.71$^q$.

8C. N1-Benzyl-4-bromo-N1-(3,3,3-trifluoropropyl)benzene-1,2-diamine

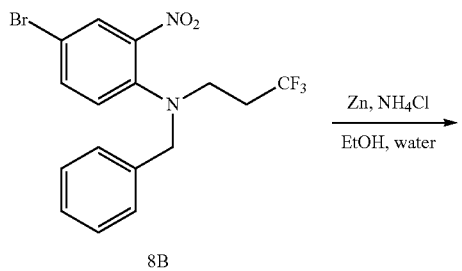

To a solution of N-benzyl-4-bromo-2-nitro-N-(3,3,3-trifluoropropyl)aniline (8B) (0.1 g, 0.248 mmol) in ethanol (6 mL) was added 1 mL of water followed by ammonium chloride (0.199 g, 3.72 mmol). The mixture was stirred 10 min. at RT then treated with zinc (0.243 g, 3.72 mmol). This mixture was stirred 30 min. at RT, diluted with dichloromethane, and filtered. The filtrate was washed with water, dried, and stripped to afford N1-benzyl-4-bromo-N1-(3,3,3-trifluoropropyl)benzene-1,2-diamine (8C) (0.09 g, 92% yield) as an amber oil. Spectra was consistent with the proposed aniline at a purity of ~95%. MS(ES): m/z=373 [M+H]$^+$, HPLC T$_r$: 4.53$^l$.

8D. 1-(2-(Benzyl(3,3,3-trifluoropropyl)amino)-5-bromophenyl)-3-(p-tolyl)urea

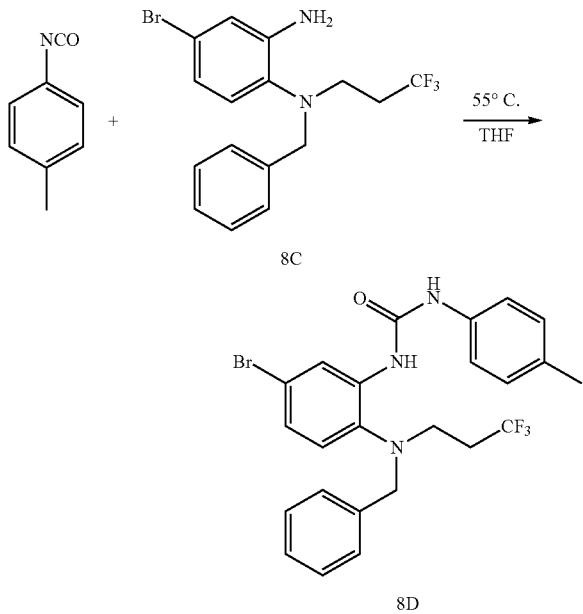

To a solution of N1-benzyl-4-bromo-N1-(3,3,3-trifluoropropyl)benzene-1,2-diamine (8C) (0.086 g, 0.23 mmol) in THF (1 mL) was added 1-isocyanato-4-methylbenzene (0.040 g, 0.299 mmol). The solution was stirred 1 h at 55° C. then cooled to RT, treated with 0.02 mL of N,N-dimethylethylenediamine, and purified by ISCO chromatography (gradient elution with EtOAc-hexanes) to afford 0.1 g (86%) of 1-(2-(benzyl(3,3,3-trifluoropropyl)amino)-5-bromophenyl)-3-(p-tolyl)urea as a white powder. MS(ES): m/z=508 [M+H]$^+$, HPLC T$_r$: 2.79$^q$.

8. 4'-(Benzyl(3,3,3-trifluoropropyl)amino)-3'-(3-(p-tolyl)ureido)-[1,1'-biphenyl]-2-carboxylic acid

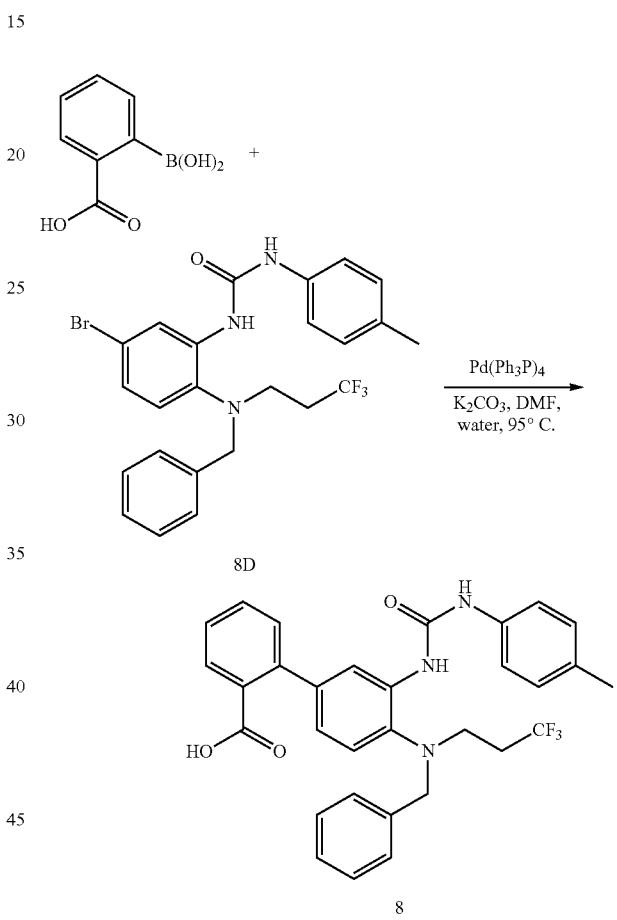

To a suspension of 2-boronobenzoic acid (0.016 g, 0.099 mmol) and 1-(2-(benzyl(3,3,3-trifluoropropyl)amino)-5-bromophenyl)-3-(p-tolyl)urea (8D) (0.025 g, 0.049 mmol) and tetrakis(triphenylphosphine)palladium(0) (5.71 mg, 4.94 µmol) in degassed DMF (1 mL) was added aq. potassium carbonate (0.165 mL, 0.247 mmol). The mixture was placed under nitrogen and heated at 95° C. for 3 h. The reaction was cooled to 60° C., brought to pH4 with glacial HOAc, filtered, and purified via preparative LC/MS with the following conditions: Column: Waters XBridge C18, 19×150 mm, 5-µm particles; Guard Column: Waters XBridge C18, 19×10 mm, 5-µm particles; Mobile Phase A: 5:95 acetonitrile:water with 10 mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation to afford 4'-(benzyl(3,3,3-trifluoropropyl)amino)-3'-(3-(p-tolyl)ureido)-[1,1'-biphenyl]-2-carboxylic acid (0.015 g, 52.7% yield). MS(ES): m/z=548 [M+H]⁺, HPLC T$_r$: 4.72$^l$.

Example 9

4'-(Benzyl(3,3,3-trifluoropropyl)amino)-5-fluoro-3'-(3-(p-tolyl)ureido)-[1,1'-biphenyl]-2-carboxylic acid

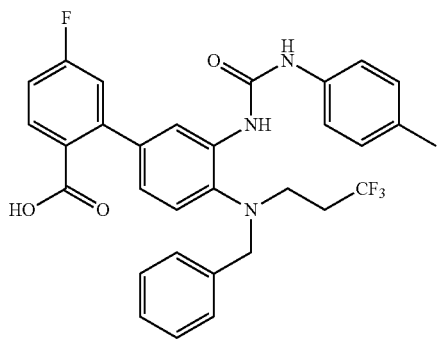 [SMILES: Cc1ccc(NC(=O)Nc2cc(-c3cc(F)ccc3C(=O)O)ccc2N(CCC(F)(F)F)Cc2ccccc2)cc1]

To a suspension of 8D (0.025 g, 0.049 mmol) and 2-borono-4-fluorobenzoic acid (0.018 g, 0.099 mmol) and tetrakis(triphenylphosphine)palladium(0) (5.71 mg, 4.94 µmol) in degassed DMF (1 mL) was added aq. potassium carbonate (0.165 mL, 0.247 mmol). The mixture was placed under nitrogen and heated at 95° C. for 3 h. The reaction was cooled to 60° C., brought to pH4 with glacial HOAc, filtered, and purified by prep. HPLC (Axia Luna 30×100 mm column, MeOH-water-TFA gradient). Concentration of the appropriate fraction afforded 0.014 g (50%) of 4'-(Benzyl (3,3,3-trifluoropropyl)amino)-5-fluoro-3'-(3-(p-tolyl) ureido)-[1,1'-biphenyl]-2-carboxylic acid. MS(ES): m/z=566 [M+H]⁺, HPLC T$_r$: 4.86$^l$.

Example 10

1-(4-(Benzyl(3,3,3-trifluoropropyl)amino)-2'-(1H-tetrazol-5-yl)-[1,1'-biphenyl]-3-yl)-3-(p-tolyl)urea

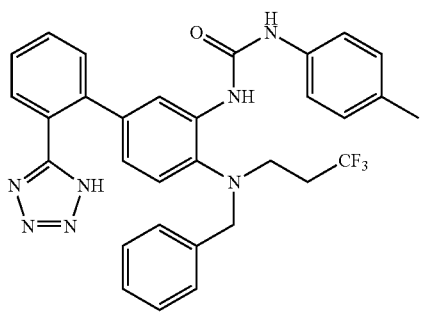 [SMILES: Cc1ccc(NC(=O)Nc2cc(-c3ccccc3-c3nnn[nH]3)ccc2N(CCC(F)(F)F)Cc2ccccc2)cc1]

The title compound was prepared from 8D and 2-tetrazolylphenylboronic acid by the procedure used for the conversion of 8D to 8. MS(ES): m/z=572 [M+H]⁺, HPLC T$_r$: 2.64$^q$.

Example 11

4'-((3-Chlorobenzyl)(3,3,3-trifluoropropyl)amino)-3'-(3-(p-tolyl)ureido)-[1,1'-biphenyl]-2-carboxylic acid

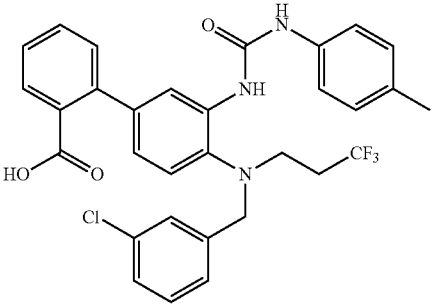

11A. 4-Bromo-N-(3-chlorobenzyl)-2-nitro-N-(3,3,3-trifluoropropyl)aniline

The title compound was prepared from 8A and 3-chlorobenzyl bromide by the general procedure used for the conversion of 8A to 8B. MS(ES): m/z=439 [M+H]⁺, HPLC T$_r$: 4.95$^l$.

11B. 4-Bromo-N1-(3-chlorobenzyl)-N1-(3,3,3-trifluoropropyl)benzene-1,2-diamine

The title compound was prepared from 11A by the general procedure used for the conversion of 8B to 8C. MS(ES): m/z=409 [M+H]⁺, HPLC T$_r$: 4.74$^l$.

11C. 1-(5-Bromo-2-((3-chlorobenzyl)(3,3,3-trifluoropropyl)amino)phenyl)-3-(p-tolyl)urea The title compound was prepared from 11B by the general procedure used for the conversion of 8C to 8D. MS(ES): m/z=542 [M+H]⁺, HPLC T$_r$: 2.84$^q$.

11. 4'-((3-Chlorobenzyl)(3,3,3-trifluoropropyl) amino)-3'-(3-(p-tolyl)ureido)-[1,1'-biphenyl]-2-carboxylic acid The title compound was prepared from 11C by the general procedure used for the conversion of 8D to 8. MS(ES): m/z=582 [M+H]⁺, HPLC T$_r$: 4.83$^l$.

Example 12

4'-((3-Chlorobenzyl)(3,3,3-trifluoropropyl)amino)-5-fluoro-3'-(3-(p-tolyl)ureido)-[1,1'-biphenyl]-2-carboxylic acid

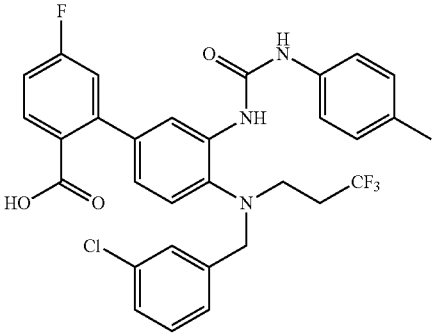 [SMILES: Cc1ccc(NC(=O)Nc2cc(-c3cc(F)ccc3C(=O)O)ccc2N(CCC(F)(F)F)Cc2cccc(Cl)c2)cc1]

The title compound was prepared from 11C and 2-carboxy-5-fluorophenylboronic acid by the general procedure for the conversion of 8D to 8. MS(ES): m/z=600 [M+H]$^+$, HPLC T$_r$: 4.94$^1$.

Example 13

1-(4-((3-Chlorobenzyl)(3,3,3-trifluoropropyl)amino)-2'-(1H-tetrazol-5-yl)-[1,1'-biphenyl]-3-yl)-3-(p-tolyl)urea

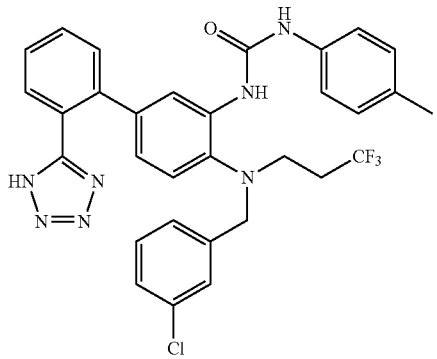 [SMILES: Cc1ccc(NC(=O)Nc2cc(-c3ccccc3-c3nnn[nH]3)ccc2N(CCC(F)(F)F)Cc2cccc(Cl)c2)cc1]

The title compound was prepared from 11C and 2-tetrazolylphenylboronic acid by the general procedure for the conversion of 8D to 8. MS(ES): m/z=606 [M+H]$^+$, HPLC T$_r$: 4.81$^1$.

Example 14

4'-((4-Chlorobenzyl)(3,3,3-trifluoropropyl)amino)-3'-(3-(p-tolyl)ureido)-[1,1'-biphenyl]-2-carboxylic acid

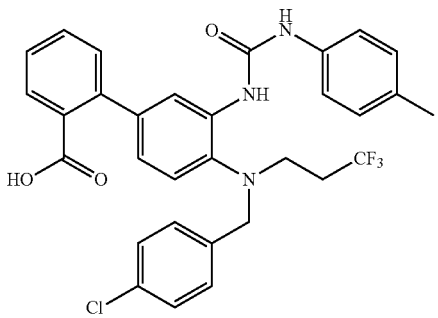 [SMILES: Cc1ccc(NC(=O)Nc2cc(-c3ccccc3C(=O)O)ccc2N(CCC(F)(F)F)Cc2ccc(Cl)cc2)cc1]

14A. 4-Bromo-N-(4-chlorobenzyl)-2-nitro-N-(3,3,3-trifluoropropyl)aniline

The title compound was prepared from 8A and 4-chlorobenzyl bromide by the general procedure used for the conversion of 8A to 8B. MS(ES): m/z=439 [M+H]$^+$, HPLC T$_r$: 4.99$^1$.

14B. 4-Bromo-N1-(4-chlorobenzyl)-N1-(3,3,3-trifluoropropyl)benzene-1,2-diamine

The title compound was prepared from 14A by the general procedure used for the conversion of 8B to 8C. MS(ES): m/z=409 [M+H]$^+$, HPLC T$_r$: 4.77$^1$.

14C. 1-(5-Bromo-2-((4-chlorobenzyl)(3,3,3-trifluoropropyl)amino)phenyl)-3-(p-tolyl)urea The title compound was prepared from 14B by the general procedure used for the conversion of 8C to 8D. MS(ES): m/z=542 [M+H]$^+$, HPLC T$_r$: 511$^1$.

14. 4'-((4-Chlorobenzyl)(3,3,3-trifluoropropyl)amino)-3'-(3-(p-tolyl)ureido)-[1,1'-biphenyl]-2-carboxylic acid The title compound was prepared from 14C by the general procedure used for the conversion of 8D to 8. MS(ES): m/z=582 [M+H]$^+$, HPLC T$_r$: 4.87$^1$ Example 15

4'-((4-Chlorobenzyl)(3,3,3-trifluoropropyl)amino)-5-fluoro-3'-(3-(p-tolyl)ureido)-[1,1'-biphenyl]-2-carboxylic acid

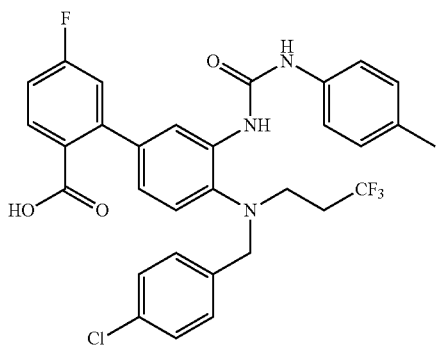 [SMILES: Cc1ccc(NC(=O)Nc2cc(-c3cc(F)ccc3C(=O)O)ccc2N(CCC(F)(F)F)Cc2ccc(Cl)cc2)cc1]

The title compound was prepared from 14C and 2-carboxy-5-fluorophenylboronic acid by the general procedure for the conversion of 8D to 8. MS(ES): m/z=600 [M+H]$^+$, HPLC T$_r$: 4.97$^1$.

Example 16

1-(4-((4-Chlorobenzyl)(3,3,3-trifluoropropyl)amino)-2'-(1H-tetrazol-5-yl)-[1,1'-biphenyl]-3-O-3-(p-tolyl)urea

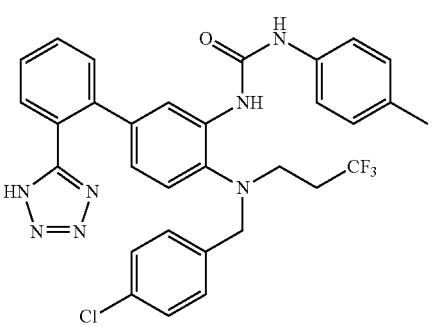 [SMILES: Cc1ccc(NC(=O)Nc2cc(-c3ccccc3-c3nnn[nH]3)ccc2N(CCC(F)(F)F)Cc2ccc(Cl)cc2)cc1]

The title compound was prepared from 14C and 2-tetrazolylphenylboronic acid by the general procedure for the conversion of 8D to 8. MS(ES): m/z=606 [M+H]$^+$, HPLC T$_r$: 2.98$^r$.

Example 17

4'-((2-Chlorobenzyl)(3,3,3-trifluoropropyl)amino)-3'-(3-(p-tolyl)ureido)-[1,1'-biphenyl]-2-carboxylic acid

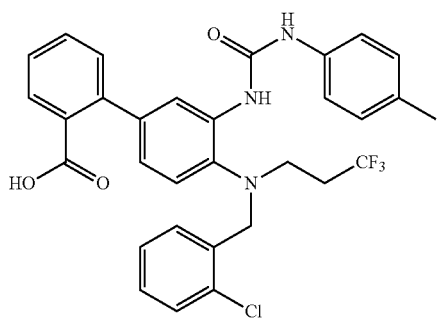 [SMILES: Cc1ccc(NC(=O)Nc2cc(-c3ccccc3C(=O)O)ccc2N(CCC(F)(F)F)Cc2ccccc2Cl)cc1]

17A. 4-Bromo-N-(2-chlorobenzyl)-2-nitro-N-(3,3,3-trifluoropropyl)aniline

The title compound was prepared from 8A and 2-chlorobenzyl bromide by the general procedure used for the conversion of 8A to 8B. MS(ES): m/z=439 [M+H]+, HPLC T$_r$: 4.94$^l$.

17B. 4-Bromo-N1-(2-chlorobenzyl)-N1-(3,3,3-trifluoropropyl)benzene-1,2-diamine The title compound was prepared from 17A by the general procedure used for the conversion of 8B to 8C. MS(ES): m/z=409 [M+H]+, HPLC T$_r$: 4.78$^l$.

17C. 1-(5-Bromo-2-((2-chlorobenzyl)(3,3,3-trifluoropropyl)amino)phenyl)-3-(p-tolyl)urea The title compound was prepared from 14B by the general procedure used for the conversion of 8C to 8D. MS(ES): m/z=542 [M+H]+, HPLC T$_r$: 3.19$^r$.

17. 4'-((2-Chlorobenzyl)(3,3,3-trifluoropropyl)amino)-3'-(3-(p-tolyl)ureido)-[1,1'-biphenyl]-2-carboxylic acid The title compound was prepared from 17C by the general procedure used for the conversion of 8D to 8. MS(ES): m/z=582 [M+H]+, HPLC T$_r$: 4.85$^l$.

Example 18

4'-((2-Chlorobenzyl)(3,3,3-trifluoropropyl)amino)-5-fluoro-3'-(3-(p-tolyl)ureido)-[1,1'-biphenyl]-2-carboxylic acid

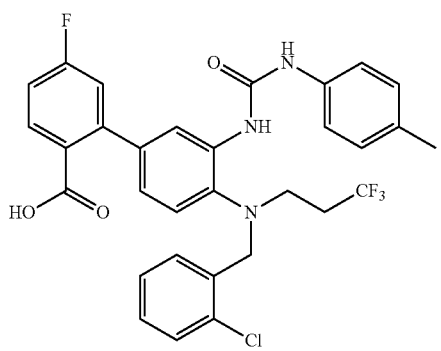 [SMILES: Cc1ccc(NC(=O)Nc2cc(-c3cc(F)ccc3C(=O)O)ccc2N(CCC(F)(F)F)Cc2ccccc2Cl)cc1]

The title compound was prepared from 17C and 2-carboxy-5-fluorophenylboronic acid by the general procedure for the conversion of 8D to 8. MS(ES): m/z=600 [M+H]+, HPLC T$_r$: 3.04$^r$.

Example 19

1-(4-((2-Chlorobenzyl)(3,3,3-trifluoropropyl)amino)-2'-(1H-tetrazol-5-yl)-[1,1'-biphenyl]-3-yl)-3-(p-tolyl)urea

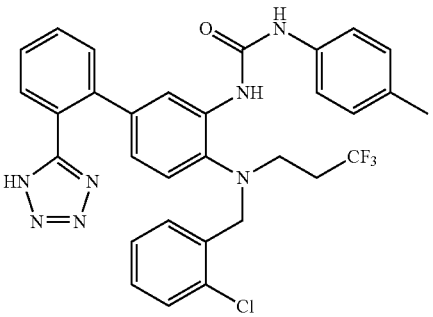 [SMILES: Cc1ccc(NC(=O)Nc2cc(-c3ccccc3-c3nnn[nH]3)ccc2N(CCC(F)(F)F)Cc2ccccc2Cl)cc1]

The title compound was prepared from 17C and 2-tetrazolylphenylboronic acid by the general procedure for the conversion of 8D to 8. MS(ES): m/z=606 [M+H]+, HPLC T$_r$: 4.81$^l$.

Example 20

4'-(Benzyl(2,2-difluoroethyl)amino)-3'-(3-(p-tolyl)ureido)-[1,1'-biphenyl]-2-carboxylic acid

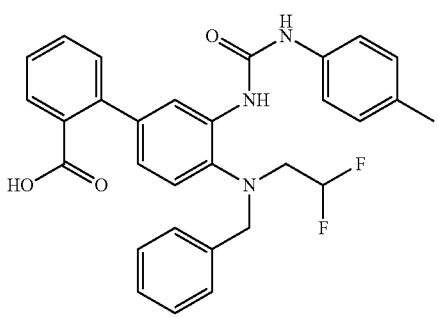 [SMILES: Cc1ccc(NC(=O)Nc2cc(-c3ccccc3C(=O)O)ccc2N(Cc2ccccc2)CC(F)F)cc1]

20A. 4-Bromo-N-(4-chlorobenzyl)-2-nitro-N-(3,3,3-trifluoropropyl)aniline

The title compound was prepared from the nitro intermediate iiik and benzyl bromide by the general procedure used for the conversion of 8A to 8B. MS(ES): m/z=371 [M+H]+, HPLC T$_r$: 2.58$^q$.

20B. N1-Benzyl-4-bromo-N1-(2,2-difluoroethyl)benzene-1,2-diamine

The title compound was prepared from 20A by the general procedure used for the conversion of 8B to 8C. MS(ES): m/z=343 [M+H]+, HPLC T$_r$: 4.15$^l$.

20C. 1-(2-(Benzyl(2,2-difluoroethyl)amino)-5-bromophenyl)-3-(p-tolyl)urea

The title compound was prepared from 20B by the general procedure used for the conversion of 8C to 8D. MS(ES): m/z=476 [M+H]$^+$, HPLC T$_r$: 2.68$^q$.

20. 4'-(Benzyl(2,2-difluoroethyl)amino)-3'-(3-(p-tolyl)ureido)-[1,1'-biphenyl]-2-carboxylic acid The title compound was prepared from 20C by the general procedure used for the conversion of 8D to 8. MS(ES): m/z=516 [M+H]$^+$, HPLC T$_r$: 2.11$^k$.

Example 21

4'-(Benzyl(2,2-difluoroethyl)amino)-5-fluoro-3'-(3-(p-tolyl)ureido)-[1,1'-biphenyl]-2-carboxylic acid

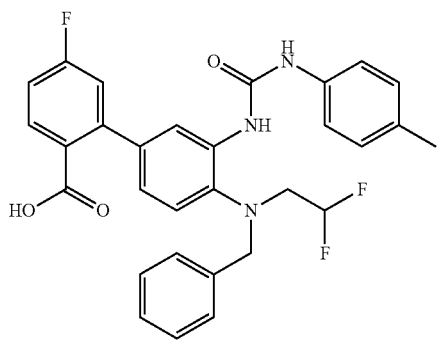 [SMILES: Cc1ccc(NC(=O)Nc2cc(-c3cc(F)ccc3C(=O)O)ccc2N(Cc2ccccc2)CC(F)F)cc1]

The title compound was prepared from 20C and 2-carboxy-5-fluorophenylboronic acid by the general procedure for the conversion of 8D to 8. MS(ES): m/z=534 [M+H]$^+$, HPLC T$_r$: 2.16$^k$.

Example 22

1-(4-(Benzyl(2,2-difluoroethyl)amino)-2'-(1H-tetrazol-5-yl)-[1,1'-biphenyl]-3-yl)-3-(p-tolyl)urea

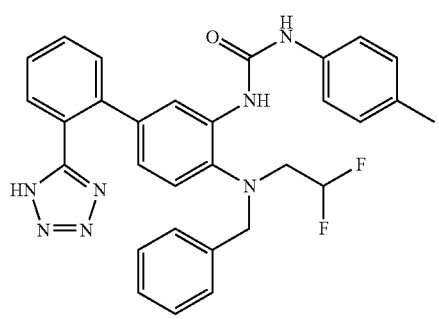 [SMILES: Cc1ccc(NC(=O)Nc2cc(-c3ccccc3-c3nnn[nH]3)ccc2N(Cc2ccccc2)CC(F)F)cc1]

The title compound was prepared from 20C and 2-tetrazolylphenylboronic acid by the general procedure for the conversion of 8D to 8. MS(ES): m/z=540 [M+H]$^+$, HPLC T$_r$: 2.07$^k$.

Example 23

5-Fluoro-4'-(isobutyl(prop-2-yn-1-yl)amino)-3'-(3-(p-tolyl)ureido)-[1,1'-biphenyl]-2-carboxylic acid

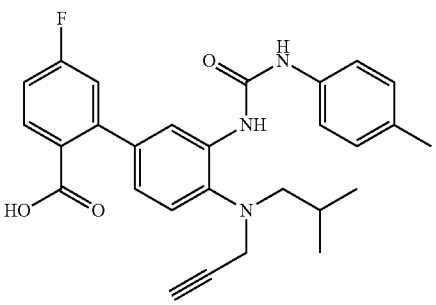 [SMILES: C#CCN(CC(C)C)c1ccc(-c2cc(F)ccc2C(=O)O)cc1NC(=O)Nc1ccc(C)cc1]

23A. 4-Bromo-N-isobutyl-2-nitro-N-(prop-2-yn-1-yl)aniline

The title compound was prepared from the nitro intermediate iiias and propargyl bromide by the general procedure used for the conversion of 8A to 8B. MS(ES): m/z=313 [M+H]$^+$, HPLC T$_r$: 4.61$^l$.

23B. 4-Bromo-N1-isobutyl-N1-(prop-2-yn-1-yl)benzene-1,2-diamine

The title compound was prepared from 23A by the general procedure used for the conversion of 8B to 8C. MS(ES): m/z=283 [M+H]$^+$, HPLC T$_r$: 213$^p$.

23C. 1-(5-Bromo-2-(isobutyl(prop-2-yn-1-yl)amino)phenyl)-3-(p-tolyl)urea

The title compound was prepared from 23B by the general procedure used for the conversion of 8C to 8D. MS(ES): m/z=416 [M+H]$^+$, HPLC T$_r$: 2.76$^q$.

23. 5-Fluoro-4'-(isobutyl(prop-2-yn-1-yl)amino)-3'-(3-(p-tolyl)ureido)-[1,1'-biphenyl]-2-carboxylic acid The title compound was prepared from 23C and 2-carboxy-5-fluorophenylboronic acid by the general procedure used for the conversion of 8D to 8. MS(ES): m/z=474 [M+H]$^+$, HPLC T$_r$: 2.66$^q$.

Example 24

1-(4-(Isobutyl(prop-2-yn-1-yl)amino)-2'-(1H-tetrazol-5-yl)-[1,1'-biphenyl]-3-yl)-3-(p-tolyl)urea

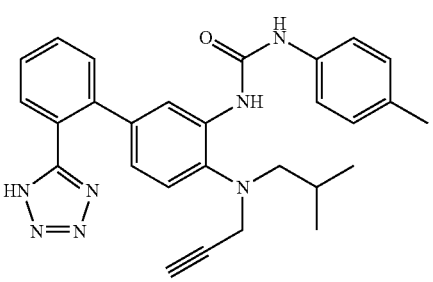 [SMILES: C#CCN(CC(C)C)c1ccc(-c2ccccc2-c2nnn[nH]2)cc1NC(=O)Nc1ccc(C)cc1]

93

The title compound was prepared from 23C and 2-tetrazolylphenylboronic acid by the general procedure for the conversion of 8D to 8. MS(ES): m/z=480 [M+H]$^+$, HPLC T$_r$: 2.55$^q$.

Example 25

1-(4-(Diisobutylamino)-2-fluoro-2'-(1H-tetrazol-5-yl)-[1,1'-biphenyl]-3-yl)-3-(p-tolyl)urea

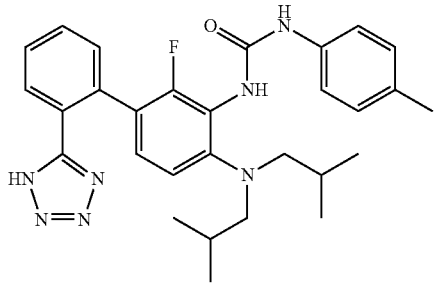 [SMILES: Cc1ccc(NC(=O)Nc2c(N(CC(C)C)CC(C)C)ccc(-c3ccccc3-c3nnn[nH]3)c2F)cc1]

25A. 3-Fluoro-N,N-diisobutyl-2-nitroaniline

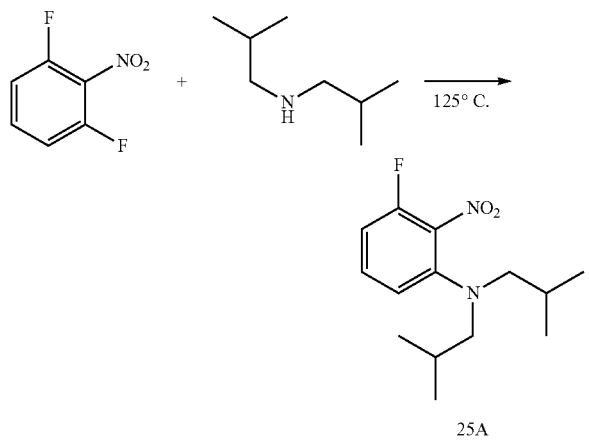

To a stirred solution of 1,3-difluoro-2-nitrobenzene (0.955 g, 6 mmol) in NMP (2 mL) was added Hunig's Base (1.153 mL, 6.60 mmol) followed by diisobutylamine (0.775 g, 6.00 mmol). The solution was stirred 30 min. at 100° C., after which time it was still pale yellow with TLC showing a tiny new spot. The temperature was raised to 125° C., stirring was continued 2 h longer, and overnight at 110° C. LCMS shows ~10% SM and essentially none of the bis-adduct; 0.1 mL more diisobutylamine was added, and the reaction was stirred 1 h longer at 125° C. The reaction was cooled and poured into aq. HOAc. This mixture was extracted with 1:1 ether-heptane, and the organic extract was washed with sat'd aq. sodium bicarbonate, dried, and stripped to afford 3-fluoro-N,N-diisobutyl-2-nitroaniline (1.5 g, 89% yield) as a dark oil. MS(ES): m/z=269 [M+H]$^+$. HPLC T$_r$: 4.83'.

94

25B. 4-Bromo-3-fluoro-N,N-diisobutyl-2-nitroaniline

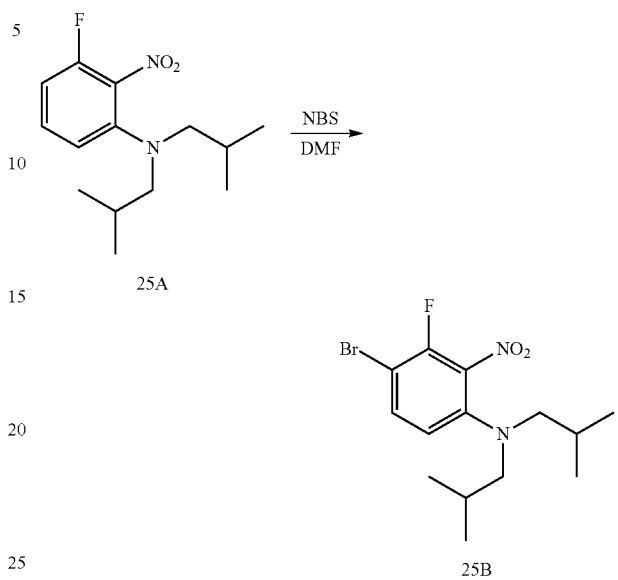

To a stirred, cooled (0° C.) solution of 3-fluoro-N,N-diisobutyl-2-nitroaniline (25A) (0.268 g, 1 mmol) in DMF (3 mL) was added N-bromosuccinimide (0.178 g, 1.000 mmol). The solution was warmed to RT, stirred an additional 15 min., and TLC taken. Most of the UV+ material was a new spot at slightly higher Rf (~0.7 in 10% ether-hexanes) than the ~10-20% SM which remains. A much smaller spot was present further down the plate. An additional 30 mg of NBS was added, and the reaction was stirred 30 min. longer then partially concentrated. Flash chromatography (gradient elution with ether-hexanes afforded 4-bromo-3-fluoro-N,N-diisobutyl-2-nitroaniline (0.32 g, 88% yield) as an orange oil. MS(ES): m/z=349 [M+H]$^+$. HPLC T$_r$: 2.89$^q$.

25C. 4-Bromo-3-fluoro-N1,N1-diisobutylbenzene-1,2-diamine

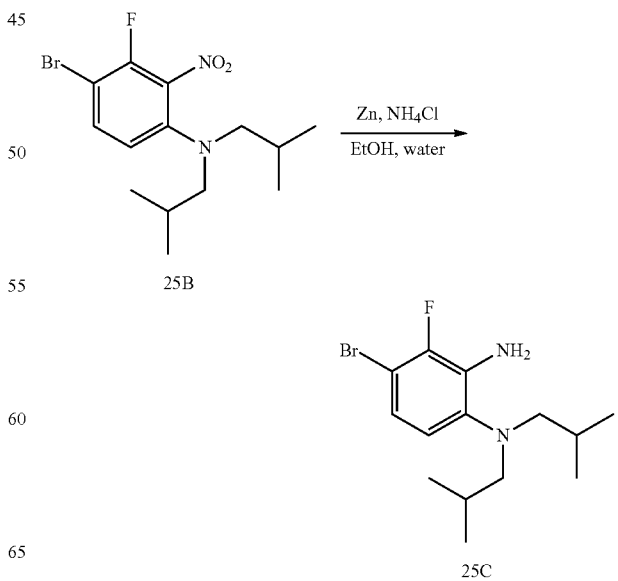

To a solution of 4-bromo-3-fluoro-N,N-diisobutyl-2-nitroaniline (25B) (0.28 g, 0.806 mmol) in ethanol (8 mL) was added 2 mL of water followed by ammonium chloride (0.259 g, 4.84 mmol). The resulting mixture was stirred 5 min. at RT then treated with zinc (0.316 g, 4.84 mmol). This mixture was stirred vigorously for 30 min. then diluted with dichloromethane and filtered. The filtrate was washed with water, dried, and stripped to afford 4-bromo-3-fluoro-N1,N1-diisobutylbenzene-1,2-diamine (0.25 g, 98% yield) as a brown oil. Spectra was consistent with the proposed aniline at the stated level of purity. MS(ES): m/z=319 [M+H]$^+$. HPLC T$_r$: 5.10$^l$.

25D. 1-(3-Bromo-6-(diisobutylamino)-2-fluorophenyl)-3-(p-tolyl)urea

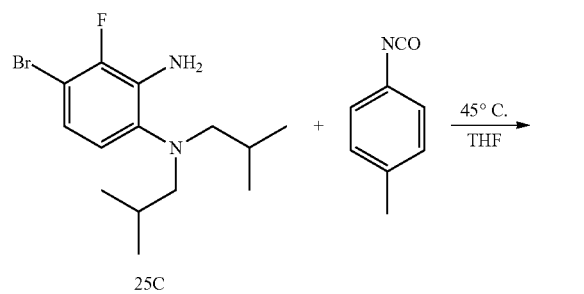

25C

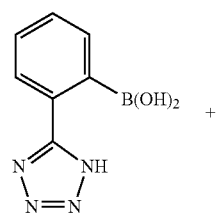

25D

A solution of crude 4-bromo-3-fluoro-N1,N1-diisobutylbenzene-1,2-diamine (0.254 g, 0.8 mmol) was dissolved in THF (1 mL), treated with 1-isocyanato-4-methylbenzene (0.138 g, 1.040 mmol), and stirred 18 h at 45° C. The reaction was quenched with 0.04 mL of N,N-dimethylethylenediamine and purified by flash chromatography (gradient elution with EtOAc-hexanes). Concentration of the appropriate fractions afforded 1-(3-bromo-6-(diisobutylamino)-2-fluorophenyl)-3-(p-tolyl)urea (0.16 g, 40.0% yield) as a tan solid. MS(ES): m/z=452 [M+H]$^+$. HPLC T$_r$: 2.74$^q$.

25. 1-(3-Bromo-6-(diisobutylamino)-2-fluorophenyl)-3-(p-tolyl)urea

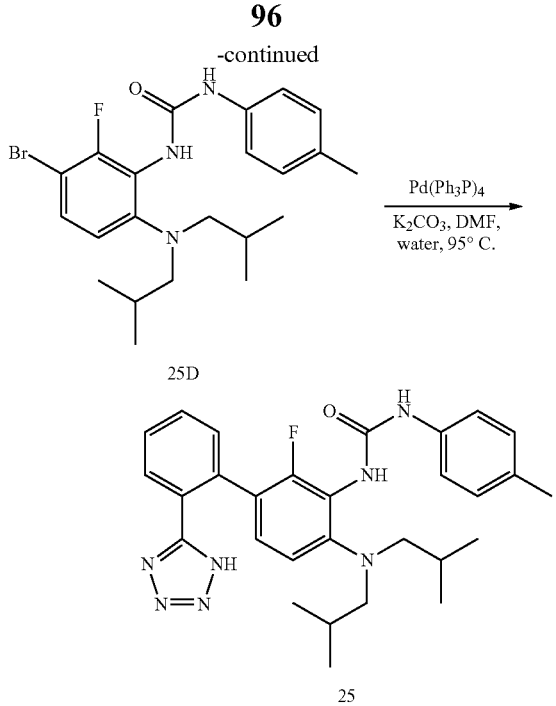

25

A suspension of (2-(1H-tetrazol-5-yl)phenyl)boronic acid (0.025 g, 0.133 mmol) and 1-(3-bromo-6-(diisobutylamino)-2-fluorophenyl)-3-(p-tolyl)urea (25D) (0.03 g, 0.067 mmol) and tetrakis(triphenylphosphine)palladium(0) (7.70 mg, 6.66 μmol) in degassed DMF (1.5 mL) was treated with aq. potassium carbonate (0.222 mL, 0.333 mmol). The reaction was heated at 95° C. for 2 h then cooled to RT and stirred overnight. The reaction was treated with glacial HOAc to pH3 then filtered and purified by prep. HPLC. (Axia Luna 30×100 mm column, MeOH-water-TFA gradient). The appropriate fraction was concentrated to afford 1-(4-(diisobutylamino)-2-fluoro-2'-(1H-tetrazol-5-yl)-[1,1'-biphenyl]-3-yl)-3-(p-tolyl)urea (0.006 g, 16% yield) as a white powder. MS(ES): m/z=516 [M+H]$^+$. HPLC T$_r$: 12.61$^d$.

Example 26

4'-(Diisobutylamino)-2'-fluoro-3'-(3-(p-tolyl)ureido)-[1,1'-biphenyl]-2-carboxylic acid

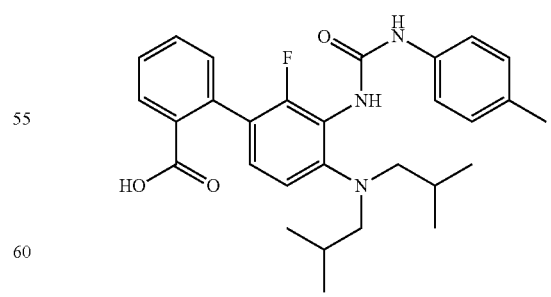

The title compound was prepared from 25D and 2-carboxyphenylboronic acid by the general procedure for the preparation of 25. MS(ES): m/z=492 [M+H]$^+$, HPLC T$_r$: 12.43$^d$.

Example 27

1-(4-(Isobutyl(4,4,4-trifluoro-2-methylbutyl)amino)-2'-(1H-tetrazol-5-yl)-[1,1'-biphenyl]-3-yl)-3-(p-tolyl)urea

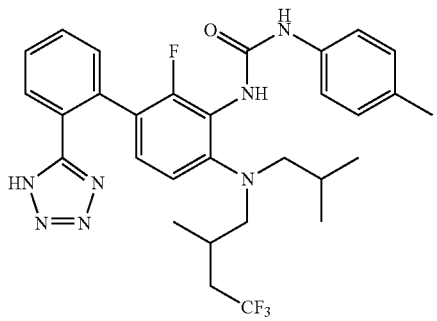 [SMILES: Cc1ccc(NC(=O)Nc2c(N(CC(C)C)CC(C)CC(F)(F)F)ccc(-c3ccccc3-c3nnn[nH]3)c2F)cc1]

27A. (+/−)-4,4,4-Trifluoro-N-isobutyl-2-methylbutanamide

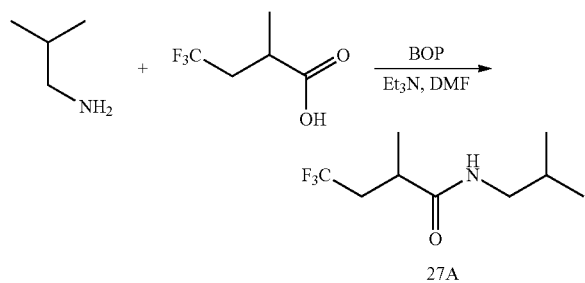

A solution of 2-methylpropan-1-amine (0.285 g, 3.90 mmol) and 4,4,4-trifluoro-2-methylbutanoic acid (0.468 g, 3 mmol) in DMF (8 mL) was treated with triethylamine (0.544 mL, 3.90 mmol) followed by BOP (1.460 g, 3.30 mmol). The solution was stirred 18 h at RT then diluted with ether and washed with 0.5 M aq. HCl and then saturated aq. sodium bicarbonate. The organic phase was dried and stripped to afford 4,4,4-trifluoro-N-isobutyl-2-methylbutanamide (0.6 g, 90% yield) as a waxy white solid. MS(ES): m/z=212 [M+H]$^+$. HPLC T$_r$: 1.60$^p$.

27B. (+/−)-4,4,4-Trifluoro-N-isobutyl-2-methylbutan-1-amine

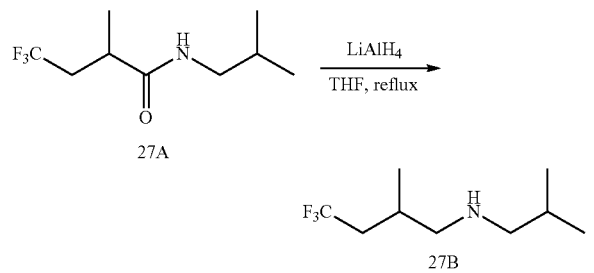

To a solution of lithium aluminum hydride (7.50 mL, 7.50 mmol) in THF was added 4,4,4-trifluoro-N-isobutyl-2-methylbutanamide (27A) (0.528 g, 2.5 mmol). The suspension was brought to reflux and stirred for 6 h. The reaction was cooled and stirred overnight at RT. The reaction was quenched using the method of Fieser, and treated with 10 mL more THF, and MgSO$_4$ and then stirred 1 h at RT. The reaction was filtered and stripped to afford 4,4,4-trifluoro-N-isobutyl-2-methylbutan-1-amine, 0.5 tetrahydrofuran (0.57 g, 93% yield) as a colorless oil. MS(ES): m/z=198 [M+H]$^+$. HPLC T$_r$: 1.27$^p$.

27C. (+/−)-4-Bromo-N-isobutyl-2-nitro-N-(4,4,4-trifluoro-2-methylbutyl)aniline

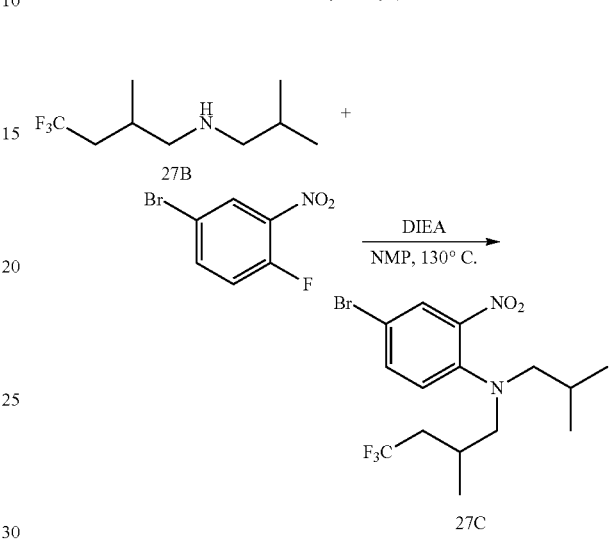

To a solution of 4-bromo-1-fluoro-2-nitrobenzene (0.220 g, 1 mmol) and 4,4,4-trifluoro-N-isobutyl-2-methylbutan-1-amine (27B), 0.5 tetrahydrofuran (0.327 g, 1.400 mmol) in N-methyl-2-pyrrolidinone (0.3 mL) was added Hunig's Base (0.210 mL, 1.200 mmol). The reaction was stirred at 130° C. for 18 h. The reaction was cooled to RT, diluted with ether and washed with 10% aq. HOAc then aq. sodium bicarbonate. The organic phase was dried and stripped to afford 4-bromo-N-isobutyl-2-nitro-N-(4,4,4-trifluoro-2-methylbutyl)aniline (0.38 g, 86% yield) as a dark orange oil. MS(ES): m/z=399 [M+H]$^+$. HPLC T$_r$: 5.05$^I$.

27D. (+/−)-4-Bromo-N1-isobutyl-N1-(4,4,4-trifluoro-2-methylbutyl)benzene-1,2-diamine

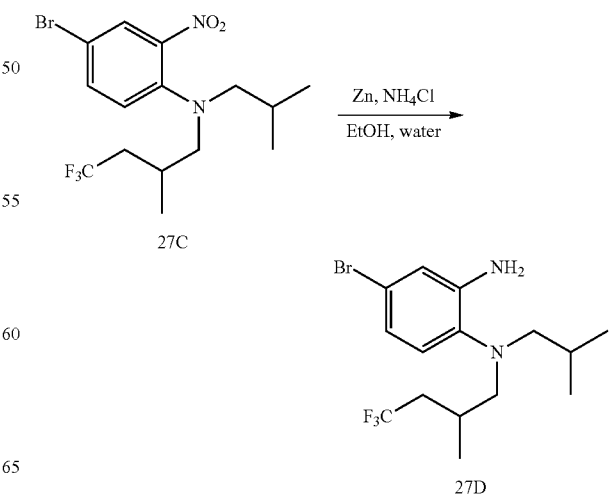

The title compound was prepared from 27C by the procedure used for the conversion of 8B to 8C. MS(ES): m/z=369 [M+H]$^+$. HPLC T$_r$: 2.76$^q$.

27E. 1-(5-Bromo-2-(isobutyl(4,4,4-trifluoro-2-methylbutyl)amino)phenyl)-3-(p-tolyl)urea

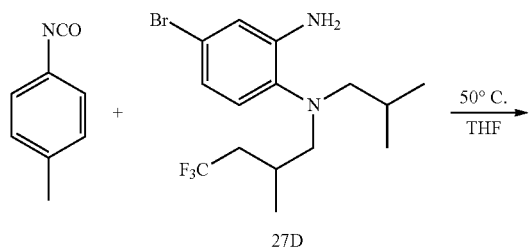

The title compound was prepared from 27D at 50° C. by the procedure used for the conversion of 8C to 8D. MS(ES): m/z=502 [M+H]$^+$. HPLC T$_r$: 3.25$^r$.

27. 1-(4-(Isobutyl(4,4,4-trifluoro-2-methylbutyl)amino)-2'-(1H-tetrazol-5-yl)-[1,1'-biphenyl]-3-yl)-3-(p-tolyl)urea

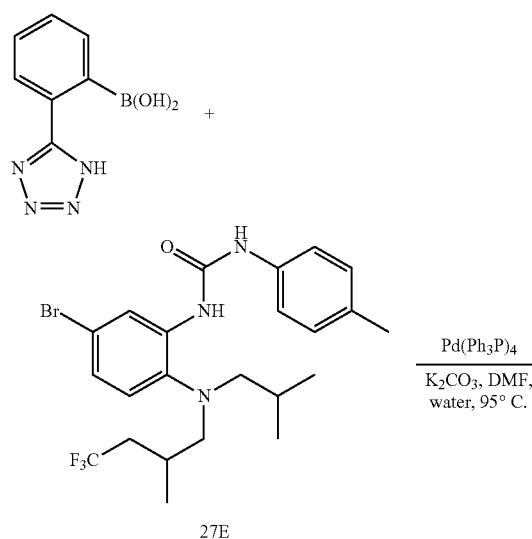

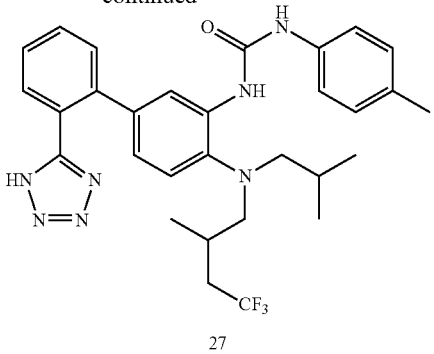

The title compound was prepared from 27E by the procedure used for the conversion of 8D to 8. MS(ES): m/z=566 [M+H]$^+$. HPLC T$_r$: 2.70$^q$.

Example 28

4'-(Isobutyl(4,4,4-trifluoro-2-methylbutyl)amino)-3'-(3-(p-tolyl)ureido)-[1,1'-biphenyl]-2-carboxylic acid

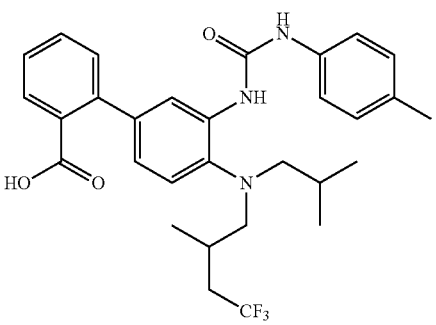 [SMILES: Cc1ccc(NC(=O)Nc2cc(-c3ccccc3C(=O)O)ccc2N(CC(C)C)CC(C)CC(F)(F)F)cc1]

The title compound was prepared from 27E and 2-carboxyphenylboronic acid by the procedure used for the conversion of 8D to 8. MS(ES): m/z=542 [M+H]$^+$. HPLC T$_r$: 2.71$^q$.

Example 29

1-(4-(Cyclohexyl(1,1-dideutero-2-methylpropyl)amino)-2'-(1H-tetrazol-5-yl)biphenyl-3-yl)-3-p-tolylurea

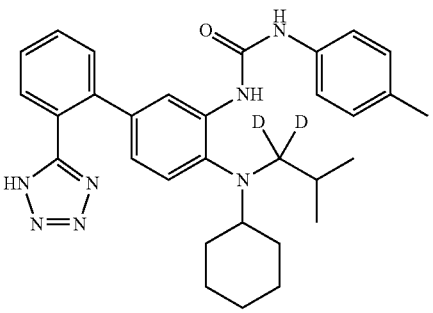 [SMILES: [2H]C([2H])(C(C)C)N(c1ccc(-c2ccccc2-c2nnn[nH]2)cc1NC(=O)Nc1ccc(C)cc1)C1CCCCC1]

29A. N-Cyclohexylisobutyramide

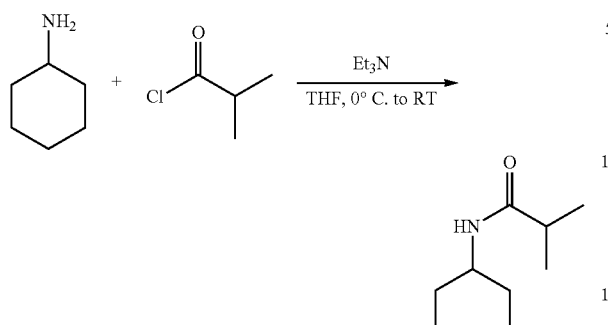

29A

To a stirred, cooled (0° C.) solution of cyclohexanamine (1.091 g, 11.00 mmol) and triethylamine (1.214 g, 12.00 mmol) in THF (Volume: 10 mL) was added isobutyryl chloride (1.066 g, 10 mmol). The resulting slurry was stirred 30 min., warming to RT then diluted with 1:1 ether-hexanes. The resulting mixture was washed with aq. HCl then sat'd aq. sodium bicarbonate, dried, and stripped to afford N-cyclohexylisobutyramide as a colorless solid. MS(ES): m/z=170 [M+H]$^+$. HPLC T$_r$: 2.61$^t$.

29B. N-(1,1-Dideutero-2-methylpropyl)cyclohexanamine

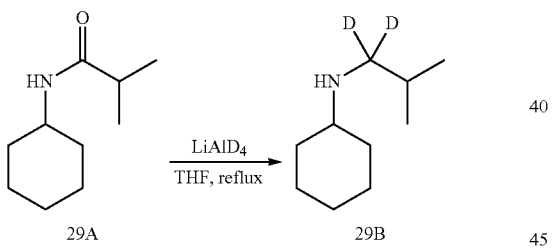

The title compound was prepared from 29A and lithium aluminum deuteride by the procedure used for the conversion of 27A to 27B. MS(ES): m/z=158 [M+H]$^+$. HPLC T$_r$: 1.56$^p$.

29C. 4-Bromo-N-cyclohexyl-N-(1,1-dideutero-2-methylpropyl)-2-nitroaniline

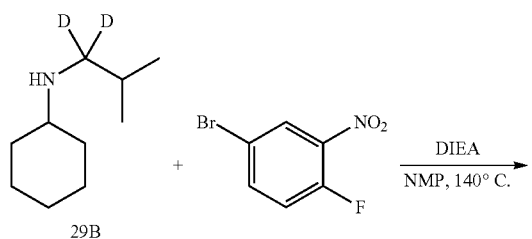

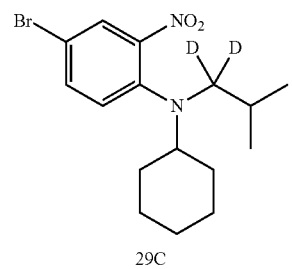

29C

The title compound was prepared from 29B at 140° C. by the procedure used for the conversion of 27B to 27C. MS(ES): m/z=359 [M+H]$^+$. HPLC T$_r$: 3.74$^q$.

29D. 4-Bromo-N1-cyclohexyl-N1-(1,1-difluoro-2-methylpropyl)benzene-1,2-diamine

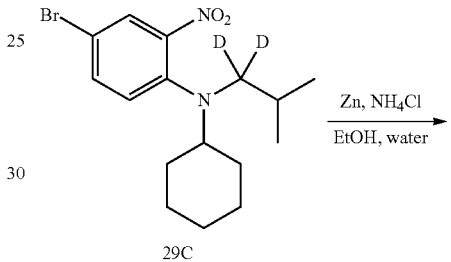

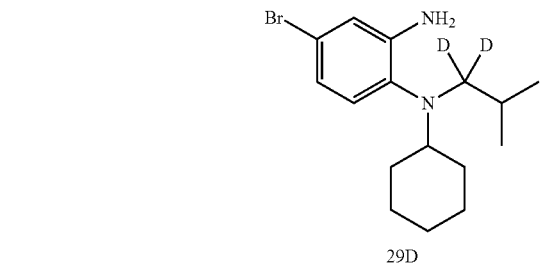

29D

The title compound was prepared from 29C by the procedure used for the conversion of 8B to 8C. MS(ES): m/z=327 [M+H]$^+$. HPLC T$_r$: 2.86$^q$.

29E. 1-(5-Bromo-2-(cyclohexyl(1,1-dideutero-2-methylpropyl)amino)phenyl)-3-p-tolylurea

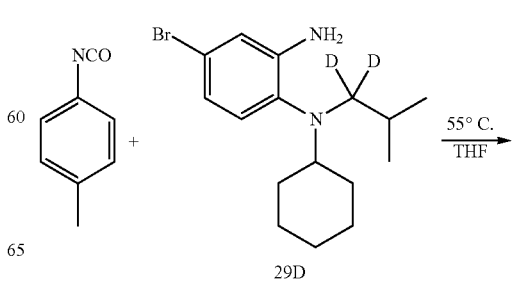

-continued

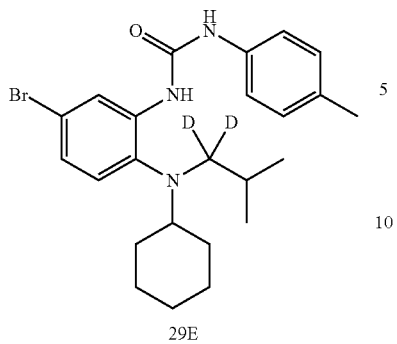

29E

The title compound was prepared from 29D at 55° C. by the procedure used for the conversion of 8C to 8D. MS(ES): m/z=462 [M+H]$^+$. HPLC T$_r$: 5.36$^l$.

29. 1-(4-(Cyclohexyl(1,1-dideutero-2-methylpropyl)amino)-2'-(1H-tetrazol-5-yl)biphenyl-3-yl)-3-p-tolylurea

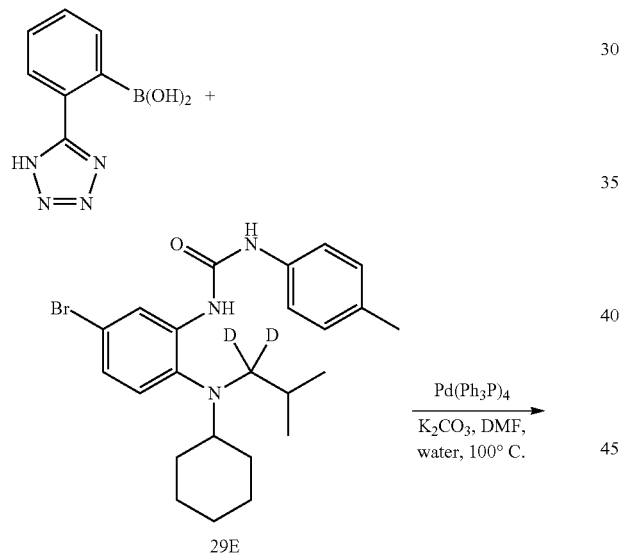

The title compound was prepared from 29E at 100° C. by the procedure used for the conversion of 8D to 8. MS(ES): m/z=526 [M+H]$^+$. HPLC T$_r$: 13.01$^d$.

Example 30

4'-(Cyclohexyl(1,1-dideutero-2-methylpropyl)amino)-3'-(3-p-tolylureido)biphenyl-2-carboxylic acid

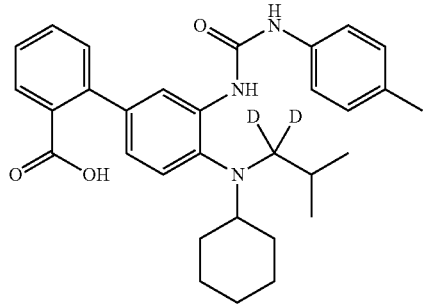 [SMILES: [2H]C([2H])(C(C)C)N(c1ccc(-c2ccccc2C(=O)O)cc1NC(=O)Nc1ccc(C)cc1)C1CCCCC1]

The title compound was prepared from 29E and 2-carboxyphenylboronic acid at 100° C. by the procedure used for the conversion of 8E to 8. MS(ES): m/z=502 [M+H]$^+$. HPLC T$_r$: 12.64$^d$.

Example 31

4'-(Cyclohexyl(1,1-dideutero-2-methylpropyl)amino)-5-fluoro-3'-(3-p-tolylureido)biphenyl-2-carboxylic acid

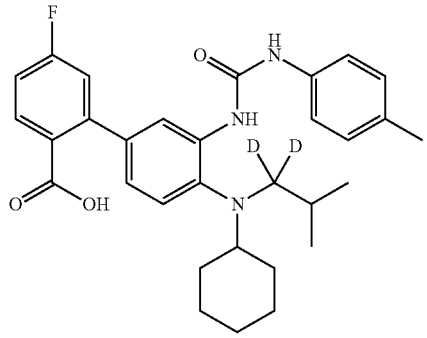 [SMILES: [2H]C([2H])(C(C)C)N(c1ccc(-c2cc(F)ccc2C(=O)O)cc1NC(=O)Nc1ccc(C)cc1)C1CCCCC1]

The title compound was prepared from 29E and 2-carboxy-5-fluorophenylboronic acid at 100° C. by the procedure used for the conversion of 8D to 8. MS(ES): m/z=520 [M+H]$^+$. HPLC T$_r$: 13.04$^d$.

Example 32

1-(4-(Cyclohexyl(1,1-dideutero-2-methylpropyl)amino)-2'-(1H-tetrazol-5-yl)biphenyl-3-yl)-3-(2-fluorophenyl)urea

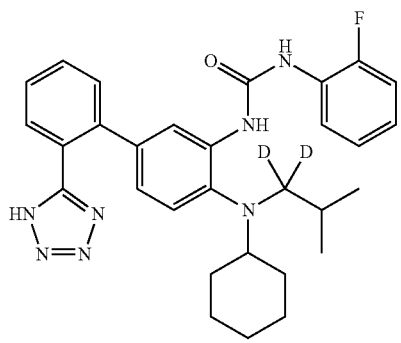 [SMILES: [2H]C([2H])(C(C)C)N(c1ccc(-c2ccccc2-c2nnn[nH]2)cc1NC(=O)Nc1ccccc1F)C1CCCCC1]

32A. 1-(5-Bromo-2-(cyclohexyl(1,1-dideutero-2-methylpropyl)amino)phenyl)-3-(2-fluorophenyl)urea

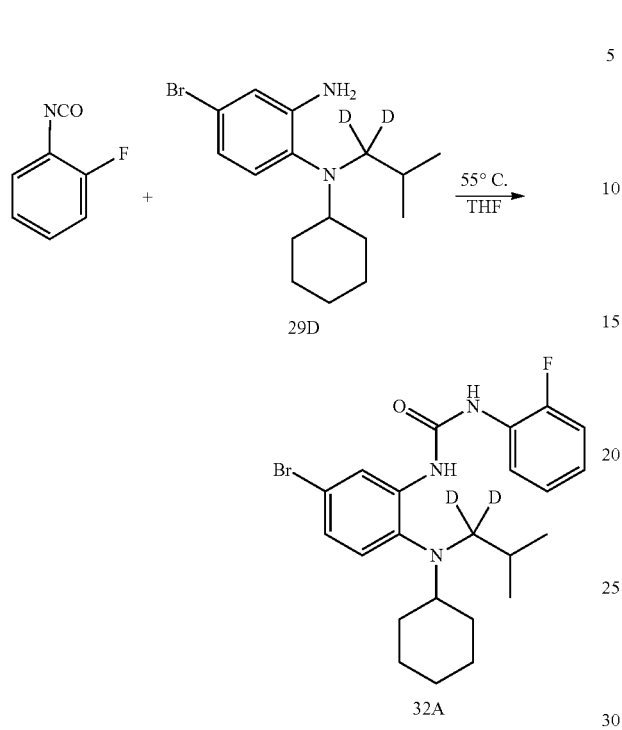

The title compound was prepared from 29D and 2-fluorophenylisocyanate at 55° C. by the procedure used for the conversion of 8C to 8D. MS(ES): m/z=466 [M+H]⁺. HPLC T$_r$: 3.43$^q$.

32. 1-(4-(Cyclohexyl(1,1-dideutero-2-methylpropyl)amino)-2'-(1H-tetrazol-5-yl)biphenyl-3-yl)-3-(2-fluorophenyl)urea

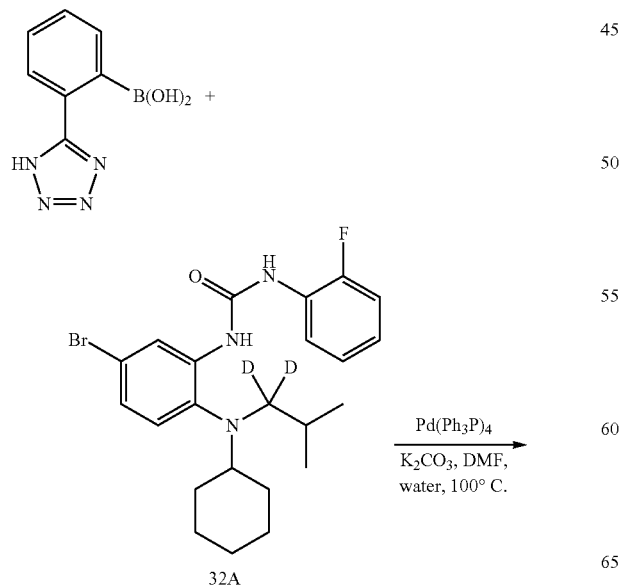

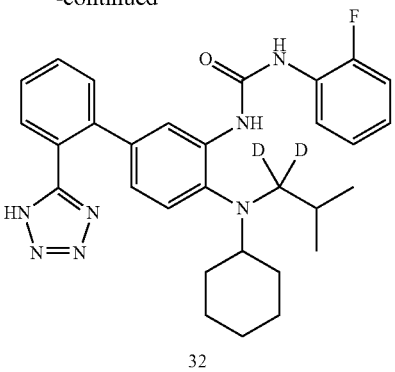

The title compound was prepared from 32A at 100° C. by the procedure used for the conversion of 8D to 8. MS(ES): m/z=530 [M+H]⁺. HPLC T$_r$: 3.05$^q$.

Example 33

4'-(Cyclohexyl(1,1-dideutero-2-methylpropyl)amino)-3'-(3-(2-fluorophenyl)ureido)biphenyl-2-carboxylic acid

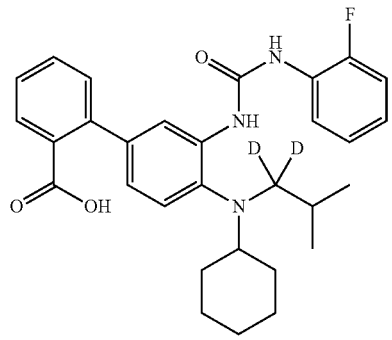 [SMILES: [2H]C([2H])(C(C)C)N(c1ccc(-c2ccccc2C(=O)O)cc1NC(=O)Nc1ccccc1F)C1CCCCC1]

The title compound was prepared from 32A and 2-carboxyphenylboronic acid at 100° C. by the procedure used for the conversion of 8D to 8. MS(ES): m/z=506 [M+H]⁺. HPLC T$_r$: 2.97$^q$.

Example 34

4'-(Cyclohexyl(1,1-dideutero-2-methylpropyl)amino)-5-fluoro-3'-(3-(2-fluorophenyl)ureido)biphenyl-2-carboxylic acid

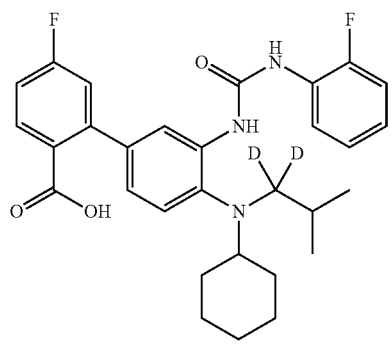 [SMILES: [2H]C([2H])(C(C)C)N(c1ccc(-c2cc(F)ccc2C(=O)O)cc1NC(=O)Nc1ccccc1F)C1CCCCC1]

The title compound was prepared from 32A and 2-carboxy-5-fluorophenylboronic acid at 100° C. by the procedure used for the conversion of 8D to 8. MS(ES): m/z=524 [M+H]+. HPLC T$_r$: 3.09$^q$.

Example 35

4-(4-(Diisobutylamino)-3-(3-p-tolylureido)phenyl)thiophene-3-carboxylic acid (Scheme 5)

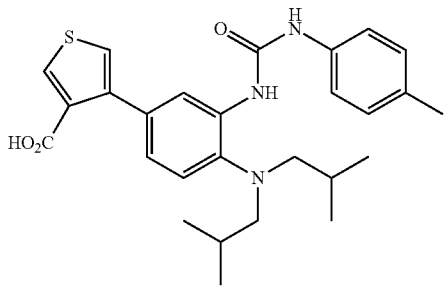 [SMILES: Cc1ccc(NC(=O)Nc2cc(-c3cscc3C(=O)O)ccc2N(CC(C)C)CC(C)C)cc1]

35A. 1-(2-(Diisobutylamino)-5-(5,5-dimethyl-1,3,2-dioxaborinan-2-yl)phenyl)-3-p-tolylurea

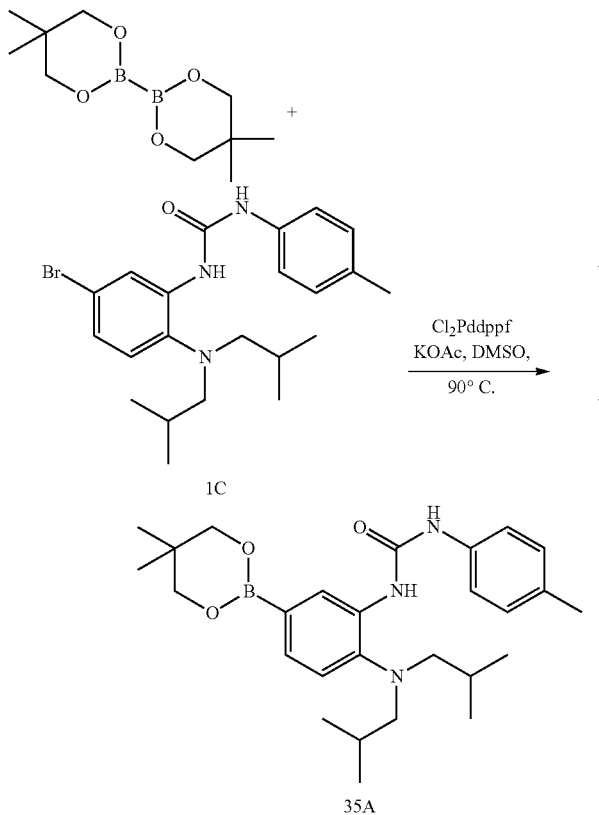

To a suspension of 1-(5-bromo-2-(diisobutylamino)phenyl)-3-p-tolylurea (0.432 g, 1 mmol) and 5,5,5',5'-tetramethyl-2,2'-bi(1,3,2-dioxaborinane) (0.294 g, 1.300 mmol) and 1,1'-bis(diphenylphosphino)ferrocene-palladium(II) dichloride dichloromethane complex (0.024 g, 0.030 mmol) in degassed DMSO (Volume: 2 mL) was added potassium acetate (0.294 g, 3.00 mmol). The mixture was placed under nitrogen and heated at 80° C. for 1.3 h. The reaction temperature was raised to 90° C., and stirring was continued for 3 h. The reaction was cooled to RT, diluted with water, and extracted with ether. The organic extract was dried, stripped, and chromatographed on silica gel (gradient elution with ether-hexanes) to afford 1-(2-(diisobutylamino)-5-(5,5-dimethyl-1,3,2-dioxaborinan-2-yl)phenyl)-3-p-tolylurea (0.37 g, 76% yield) as a white powder. $^1$H NMR (400 MHz, DMSO-d$_6$) δ ppm 9.26 (s, 1H), 8.22 (d, 1H, J=1.5 Hz); 7.66 (s, 1H); 7.35 (d, 2H, J=8.4 Hz); 7.28 (dd, 1H, J=7.9, 1.3 Hz); 7.13 (d, 1H, J=8.1 Hz); 7.07 (d, 2H, J=8.4 Hz); 3.72 (s, 4H); 2.71 (d, 4H, J=7.0 Hz); 2.24 (s, 3H); 1.60-1.71 (m, 2H); 0.95 (s, 6H); 0.82 (d, 12H, J=6.6 Hz). MS(ES): m/z=398 [M+H-C$_5$H$_8$]+.

35. 4-(4-(Diisobutylamino)-3-(3-p-tolylureido)phenyl)thiophene-3-carboxylic acid

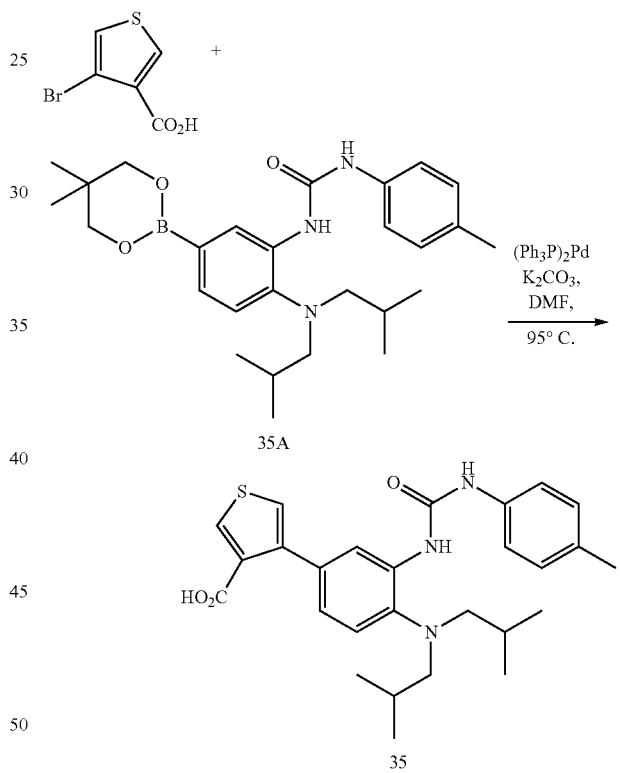

A suspension of 4-bromothiophene-3-carboxylic acid (0.036 g, 0.17 mmol) and 1-(2-(diisobutylamino)-5-(5,5-dimethyl-1,3,2-dioxaborinan-2-yl)phenyl)-3-p-tolylurea (35A) (0.04 g, 0.086 mmol) and tetrakis(triphenylphosphine)palladium(0) (9.93 mg, 8.59 μmol) in degassed DMF (Volume: 1 mL) was treated with aq. potassium carbonate (0.29 mL, 0.43 mmol). The suspension was placed under nitrogen and heated at 95° C. for 2 h. The reaction was cooled, brought to pH 5 with glacial HOAc, filtered, and purified by prep. HPLC (Axia 30×100 mm column, MeOH-water-TFA gradient). Concentration of the appropriate fraction afforded 4-(4-(diisobutylamino)-3-(3-p-tolylureido)phenyl)thiophene-3-carboxylic acid (0.008 g, 0.016 mmol, 18% yield) as a white powder. $^1$H NMR (400 MHz, DMSO-d$_6$) δ ppm 9.33 (s, 1H), 8.23 (d, 1H, J=3.3 Hz); 7.97 (d, 1H, J=1.8 Hz); 7.83 (s, 1H); 7.47 (d, 1H, J=3.3 Hz); 7.34 (d, 2H, J=8.4 Hz); 7.18 (d, 1H, J=8.4 Hz); 7.07 (d, 2H, J=8.1 Hz); 6.94 (dd, 1H, J=8.1, 1.8 Hz); 2.68 (d, 4H, J=6.8 Hz); 2.23 (s, 3H); 1.61-1.76 (m, 2H); 0.86 (d, 12H, J=6.6 Hz). MS(ES): m/z=480 [M+H]$^+$.

Example 36

2-(4-(Cyclohexyl(1,1-dideutero-2-methylpropyl)amino)-3-(3-(2-fluorophenyl)ureido)phenyl)thiophene-3-carboxylic acid

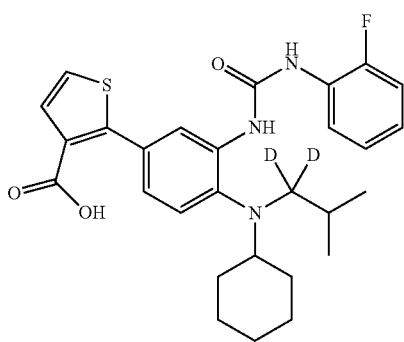 [SMILES: [2H]C([2H])(C(C)C)N(c1ccc(-c2sccc2C(=O)O)cc1NC(=O)Nc1ccccc1F)C1CCCCC1]

The title compound was prepared from 32A and 2-boronothiophene-3-carboxylic acid at 100° C. by the procedure used for the conversion of 8D to 8. MS(ES): m/z=512 [M+H]$^+$. HPLC T$_r$: 3.10$^q$.

Example 37

1-(5-(2-(1H-Tetrazol-5-yl)phenyl)-2-(cyclohexyl(methyl)amino)pyridin-3-yl)-3-(2-fluorophenyl)urea

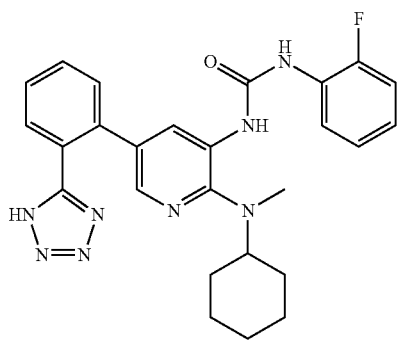 [SMILES: CN(c1ncc(-c2ccccc2-c2nnn[nH]2)cc1NC(=O)Nc1ccccc1F)C1CCCCC1]

37A. 5-Bromo-N-cyclohexyl-N-methyl-3-nitropyridin-2-amine

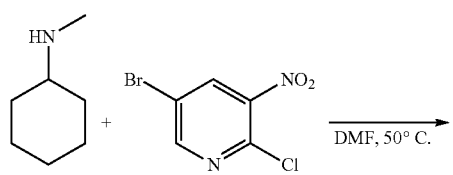

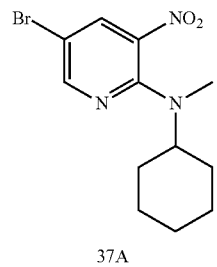

The title compound was prepared from 5-bromo-2-chloro-3-nitropyridine and N-methylcyclohexylamine (2.2 eq.) in DMF (~0.3 M) at 50° C. by the procedure used for the preparation of 1A. MS(ES): m/z=316 [M+H]$^+$. HPLC T$_r$: 5.01$^l$.

37B. 5-Bromo-N2-cyclohexyl-N2-methylpyridine-2,3-diamine

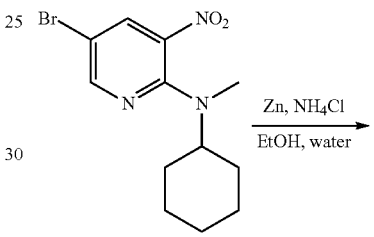

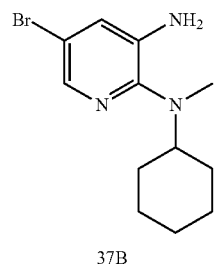

The title compound was prepared from 37A by the procedure used for the preparation of 1B. MS(ES): m/z=284 [M+H]$^+$. HPLC T$_r$: 2.88$^l$.

37C. 1-(5-Bromo-2-(cyclohexyl(methyl)amino)pyridin-3-yl)-3-(2-fluorophenyl)urea

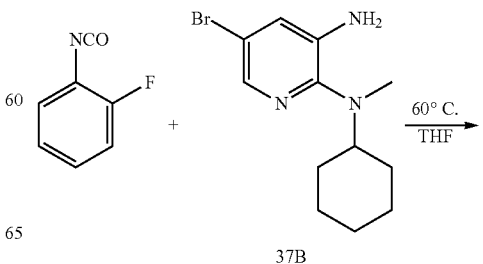

-continued

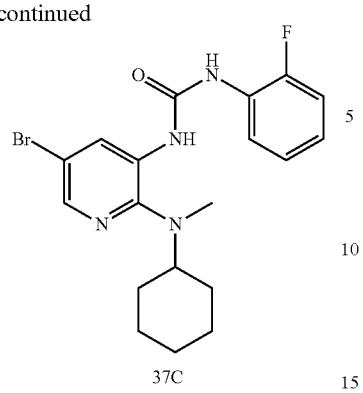

37C

The title compound was prepared from 37B and 2-fluorophenyl isocyanate at 60° C. by the procedure used for the conversion of 8C to 8D. MS(ES): m/z=423 [M+H]+. HPLC T$_r$: 4.85[l].

37. 1-(5-(2-(1H-Tetrazol-5-yl)phenyl)-2-(cyclohexyl(methyl)amino)pyridin-3-yl)-3-(2-fluorophenyl)urea

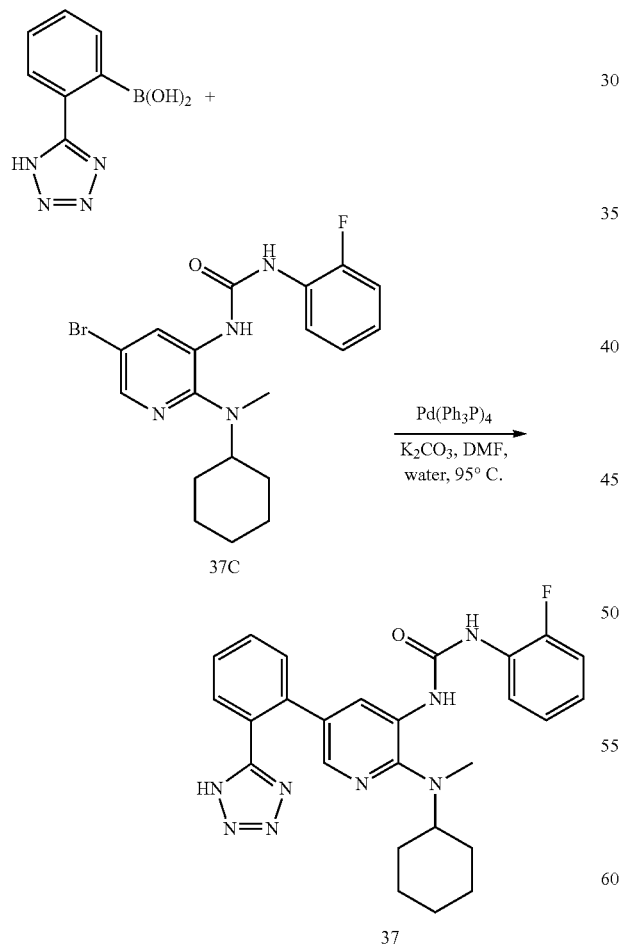

The title compound was prepared from 37C at 95° C. by the procedure used for the conversion of 8D to 8. MS(ES): m/z=487 [M+H]+. HPLC T$_r$: 11.53[d].

Example 38

1-(4-Bromo-2-fluorophenyl)-3-(4-(diisobutylamino)-2'-(1H-tetrazol-5-yl)biphenyl-3-yl)urea

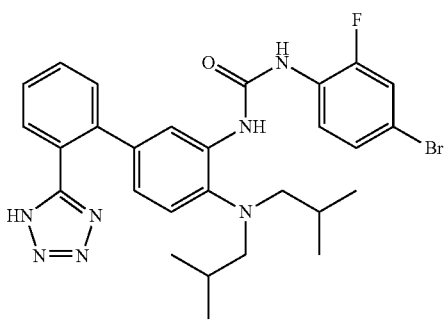 [SMILES: CC(C)CN(CC(C)C)c1ccc(-c2ccccc2-c2nnn[nH]2)cc1NC(=O)Nc1ccc(Br)cc1F]

38A. N4,N4-Diisobutyl-2'-(2-trityl-2H-tetrazol-5-yl)biphenyl-3,4-diamine

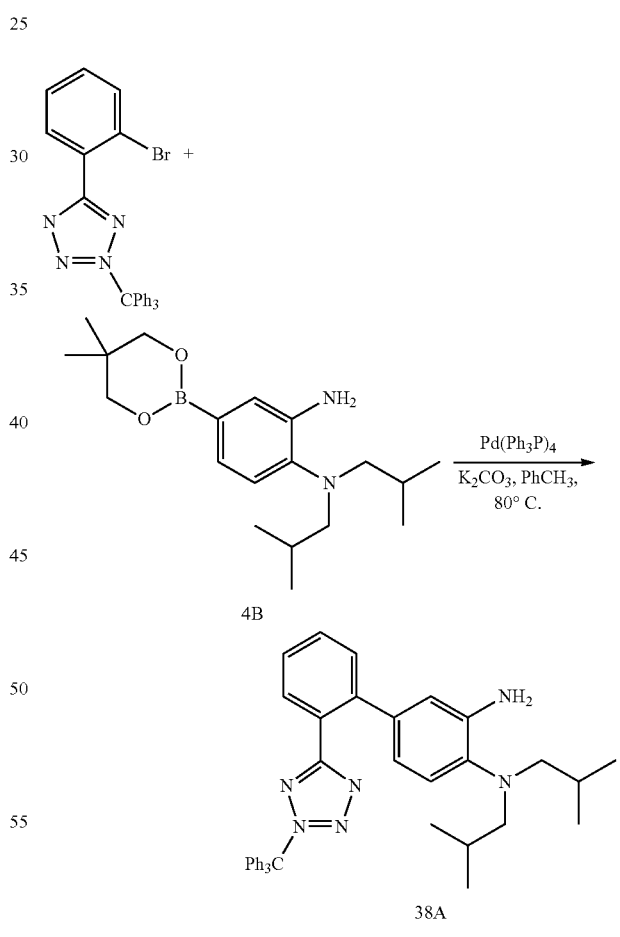

A mixture of toluene (Ratio: 2.250, Volume: 9 mL) and water (Ratio: 1.000, Volume: 4 mL) was degassed by purges with nitrogen (3×). 4-(5,5-dimethyl-1,3,2-dioxaborinan-2-yl)-N1,N1-diisobutylbenzene-1,2-diamine (4B) (2 g, 6.02 mmol), 5-(2-bromophenyl)-2-trityl-2H-tetrazole (2.56 g, 5.47 mmol) and sodium carbonate (1.160 g, 10.94 mmol) were added, and the reaction mixture was purged with nitrogen. Pd(Ph₃P)₄ (0.632 g, 0.547 mmol) was added, the mixture was degassed (3×), and the reaction mixture was heated at 80° C. under a nitrogen atmosphere for 14 h. The reaction was cooled to room temperature, and the resulting mixture was extracted with DCM (3×60 ml), washed with water and brine, dried over anhydrous Na₂SO₄. Purification by ISCO chromatography (gradient elution with ethyl acetate-hexanes) afforded N4,N4-diisobutyl-2'-(2-trityl-2H-tetrazol-5-yl)biphenyl-3,4-diamine (2.37 g, 3.91 mmol, 71.4% yield) as white solid. MS(ES): m/z=607 [M+H]⁺. HPLC T$_r$: 1.28$^k$.

38. 1-(4-Bromo-2-fluorophenyl)-3-(4-(diisobutylamino)-2'-(1H-tetrazol-5-yl)biphenyl-3-yl)urea

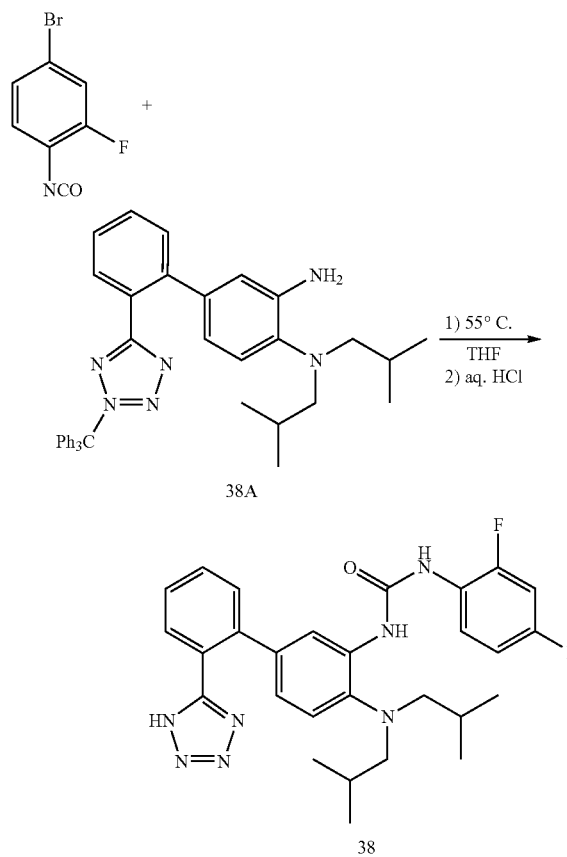

A solution of N4,N4-diisobutyl-2'-(1-trityl-1H-tetrazol-5-yl)-[1,1'-biphenyl]-3,4-diamine (38A) (0.2 g, 0.330 mmol) in THF (1 mL) was treated with 4-bromo-2-fluoro-1-isocyanatobenzene (0.093 g, 0.428 mmol) and warmed to 55° C. After 1 h, the solution was treated with 0.3 mL of 4 M aq. HCl and stirred 3 h at RT. This mixture was treated with ~0.3 mL of DMF and a few drops of EtOH to give a solution, and then it was chromatographed on silica gel (elution with 1:1 ether-hexanes, 1% HOAc, gradient of EtOH from 0% to 5%). Concentration of the appropriate fractions afforded 1-(4-bromo-2-fluorophenyl)-3-(4-(diisobutylamino)-2'-(1H-tetrazol-5-yl)-[1,1'-biphenyl]-3-yl)urea (0.058 g, 27.3% yield) as a colorless foam. MS(ES): m/z=580 [M+H]⁺. HPLC T$_r$: 13.18$^d$.

Example 39

1-(5-Chloro-4-(diisobutylamino)-2'-(1H-tetrazol-5-yl)biphenyl-3-yl)-3-p-tolylurea

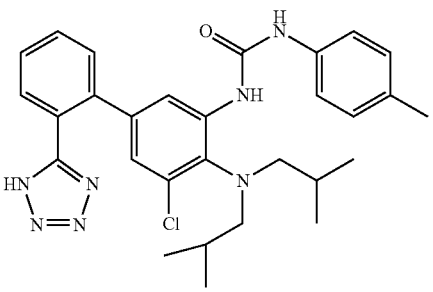 [SMILES: Cc1ccc(NC(=O)Nc2cc(-c3ccccc3-c3nnn[nH]3)cc(Cl)c2N(CC(C)C)CC(C)C)cc1]

39A.
4-Bromo-2-chloro-N,N-diisobutyl-6-nitroaniline

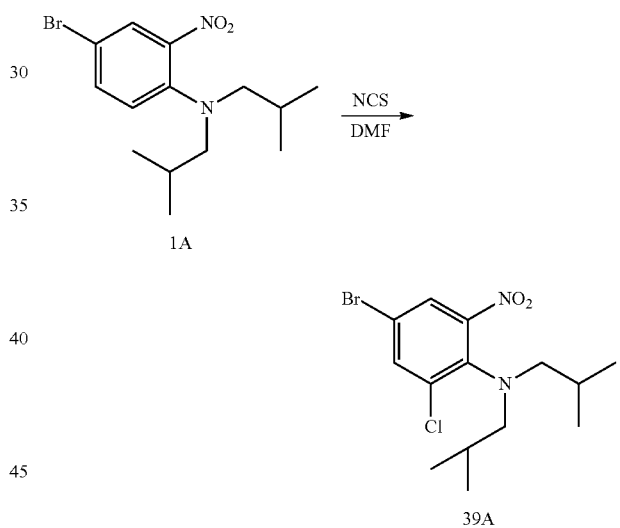

A stirred, cooled (0° C.) solution of 4-bromo-N,N-diisobutyl-2-nitroaniline (1A) (0.494 g, 1.5 mmol) in DMF (4 mL) was treated with N-chlorosuccinimide (0.220 g, 1.650 mmol). The orange solution was warmed to RT and stirred 15 min. LCMS indicates that LTN reaction has occurred. The reaction was warmed with a heat gun to ~60° C. for a few seconds then cooled to RT with stirring over 10 min. TLC indicates SM and one spot at lower Rf and one spot at higher Rf. The reaction was treated with an additional 150 mg. of NCS and re-warmed to 60° C. The reaction was then stirred overnight at RT. The reaction was purified by prep. HPLC (Axia Luna 30×100 mm column, gradient elution with MeOH-water-TFA, four injections). Concentration of the appropriate fractions afforded 4-bromo-2-chloro-N,N-diisobutyl-6-nitroaniline (0.27 g, 47.0% yield) as an orange oil. MS(ES): m/z=363 [M+H]⁺. HPLC T$_r$: 5.52$^l$.

39B. 1-(5-Bromo-3-chloro-2-(diisobutylamino)phenyl)-3-p-tolylurea

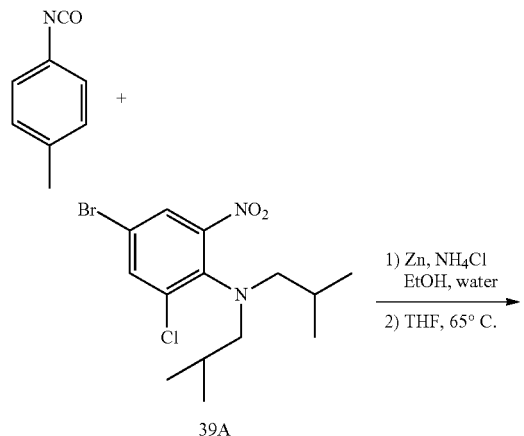

The title compound was prepared from 39A using the procedures for the conversion of 1A into 1C. MS(ES): m/z=468 [M+H]$^+$. HPLC T$_r$: 5.49$^f$.

39. 1-(5-Chloro-4-(diisobutylamino)-2'-(1H-tetrazol-5-yl)biphenyl-3-yl)-3-p-tolylurea

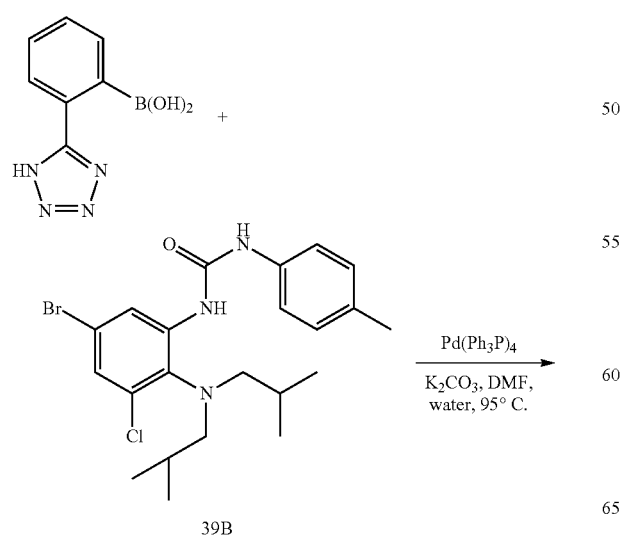

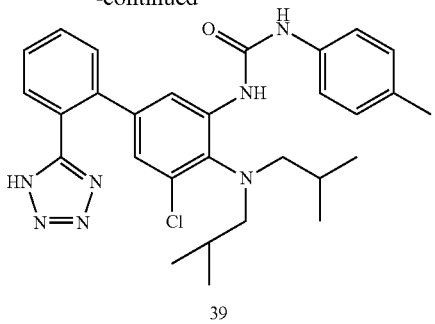

The title compound was prepared from 39B using the procedures for the conversion of 8D to 8. MS(ES): m/z=532 [M+H]$^+$. HPLC T$_r$: 5.00$^f$.

Example 40

3'-Chloro-4'-(diisobutylamino)-5'-(3-p-tolylureido)biphenyl-2-carboxylic acid

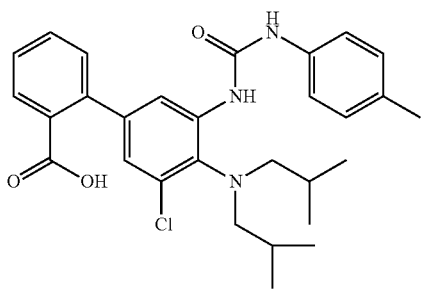 [SMILES: Cc1ccc(NC(=O)Nc2cc(-c3ccccc3C(=O)O)cc(Cl)c2N(CC(C)C)CC(C)C)cc1]

The title compound was prepared from 39B and 2-carboxyphenylboronic acid by the procedure described for the conversion of 8D to 8. MS(ES): m/z=508 [M+H]$^+$. HPLC T$_r$: 13.34$^d$.

Example 41

3'-Chloro-4'-(diisobutyl amino)-5-fluoro-5'-(3-p-tolylureido)biphenyl-2-carboxylic acid

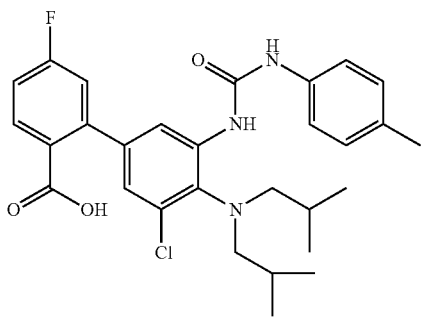 [SMILES: Cc1ccc(NC(=O)Nc2cc(-c3cc(F)ccc3C(=O)O)cc(Cl)c2N(CC(C)C)CC(C)C)cc1]

The title compound was prepared from 39B and 2-borono-4-fluorobenzoic acid by the procedure described for the conversion of 8D to 8. MS(ES): m/z=526 [M+H]$^+$. HPLC T$_r$: 5.23$^f$.

Using the methods described for the preparation of 27B and 29B, amines RNH$_2$ and carboxylic acids R'CO$_2$H are coupled to give amides which are further transformed by the action of LiAlH$_4$ into secondary amines RNHCH$_2$R' (lx, Table 2) useful as intermediates in the synthesis of compounds of the present invention.

TABLE 2

Amine Starting Materials Made by Hydride Reduction of Amides $$RNH_2 \xrightarrow[\substack{\text{or R'COCl, Et}_3\text{N, THF,} \\ 0°\text{ C. to RT} \\ \text{2) LiAlH}_4\text{, THF, reflux}}]{\substack{\text{1) R'CO}_2\text{H, Et}_3\text{N} \\ \text{Bop, DMF}}} R\text{-NH-CH}_2\text{-R'} \quad \text{Ix}$$

| | R | R' | Coupling method | (M + H)$^+$ | T$_r$ |
|---|---|---|---|---|---|
| lxa | cyclohexyl-CH$_2$- | -CH(CH$_3$)$_2$ | acid chloride | 156 | 1.46$^o$ |
| lxb | cyclobutyl-CH$_2$- | -CH(CH$_3$)$_2$ | acid chloride | used in subsequent step without purification or characterization | |
| lxc | cyclopentyl-CH$_2$- | -CH(CH$_3$)$_2$ | acid chloride | 142 | 1.22$^o$ |
| lxd | cyclopentyl-CH$_2$- | -CH$_2$CH$_2$CH$_3$ | acid chloride | $^1$H NMR (400 MHz, DMSO-d$_6$) δ ppm 2.89-2.98 (m, 1H); 2.41 (t, 2H, J = 7.0 Hz); 1.20-1.72 (m, 10H); 0.84 (t, 3H, J = 7.4 Hz). | |
| lxe | cyclohexyl-CH$_2$- | -CH$_2$CF$_3$ | acid chloride | 196 | 1.24$^q$ |
| lxf | cyclohexyl-CH$_2$- | -CH$_2$CH(CH$_3$)CH$_2$CF$_3$ | Bop | 224 | 1.36$^o$ |
| lxg | CF$_3$CH$_2$- | -CH(CH$_3$)$_2$ | acid chloride | 170 | 0.60$^p$ |
| lxq | (CH$_3$CH$_2$)$_2$CH- | -CH(CH$_3$)$_2$ | acid chloride | 144 | 0.98$^p$ |
| lxr | (CH$_3$)$_2$CHOCH$_2$CH$_2$- | -CH(CH$_3$)$_2$ | acid chloride | 160 | 0.80$^p$ |

TABLE 2-continued

Amine Starting Materials Made by Hydride Reduction of Amides $$RNH_2 \xrightarrow[\substack{\text{or R'COCl, Et}_3\text{N, THF,} \\ 0°\text{C. to RT} \\ \text{2) LiAlH}_4\text{, THF, reflux}}]{\substack{\text{1) R'CO}_2\text{H, Et}_3\text{N} \\ \text{Bop, DMF}}} R-\underset{H}{N}-R' \quad \text{Ix}$$

| | R | R' | Coupling method | (M + H)+ | $T_r$ |
|---|---|---|---|---|---|
| lxs | cyclohexyl | –CH₂CH₂CH₂CF₃ | Bop | 210 | 0.81[P] |

Additional secondary amines RNHCHR'R"(lx) useful as intermediates in the synthesis of compounds of the present invention may be prepared by the scheme below. Some Examples prepared by this method are shown in Table 3a. The Example below utilizing sodium cyanoborohydride as the reducing agent and acetic acid as a proton source is representative and not intended to be limiting. Additional proton sources could include any number of inorganic acids such as HCl or HBr and other organic acids. Other reducing agents utilized for this transformation include but are not limited to sodium triacetoxyborohydride and sodium borohydride.

Example lxi

N-(2,2-Difluoroethyl)cyclohexanamine, HCl

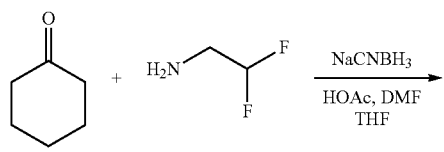

To a stirred solution of 2,2-difluoroethanamine (0.446 g, 5.50 mmol) in DMF (5 mL) and acetic acid (0.572 mL, 10.00 mmol) was added cyclohexanone (0.491 g, 5 mmol) followed by a solution of sodium cyanoborohydride (6.00 mL, 6.00 mmol) in THF. The solution was stirred overnight at RT. The reaction was diluted with ether and treated with 0.5M aq. HCl. The phases were stirred together for 1 h, separated, and the aq. phase was brought to pH 10 with sat. aq. sodium carbonate. The resulting mixture was extracted with ether, and the organic extract was dried and concentrated to afford a colorless oil. This oil was dissolved in ether, treated with 2 mL of 4M HCl in dioxane, and the resulting solid was filtered, rinsed with ether, and air-dried to afford N-(2,2-difluoroethyl)cyclohexanamine, HCl (0.5 g, 47.6% yield) as a white powder. MS(ES): m/z=164 [M+H]+. HPLC $T_r$: 0.55[P].

Using the methods described for the preparation of lxi, amines RNH₂ and aldehydes/ketones R'COR" are condensed to secondary amines RNHCHR'R" (lx, Table 3a) useful as intermediates in the synthesis of compounds of the present invention.

TABLE 3a

Amine Starting Materials Made by Reductive Amination $$RNH_2 + R'\underset{\underset{R''}{\|}}{\overset{O}{C}} \xrightarrow[\substack{\text{CH}_3\text{CO}_2\text{H} \\ \text{DMF—THF}}]{NaCNBH_3} R-\underset{H}{\overset{N}{|}}-\underset{R''}{\overset{R'}{|}} \quad \text{Ix}$$

| Entry | RNH₂ | R'COR" | (M + H)+ | $T_r$ |
|---|---|---|---|---|
| lxj | F₃C-CH₂CH₂-NH₂ | cyclohexanone | 196 | 1.00[P] |

TABLE 3a-continued

Amine Starting Materials Made by Reductive Amination $$RNH_2 + R'COR'' \xrightarrow[\text{DMF—THF}]{\text{NaCNBH}_3, \text{CH}_3\text{CO}_2\text{H}} R-NH-CHR'R''$$
Ix

| Entry | RNH₂ | R'COR" | (M + H)⁺ | T_r |
|---|---|---|---|---|
| 1xk | cyclohexylamine | CF₃CH₂CH₂CHO | 210 | 1.18^p |
| 1xl | cyclopropylmethyl-CH₂NH₂ | (CH₃)₂CHCHO | 142 (Crude product was derivatized as the t-butyl carbamate for purification, then deprotected to give the desired amine HCl.) | 1.36^p |

Additional secondary amines RNHCHR'R"(lx) useful as intermediates in the synthesis of compounds of the present invention may be prepared by the scheme below. Some Examples prepared by this method are shown in Table 3b.

Example lxs 4,4,4-trifluoro-N-(2-methylallyl)butan-1-amine

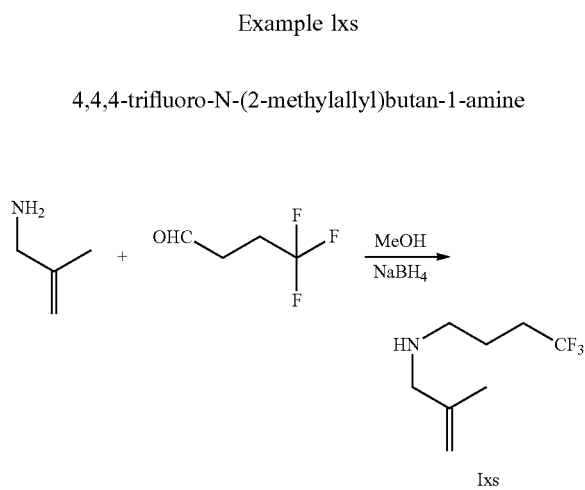

A solution of 4,4,4-trifluorobutanal (3.72 g, 29.5 mmol) and 2-methylprop-2-en-1-amine (2, 28.1 mmol) in MeOH (14.06 ml) was warmed to 40° C. for 30 min. then cooled to RT. This solution was treated with sodium borohydride (1.596 g, 42.2 mmol) and stirred ON at RT. The reaction was diluted with water and extracted twice with ether. The comb. org. ext. dried and stripped to afford 4,4,4-trifluoro-N-(2-methylallyl)butan-1-amine (2.9 g, 14.40 mmol, 51.2% yield) as a colorless oil. MS(ES): m/z=182 [M+H]⁺. HPLC T_r: 0.53^k.

Using the methods described for the preparation of lxs, amines RNH₂ and aldehydes/ketones R'COR" are converted to secondary amines RNHCHR'R" (lx, Table 3b) useful as intermediates in the synthesis of compounds of the present invention.

TABLE 3b

Amine Starting Materials Made by Reductive Amination $$RNH_2 + R'COR'' \xrightarrow[\text{NaBH}_4]{\text{MeOH}} R-NH-CHR'R''$$
Ix

| Entry | RNH₂ | R'COR" | (M + H)⁺ | T_r |
|---|---|---|---|---|
| 1xt | methoxy-neopentyl-NH₂ | cyclohexanone | 200 | 1.12^p |
| 1xu | methoxy-neopentyl-NH₂ | F₃C(CH₂)₃CHO | 228 | 1.02^p |
| 1xv | (S)-1-methoxy-propan-2-amine | F₃C(CH₂)₃CHO | 200 | 0.49^k |
| 1xw | hydroxy-neopentyl-NH₂ | 4-chlorobenzaldehyde | 226 (M − H)⁻ | 1.31^w |

TABLE 3b-continued

Amine Starting Materials Made by Reductive Amination $$RNH_2 + R'\overset{O}{\underset{}{\|}}R'' \xrightarrow{\text{MeOH}}{\text{NaBH}_4} R\overset{H}{\underset{}{N}}\overset{R'}{\underset{R''}{|}}$$

Ix

| Entry | RNH$_2$ | R'COR'' | (M + H)$^+$ | T$_r$ |
|---|---|---|---|---|
| 1xy | isobutylamine | 4-trifluoromethylcyclohexanone | 224 | 0.64$^s$ |

Additional secondary amines RNHCHR'R'' (Ix, R''=H) useful as intermediates in the synthesis of compounds of the present invention may be prepared by carbamate N-alkylation followed by carbamate deprotection as shown in the scheme below. Some Examples prepared by this method are shown in Table 4. The Example below utilizing a t-butyl carbamate with sodium hydride as the base is representative and not intended to be limiting. Benzyl carbamates are also suitable groups for activating amines for alkylation and are removed under reducing conditions. Other bases of suitable strength include lithium dialkylamides and the related disilylazides and others known to those skilled in the art of organic/medicinal chemistry.

Example 1xm

N-(Cyclopropylmethyl)-2,2-difluoroethanamine, HCl

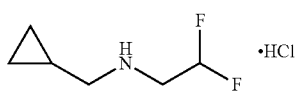

1xm, Part A. tert-Butyl 2,2-difluoroethylcarbamate

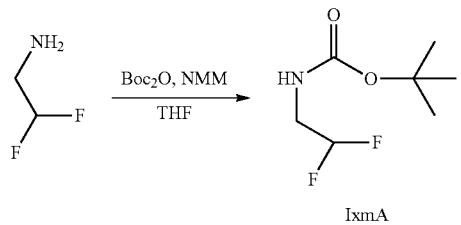

A solution of 2,2-difluoroethanamine (0.892 g, 11.00 mmol) in THF (Volume: 10 mL) was treated with di-tert-butyl dicarbonate (2.182 g, 10 mmol) followed by N-methylmorpholine (1.099 mL, 10.00 mmol). The solution was stirred 1.5 h at RT then diluted with ether. This solution was washed with diluted aq. HOAc then aq. sodium bicarbonate, dried, and concentrated to afford tert-butyl 2,2-difluoroethylcarbamate (1.8 g, 94% yield) as a colorless crystalline solid. MS(ES): m/z=182 [M+H]$^+$. HPLC T$_r$: 2.24$^t$.

1xm, Part B. tert-Butyl cyclopropylmethyl(2,2-difluoroethyl)carbamate

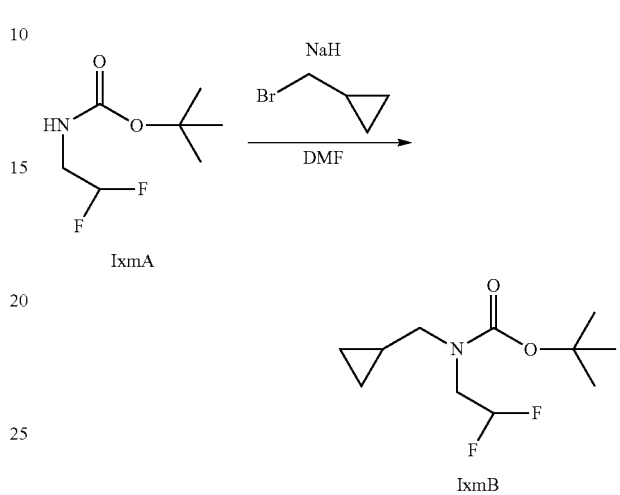

To a stirred solution of tert-butyl 2,2-difluoroethylcarbamate (0.544 g, 3 mmol) in DMF (Volume: 4 mL) was added sodium hydride (0.180 g, 4.50 mmol). The mixture was placed under nitrogen and stirred for 10 min. then treated with (bromomethyl)cyclopropane (0.567 g, 4.20 mmol). The reaction was stirred 1.5 h at RT then quenched with diluted aq. HOAc. The resulting mixture was diluted with ether and washed with water then sat. aq. sodium bicarbonate. The organic phase was dried and concentrated to afford tert-butyl cyclopropylmethyl(2,2-difluoroethyl) carbamate (0.64 g, 86% yield) as a colorless oil. MS(ES): m/z=180 [M+H-isobutylene]$^+$. HPLC T$_r$: 1.85°.

1xm. N-(Cyclopropylmethyl)-2,2-difluoroethanamine, HCl

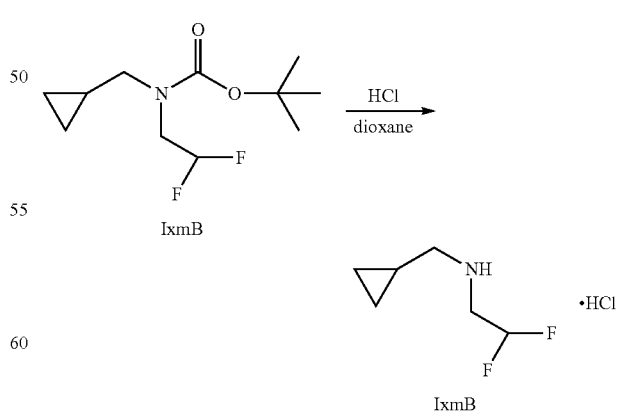

tert-Butyl cyclopropylmethyl(2,2-difluoroethyl)carbamate (0.6 g, 2.55 mmol) was treated with a solution of HCl (2.55 ml, 10.20 mmol) in dioxane. The solution was stirred 1 h at RT then concentrated under reduced pressure to afford an oily white solid. This material was suspended in 30% ether-hexanes and filtered, rinsed with 30% ether-hexanes, and air-dried to afford N-(cyclopropylmethyl)-2,2-difluoroethanamine, HCl (0.37 g, 80% yield) as a colorless solid. MS(ES): m/z=180 [M+H]$^+$. HPLC T$_r$: 0.28°.

Using the methods described for the preparation of lxm, amines RNH$_2$ are derivatized as t-butyl carbamates, alkylated, and then deprotected to afford secondary amine hydrochloride salts RNHCH$_2$R'HCl (lx, Table 4) useful as intermediates in the synthesis of compounds of the present invention.

TABLE 4

Amine Starting Materials Made by Carbamate Alkylation

| | RNH$_2$ | R'CH$_2$X" | (M + H)$^+$ | T$_r$ |
|---|---|---|---|---|
| lxn | | | 142 | 0.99$^p$ |
| lxo | | | $^1$H NMR (400 MHz, DMSO-d$_6$) δ ppm 0.84 (br. s, 1H); 2.91-3.0 (m, 2H); 2.71-2.75 (br. s, 2H); 1.26 (t, 3H, J = 7.3 Hz); 1.01 (s, 9H). | 1.18$^p$ |
| lxp | | | 154 | 1.47$^l$ |

Using the methods described for the conversion of 1B to 1C, aniline intermediates iii and the appropriate isocyanate R$^9$NCO are converted to the urea intermediates iv (Table 5, Z=NR$^7$R$^8$).

TABLE 5

Bromourea Intermediates Made by Scheme 1

(Scheme 1)

| | R$^9$ | NR$^7$R$^8$ | Temp. (° C.) | (M +H)$^+$ | T$_r$ |
|---|---|---|---|---|---|
| iva | 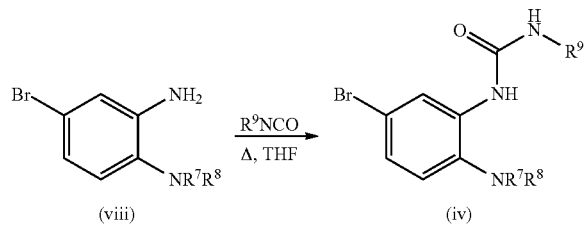 | | 60 | 418 | 4.58$^l$ |

TABLE 5-continued

Bromourea Intermediates Made by Scheme 1

Scheme 1: Compound (viii) with NH₂ and NR⁷R⁸ groups on a bromo-substituted benzene reacts with R⁹NCO (Δ, THF) to give compound (iv), a urea derivative.

| | R⁹ | NR⁷R⁸ | Temp. (° C.) | (M +H)⁺ | T$_r$ |
|---|---|---|---|---|---|
| ivb | 2-chlorobenzyl | N-methyl-N-cyclohexyl | 60 | 438 | 4.51$^l$ |
| ivd | 4-methylbenzyl | trans-decahydroquinolin-1-yl | 50 | 444 | 5.05$^l$ |
| ive | 4-methylbenzyl | N-methyl-N-(tetrahydropyran-4-yl) | 50 | 420 | 4.38$^l$ |
| ivg | 4-methylbenzyl | N-methyl-N-(2,2-dimethoxyethyl) | 55 | 424 | 4.03$^l$ |
| ivh | 4-methylbenzyl | N,N-bis(2-methoxyethyl) | 60 | 438 | 4.07$^l$ |
| ivi | 4-methylbenzyl | N-propyl-N-(cyclopropylmethyl) | 50 | 418 | 3.97$^l$ |

TABLE 5-continued

Bromourea Intermediates Made by Scheme 1

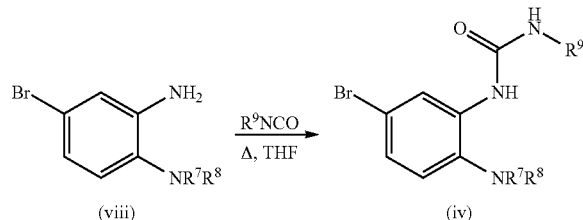

(Scheme 1)

| | R⁹ | NR⁷R⁸ | Temp. (° C.) | (M +H)⁺ | T$_r$ |
|---|---|---|---|---|---|
| ivk | 4-methylphenyl | N(CH₂CHF₂)(CH₂-cyclopropyl) | 55 | 440 | 4.77$^I$ |
| ivl | 4-methylphenyl | N(CH₂CH₂CF₃)(CH₂-cyclopropyl) | 55 | 472 | 5.07$^I$ |
| ivm | 4-methylphenyl | N(CH₂-cyclopropyl)₂ | 55 | 430 | 5.43$^I$ |
| ivn | 4-methylphenyl | N(Et)(CH₂CH₂OMe) | 45 | 408 | 1.93$^o$ |
| ivo | 4-methylphenyl | N(Me)(cycloheptyl) | 55 | 432 | 4.65$^I$ |
| ivp | 4-methylphenyl | N(CH₂-cyclopropyl)(cyclohexyl) | 55 | 458 | 2.25$^o$ |

TABLE 5-continued

Bromourea Intermediates Made by Scheme 1

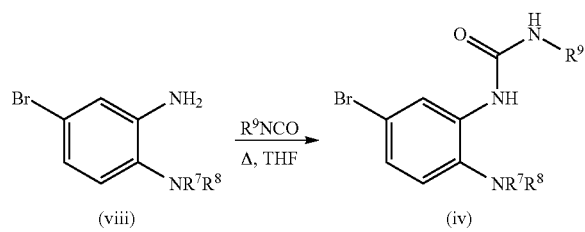

(Scheme 1)

| | R⁹ | NR⁷R⁸ | Temp. (° C.) | (M +H)⁺ | $T_r$ |
|---|---|---|---|---|---|
| ivq | 4-methylphenyl | N(propyl)(cyclohexyl) | 55 | 446 | 2.45$^p$ |
| ivr | 4-methylphenyl | N(butyl)(pentyl) | 55 | 434 | 2.47$^p$ |
| ivs | 4-methylphenyl | N(isobutyl)(cyclopropylmethyl) | 55 | 432 | 2.47$^p$ |
| ivt | 4-methylphenyl | N(isobutyl)(cyclobutylmethyl) | 60 | 446 | 2.57$^p$ |
| ivu | 4-methylphenyl | N(methyl)(4,4-difluorocyclohexyl) | 60 | 454 | 2.87$^p$ |
| ivv | 2-fluorophenyl | N(ethyl)(neopentyl) | 60 | 424 | 2.96$^p$ |

TABLE 5-continued

Bromourea Intermediates Made by Scheme 1

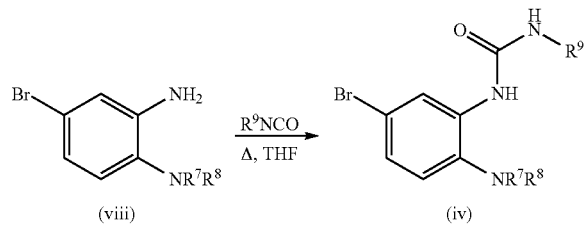

(Scheme 1)

| | R⁹ | NR⁷R⁸ | Temp. (° C.) | (M +H)⁺ | T$_r$ |
|---|---|---|---|---|---|
| ivw | 2-fluorophenyl | 2-ethylpiperidin-1-yl | 60 | 422 | 2.82$^p$ |
| ivx | 4-methylphenyl | N-ethyl-N-neopentyl | 60 | 420 | 3.01$^p$ |
| ivy | 4-methylphenyl | 2-ethylpiperidin-1-yl | 60 | 418 | 2.87$^p$ |
| ivz | 4-methylphenyl | N-cyclohexyl-N-isobutyl | 55 | 460 | 3.51$^q$ |
| ivaa | 2-fluorophenyl | N-cyclohexyl-N-isobutyl | 55 | 464 | 3.43$^q$ |
| ivac | 4-methylphenyl | N-(2-cyclopropylethyl)-N-isobutyl | 55 | 446 | 3.43$^q$ |

TABLE 5-continued
Bromourea Intermediates Made by Scheme 1
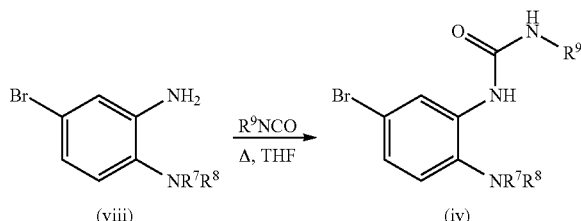
(Scheme 1)
| | R⁹ | NR⁷R⁸ | Temp. (° C.) | (M +H)⁺ | T$_r$ |
|---|---|---|---|---|---|
| ivad | 2-F-phenyl | N(CH₂-cyclopropyl)(isobutyl) | 55 | 450 | 3.38$^q$ |
| ivae | 2,4-diF-phenyl | N(isobutyl)₂ | 55 | 456 | 3.42$^q$ |
| ivag | 4-methylphenyl | N(isobutyl)(isopropyl) | 60 | 420 | 3.31$^q$ |
| ivah | 2-F-phenyl | N(isobutyl)(isopropyl) | 60 | 424 | 3.23$^q$ |
| ivai | 2,4-diF-phenyl | N(isobutyl)(isopropyl) | 60 | 442 | 3.27$^q$ |
| ivaj | 2-Cl-phenyl | N(isobutyl)(cyclohexyl) | 50 | 514 | 3.48$^q$ |

TABLE 5-continued
Bromourea Intermediates Made by Scheme 1
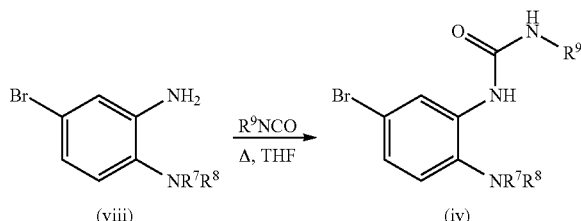
(Scheme 1)
| | R[9] | NR[7]R[8] | Temp. (° C.) | (M +H)[+] | T[r] |
|---|---|---|---|---|---|
| ival | 4-methylphenyl | N(ethyl)(cyclopentyl) | 55 | 418 | 4.56[l] |
| ivam | 4-methylphenyl | N(propyl)(cyclopentyl) | 45 | 432 | 3.25[q] |
| ivan | 2-fluorophenyl | N(propyl)(cyclopentyl) | 45 | 434 | 3.21[q] |
| ivao | 2-fluorophenyl | isoindolin-2-yl | 45 | 428 | 3.20[q] |
| ivap | 4-methylphenyl | N(propyl)(cyclopentyl) | 45 | 446 | 2.89[q] |
| ivaq | 2-fluorophenyl | N(propyl)(cyclopentyl) | 45 | 450 | 2.84[q] |

TABLE 5-continued

Bromourea Intermediates Made by Scheme 1

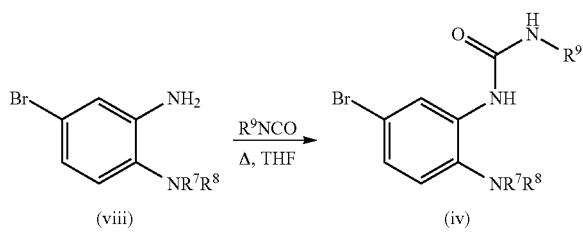

(Scheme 1)

| | R⁹ | NR⁷R⁸ | Temp. (° C.) | (M +H)⁺ | $T_r$ |
|---|---|---|---|---|---|
| ivar | 4-methylphenyl | N-butyl-N-cyclohexyl | 60 | 460 | 2.85$^q$ |
| ivas | 4-methylphenyl | N-methyl-N-isobutyl | 60 | 392 | 2.65$^q$ |
| ivat | 4-methylphenyl | N-isobutyl-N-cyclobutyl | 45 | 432 | 2.85$^q$ |
| ivau | 4-methylphenyl | N-propyl-N-benzyl | 50 | 454 | 1.23$^k$ |
| ivav | 4-methylphenyl | N-cyclohexyl-N-(3,3,3-trifluoro-2-methylpropyl) | 60 | 528 | 2.94$^q$ |
| ivaw | 4-methylphenyl | N-isobutyl-N-(3,3,3-trifluoro-2-methylpropyl) | 50 | 502 | 3.25$^r$ |

TABLE 5-continued

Bromourea Intermediates Made by Scheme 1

(viii) → (iv)  R⁹NCO, Δ, THF (Scheme 1)

| | R⁹ | NR⁷R⁸ | Temp. (° C.) | (M +H)⁺ | $T_r$ |
|---|---|---|---|---|---|
| ivax | 4-methylphenyl | N(CH₂CH₂OCH₃)(4-chlorobenzyl) | 45 | 504 | 2.80$^q$ |
| ivay | 4-methylphenyl | N(CH₂CHF₂)(cyclohexyl) | 45 | 468 | 2.79$^q$ |
| ivaz | 4-methylphenyl | N(CH₂CF₃)(cyclohexyl) | 45 | 500 | 3.28$^r$ |
| ivba | 4-methylphenyl | N(CH₂CF₃)(isobutyl) | 50 | 474 | 2.84$^q$ |
| ivbb | 2-fluorophenyl | N(isobutyl)(CH₂CH(CH₃)CF₃) | 45 | 506 | 2.86$^q$ |
| ivbc | 4-methylphenyl | N(isobutyl)(CH₂CH(CH₃)CF₃) | 45 | 502 | 1.31$^k$ |

TABLE 5-continued

Bromourea Intermediates Made by Scheme 1

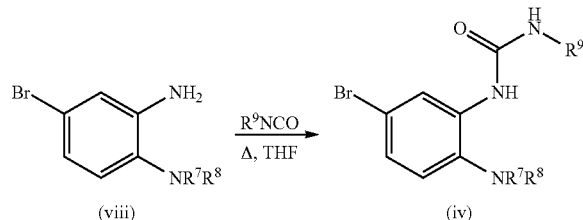

(Scheme 1)

| | R⁹ | NR⁷R⁸ | Temp. (° C.) | (M +H)⁺ | T$_r$ |
|---|---|---|---|---|---|
| ivbd | 4-methylphenyl | 2-tert-butylphenyl-NH | 45 | 454 | 3.21$^r$ |
| ivbe | 2-fluorophenyl | N-methyl-2-tert-butylphenyl | 50 | 470 | 1.22$^k$ |
| ivbf | 4-methylphenyl | N-methyl-2-tert-butylphenyl | 50 | 468 | 3.18$^r$ |
| ivbg | 4-methylphenyl | N-(4,4,4-trifluorobutyl)-N-(2-methylallyl) | RT | 484 | 5.16$^l$ |
| ivbh | 4-methylphenyl | N-(4,4,4-trifluorobutyl)-N-(3-methoxy-3-methylbutyl) | RT | 532 | 5.04$^l$ |
| ivbi | 4-methylphenyl | N-cyclohexyl-N-(3-methoxy-3-methylbutyl) | RT | 504 | 5.04$^l$ |

TABLE 5-continued

Bromourea Intermediates Made by Scheme 1

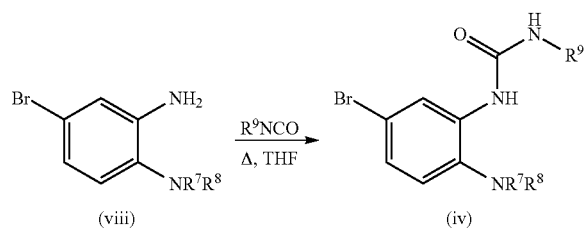

(Scheme 1)

| | R⁹ | NR⁷R⁸ | Temp. (° C.) | (M +H)⁺ | T$_r$ |
|---|---|---|---|---|---|
| ivbj | 4-methylphenyl | N(CH(CH₃)CH₂OCH₃)(CH₂CH₂CH₂CF₃) | RT | 504 | 1.23[k] |
| ivbk | 4-methylphenyl | N(isobutyl)(pentan-3-yl) | 50 | 448 | 5.21[l] |
| ivbl | 4-chloro-2-fluorophenyl | N(isobutyl)(pentan-3-yl) | 50 | 486 | 5.39[l] |
| ivbm | 2-fluorophenyl | N(isobutyl)(pentan-3-yl) | 50 | 452 | 5.11[l] |
| ivbn | 4-methylphenyl | N(2-methoxyethyl)(cyclohexyl) | 50 | 462 | 4.97[l] |
| ivbo | 4-chloro-2-fluorophenyl | N(2-methoxyethyl)(cyclohexyl) | 50 | 500 | 5.33[l] |

TABLE 5-continued
Bromourea Intermediates Made by Scheme 1
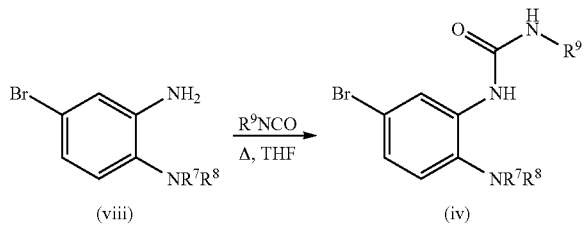
(Scheme 1)
| | R⁹ | NR⁷R⁸ | Temp. (° C.) | (M +H)⁺ | T$_r$ |
|---|---|---|---|---|---|
| ivbp | 4-methylphenyl | N(cyclohexyl)(2-methylallyl) | RT | 458 | 5.18[l] |
| ivbq | 4-methylphenyl | N(isobutyl)(2-isopropoxyethyl) | RT | 464 | 4.57[l] |
| ivbr | 4-methylphenyl | N(cyclohexyl)(4,4,4-trifluorobutyl) | RT | 512 | 1.28[k] |
| ivbs | 4-methylphenyl | N(cyclohexyl)(4-chlorobenzyl) | 55 | 528 | 5.35[l] |

TABLE 5-continued

Bromourea Intermediates Made by Scheme 1

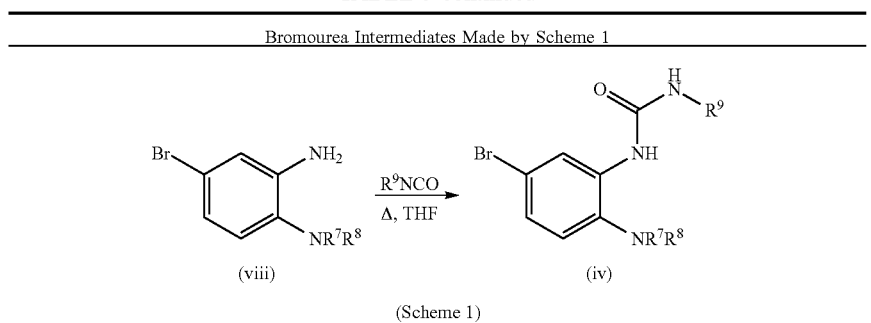

(Scheme 1)

| | $R^9$ | $NR^7R^8$ | Temp. (° C.) | (M +H)$^+$ | T$_r$ |
|---|---|---|---|---|---|
| ivbt | 2-fluorophenyl | N-(4-chlorobenzyl)-N-cyclohexyl | 55 | 532 | 5.27[l] |

Using the method described for the conversion of 2A to 2B, bromide intermediates viii and the appropriate arylboronic acid are converted to the biaryl intermediates x (Table 6, $Z=NR_7R_8$).

TABLE 6

Biaryldiamine Intermediates Made by Scheme 2

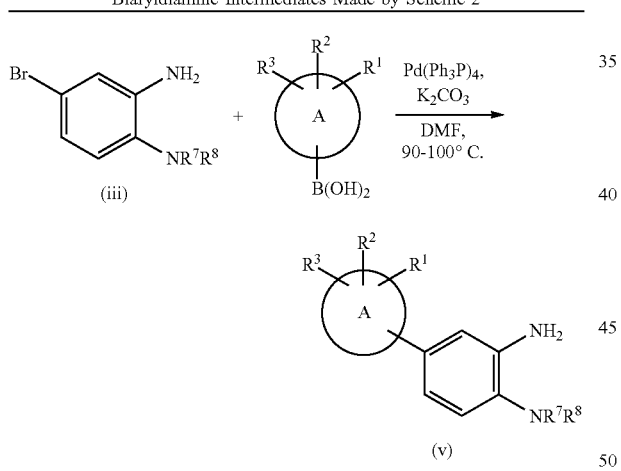

(Scheme 2)

| | B(OH)$_2$ | —NR$^7$R$^8$ | (M + H)$^+$ | T$_r$ |
|---|---|---|---|---|
| va | 3-CO₂H, 4-OMe phenyl | N-methyl-N-(2-tert-butylphenyl) | 391 | 3.93[l] |

TABLE 6-continued

| | B(OH)$_2$ | —NR$^7$R$^8$ | (M + H)$^+$ | T$_r$ |
|---|---|---|---|---|
| vb | 2-CO₂H phenyl | N-methyl-N-cyclohexyl | 325 | 2.88[l] |
| vc | 2-(1H-tetrazol-5-yl)phenyl | N-ethyl-N-cyclohexyl | 363 | 2.59[l] |
| vd | 2-CO₂H phenyl | N,N-diisobutyl | 341 | 2.67[q] |

Using the methods described for the conversion of 1B to 1C, aniline intermediates iii and the appropriate isocyanate R$^9$NCO are converted to the urea intermediates iv.

TABLE 7
B5F Bromourea Intermediates Made by Scheme 1
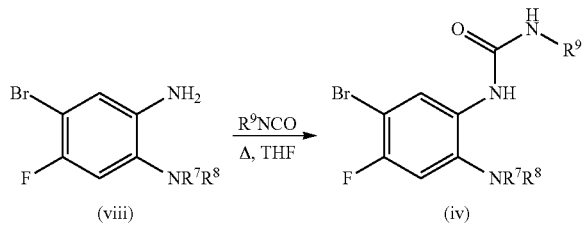
(Scheme 1)
| Ex. | R⁹ | —NR⁷R⁸ | Temp. (° C.) | (M + H)⁺ | $T_r$ |
|---|---|---|---|---|---|
| ivca | 4-methylphenyl | N(Me)(cyclohexyl) | 60 | 436 | 5.05[l] |
| ivcb | 4-methylphenyl | N(CH₂-cyclopropyl)(CH₂CHF₂) | 55 | 4.58 | 4.22[l] |
| ivcc | 4-methylphenyl | N(isobutyl)(cyclohexyl) | 55 | 478 | 3.65[q] |
| ivcd | 2-fluorophenyl | N(isobutyl)(cyclohexyl) | 45 | 482 | 3.60[q] |
| ivce | 2,4-difluorophenyl | N(isobutyl)(cyclohexyl) | 45 | 500 | 3.65[q] |

TABLE 7-continued

B5F Bromourea Intermediates Made by Scheme 1

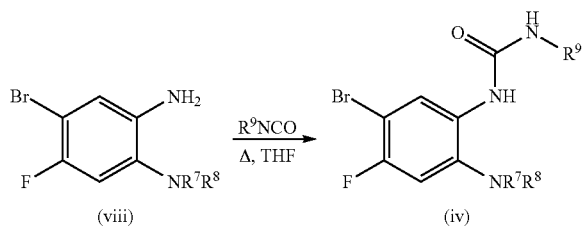

(Scheme 1)

| Ex. | R⁹ | —NR⁷R⁸ | Temp. (° C.) | (M + H)⁺ | T_r |
|---|---|---|---|---|---|
| ivcf | 4-methylphenyl | N(isobutyl)(isobutyl) | 45 | 452 | 5.22[l] |
| ivcg | 4-chloro-2-fluorophenyl | N(isobutyl)(isobutyl) | 45 | 490 | 5.39[l] |

Using the method described for the conversion of 1B to 1C, aniline intermediates (iii) and the appropriate isocyanate R⁹NCO are converted to the urea intermediates (iv).

TABLE 8

| Ex. | R⁹ | —NR⁷R⁸ | Temp. (° C.) | (M + H)⁺ | T_r |
|---|---|---|---|---|---|
| ivda | 2-fluorophenyl | N(isobutyl)(cyclohexyl) | 50 | 482 | 5.49[l] |
| ivdb | 4-methylphenyl | N(isobutyl)(cyclohexyl) | 50 | 478 | 5.59[l] |

TABLE 8-continued

| Ex. | R⁹ | —NR⁷R⁸ | Temp. (° C.) | (M + H)⁺ | T_r |
|---|---|---|---|---|---|
| ivdc | 4-chloro-2-fluorophenyl | N(isobutyl)(cyclohexyl) | 50 | 516 | 5.75[q] |

Examples 42 to 210

The following compounds of the invention set out in Table 9 were prepared employing the process set out below

TABLE 9

| Ex. No. | Name | A (R¹, R², R³) | R⁹ | —NR⁷R⁸ | Tr^method | (M +H)⁺ |
|---|---|---|---|---|---|---|
| 42 | 3'-(3-(2-chlorophenyl)ureido)-4'-(cyclohexyl(methyl)amino)-4-methoxybiphenyl-3-carboxylic acid | 2-methoxy-5-yl-benzoic acid (HO₂C, OMe substituted phenyl) | 2-chlorophenyl | N-methyl-N-cyclohexyl | 11.53[b] | 508 |
| 43 | 4'-(cyclohexyl(methyl)amino)-4-methoxy-3'-(3-p-tolylureido)biphenyl-3-carboxylic acid | 2-methoxy-5-yl-benzoic acid (HO₂C, OMe substituted phenyl) | 4-methylphenyl | N-methyl-N-cyclohexyl | 11.61[b] | 488 |
| 44 | 1-(4-(cyclohexyl(methyl)amino)-2'-(1H-tetrazol-5-yl)biphenyl-3-yl)-3-p-tolylurea | 2-(1H-tetrazol-5-yl)phenyl | 4-methylphenyl | N-methyl-N-cyclohexyl | 11.77[b] | 482 |
| 45 | 1-(2-chlorophenyl)-3-(4-(cyclohexyl(methyl)amino)-2'-(1H-tetrazol-5-yl)biphenyl-3-yl)urea | 2-(1H-tetrazol-5-yl)phenyl | 2-chlorophenyl | N-methyl-N-cyclohexyl | 11.67[b] | 502 |
| 46 | 1-(4-(cyclohexylamino)-2'-(1H-tetrazol-5-yl)biphenyl-3-yl)-3-p-tolylurea | 2-(1H-tetrazol-5-yl)phenyl | 4-methylphenyl | N-H cyclohexyl | 11.76[b] | 468 |

TABLE 9-continued

| Ex. No. | Name | R⁹ | | —NR⁷R⁸ | Tr^method | (M +H)⁺ |
|---|---|---|---|---|---|---|
| 47 | 1-(4-((4aS,8aS)-octahydroquinolin-1(2H)-yl)-2'-(1H-tetrazol-5-yl)biphenyl-3-yl)-3-p-tolylurea | 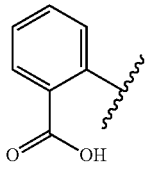 [SMILES: *c1ccccc1C(=O)O] | 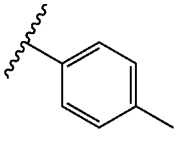 [SMILES: *c1ccc(C)cc1] | 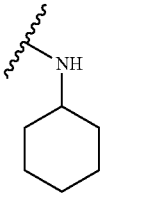 [SMILES: *NC1CCCCC1] | 13.09[b] | 508 |
| 48 | 4'-(cyclohexyl-amino)-3'-(3-p-tolylureido)biphenyl-2-carboxylic acid | 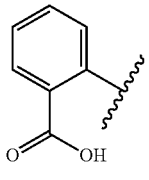 [SMILES: *c1ccccc1C(=O)O] | 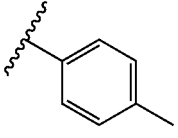 [SMILES: *c1ccc(C)cc1] | 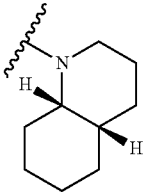 [SMILES: *N1CCC[C@@H]2CCCC[C@@H]21] | 11.16[b] | 444 |
| 49 | 4'-((4aS,8aS)-octahydroquinolin-1(2H)-yl)-3'-(3-p-tolylureido)biphenyl-2-carboxylic acid | 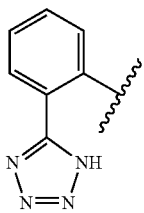 [SMILES: *c1ccccc1-c1nnn[nH]1] | 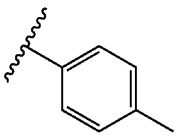 [SMILES: *c1ccc(C)cc1] | 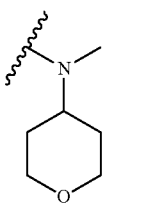 [SMILES: *N(C)C1CCOCC1] | 12.42[b] | 484 |
| 50 | 1-(4-(methyl(tetra-hydro-2H-pyran-4-yl)amino)-2'-(1H-tetrazol-5-yl)biphenyl-3-yl)-3-p-tolylurea | 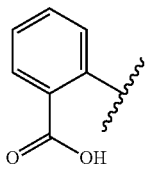 [SMILES: *c1ccccc1C(=O)O] | 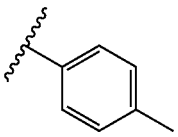 [SMILES: *c1ccc(C)cc1] | 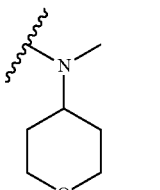 | 11.65[b] | 484 |
| 51 | 4'-(methyl(tetra-hydro-2H-pyran-4-yl)amino)-3'-(3-p-tolylureido)biphenyl-2-carboxylic acid | 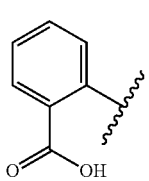 [SMILES: *c1ccccc1C(=O)O] | 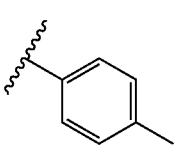 [SMILES: *c1ccc(C)cc1] | 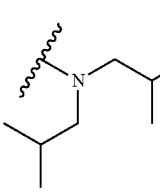 | 11.54[b] | 460 |
| 52 | 4'-(diisobutyl-amino)-3'-(3-p-tolylureido)biphenyl-2-carboxylic acid | | | | 13.35[b] | 474 |

TABLE 9-continued

| Ex. No. | Name | A | R⁹ | —NR⁷R⁸ | Tr$^{method}$ | (M +H)⁺ |
|---|---|---|---|---|---|---|
| 53 | 1-(4-(cyclohexyl(ethyl)amino)-2'-(1H-tetrazol-5-yl)biphenyl-3-yl)-3-(2-fluorophenyl)urea | 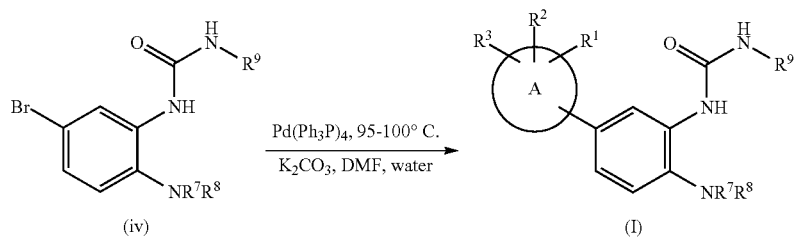 | 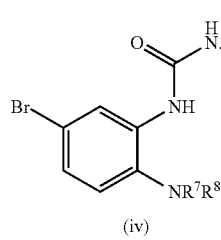 | 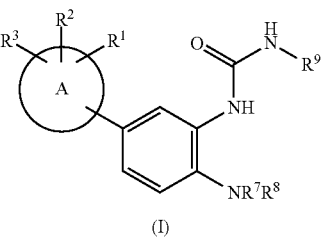 | 11.38$^b$ | 500 |
| 54 | 4'-((2,2-dimethoxyethyl)(methyl)amino)-3'-(3-p-tolylureido)biphenyl-2-carboxylic acid | 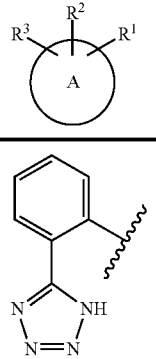 | 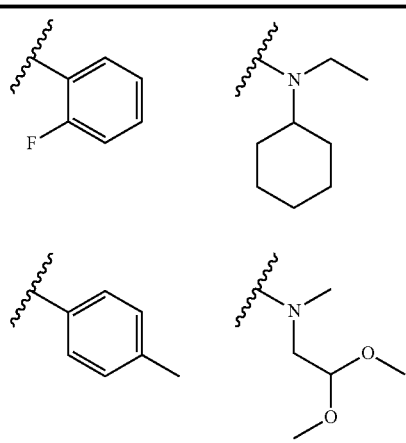 | 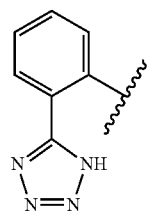 [SMILES: *c1ccccc1-c1nnn[nH]1] | 11.99$^b$ | 464 |
| 55 | 1-(4-((2,2-dimethoxyethyl)(methyl)amino)-2'-(1H-tetrazol-5-yl)biphenyl-3-yl)-3-p-tolylurea | 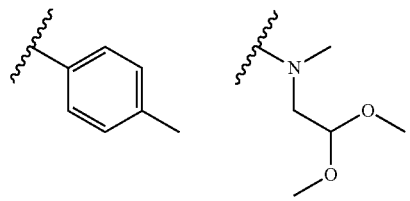 | 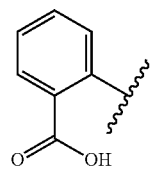 [SMILES: *c1ccccc1C(=O)O] | 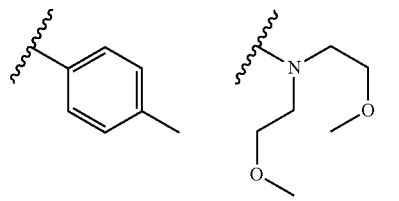 | 11.95$^b$ | 488 |
| 56 | 4'-(bis(2-methoxyethyl)amino)-3'-(3-p-tolylureido)biphenyl-2-carboxylic acid | 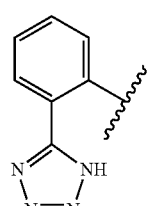 | 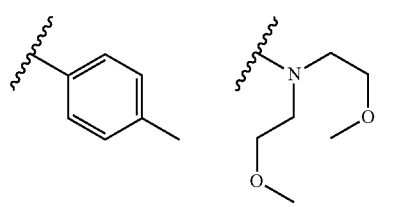 | 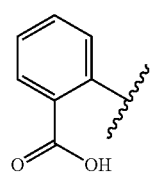 [SMILES: *c1ccccc1C(=O)O] | 12.13$^b$ | 478 |
| 57 | 1-(4-(bis(2-methoxyethyl)amino)-2'-(1H-tetrazol-5-yl)biphenyl-3-yl)-3-p-tolylurea | | | | 12.01$^b$ | 502 |
| 58 | 4'-((cyclopropylmethyl)(propyl)amino)-3'-(3-p-tolylureido)biphenyl-2-carboxylic acid | 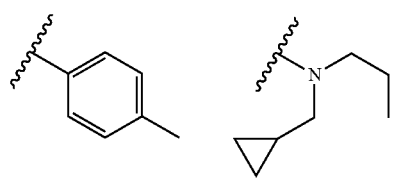 | | | 11.36$^d$ | 458 |

TABLE 9-continued

| Ex. No. | Name | A | R⁹ | —NR⁷R⁸ | Tr$^{method}$ | (M +H)⁺ |
|---|---|---|---|---|---|---|
| 59 | 1-(4-((cyclopropylmethyl)(propyl)amino)-2'-(1H-tetrazol-5-yl)biphenyl-3-yl)-3-p-tolylurea | 2-(1H-tetrazol-5-yl)phenyl | p-tolyl | N(CH₂-cyclopropyl)(propyl) | 11.71$^b$ | 482 |
| 60 | 1-(4-((cyclopropylmethyl)(2,2-difluoroethyl)amino)-2'-(1H-tetrazol-5-yl)biphenyl-3-yl)-3-p-tolylurea | 2-(1H-tetrazol-5-yl)phenyl | p-tolyl | N(CH₂-cyclopropyl)(CH₂CHF₂) | 16.81$^a$ | 504 |
| 61 | 4'-((cyclopropylmethyl)(2,2-difluoroethyl)amino)-3'-(3-p-tolylureido)biphenyl-2-carboxylic acid | 2-carboxyphenyl | p-tolyl | N(CH₂-cyclopropyl)(CH₂CHF₂) | 17.15$^a$ | 480 |
| 62 | 4'-((cyclopropylmethyl)(2,2-difluoroethyl)amino)-4-methoxy-3'-(3-p-tolylureido)biphenyl-3-carboxylic acid | 2-methoxy-5-carboxyphenyl | p-tolyl | N(CH₂-cyclopropyl)(CH₂CHF₂) | 17.05$^a$ | 510 |
| 63 | 1-(4-((cyclopropylmethyl)(3,3,3-trifluoropropyl)amino)-2'-(1H-tetrazol-5-yl)biphenyl-3-yl)-3-p-tolylurea | 2-(1H-tetrazol-5-yl)phenyl | p-tolyl | N(CH₂-cyclopropyl)(CH₂CH₂CF₃) | 12.86$^b$ | 536 |
| 64 | 4'-((cyclopropylmethyl)(3,3,3-trifluoropropyl)amino)-3'-(3-p-tolylureido)biphenyl-2-carboxylic acid | 2-carboxyphenyl | p-tolyl | N(CH₂-cyclopropyl)(CH₂CH₂CF₃) | 17.66$^a$ | 512 |

TABLE 9-continued

| Ex. No. | Name | A (R¹, R², R³) | R⁹ | —NR⁷R⁸ | Tr$^{method}$ | (M +H)⁺ |
|---|---|---|---|---|---|---|
| 65 | 4'-((cyclopropylmethyl)(3,3,3-trifluoropropyl)amino)-4-methoxy-3'-(3-p-tolylureido)biphenyl-3-carboxylic acid | 2-methoxy-5-yl-benzoic acid | p-tolyl | N(CH₂-cyclopropyl)(CH₂CH₂CF₃) | 13.01$^b$ | 542 |
| 66 | 1-(4-(bis(cyclopropylmethyl)amino)-2'-(1H-tetrazol-5-yl)biphenyl-3-yl)-3-p-tolylurea | 2-(1H-tetrazol-5-yl)phenyl | p-tolyl | N(CH₂-cyclopropyl)₂ | 15.24$^a$ | 494 |
| 67 | 4'-(bis(cyclopropylmethyl)amino)-3'-(3-p-tolylureido)biphenyl-2-carboxylic acid | 2-carboxyphenyl | p-tolyl | N(CH₂-cyclopropyl)₂ | 14.54$^a$ | 470 |
| 68 | 3'-(3-(2-chlorophenyl)ureido)-4'-(diisobutylamino)-4-fluorobiphenyl-2-carboxylic acid | 4-fluoro-2-carboxyphenyl | 2-chlorophenyl | N(iBu)₂ | 7.27$^m$ | 512 |
| 69 | 4'-(diisobutylamino)-3-fluoro-3'-(3-o-tolylureido)biphenyl-2-carboxylic acid | 5-fluoro-2-carboxyphenyl | o-tolyl | N(iBu)₂ | 7.14$^m$ | 492 |
| 70 | 4'-(diisobutylamino)-4-fluoro-3'-(3-p-tolylureido)biphenyl-2-carboxylic acid | 4-fluoro-2-carboxyphenyl | p-tolyl | N(iBu)₂ | 7.10$^m$ | 492 |

TABLE 9-continued

| Ex. No. | Name | A (with R1, R2, R3) | R9 | —NR7R8 | Tr method | (M +H)+ |
|---|---|---|---|---|---|---|
| 71 | N-(4'-(diisobutylamino)-4-methoxy-3'-(3-p-tolylureido)biphenyl-2-yl)-1,1,1-trifluoromethane-sulfonamide | 2-(trifluoromethylsulfonamido)-4-methoxyphenyl | p-tolyl | N(iBu)2 | 7.94 $^m$ | 607 |
| 72 | 4'-(ethyl(2-methoxyethyl)amino)-3'-(3-p-tolylureido)biphenyl-2-carboxylic acid | 2-carboxyphenyl | p-tolyl | N(Et)(CH2CH2OMe) | 15.32 $^a$ | 448 |
| 73 | 1-(4-(ethyl(2-methoxyethyl)amino)-2'-(1H-tetrazol-5-yl)biphenyl-3-yl)-3-p-tolylurea | 2-(1H-tetrazol-5-yl)phenyl | p-tolyl | N(Et)(CH2CH2OMe) | 15.79 $^a$ | 472 |
| 74 | N-(4'-(diisobutylamino)-3'-(3-p-tolylureido)biphenyl-2-yl)methanesulfonamide | 2-(methanesulfonamido)phenyl | p-tolyl | N(iBu)2 | 7.01 $^m$ | 523 |
| 75 | 1-(4-(cyclopentyl(ethyl)amino)-2'-(1H-tetrazol-5-yl)biphenyl-3-yl)-3-p-tolylurea | 2-(1H-tetrazol-5-yl)phenyl | p-tolyl | N(Et)(cyclopentyl) | 15.60 $^a$ | 482 |

TABLE 9-continued

| Ex. No. | Name | A (with R1, R2, R3) | R9 | —NR7R8 | Tr method | (M +H)+ |
|---|---|---|---|---|---|---|
| 76 | 4'-(cyclopentyl(ethyl)amino)-3'-(3-p-tolylureido)biphenyl-2-carboxylic acid | 2-carboxyphenyl | p-tolyl | N(ethyl)(cyclopentyl) | 14.90[a] | 458 |
| 77 | 4'-(cyclopentyl(ethyl)amino)-4-methoxy-3'-(3-p-tolylureido)biphenyl-3-carboxylic acid | 4-methoxy-3-carboxyphenyl | p-tolyl | N(ethyl)(cyclopentyl) | 13.56[a] | 488 |
| 78 | 4'-(cycloheptyl(methyl)amino)-4-methoxy-3'-(3-p-tolylureido)biphenyl-3-carboxylic acid | 4-methoxy-3-carboxyphenyl | p-tolyl | NH-cycloheptyl | 16.00[a] | 502 |
| 79 | 1-(4-(cycloheptyl(methyl)amino)-2'-(1H-tetrazol-5-yl)biphenyl-3-yl)-3-p-tolylurea | 2-(1H-tetrazol-5-yl)phenyl | p-tolyl | NH-cycloheptyl | 16.29[a] | 496 |
| 80 | 4'-(cycloheptyl(methyl)amino)-3'-(3-p-tolylureido)biphenyl-2-carboxylic acid | 2-carboxyphenyl | p-tolyl | NH-cycloheptyl | 15.42[a] | 472 |

TABLE 9-continued

| Ex. No. | Name | A (with R1, R2, R3) | R9 | —NR7R8 | Tr method | (M+H)+ |
|---|---|---|---|---|---|---|
| 81 | N-(4'-(diisobutylamino)-4-fluoro-3'-(3-p-tolylureido)biphenyl-2-yl)-1,1,1-trifluoromethane-sulfonamide | 4-fluoro-2-(F3C-SO2-NH-) phenyl | p-tolyl | N(isobutyl)2 | 8.32[m] | 595 |
| 82 | 1-(4-(cyclohexyl(cyclopropylmethyl)amino)-2'-(1H-tetrazol-5-yl)biphenyl-3-yl)-3-p-tolylurea | 2-(1H-tetrazol-5-yl)phenyl | p-tolyl | N(cyclohexyl)(CH2-cyclopropyl) | 16.55[a] | 522 |
| 83 | 4'-(cyclohexyl(cyclopropylmethyl)amino)-3'-(3-p-tolylureido)biphenyl-2-carboxylic acid | 2-carboxyphenyl | p-tolyl | N(cyclohexyl)(CH2-cyclopropyl) | 15.81[a] | 498 |
| 84 | N-(4'-(diisobutylamino)-3'-(3-p-tolylureido)biphenyl-2-yl)-2,2,2-trifluoroethane-sulfonamide | 2-(F3C-CH2-SO2-NH-)phenyl | p-tolyl | N(isobutyl)2 | 7.67[m] | 591 |
| 85 | 1-(4-(cyclohexyl(propyl)amino)-2'-(1H-tetrazol-5-yl)biphenyl-3-yl)-3-p-tolylurea | 2-(1H-tetrazol-5-yl)phenyl | p-tolyl | N(cyclohexyl)(propyl) | 16.81[a] | 510 |

TABLE 9-continued

| Ex. No. | Name | A (R1, R2, R3) | R9 | —NR7R8 | Tr method | (M +H)+ |
|---|---|---|---|---|---|---|
| 86 | 4'-(cyclohexyl(propyl)amino)-3'-(3-p-tolylureido)biphenyl-2-carboxylic acid | 2-carboxyphenyl | p-tolyl | N(propyl)(cyclohexyl) | 16.09[a] | 486 |
| 87 | 4'-(cyclohexyl(propyl)amino)-5-fluoro-3'-(3-p-tolylureido)biphenyl-2-carboxylic acid | 4-fluoro-2-carboxyphenyl | p-tolyl | N(propyl)(cyclohexyl) | 17.11[a] | 504 |
| 88 | 1-(4-(dibutylamino)-2'-(1H-tetrazol-5-yl)biphenyl-3-yl)-3-p-tolylurea | 2-(1H-tetrazol-5-yl)phenyl | p-tolyl | N(butyl)(butyl) | 12.48[b] | 498 |
| 89 | 4'-(dibutylamino)-3'-(3-p-tolylureido)biphenyl-2-carboxylic acid | 2-carboxyphenyl | p-tolyl | N(butyl)(butyl) | 16.27[a] | 474 |
| 90 | 4'-(dibutylamino)-5-fluoro-3'-(3-p-tolylureido)biphenyl-2-carboxylic acid | 4-fluoro-2-carboxyphenyl | p-tolyl | N(butyl)(butyl) | 17.28[a] | 492 |

TABLE 9-continued

| Ex. No. | Name | A (with R¹, R², R³) | R⁹ | —NR⁷R⁸ | Tr^method | (M +H)⁺ |
|---|---|---|---|---|---|---|
| 91 | 2-(4-(dibutylamino)-3-(3-p-tolylureido)phenyl)thiophene-3-carboxylic acid | thiophene-3-carboxylic acid | p-tolyl | N(dibutyl) | 17.46[a] | 480 |
| 92 | 1-(4-((cyclopropylmethyl)(isobutyl)amino)-2'-(1H-tetrazol-5-yl)biphenyl-3-yl)-3-p-tolylurea | 2-(1H-tetrazol-5-yl)phenyl | p-tolyl | N(isobutyl)(cyclopropylmethyl) | 1.90[k] | 496 |
| 93 | 4'-((cyclopropylmethyl)(isobutyl)amino)-3'-(3-p-tolylureido)biphenyl-2-carboxylic acid | 2-carboxyphenyl | p-tolyl | N(isobutyl)(cyclopropylmethyl) | 1.87[k] | 472 |
| 96 | 1-(2'-(2-cyano-2-(methylsulfonyl)acetyl)-4-(diisobutylamino)biphenyl-3-yl)-3-p-tolylurea | 2-(2-cyano-2-(methylsulfonyl)acetyl)phenyl | p-tolyl | N(diisobutyl) | 5.50[m] | 575 |
| 97 | 4'-((cyclobutylmethyl)(isobutyl)amino)-3'-(3-p-tolylureido)biphenyl-3-carboxylic acid | 3-carboxyphenyl | p-tolyl | N(isobutyl)(cyclobutylmethyl) | 1.57[k] | 486 |
| 98 | 1-(4-((cyclobutylmethyl)(isobutyl)amino)-2'-(1H-tetrazol-5-yl)biphenyl-3-yl)-3-p-tolylurea | 2-(1H-tetrazol-5-yl)phenyl | p-tolyl | N(isobutyl)(cyclobutylmethyl) | 2.79[i] | 510 |

TABLE 9-continued

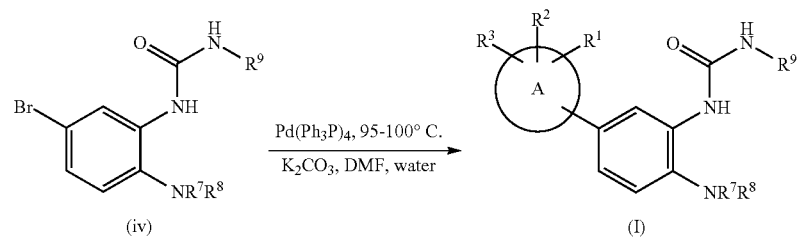

| Ex. No. | Name | | R⁹ | —NR⁷R⁸ | Tr^method | (M +H)⁺ |
|---|---|---|---|---|---|---|
| 99 | 4'-((cyclobutylmethyl) (isobutyl)amino)-5-fluoro-3'-(3-p-tolylureido)biphenyl-2-carboxylic acid | (4-fluoro-2-carboxyphenyl) | p-tolyl | N(isobutyl)(cyclobutylmethyl) | 2.86$^i$ | 504 |
| 100 | 4'-((cyclobutylmethyl) (isobutyl)amino)-3'-(3-p-tolylureido)biphenyl-2-carboxylic acid | (2-carboxyphenyl) | p-tolyl | N(isobutyl)(cyclobutylmethyl) | 1.59$^k$ | 486 |
| 101 | 4'-(diisobutylamino)-6-(dimethylamino)-3'-(3-p-tolylureido) biphenyl-2-carboxylic acid | (3-dimethylamino-2-carboxyphenyl) | p-tolyl | N(isobutyl)₂ | 2.29$^j$ | 517 |
| 102 | 4-(4-(diisobutylamino)-3-(3-p-tolylureido) phenyl)-1-ethyl-3-methyl-1H-pyrazole-5-carboxylic acid | 1-ethyl-3-methyl-5-carboxy-1H-pyrazol-4-yl | p-tolyl | N(isobutyl)₂ | 1.95$^k$ | 506 |
| 103 | 5-(4-(diisobutylamino)-3-(3-p-tolylureido) phenyl)thiazole-4-carboxylic acid | 4-carboxythiazol-5-yl | p-tolyl | N(isobutyl)₂ | 2.05$^k$ | 481 |
| 104 | 4'-((4,4-difluoro-cyclohexyl) (methyl)amino)-3'-(3-p-tolylureido)biphenyl-2-carboxylic acid | (2-carboxyphenyl) | p-tolyl | N(methyl)(4,4-difluorocyclohexyl) | 16.82$^a$ | 494 |

TABLE 9-continued

| Ex. No. | Name | A (with R1, R2, R3) | R9 | —NR7R8 | Tr^method | (M+H)+ |
|---|---|---|---|---|---|---|
| 105 | 4'-((4,4-difluorocyclohexyl)(methyl)amino)-5-fluoro-3'-(3-p-tolylureido)biphenyl-2-carboxylic acid | 4-fluoro-2-(carboxylic acid)phenyl | p-tolyl | N-methyl-(4,4-difluorocyclohexyl)amino | 17.35^a | 512 |
| 106 | 1-(4-((4,4-difluorocyclohexyl)(methyl)amino)-2'-(1H-tetrazol-5-yl)biphenyl-3-yl)-3-p-tolylurea | 2-(1H-tetrazol-5-yl)phenyl | p-tolyl | N-methyl-(4,4-difluorocyclohexyl)amino | 16.74^a | 518 |
| 107 | 4'-(2-ethylpiperidin-1-yl)-3'-(3-p-tolylureido)biphenyl-2-carboxylic acid | 2-(carboxylic acid)phenyl | p-tolyl | 2-ethylpiperidin-1-yl | 1.76^k | 458 |
| 108 | 4'-(ethyl(neopentyl)amino)-3'-(3-(2-fluorophenyl)ureido)biphenyl-2-carboxylic acid | 2-(carboxylic acid)phenyl | 2-fluorophenyl | N-ethyl-N-neopentylamino | 1.95^k | 464 |
| 109 | 1-(4-(2-ethylpiperidin-1-yl)-2'-(1H-tetrazol-5-yl)biphenyl-3-yl)-3-(2-fluorophenyl)urea | 2-(1H-tetrazol-5-yl)phenyl | 2-fluorophenyl | 2-ethylpiperidin-1-yl | 1.63^k | 486 |

TABLE 9-continued

| Ex. No. | Name | A | R⁹ | —NR⁷R⁸ | Tr$^{method}$ | (M +H)⁺ |
|---|---|---|---|---|---|---|
| 110 | 1-(4-(ethyl(neopentyl)amino)-2'-(1H-tetrazol-5-yl)biphenyl-3-yl)-3-p-tolylurea | 2-(1H-tetrazol-5-yl)phenyl | p-tolyl | N(ethyl)(neopentyl) | 2.10$^k$ | 484 |
| 111 | 4'-(ethyl(neopentyl)amino)-3'-(3-p-tolylureido)biphenyl-2-carboxylic acid | 2-carboxyphenyl | p-tolyl | N(ethyl)(neopentyl) | 2.04$^k$ | 460 |
| 112 | 1-(4-(ethyl(neopentyl)amino)-2'-(1H-tetrazol-5-yl)biphenyl-3-yl)-3-(2-fluorophenyl)urea | 2-(1H-tetrazol-5-yl)phenyl | 2-fluorophenyl | N(ethyl)(neopentyl) | 2.01$^k$ | 488 |
| 113 | 4'-(ethyl(neopentyl)amino)-5-fluoro-3'-(3-p-tolylureido)biphenyl-2-carboxylic acid | 4-fluoro-2-carboxyphenyl | p-tolyl | N(ethyl)(neopentyl) | 2.16$^k$ | 478 |
| 114 | 1-(4-(2-ethylpiperidin-1-yl)-2'-(1H-tetrazol-5-yl)biphenyl-3-yl)-3-p-tolylurea | 2-(1H-tetrazol-5-yl)phenyl | p-tolyl | 2-ethylpiperidin-1-yl | 1.75$^k$ | 482 |

TABLE 9-continued

| Ex. No. | Name | A (with R1, R2, R3) | R9 | —NR7R8 | Tr^method | (M+H)+ |
|---|---|---|---|---|---|---|
| 115 | 4'-(ethyl(neopentyl)amino)-5-fluoro-3'-(3-(2-fluorophenyl)ureido)biphenyl-2-carboxylic acid | 4-fluoro-2-(carboxy)phenyl | 2-fluorophenyl | N(ethyl)(neopentyl) | 2.09$^k$ | 482 |
| 116 | 4'-(2-ethylpiperidin-1-yl)-3'-(3-(2-fluorophenyl)ureido)biphenyl-2-carboxylic acid | 2-(carboxy)phenyl | 2-fluorophenyl | 2-ethylpiperidin-1-yl | 1.64$^k$ | 462 |
| 117 | 1-(4-(diisobutylamino)-4'-methoxy-2'-(1H-tetrazol-5-yl)biphenyl-3-yl)-3-p-tolylurea | 4-methoxy-2-(1H-tetrazol-5-yl)phenyl | p-tolyl | N(isobutyl)(isobutyl) | 7.23$^m$ | 528 |
| 118 | 1-(4-(cyclohexyl(isobutyl)amino)-2'-(1H-tetrazol-5-yl)biphenyl-3-yl)-3-p-tolylurea | 2-(1H-tetrazol-5-yl)phenyl | p-tolyl | N(isobutyl)(cyclohexyl) | 18.20$^a$ | 524 |
| 119 | 4'-(cyclohexyl(isobutyl)amino)-3'-(3-p-tolylureido)biphenyl-2-carboxylic acid | 2-(carboxy)phenyl | p-tolyl | N(isobutyl)(cyclohexyl) | 17.91$^a$ | 500 |

TABLE 9-continued

| Ex. No. | Name | A (with R¹, R², R³) | R⁹ | —NR⁷R⁸ | Tr^method | (M+H)⁺ |
|---|---|---|---|---|---|---|
| 120 | 4-chloro-4'-(cyclohexyl(isobutyl)amino)-3'-(3-p-tolylureido)biphenyl-2-carboxylic acid | 5-chloro-2-carboxyphenyl | p-tolyl | N-isobutyl-N-cyclohexyl | 19.73ᵃ | 534 |
| 121 | 1-(4-(cyclohexyl(isobutyl)amino)-2'-(1H-tetrazol-5-yl)biphenyl-3-yl)-3-(2-fluorophenyl)urea | 2-(1H-tetrazol-5-yl)phenyl | 2-fluorophenyl | N-isobutyl-N-cyclohexyl | 17.79ᵃ | 528 |
| 122 | 4'-(cyclohexyl(isobutyl)amino)-3'-(3-(2-fluorophenyl)ureido)biphenyl-2-carboxylic acid | 2-carboxyphenyl | 2-fluorophenyl | N-isobutyl-N-cyclohexyl | 17.53ᵃ | 504 |
| 123 | 4-chloro-4'-(cyclohexyl(isobutyl)amino)-3'-(3-(2-fluorophenyl)ureido)biphenyl-2-carboxylic acid | 5-chloro-2-carboxyphenyl | 2-fluorophenyl | N-isobutyl-N-cyclohexyl | 19.11ᵃ | 538 |
| 124 | 4'-(cyclohexyl(isobutyl)amino)-5-fluoro-3'-(3-p-tolylureido)biphenyl-2-carboxylic acid | 4-fluoro-2-carboxyphenyl | p-tolyl | N-isobutyl-N-cyclohexyl | 2.26ᵏ | 518 |

TABLE 9-continued

| Ex. No. | Name | A (R¹, R², R³) | R⁹ | —NR⁷R⁸ | Tr^method | (M+H)⁺ |
|---|---|---|---|---|---|---|
| 125 | 4'-(cyclohexyl(isobutyl)amino)-5-fluoro-3'-(3-(2-fluorophenyl)ureido)biphenyl-2-carboxylic acid | 4-F, 2-COOH phenyl | 2-fluorophenyl | N(isobutyl)(cyclohexyl) | 2.18^k | 522 |
| 126 | 4'-(diisobutylamino)-5-fluoro-3'-(3-p-tolylureido)biphenyl-2-carboxylic acid | 4-F, 2-COOH phenyl | p-tolyl | N(isobutyl)₂ | 2.28^k | 492 |
| 127 | 4-chloro-4'-(diisobutylamino)-3'-(3-p-tolylureido)biphenyl-2-carboxylic acid | 4-Cl, 2-COOH phenyl | p-tolyl | N(isobutyl)₂ | 2.36^k | 508 |
| 128 | 4'-(diisobutylamino)-5-methoxy-3'-(3-p-tolylureido)biphenyl-2-carboxylic acid | 4-OMe, 2-COOH phenyl | p-tolyl | N(isobutyl)₂ | 17.91^a | 504 |
| 129 | 1-(4-((2-cyclopropylethyl)(isobutyl)amino)-2'-(1H-tetrazol-5-yl)biphenyl-3-yl)-3-p-tolylurea | 2-(1H-tetrazol-5-yl)phenyl | p-tolyl | N(isobutyl)(2-cyclopropylethyl) | 17.77^a | 510 |

TABLE 9-continued

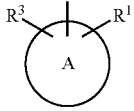

| Ex. No. | Name | A (R1,R2,R3) | R9 | —NR7R8 | Tr method | (M +H)+ |
|---|---|---|---|---|---|---|
| 130 | 4'-((2-cyclopropylethyl)(isobutyl)amino)-5-fluoro-3'-(3-p-tolylureido)biphenyl-2-carboxylic acid | 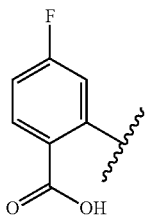 [SMILES: *c1cc(F)ccc1C(=O)O] | 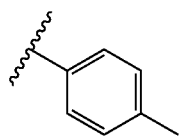 [SMILES: *c1ccc(C)cc1] | 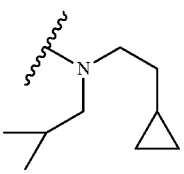 | 18.33<sup>a</sup> | 504 |
| 131 | 2-(4-((2-cyclopropylethyl)(isobutyl)amino)-3-(3-p-tolylureido)phenyl)thiophene-3-carboxylic acid | 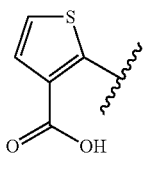 [SMILES: *c1sccc1C(=O)O] | 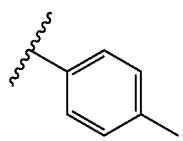 [SMILES: *c1ccc(C)cc1] | 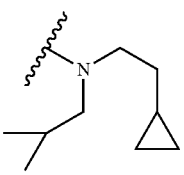 [SMILES: *N(CCC1CC1)CC(C)C] | 18.32<sup>a</sup> | 492 |
| 132 | 4'-((2-cyclopropylethyl)(isobutyl)amino)-3'-(3-p-tolylureido)biphenyl-2-carboxylic acid | 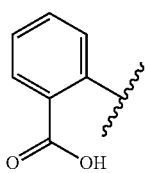 [SMILES: *c1ccccc1C(=O)O] | 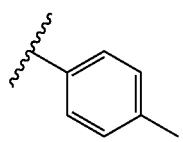 [SMILES: *c1ccc(C)cc1] | 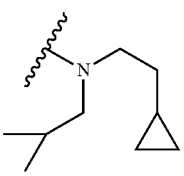 [SMILES: *N(CCC1CC1)CC(C)C] | 17.50<sup>a</sup> | 486 |
| 133 | 1-(4-((2-cyclopropylethyl)(isobutyl)amino)-2'-(1H-tetrazol-5-yl)biphenyl-3-yl)-3-(2-fluorophenyl)urea | 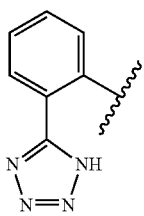 | 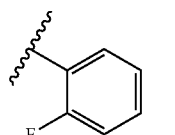 | 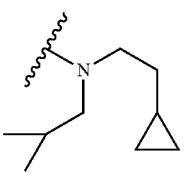 [SMILES: *N(CCC1CC1)CC(C)C] | 2.10<sup>k</sup> | 514 |
| 134 | 4'-((2-cyclopropylethyl)(isobutyl)amino)-3'-(3-(2-fluorophenyl)ureido)biphenyl-2-carboxylic acid | 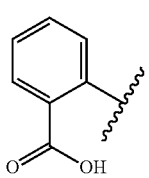 [SMILES: *c1ccccc1C(=O)O] | 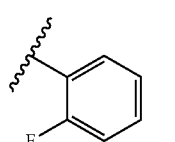 | 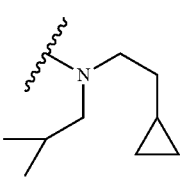 [SMILES: *N(CCC1CC1)CC(C)C] | 2.05<sup>k</sup> | 490 |
| 135 | 4'-((2-cyclopropylethyl)(isobutyl)amino)-5-fluoro-3'-(3-(2-fluorophenyl)ureido)biphenyl-2-carboxylic acid | 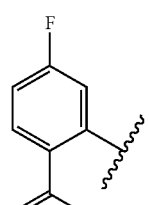 | 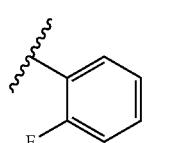 | 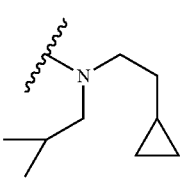 [SMILES: *N(CCC1CC1)CC(C)C] | 2.18<sup>k</sup> | 508 |

TABLE 9-continued

| Ex. No. | Name | A (structure) | R⁹ | —NR⁷R⁸ | Tr^method | (M+H)⁺ |
|---|---|---|---|---|---|---|
| 136 | 2-(4-((2-cyclopropylethyl)(isobutyl)amino)-3-(3-(2-fluorophenyl)ureido)phenyl)thiophene-3-carboxylic acid | thiophene-3-carboxylic acid | 2-fluorophenyl | N(isobutyl)(2-cyclopropylethyl) | 2.22$^k$ | 496 |
| 137 | 1-(2,4-difluorophenyl)-3-(4-(diisobutylamino)-2'-(1H-tetrazol-5-yl)biphenyl-3-yl)urea | 2-(1H-tetrazol-5-yl)phenyl | 2,4-difluorophenyl | N(isobutyl)₂ | 13.23$^b$ | 520 |
| 138 | 3'-(3-(2,4-difluorophenyl)ureido)-4'-(diisobutylamino)biphenyl-2-carboxylic acid | 2-carboxyphenyl | 2,4-difluorophenyl | N(isobutyl)₂ | 13.21$^b$ | 496 |
| 139 | 1-cyclopropyl-3-(4-(diisobutylamino)-2'-(1H-tetrazol-5-yl)biphenyl-3-yl)urea | 2-(1H-tetrazol-5-yl)phenyl | cyclopropyl | N(isobutyl)₂ | 2.16$^i$ | 448 |
| 140 | 1-cyclohexyl-3-(4-(diisobutylamino)-2'-(1H-tetrazol-5-yl)biphenyl-3-yl)urea | 2-(1H-tetrazol-5-yl)phenyl | cyclohexyl | N(isobutyl)₂ | 2.59$^i$ | 490 |
| 141 | 1-(4-(diisobutylamino)-2'-(1H-tetrazol-5-yl)biphenyl-3-yl)-3-neopentylurea | 2-(1H-tetrazol-5-yl)phenyl | neopentyl | N(isobutyl)₂ | 2.51$^i$ | 478 |

TABLE 9-continued

| Ex. No. | Name | | R⁹ | —NR⁷R⁸ | Tr^method | (M +H)⁺ |
|---|---|---|---|---|---|---|
| 142 | 1-(cyclopropylmethyl)-3-(4-(diisobutylamino)-2'-(1H-tetrazol-5-yl)biphenyl-3-yl)urea | | cyclopropylmethyl | diisobutylamino | 2.29[i] | 462 |
| 143 | 1-(benzo[d]thiazol-6-yl)-3-(4-(diisobutylamino)-2'-(1H-tetrazol-5-yl)biphenyl-3-yl)urea | | benzo[d]thiazol-6-yl | diisobutylamino | 2.26[i] | 541 |
| 144 | methyl 2-(3-(4-(diisobutylamino)-2'-(1H-tetrazol-5-yl)biphenyl-3-yl)ureido)thiazole-5-carboxylate | | methyl thiazole-5-carboxylate | diisobutylamino | 2.26[i] | 549 |
| 145 | 1-(4-(diisobutylamino)-2'-(1H-tetrazol-5-yl)biphenyl-3-yl)-3-(1,3,4-thiadiazol-2-yl)urea | | 1,3,4-thiadiazol-2-yl | diisobutylamino | 1.91[i] | 492 |
| 146 | 3'-(3-(2,4-difluorophenyl)ureido)-4'-(diisobutylamino)-5-fluorobiphenyl-2-carboxylic acid | | 2,4-difluorophenyl | diisobutylamino | 13.84[b] | 514 |

TABLE 9-continued

| Ex. No. | Name | A (R¹,R²,R³) | R⁹ | —NR⁷R⁸ | Tr$^{method}$ | (M +H)⁺ |
|---|---|---|---|---|---|---|
| 147 | 1-(4-(isobutyl(isopropyl) amino)-2'-(1H-tetrazol-5-yl)biphenyl-3-yl)-3-p-tolylurea | 2-(1H-tetrazol-5-yl)phenyl | p-tolyl | N(iBu)(iPr) | 12.68$^b$ | 484 |
| 148 | 4'-(isobutyl(isopropyl) amino)-3'-(3-p-tolylureido)biphenyl-2-carboxylic acid | 2-carboxyphenyl | p-tolyl | N(iBu)(iPr) | 12.28$^b$ | 460 |
| 149 | 5-fluoro-4'-(isobutyl(isopropyl) amino)-3'-(3-p-tolylureido)biphenyl-2-carboxylic acid | 4-fluoro-2-carboxyphenyl | p-tolyl | N(iBu)(iPr) | 12.99$^b$ | 478 |
| 150 | 4'-(diisobutylamino)-3-fluoro-3'-(3-p-tolylureido)biphenyl-2-carboxylic acid | 3-fluoro-2-carboxyphenyl | p-tolyl | N(iBu)₂ | 2.06$^j$ | 492 |
| 151 | 3-(4-(diisobutylamino)-3-(3-p-tolylureido)phenyl) isonicotinic acid | pyridyl-carboxylic acid | p-tolyl | N(iBu)₂ | 1.89$^k$ | 475 |
| 152 | 3-(4-(diisobutylamino)-3-(3-p-tolylureido) phenyl)furan-2-carboxylic acid | furan-2-carboxylic acid | p-tolyl | N(iBu)₂ | 2.70$^k$ | 464 |

TABLE 9-continued

| Ex. No. | Name | A (R1, R2, R3) | R9 | —NR7R8 | Tr^method | (M +H)+ |
|---|---|---|---|---|---|---|
| 153 | 1-(2-fluorophenyl)-3-(4-(isobutyl(isopropyl)amino)-2'-(1H-tetrazol-5-yl)biphenyl-3-yl)urea | phenyl with tetrazole | 2-fluorophenyl | N(isobutyl)(isobutyl) | 1.97$^k$ | 488 |
| 154 | 3'-(3-(2-fluorophenyl)ureido)-4'-(isobutyl(isopropyl)amino)biphenyl-2-carboxylic acid | 2-carboxyphenyl | 2-fluorophenyl | N(isobutyl)(isobutyl) | 1.93$^k$ | 464 |
| 155 | 5-fluoro-3'-(3-(2-fluorophenyl)ureido)-4'-(isobutyl(isopropyl)amino)biphenyl-2-carboxylic acid | 4-fluoro-2-carboxyphenyl | 2-fluorophenyl | N(isobutyl)(isobutyl) | 2.06$^k$ | 482 |
| 156 | 1-(2,4-difluorophenyl)-3-(4-(isobutyl(isopropyl)amino)-2'-(1H-tetrazol-5-yl)biphenyl-3-yl)urea | phenyl with tetrazole | 2,4-difluorophenyl | N(isobutyl)(isobutyl) | 2.02$^k$ | 506 |
| 157 | 3'-(3-(2,4-difluorophenyl)ureido)-4'-(isobutyl(isopropyl)amino)biphenyl-2-carboxylic acid | 2-carboxyphenyl | 2,4-difluorophenyl | N(isobutyl)(isobutyl) | 1.98$^k$ | 482 |
| 158 | 3'-(3-(2,4-difluorophenyl)ureido)-5-fluoro-4'-(isobutyl(isopropyl)amino)biphenyl-2-carboxylic acid | 4-fluoro-2-carboxyphenyl | 2,4-difluorophenyl | N(isobutyl)(isobutyl) | 2.09$^k$ | 500 |

TABLE 9-continued

| Ex. No. | Name | A (with R¹, R², R³) | R⁹ | —NR⁷R⁸ | Tr^method | (M +H)⁺ |
|---|---|---|---|---|---|---|
| 159 | 4-(4-(diisobutylamino)-3-(3-p-tolylureido)phenyl)nicotinic acid | pyridine with COOH (nicotinic acid) | p-tolyl (4-methylphenyl) | N(isobutyl)₂ | 2.00$^k$ | 475 |
| 160 | 3'-(3-(2,4-difluorophenyl)ureido)-4'-(diisobutylamino)-5-methoxybiphenyl-2-carboxylic acid | 4-OMe, 2-COOH phenyl | 2,4-difluorophenyl | N(isobutyl)₂ | 2.28$^k$ | 526 |
| 161 | 1-(4-(cyclohexyl(isobutyl)amino)-2'-(1H-tetrazol-5-yl)biphenyl-3-yl)-3-(2-(trifluoromethyl)phenyl)urea | 2-(1H-tetrazol-5-yl)phenyl | 2-(trifluoromethyl)phenyl | N(isobutyl)(cyclohexyl) | 2.37$^k$ | 578 |
| 162 | 4'-(cyclohexyl(isobutyl)amino)-3'-(3-(2-(trifluoromethyl)phenyl)ureido)biphenyl-2-carboxylic acid | 2-COOH phenyl | 2-(trifluoromethyl)phenyl | N(isobutyl)(cyclohexyl) | 2.38$^k$ | 554 |
| 163 | 4'-(cyclohexyl(isobutyl)amino)-5-fluoro-3'-(3-(2-(trifluoromethyl)phenyl)ureido)biphenyl-2-carboxylic acid | 4-F, 2-COOH phenyl | 2-(trifluoromethyl)phenyl | N(isobutyl)(cyclohexyl) | 2.49$^k$ | 572 |

TABLE 9-continued

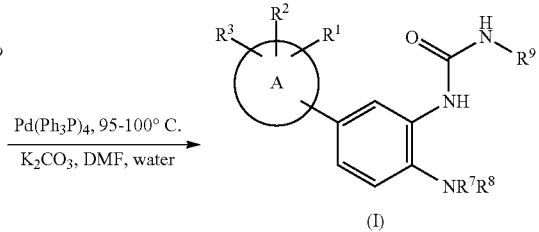

| Ex. No. | Name | A | R⁹ | —NR⁷R⁸ | Tr^method | (M +H)⁺ |
|---|---|---|---|---|---|---|
| 164 | 1-(5-(2-(1H-tetrazol-5-yl)cyclopent-1-enyl)-2-(diisobutylamino)phenyl)-3-p-tolylurea | 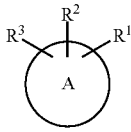 | 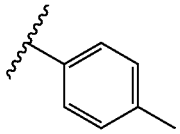 [SMILES: *c1ccc(C)cc1] | 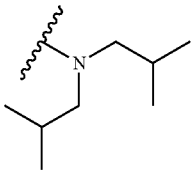 [SMILES: *N(CC(C)C)CC(C)C] | 2.21^k | 488 |
| 165 | 4'-(cyclopentyl(propyl)amino)-3'-(3-p-tolylureido)biphenyl-2-carboxylic acid | 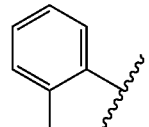 | 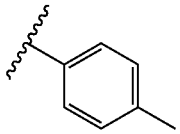 [SMILES: *c1ccc(C)cc1] | 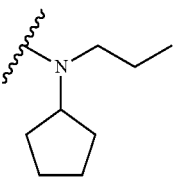 | 2.85^q | 472 |
| 166 | 4'-(cyclopentyl(propyl)amino)-5-fluoro-3'-(3-p-tolylureido)biphenyl-2-carboxylic acid | 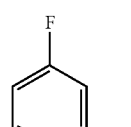 | 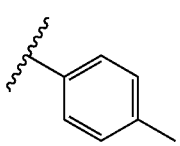 [SMILES: *c1ccc(C)cc1] | 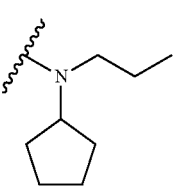 [SMILES: *N(CCC)C1CCCC1] | 2.95^q | 490 |
| 167 | 4'-(cyclopentyl(propyl)amino)-5-fluoro-3'-(3-(2-fluorophenyl)ureido)biphenyl-2-carboxylic acid | 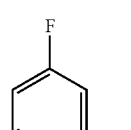 | 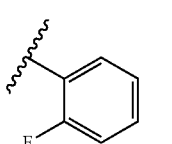 | 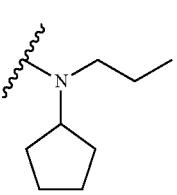 [SMILES: *N(CCC)C1CCCC1] | 1.77^k | 494 |
| 168 | 4'-(cyclopentyl(propyl)amino)-3'-(3-(2-fluorophenyl)ureido)biphenyl-2-carboxylic acid | 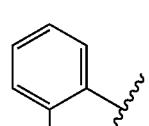 | 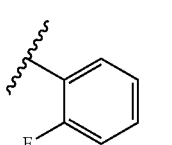 | 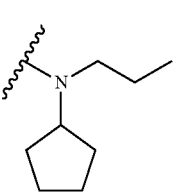 [SMILES: *N(CCC)C1CCCC1] | 2.75^q | 476 |
| 169 | 1-(4-(cyclopentyl(propyl)amino)-2'-(1H-tetrazol-5-yl)biphenyl-3-yl)-3-p-tolylurea | 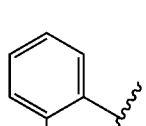 | 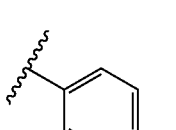 | 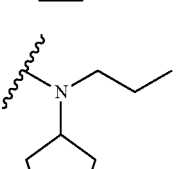 | 2.87^q | 496 |

TABLE 9-continued

| Ex. No. | Name | A (R¹, R², R³) | R⁹ | —NR⁷R⁸ | Tr^method | (M +H)⁺ |
|---|---|---|---|---|---|---|
| 170 | 1-(4-(cyclopentyl(propyl) amino)-2'-(1H-tetrazol-5-yl)biphenyl-3-yl)-3-(2-fluorophenyl)urea | 2-(1H-tetrazol-5-yl)phenyl | 2-fluorophenyl | N-propyl-N-cyclopentyl | 2.76$^q$ | 500 |
| 171 | 4'-(cyclopentyl(isobutyl) amino)-5-fluoro-3'-(3-p-tolylureido)biphenyl-2-carboxylic acid | 4-fluoro-2-carboxyphenyl | p-tolyl | N-isobutyl-N-cyclopentyl | 2.04$^k$ | 504 |
| 172 | 4'-(cyclopentyl(isobutyl) amino)-3'-(3-p-tolylureido)biphenyl-2-carboxylic acid | 2-carboxyphenyl | p-tolyl | N-isobutyl-N-cyclopentyl | 2.41$^q$ | 486 |
| 173 | 4'-(cyclopentyl(isobutyl) amino)-3'-(3-(2-fluorophenyl)ureido) biphenyl-2-carboxylic acid | 2-carboxyphenyl | 2-fluorophenyl | N-isobutyl-N-cyclopentyl | 1.85$^k$ | 490 |
| 174 | 1-(4-(cyclopentyl (isobutyl) amino)-2'-(1H-tetrazol-5-yl)biphenyl-3-yl)-3-p-tolylurea | 2-(1H-tetrazol-5-yl)phenyl | p-tolyl | N-isobutyl-N-cyclopentyl | 2.47$^q$ | 510 |
| 175 | 1-(4-(cyclopentyl (isobutyl) amino)-2'-(1H-tetrazol-5-yl)biphenyl-3-yl)-3-(2-fluorophenyl)urea | 2-(1H-tetrazol-5-yl)phenyl | 2-fluorophenyl | N-isobutyl-N-cyclopentyl | 1.91$^k$ | 514 |

TABLE 9-continued

| Ex. No. | Name | A (with R1, R2, R3) | R9 | —NR7R8 | Tr method | (M +H)+ |
|---|---|---|---|---|---|---|
| 176 | 4'-(cyclopentyl(isobutyl)amino)-5-fluoro-3'-(3-(2-fluorophenyl)ureido)biphenyl-2-carboxylic acid | 4-fluoro-2-carboxyphenyl | 2-fluorophenyl | N(isobutyl)(cyclopentyl) | 2.47$^q$ | 508 |
| 177 | 4'-(butyl(cyclohexyl)amino)-3'-(3-(p-tolyl)ureido)-[1,1'-biphenyl]-2-carboxylic acid | 2-carboxyphenyl | p-tolyl | N(butyl)(cyclohexyl) | 4.21$^l$ | 500 |
| 178 | 4'-(butyl(cyclohexyl)amino)-5-fluoro-3'-(3-(p-tolyl)ureido)-[1,1'-biphenyl]-2-carboxylic acid | 4-fluoro-2-carboxyphenyl | p-tolyl | N(butyl)(cyclohexyl) | 4.41$^l$ | 518 |
| 179 | 1-(4-(isobutyl(methyl)amino)-2'-(1H-tetrazol-5-yl)-[1,1'-biphenyl]-3-yl)-3-(p-tolyl)urea | 2-(1H-tetrazol-5-yl)phenyl | p-tolyl | N(isobutyl)(methyl) | 2.21$^q$ | 456 |
| 180 | 4'-(isobutyl(methyl)amino)-3'-(3-(p-tolyl)ureido)-[1,1'-biphenyl]-2-carboxylic acid | 2-carboxyphenyl | p-tolyl | N(isobutyl)(methyl) | 2.17$^q$ | 432 |

TABLE 9-continued

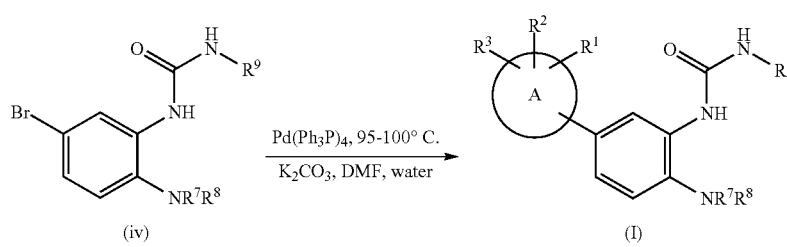

| Ex. No. | Name | | R⁹ | —NR⁷R⁸ | Tr^method | (M +H)⁺ |
|---|---|---|---|---|---|---|
| 181 | 5-fluoro-4'-(isobutyl(methyl)amino)-3'-(3-(p-tolyl)ureido)-[1,1'-biphenyl]-2-carboxylic acid | 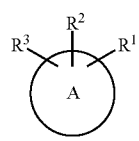 | 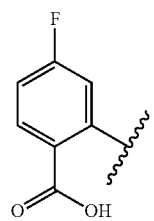 [SMILES: *c1cc(F)ccc1C(=O)O] | 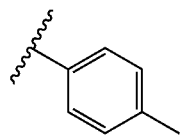 [SMILES: *c1ccc(C)cc1] | 2.31^q | 450 |
| 182 | 4'-(cyclobutyl(isobutyl)amino)-5-fluoro-3'-(3-(p-tolyl)ureido)-[1,1'-biphenyl]-2-carboxylic acid | 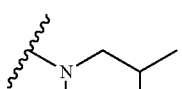 | 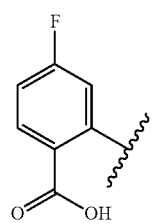 [SMILES: *c1cc(F)ccc1C(=O)O] | 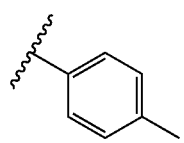 [SMILES: *c1ccc(C)cc1] | 2.55^q | 490 |
| 183 | 4'-(cyclobutyl(isobutyl)amino)-3'-(3-(p-tolyl)ureido)-[1,1'-biphenyl]-2-carboxylic acid | 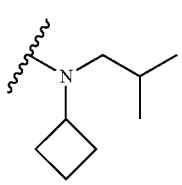 [SMILES: *N(CC(C)C)C1CCC1] | 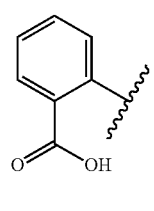 [SMILES: *c1ccccc1C(=O)O] | 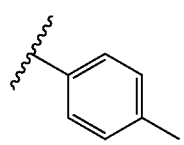 [SMILES: *c1ccc(C)cc1] | 2.41^q | 472 |
| 184 | 1-(4-(cyclobutyl(isobutyl)amino)-2'-(1H-tetrazol-5-yl)-[1,1'-biphenyl]-3-yl)-3-(p-tolyl)urea | 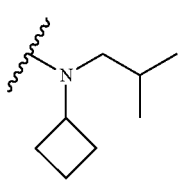 [SMILES: *N(CC(C)C)C1CCC1] | 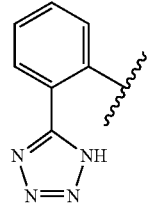 [SMILES: *c1ccccc1-c1nnn[nH]1] | 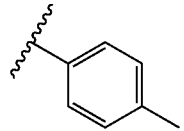 [SMILES: *c1ccc(C)cc1] | 2.49^q | 496 |
| 185 | 1-(4-(benzyl(propyl)amino)-2'-(1H-tetrazol-5-yl)-[1,1'-biphenyl]-3-yl)-3-(p-tolyl)urea | 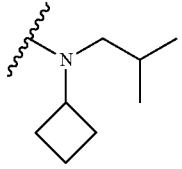 [SMILES: *N(CC(C)C)C1CCC1] | 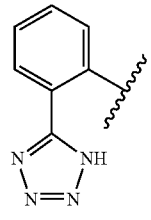 [SMILES: *c1ccccc1-c1nnn[nH]1] | 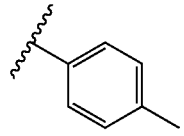 [SMILES: *c1ccc(C)cc1] | 2.52^q | 518 |

TABLE 9-continued

| Ex. No. | Name | A (R¹, R², R³) | R⁹ | —NR⁷R⁸ | Tr$^{method}$ | (M +H)⁺ |
|---|---|---|---|---|---|---|
| 186 | 4'-(benzyl(propyl)amino)-5-fluoro-3'-(3-(p-tolyl)ureido)-[1,1'-biphenyl]-2-carboxylic acid | 4-fluoro-2-carboxyphenyl | p-tolyl | N(benzyl)(propyl) | 2.56$^q$ | 512 |
| 187 | 4'-(benzyl(propyl)amino)-3'-(3-(p-tolyl)ureido)-[1,1'-biphenyl]-2-carboxylic acid | 2-carboxyphenyl | p-tolyl | N(benzyl)(propyl) | 2.43$^q$ | 494 |
| 188 | 4'-(cyclohexyl(4,4,4-trifluoro-3-methylbutyl)amino)-3'-(3-(p-tolyl)ureido)-[1,1'-biphenyl]-2-carboxylic acid | 2-carboxyphenyl | p-tolyl | N(cyclohexyl)(4,4,4-trifluoro-3-methylbutyl) | 2.66$^q$ | 568 |
| 189 | 4'-(cyclohexyl(4,4,4-trifluoro-3-methylbutyl)amino)-5-fluoro-3'-(3-(p-tolyl)ureido)-[1,1'-biphenyl]-2-carboxylic acid | 4-fluoro-2-carboxyphenyl | p-tolyl | N(cyclohexyl)(4,4,4-trifluoro-3-methylbutyl) | 2.75$^q$ | 586 |
| 190 | 1-(4-(cyclohexyl(4,4,4-trifluoro-3-methylbutyl)amino)-2'-(1H-tetrazol-5-yl)-[1,1'-biphenyl]-3-yl)-3-(p-tolyl)urea | 2-(1H-tetrazol-5-yl)phenyl | p-tolyl | N(cyclohexyl)(4,4,4-trifluoro-3-methylbutyl) | 3.01$^r$ | 592 |

TABLE 9-continued

| Ex. No. | Name | R[9] | —NR[7]R[8] | Tr[method] | (M +H)+ |
|---|---|---|---|---|---|
| 191 | 1-(4-((4-chlorobenzyl)(2-methoxyethyl)amino)-2'-(1H-tetrazol-5-yl)-[1,1'-biphenyl]-3-yl)-3-(p-tolyl)urea | 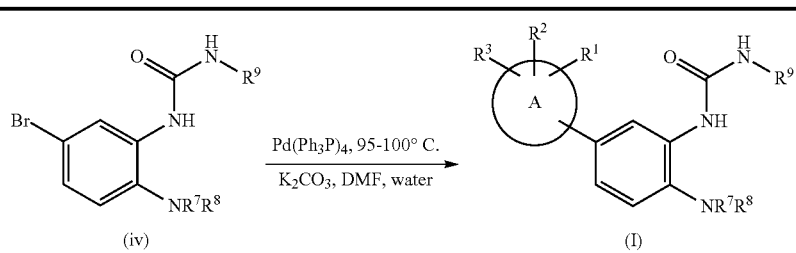 | 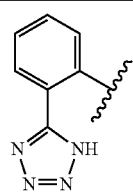 | 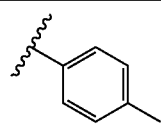 | 2.62[q] | 568 |
| 192 | 4'-((4-chlorobenzyl)(2-methoxyethyl)amino)-3'-(3-(p-tolyl)ureido)-[1,1'-biphenyl]-2-carboxylic acid | 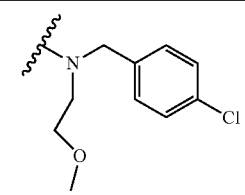 | 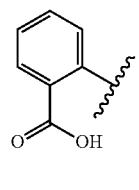 [SMILES: *c1ccccc1C(=O)O] | 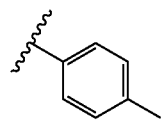 | 2.64[q] | 544 |
| 193 | 4'-((4-chlorobenzyl)(2-methoxyethyl)amino)-5-fluoro-3'-(3-(p-tolyl)ureido)-[1,1'-biphenyl]-2-carboxylic acid | 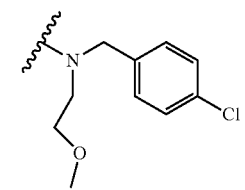 [SMILES: *N(CCOC)Cc1ccc(Cl)cc1] | 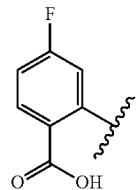 [SMILES: *c1cc(F)ccc1C(=O)O] | 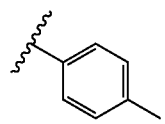 [SMILES: *c1ccc(C)cc1] | 2.72[q] | 562 |
| 194 | 1-(4-(cyclohexyl(2,2-difluoroethyl)amino)-2'-(1H-tetrazol-5-yl)-[1,1'-biphenyl]-3-yl)-3-(p-tolyl)urea | 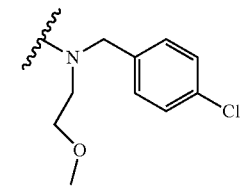 [SMILES: *N(CCOC)Cc1ccc(Cl)cc1] | 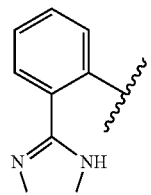 | 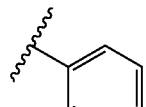 | 2.60[q] | 532 |
| 195 | 1-(4-(cyclohexyl(3,3,3-trifluoropropyl)amino)-2'-(1H-tetrazol-5-yl)-[1,1'-biphenyl]-3-yl)-3-(p-tolyl)urea | 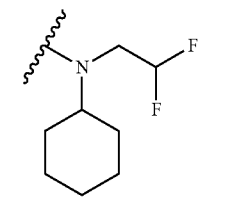 [SMILES: *N(CC(F)F)C1CCCCC1] | 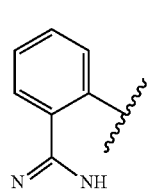 | 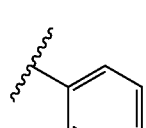 | 2.96[r] | 564 |
| 196 | 4'-(cyclohexyl(2,2-difluoroethyl)amino)-3'-(3-(p-tolyl)ureido)-[1,1'-biphenyl]-2-carboxylic acid | 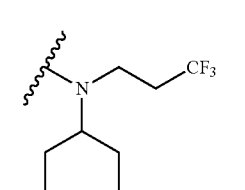 | 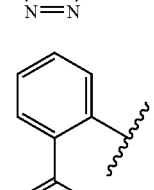 | 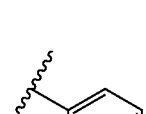 | 2.66[q] | 508 |

TABLE 9-continued

| Ex. No. | Name | A (R1, R2, R3) | R9 | —NR7R8 | Tr method | (M +H)+ |
|---|---|---|---|---|---|---|
| 197 | 4'-(cyclohexyl(3,3,3-trifluoropropyl)amino)-3'-(3-(p-tolyl)ureido)-[1,1'-biphenyl]-2-carboxylic acid | 2-carboxyphenyl | p-tolyl | N(CH2CH2CF3)(cyclohexyl) | 2.75$^q$ | 540 |
| 198 | 4'-(isobutyl(3,3,3-trifluoropropyl)amino)-3'-(3-(p-tolyl)ureido)-[1,1'-biphenyl]-2-carboxylic acid | 2-carboxyphenyl | p-tolyl | N(CH2CH2CF3)(isobutyl) | 2.90$^r$ | 514 |
| 199 | 1-(4-(isobutyl(3,3,3-trifluoropropyl)amino)-2'-(1H-tetrazol-5-yl)-[1,1'-biphenyl]-3-yl)-3-(p-tolyl)urea | 2-(1H-tetrazol-5-yl)phenyl | p-tolyl | N(CH2CH2CF3)(isobutyl) | 2.23$^k$ | 538 |
| 200 | 5-fluoro-4'-(isobutyl(3,3,3-trifluoropropyl)amino)-3'-(3-(p-tolyl)ureido)-[1,1'-biphenyl]-2-carboxylic acid | 4-fluoro-2-carboxyphenyl | p-tolyl | N(CH2CH2CF3)(isobutyl) | 2.99$^r$ | 532 |
| 201 | 1-(2-fluorophenyl)-3-(4'-(isobutyl(4,4,4-trifluoro-3-methylbutyl)amino)-2'-(1H-tetrazol-5-yl)-[1,1'-biphenyl]-3-yl)urea | 2-(1H-tetrazol-5-yl)phenyl | 2-fluorophenyl | N(isobutyl)(CH2CH2CH(CH3)CF3) | 2.63$^q$ | 570 |

TABLE 9-continued

| Ex. No. | Name | A (R¹, R², R³) | R⁹ | —NR⁷R⁸ | Tr^method | (M+H)⁺ |
|---|---|---|---|---|---|---|
| 202 | 1-(4-(isobutyl(4,4,4-trifluoro-3-methylbutyl)amino)-2'-(1H-tetrazol-5-yl)-[1,1'-biphenyl]-3-yl)-3-(p-tolyl)urea | 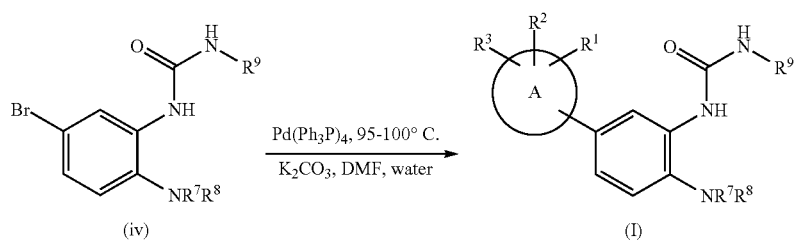 | 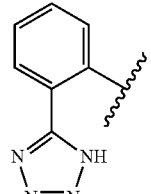 | 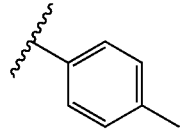 [SMILES: *c1ccc(C)cc1] | 2.66^q | 566 |
| 203 | 5-fluoro-4'-(isobutyl(4,4,4-trifluoro-3-methylbutyl)amino)-3'-(3-(p-tolyl)ureido)-[1,1'-biphenyl]-2-carboxylic acid | 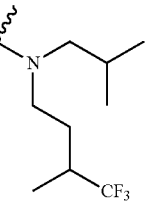 | 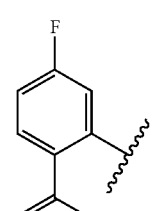 | 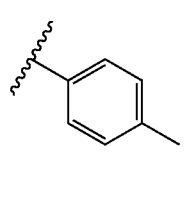 [SMILES: *c1ccc(C)cc1] | 2.74^q | 560 |
| 204 | 5-fluoro-3'-(3-(2-fluorophenyl)ureido)-4'-(isobutyl(4,4,4-trifluoro-3-methylbutyl)amino)-[1,1'-biphenyl]-2-carboxylic acid | 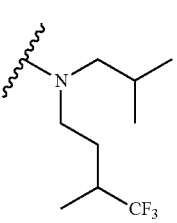 [SMILES: *N(CCC(C)C(F)(F)F)CC(C)C] | 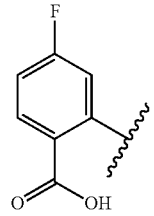 [SMILES: *c1cc(F)ccc1C(=O)O] | 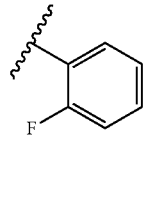 [SMILES: *c1ccccc1F] | 2.71^q | 564 |
| 205 | 4'-(isobutyl(4,4,4-trifluoro-3-methylbutyl)amino)-3'-(3-(p-tolyl)ureido)-[1,1'-biphenyl]-2-carboxylic acid | 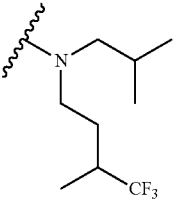 [SMILES: *N(CCC(C)C(F)(F)F)CC(C)C] | 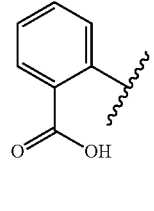 [SMILES: *c1ccccc1C(=O)O] | 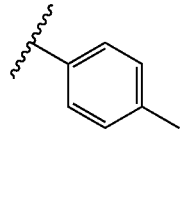 [SMILES: *c1ccc(C)cc1] | 2.66^q | 542 |
| 206 | 4'((2-(tert-butyl)phenyl)amino)-3'-(3-(p-tolyl)ureido)-[1,1'-biphenyl]-2-carboxylic acid | 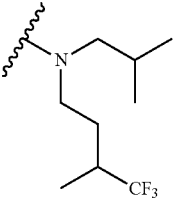 [SMILES: *N(CCC(C)C(F)(F)F)CC(C)C] | 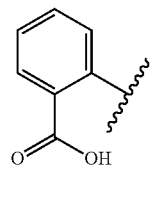 [SMILES: *c1ccccc1C(=O)O] | 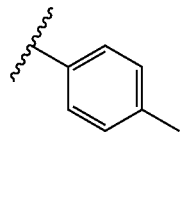 [SMILES: *c1ccc(C)cc1] | 2.34^k | 494 |

TABLE 9-continued

| Ex. No. | Name | A (with R1, R2, R3) | R9 | —NR7R8 | Tr method | (M +H)+ |
|---|---|---|---|---|---|---|
| 207 | 1-(4-((2-(tert-butyl)phenyl)(methyl)amino)-2'-(1H-tetrazol-5-yl)-[1,1'-biphenyl]-3-yl)-3-(2-fluorophenyl)urea | phenyl substituted with tetrazole | 2-fluorophenyl | N(Me)(2-tert-butylphenyl) | 4.71[l] | 536 |
| 208 | 1-(4-((2-(tert-butyl)phenyl)amino)-2'-(1H-tetrazol-5-yl)-[1,1'-biphenyl]-3-yl)-3-(p-tolyl)urea | phenyl substituted with tetrazole | p-tolyl | NH(2-tert-butylphenyl) | 2.27[k] | 518 |
| 209 | 4'-((2-(tert-butyl)phenyl)(methyl)amino)-3'-(3-(2-fluorophenyl)ureido)-4-methoxy-[1,1'-biphenyl]-3-carboxylic acid | 2-methoxy-5-carboxyphenyl | 2-fluorophenyl | N(Me)(2-tert-butylphenyl) | 2.68[q] | 542 |
| 210 | 1-(4-((2-(tert-butyl)phenyl)(methyl)amino)-2'-(1H-tetrazol-5-yl)-[1,1'-biphenyl]-3-yl)-3-(p-tolyl)urea | phenyl substituted with tetrazole | p-tolyl | N(Me)(2-tert-butylphenyl) | 2.69[q] | 532 |

Examples 211 to 219

Using the methods described herein (the preparation of Example 2 from 2A is representative), the following compounds of the invention were prepared from aniline intermediates (v) and the appropriate isocyanates R9NCO.

TABLE 10

| Ex. No. Name | A (with R1, R2, R3) | R9 | —NR7R8 | Tr^method | (M + H)+ |
|---|---|---|---|---|---|
| 211 1-(4-(cyclohexyl(methyl)amino)-2'-(1H-tetrazol-5-yl)biphenyl-3-yl)-3-m-tolylurea | 2-(1H-tetrazol-5-yl)phenyl | 3-methylphenyl | N(Me)(cyclohexyl) | 11.83[b] | 482 |
| 212 1-(4-(cyclohexyl(methyl)amino)-2'-(1H-tetrazol-5-yl)biphenyl-3-yl)-3-(2-(trifluoromethyl)phenyl)urea | 2-(1H-tetrazol-5-yl)phenyl | 2-(trifluoromethyl)phenyl | N(Me)(cyclohexyl) | 11.69[b] | 536 |
| 213 4'-(cyclohexyl(methyl)amino)-3'-(3-p-tolylureido)biphenyl-2-carboxylic acid | 2-carboxyphenyl | 4-methylphenyl | N(Me)(cyclohexyl) | 11.14[b] | 458 |
| 214 1-(4-(cyclohexyl(methyl)amino)-2'-(1H-tetrazol-5-yl)biphenyl-3-yl)-3-(2-fluorophenyl)urea | 2-(1H-tetrazol-5-yl)phenyl | 2-fluorophenyl | N(Me)(cyclohexyl) | 11.47[b] | 486 |

TABLE 10-continued

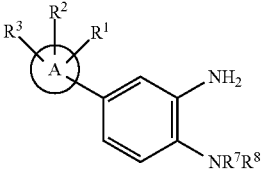

| Ex. No. | Name | A with R¹R²R³ | R⁹ | —NR⁷R⁸ | Tr^method | (M + H)⁺ |
|---|---|---|---|---|---|---|
| 215 | 3'-(3-(2-chlorophenyl)ureido)-4'-(cyclohexyl(methyl)amino)biphenyl-2-carboxylic acid | 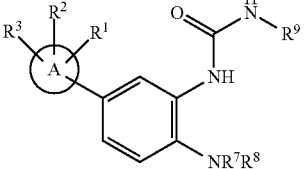 | 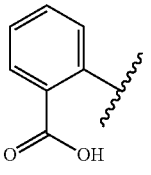 [SMILES: *c1ccccc1C(=O)O] | 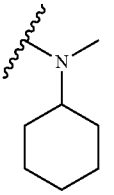 | 3.66[i] | 478 |
| 216 | 1-(4-(cyclohexyl(ethyl)amino)-2'-(1H-tetrazol-5-yl)biphenyl-3-yl)-3-p-tolylurea | 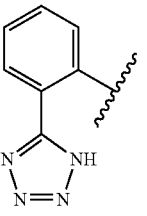 | 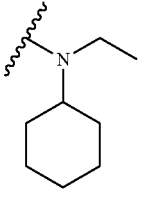 [SMILES: *N(CC)C1CCCCC1] | 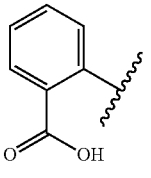 [SMILES: *c1ccccc1C(=O)O] | 11.75[b] | 496 |
| 218 | 4'-(cyclohexyl(methyl)amino)-3'-(3-phenylureido)biphenyl-2-carboxylic acid | 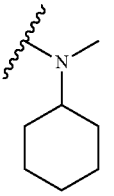 | 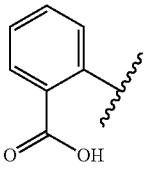 | 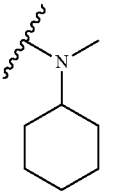 [SMILES: *N(C)C1CCCCC1] | 10.78[b] | 444 |
| 219 | 4'-(cyclohexyl(methyl)amino)-3'-(3-(2-fluorophenyl)ureido)biphenyl-2-carboxylic acid | | | | 10.90[b] | 462 |

Examples 220 to 231

Using the methods described below, the following compounds of the invention were prepared.

TABLE 11

| Ex. No. | Name | R³ R² R¹ (A) | R⁹ | —NR⁷R⁸ | HPLC T_r | (M + H)⁺ |
|---|---|---|---|---|---|---|
| 220 | 4'-(cyclohexyl(methyl)amino)-2'-fluoro-4-methoxy-5'-(3-p-tolylureido)biphenyl-3-carboxylic acid | 2-methoxy-5-yl benzoic acid (HO₂C, OMe) | p-tolyl | N(Me)(cyclohexyl) | 13.05[b] | 506 |
| 221 | 4'-(cyclohexyl(methyl)amino)-2'-fluoro-5'-(3-p-tolylureido)biphenyl-2-carboxylic acid | 2-carboxyphenyl | p-tolyl | N(Me)(cyclohexyl) | 12.49[b] | 476 |
| 222 | 1-(4-(cyclohexyl(methyl)amino)-6-fluoro-2'-(1H-tetrazol-5-yl)biphenyl-3-yl)-3-p-tolylurea | 2-(1H-tetrazol-5-yl)phenyl | p-tolyl | N(Me)(cyclohexyl) | 12.59[b] | 500 |
| 223 | 1-(4-((cyclopropylmethyl)(2,2-difluoroethyl)amino)-6-fluoro-2'-(1H-tetrazol-5-yl)biphenyl-3-yl)-3-p-tolylurea | 2-(1H-tetrazol-5-yl)phenyl | p-tolyl | N(CH₂-cyclopropyl)(CH₂CHF₂) | 12.26[b] | 522 |
| 224 | 4'-((cyclopropylmethyl)(2,2-difluoroethyl)amino)-2'-fluoro-5'-(3-p-tolylureido)biphenyl-2-carboxylic acid | 2-carboxyphenyl | p-tolyl | N(CH₂-cyclopropyl)(CH₂CHF₂) | 12.47[b] | 498 |

TABLE 11-continued

| Ex. No. | Name | ⟨A⟩ with R¹ R² R³ | R⁹ | —NR⁷R⁸ | HPLC T_r | (M + H)⁺ |
|---|---|---|---|---|---|---|
| 225 | 4'-(cyclohexyl)(isobutyl)amino)-2'-fluoro-5'-(3-p-tolylureido)biphenyl-2-carboxylic acid | 2-carboxyphenyl | 4-methylphenyl | N(isobutyl)(cyclohexyl) | 13.94[b] | 518 |
| 226 | 4'-(cyclohexyl(isobutyl)amino)-5'-(3-(2,4-difluorophenyl)ureido)-2',5-difluoro-[1,1'-biphenyl]-2-carboxylic acid | 4-fluoro-2-carboxyphenyl | 2,4-difluorophenyl | N(isobutyl)(cyclohexyl) | 3.30[q] | 558 |
| 227 | 1-(4-(cyclohexyl(isobutyl)amino)-6-fluoro-2'-(1H-tetrazol-5-yl)biphenyl-3-yl)-3-p-tolylurea | 2-(1H-tetrazol-5-yl)phenyl | 4-methylphenyl | N(isobutyl)(cyclohexyl) | 3.22[q] | 542 |
| 228 | 4'-(cyclohexyl(isobutyl)amino)-2'-fluoro-5'-(3-(2-fluorophenyl)ureido)biphenyl-2-carboxylic acid | 2-carboxyphenyl | 2-fluorophenyl | N(isobutyl)(cyclohexyl) | 3.16[q] | 522 |
| 229 | 4'-(cyclohexyl(isobutyl)amino)-2',5-difluoro-5'-(3-(2-fluorophenyl)ureido)biphenyl-2-carboxylic acid | 4-fluoro-2-carboxyphenyl | 2-fluorophenyl | N(isobutyl)(cyclohexyl) | 3.26[q] | 540 |

TABLE 11-continued

| Ex. No. | Name | A (R¹,R²,R³) | $R^9$ | —$NR^7R^8$ | HPLC $T_r$ | $(M + H)^+$ |
|---|---|---|---|---|---|---|
| 230 | 4'-(cyclohexyl(isobutyl)amino)-5'-(3-(2,4-difluorophenyl)ureido)-2'-fluorobiphenyl-2-carboxylic acid | 2-carboxyphenyl | 2,4-difluorophenyl | N(cyclohexyl)(isobutyl) | $3.21^q$ | 540 |
| 231 | 4'-(cyclohexyl)(isobutyl)amino)-2',5-difluoro-5'-(3-(p-tolyl)ureido)-[1,1'-biphenyl]-2-carboxylic acid | 4-fluoro-2-carboxyphenyl | p-tolyl | N(cyclohexyl)(isobutyl) | $3.32^q$ | 536 |

Example 232

4'-(Diisobutylamino)-N-(methylsulfonyl)-3'-(3-(p-tolyl)ureido)-[1,1'-biphenyl]-2-carboxamide

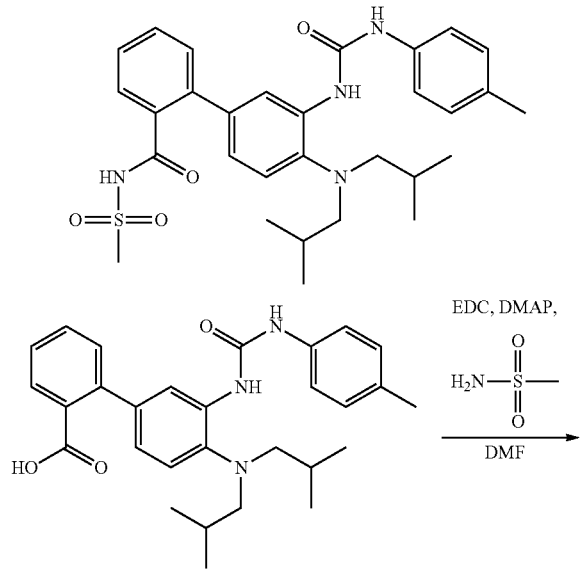

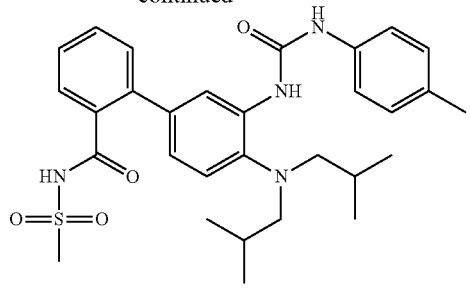

To a solution of 4'-(diisobutylamino)-3'-(3-(p-tolyl)ureido)-[1,1'-biphenyl]-2-carboxylic acid (Example 52) (40 mg, 0.084 mmol) in DMF (1 mL) was added DMAP (77 mg, 0.633 mmol), then EDC (162 mg, 0.845 mmol) and methanesulfonamide (121 mg, 1.267 mmol). The mixture was stirred at room temperature for 18 h, filtered and purified by HPLC PHENOMENEX® Axia (Luna 5μ 30×100 mm) 35% B (Solvent B=90% MeOH-10% $H_2O$-0.1% TFA) to 100% B in A (Solvent A=10% MeOH-90% $H_2O$-0.1% TFA) in 20 minutes and concentrated to obtain the product 4'-(diisobutylamino)-N-(methylsulfonyl)-3'-(3-(p-tolyl)ureido)-[1,1'-biphenyl]-2-carboxamide (19.4 mg, 0.035 mmol, 41.7% yield) LC/MS, m/z=551.5 (M+1). HPLC Rt=1.04 min. LC/MS (BEH C18 2.1×50 mm, 1.7 u, 0 to 100 B in 1 min with 0.5 min hold time, Flow rate=1 ml/min, detection at 254 nm, Solvent A: 100% water/0.1% TFA; Solvent B: 100% ACN/0.1% TFA). $^1$H NMR (500 MHz, methanol-$d_4$) δ 8.05 (d, J=2.0 Hz, 1H), 7.59-7.46 (m, 3H), 7.44-7.36 (m, 1H), 7.29 (d, J=8.4 Hz, 2H), 7.22 (d, J=7.9 Hz, 1H), 7.11 (d, J=7.9 Hz, 2H), 7.08-7.01 (m, 1H), 3.10 (s, 3H), 2.68 (d, J=6.9 Hz, 4H), 2.31 (s, 3H), 1.85-1.56 (m, 2H), 0.87 (d, J=6.4 Hz, 12H).

Following the procedure of Example 232, the following compounds were prepared.

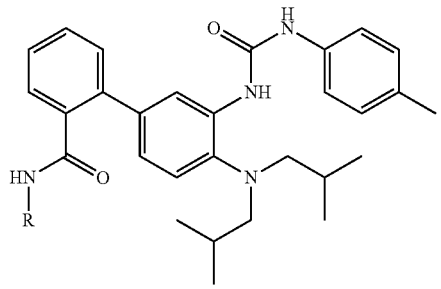

| Example No. | R | [M + H]$^+$ | HPLC RT |
|---|---|---|---|
| 223 | 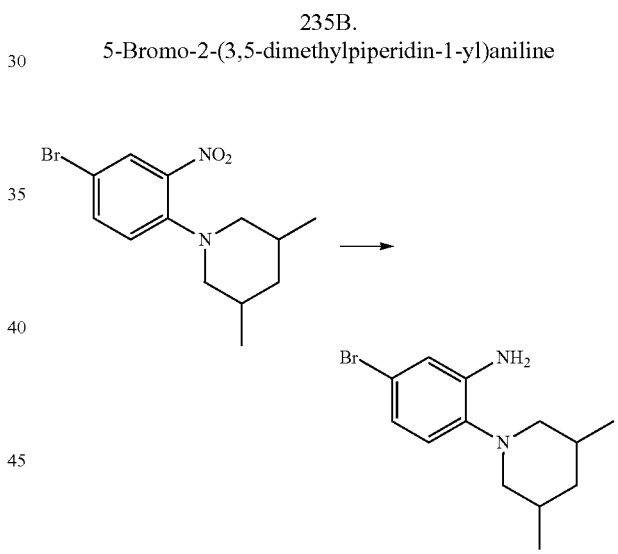 | 577.5 | 1.06$^v$ |
| 234 |  | 605.5 | 1.04$^v$ |

Example 235

1-(4-(3,5-Dimethylpiperidin-1-yl)-2'-(1H-tetrazol-5-yl)-[1,1'-biphenyl]-3-yl)-3-(p-tolyl)urea

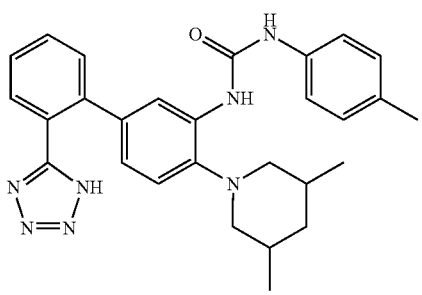 [SMILES: Cc1ccc(NC(=O)Nc2cc(-c3ccccc3-c3nnn[nH]3)ccc2N2CC(C)CC(C)C2)cc1]

235A.
1-(4-Bromo-2-nitrophenyl)-3,5-dimethylpiperidine

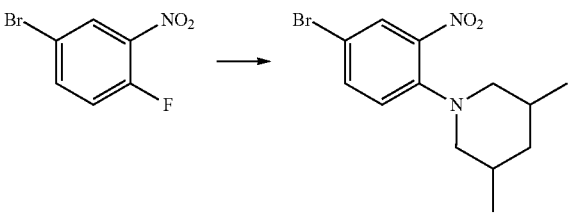 [SMILES: O=[N+]([O-])c1cc(Br)ccc1F ; CC1CC(C)CN(c2ccc(Br)cc2[N+](=O)[O-])C1]

A mixture of 4-bromo-1-fluoro-2-nitrobenzene (4 g, 18.18 mmol) and 3,5-dimethylpiperidine (2.058 g, 18.18 mmol) was heated at 130° C. for 3 h, cooled to rt, diluted with DCM (5 ml) and purified by Column chromatography (0-20% EtOAc/hexane; 220 g column) to obtain 1-(4-bromo-2-nitrophenyl)-3,5-dimethylpiperidine (5.03 g, 16.06 mmol, 88% yield) as an orange oil. LC/MS, m/z=314.4 (M+1). HPLC Rt=1.26 min. LC/MS (BEH C18 2.1×50 mm, 1.7 u, 0 to 100 B in 1 min with 0.5 min hold time, Flow rate=1 ml/min, detection at 254 nm, Solvent A: 100% water/0.1% TFA; Solvent B: 100% ACN/0.1% TFA).

235B.
5-Bromo-2-(3,5-dimethylpiperidin-1-yl)aniline 1-(4-Bromo-2-nitrophenyl)-3,5-dimethylpiperidine (235A) (6 g, 19.16 mmol) was taken up in EtOH (Ratio: 10.00, Volume: 60 mL) and water (Ratio: 1.000, Volume: 6 mL), zinc (12.53 g, 192 mmol) and ammonium chloride (10.25 g, 192 mmol) were added. The resulting exothermic reaction was stirred at room temperature for 30 minutes. The resulting solution turned to clear from orange color, was cooled at room temperature and filtered through a CELITE® pad, washed with additional 30 ml of DCM and the filtrate concentrated and purified by column chromatography (0-10% EtOAc/hexane; 120 g column) 5-Bromo-2-(3,5-dimethylpiperidin-1-yl)aniline (4.97 g, 17.55 mmol, 92% yield) was obtained as a light yellow oil. LC/MS, m/z=283.0 (M+1). HPLC Rt=1.01 min. LC/MS (BEH C18 2.1×50 mm, 1.7 u, 0 to 100 B in 1 min with 0.5 min hold time, Flow rate=1 ml/min, detection at 254 nm, Solvent A: 100% water/0.1% TFA; Solvent B: 100% ACN/0.1% TFA).

235C. 5-(5,5-Dimethyl-1,3,2-dioxaborinan-2-yl)-2-(3,5-dimethylpiperidin-1-yl)aniline

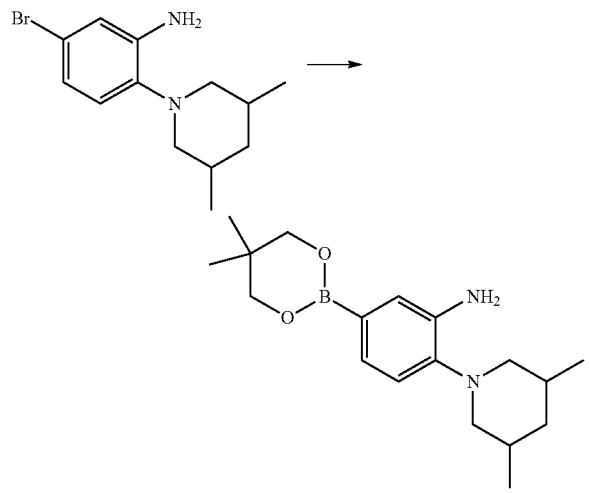

A mixture of 5-bromo-2-(3,5-dimethylpiperidin-1-yl)aniline (235B) (4.8 g, 16.95 mmol), 5,5,5',5'-tetramethyl-2,2'-bi(1,3,2-dioxaborinane) (4.98 g, 22.03 mmol), PdCl$_2$(dppf)-CH$_2$Cl$_2$ Adduct (0.372 g, 0.508 mmol) and potassium acetate (4.99 g, 50.8 mmol) in DMSO (Volume: 30 mL) was evacuated and filled with nitrogen three times, then heated at 80° C. for 4 h. The completed reaction was cooled to rt and the reaction mixture loaded on a silica gel plug (300 g), and washed with (20% EtOAc/hexane). The resulting organic solution was concentrated and redissolved in DCM (5 ml), and purified by column chromatography (0-20% EtOAc/hexane; 120 g column) 5-(5,5-Dimethyl-1,3,2-dioxaborinan-2-yl)-2-(3,5-dimethylpiperidin-1-yl)aniline (4.07 g, 12.87 mmol, 76% yield) was obtained as a light brown solid. LC/MS, m/z=249.0 (M+1). HPLC Rt=0.64 min. (boronic acid) LC/MS (BEH C18 2.1×50 mm, 1.7 u, 0 to 100 B in 1 min with 0.5 min hold time, Flow rate=1 ml/min, detection at 254 nm, Solvent A: 100% water/0.1% TFA; Solvent B: 100% ACN/0.1% TFA).

235D. 4-(3,5-Dimethylpiperidin-1-yl)-2'-(2-trityl-2H-tetrazol-5-yl)biphenyl-3-amine

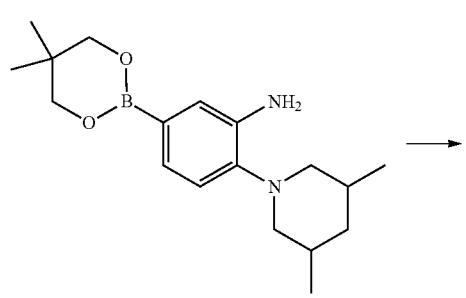

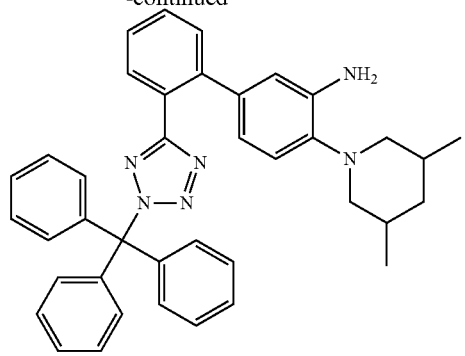

A mixture of toluene (Ratio: 2.250, Volume: 18 mL) and water (Ratio: 1.000, Volume: 8 mL) was degassed by purges with nitrogen (3×). 5-(5,5-Dimethyl-1,3,2-dioxaborinan-2-yl)-2-(3,5-dimethylpiperidin-1-yl)aniline (235C) (3 g, 9.49 mmol), 5-(2-bromophenyl)-2-trityl-2H-tetrazole (4.03 g, 8.62 mmol) and sodium carbonate (1.828 g, 17.25 mmol) were added, and the reaction mixture was purged (bubble) with nitrogen. Pd(Ph$_3$P)$_4$ (0.997 g, 0.862 mmol) was added at last. This mixture was degassed (3×) and the reaction mixture was heated at 80° C. under a nitrogen atmosphere for 14 h, cooled to room temperature, and the resulting mixture was extracted with DCM (3×60 ml), washed with water and brine, dried over anhydrous Na$_2$SO$_4$ and the residue was purified by column chromatography (120 g, 0% to 30% EtOAc in hexane) to obtain the product 4-(3,5-dimethylpiperidin-1-yl)-2'-(2-trityl-2H-tetrazol-5-yl)biphenyl-3-amine (3.31 g, 5.60 mmol, 65.0% yield) as a light yellow solid. LC/MS, m/z=591.3 (M+1). HPLC Rt=1.18 min. LC/MS (BEH C18 2.1×50 mm, 1.7 u, 0 to 100 B in 1 min with 0.5 min hold time, Flow rate=1 ml/min, detection at 254 nm, Solvent A: 100% water/0.1% TFA; Solvent B: 100% ACN/0.1% TFA).

235E. 1-(4-((3,5-Dimethylpiperidin-1-yl)-2'-(1H-tetrazol-5-yl)-[1,1'-biphenyl]-3-yl)-3-(p-tolyl)urea

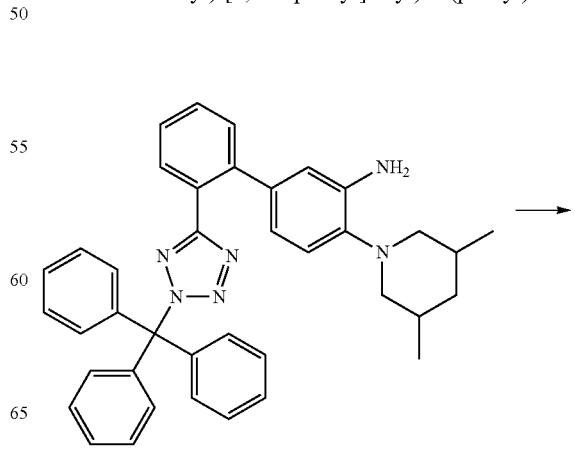

-continued

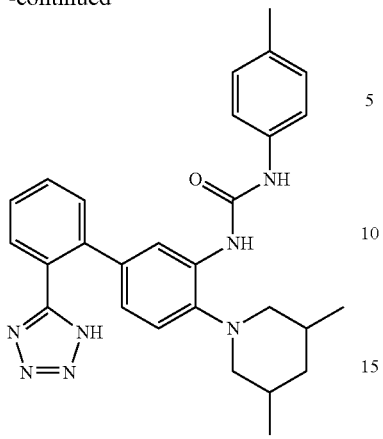

To a solution of 4-(3,5-dimethylpiperidin-1-yl)-2'-(2-trityl-2H-tetrazol-5-yl)-[1,1'-biphenyl]-3-amine (235D) (59 mg, 0.100 mmol) in THF (1 mL) was added 1-isocyanato-4-methylbenzene (0.016 mL, 0.130 mmol). The solution was stirred 2 h at RT. 4N HCl in dioxane (0.100 mL, 0.399 mmol) was added to the reaction mixture and the resulting mixture was heated at 50° C. for 10 min, cooled to room temperature and concentrated. The residue was purified by HPLC, Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 20-100% B over 25 minutes, then a 5-minute hold at 100% B; Flow: 20 mL/min. Fractions containing the desired product were combined and dried via centrifugal evaporation to obtain 1-(4-((3,5-dimethylpiperidin-1-yl)-2'-(1H-tetrazol-5-yl)-[1,1'-biphenyl]-3-yl)-3-(p-tolyl)urea (37.8 mg, 78% yield). LC/MS, m/z=482.5 (M+1). HPLC Rt=0.94 min. LC/MS (BEH C18 2.1×50 mm, 1.7 u, 0 to 100 B in 1 min with 0.5 min hold time, Flow rate=1 ml/min, detection at 254 nm, Solvent A: 100% water/0.1% TFA; Solvent B: 100% ACN/0.1% TFA). $^1$H NMR (500 MHz, methanol-$d_4$) δ 8.01-7.94 (m, 1H), 7.75-7.70 (m, 1H), 7.68-7.62 (m, 3H), 7.60-7.50 (m, 2H), 7.32 (d, J=8.4 Hz, 2H), 7.15 (d, J=8.4 Hz, 2H), 3.01 (s, 2H), 2.94-2.80 (m, 2H), 2.32 (s, 3H), 2.21-1.92 (m, 2H), 1.59-1.39 (m, 2H), 1.16-0.86 (m, 6H).

Examples 236 and 237

Following the procedure of Example 235, Part E, employing the R$^9$NCO substituent listed below, the following compounds were obtained.

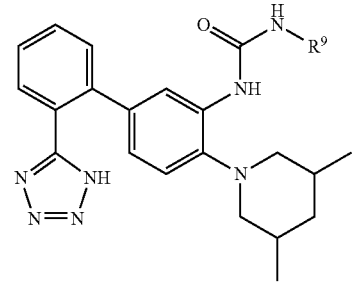

| Example No. | R$^9$ | [M + H]$^+$ | HPLC RT |
|---|---|---|---|
| 236 | 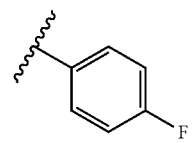 | 486.4 | 0.92$^v$ |
| 237 | F (2-fluorophenyl) | 486.4 | 0.91$^v$ |

Example 238

1,1-(4-(Diisobutylamino)-2'-(1H-tetrazol-5-yl)biphenyl-3-yl)-3-(pyridin-2-yl)urea

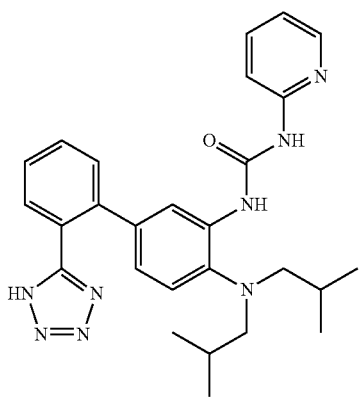 [SMILES: CC(C)CN(CC(C)C)c1ccc(-c2ccccc2-c2nnn[nH]2)cc1NC(=O)Nc1ccccn1]

238A. 4-(5,5-Dimethyl-1,3,2-dioxaborinan-2-yl)-N1,N1-diisobutylbenzene-1,2-diamine

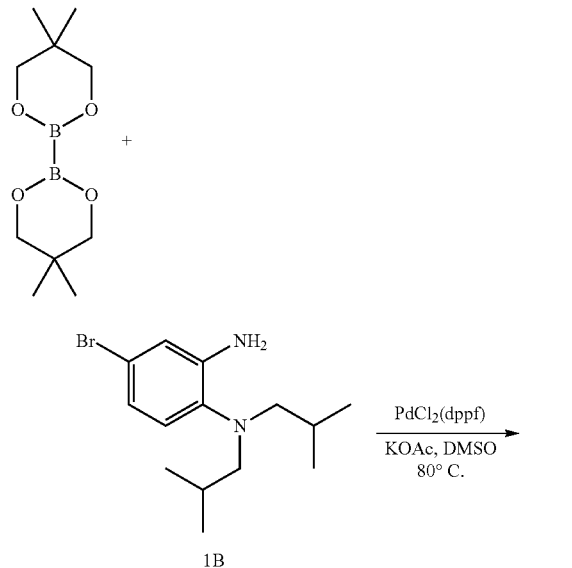

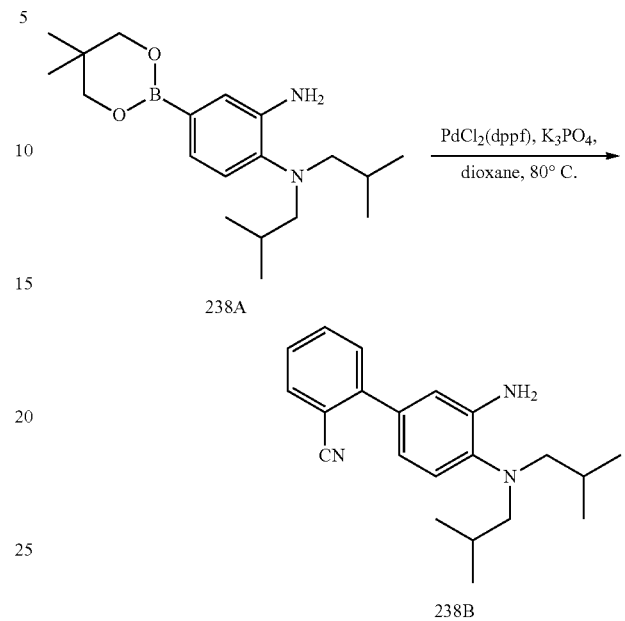

4-Bromo-N1,N1-diisobutylbenzene-1,2-diamine (15.0 g, 50.1 mmol), 5,5,5',5'-tetramethyl-2,2'-bi(1,3,2-dioxaborinane) (20.38 g, 90.0 mmol), PdCl$_2$(dppf)-CH$_2$Cl$_2$Adduct (1.842 g, 2.256 mmol), and potassium acetate (22.14 g, 226 mmol) were combined in a 250 mL RB flask, and DMSO (Volume: 150 mL) was added. The flask was evacuated and filled with argon 3×, then heated at 80° C. for 16 h. The reaction was cooled to RT diluted with ethyl acetate and filtered. The filtrate was washed with water, dried, and concentrated to afford crude solid. Chromatography on silica gel (EtOAc-hexanes gradient) afforded 4-(5,5-dimethyl-1,3,2-dioxaborinan-2-yl)-N1,N1-diisobutylbenzene-1,2-diamine (13.0 g, 78% yield) as a white solid. MS(ES): m/z=265. (These mass spectra correspond to [M+H]$^+$ for free boronic acid. No significant [M+H]$^+$ is seen for the parent compound.) $^1$H NMR (400 MHz, DMSO-d$_6$) δ ppm 7.07 (d, 1H, J=1.2 Hz), 6.92-6.96 (m, 2H), 4.66 (brs, 2H), 3.70 (s, 4H), 2.57 (d, 4H, J=7.2 Hz), 1.66-1.69 (m, 2H), 0.94 (s, 6H), 0.84 (d, 12H, J=6.8 Hz).

238B. 3'-Amino-4'-(diisobutylamino)biphenyl-2-carbonitrile

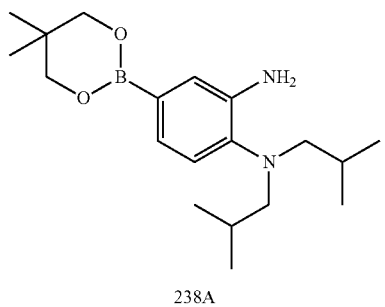

4-(5,5-Dimethyl-1,3,2-dioxaborinan-2-yl)-N1,N1-diisobutylbenzene-1,2-diamine (238A) (7.5 g, 22.57 mmol), 2-bromobenzonitrile (4.93 g, 27.1 mmol), PdCl$_2$(dppf)-CH$_2$Cl$_2$Adduct (3.69 g, 4.51 mmol) and potassium phosphate, tribasic (14.37 g, 67.7 mmol) were added to a 250 mL RB flask, which was evacuated and filled with argon 3× followed by 2 mL of dioxane. The reaction mixture was heated at 80° C. for 16 h. The reaction was cooled to room temperature, concentrated in dioxane, diluted with ethyl acetate, washed with water, dried, and concentrated to afford crude solid. Chromatography on silica gel (EtOAc-hexanes gradient) afforded 3'-amino-4'-(diisobutylamino)biphenyl-2-carbonitrile (6.2 g, 85.0% yield). $^1$H NMR (400 MHz, CDCl$_3$) δ ppm 7.72 (dd, 1H, J=8.0, 1.2 Hz), 7.58-7.61 (m, 1H), 7.50 (dd, 1H, J=8.0, 1.2 Hz), 7.37-7.39 (m, 1H), 7.14 (t, 1H), 7.13-7.15 (m, 1H), 6.89-6.92 (m, 2H), 4.12 (2H, brs), 2.65 (d, 4H, J=7.2 Hz), 1.77-1.84 (m, 2H), 0.92 (d, 12H, J=6.4 Hz). MS(ES): m/z=322.2 [M+H]$^+$.

238C. N4,N4-Diisobutyl-2'-(1H-tetrazol-5-yl)biphenyl-3,4-diamine

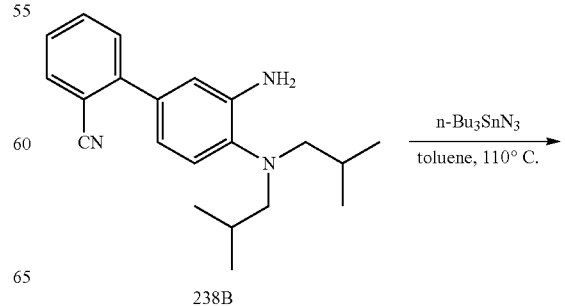

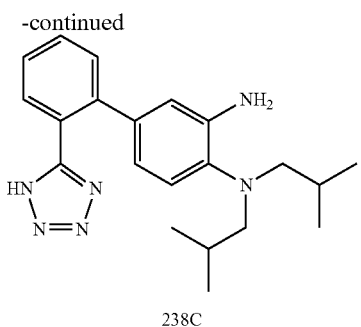

238C

3′-Amino-4′-(diisobutylamine)biphenyl-2-carbonitrile (238B) (3.0 g, 9.33 mmol) and azidotributyltin (17.90 mL, 65.33 mmol) in toluene (60 mL) were heated at 110° C. for 40 hours, cooled to room temperature and washed with 10% KF aqueous solution, dried and concentrated to afford crude liquid product. Chromatography on silica gel (EtOAc-hexanes gradient) afforded N4,N4-diisobutyl-2′-(1H-tetrazol-5-yl) biphenyl-3,4-diamine (3.5 g) as yellow oil. MS(ES): m/z=365.2 [M+H]$^+$.

238. 1-(4-(Diisobutylamino)-2′-(1H-tetrazol-5-yl)-[1,1′-biphenyl]-3-yl)-3-(pyridin-2-yl)urea

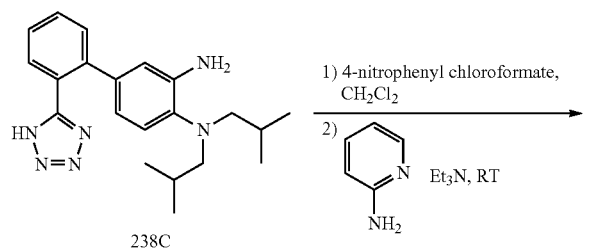

238

To the stirred solution of N4,N4-diisobutyl-2′-(1H-tetrazol-5-yl)biphenyl-3,4-diamine (238C) (500 mg, 1.372 mmol) in DCM (3.0 mL) was added 4-nitrophenyl carbonochloridate (332 mg, 1.646 mmol) dropwise and refluxed for 1 h. Reaction progress was detected by TLC and LCMS. The reaction mixture was concentrated to afford the crude carbamate. (Note: This intermediate was carried forward for the next step without purification.) The yellow residue (4-nitrophenyl(4-(diisobutylamino)-2′-(1H-tetrazol-5-yl)-[1,1′-biphenyl]-3-yl)carbamate, 60.0 mg, 0.113 mmol) was taken up in DCE (1.0 mL). The solution was treated with Et$_3$N (0.016 mL, 0.113 mmol) then pyridin-2-amine (10.66 mg, 0.113 mmol), stirred overnight at RT, and purified by preparative HPLC. Concentration of appropriate fractions afforded 1-(4-(diisobutylamino)-2′-(1H-tetrazol-5-yl)-[1,1′-biphenyl]-3-yl)-3-(pyridin-2-yl)urea (18 mg, 32.5% yield) as an off-white solid. $^1$H NMR (400 MHz, DMSO-d$_6$) δ ppm 11.30 (brs, 1H), 9.84 (s, 1H), 8.22 (dd, 1H, J=18.4, 1.2 Hz), 7.53-7.76 (m, 5H), 7.08-7.14 (m, 2H), 6.99-7.02 (m, 1H), 6.57 (dd, 1H, J=8.4, 2.4 Hz), 2.84 (d, 4H, J=6.8 Hz), 1.67-1.73 (m, 2H), 0.80 (d, 12H, J=6.8 Hz). MS(ES): m/z=485.4 [M+H]$^+$.

Example 239

1-(4-(Diisobutylamino)-2′-(1H-tetrazol-5-yl)-[1,1′-biphenyl]-3-yl)-3-(pyrimidin-2-yl)urea

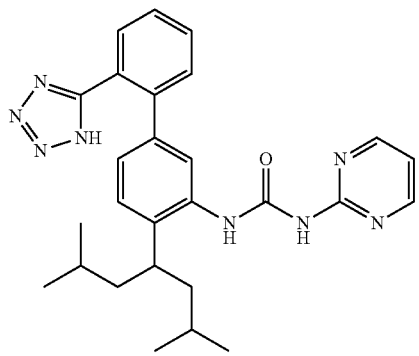 [SMILES: CC(C)CC(CC(C)C)c1ccc(-c2ccccc2-c2nnn[nH]2)cc1NC(=O)Nc1ncccn1]

239A. N4,N4-diisobutyl-2′-(2-trityl-2H-tetrazol-5-yl)-[1,1′-biphenyl]-3,4-diamine

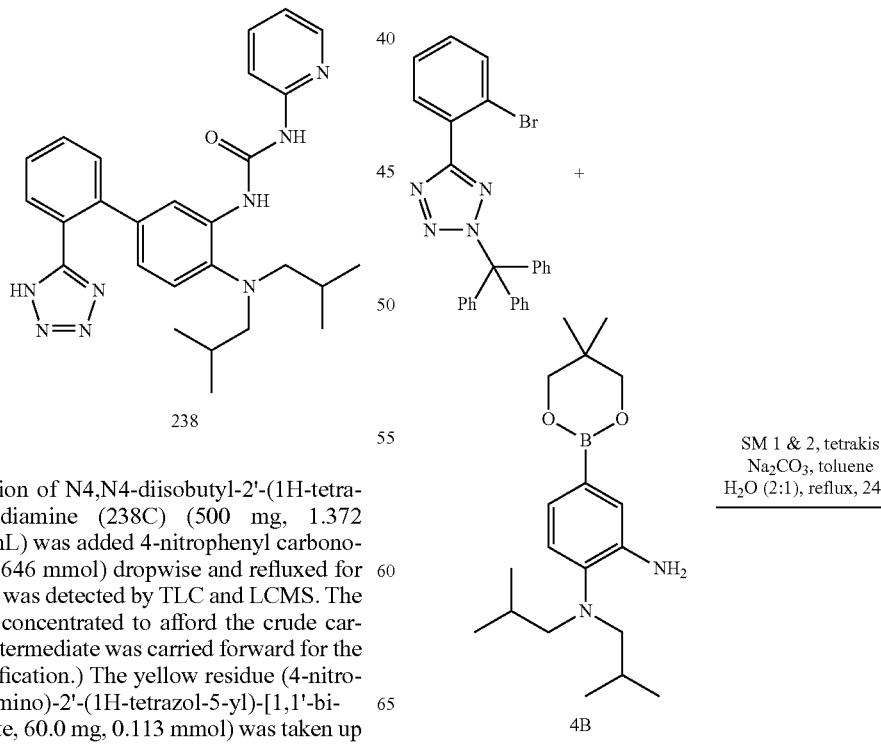

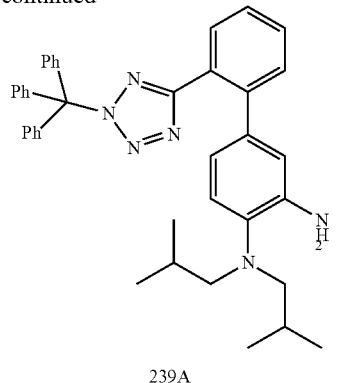

239A

A mixture of toluene (12.5 mL) and water (5.0 mL) was degassed for 10 minutes. 4-(5,5-Dimethyl-1,3,2-dioxaborinan-2-yl)-N1,N1-diisobutylbenzene-1,2-diamine (2.48 g, 7.49 mmol), 5-(2-bromophenyl)-2-trityl-2H-tetrazole (2.5 g, 5.35 mmol), sodium carbonate (1.13 g, 10.70 mmol) and tetrakis(triphenylphosphine)palladium(0) (0.371 g, 0.321 mmol) were added. This mixture was degassed under $N_2$ atmosphere and heated at 80° C. for overnight. The reaction was cooled to room temperature, concentrated in toluene, and the residue was dissolved in ethyl acetate, washed with water, dried, concentrated and purified on silica gel (EtOAc/hexane gradient) to afford N4,N4-diisobutyl-2'-(2-trityl-2H-tetrazol-5-yl)-[1,1'-biphenyl]-3,4-diamine (2.4 g) as an off-white solid. MS(ES): m/z=607.4 [M+H]+.

239B. 4-Nitrophenyl (4-(diisobutylamino)-2'-(2-trityl-2H-tetrazol-5-yl)-[1,1'-biphenyl]-3-yl)carbamate

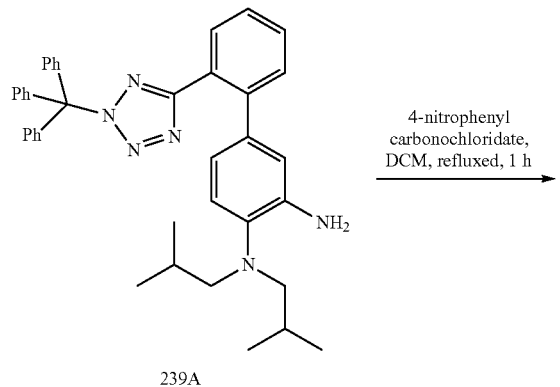

N4,N4-Diisobutyl-2'-(2-trityl-2H-tetrazol-5-yl)-[1,1'-biphenyl]-3,4-diamine (0.1 g, 0.165 mmol) and 4-nitrophenyl carbonochloridate (0.033 g, 0.165 mmol) were taken in DCM (1 mL) and refluxed for 1 h. The progress of the reaction was checked by LCMS. The solvent was removed to give 4-nitrophenyl (4-(diisobutylamino)-T-(2-trityl-2H-tetrazol-5-yl)-[1,1'-biphenyl]-3-yl)carbamate (0.110 g). MS(ES): m/z=772.2 [M+H]+.

239C. 1-(4-(Diisobutylamino)-2'-(2-trityl-2H-tetrazol-5-yl)-[1,1'-biphenyl]-3-yl)-3-(pyrimidin-2-yl) urea

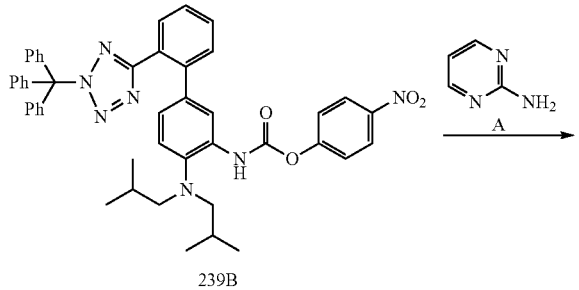

239B

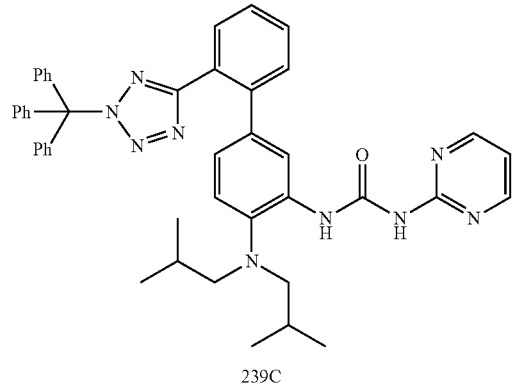

239C

To a slurry of sodium hydride (4.76 mg, 0.194 mmol) in THF (0.5 mL) was added a solution of pyrimidin-2-amine (8.87 mg, 0.093 mmol) in THF (0.5 mL) at 0° C. The reaction mixture was stirred for 15 minutes, and 4-nitrophenyl (4-(diisobutylamino)-2'-(2-trityl-2H-tetrazol-5-yl)-[1,1'-biphenyl]-3-yl)carbamate (60 mg, 0.078 mmol) in THF (1.0 mL) added. The reaction mixture was slowly brought to room temperature, and stirred for 1 h. The progress of the reaction was checked by TLC. No starting material was observed. The reaction mixture was quenched with ice cold water, extracted with ethyl acetate twice, the combined organic layer was washed with water, brine, dried over sodium sulfate and concentrated to give 1-(4-(diisobutylamino)-2'-(2-trityl-2H-tetrazol-5-yl)-[1,1'-biphenyl]-3-yl)-3-(pyrimidin-2-yl) urea (60 mg). MS(ES): m/z=728.8 [M+H]+.

239. 1-(4-(Diisobutylamino)-2'-(1H-tetrazol-5-yl)-[1,1'-biphenyl]-3-yl)-3-(pyrimidin-2-yl)urea

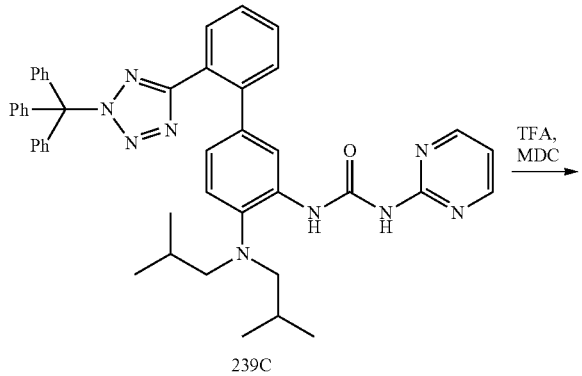

239C

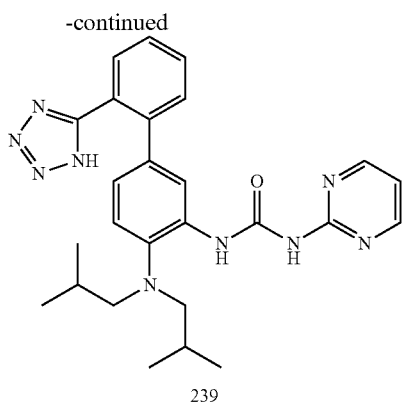

239

To a solution of 1-(4-(diisobutylamino)-2'-(2-trityl-2H-tetrazol-5-yl)-[1,1'-biphenyl]-3-yl)-3-(pyrimidin-2-yl)urea (100 mg, 0.137 mmol) in DCM (1 mL) was added TFA (0.5 mL, 6.49 mmol) at 0° C. The reaction mixture was brought to RT and stirred for 1 h. The progress of the reaction was monitored by TLC. The complete conversion of starting material was observed. The reaction mixture was purified by silica gel column chromatography (230-400 mesh) using EtOAc/pet ether gradient. The fractions were concentrated to give the 1-(4-(diisobutylamino)-2'-(1H-tetrazol-5-yl)-[1,1'-biphenyl]-3-yl)-3-(pyrimidin-2-yl)urea (50 mg; 67.6% by LCMS), which was purified by reverse phase HPLC and freeze-dried to give 1-(4-(diisobutylamino)-2'-(1H-tetrazol-5-yl)-[1,1'-biphenyl]-3-yl)-3-(pyrimidin-2-yl)urea (12 mg) as an off-white solid. MS(ES): m/z=486.2 [M+H]$^+$.

Examples 240 to 249

Following the procedure of Example 239 using appropriate trityl-tetrazole and dioxaborinane starting materials, the following compounds were prepared.

TABLE 12

| Ex. No. | Name | NR$^7$R$^8$ | R$^9$ | HPLC Ret Time | (M + H)$^+$/(M − 1) |
|---|---|---|---|---|---|
| 240 | 1-(4-(diisobutylamino)-2'-(2H-tetrazol-5-yl)-[1,1'-biphenyl]-3-yl)-3-(1-(4-fluorophenyl)-2-methylpropan-2-yl)urea | diisobutylamino | 1-(4-fluorophenyl)-2-methylpropan-2-yl | 20.07$^r$ | 558.4 |
| 241 | 1-(4-(diisobutylamino)-2'-(1H-tetrazol-5-yl)-[1,1'-biphenyl]-3-yl)-3-(3-ethynylphenyl)urea | diisobutylamino | 3-ethynylphenyl | 19.86$^r$ | 508.2 |
| 242 | 1-(4-(diisobutylamino)-2'-(1H-tetrazol-5-yl)-[1,1'-biphenyl]-3-yl)-3-(3-(prop-2-yn-1-yloxy)phenyl)urea | diisobutylamino | 3-(prop-2-yn-1-yloxy)phenyl | 19.54$^r$ | 538.4 |
| 243 | 1-(4-chloro-2,6-difluorophenyl)-3-(4-(diisobutylamino)-2'-(1H-tetrazol-5-yl)-[1,1'-biphenyl]-3-yl)urea | diisobutylamino | 4-chloro-2,6-difluorophenyl | 19.96$^r$ | 554 |

TABLE 12-continued

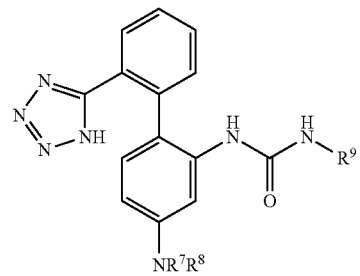

| Ex. No. Name | NR⁷R⁸ | R⁹ | HPLC Ret Time | (M + H)⁺/ (M − 1) |
|---|---|---|---|---|
| 244 1-(4-diisobutylamino)-2'-(1H-tetrazol-5-yl)-[1,1'-biphenyl]-3-yl)-3-(4-(prop-2-yn-1-yloxy)phenyl)urea | diisobutylamino | 4-(prop-2-yn-1-yloxy)phenyl | 18.91ʳ | 536.2 |
| 245 1-(4-(diisobutylamino)-2'-(1H-tetrazol-5-yl)-[1,1'-biphenyl]-3-yl)-3-isobutylurea | diisobutylamino | isobutyl | 10.80ʳ | 464.4 |
| 246 1-(4-(diisobutylamino)-2'-(1H-tetrazol-5-yl)-[1,1'-biphenyl]-3-yl)-3-isopropylurea | diisobutylamino | isopropyl | 10.27ʳ | 450.4 |
| 247 1-(4-(diisobutylamino)-2'-(1H-tetrazol-5-yl)-[1,1'-biphenyl]-3-yl)-3-(isoquinolin-5-yl)urea | diisobutylamino | isoquinolin-5-yl | 8.80ʳ | 533.2 |
| 248 2-(3-(4-(diisobutylamino)-2'-(1H-tetrazol-5-yl)-[1,1'-biphenyl]-3-yl)ureido)-N-methylbenzamide | diisobutylamino | 2-(N-methylcarbamoyl)phenyl | 18.33ʳ | 539.2 |
| 249 1-(4-(diisobutylamino)-2'-1H-tetrazol-5-yl)biphenyl-3-yl)-3-(4-trifluoromethyl)phenyl)urea | diisobutylamino | 4-(trifluoromethyl)phenyl | 23.41ʳ | 550.0 |

Example 250

1-(3-Cyano-4-fluorophenyl-3-(4-diisobutylamino)-2'-(1H-tetrazol-5-yl)-[1,1'-biphenyl]-3-yl)urea

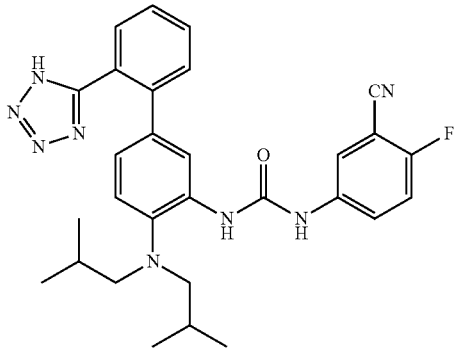

To the stirred solution of N4,N4-(diisobutylamino)-2'-(1H-tetrazol-5-yl)biphenyl-3-yl)-3,4-diamine (238E) (30 mg, 0.081 mmol) in DCM (2.0 mL) was added 2-fluoro-5-isocyanatobenzonitrile (13 mg, 0.082 mmol). The reaction was stirred at RT for 16 h. Solvent was removed in vacuo and the residue purified by prep. HPLC. The concentration of the appropriate fractions and freeze drying afforded 1-(3-cyano-4-fluorophenyl)-3-(4-(diisobutylamino)-2'-(1H-tetrazol-5-yl)-[1,1'-biphenyl]-3-yl)urea (43.0 mg, 100% yield) as an off-white solid. $^1$H NMR (400 MHz, DMSO-$d_6$) δ ppm 9.82 (s, 1H), 7.97-8.01 (m, 2H), 7.88 (d, 1H, J=2.0 Hz), 7.47-7.71 (m, 6H), 7.48 (d, 1H, J=8.4 Hz), 6.44 (dd, 1H, J=8.0, 2.0 Hz), 2.68 (d, 4H, J=6.8 Hz), 1.64-1.67 (m, 2H), 0.84 (d, 12H, J=6.4 Hz). MS(ES): m/z=527.2 [M+H]$^+$.

Synthesis of 2-fluoro-5-isocyanatobenzonitrile

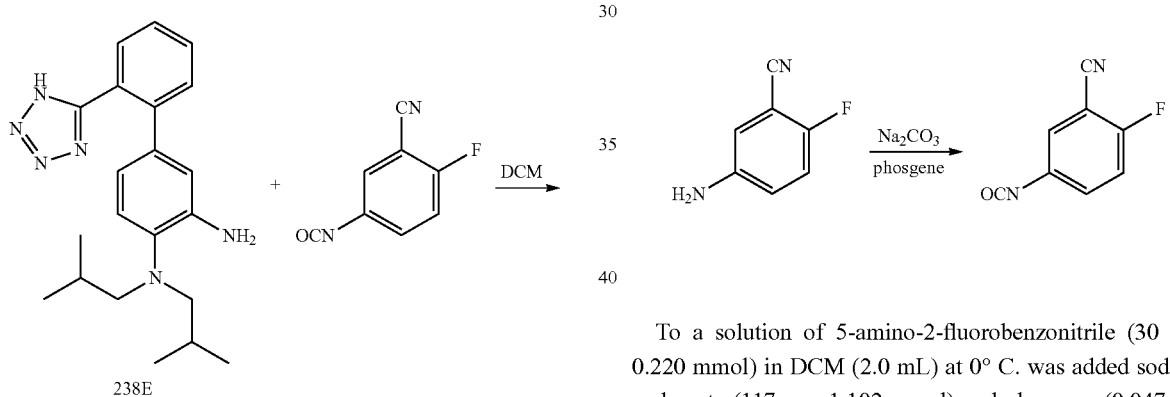

To a solution of 5-amino-2-fluorobenzonitrile (30 mg, 0.220 mmol) in DCM (2.0 mL) at 0° C. was added sodium carbonate (117 mg, 1.102 mmol) and phosgene (0.047 mL 0.441 mmol). The reaction was stirred at RT for 1 h. MS(ES): m/z=195, (These mass spectra correspond to [M+H]$^+$ for methyl carbamate of the product. No significant [M+H]$^+$ was seen for the parent compound. The above reaction mixture was filtered, concentrated under reduced pressure and used for the next step without purification.

Examples 251 to 276

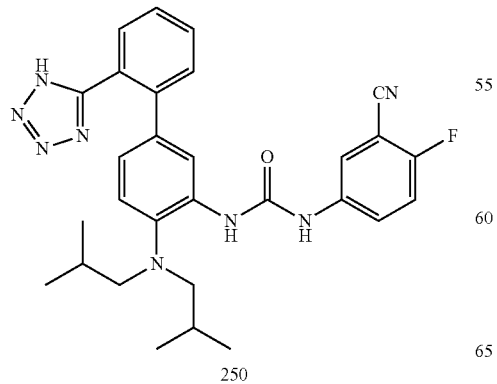

Following the procedure of Example 250 employing the appropriate R$^9$NCO, the following compounds were prepared.

TABLE 13

| Ex. No. | Name | NR⁷R⁸ | R⁹ | HPLC Ret Time | (M + H)⁺/(M − 1) |
|---|---|---|---|---|---|
| 251 | 1-(3-chloro-5-fluorophenyl)-3-(4-(diisobutylamino)-2'-(1H-tetrazol-5-yl)-[1,1'-biphenyl]-3-yl)urea | diisobutylamino | 3-chloro-5-fluorophenyl | 20.97$^t$ | 536.2 |
| 252 | 1-(4-(diisobutylamino)-2'-(1H-tetrazol-5-yl)-[1,1'-biphenyl]-3-yl)-3-(4-fluoro-3-methoxyphenyl)urea | diisobutylamino | 4-fluoro-3-methoxyphenyl | 18.81$^t$ | 532.3 |
| 253 | 1-(4-(diisobutylamino)-2'-(1H-tetrazol-5-yl)-[1,1'-biphenyl]-3-yl)-3-(3-(oxazol-5-yl)phenyl)urea | diisobutylamino | 3-(oxazol-5-yl)phenyl | 11.34$^t$ | 549.2 |
| 254 | 4-chloro-3-(3-(4-(diisobutylamino)-2'-(1H-tetrazol-5-yl)-[1,1'-biphenyl]-3-yl)ureido)benzamide | diisobutylamino | 4-chloro-3-carbamoylphenyl | 10.54$^t$ | 559 |
| 255 | 1-(4-(diisobutylamino)-2'-(1H-tetrazol-5-yl)-[1,1'-biphenyl]-3-yl)-3-(4-(oxazol-5-yl)phenyl)urea | diisobutylamino | 4-(oxazol-5-yl)phenyl | 18.21$^t$ | 549.2 |
| 256 | 1-(2-(1H-1,2,4-triazol-1-yl)phenyl)-3-(4-(diisobutylamino)-2'-(1H-tetrazol-5-yl)-[1,1'-biphenyl]-3-yl)urea | diisobutylamino | 2-(1H-1,2,4-triazol-1-yl)phenyl | 10.81$^t$ | 551.3 |
| 257 | 1-(3-azidophenyl)-3-(4-(diisobutylamino)-2'-(1H-tetrazol-5-yl)-[1,1'-biphenyl]-3-yl)urea | diisobutylamino | 3-azidophenyl | 20.10$^t$ | 525.4 |

TABLE 13-continued

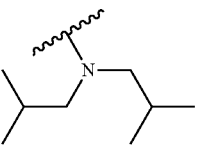

| Ex. No. | Name | NR⁷R⁸ | R⁹ | HPLC Ret Time | (M + H)⁺/ (M − 1) |
|---|---|---|---|---|---|
| 258 | 1-(3-bromo-4-fluorophenyl)-3-(4-(diisobutylamino)-2'-(1H-tetrazol-5-yl)-[1,1'-biphenyl]-3-yl)urea | 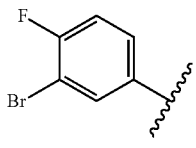 | 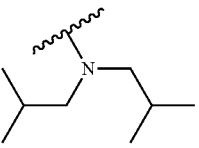 [SMILES: *N(CC(C)C)CC(C)C] | 20.54ʳ | 580.2 |
| 259 | 1-(benzo[b]thiophen-5-yl)-3-(4-(diisobutylamino)-2'-(1H-tetrazol-5-yl)-[1,1'-biphenyl]-3-yl)urea | 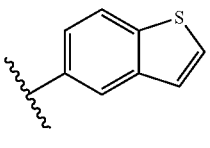 [SMILES: *c1ccc2sccc2c1] | 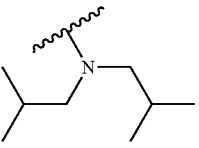 [SMILES: *N(CC(C)C)CC(C)C] | 20.10ʳ | 538.0 |
| 260 | 1-(4-cyano-2-fluorophenyl)-3-(4-(diisobutylamino)-2'-(1H-tetrazol-5-yl-[1,1'-biphenyl]-3-yl)urea | 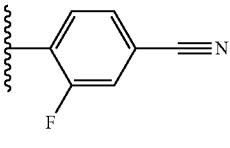 | 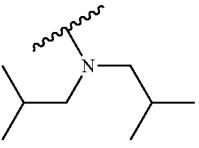 | 19.19ʳ | 527.2 |
| 261 | 1-(4-cyano-3-methoxyphenyl)-3-(4-(diisobutylamino)-2'-(1H-tetrazol-5-yl)-[1,1'-biphenyl]-3-yl)urea | 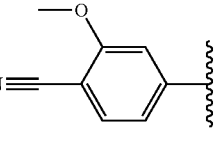 | 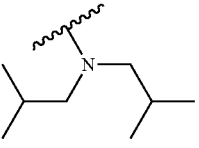 | 18.97ʳ | 537.2 |
| 262 | 1-(4-(diisobutylamino)-2'-(1H-tetrazol-5-yl)-[1,1'-biphenyl]-3-yl)-3-(3-(dimethylamino)phenyl)urea | 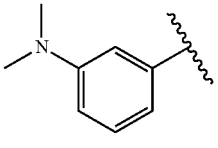 [SMILES: *c1cccc(N(C)C)c1] | 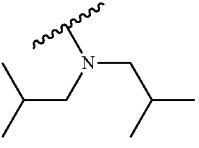 [SMILES: *N(CC(C)C)CC(C)C] | 9.61ʳ | 527.2 |
| 263 | 1-(2,3-difluorophenyl)-3-(4-(diisobutylamino)-2'-(1H-tetrazol-5-yl)-[1,1'-biphenyl]-3-yl)urea | 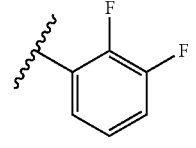 [SMILES: *c1cccc(F)c1F] | 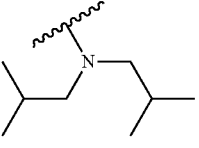 | 19.62ʳ | 520.2 |
| 264 | 1-(4-(diisobutylamino)-2'-(1H-tetrazol-5-yl)-[1,1'-biphenyl]-3-yl)-3-(2-fluoro-4-methylphenyl)urea | 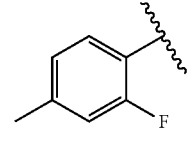 [SMILES: *c1ccc(C)cc1F] | 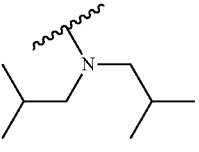 [SMILES: *N(CC(C)C)CC(C)C] | 19.68ʳ | 516.2 |
| 266 | 3-(3-(4-(diisobutylamino)-2'-(1H-tetrazol-5-yl)-[1,1'-biphenyl]-3-yl)ureido)benzenesulfonamide | 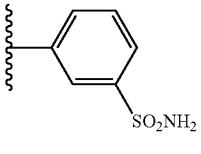 [SMILES: *c1cccc(S(N)(=O)=O)c1] | | 10.42ʳ | 563.2 |

TABLE 13-continued

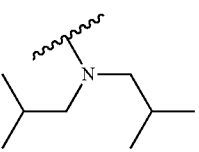 [SMILES: *N(CC(C)C)CC(C)C]

| Ex. No. | Name | NR⁷R⁸ | R⁹ | HPLC Ret Time | (M + H)⁺/ (M − 1) |
|---|---|---|---|---|---|
| 267 | 1-(3-(1H-imidazol-1-yl)phenyl)-3-(4-(diisobutylamino)-2'-(1H-tetrazol-5-yl)-[1,1'-biphenyl]-3-yl)urea | 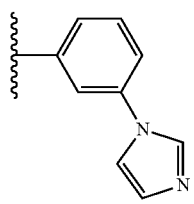 [SMILES: *c1cccc(-n2ccnc2)c1] | 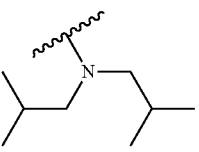 | 9.49$^t$ | 550.4 |
| 268 | 1-(cyclohexylmethyl)-3-(4-(diisobutylamino)-2'-(1H-tetrazol-5-yl)-[1,1'-biphenyl]-3-yl)urea | 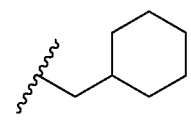 [SMILES: *CC1CCCCC1] | 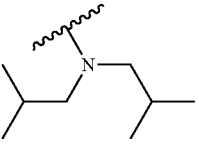 [SMILES: *N(CC(C)C)CC(C)C] | 20.03$^t$ | 502.2 |
| 269 | 1-(4-(diisobutylamino)-2'-(2H-tetrazol-5-yl)-[1,1'-biphenyl]-3-yl)-3-(2-(prop-2-yn-1-yloxy)phenyl)urea | 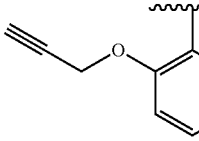 | 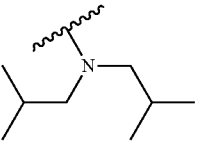 | 19.71$^t$ | 538.4 |
| 270 | 2-(4-(diisobutylamino)-2'-(1H-tetrazol-5-yl)-[1,1'-biphenyl]-3-yl)-3-(2-(piperidin-1-yl)phenyl)urea | 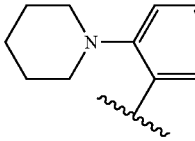 | 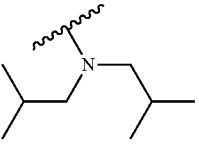 | 18.26$^t$ | 567.4 |
| 271 | 1-(4-(diisobutylamino)-2'-(1H-tetrazol-5-yl)-[1,1'-biphenyl]-3-yl)-3-(4-fluoro-3-(trifluoromethyl)phenyl)urea | 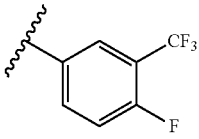 [SMILES: *c1ccc(F)c(C(F)(F)F)c1] | 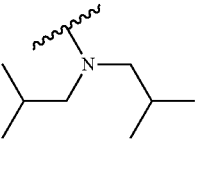 [SMILES: *N(CC(C)C)CC(C)C] | 20.47$^t$ | 570.2 |
| 272 | 1-(4-(diisobutylamino)-2'-(1H-tetrazol-5-yl)-[1,1'-biphenyl]-3-yl)-3-(4-fluoro-2-isopropoxyphenyl)urea | 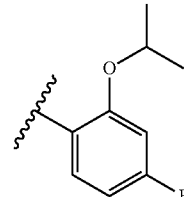 | 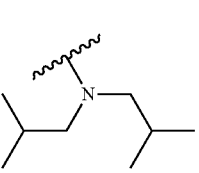 [SMILES: *N(CC(C)C)CC(C)C] | 20.69$^t$ | 560.2 |
| 273 | 1-(4-(diisobutylamino)-2'-(1H-tetrazol-5-yl)-[1,1'-biphenyl]-3-yl)-3-(3-(trifluoromethoxy)phenyl)urea | 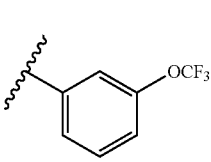 [SMILES: *c1cccc(OC(F)(F)F)c1] | | 20.38$^t$ | 568.2 |

TABLE 13-continued

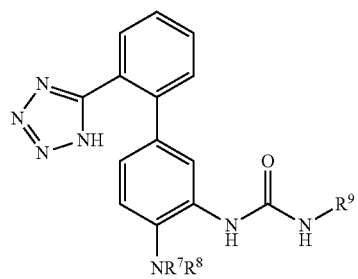

| Ex. No. Name | NR⁷R⁸ | R⁹ | HPLC Ret Time | (M + H)⁺/ (M − 1) |
|---|---|---|---|---|
| 274 1-(2-cyclopropylphenyl)-3-(4-(diisobutylamino)-2'-(1H-tetrazol-5-yl)-[1,1'-biphenyl]-3-yl)urea | diisobutylamino | 2-cyclopropylphenyl | 20.70$^t$ | 524.2 |
| 275 1-(4-(diisobutylamino)-2'-(1H-tetrazol-5-yl)-[1,1'-biphenyl]-3-yl)-3-(3-fluoro-2-hydroxyphenyl)urea | diisobutylamino | 3-fluoro-2-hydroxyphenyl | 17.98$^t$ | 516.2 |
| 276 1-(2,3-dihydro-1H-inden-4-yl)-3-(4-(diisobutylamino)-2'-(1H-tetrazol-5-yl)-[1,1'-biphenyl]-3-yl)urea | diisobutylamino | 2,3-dihydro-1H-inden-4-yl | 20.12$^t$ | 524.2 |

The urea analogs of Examples 277 to 279 were prepared by the following procedure.

TABLE 14

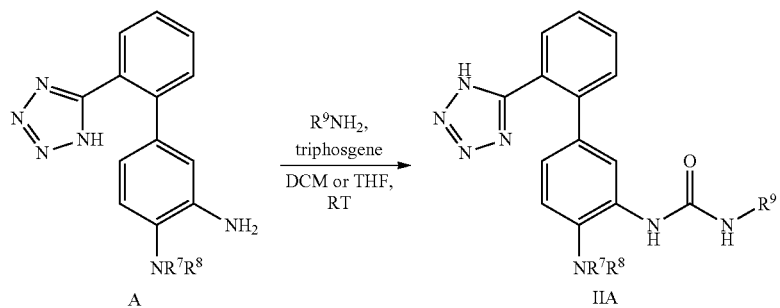

| Ex. No. Name | NR⁷R⁸ | R⁹ | HPLC Ret Time | (M + H)⁺/ (M − 1) |
|---|---|---|---|---|
| 277 1-(4-(diisobutylamino)-2'-(1H-tetrazol-5-yl)-[1,1'-biphenyl]-3-yl)-3-(2-ethynylphenyl)urea | diisobutylamino | 2-ethynylphenyl | 20.16$^t$ | 506.2 |

TABLE 14-continued

| Ex. No. | Name | NR⁷R⁸ | R⁹ | HPLC Ret Time | (M + H)⁺/(M − 1) |
|---|---|---|---|---|---|
| 278 | 1-(4-(diisobutylamino)-2'-(1H-tetrazol-5-yl)-[1,1'-biphenyl]-3-yl)-3-(4-ethynylphenyl)urea | diisobutylamino | 4-ethynylphenyl | 19.98ʳ | 506.2 |
| 279 | 1-(4-(diisobutylamino)-2'-(1H-tetrazol-5-yl)-[1,1'-biphenyl]-3-yl)-3-(4-fluoro-3-(methylsulfonyl)phenyl)urea | diisobutylamino | 4-fluoro-3-(methylsulfonyl)phenyl | 18.02ʳ | 578.2 |

The urea analogs of Examples 280 to 287 were prepared using the method described herein, i.e., the preparation of 2 from 2A, from aniline intermediates A and the appropriate isocyanates R⁹NCO.

TABLE 15

| Ex. No. | Name | NR⁷R⁸ | R⁹ | HPLC Ret Time | (M + H)⁺/(M − 1) |
|---|---|---|---|---|---|
| 280 | 1-(2-(difluoromethoxy)phenyl)-3-(4-(diisobutylamino)-2'-(1H-tetrazol-5-yl)biphenyl-3-yl)urea | diisobutylamino | 2-(OCF₂)phenyl | 19.84ʳ | 550.3 |

TABLE 15-continued

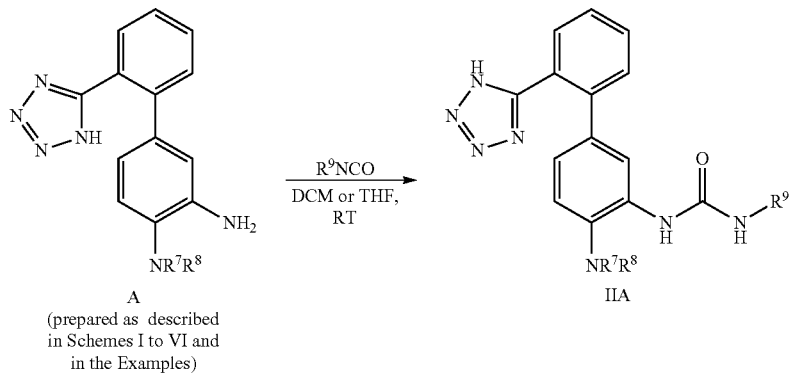

A
(prepared as described in Schemes I to VI and in the Examples)

IIA

| Ex. No. Name | NR⁷R⁸ | R⁹ | HPLC Ret Time | (M + H)⁺/ (M − 1) |
|---|---|---|---|---|
| 281 1-(4-(diisobutylamino)-2'-(1H-tetrazol-5-yl)biphenyl-3-yl)-3-(2-methoxyphenyl)urea | diisobutylamino | 2-methoxyphenyl | 19.27$^t$ | 514.3 |
| 282 1-(4-(diisobutylamino)-2'-(1H-tetrazol-5-yl)-[1,1'-biphenyl]-3-yl)-3-(2,4,6-trifluorophenyl)urea | diisobutylamino | 2,4,6-trifluorophenyl | 18.89$^t$ | 536.2 |
| 283 1-(2,6-difluorophenyl)-3-(4-(diisobutylamino)-2'-(2H-tetrazol-5-yl)-[1,1'-biphenyl]-3-yl)urea | diisobutylamino | 2,6-difluorophenyl | 18.72$^t$ | 518.2 |
| 284 1-(4-(diisobutylamino)-2'-(1H-tetrazol-5-yl)-[1,1'-biphenyl]-3-yl)-3-(2-fluoro-4-(methylsulfonyl)phenyl)urea | diisobutylamino | 2-fluoro-4-(SO₂Me)phenyl | 17.93$^t$ | 580.1 |
| 285 1-(4-azidophenyl)-3-(4-(diisobutylamino)-2'-(1H-tetrazol-5-yl)-[1,1'-biphenyl]-3-yl)urea | diisobutylamino | 4-azidophenyl | 19.63$^t$ | 523.2 |
| 286 1-(3-chloro-4-fluorophenyl)-3-(4-(diisobutylamino)-2'-(1H-tetrazol-5-yl)biphenyl-3-yl)urea | diisobutylamino | 3-chloro-4-fluorophenyl | 20.51$^t$ | 534.0 |

TABLE 15-continued

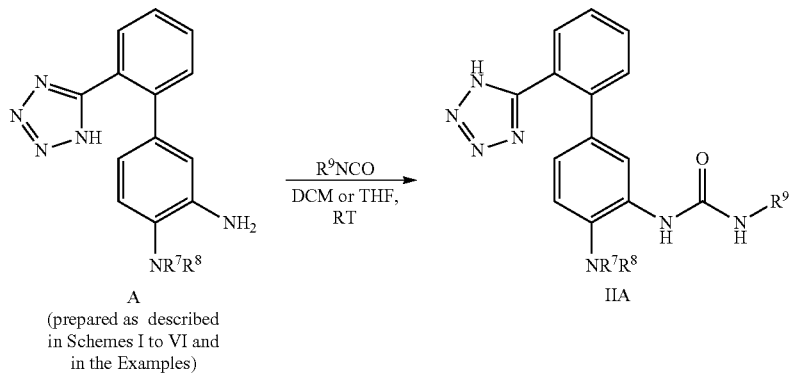

A
(prepared as described in Schemes I to VI and in the Examples)

IIA

| Ex. No. | Name | NR⁷R⁸ | R⁹ | HPLC Ret Time | (M + H)⁺/ (M − 1) |
|---|---|---|---|---|---|
| 287 | 1-(4-(diisobutylamino)-2'-(1H-tetrazol-5-yl)-[1,1'-biphenyl]-3-yl)-3-(3-fluoro-4-methylphenyl)urea | (diisobutylamino group) | (3-fluoro-4-methylphenyl) | 19.75ʳ | 516.2 |

Example 288

1-(4-(Diisobutylamino)-2'-(1H-tetrazol-5-yl)-[1,1'-biphenyl]-3-yl)-3-(2,4,4-trimethylpentan-2-yl)urea

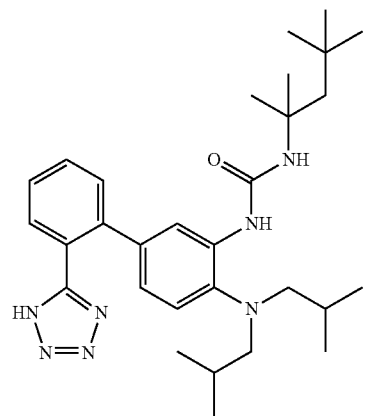

+

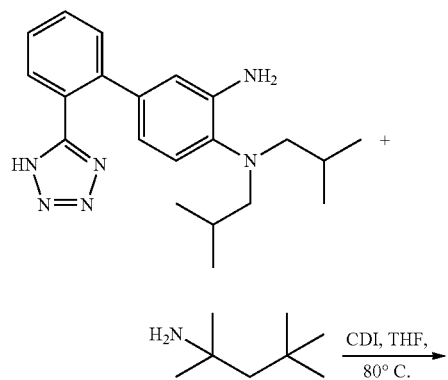

CDI, THF,
80° C.

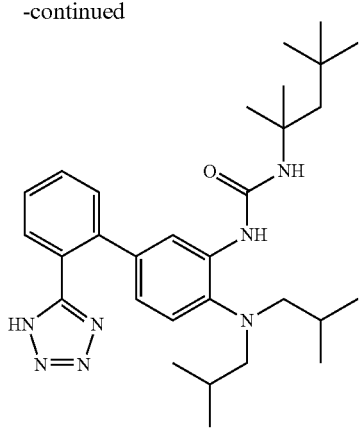

288

To a solution of N4,N4-diisobutyl-2'-(1H-tetrazol-5-yl)-[1,1'-biphenyl]-3,4-diamine (30 mg, 0.082 mmol) in THF (0.3 mL) was added 2,4,4-trimethylpentan-2-amine (15.96 mg, 0.123 mmol) and CDI (40 mg, 0.247 mmol). The reaction mixture was refluxed overnight. The progress of the reaction was checked by TLC and O-LCMS. Unreacted starting material was observed. CDI (1.0 eq) was added to the reaction mixture which was refluxed. The complete consumption of starting material was observed. The reaction mixture was diluted with EtOAc, washed with water, the organic layer collected, dried over anhydrous Na₂SO₄, filtered and excess solvent was evaporated under reduced pressure. The resultant crude material was purified by reverse phase HPLC and freeze-drying afforded 1-(4-(diisobutylamino)-2'-(1H-tetrazol-5-yl)-[1,1'-biphenyl]-3-yl)-3-(2,4,4-trimethylpentan-2-yl)urea (6.0 mg, 13.27% yield) as a pale yellow solid. LCMS MS(ES): m/z=520.2 [M+H]⁺.

Example 289

1-(4-(Benzyl(isobutyl)amino)-2'-(1H-tetrazol-5-yl)-[1,1'-biphenyl]-3-yl)-3-(p-tolyl)urea

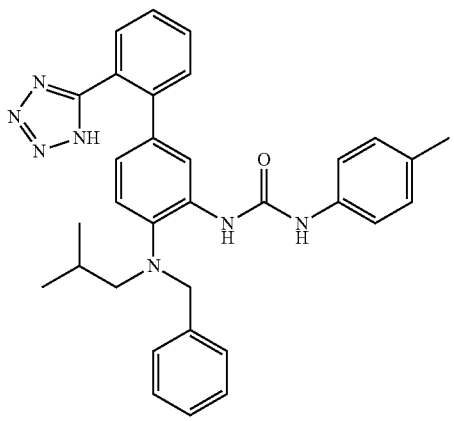 [SMILES: Cc1ccc(NC(=O)Nc2cc(-c3ccccc3-c3nnn[nH]3)ccc2N(Cc2ccccc2)CC(C)C)cc1]

The compound was prepared from N4-benzyl-N4-isobutyl-2'-(2-trityl-2H-tetrazol-5-yl) biphenyl-3, 4-diamine by the general procedure used for the conversion of A to IIA as set out prior to Examples 280 to 287 and followed by detritylation (DCM, TFA, 1 hr). MS(ES): m/z=531.2 [M+H]⁺, HPLC Tr: 19.8.

Example 290

1-(4-(Benzyl(isobutyl)amino)-2'-(1H-tetrazol-5-yl)-[1,1'-biphenyl]-3-yl)-3-(4-(trifluoromethoxy)phenyl)urea

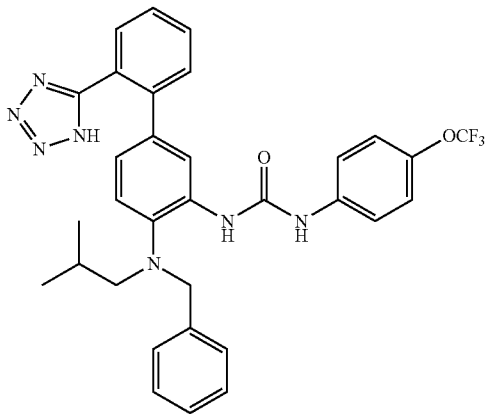 [SMILES: CC(C)CN(Cc1ccccc1)c1ccc(-c2ccccc2-c2nnn[nH]2)cc1NC(=O)Nc1ccc(OC(F)(F)F)cc1]

The compound was prepared from N4-benzyl-N4-isobutyl-2'-(2-trityl-2H-tetrazol-5-yl) biphenyl-3, 4-diamine by the general procedure used for the conversion of A to IIA as set out prior to Examples 280 to 287 and followed by detritylation (DCM, TFA, 1 hr). MS(ES): m/z=602.2 [M+H]⁺, HPLC Tr: 20.52.

Example 291

1-(4-(Benzyl(isobutyl)amino)-2'-(1H-tetrazol-5-yl)-[1,1'-biphenyl]-3-yl)-3-(4-cyclopropylphenyl)urea

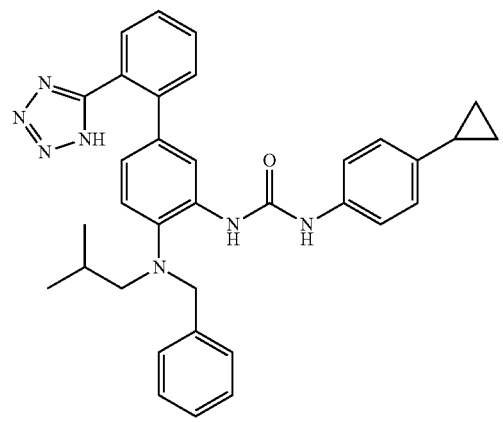 [SMILES: CC(C)CN(Cc1ccccc1)c1ccc(-c2ccccc2-c2nnn[nH]2)cc1NC(=O)Nc1ccc(C2CC2)cc1]

The compound was prepared from N4-benzyl-N4-isobutyl-2'-(2-trityl-2H-tetrazol-5-yl) biphenyl-3, 4-diamine by the general procedure used for the synthesis of Example 250 and followed by detritylation (DCM, TFA, 1 hr). MS(ES): m/z=556.2 [M–H], HPLC Tr: 21.03.

Compound 292 was prepared employing methodology described herein.

TABLE 16

| Ex No. | Name | NR⁷R⁸ | R⁹ | HPLC Ret Time | (M + H)⁺/(M − 1) |
|---|---|---|---|---|---|
| 292 | 1-(4-(benzyl(isobutyl)amino)-2'-(1H-tetrazol-5-yl)-[1,1'-biphenyl]-3-yl)-3-(p-tolyl)urea | *N(CH₂CH(CH₃)₂)(CH₂Ph)* | *4-methylphenyl* | 19.80ᶠ | 531.2 |

Example 295

1-(4-(Phenethyl(3,3,3-trifluoropropyl)amino)-2'-(1H-tetrazol-5-yl)biphenyl-3-yl)-3-(2-(trifluoromethyl)phenyl)urea

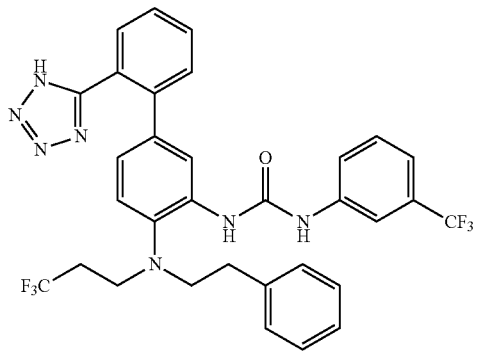 [SMILES: O=C(Nc1cccc(C(F)(F)F)c1)Nc1cc(-c2ccccc2-c2nnn[nH]2)ccc1N(CCc1ccccc1)CCC(F)(F)F]

295A. 1-(5-Bromo-2-(phenethyl(3,3,3-trifluoropropyl)amino)phenyl)-3-(2-(trifluoromethyl)phenyl)urea

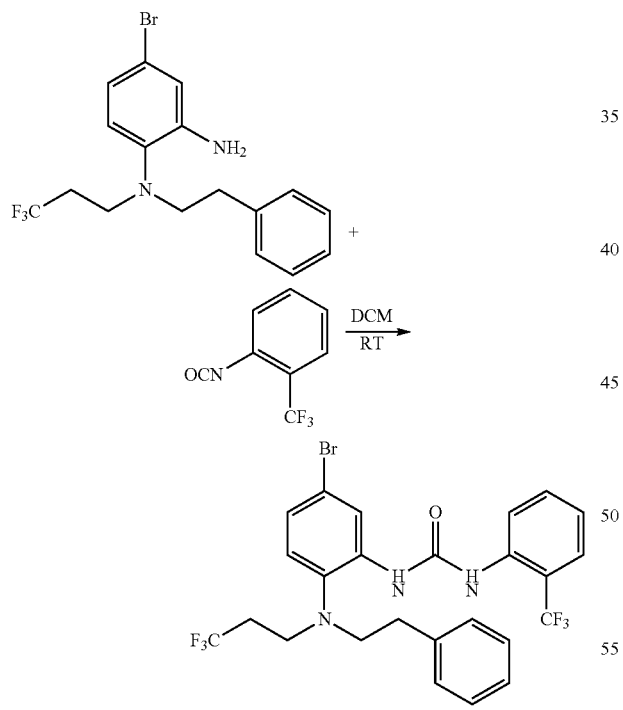

To a stirred solution of 4-bromo-N1-phenethyl-N1-(3,3,3-trifluoropropyl)benzene-1,2-diamine (30 mg, 0.077 mmol) in DCM was added 1-isocyanato-2-(trifluoromethyl)benzene (17 mg, 0.093 mmol). The reaction mixture was stirred overnight. The reaction mixture was concentrated to give 1-(5-bromo-2-(phenethyl(3,3,3-trifluoropropyl)amino)phenyl)-3-(2-(trifluoromethyl)phenyl)urea (35 mg). MS(ES): m/z=576.1 [M+H]$^+$.

295. 1-(4-(Phenethyl(3,3,3-trifluoropropyl)amino)-2'-(1H-tetrazol-5-yl)biphenyl-3-yl)-3-(2-(trifluoromethyl)phenyl)urea Employing procedures described here, the title compound was prepared from 1-(5-bromo-2-(phenethyl(3,3,3-trifluoropropyl)amino)phenyl)-3-(2-(trifluoromethyl)phenyl)urea (295A). MS(ESI$^-$) m/z=638.2 [M−H].

Example 296

1-(4-Cyclopropyl-3-fluorophenyl)-3-(4-phenethyl(3,3,3-trifluoropropyl)amino)-2'-(1H-tetrazol-5-yl)biphenyl-3-yl)urea

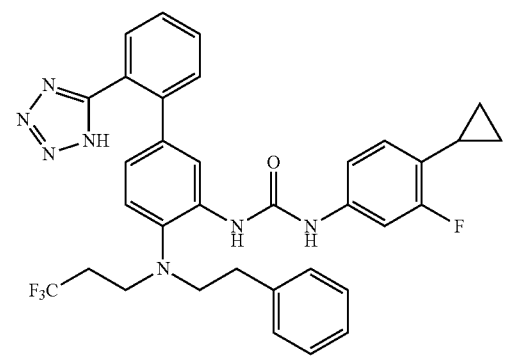 [SMILES: O=C(Nc1ccc(C2CC2)c(F)c1)Nc1cc(-c2ccccc2-c2nnn[nH]2)ccc1N(CCc1ccccc1)CCC(F)(F)F]

296A. 1-(5-Bromo-2-(phenethyl(3,3,3-trifluoropropyl)amino)phenyl)-3-(4-cyclopropyl-3-fluorophenyl)urea

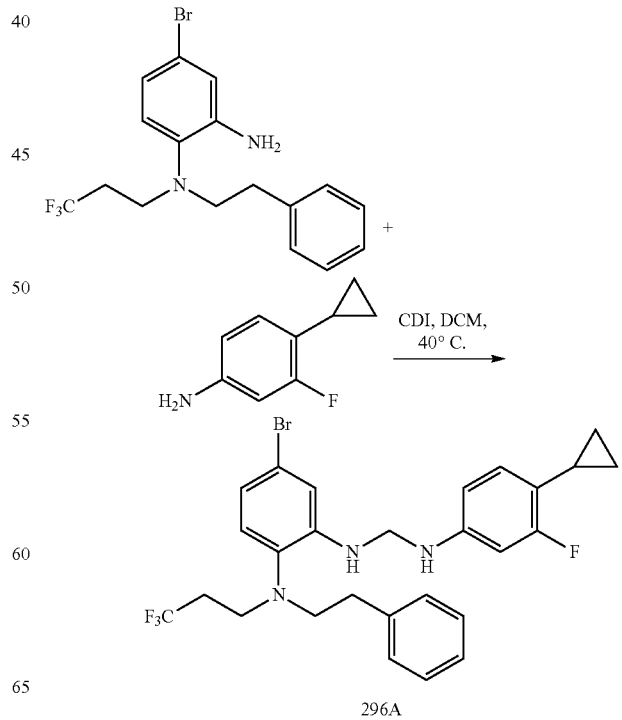

To a stirred solution of 4-bromo-N1-phenethyl-N1-(3,3,3-trifluoropropyl)benzene-1,2-diamine (30 mg, 0.077 mmol) in DCM added 4-cyclopropyl-3-fluoroaniline (14 mg, 0.093 mmol) and CDI (25 mg, 0.155 mmol). The reaction mixture was heated at 40° C. for 48 hours. The reaction mixture was diluted with DCM and washed with water, brine solution, the organic layer dried over Na$_2$SO$_4$ and concentrated to provide 1-(5-bromo-2-(phenethyl(3,3,3-trifluoropropyl)amino)phenyl)-3-(4-cyclopropyl-3-fluorophenyl)urea (35 mg). $^1$H NMR (400 MHz, CDCl$_3$) δ ppm 8.49 (d, 1H, J=2.4 Hz), 7.36-7.40 (m, 2H), 7.21-7.31 (m, 4H), 7.12-7.15 (m, 2H), 7.06 (d, 1H, J=8.4 Hz), 6.81-6.90 (m, 2H), 3.15-3.21 (m, 4H), 2.72-2.76 (m, 2H), 2.01-2.08 (m, 2H), 1.22-1.25 (m, 1H), 0.92-0.97 (m, 2H), 0.66-0.70 (m, 2H). MS(ES): m/z=564.2 [M+H]$^+$.

296. 1-(4-Cyclopropyl-3-fluorophenyl)-3-(4-(phenethyl(3,3,3-trifluoropropyl)amino)-2'-(1H-tetrazol-5-yl)biphenyl-3-yl)urea

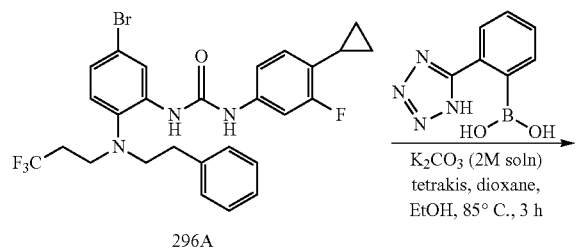

296A

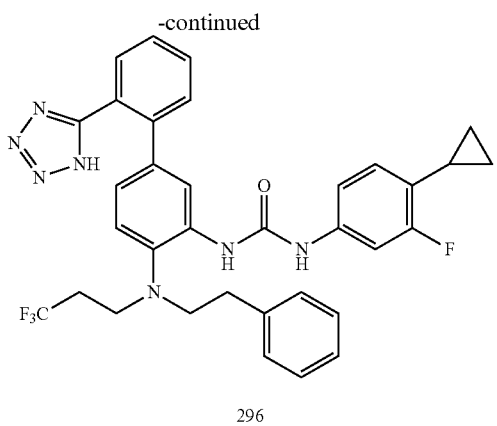

296

The title compound was prepared from 1-(5-bromo-2-(phenethyl(3,3,3-trifluoropropyl)amino)phenyl)-3-(4-cyclopropyl-3-fluorophenyl)urea (296A) as outlined above. $^1$H NMR (400 MHz, DMSO-d$_6$) δ ppm 9.53 (s, 1H), 8.38 (s, 1H), 8.15 (s, 1H), 7.56-7.72 (m, 4H), 7.43 (dd, 1H, J=12.8, 2.0 Hz), 7.41-7.45 (m, 3H), 7.13-7.17 (m, 3H), 6.89-7.00 (m, 2H), 6.62 (dd, 1H, J=8.4, 2.0 Hz), 3.15-3.22 (m, 4H), 2.51-2.63 (m, 2H), 2.33-2.39 (m, 2H), 1.93-1.97 (m, 1H), 0.89-0.93 (m, 2H), 0.65-0.67. MS(ES): m/z=630.2 [M+H]$^+$.

Examples 297 to 304

The following compounds were prepared using the procedure shown below with the appropriate starting materials.

TABLE 17

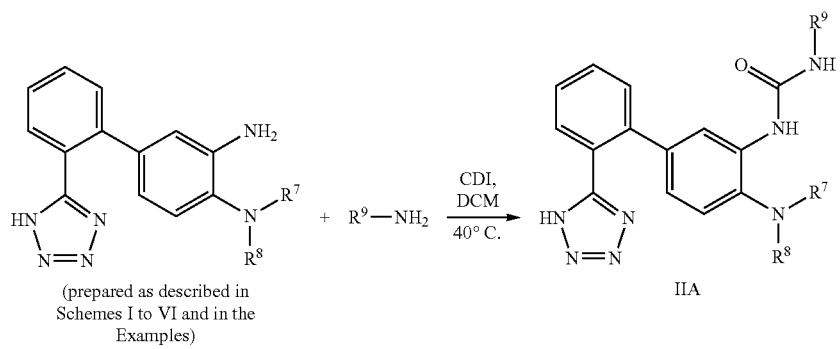

| Ex No. | Name | NR$^7$R$^8$ | R$^9$ | HPLC Ret Time | (M + H)$^+$/ (M − 1) |
|---|---|---|---|---|---|
| 297 | 1-(4-((4-chlorobenzyl)(4,4,4-trifluorobutyl)amino)-2'-(1H-tetrazol-5-yl)-[1,1'-biphenyl]-3-yl)-3-(4-cyclopropyl-3-fluorophenyl)urea | [F$_3$C-(CH$_2$)$_3$-N(-CH$_2$-C$_6$H$_4$-4-Cl)-] | [4-cyclopropyl-3-fluorophenyl] | 21.77$^t$ | 664.2 |

TABLE 17-continued

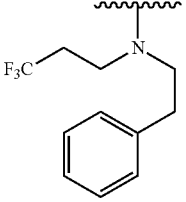 [SMILES: *N(CCc1ccccc1)CCC(F)(F)F]

(prepared as described in Schemes I to VI and in the Examples) + R⁹—NH₂ →(CDI, DCM, 40° C.) IIA

| Ex No. | Name | NR⁷R⁸ | R⁹ | HPLC Ret Time | (M + H)⁺/ (M − 1) |
|---|---|---|---|---|---|
| 298 | 1-(4-cyclopropylphenyl)-3-(4-(phenethyl(3,3,3-trifluoropropyl)amino)-2'-(1H-tetrazol-5-yl)-[1,1'-biphenyl]-3-yl)urea | 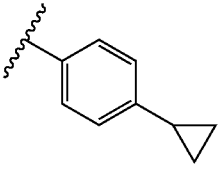 [SMILES: *c1ccc(C2CC2)cc1] | 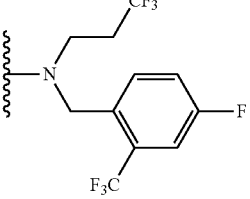 | 20.27ᵗ | 612.4 |
| 299 | 1-(4-cyclopropylphenyl)-3-(4-((4-fluoro-2-(trifluoromethyl)benzyl)(3,3,3-trifluoropropyl)amino)-2'-(1H-tetrazol-5-yl)-[1,1'-biphenyl]-3-yl)urea | 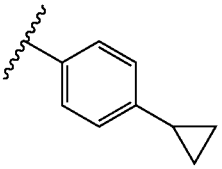 | 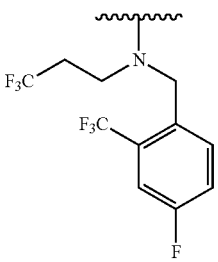 [SMILES: *N(CCC(F)(F)F)Cc1ccc(F)cc1C(F)(F)F] | 20.98ᵗ | 684.5 |
| 300 | 1-(4-((4-fluoro-2-(trifluoromethyl)benzyl)(3,3,3-trifluoropropyl)amino)-2'-(1H-tetrazol-5-yl)-[1,1'-biphenyl]-3-yl)-3-(2-fluoro-4-(trifluoromethyl)phenyl)urea | 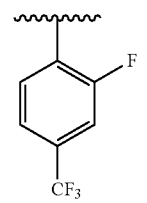 | 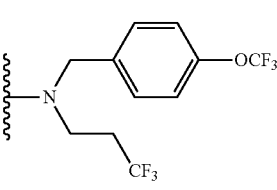 [SMILES: *N(CCC(F)(F)F)Cc1ccc(OC(F)(F)F)cc1] | 20.79ᵗ | 730.4 |
| 301 | 1-(2'-(1H-tetrazol-5-yl)-4-((4-(trifluoromethoxy)benzyl)(3,3,3-trifluoropropyl)amino)-[1,1'-biphenyl]-3-yl)-3-(2-fluoro-4-(trifluoromethyl)phenyl)urea | 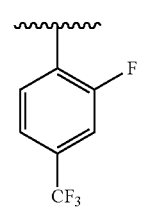 | 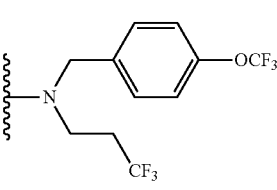 [SMILES: *N(CCC(F)(F)F)Cc1ccc(OC(F)(F)F)cc1] | 20.71ᵗ | 728.3 |

TABLE 17-continued

| Ex No. | Name | NR⁷R⁸ | R⁹ | HPLC Ret Time | (M + H)⁺/ (M − 1) |
|---|---|---|---|---|---|
| 302 | 1-(2'-(1H-tetrazol-5-yl)-4-((4-(trifluoromethoxy)benzyl)(3,3,3-trifluoropropyl)amino)-[1,1'-biphenyl]-3-yl)-3-(4-cyclopropylphenyl)urea | (4-OCF₃-benzyl)(CH₂CH₂CF₃)N– | 4-cyclopropylphenyl | 21.21ʳ | 682.5 |
| 303 | 1-(2-fluoro-4-(trifluoromethyl)phenyl)-3-(4-((pyridin-2-ylmethyl)(3,3,3-trifluoropropyl)amino)-2'-(1H-tetrazol-5-yl)-[1,1'-biphenyl]-3-yl)urea | (pyridin-2-ylmethyl)(CH₂CH₂CF₃)N– | 2-fluoro-4-(trifluoromethyl)phenyl | 16.28ʳ | 645.3 |
| 304 | 1-(4-cyclopropylphenyl)-3-(4-((pyridin-2-ylmethyl)(3,3,3-trifluoropropyl)amino)-2'-(1H-tetrazol-5-yl)-[1,1'-biphenyl]-3-yl)urea | (pyridin-2-ylmethyl)(CH₂CH₂CF₃)N– | 4-cyclopropylphenyl | 15.60ʳ | 599.4 |

Examples 305 to 307

Starting from cis-N-isobutyl-4-(trifluoromethyl)cyclohexanamine (lxy, Table 3b) and 2-fluoro-5-bromonitrobenzene the following compounds of the generic structure below with substituents specified in the table were prepared using the procedure for the conversion of 1B to Example 1.

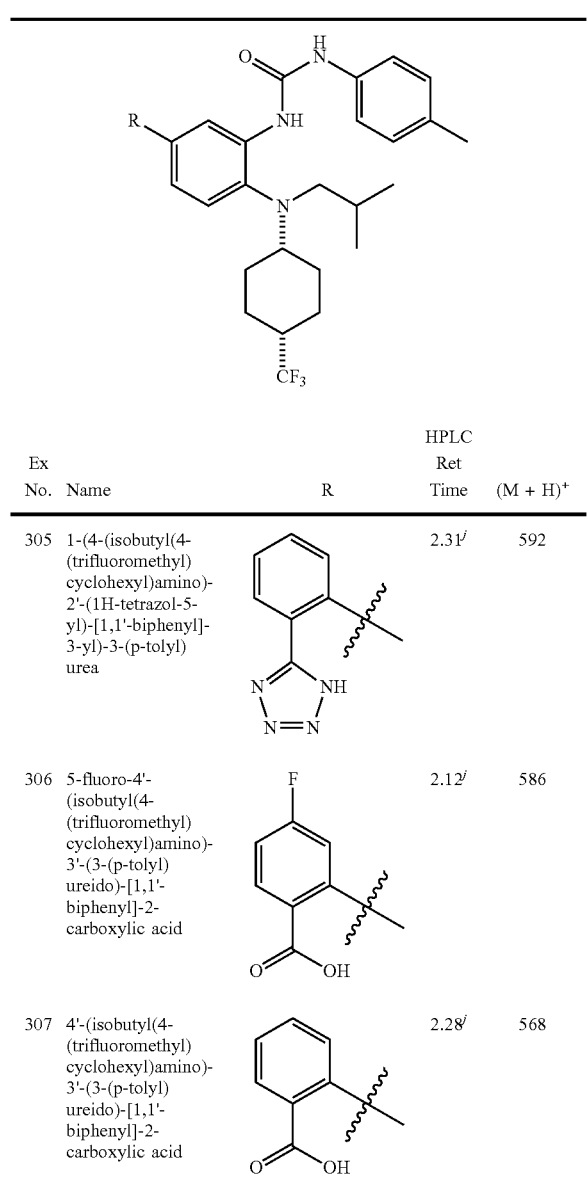

| Ex No. | Name | R | HPLC Ret Time | (M + H)+ |
|---|---|---|---|---|
| 305 | 1-(4-(isobutyl(4-(trifluoromethyl)cyclohexyl)amino)-2'-(1H-tetrazol-5-yl)-[1,1'-biphenyl]-3-yl)-3-(p-tolyl)urea | | 2.31[j] | 592 |
| 306 | 5-fluoro-4'-(isobutyl(4-(trifluoromethyl)cyclohexyl)amino)-3'-(3-(p-tolyl)ureido)-[1,1'-biphenyl]-2-carboxylic acid | | 2.12[j] | 586 |
| 307 | 4'-(isobutyl(4-(trifluoromethyl)cyclohexyl)amino)-3'-(3-(p-tolyl)ureido)-[1,1'-biphenyl]-2-carboxylic acid | | 2.28[j] | 568 |

Example 308

1-(4-(diisobutylamino)-2'-(2H-tetrazol-5-yl)-[1,1'-biphenyl]-3-yl)-3-(5-methylpyrazin-2-yl)urea

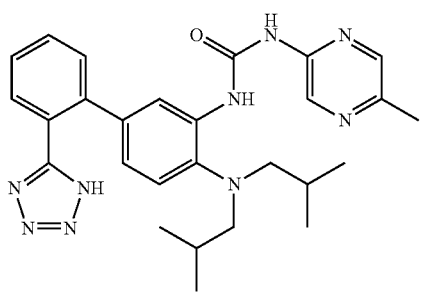

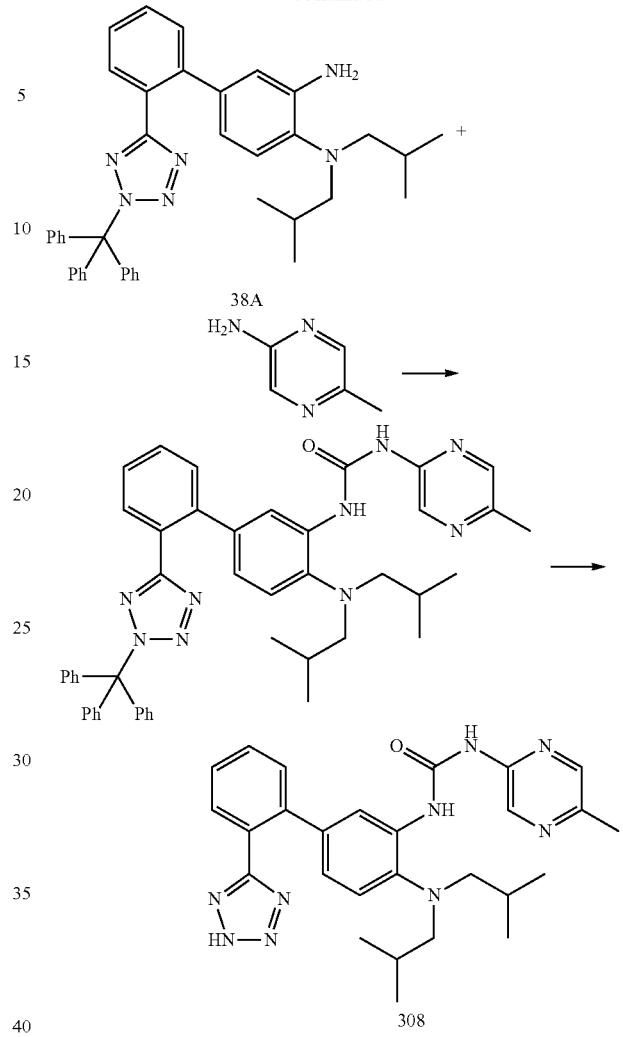

A reaction vial was charged with N4,N4-diisobutyl-2'-(2-trityl-2H-tetrazol-5-yl)-[1,1'-biphenyl]-3,4-diamine ((38A), 99.3 mg, 0.164 mmol) in dry THF (2 mL) under nitrogen. This solution was treated with 4-nitrophenyl chloroformate (36.3 mg, 0.180 mmol) and stirred for 0.5 hours. The reaction was then treated with 5-methylpyrazin-2-amine (53.6 mg, 0.491 mmol) and triethylamine (68.4 µl, 0.491 mmol). The reaction was warmed to 50° C. overnight then cooled and treated with 100 uL of 5-6 M HCl in isopropanol. This mixture was briefly warmed to 50° C., stirred overnight at RT, then concentrated and partially purified by reverse-phase HPLC (methanol-water gradient+0.1% TFA). This material was further purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-80% B over 20 minutes, then a 5-minute hold at 100% B; Flow: 20 mL/min. Fractions containing the desired product were combined and dried via centrifugal evaporation to afford 0.012 g (15%) of 1-(4-(diisobutylamino)-2'-(2H-tetrazol-5-yl)-[1,1'-biphenyl]-3-yl)-3-(5-methylpyrazin-2-yl)urea. MS(ES): m/z=500 [M+H]⁺. HPLC ret. time: 1.71$^J$.

Example 309

4'-(Diisobutylamino)-3-methyl-3'-(3-(4-(trifluoromethoxy)phenyl)ureido)-[1,1'-biphenyl]-2-carboxylic acid

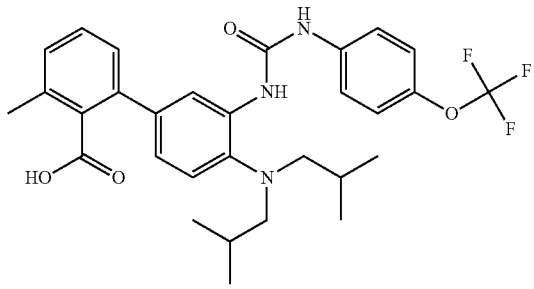 [SMILES: Cc1cccc(-c2ccc(N(CC(C)C)CC(C)C)c(NC(=O)Nc3ccc(OC(F)(F)F)cc3)c2)c1C(=O)O]

309A 4'-Fluoro-3'-nitro-[1,1'-biphenyl]-2-carboxylic acid

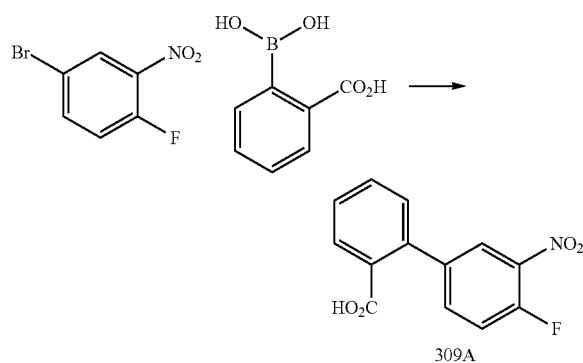

A reaction vial was charged with DMF (5.0 mL), 4-bromo-1-fluoro-2-nitrobenzene (304 mg, 1.382 mmol) and 2-boronobenzoic acid (459 mg, 2.76 mmol). Nitrogen was bubbled through the solution for 20 minutes. A solution of potassium carbonate (2764 µl, 2.76 mmol) (1.0 M solution) was added and bubbling with nitrogen continued for a few more minutes. Tetrakis(triphenylphosphine)palladium (0) (80 mg, 0.069 mmol) was added and the vial was sealed. The reaction was heated to 90° C. for 3 hours. The light orange reaction was cooled and quenched with 10% acetic acid. Some precipitate formed. The reaction was concentrated under a stream of nitrogen. The reaction was filtered and the yellow solid rinsed with water. This first crop contained product but was not pure by TLC on silica gel (1:1 ethyl acetate-hexanes+0.5% acetic acid). After standing, additional solid precipitates from the mother liquor. Filtration provided 4'-fluoro-3'-nitro-[1,1'-biphenyl]-2-carboxylic acid (153 mg, 42%) as a pale yellow solid. ¹H NMR (400 MHz, DMSO-d₆) δ 13.10-12.87 (m, 1H), 8.06 (dd, J=7.1, 2.3 Hz, 1H), 7.90 (dd, J=7.8, 1.2 Hz, 1H), 7.77 (ddd, J=8.6, 4.4, 2.4 Hz, 1H), 7.70-7.61 (m, 2H), 7.70-7.61 (m, 2H), 7.59-7.52 (m, 1H), 7.46 (dd, J=7.6, 0.9 Hz, 1H).

309B 4'-Fluoro-3-methyl-3'-nitro-[1,1'-biphenyl]-2-carboxylic acid

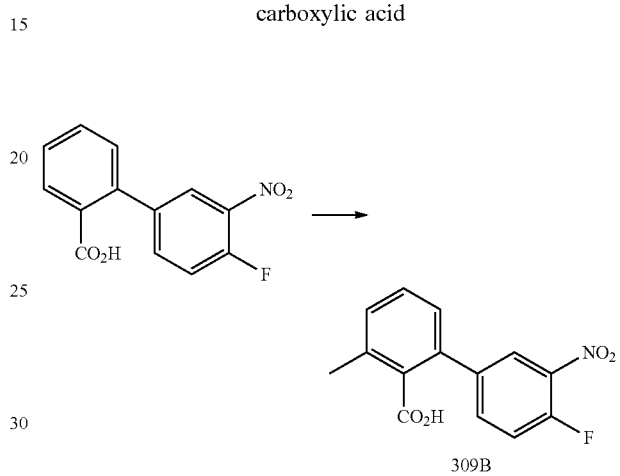

A reaction vial was charged with 4'-fluoro-3'-nitro-[1,1'-biphenyl]-2-carboxylic acid (111 mg, 0.425 mmol), palladium(II) acetate (9.5 mg, 0.042 mmol), silver carbonate (234 mg, 0.850 mmol), lithium carbonate (62.8 mg, 0.850 mmol), t-Boc-L-phenylalanine (22.6 mg, 0.085 mmol), potassium methyltrifluoroborate (155 mg, 1.275 mmol). DMF (32.9 µL, 0.425 mmol) and a stirring bar. t-Butanol (3.0 mL) was added and the vial was evacuated and filled with nitrogen three times. The vial was sealed, and the reaction was stirred for 5 minutes at ambient temperature. The reaction was then warmed to 90° C. for three days. The cooled reaction was quenched with 2 mL 1 N hydrochloric acid and sonicated. Methylene chloride was added, and the reaction was filtered. The filtrate was transferred to a separatory funnel and partitioned between methylene chloride and water. The organic phase was dried over magnesium sulfate, filtered and evaporated. The crude product was purified by RP-HPLC (methanol-water gradient+0.1% TFA). Evaporation of the appropriate fractions gave 4'-fluoro-3-methyl-3'-nitro-[1,1'-biphenyl]-2-carboxylic acid (26 mg, 0.094 mmol, 22% yield) as a yellow solid. ¹H NMR (400 MHz, DMSO-d₆) δ 13.31 (s, 1H), 8.11 (dd, J=7.1, 2.3 Hz, 1H), 7.82 (ddd, J=8.7, 4.4, 2.3 Hz, 1H), 7.70 (dd, J=11.2, 8.7 Hz, 1H), 7.49-7.43 (m, 1H), 7.38 (d, J=6.0 Hz, 1H), 7.31 (d, J=7.6 Hz, 1H), 2.38 (s, 3H). ¹⁹F NMR (376 MHz, DMSO-d₆) δ −121.18.

309C 4'-(Diisobutylamino)-3-methyl-3'-nitro-[1,1'-biphenyl]-2-carboxylic acid

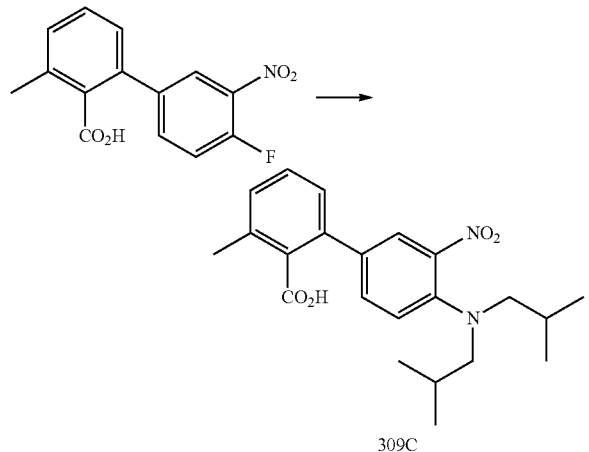

309C

4'-Fluoro-3-methyl-3'-nitro-[1,1'-biphenyl]-2-carboxylic acid (32 mg, 0.116 mmol) was dissolved in DMF (1 mL) and diisobutylamine (1 mL). The reaction was warmed to 110° C. and stirred for 4 hours. The cooled reaction was quenched with 10% acetic acid. A nice solid formed. The solid was filtered and rinsed with water. Air drying provided 4'-(diisobutylamino)-3-methyl-3'-nitro-[1,1'-biphenyl]-2-carboxylic acid (27.9 mg, 62%) as an orange solid. MS(ES): m/z=385 [M+H]+.

309D 3'-Amino-4'-(diisobutylamino)-3-methyl-[1,1'-biphenyl]-2-carboxylic acid

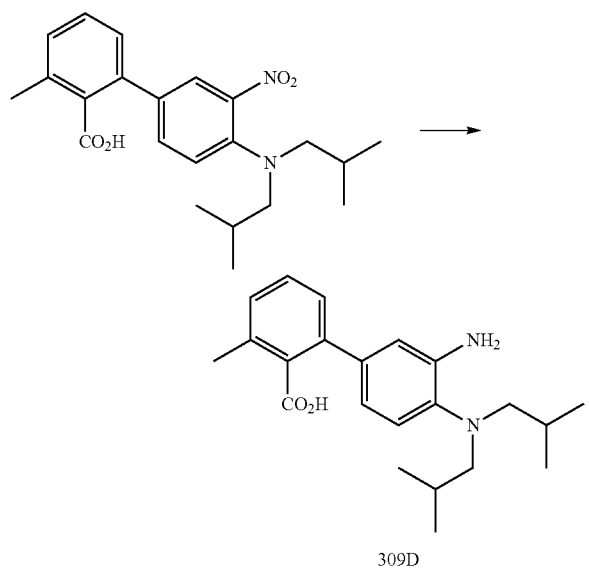

309D

A Parr bottle was charged with 4'-(diisobutylamino)-3-methyl-3'-nitro-[1,1'-biphenyl]-2-carboxylic acid (26 mg, 0.068 mmol) in ethyl acetate (ca. 10 mL). 10% Pd/C (26 mg) was added and the vessel pressurized with 45 psi hydrogen. After 3 hours, the reaction was filtered and evaporated to give 20 mg of an orange solid. This material was used without purification in the subsequent reaction. MS(ES): m/z=355 [M+H]+.

309 4'-(Diisobutylamino)-3-methyl-3'-(3-(4-(trifluoromethoxy)phenyl)ureido)-[1,1'-biphenyl]-2-carboxylic acid

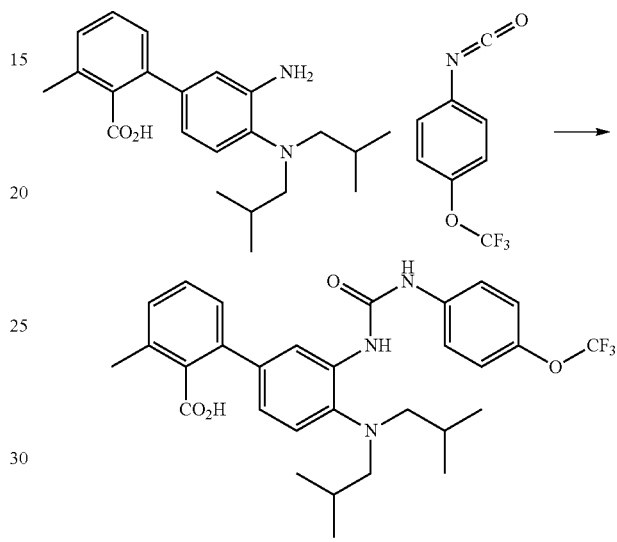

3'-Amino-4'-(diisobutylamino)-3-methyl-[1,1'-biphenyl]-2-carboxylic acid (10 mg, 0.028 mmol) was dissolved in dry DMF (0.25 mL). 1-Isocyanato-4-(trifluoromethoxy)benzene (10 uL) was added and stirring continued for 4 hours. The reaction was then diluted with DMF (1.75 mL). The crude material was purified via preparative LC/MS with the following conditions: Column: Waters XBridge C18, 19×200 mm, 5 μm particles; Mobile Phase A: 5:95 acetonitrile: water with 10-mM ammonium acetate; Mobile Phase B: 95:5 acetonitrile: water with 10-mM ammonium acetate; Gradient: 25-80% B over 20 minutes, then a 5-minute hold at 100% B; Flow: 20 mL/min. Fractions containing the desired product were combined and dried via centrifugal evaporation to give 4'-(diisobutylamino)-3-methyl-3'-(3-(4-(trifluoro methoxy)phenyl)ureido)-[1,1'-biphenyl]-2-carboxylic acid (8.0 mg, 50%).

$^1$H NMR (500 MHz, DMSO-$d_6$) δ 9.72 (s, 1H), 8.04 (s, 1H), 7.96 (s, 1H), 7.59 (d, J=8.8 Hz, 2H), 7.46-7.34 (m, 1H), 7.30 (d, J=8.8 Hz, 2H), 7.28-7.22 (m, 2H), 7.19 (d, J=7.4 Hz, 1H), 7.03 (d, J=7.1 Hz, 1H), 2.71 (d, J=6.7 Hz, 4H), 2.34 (s, 3H), 1.70 (dt, J=13.1, 6.6 Hz, 2H), 0.89 (d, J=6.4 Hz, 12H). MS(ES): m/z=558 [M+H]+.

Examples 315 to 345

Using the method shown below, the following compounds of the invention were prepared from aniline intermediates L and the appropriate isocyanate R$^9$NCO.

TABLE 18

| Ex. No. Name | NR⁷R⁸ | R⁹ | HPLC Ret Time | (M + H)⁺/ (M − 1) |
|---|---|---|---|---|
| 315 1-(4-(3,3-difluoropyrrolidin-1-yl)-2'-(1H-tetrazol-5-yl)-[1,1'-biphenyl]-3-yl)-3-(p-tolyl)urea | 3,3-difluoropyrrolidin-1-yl | p-tolyl | 16.93ᵗ | 476.2 |
| 316 1-(4-(3,3-difluoropyrrolidin-1-yl)-2'-(1H-tetrazol-5-yl)-[1,1'-biphenyl]-3-yl)-3-(4-(trifluoromethoxy)phenyl)urea | 3,3-difluoropyrrolidin-1-yl | 4-(trifluoromethoxy)phenyl | 18.18ᵗ | 544.0 |
| 317 1-(4-(5-benzyl-2,5-diazabicyclo[2.2.1]heptan-2-yl)-2'-(1H-tetrazol-5-yl)-[1,1'-biphenyl]-3-yl)-3-(p-tolyl)urea | 5-benzyl-2,5-diazabicyclo[2.2.1]heptan-2-yl | p-tolyl | 8.80ᵗ | 555.2 |
| 318 1-(4-(5-benzyl-2,5-diazabicyclo[2.2.1]heptan-2-yl)-2'-(1H-tetrazol-5-yl)-[1,1'-biphenyl]-3-yl)-3-(4-(trifluoromethoxy)phenyl)urea | 5-benzyl-2,5-diazabicyclo[2.2.1]heptan-2-yl | 4-(trifluoromethoxy)phenyl | 14.93ᵗ | 627.2 |
| 319 1-(4-((4-chlorobenzyl)(4,4,4-trifluorobutyl)amino)-2'-(1H-tetrazol-5-yl)-[1,1'-biphenyl]-3-yl)-3-(2,4-difluorophenyl)urea | N-(4-chlorobenzyl)-N-(4,4,4-trifluorobutyl)amino | 2,4-difluorophenyl | 20.55ᵗ | 642 |
| 320 1-(4-((4-chlorobenzyl)(4,4,4-trifluorobutyl)amino)-2'-(1H-tetrazol-5-yl)-[1,1'-biphenyl]-3-yl)-3-(p-tolyl)urea | N-(4-chlorobenzyl)-N-(4,4,4-trifluorobutyl)amino | p-tolyl | 21.06ᵗ | 620.2 |

TABLE 18-continued

| Ex. No. | Name | NR⁷R⁸ | R⁹ | HPLC Ret Time | (M + H)⁺/ (M − 1) |
|---|---|---|---|---|---|
| 321 | 1-(4-((4-chlorobenzyl)(4,4,4-trifluorobutyl)amino)-2'-(1H-tetrazol-5-yl)-[1,1'-biphenyl]-3-yl)-3-(2-(trifluoromethyl)phenyl)urea | N-benzyl(4-Cl), N-CH₂CH₂CH₂CF₃ | 2-CF₃-phenyl | 12.33ʳ | 674.2 |
| 322 | 1-(4-((4-chlorobenzyl)(4,4,4-trifluorobutyl)amino)-2'-(1H-tetrazol-5-yl)-[1,1'-biphenyl]-3-yl)-3-(4-(trifluoromethoxy)phenyl)urea | N-benzyl(4-Cl), N-CH₂CH₂CH₂CF₃ | 4-OCF₃-phenyl | 21.02ʳ | 688.2 |
| 323 | 1-(4-((4-fluorobenzyl)(3,3,3-trifluoropropyl)amino)-2'-(1H-tetrazol-5-yl)-[1,1'-biphenyl]-3-yl)-3-(4-(trifluoromethoxy)phenyl)urea | N-benzyl(4-F), N-CH₂CH₂CF₃ | 4-OCF₃-phenyl | 20.13ʳ | 660.2 |
| 324 | 1-(2,4-difluorophenyl)-3-(4-((4-fluorobenzyl)(3,3,3-trifluoropropyl)amino)-2'-(1H-tetrazol-5-yl)-[1,1'-biphenyl]-3-yl)urea | N-benzyl(4-F), N-CH₂CH₂CF₃ | 2,4-diF-phenyl | 19.25ʳ | 612 |

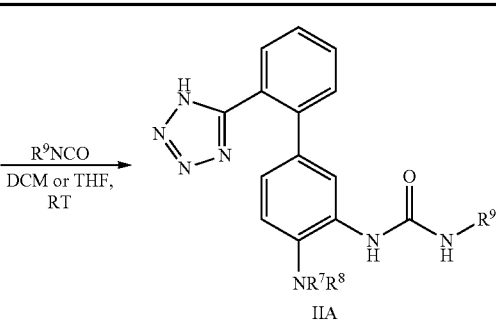

TABLE 18-continued

| Ex. No. Name | NR⁷R⁸ | R⁹ | HPLC Ret Time | (M + H)⁺/ (M − 1) |
|---|---|---|---|---|
| 329 1-(2'-(1H-tetrazol-5-yl)-4-((4-(trifluoromethyl)benzyl)(3,3,3-trifluoropropyl)amino)-[1,1'-biphenyl]-3-yl)-3-(p-tolyl)urea | F₃C–propyl–N–benzyl–(4-CF₃-phenyl) | 4-methylphenyl | 20.64ʳ | 640.2 |
| 330 1-(2'-(1H-tetrazol-5-yl)-4-((4-(trifluoromethyl)benzyl)(3,3,3-trifluoropropyl)amino)-[1,1'-biphenyl]-3-yl)-3-(2,4-difluorophenyl)urea | F₃C–propyl–N–benzyl–(4-CF₃-phenyl) | 2,4-difluorophenyl | 20.43ʳ | 662.2 |
| 331 1-(4-(phenethyl(3,3,3-trifluoropropyl)amino)-2'-(1H-tetrazol-5-yl)-[1,1'-biphenyl]-3-yl)-3-(4-(trifluoromethoxy)phenyl)urea | F₃C–propyl–N–phenethyl | 4-OCF₃-phenyl | 20.85ʳ | 656.4 |
| 332 1-(2,4-difluorophenyl)-3-(4-(phenethyl(3,3,3-trifluoropropyl)amino)-2'-(1H-tetrazol-5-yl)-[1,1'-biphenyl]-3-yl)urea | F₃C–propyl–N–phenethyl | 2,4-difluorophenyl | 19.51ʳ | 608.2 |
| 333 1-(4-(phenethyl(3,3,3-trifluoropropyl)amino)-2'-(1H-tetrazol-5-yl)-[1,1'-biphenyl]-3-yl)-3-(2-(trifluoromethyl)phenyl)urea | F₃C–propyl–N–phenethyl | 2-CF₃-phenyl | 20.16ʳ | 638.2 (M − 1)⁻ |

TABLE 18-continued

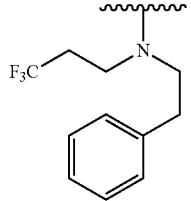

| Ex. No. | Name | NR⁷R⁸ | R⁹ | HPLC Ret Time | (M + H)⁺/ (M − 1) |
|---|---|---|---|---|---|
| 334 | 1-(4-(phenethyl(3,3,3-trifluoropropyl)amino)-2'-(1H-tetrazol-5-yl)-[1,1'-biphenyl]-3-yl)-3-(p-tolyl)urea | 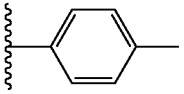 [SMILES: *c1ccc(C)cc1] | 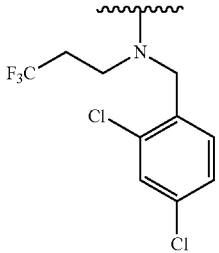 [SMILES: *N(CCC(F)(F)F)Cc1ccc(Cl)cc1Cl] | 19.79ʳ | 586.2 |
| 335 | 1-(4-((2,4-dichlorobenzyl)(3,3,3-trifluoropropyl)amino)-2'-(1H-tetrazol-5-yl)-[1,1'-biphenyl]-3-yl)-3-(2-(trifluoromethyl)phenyl)urea | 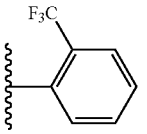 [SMILES: *c1ccccc1C(F)(F)F] | 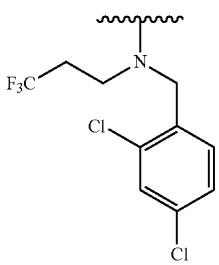 [SMILES: *N(CCC(F)(F)F)Cc1ccc(Cl)cc1Cl] | 20.46ʳ | 694.9 |
| 336 | 1-(4-((2,4-dichlorobenzyl)(3,3,3-trifluoropropyl)amino)-2'-(1H-tetrazol-5-yl)-[1,1'-biphenyl]-3-yl)-3-(2,4-difluorophenyl)urea | 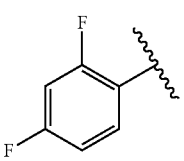 | 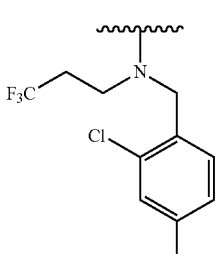 | 20.58ʳ | 662 |
| 337 | 1-(4-((2,4-dichlorobenzyl)(3,3,3-trifluoropropyl)amino)-2'-(1H-tetrazol-5-yl)-[1,1'-biphenyl]-3-yl)-3-(4-(trifluoromethoxy)phenyl)urea | 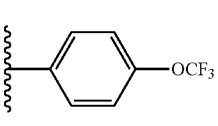 | | 21.25ʳ | 710.9 |

TABLE 18-continued

| Ex. No. | Name | NR⁷R⁸ | R⁹ | HPLC Ret Time | (M + H)⁺/ (M − 1) |
|---|---|---|---|---|---|
| 338 | 1-(4-((4-fluoro-2-(trifluoromethyl)benzyl)(3,3,3-trifluoropropyl)amino)-2'-(1H-tetrazol-5-yl)-[1,1'-biphenyl]-3-yl)-3-(2-(trifluoromethyl)phenyl)urea | (4-fluoro-2-(trifluoromethyl)benzyl)(3,3,3-trifluoropropyl)amino | 2-(trifluoromethyl)phenyl | 19.83ᵗ | 712.3 |
| 339 | 1-(4-((4-fluoro-2-(trifluoromethyl)benzyl)(3,3,3-trifluoropropyl)amino)-2'-(1H-tetrazol-5-yl)-[1,1'-biphenyl]-3-yl)-3-(4-(trifluoromethoxy)phenyl)urea | (4-fluoro-2-(trifluoromethyl)benzyl)(3,3,3-trifluoropropyl)amino | 4-(trifluoromethoxy)phenyl | 20.46ᵗ | 728.3 |
| 340 | 1-(2,4-difluorophenyl)-3-(4-((4-fluoro-2-(trifluoromethyl)benzyl)(3,3,3-trifluoropropyl)amino)-2'-(1H-tetrazol-5-yl)-[1,1'-biphenyl]-3-yl)urea | (4-fluoro-2-(trifluoromethyl)benzyl)(3,3,3-trifluoropropyl)amino | 2,4-difluorophenyl | 19.58ᵗ | 680.3 |
| 341 | 1-(2'-(1H-tetrazol-5-yl)-4-((4-(trifluoromethoxy)benzyl)(3,3,3-trifluoropropyl)amino)-[1,1'-biphenyl]-3-yl)-3-(p-tolyl)urea | (4-(trifluoromethoxy)benzyl)(3,3,3-trifluoropropyl)amino | p-tolyl | 20.57ᵗ | 654 |

TABLE 18-continued

| Ex. No. | Name | NR⁷R⁸ | R⁹ | HPLC Ret Time | (M + H)⁺/(M − 1) |
|---|---|---|---|---|---|
| 342 | 1-(2'-(1H-tetrazol-5-yl)-4-((4-(trifluoromethoxy)benzyl)(3,3,3-trifluoropropyl)amino)-[1,1'-biphenyl]-3-yl)-3-(2-(trifluoromethyl)phenyl)urea | (4-OCF₃-benzyl)(CH₂CH₂CF₃)N– | 2-CF₃-phenyl | 20.10ʳ | 708.2 |
| 343 | 1-(4-((pyridin-2-ylmethyl)(3,3,3-trifluoropropyl)amino)-2'-(1H-tetrazol-5-yl)-[1,1'-biphenyl]-3-yl)-3-(4-(trifluoromethoxy)phenyl)urea | (pyridin-2-ylmethyl)(CH₂CH₂CF₃)N– | 4-OCF₃-phenyl | 16.06ʳ | 643.3 |
| 344 | 1-(2,4-difluorophenyl)-3-(4-((pyridin-2-ylmethyl)(3,3,3-trifluoropropyl)amino)-2'-(1H-tetrazol-5-yl)-[1,1'-biphenyl]-3-yl)urea | (pyridin-2-ylmethyl)(CH₂CH₂CF₃)N– | 2,4-difluorophenyl | 14.48ʳ | 595.3 |
| 345 | 1-(4-((pyridin-2-ylmethyl)(3,3,3-trifluoropropyl)amino)-2'-(1H-tetrazol-5-yl)-[1,1'-biphenyl]-3-yl)-3-(2-(trifluoromethyl)phenyl)urea | (pyridin-2-ylmethyl)(CH₂CH₂CF₃)N– | 2-CF₃-phenyl | 14.63ʳ | 627.3 |

Examples 346 to 354

The following compounds were prepared employing the method outlined below employing appropriate starting materials.

TABLE 19

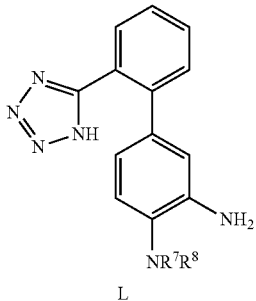

| Ex. No. Name | NR⁷R⁸ | R⁹ | HPLC Ret Time (M + H)⁺/ (M − 1) |
|---|---|---|---|
| 346 1-(3-chloro-5-fluorophenyl)-3-(4-(diisobutylamino)-2'-(1H-tetrazol-5-yl)-[1,1'-biphenyl]-3-yl)urea | 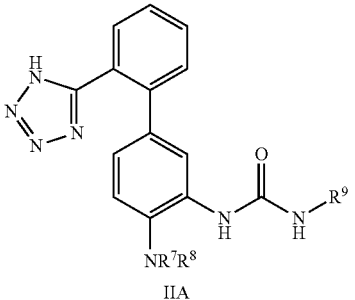 | 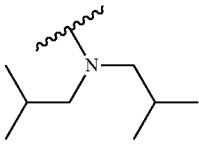 [SMILES: *N(CC(C)C)CC(C)C] | 20.97ᵗ 536.2 |
| 347 1-(4-cyclopropylphenyl)-3-(4-(3,3-difluoropyrrolidin-1-yl)-2'-(1H-tetrazol-5-yl)-[1,1'-biphenyl]-3-yl)urea | 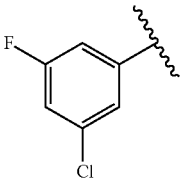 [SMILES: *c1cc(F)cc(Cl)c1] | 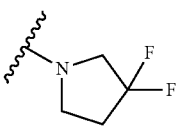 [SMILES: *N1CCC(F)(F)C1] | 17.98ᵗ 502.2 |
| 348 1-(4-(5-benzyl-2,5-diazabicyclo[2.2.1]heptan-2-yl)-2'-(2H-tetrazol-5-yl)-[1,1'-biphenyl]-3-yl)-3-(4-cyclopropylphenyl)urea | 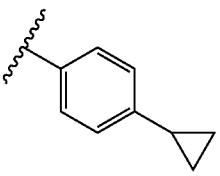 [SMILES: *c1ccc(C2CC2)cc1] | 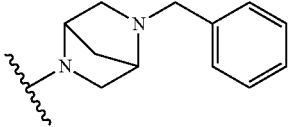 [SMILES: *N1CC2CC1CN2Cc1ccccc1] | 9.41ᵗ 583.4 |
| 349 1-(4-((4-chlorobenzyl)(4,4,4-trifluorobutyl)amino)-2'-(1H-tetrazol-5-yl)-[1,1'-biphenyl]-3-yl)-3-(4-cyclopropylphenyl)urea | 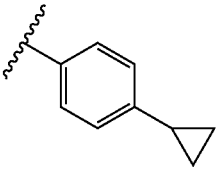 [SMILES: *c1ccc(C2CC2)cc1] | 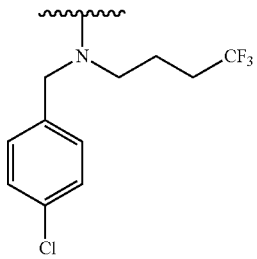 [SMILES: *N(CCCC(F)(F)F)Cc1ccc(Cl)cc1] | 21.33ᵗ 646.2 |
| 350 1-(4-cyclopropylphenyl)-3-(4-((4-fluorobenzyl)(3,3,3-trifluoropropyl)amino)-2'-(1H-tetrazol-5-yl)-[1,1'-biphenyl]-3-yl)urea | 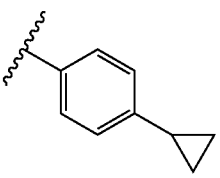 [SMILES: *c1ccc(C2CC2)cc1] | 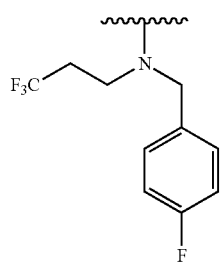 [SMILES: *N(CCC(F)(F)F)Cc1ccc(F)cc1] | 20.67ᵗ 616.2 |

TABLE 19-continued

| Ex. No. | Name | NR⁷R⁸ | R⁹ | HPLC Ret Time | (M + H)⁺/ (M − 1) |
|---|---|---|---|---|---|
| 351 | 1-(4-cyclopropyl-3-fluorophenyl)-3-(4-((2,4-dichlorobenzyl)(3,3,3-trifluoropropyl)amino)-2'-(1H-tetrazol-5-yl)-[1,1'-biphenyl]-3-yl)urea | | | 16.70ᵗ | 684.9 |
| 352 | 1-(4-cyclopropyl-3-fluorophenyl)-3-(4-((4-fluoro-2-(trifluoromethyl)benzyl)(3,3,3-trifluoropropyl)amino)-2'-(1H-tetrazol-5-yl)-[1,1'-biphenyl]-3-yl)urea | | | 20.85ᵗ | 700.2 (M − 1)⁻ |
| 353 | 1-(2'-(1H-tetrazol-5-yl)-4-((4-(trifluoromethoxy)benzyl)(3,3,3-trifluoropropyl)amino)-[1,1'-biphenyl]-3-yl)-3-(4-cyclopropyl-3-fluorophenyl)urea | | | 20.79ᵗ | 698 (M − 1)⁻ |
| 354 | 1-(4-cyclopropyl-3-fluorophenyl)-3-(4-((pyridin-2-ylmethyl)(3,3,3-trifluoropropyl)amino)-2'-(1H-tetrazol-5-yl)-[1,1'-biphenyl]-3-yl)urea | | | 15.91ᵗ | 617.5 |

Example 355

1-(4-(cyclohexyhisobutyl)amino)-5',6-difluoro-2'-(1H-tetrazol-5-yl)-[1,1'-biphenyl]-3-yl)-3-(p-tolyl)urea

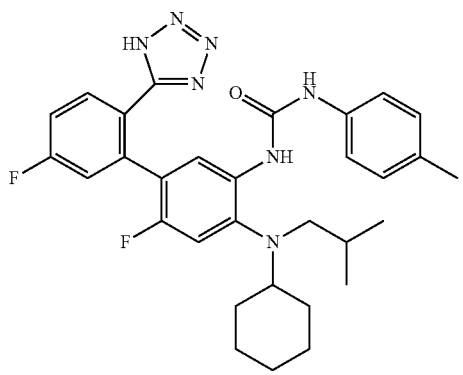 [SMILES: Cc1ccc(NC(=O)Nc2cc(-c3cc(F)ccc3-c3nnn[nH]3)c(F)cc2N(CC(C)C)C2CCCCC2)cc1]

Part A: 1-(2'-cyano-4-(cyclohexyl(isobutyl)amino)-5',6-difluoro-[1,1'-biphenyl]-3-yl)-3-(p-tolyl)urea

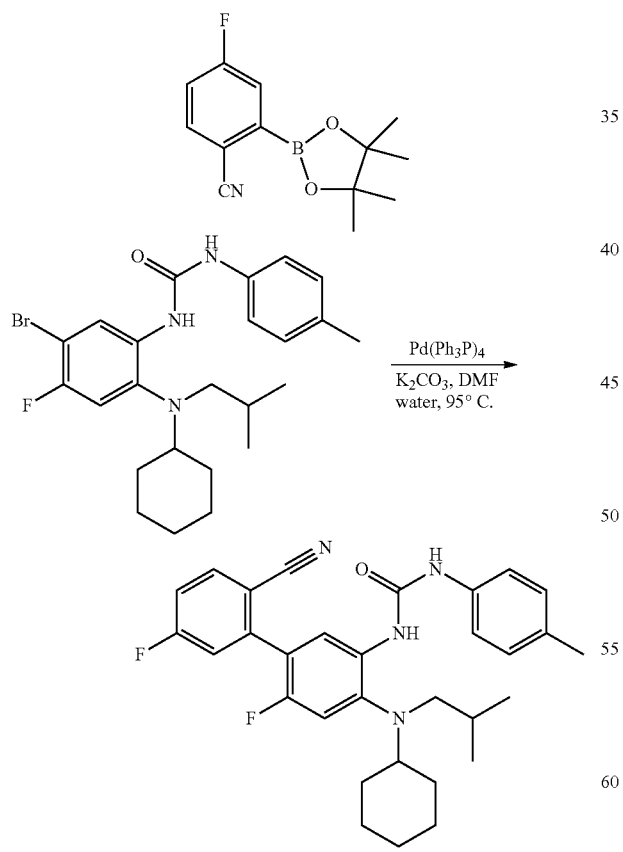

The above compound was prepared from 1-(5-bromo-2-(cyclohexyl(isobutyl)amino)-4-fluorophenyl)-3-(p-tolyl)urea (Table 7) and 4-fluoro-2-(4,4,5,5-tetramethyl-1,3,2-dioxaborolan-2-yl)benzonitrile by the procedure used for conversion of 1C to 1. MS(ES): m/z=517[M+H]$^+$. HPLC Tr: 5.17$^l$.

355. 1-(4-(cyclohexyl(isobutyl)amino)-5',6-difluoro-2'-(1H-tetrazol-5-yl)-[1,1'-biphenyl]-3-yl)-3-(p-tolyl)urea

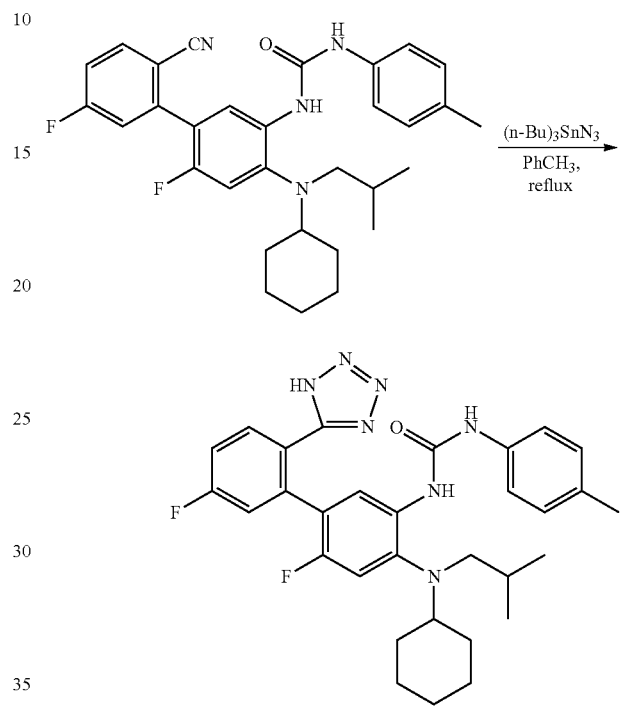

355: 1-(4-(cyclohexyl(isobutyl)amino)-5',6-difluoro-2'-(1H-tetrazol-5-yl)-[1,1'-biphenyl]-3-yl)-3-(p-tolyl)urea The compound was prepared from 1-(2'-cyano-4-(cyclohexyl(isobutyl)amino)-5',6-difluoro-[1,1'-biphenyl]-3-yl)-3-(p-tolyl)urea by the general procedure used for the conversion of 7A into 7B. MS(ES): m/z=560[M+H]$^p$. HPLC Tr: 2.94$^q$.

Example 356

1-(4-(cyclohexyl(2,2-difluoropropyl)amino)-2'-(1H-tetrazol-5-yl)-[1,1'-biphenyl]-3-yl)-3-(p-tolyl)urea

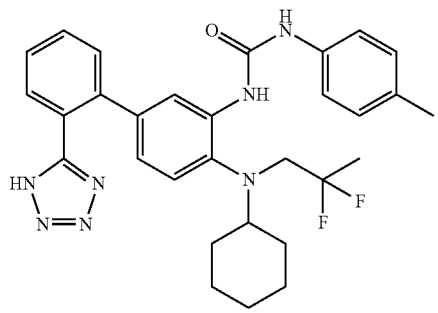 [SMILES: Cc1ccc(NC(=O)Nc2cc(-c3ccccc3-c3nnn[nH]3)ccc2N(CC(C)(F)F)C2CCCCC2)cc1]

295

Part A: 1-((4-bromo-2-nitrophenyl)(cyclohexyl)amino)propan-2-one

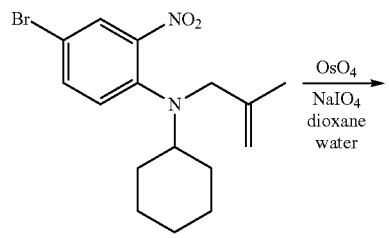

A solution of 4-bromo-N-cyclohexyl-N-(2-methylallyl)-2-nitroaniline (0.05 g, 0.142 mmol) in dioxane (2 mL) was treated with osmium tetroxide (0.072 g, 7.08 µmol) and 2,6-lutidine (0.016 mL, 0.142 mmol) followed by a slurry of sodium periodate (0.121 g, 0.566 mmol) in water (0.5 mL). This mixture was stirred 3 h at RT. then diluted with ether and washed twice with water. The org. phase was dried, stripped, and chromatographed on silica gel (gradient elution with ether-hexanes). Concentration of the appropriate fractions afforded 1-((4-bromo-2-nitrophenyl)(cyclohexyl)amino)propan-2-one as an oil. MS(ES): m/z=275 [M+H]$^p$. HPLC Tr: 4.47$^l$.

Part B: 4-bromo-N-cyclohexyl-N-(2,2-difluoropropyl)-2-nitroaniline

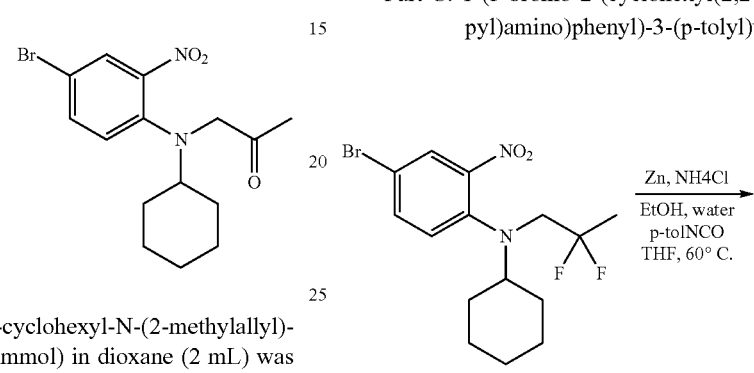

A solution of 1-((4-bromo-2-nitrophenyl)(cyclohexyl)amino)propan-2-one (0.045 g, 0.127 mmol) in dichloromethane (0.5 ml) was treated with DAST (0.067 ml, 0.507 mmol) and stirred at RT. After 24 h, additional DAST (0.1 mL) was added, and the reaction was stirred an additional 24 h. The reaction was applied to a silica gel column (hexane) and eluted with a gradient of ether-hexane. Concentration of the appropriate fractions afforded 4-bromo-N-cyclohexyl-N-(2,2-difluoropropyl)-2-nitroaniline (0.04 g, 0.101 mmol, 80% yield) as an orange oil. MS(ES): m/z=297[M+1-1]$^+$. HPLC Tr: 2.30$^p$.

Part C: 1-(5-bromo-2-(cyclohexyl(2,2-difluoropropyl)amino)phenyl)-3-(p-tolyl)urea

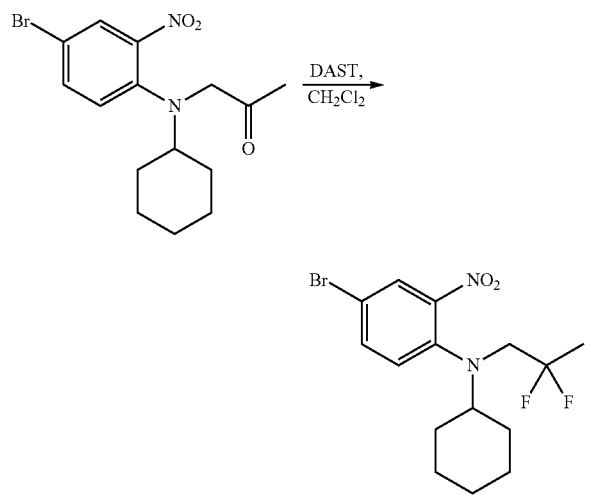

A solution of 4-bromo-N-cyclohexyl-N-(2,2-difluoropropyl)-2-nitroaniline (0.037 g, 0.098 mmol) in ethanol (3 mL) was treated with ammonium chloride (0.079 g, 1.471 mmol) and 0.3 mL of water. This mixture was stirred 10 min. at RT then treated with zinc (0.096 g, 1.471 mmol). The reaction was stirred 5 min. at RT then diluted with dichloromethane and filtered. The filtrate was washed with water, dried, and stripped to afford an oil. This was dissolved in 0.5 mL of THF and treated with 0.03 mL of p-tolyl isocyanate. The reaction was stirred 1 h at RT. LCMS of the first step indicates that much hydroxylamine intermediate was present. The second step has proceeded to give a mixture of the desired urea and N-hydroxy urea. The reaction was diluted with 2 mL of ethanol and 0.2 mL of water followed by 0.05 g of ammonium chloride and 0.1 g of zinc. The reaction was stirred ON at RT. The reaction was concentrated and applied to a silica gel column. Gradient elution with ether-hexanes afforded 0.016 g (34%) of 1-(5-bromo-2-(cyclohexyl(2,2-difluoropropyl)amino)phenyl)-3-(p-tolyl)urea as a glass. MS(ES): m/z=482[M+H]$^+$. HPLC Tr: 4.46$^l$.

356: 1-(4-(cyclohexyl(2,2-difluoropropyl)amino)-2'-(1H-tetrazol-5-yl)-[1,1'-biphenyl]-3-yl)-3-(p-tolyl)urea

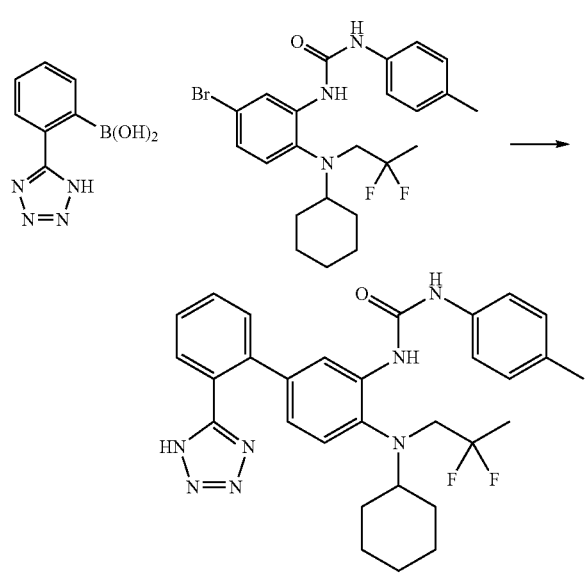

The title compound was prepared from 1-(5-bromo-2-(cyclohexyl(2,2-difluoropropyl)amino)phenyl)-3-(p-tolyl)urea and (2-(1H-tetrazol-5-yl)phenyl)boronic acid by the procedure used for conversion of 1C to 1. MS(ES): m/z=546 [M+H]$^+$. HPLC Tr: 4.02$^I$.

Example 357

1-(2-fluorophenyl)-3-(4-(isobutylamino)-5-(1-phenylallyl)-2'-(1H-tetrazol-5-yl)-[1,1'-biphenyl]-3-yl)urea

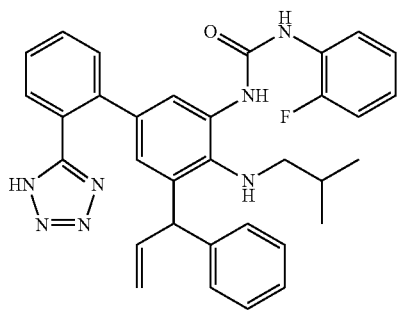 [SMILES: C=CC(c1ccccc1)c1cc(-c2ccccc2-c2nnn[nH]2)cc(NC(=O)Nc2ccccc2F)c1NCC(C)C]

Part A: 4-Bromo-1-(cinnamyloxy)-2-nitrobenzene

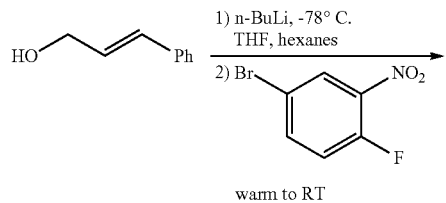

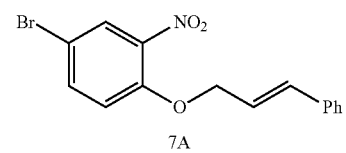

To a stirred, cooled (−78° C.) solution of (E)-3-phenyl-prop-2-en-1-ol (2.415 g, 18.00 mmol) in THF (3 mL) was added n-butyllithium (5.76 mL, 14.40 mmol), dropwise over 4-5 min. The solution was stirred for 5 min. at −78° C. then treated with 4-bromo-1-fluoro-2-nitrobenzene (2.64 g, 12 mmol) and allowed to warm to RT with stirring. Stirring at RT was continued for 30 min, after which time the reaction was transferred into aq. HCl, and this mixture was extracted with ether. The organic extract was dried, stripped, and chromatographed on silica gel (gradient elution with ether-hexanes). Concentration of the appropriate fractions afforded an oily yellow solid. This was triturated with heptane to afford 4-bromo-1-(cinnamyloxy)-2-nitrobenzene (2.2 g, 52.1% yield) as a pale yellow powder, mp 95-97° C. $^1$H NMR (400 MHz, DMSO-d$_6$) δ ppm 8.13 (d, 1H, J=2.4 Hz); 7.84 (dd, 1H, J=9.0, 2.4 Hz); 7.47 (d, 2H, J=7.3 Hz); 7.42 (d, 1H, J=9.2 Hz); 7.35 (t, 2H, J=7.4 Hz); 7.28 (t, 1H, J=7.8 Hz); 6.78 (d, 1H, J=16.1 Hz); 6.46 (dt, 1H, J=16.1, 5.8 Hz); 4.92 (d, 2H, J=5.9 Hz).

Part B: (+/−)-4-Bromo-2-nitro-6-(1-phenylallyl)phenol

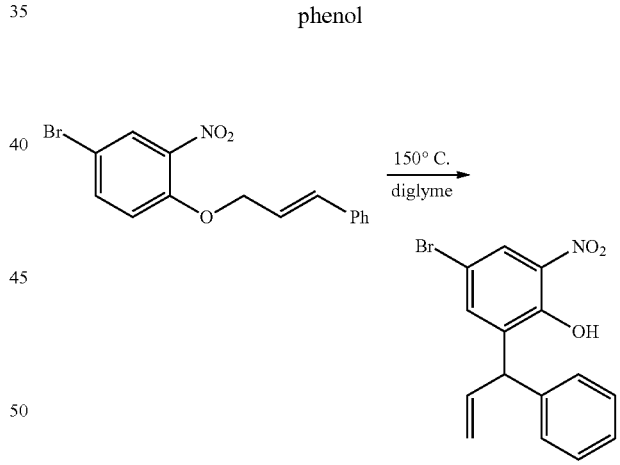

A solution of 4-bromo-1-(cinnamyloxy)-2-nitrobenzene (8A) (1.5 g, 4.49 mmol) in diglyme (3 mL) was placed under nitrogen and heated to 150° C. for 36 h. The reaction was cooled and purified by flash chromatography (gradient elution with hexanes up to 15% ether-hexanes). Concentration of the appropriate fractions afforded 4-bromo-2-nitro-6-(1-phenylallyl)phenol (1.08 g, 68.4% yield) as an oily yellow solid. $^1$H NMR (400 MHz, DMSO-d$_6$) δ ppm 10.73 (br. s, 1H); 8.04 (d, 1H, J=2.4 Hz) 7.62 (d, 1H, J=2.4 Hz); 7.31 (t, 2H, J=7.4 Hz); 7.16-7.25 (m, 3H); 6.39 (ddd, 1H, J=17.1, 10.1, 7.5 Hz); 5.23 (d, 1H, J=10.1 Hz); 5.15 (d, 1H, J=7.3 Hz); 5.00 (d, 1H, J=17.2 Hz).

Part C: 2-(allyloxy)-5-bromo-1-nitro-3-(1-phenylallyl)benzene

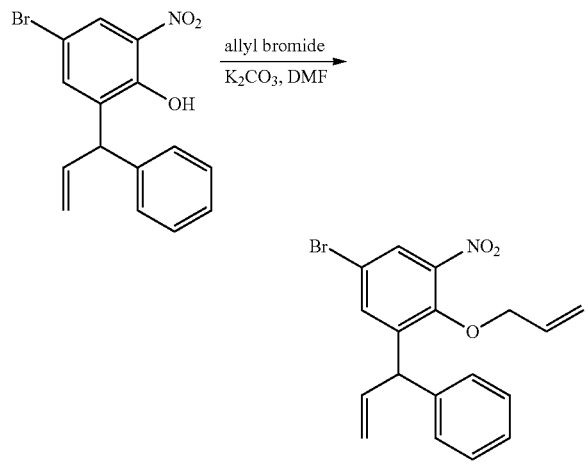

To a solution of 4-bromo-2-nitro-6-(1-phenylallyl)phenol (0.1 g, 0.299 mmol) in DMF (1 mL) was added potassium carbonate (0.124 g, 0.898 mmol) followed by 3-bromoprop-1-ene (0.145 g, 1.197 mmol). This mixture was brought to 60° C. and stirred for 17 h. The reaction was cooled, quenched with glacial HOAc, and purified by flash chromatography (gradient elution with ether-hexanes). Concentration of the appropriate fractions afforded 2-(allyloxy)-5-bromo-1-nitro-3-(1-phenylallyl)benzene (0.105 g, 89% yield) as a colorless oil. $^1$H NMR (400 MHz, DMSO-$d_6$) δ ppm 8.08 (d, 1H, J=2.2 Hz) 7.69 (d, 1H, J=2.2 Hz); 7.33 (dd, 2H, J=7.5, 7.3 Hz); 7.24 (td, 1H, J=7.5, 1.8 Hz); 7.19 (d, 2H, J=7.7 Hz); 6.34-6.44 (m, 1H); 5.84-5.95 (m, 1H); 5.21-5.32 (m, 3H); 5.13 (d, 1H, J=7.0 Hz); 5.02 (dd, 1H, J=17.0, 1.1 Hz); 4.25-4.41 (m, 2H).

Part D: 4-bromo-N-isobutyl-2-nitro-6-(1-phenylallyl)aniline

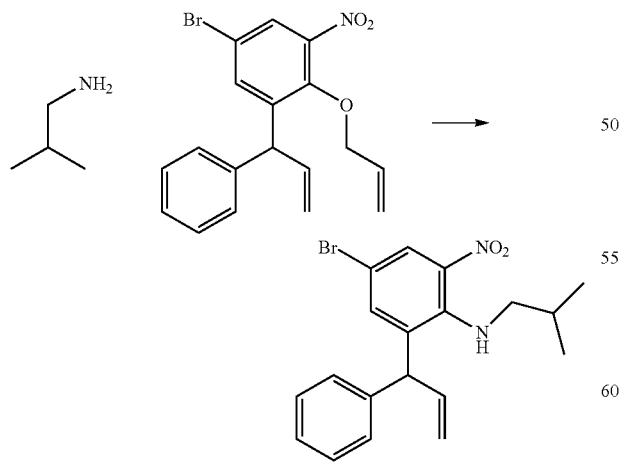

A solution of 2-(allyloxy)-5-bromo-1-nitro-3-(1-phenylallyl)benzene (0.09 g, 0.240 mmol) in NMP (0.2 mL) was heated at 60° C. for 20 min. LCMS suggests that LTN reaction has occurred. The solution was treated with 0.05 mL more isobutylamine and heated to 80° C. for 2 h. LCMS suggests that reaction is occurring to give two products. The reaction was cooled and purified by prep. HPLC (Axia Luna 30×100 mm column, MeOH-water-TFA gradient). Concentration of the appropriate (earlier-eluting) fractions afforded 4-bromo-N-isobutyl-2-nitro-6-(1-phenylallyl)aniline as a yellow oil. MS(ES): m/z=391 [M+H]$^+$. HPLC Tr: 5.43$^I$.

Part E: 4-bromo-N1-isobutyl-6-(1-phenylallyl)benzene-1,2-diamine

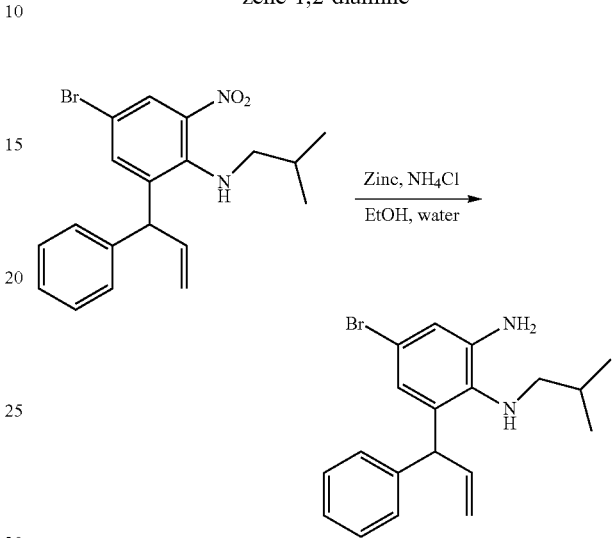

A solution of 4-bromo-N-isobutyl-2-nitro-6-(1-phenylallyl)aniline (0.06 g, 0.154 mmol) in ethanol (4 mL) was treated with 0.4 mL of water, and the resulting mixture was stirred for 5 min. at RT. This stirred suspension was treated with zinc (0.151 g, 2.312 mmol), and after stirring 30 min. the reaction was diluted with dichloromethane and filtered. The filtrate was washed with water, dried, and stripped to afford 4-bromo-N1-isobutyl-6-(1-phenylallyl)benzene-1,2-diamine (0.055 g, 92% yield) as a pale amber oil. MS(ES): m/z=359[M+H]$^+$. HPLC Tr: 4.35$^I$.

Part F: 1-(5-bromo-2-(isobutylamino)-3-(1-phenylallyl)phenyl)-3-(2-fluorophenyl)urea

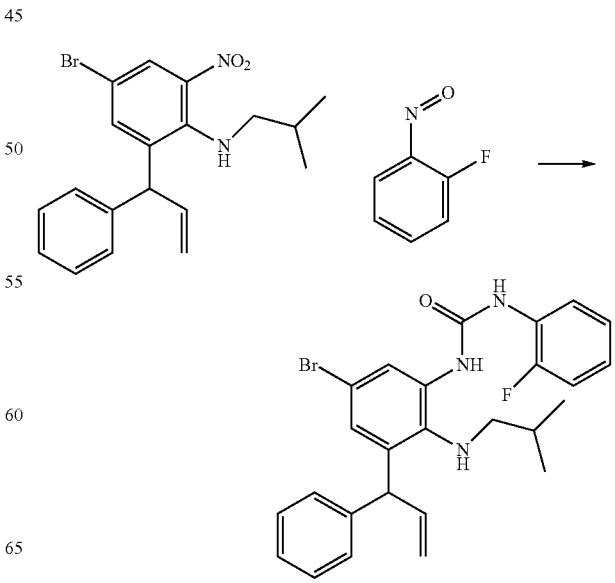

301

A solution of 4-bromo-N1-isobutyl-6-(1-phenylallyl)benzene-1,2-diamine (0.033 g, 0.092 mmol) in THF (0.8 mL) was treated with 1-fluoro-2-isocyanatobenzene (0.025 g, 0.184 mmol). The reaction was stirred 30 min. at 60° C. then cooled, concentrated, and purified by flash chromatography (gradient elution with ether-hexanes). Concentration of the appropriate fractions afforded 1-(5-bromo-2-(isobutylamino)-3-(1-phenylallyl)phenyl)-3-(2-fluorophenyl)urea (0.04 g, 88% yield) as a colorless solid. MS(ES): m/z=498 [M+H]$^+$. HPLC Tr: 5.23$^I$.

357. 1-(2-fluorophenyl)-3-(4-(isobutylamino)-5-(1-phenylallyl)-2'-(1H-tetrazol-5-yl)-[1,1'-biphenyl]-3-yl)urea

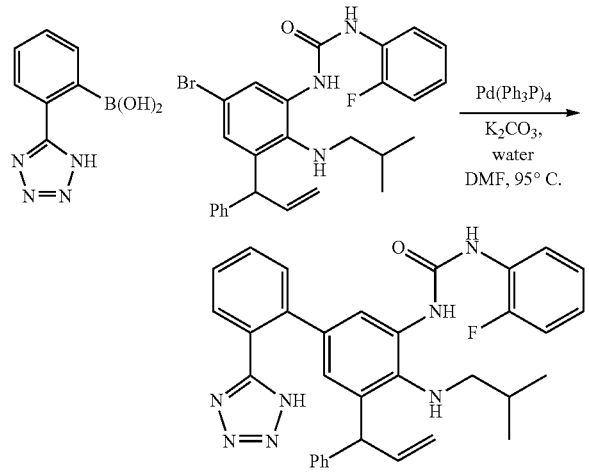

The title compound was prepared from 1-(5-bromo-2-(isobutylamino)-3-(1-phenylallyl)phenyl)-3-(2-fluorophenyl)urea and (2-(1H-tetrazol-5-yl)phenyl)boronic acid by the procedure used for conversion of 1C to 1. MS(ES): m/z=562[M+H]$^P$. HPLC Tr: 4.02$^I$.

Example 358

1-(4-(isobutylamino)-5-(1-phenylallyl)-2'-(1H-tetrazol-5-yl)-[1,1'-biphenyl]-3-yl)-3-(p-tolyl)urea

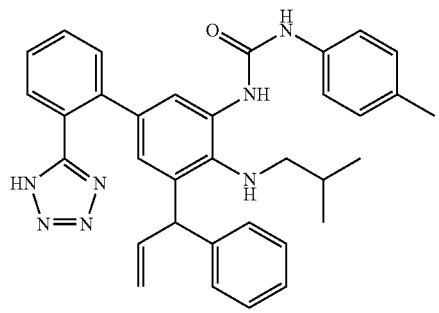 [SMILES: C=CC(c1ccccc1)c1cc(-c2ccccc2-c2nnn[nH]2)cc(NC(=O)Nc2ccc(C)cc2)c1NCC(C)C]

302

Part A: 1-(5-bromo-2-(isobutylamino)-3-(1-phenylallyl)phenyl)-3-(p-tolyl)urea

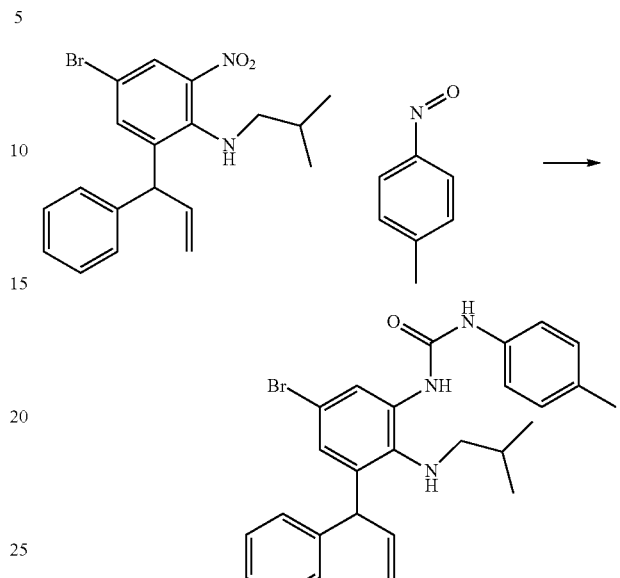

The title compound was prepared from 4-bromo-N1-isobutyl-6-(1-phenylallyl)benzene-1,2-diamine and 1-isocyanato-4-methylbenzene by the procedure used to prepare 1-(5-bromo-2-(isobutylamino)-3-(1-phenylallyl)phenyl)-3-(2-fluorophenyl)urea. MS(ES): m/z=492[M+H]$^+$. HPLC Tr: 5.09$^I$.

358: 1-(4-(isobutylamino)-5-(1-phenylallyl)-2'-(1H-tetrazol-5-yl)-[1,1'-biphenyl]-3-yl)-3-(p-tolyl)urea

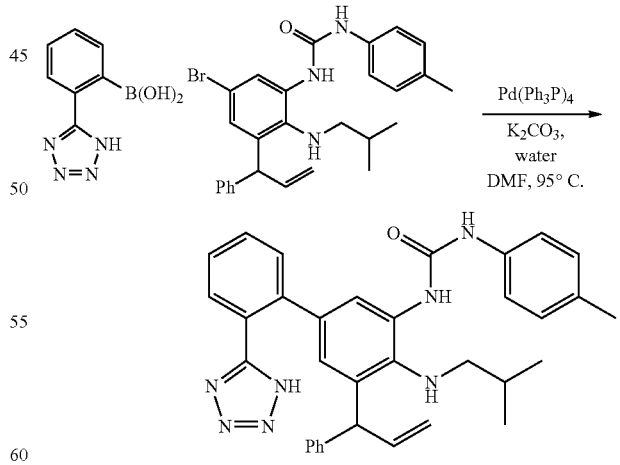

The title compound was prepared from 1-(5-bromo-2-(isobutylamino)-3-(1-phenylallyl)phenyl)-3-(p-tolyl)urea and (2-(1H-tetrazol-5-yl)phenyl)boronic acid by the procedure used for conversion of 1C to 1. MS(ES): m/z=558[M+H]$^+$. HPLC Tr: 4.48$^I$.

Example 359

4-Chloro-3'-(3-(6-cyanopyridin-3-yl)ureido)-4'-(diisobutylamino)-[1,1'-biphenyl]-2-carboxylic acid

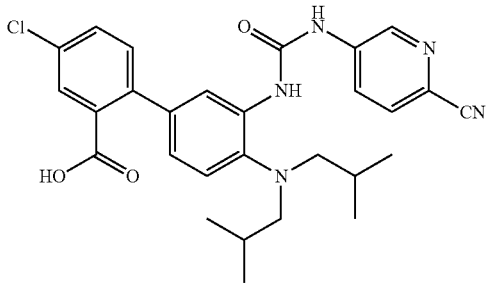 [SMILES: CC(C)CN(CC(C)C)c1ccc(-c2ccc(Cl)cc2C(=O)O)cc1NC(=O)Nc1ccc(C#N)nc1]

A. Methyl 3'-amino-4-chloro-4'-(diisobutylamino)-[1,1'-biphenyl]-2-carboxylate

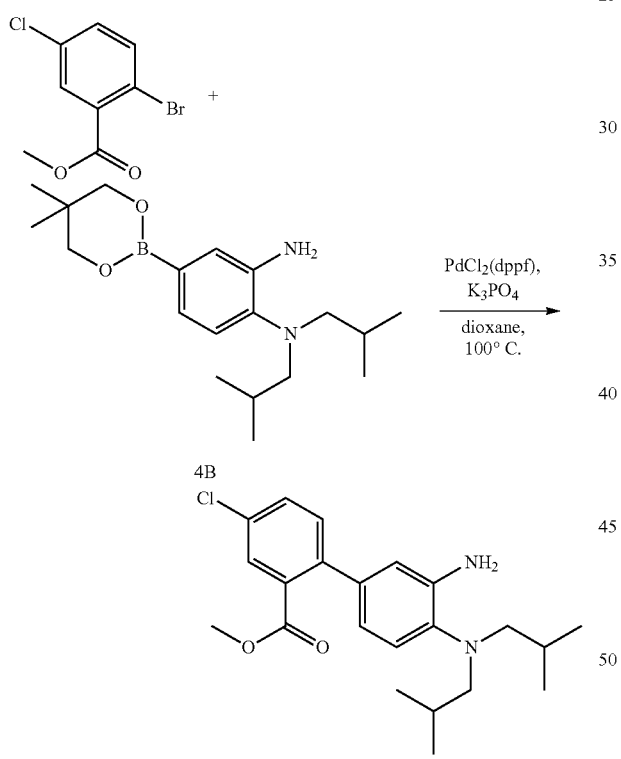

4-(5,5-Dimethyl-1,3,2-dioxaborinan-2-yl)-N1,N1-diisobutylbenzene-1,2-diamine (4B) (128 mg, 0.385 mmol), methyl 2-bromo-5-chlorobenzoate (80 mg, 0.321 mmol), PdCl$_2$(dppf)-CH$_2$Cl$_2$Adduct (23.5 mg, 0.032 mmol) and potassium phosphate, tribasic (204 mg, 0.962 mmol) were added to a 2 dram vial which was then evacuated and filled with nitrogen 3×. Dioxane (2 mL) was added and the resultant mixture was purged with nitrogen for five minutes. The mixture was then heated at 100° C. for 20 h. The reaction was cooled to rt, filtered and concentrated in vacuo before being purified via ISCO Companion (12 g silica gel column with 0-10% EtOAc/hexane gradient) to afford the title compound as a clear oil (99.4 mg, 75%). $^1$H NMR (500 MHz, CDCl$_3$) δ 7.71 (d, J=2.2 Hz, 1H), 7.45 (dd, J=8.2, 2.1 Hz, 1H), 7.33 (d, J=8.0 Hz, 1H), 7.06 (d, J=8.0 Hz, 1H), 6.66 (d, J=1.9 Hz, 1H), 6.60 (dd, J=8.0, 1.9 Hz, 1H), 4.17 (br. s., 2H), 2.65 (d, J=7.2 Hz, 4H), 1.79 (m, 2H), 0.93 (d, J=6.7 Hz, 12H). MS(ES): m/z=389 [M+H]$^+$.

B. 3'-Amino-4-chloro-4'-(diisobutylamino)-[1,1'-biphenyl]-2-carboxylic acid

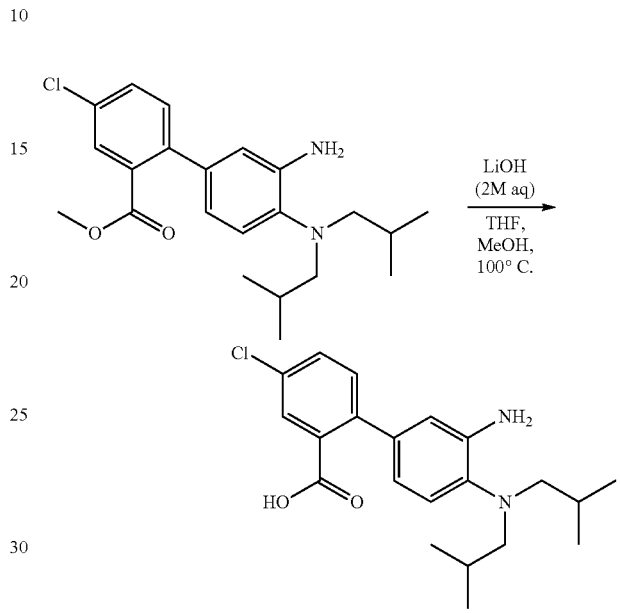

To a mixture of methyl 3'-amino-4-chloro-4'-(diisobutylamino)-[1,1'-biphenyl]-2-carboxylate (99.4 mg, 0.256 mmol) in MeOH (1 mL) and THF (0.6 mL) was added LiOH (2M aq solution, 1.28 mL, 2.56 mmol). The resulting mixture was heated at 100° C. for thirty minutes, then cooled to room temperature and neutralized with HCl (1N in diethyl ether, 2.56 mL, 2.56 mmol). The mixture was concentrated to remove volatiles, then extracted with EtOAc (3×). The combined organic layers were concentrated in vacuo to afford the title compound as a brown solid (75 mg, 77%) which was used without further purification. MS(ES): m/z=375 [M+H]$^+$.

359. 4-Chloro-3'-(3-(6-cyanopyridin-3-yl)ureido)-4'-(diisobutylamino)-[1,1'-biphenyl]-2-carboxylic acid

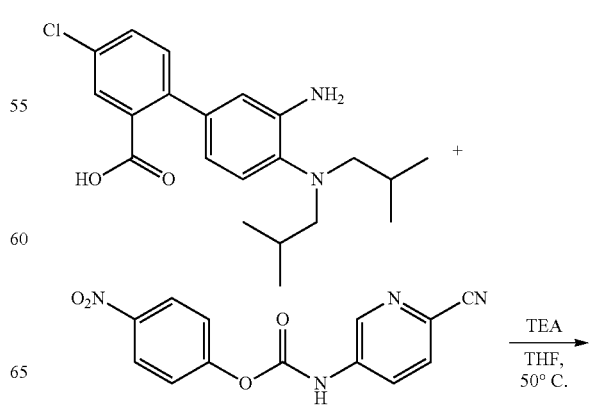

305

-continued

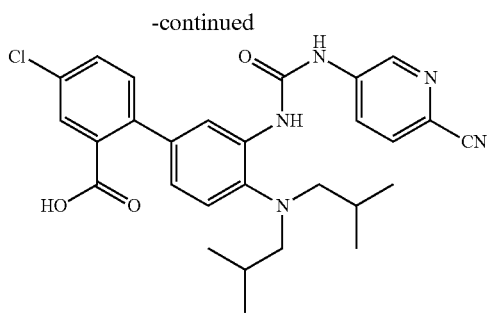

To a mixture of 5-aminopicolinonitrile (20 mg, 0.168 mmol) in anhydrous THF (1 mL) was added 4-nitrophenyl carbonochloridate (41 mg, 0.201 mmol). The mixture was stirred at 35° C. for twenty minutes to afford 4-nitrophenyl (6-cyanopyridin-3-yl) carbamate. MS(ESI+) m/z 285.2 (M+H)+. The entire reaction mixture was used without further purification.

To the 4-nitrophenyl (6-cyanopyridin-3-yl) carbamate reaction mixture was added 3'-amino-4-chloro-4'-(diisobutylamino)-[1,1'-biphenyl]-2-carboxylic acid (25 mg, 0.067 mmol), followed by TEA (0.04 mL, 0.267 mmol). The resulting mixture was stirred at 50° C. for twenty minutes. After cooling to room temperature, the compound was purified via via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10 mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation to afford the title compound (17.7 mg, 51% yield). MS(ES): m/z=520 [M+H]+, HPLC T$_r$: 1.73$^j$.

Example 360

4-Chloro-3'-(3-(4-chloro-2-fluorophenyl)ureido)-4'-(diisobutylamino)-[1,1'-biphenyl]-2-carboxylic acid

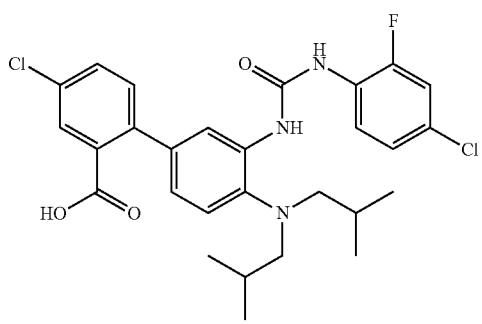 [SMILES: CC(C)CN(CC(C)C)c1ccc(-c2ccc(Cl)cc2C(=O)O)cc1NC(=O)Nc1ccc(Cl)cc1F]

To a mixture of 3'-amino-4-chloro-4'-(diisobutylamino)-[1,1'-biphenyl]-2-carboxylic acid (25 mg, 0.067 mmol) in anhydrous THF (0.5 mL) was added 4-chloro-2-fluoro-1-isocyanatobenzene (19 mg, 0.113 mmol). The resulting mixture was stirred at 50° C. for ten minutes. After cooling to room temperature, the compound was purified via via preparative LC/MS with the following conditions: Column: Waters XBridge C18, 19×150 mm, 5-μm particles; Guard

306

Column: Waters XBridge C18, 19×10 mm, 5-μm particles; Mobile Phase A: 5:95 acetonitrile:water with 10 mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation to afford the title compound (28.1 mg, 76% yield). MS(ES): m/z=546 [M+H]+, HPLC T$_r$: 2.03$^j$.

Example 361

1-(4-(3,4-Dihydroquinolin-1(2H)-yl)-2'-(1H-tetrazol-5-yl)-[1,1'-biphenyl]-3-yl)-3-(p-tolyl)urea

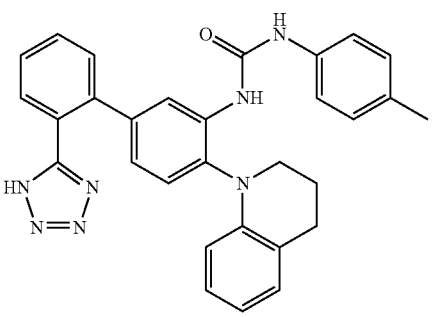 [SMILES: Cc1ccc(NC(=O)Nc2cc(-c3ccccc3-c3nnn[nH]3)ccc2N2CCCc3ccccc32)cc1]

A. 1-(4-Bromo-2-nitrophenyl)-1,2,3,4-tetrahydroquinoline

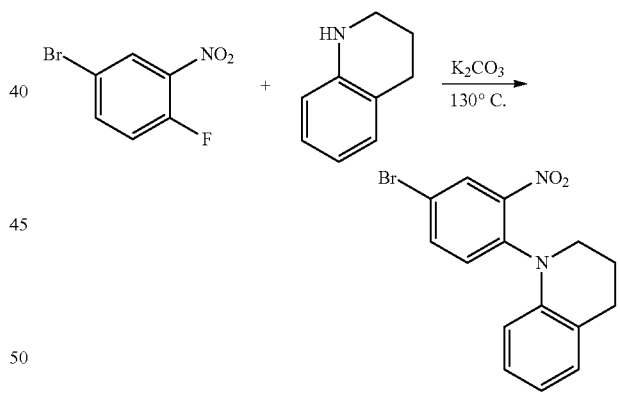

To a mixture of 4-bromo-1-fluoro-2-nitrobenzene (2.02 ml, 16.4 mmol) and 1,2,3,4-tetrahydroquinoline (8.72 g, 65.5 mmol), in a 100 mL pressure flask, was added K$_2$CO$_3$ (11.31 g, 82.0 mmol). The flask was sealed and the resulting mixture was heated at 130° C. for 16 hours, before being cooled to rt, then partitioned between water and EtOAc. The layers were separated and the aqueous layer was extracted twice more with EtOAc. These organic extracts were combined with the original organic layer and were washed with brine, then dried over anhydrous sodium sulfate. The crude material was filtered, then concentrated in vacuo to afford a residue which was treated with 1-methylpiperazine (1.64 g, 16.4 mmol). The resultant mixture was heated at 80° C. for one hour then cooled to room temperature. The crude

B. 4'-(3,4-Dihydroquinolin-1(2H)-yl)-3'-nitro-[1,1'-biphenyl]-2-carbonitrile

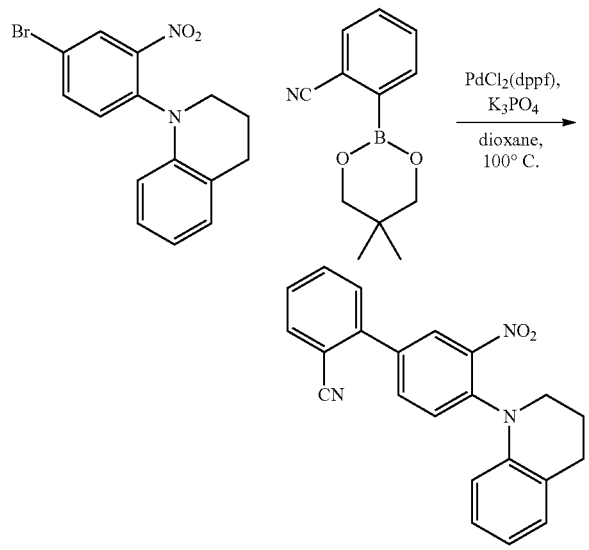

To a solution of 1-(4-bromo-2-nitrophenyl)-1,2,3,4-tetrahydroquinoline (1.43 g, 4.3 mmol) in dioxane (14.3 mL), in a sealable reaction vial, was added 2-(5,5-dimethyl-1,3,2-dioxaborinan-2-yl)benzonitrile (1.20 g, 5.6 mmol), $PdCl_2$(dppf)-$CH_2Cl_2$ adduct (0.18 g, 0.22 mmol) and potassium phosphate, tribasic (2.24 g, 12.9 mmol). The mixture was purged with nitrogen for five minutes before the vial was sealed and the reaction heated at 100° C. for two hours. The reaction was cooled to room temperature and the solids were removed by vacuum filtration through a fritted glass funnel. The filtrate was concentrate in vacuo and the crude reaction mixture was purified by flash chromatography to afford the title compound as a dark red solid (1.26 g, 83%). MS(ES): m/z=356 [M+H]$^+$, HPLC T$_r$: 4.40$^l$.

C. 1-(3-Nitro-2'-(1H-tetrazol-5-yl)-[1,1'-biphenyl]-4-yl)-1,2,3,4-tetrahydroquinoline

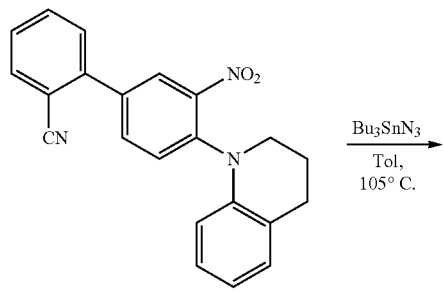

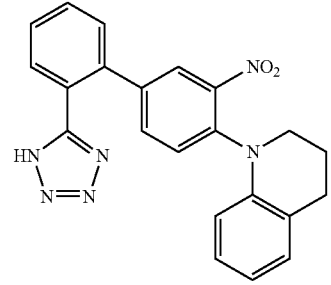

To a solution of 4'-(3,4-dihydroquinolin-1(2H)-yl)-3'-nitro-[1,1'-biphenyl]-2-carbonitrile (0.6 g, 1.7 mmol) in toluene (7 mL), in a sealable reaction vial, was added azidotributylstannane (3 ml, 10.9 mmol). The reaction was then heated at 105° C. for 16 hours before being cooled to room temperature. The solvent was removed under reduced pressure, and the resultant residue was purified by flash chromatography to afford the title compound (0.61 g, 86%). MS(ES): m/z=399 [M+H]$^+$, HPLC T$_r$: 4.07$^l$.

D. 4-(3,4-Dihydroquinolin-1(2H)-yl)-2'-(1H-tetrazol-5-yl)-[1,1'-biphenyl]-3-amine

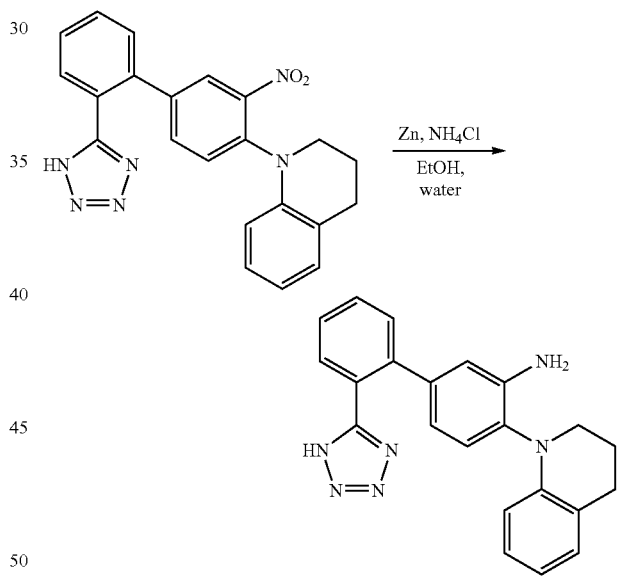

To a solution of ammonium chloride (0.49 g, 9.2 mmol) in water (0.92 mL) was added EtOH (6.4 mL). The mixture was cooled to 0° C. then treated with zinc (325 mesh flake, 0.83 g, 12.6 mmol). To this mixture was added a solution of 1-(3-nitro-2'-(1H-tetrazol-5-yl)-[1,1'-biphenyl]-4-yl)-1,2,3,4-tetrahydroquinoline (0.61 g, 1.53 mmol) in EtOH (1 mL). The mixture was allowed to warm to room temperature and was stirred for 1.5 hours. After that time, the reaction mixture was filtered through a pad of Celite and the isolated solids were thoroughly rinsed with DCM. The combined filtrates were concentrated in vacuo to remove volatiles then partitioned between water and DCM. The layers were separated and the organic layer was dried over anhydrous sodium sulfate, filtered and concentrated in vacuo to afford a brown residue. Purification by flash chromatography, followed by treatment with DCM, removal of remaining solids and concentration in vacuo afforded the title compound (0.21 g, 29%), which was used without further purification. MS(ES): m/z=369 [M+H]⁺, HPLC T$_r$: 3.57$^l$.

E. 4-Nitrophenyl (4-(3,4-dihydroquinolin-1(2H)-yl)-2'-(1H-tetrazol-5-yl)-[1,1'-biphenyl]-3-yl)carbamate

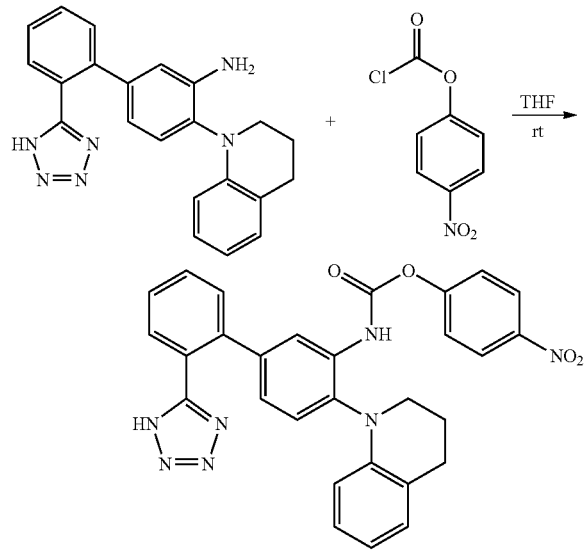

To a homogeneous mixture of 4-(3,4-dihydroquinolin-1 (2H)-yl)-2'-(1H-tetrazol-5-yl)-[1,1'-biphenyl]-3-amine (0.03 g, 0.08 mmol) in anhydrous THF (1.3 mL) was added 4-nitrophenyl carbonochloridate (0.02 g, 0.10 mmol). The mixture was stirred at room temperature for twenty minutes to afford 4-nitrophenyl (4-(3,4-dihydroquinolin-1(2H)-yl)-2'-(1H-tetrazol-5-yl)-[1,1'-biphenyl]-3-yl)carbamate. MS(ES): m/z=534 [M+H]⁺, HPLC T$_r$: 4.50$^l$. The entire reaction mixture was used without further purification.

361. 1-(4-(3,4-Dihydroquinolin-1(2H)-yl)-2'-(1H-tetrazol-5-yl)-[1,1'-biphenyl]-3-yl)-3-(p-tolyl)urea

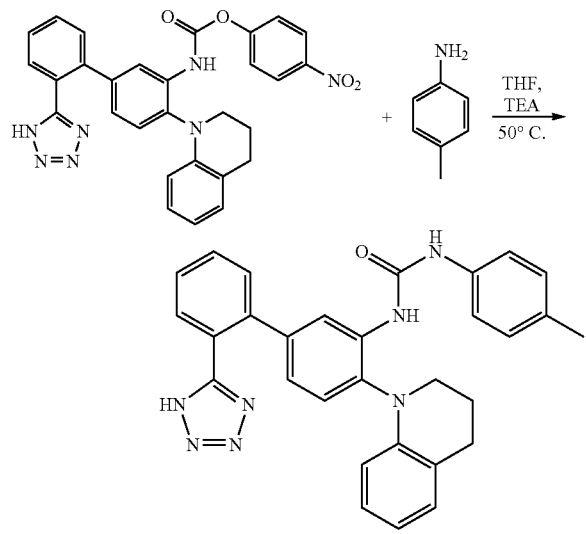

To the reaction mixture from Step E, containing 4-nitrophenyl (4-(3,4-dihydroquinolin-1(2H)-yl)-2'-(1H-tetrazol-5-yl)-[1,1'-biphenyl]-3-yl)carbamate, was added p-toluidine (12 mg, 0.11 mmol) followed by triethylamine (0.05 mL, 0.33 mmol). The mixture was then heated at 50° C. for thirty minutes. After cooling to room temperature, the reaction mixture was concentrated in vacuo then redissolved in DMF (1 mL) before being purified via via preparative LC/MS with the following conditions: Column: Waters XBridge C18, 19×150 mm, 5-µm particles; Guard Column: Waters XBridge C18, 19×10 mm, 5-µm particles; Mobile Phase A: 5:95 acetonitrile:water with 10 mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to afford the title compound (11.9 mg, 29% yield). MS(ES): m/z=502 [M+H]⁺, HPLC T$_r$: 1.66$^j$.

Example 362

1-(4-(3,4-Dihydroquinolin-1(2H)-yl)-2'-(1H-tetrazol-5-yl)-[1,1'-biphenyl]-3-yl)-3-(6-methylpyridin-3-yl) urea

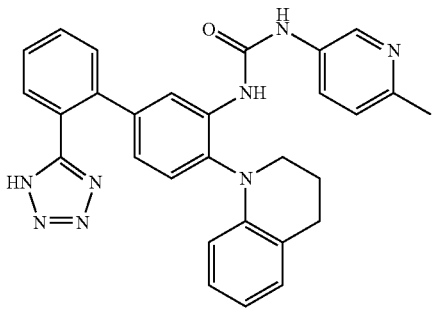 [SMILES: Cc1ccc(NC(=O)Nc2cc(-c3ccccc3-c3nnn[nH]3)ccc2N2CCCc3ccccc32)cn1]

The title compound (25.2 mg, 60%) was prepared following a procedure analogous to that for the synthesis of Example 361, except that 6-methylpyridin-3-amine (12 mg, 0.11 mmol) was used instead of p-toluidine. MS(ES): m/z=503 [M+H]⁺, HPLC T$_r$: 1.36$^j$.

Example 363

1-(4-(3,4-Dihydroquinolin-1(2H)-yl)-2'-(1H-tetrazol-5-yl)-[1,1'-biphenyl]-3-yl)-3-(4-(trifluoromethoxy) phenyl)urea

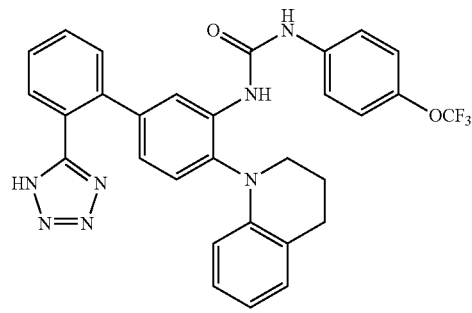 [SMILES: O=C(Nc1ccc(OC(F)(F)F)cc1)Nc1cc(-c2ccccc2-c2nnn[nH]2)ccc1N1CCCc2ccccc21]

The title compound (5.4 mg, 12%) was prepared following a procedure analogous to that for the synthesis of Example 361, except that 4-(trifluoromethoxy)aniline (20 mg, 0.11 mmol) was used instead of p-toluidine. MS(ES): m/z=572 [M+H]⁺, HPLC T$_r$: 1.82$^j$.

Example 364

1-(4-(3,4-Dihydroquinolin-1(2H)-yl)-2'-(1H-tetrazol-5-yl)-[1,1'-biphenyl]-3-yl)-3-(2-fluoro-4-(trifluoromethyl)phenyl)urea

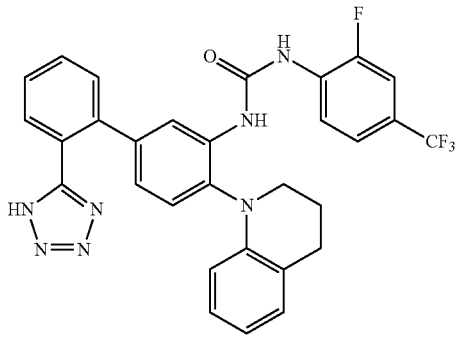 [SMILES: O=C(Nc1ccc(C(F)(F)F)cc1F)Nc1cc(-c2ccccc2-c2nnn[nH]2)ccc1N1CCCc2ccccc21]

The title compound (9.3 mg, 20%) was prepared following a procedure analogous to that for the synthesis of Example 361, except that 2-fluoro-4-(trifluoromethyl)aniline (20 mg, 0.11 mmol) was used instead of p-toluidine. MS(ES): m/z=574 [M+H]⁺, HPLC T$_r$: 1.86$^j$.

Example 365

1-(4-(3,4-Dihydroquinolin-1(2H)-yl)-2'-(1H-tetrazol-5-yl)-[1,1'-biphenyl]-3-yl)-3-(6-fluoropyridin-3-yl)urea

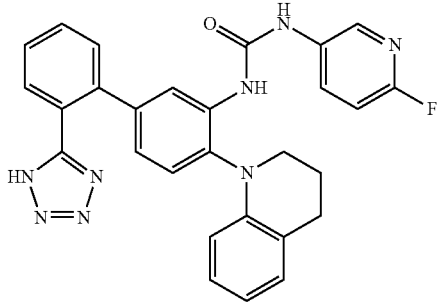 [SMILES: O=C(Nc1ccc(F)nc1)Nc1cc(-c2ccccc2-c2nnn[nH]2)ccc1N1CCCc2ccccc21]

The title compound (24.7 mg, 59%) was prepared following a procedure analogous to that for the synthesis of Example 361, except that 6-fluoropyridin-3-amine (13 mg, 0.11 mmol) was used instead of p-toluidine. MS(ES): m/z=507 [M+H]⁺, HPLC T$_r$: 1.42$^j$.

Example 366

1-(4-(3,4-Dihydroquinolin-1(2H)-yl)-2'-(1H-tetrazol-5-yl)-[1,1'-biphenyl]-3-yl)-3-(3-methylisoxazol-5-yl)urea

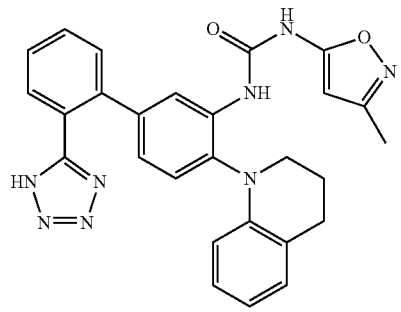 [SMILES: Cc1cc(NC(=O)Nc2cc(-c3ccccc3-c3nnn[nH]3)ccc2N2CCCc3ccccc32)on1]

The title compound (11.5 mg, 26%) was prepared following a procedure analogous to that for the synthesis of Example 361, except that 3-methylisoxazol-5-amine (11 mg, 0.11 mmol) was used instead of p-toluidine. MS(ES): m/z=493 [M+H]⁺, HPLC T$_r$: 1.39$^j$.

Example 367

(±)-1-(4-(3-Phenylpyrrolidin-1-yl)-2'-(1H-tetrazol-5-yl)-[1,1'-biphenyl]-3-yl)-3-(p-tolyl)urea

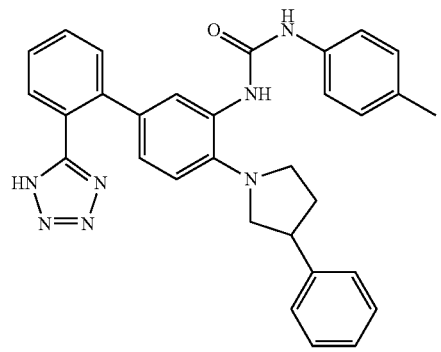 [SMILES: Cc1ccc(NC(=O)Nc2cc(-c3ccccc3-c3nnn[nH]3)ccc2N2CCC(c3ccccc3)C2)cc1]

A. (±)-1-(4-Bromo-2-nitrophenyl)-3-phenylpyrrolidine

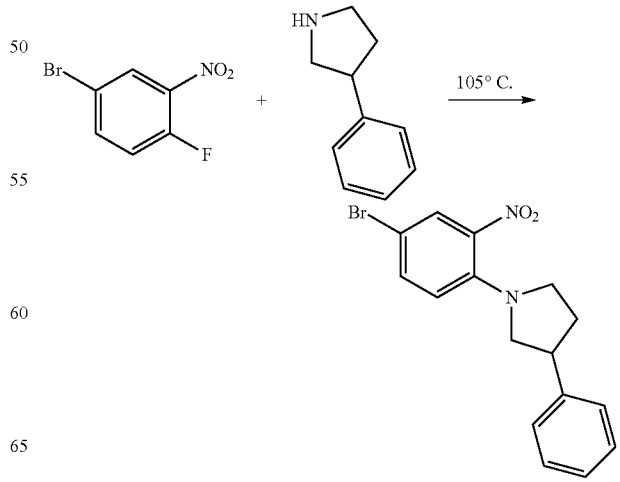

A mixture of 4-bromo-1-fluoro-2-nitrobenzene (0.39 ml, 3.2 mmol) and 3-phenylpyrrolidine (1.0 g, 6.79 mmol), in a sealable vial with pressure release cap, was heated at 105° C. for 16 hours before being cooled to room temperature. The crude reaction mixture was purified by flash chromatography to afford the title compound (1.04 g, 94%). $^1$H NMR (400 MHz, CDCl$_3$) δ 7.90 (d, J=2.4 Hz, 1H), 7.46 (dd, J=9.2, 2.4 Hz, 1H), 7.40-7.32 (m, 2H), 7.31-7.21 (m, 3H), 6.83 (d, J=9.2 Hz, 1H), 3.59-3.39 (m, 4H), 3.28 (ddd, J=10.1, 7.5, 2.9 Hz, 1H), 2.41 (dtd, J=12.1, 6.1, 2.6 Hz, 1H), 2.16 (dtd, J=12.0, 9.7, 7.7 Hz, 1H). MS(ES): m/z=347 [M+H]$^+$, HPLC T$_r$: 4.81$^l$.

367. (±)-1-(4-(3-Phenylpyrrolidin-1-yl)-2'-(1H-tetrazol-5-yl)-[1,1'-biphenyl]-3-yl)-3-(p-tolyl)urea

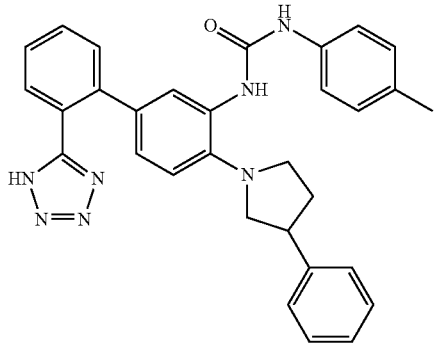 [SMILES: Cc1ccc(NC(=O)Nc2cc(-c3ccccc3-c3nnn[nH]3)ccc2N2CCC(c3ccccc3)C2)cc1]

The title compound (19.8 mg, 52%) was prepared following a procedure analogous to that for the synthesis of Example 361, except that (±)-1-(4-bromo-2-nitrophenyl)-3-phenylpyrrolidine was used instead of 1-(4-bromo-2-nitrophenyl)-1,2,3,4-tetrahydroquinoline. MS(ES): m/z=516 [M+H]$^+$, HPLC T$_r$: 1.65$^j$.

Example 368

(±)-1-(6-Methylpyridin-3-yl)-3-(4-(3-phenylpyrrolidin-1-yl)-2'-(1H-tetrazol-5-yl)-[1,1'-biphenyl]-3-yl)urea

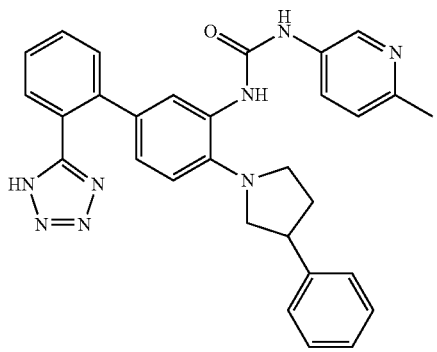 [SMILES: Cc1ccc(NC(=O)Nc2cc(-c3ccccc3-c3nnn[nH]3)ccc2N2CCC(c3ccccc3)C2)cn1]

The title compound (20.6 mg, 54%) was prepared following a procedure analogous to that for the synthesis of Example 362, except that (±)-1-(4-bromo-2-nitrophenyl)-3-phenylpyrrolidine was used instead of 1-(4-bromo-2-nitrophenyl)-1,2,3,4-tetrahydroquinoline. MS(ES): m/z=517 [M+H]$^+$, HPLC T$_r$: 1.30.

Example 369

(±)-1-(4-(3-Phenylpyrrolidin-1-yl)-2'-(1H-tetrazol-5-yl)-[1,1'-biphenyl]-3-yl)-3-(4-(trifluoromethoxy)phenyl)urea

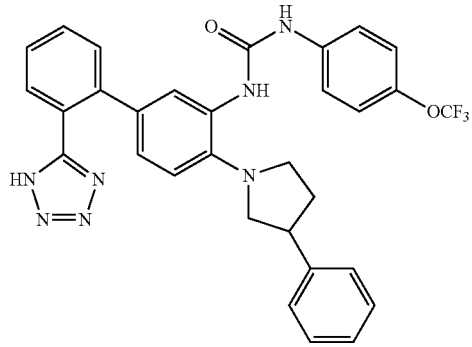 [SMILES: O=C(Nc1ccc(OC(F)(F)F)cc1)Nc1cc(-c2ccccc2-c2nnn[nH]2)ccc1N1CCC(c2ccccc2)C1]

The title compound (22.6 mg, 52%) was prepared following a procedure analogous to that for the synthesis of Example 363, except that (±)-1-(4-bromo-2-nitrophenyl)-3-phenylpyrrolidine was used instead of 1-(4-bromo-2-nitrophenyl)-1,2,3,4-tetrahydroquinoline. MS(ES): m/z=586 [M+H]$^+$, HPLC T$_r$: 1.79$^j$.

Example 370

(±)-1-(2-Fluoro-4-(trifluoromethyl)phenyl)-3-(4-(3-phenylpyrrolidin-1-yl)-2'-(1H-tetrazol-5-yl)-[1,1'-biphenyl]-3-yl)urea

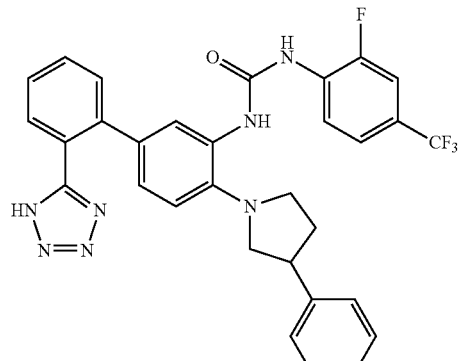

The title compound (9.5 mg, 22%) was prepared following a procedure analogous to that for the synthesis of Example 364, except that (±)-1-(4-bromo-2-nitrophenyl)-3-phenylpyrrolidine was used instead of 1-(4-bromo-2-nitrophenyl)-1,2,3,4-tetrahydroquinoline. MS(ES): m/z=588 [M+H]$^+$, HPLC T$_r$: 1.85$^j$.

Example 371

(±)-1-(6-Fluoropyridin-3-yl)-3-(4-(3-phenylpyrrolidin-1-yl)-2'-(1H-tetrazol-5-yl)-[1,1'-biphenyl]-3-yl)urea

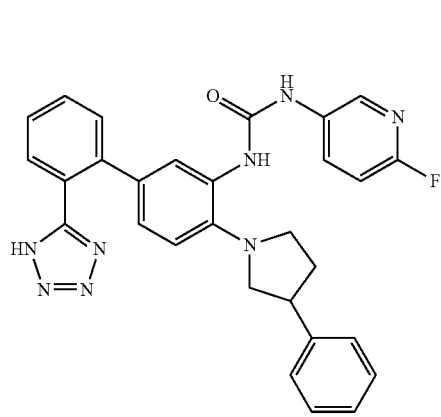 [SMILES: O=C(Nc1ccc(F)nc1)Nc1cc(-c2ccccc2-c2nnn[nH]2)ccc1N1CCC(c2ccccc2)C1]

The title compound (11.8 mg, 31%) was prepared following a procedure analogous to that for the synthesis of Example 365, except that (±)-1-(4-bromo-2-nitrophenyl)-3-phenylpyrrolidine was used instead of 1-(4-bromo-2-nitrophenyl)-1,2,3,4-tetrahydroquinoline. MS(ES): m/z=521 [M+H]$^+$, HPLC T$_r$: 1.42$^j$.

Example 372

(±)-1-(3-Methylisoxazol-5-yl)-3-(4-(3-phenylpyrrolidin-1-yl)-2'-(1H-tetrazol-5-yl)-[1,1'-biphenyl]-3-yl)urea

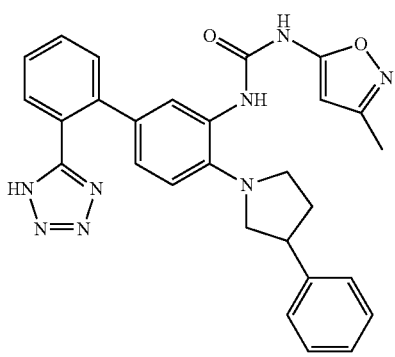 [SMILES: Cc1cc(NC(=O)Nc2cc(-c3ccccc3-c3nnn[nH]3)ccc2N2CCC(c3ccccc3)C2)on1]

The title compound (8.8 mg, 23%) was prepared following a procedure analogous to that for the synthesis of Example 366, except that (±)-1-(4-bromo-2-nitrophenyl)-3-phenylpyrrolidine was used instead of 1-(4-bromo-2-nitrophenyl)-1,2,3,4-tetrahydroquinoline. MS(ES): m/z=507 [M+H]$^+$, HPLC T$_r$: 1.38$^j$.

Example 373

4'-(3,4-Dihydroquinolin-1(2H)-yl)-5-fluoro-3'-(3-(p-tolyl)ureido)-[1,1'-biphenyl]-2-carboxylic acid

A. 4'-(3,4-Dihydroquinolin-1(2H)-yl)-5-fluoro-3'-nitro-[1,1'-biphenyl]-2-carboxylic acid

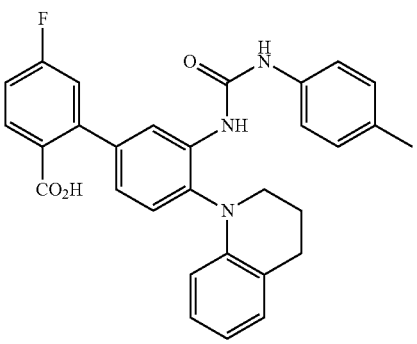 [SMILES: Cc1ccc(NC(=O)Nc2cc(-c3cc(F)ccc3C(=O)O)ccc2N2CCCc3ccccc32)cc1]

To a solution of 1-(4-bromo-2-nitrophenyl)-1,2,3,4-tetrahydroquinoline (0.40 g, 1.20 mmol) in DMF (10.5 mL), in a sealable reaction vial, was added 2-borono-4-fluorobenzoic acid (0.29 g, 1.57 mmol), K$_2$CO$_3$ (0.83 g, 6.02 mmol) and water (1.5 ml). The heterogenous mixture was purged with nitrogen for 15 minutes, before tetrakis(tri-phenylphophine)palladium(0) (0.07 g, 0.06 mmol) was added to the flask. The mixture was purged with nitrogen for an additional five minutes before the vial was sealed and the reaction heated at 100° C. for three hours. The reaction mixture was cooled to room temperature before being treated with Et$_2$O and water. Aqueous HCl (1N) was added until the aqueous layer reached pH 4. The mixture was thoroughly extracted with Et$_2$O and these organic extracts were combined, washed with water then brine, and dried over anhydrous sodium sulfate. The drying agent was removed by filtration and the filtrate was concentrated in vacuo to afford the crude product which was purified by flash chromatography to afford the title compound (0.34 g, 72%). MS(ES): m/z=393 [M+H]$^+$, HPLC T$_r$: 1.27$^l$.

373. 4'-(3,4-Dihydroquinolin-1(2H)-yl)-5-fluoro-3'-(3-(p-tolyl)ureido)-[1,1'-biphenyl]-2-carboxylic acid

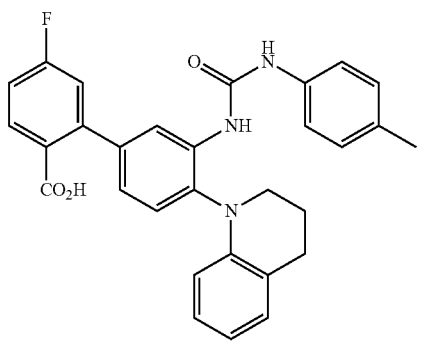 [SMILES: Cc1ccc(NC(=O)Nc2cc(-c3cc(F)ccc3C(=O)O)ccc2N2CCCc3ccccc32)cc1]

The title compound (11.8 mg, 41%) was prepared following a procedure analogous to that for the synthesis of Example 361, except that 4'-(3,4-dihydro-quinolin-1(2H)-yl)-5-fluoro-3'-nitro-[1,1'-biphenyl]-2-carboxylic acid was used instead of 1-(3-nitro-2'-(1H-tetrazol-5-yl)-[1,1'-biphenyl]-4-yl)-1,2,3,4-tetrahydroquinoline. MS(ES): m/z=496 [M+H]$^+$, HPLC T$_r$: 1.67$^j$.

Using the methods described herein, the following additional compounds of the invention were prepared.

| Example No. | Compound | HPLC T$_r$ | (M + H)$^+$ |
|---|---|---|---|
| 374 | 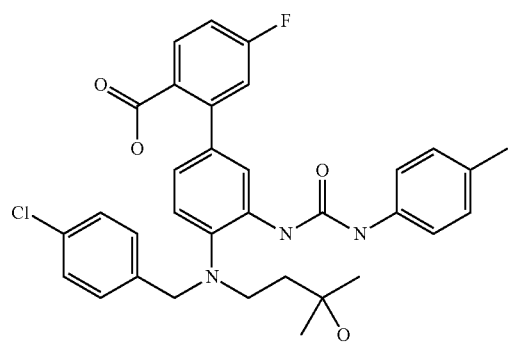 [SMILES: Cc1ccc(NC(=O)Nc2cc(-c3cc(F)ccc3C(=O)O)ccc2N(CCC(C)(C)O)Cc2ccc(Cl)cc2)cc1] | 1.86$^j$ | 590 |
| 375 | 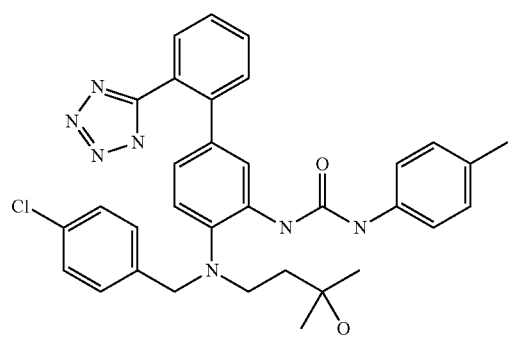 [SMILES: Cc1ccc(NC(=O)Nc2cc(-c3ccccc3-c3nnn[nH]3)ccc2N(CCC(C)(C)O)Cc2ccc(Cl)cc2)cc1] | 1.92$^j$ | 596 |
| 376 | 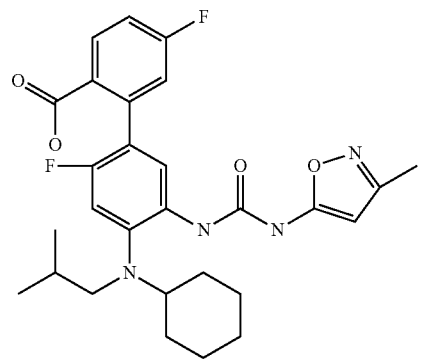 [SMILES: Cc1cc(NC(=O)Nc2cc(-c3cc(F)ccc3C(=O)O)c(F)cc2N(CC(C)C)C2CCCCC2)on1] | 1.74$^j$ | 527 |

-continued

| Example No. | Compound | HPLC T_r | (M + H)+ |
|---|---|---|---|
| 377 | | 1.64$^j$ | 491 |
| 378 | | 1.53$^j$ | 502 |
| 379 | | 1.65$^j$ | 526 |
| 380 | | 2.52$^j$ | 540 |

| Example No. | Compound | HPLC T_r | (M + H)+ |
|---|---|---|---|
| 381 | 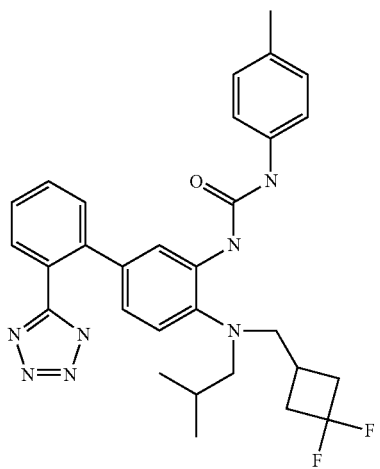 [SMILES: Cc1ccc(NC(=O)Nc2cc(-c3ccccc3-c3nnn[nH]3)ccc2N(CC(C)C)CC2CC(F)(F)C2)cc1] | 1.90[j] | 546 |
| 382 | 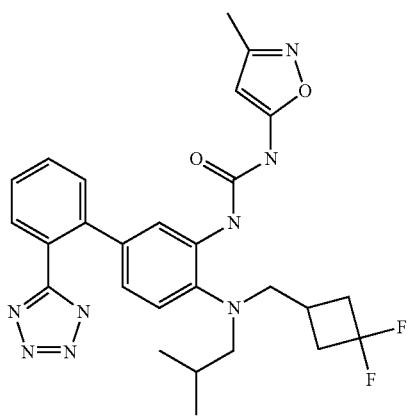 [SMILES: Cc1cc(NC(=O)Nc2cc(-c3ccccc3-c3nnn[nH]3)ccc2N(CC(C)C)CC2CC(F)(F)C2)on1] | 1.53[j] | 537 |
| 383 | 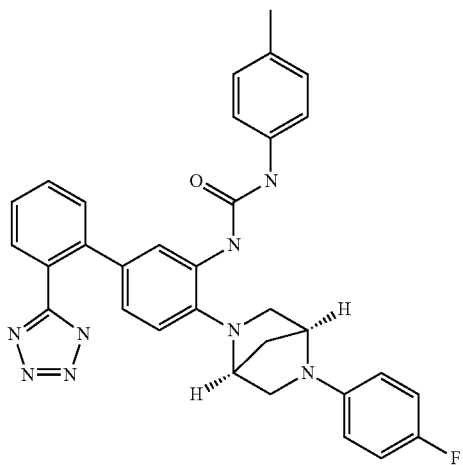 [SMILES: Cc1ccc(NC(=O)Nc2cc(-c3ccccc3-c3nnn[nH]3)ccc2N2C[C@@H]3C[C@H]2CN3c2ccc(F)cc2)cc1] | 1.64[j] | 561 |

-continued

| Example No. | Compound | HPLC T$_r$ | (M + H)$^+$ |
|---|---|---|---|
| 384 | | 1.70$^j$ | 565 |
| 385 | | 2.14$^j$ | 539 |
| 386 | | 1.67$^j$ | 534 |
| 387 | | 1.38$^j$ | 535 |

| Example No. | Compound | HPLC T$_r$ | (M + H)$^+$ |
|---|---|---|---|
| 388 | 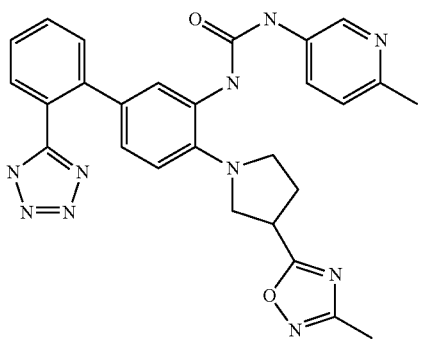 [SMILES: Cc1ccc(NC(=O)Nc2cc(-c3ccccc3-c3nnn[nH]3)ccc2N2CCC(c3nc(C)no3)C2)cn1] | 1.08$^j$ | 523 |
| 389 | 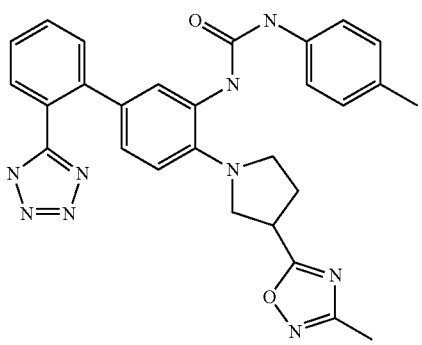 [SMILES: Cc1ccc(NC(=O)Nc2cc(-c3ccccc3-c3nnn[nH]3)ccc2N2CCC(c3nc(C)no3)C2)cc1] | 1.38$^j$ | 522 |
| 390 | 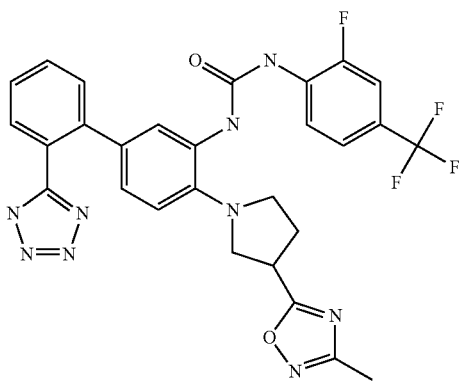 [SMILES: Cc1noc(C2CCN(c3ccc(-c4ccccc4-c4nnn[nH]4)cc3NC(=O)Nc3ccc(C(F)(F)F)cc3F)C2)n1] | 1.59$^j$ | 594 |
| 391 | 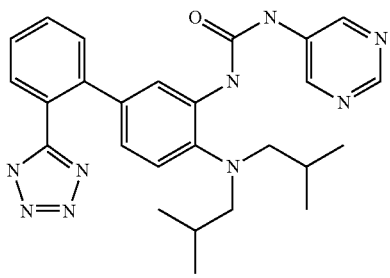 [SMILES: CC(C)CN(CC(C)C)c1ccc(-c2ccccc2-c2nnn[nH]2)cc1NC(=O)Nc1cncnc1] | 1.51$^j$ | 486 |

-continued
| Example No. | Compound | HPLC T$_r$ | (M + H)$^+$ |
|---|---|---|---|
| 392 | 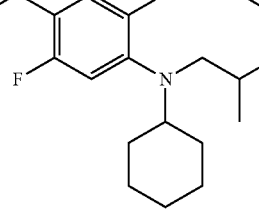 | 2.28$^j$ | 608 |
| 393 | 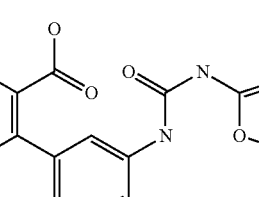 | 2.13$^j$ | 581 |
| 394 | 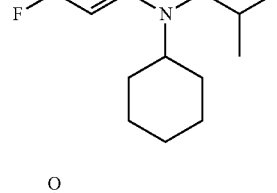 | 1.74$^j$ | 537 |
| 395 | 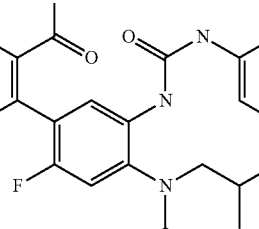 | 1.61$^j$ | 499 |
| 396 | 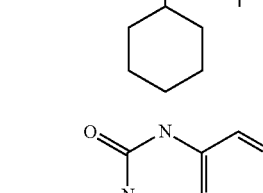 | 1.40$^j$ | 489 |

| Example No. | Compound | HPLC T$_r$ | (M + H)$^+$ |
|---|---|---|---|
| 397 | 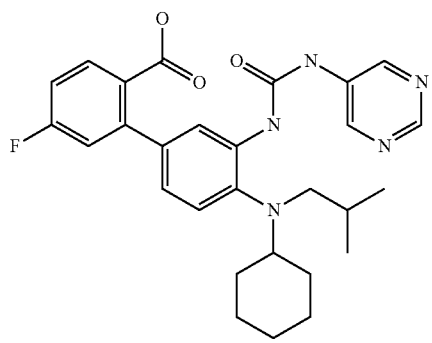 [SMILES: CC(C)CN(c1ccc(-c2cc(F)ccc2C(=O)O)cc1NC(=O)Nc1cncnc1)C1CCCCC1] | 1.64$^j$ | 506 |
| 398 | 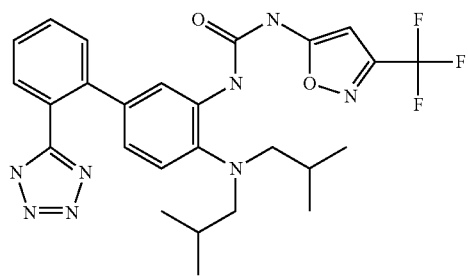 [SMILES: CC(C)CN(CC(C)C)c1ccc(-c2ccccc2-c2nnn[nH]2)cc1NC(=O)Nc1cc(C(F)(F)F)no1] | 1.92$^j$ | 543 |
| 399 | 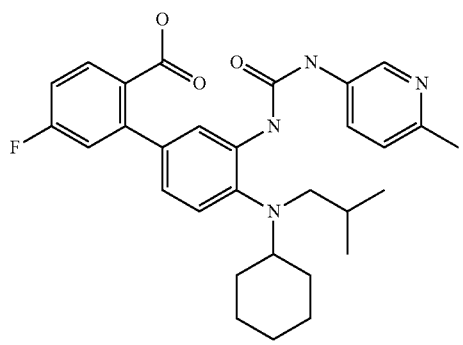 [SMILES: Cc1ccc(NC(=O)Nc2cc(-c3cc(F)ccc3C(=O)O)ccc2N(CC(C)C)C2CCCCC2)cn1] | 1.46$^j$ | 519 |
| 400 | 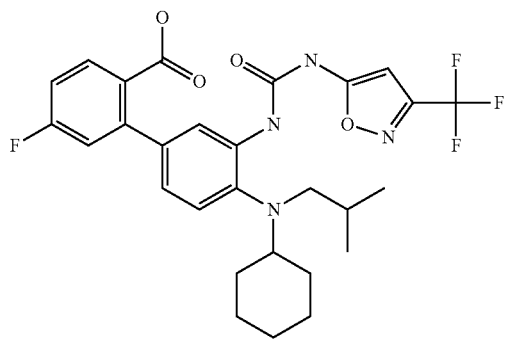 [SMILES: CC(C)CN(c1ccc(-c2cc(F)ccc2C(=O)O)cc1NC(=O)Nc1cc(C(F)(F)F)no1)C1CCCCC1] | 1.73$^j$ | 563 |

-continued
| Example No. | Compound | HPLC T$_r$ | (M + H)$^+$ |
|---|---|---|---|
| 401 | 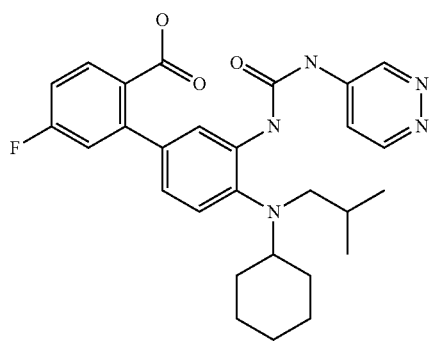 [SMILES: CC(C)CN(c1ccc(-c2cc(F)ccc2C(=O)O)cc1NC(=O)Nc1ccnnc1)C1CCCCC1] | 0.82$^j$ | 506 |
| 402 | 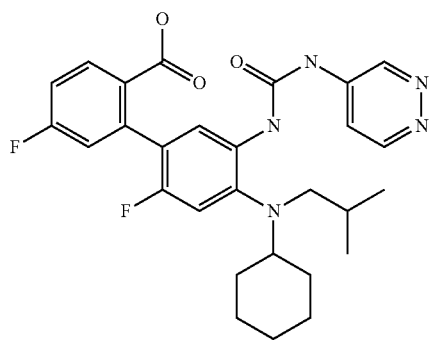 [SMILES: CC(C)CN(c1cc(F)c(-c2cc(F)ccc2C(=O)O)cc1NC(=O)Nc1ccnnc1)C1CCCCC1] | 1.37$^j$ | 524 |
| 403 | 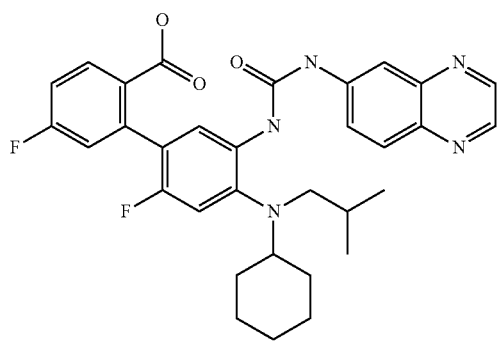 [SMILES: CC(C)CN(c1cc(F)c(-c2cc(F)ccc2C(=O)O)cc1NC(=O)Nc1ccc2nccnc2c1)C1CCCCC1] | 1.51$^j$ | 574 |
| 404 | 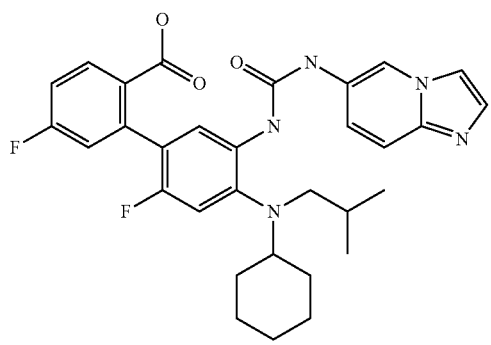 [SMILES: CC(C)CN(c1cc(F)c(-c2cc(F)ccc2C(=O)O)cc1NC(=O)Nc1ccc2nccn2c1)C1CCCCC1] | 1.41$^j$ | 562 |

| Example No. | Compound | HPLC T$_r$ | (M + H)$^+$ |
|---|---|---|---|
| 405 | 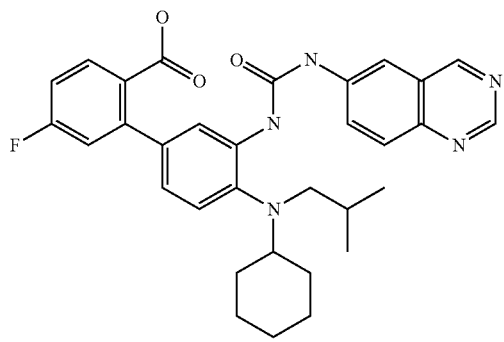 [SMILES: CC(C)CN(c1ccc(-c2cc(F)ccc2C(=O)O)cc1NC(=O)Nc1ccc2ncncc2c1)C1CCCCC1] | 1.68$^j$ | 556 |
| 406 | 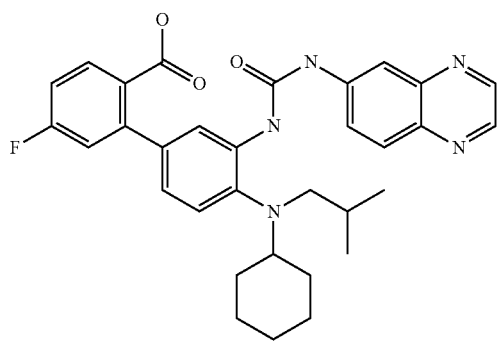 [SMILES: CC(C)CN(c1ccc(-c2cc(F)ccc2C(=O)O)cc1NC(=O)Nc1ccc2nccnc2c1)C1CCCCC1] | 1.47$^j$ | 556 |
| 407 | 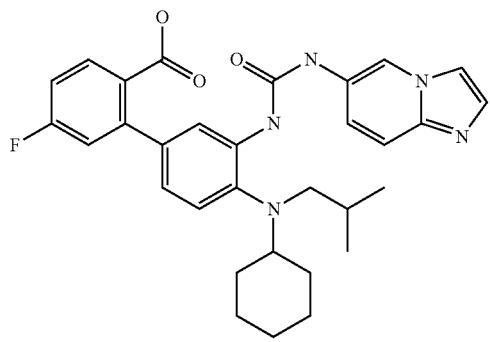 [SMILES: CC(C)CN(c1ccc(-c2cc(F)ccc2C(=O)O)cc1NC(=O)Nc1ccc2nccn2c1)C1CCCCC1] | 1.40$^j$ | 544 |
| 408 | 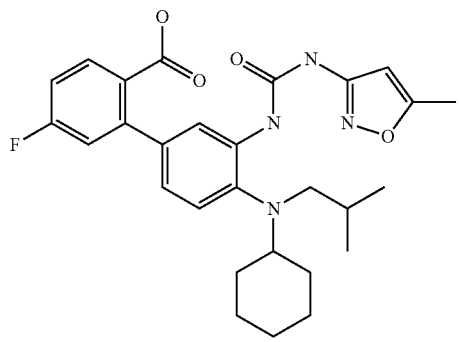 [SMILES: Cc1cc(NC(=O)Nc2cc(-c3cc(F)ccc3C(=O)O)ccc2N(CC(C)C)C2CCCCC2)no1] | 1.59$^j$ | 509 |

| Example No. | Compound | HPLC $T_r$ | $(M + H)^+$ |
|---|---|---|---|
| 409 | 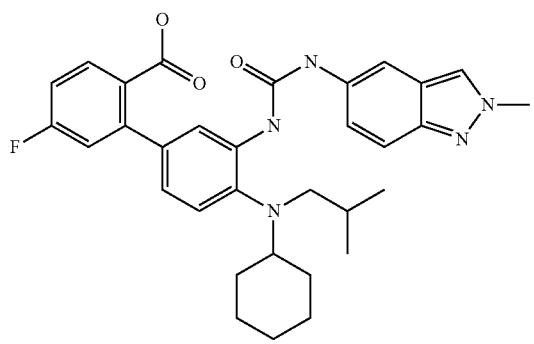 [SMILES: CC(C)CN(c1ccc(-c2cc(F)ccc2C(=O)O)cc1NC(=O)Nc1ccc2nn(C)cc2c1)C1CCCCC1] | 1.68[j] | 558 |
| 410 | 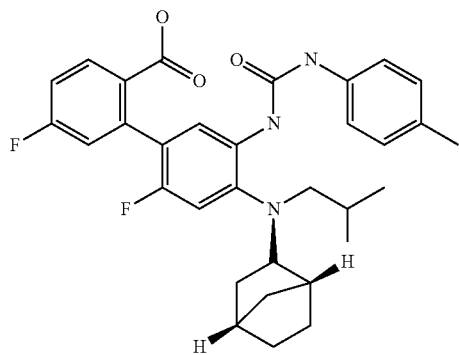 | 2.19[j] | 548 |
| 411 | 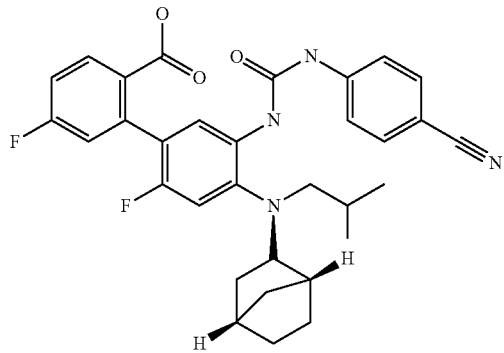 | 1.72[j] | 559 |
| 412 | 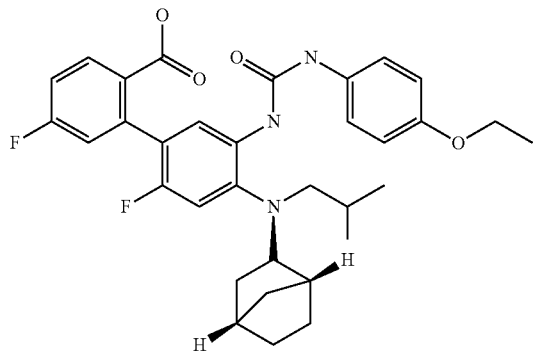 | 2.10[j] | 578 |

| Example No. | Compound | HPLC T$_r$ | (M + H)$^+$ |
|---|---|---|---|
| 413 | 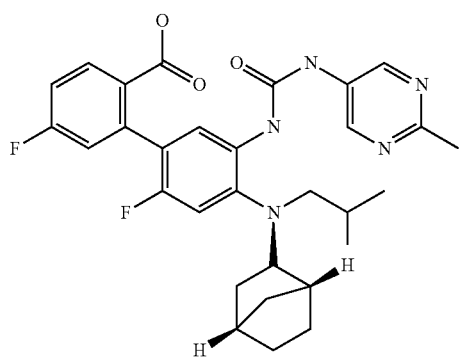 | 1.49$^j$ | 550 |
| 414 | 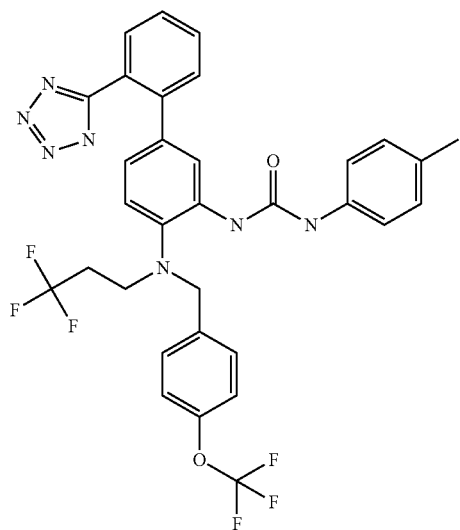 [SMILES: Cc1ccc(NC(=O)Nc2cc(-c3ccccc3-c3nnn[nH]3)ccc2N(CCC(F)(F)F)Cc2ccc(OC(F)(F)F)cc2)cc1] | 2.13$^v$ | 654 |
| 415 | 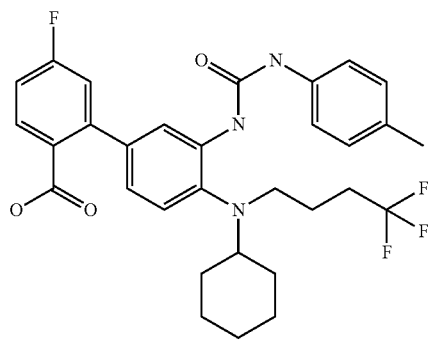 [SMILES: Cc1ccc(NC(=O)Nc2cc(-c3cc(F)ccc3C(=O)O)ccc2N(CCCC(F)(F)F)C2CCCCC2)cc1] | 1.67$^j$ | 572 |
| 416 | 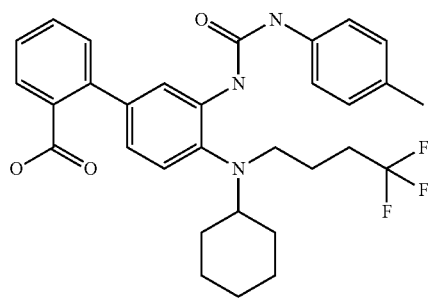 [SMILES: Cc1ccc(NC(=O)Nc2cc(-c3ccccc3C(=O)O)ccc2N(CCCC(F)(F)F)C2CCCCC2)cc1] | 1.92$^j$ | 554 |

| Example No. | Compound | HPLC T$_r$ | (M + H)$^+$ |
|---|---|---|---|
| 417 | | 17.27$^a$ | 550 |
| 418 | | 1.84$^j$ | 526 |
| 419 | | 1.87$^j$ | 544 |
| 420 | | 1.95$^j$ | 544 |
| 421 | | 1.97$^k$ | 562 |

-continued

| Example No. | Compound | HPLC T_r | (M + H)+ |
|---|---|---|---|
| 422 | | 2.00[k] | 572 |
| 423 | Chiral | 1.80[j] | 568 |
| 424 | | 17.73[a] | 502 |
| 425 | | 1.94[j] | 492 |
| 426 | | 1.96[j] | 510 |

| Example No. | Compound | HPLC T_r | (M + H)+ |
|---|---|---|---|
| 427 | 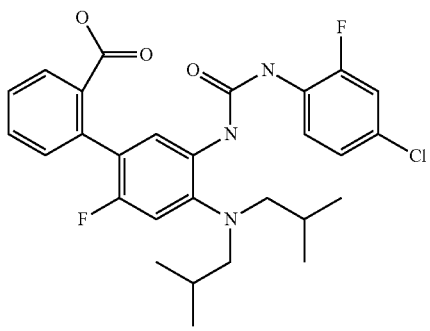 [SMILES: CC(C)CN(CC(C)C)c1cc(F)c(-c2ccccc2C(=O)O)cc1NC(=O)Nc1ccc(Cl)cc1F] | 1.77[j] | 530 |
| 428 | 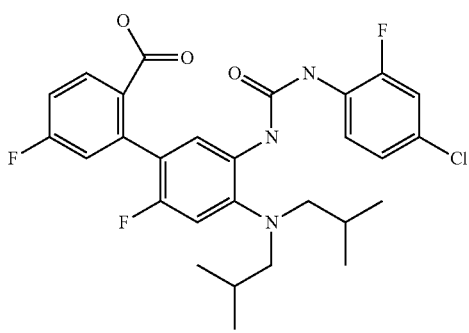 [SMILES: CC(C)CN(CC(C)C)c1cc(F)c(-c2cc(F)ccc2C(=O)O)cc1NC(=O)Nc1ccc(Cl)cc1F] | 2.05[j] | 548 |
| 429 | 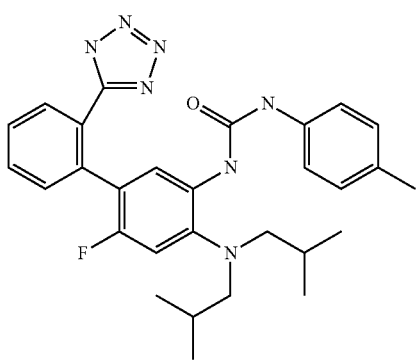 [SMILES: Cc1ccc(NC(=O)Nc2cc(-c3ccccc3-c3nnn[nH]3)c(F)cc2N(CC(C)C)CC(C)C)cc1] | 2.27[k] | 516 |
| 430 | 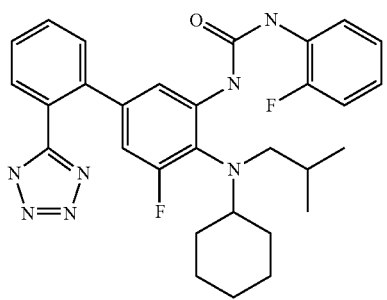 [SMILES: CC(C)CN(c1c(F)cc(-c2ccccc2-c2nnn[nH]2)cc1NC(=O)Nc1ccccc1F)C1CCCCC1] | 1.66j | 546 |

| Example No. | Compound | HPLC T_r | (M + H)+ |
|---|---|---|---|
| 431 | | 1.71$^j$ | 540 |
| 432 | | 1.69$^j$ | 522 |
| 433 | | 2.00$^j$ | 542 |
| 434 | | 2.12$^j$ | 574 |

| Example No. | Compound | HPLC T$_r$ | (M + H)$^+$ |
|---|---|---|---|
| 435 | | 2.06$^j$ | 536 |
| 436 | | 2.08$^j$ | 580 |
| 437 | | 2.03$^j$ | 518 |
| 438 | | 2.10j | 556 |
| 439 | | 1.67$^j$ | 506 |

-continued
| Example No. | Compound | HPLC $T_r$ | $(M + H)^+$ |
|---|---|---|---|
| 440 | 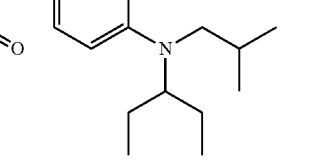 | 1.72[j] | 526 |
| 441 | 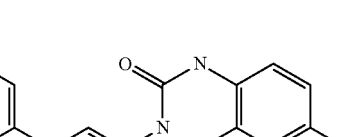 | 1.73[j] | 550 |
| 442 | 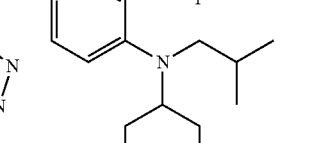 | 174[j] | 544 |
| 443 | 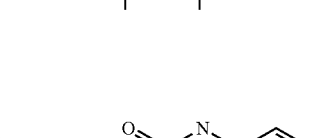 | 1.66[j] | 488 |
| 444 | 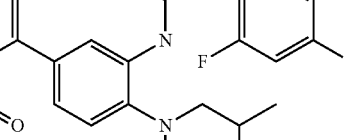 | 1.65[j] | 512 |

| Example No. | Compound | HPLC T$_r$ | (M + H)$^+$ |
|---|---|---|---|
| 445 | 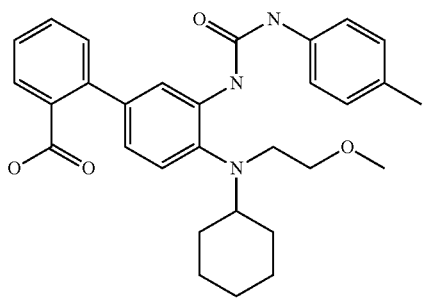 [SMILES: COCCN(c1ccc(-c2ccccc2C(=O)O)cc1NC(=O)Nc1ccc(C)cc1)C1CCCCC1] | 1.69$^j$ | 502 |
| 446 | 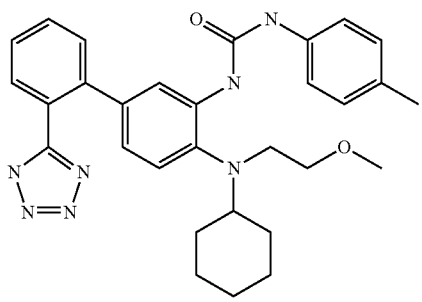 [SMILES: COCCN(c1ccc(-c2ccccc2-c2nnn[nH]2)cc1NC(=O)Nc1ccc(C)cc1)C1CCCCC1] | 1.51$^j$ | 526 |
| 447 | 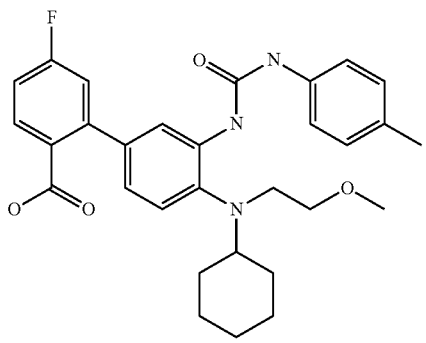 [SMILES: COCCN(c1ccc(-c2cc(F)ccc2C(=O)O)cc1NC(=O)Nc1ccc(C)cc1)C1CCCCC1] | 1.51$^j$ | 520 |
| 448 | 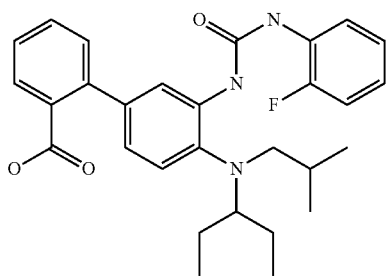 [SMILES: CCC(CC)N(CC(C)C)c1ccc(-c2ccccc2C(=O)O)cc1NC(=O)Nc1ccccc1F] | 1.91$^j$ | 492 |
| 449 | 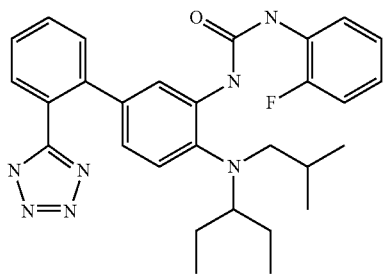 [SMILES: CCC(CC)N(CC(C)C)c1ccc(-c2ccccc2-c2nnn[nH]2)cc1NC(=O)Nc1ccccc1F] | 1.93$^j$ | 516 |

| Example No. | Compound | HPLC T$_r$ | (M + H)$^+$ |
|---|---|---|---|
| 450 | | 1.93$^j$ | 510 |
| 451 | | 1.89$^j$ | 558 |
| 452 | | 1.90$^j$ | 564 |
| 453 | | 1.92$^j$ | 550 |
| 454 | | 1.93$^j$ | 528 |

| Example No. | Compound | HPLC T$_r$ | (M + H)$^+$ |
|---|---|---|---|
| 455 | 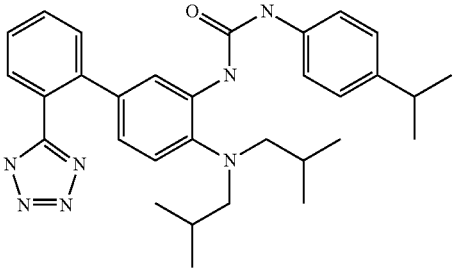 | 1.60$^k$ | 526 |
| 456 | 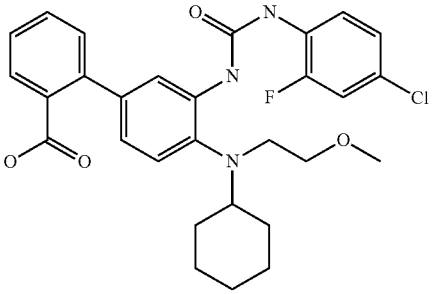 [SMILES: COCCN(c1ccc(-c2ccccc2C(=O)O)cc1NC(=O)Nc1ccc(Cl)cc1F)C1CCCCC1] | 4.56$^l$ | 540 |
| 457 | 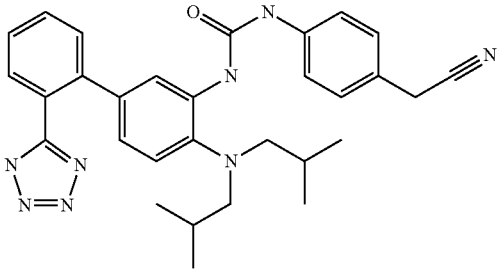 [SMILES: CC(C)CN(CC(C)C)c1ccc(-c2ccccc2-c2nnn[nH]2)cc1NC(=O)Nc1ccc(CC#N)cc1] | 1.75$^j$ | 523 |
| 458 | 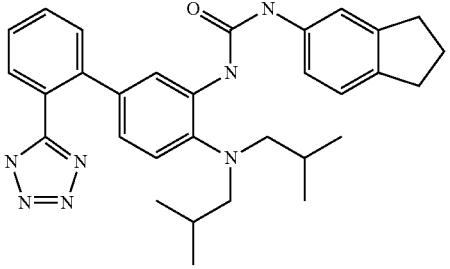 [SMILES: CC(C)CN(CC(C)C)c1ccc(-c2ccccc2-c2nnn[nH]2)cc1NC(=O)Nc1ccc2c(c1)CCC2] | 2.08$^j$ | 524 |
| 459 | 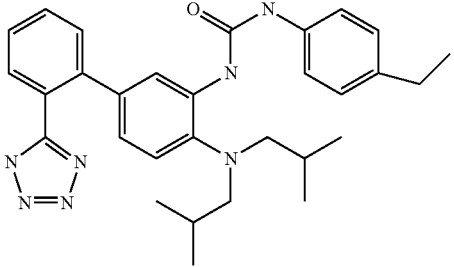 [SMILES: CCc1ccc(NC(=O)Nc2cc(-c3ccccc3-c3nnn[nH]3)ccc2N(CC(C)C)CC(C)C)cc1] | 2.05$^j$ | 512 |

| Example No. | Compound | HPLC T$_r$ | (M + H)$^+$ |
|---|---|---|---|
| 460 | 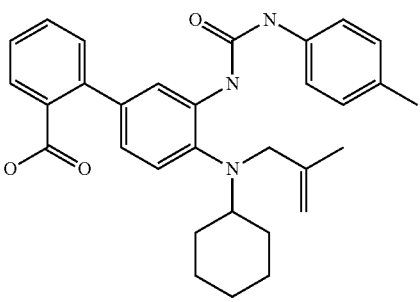 [SMILES: C=C(C)CN(c1ccc(-c2ccccc2C(=O)O)cc1NC(=O)Nc1ccc(C)cc1)C1CCCCC1] | 1.93$^j$ | 498 |
| 461 | 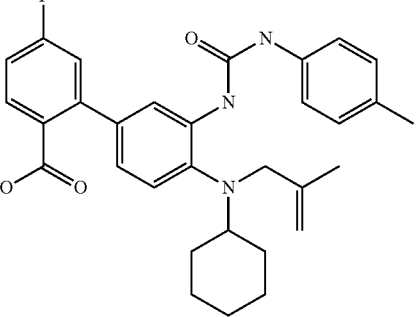 | 1.95$^j$ | 516 |
| 462 | 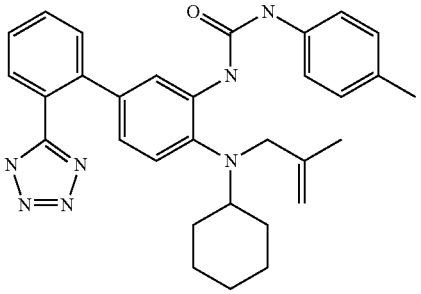 [SMILES: C=C(C)CN(c1ccc(-c2ccccc2-c2nnn[nH]2)cc1NC(=O)Nc1ccc(C)cc1)C1CCCCC1] | 1.95j | 522 |
| 463 | 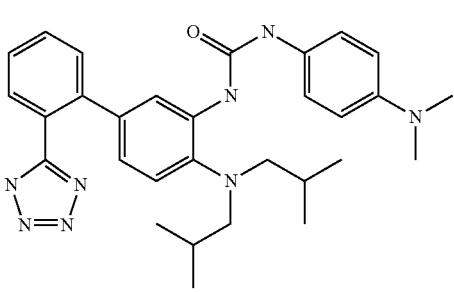 | 1.89$^j$ | 527 |
| 464 | 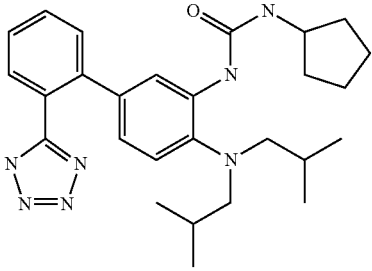 [SMILES: CC(C)CN(CC(C)C)c1ccc(-c2ccccc2-c2nnn[nH]2)cc1NC(=O)NC1CCCC1] | 1.88$^j$ | 476 |

-continued

| Example No. | Compound | HPLC T_r | (M + H)+ |
|---|---|---|---|
| 465 | | 1.90[j] | 528 |
| 466 | | 1.92[j] | 522 |
| 467 | | 17.73[a] | 578 |
| 468 | | 2.11[j] | 592 |
| 469 | | 2.05[j] | 586 |

| Example No. | Compound | HPLC $T_r$ | $(M + H)^+$ |
| --- | --- | --- | --- |
| 470 | | $1.97^j$ | 590 |
| 471 | | $4.53^l$ | 498 |
| 472 | | $4.45^l$ | 522 |
| 473 | | $4.68^l$ | 516 |
| 474 | | $4.64^l$ | 500 |

| Example No. | Compound | HPLC T_r | (M + H)+ |
|---|---|---|---|
| 475 | | 4.58[l] | 524 |
| 476 | | 4.80[l] | 518 |
| 477 | | 2.78[q] | 496 |
| 478 | | 2.67[q] | 478 |
| 479 | | 2.73[q] | 530 |

-continued

| Example No. | Compound | HPLC T$_r$ | (M + H)$^+$ |
|---|---|---|---|
| 480 | | 2.68$^q$ | 512 |
| 481 | | 2.36$^k$ | 508 |
| 482 | | 4.81$^l$ | 606 |
| 483 | | 4.75$^l$ | 516 |
| 484 | | 4.64$^l$ | 520 |

-continued
| Example No. | Compound | HPLC $T_r$ | $(M + H)^+$ |
|---|---|---|---|
| 485 | 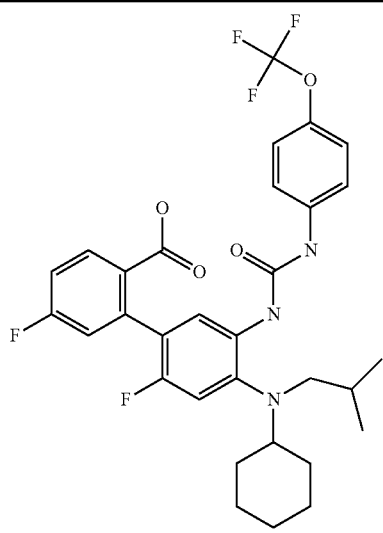 | $1.64^w$ | 606 |
| 486 | 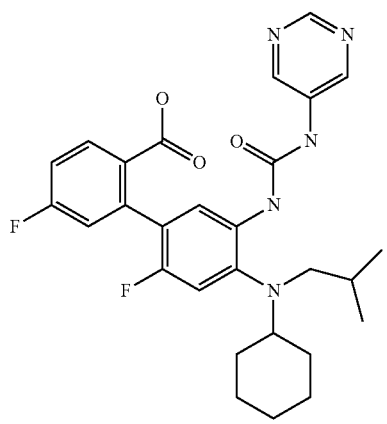 [SMILES: CC(C)CN(c1cc(F)c(-c2cc(F)ccc2C(=O)O)cc1NC(=O)Nc1cncnc1)C1CCCCC1] | $1.26^w$ | 524 |
| 487 | 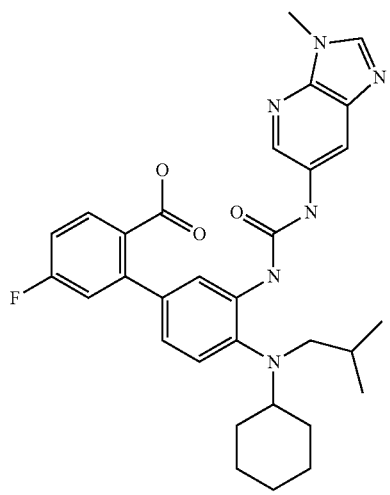 [SMILES: CC(C)CN(c1ccc(-c2cc(F)ccc2C(=O)O)cc1NC(=O)Nc1cnc2c(c1)ncn2C)C1CCCCC1] | $4.21^x$ | 559 |

-continued
| Example No. | Compound | HPLC T_r | (M + H)+ |
|---|---|---|---|
| 488 | 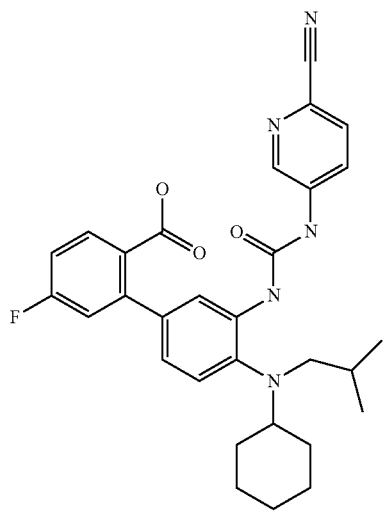 [SMILES: CC(C)CN(c1ccc(-c2cc(F)ccc2C(=O)O)cc1NC(=O)Nc1ccc(C#N)nc1)C1CCCCC1] | 4.75[x] | 530 |
| 489 | 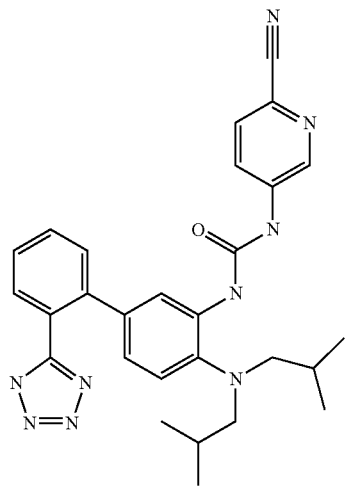 [SMILES: CC(C)CN(CC(C)C)c1ccc(-c2ccccc2-c2nnn[nH]2)cc1NC(=O)Nc1ccc(C#N)nc1] | 4.38[x] | 510 |
| 491 | 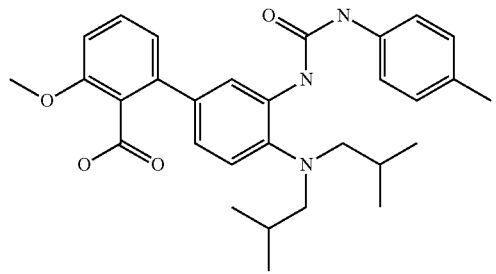 | 1.18[y] | 518 |

-continued

| Example No. | Compound | HPLC $T_r$ | $(M + H)^+$ |
|---|---|---|---|
| 492 | | $2.15^k$ | 508 |
| 493 | | $2.24^k$ | 508 |
| 494 | | $1.09^y$ | 542 |
| 495 | | $4.97^x$ | 558 |

-continued
| Example No. | Compound | HPLC T$_r$ | (M + H)$^+$ |
|---|---|---|---|
| 496 | 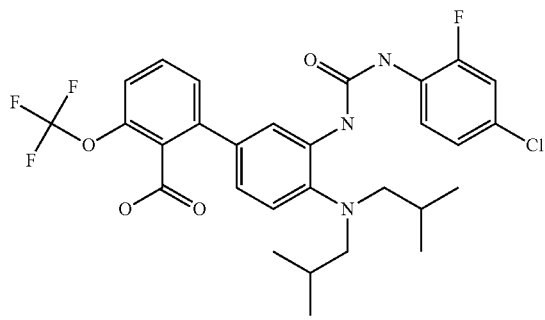 [SMILES: CC(C)CN(CC(C)C)c1ccc(-c2cccc(OC(F)(F)F)c2C(=O)O)cc1NC(=O)Nc1ccc(Cl)cc1F] | 5.17$^x$ | 596 |
| 497 | 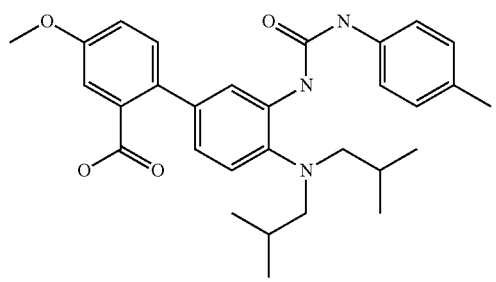 | 2.02$^k$ | 504 |
| 498 | 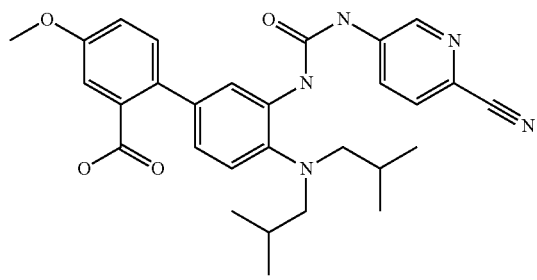 [SMILES: COc1ccc(-c2ccc(N(CC(C)C)CC(C)C)c(NC(=O)Nc3ccc(C#N)nc3)c2)c(C(=O)O)c1] | 1.93$^k$ | 516 |
| 499 | 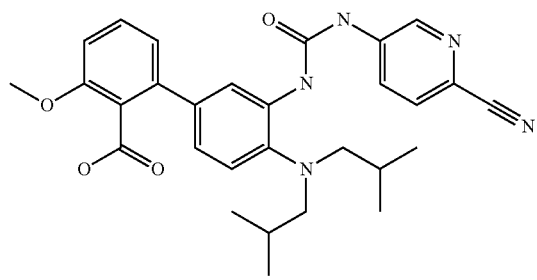 [SMILES: COc1cccc(-c2ccc(N(CC(C)C)CC(C)C)c(NC(=O)Nc3ccc(C#N)nc3)c2)c1C(=O)O] | 1.26$^w$ | 516 |
| 500 | 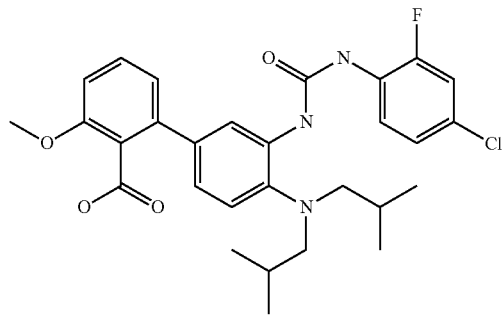 [SMILES: COc1cccc(-c2ccc(N(CC(C)C)CC(C)C)c(NC(=O)Nc3ccc(Cl)cc3F)c2)c1C(=O)O] | 4.81$^x$ | 542 |

| Example No. | Compound | HPLC T_r | (M + H)+ |
|---|---|---|---|
| 501 | 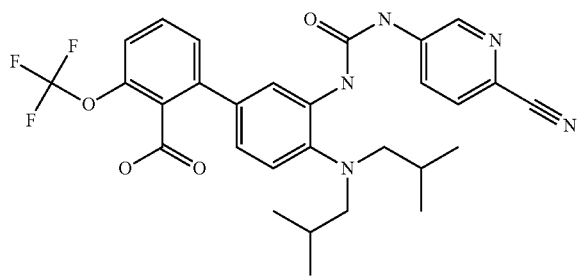 [SMILES: CC(C)CN(CC(C)C)c1ccc(-c2cccc(OC(F)(F)F)c2C(=O)O)cc1NC(=O)Nc1ccc(C#N)nc1] | 4.90[x] | 570 |

Example 502

1-(4-((4-fluoro-2-(trifluoromethyl)benzyl)(3,3,3-trifluoropropyl)amino)-2'-(1H-tetrazol-5-yl)-[1,1'-biphenyl]-3-yl)-3-(p-tolyl)urea

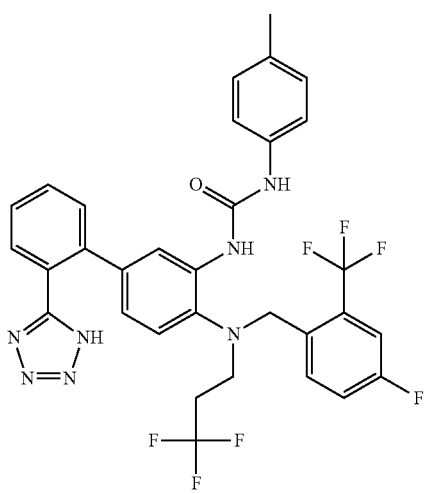 [SMILES: Cc1ccc(NC(=O)Nc2cc(-c3ccccc3-c3nnn[nH]3)ccc2N(CCC(F)(F)F)Cc2ccc(F)cc2C(F)(F)F)cc1]

502A. 3,3,3-Trifluoro-N-(4-fluoro-2-(trifluoromethyl)benzyl)propanamide

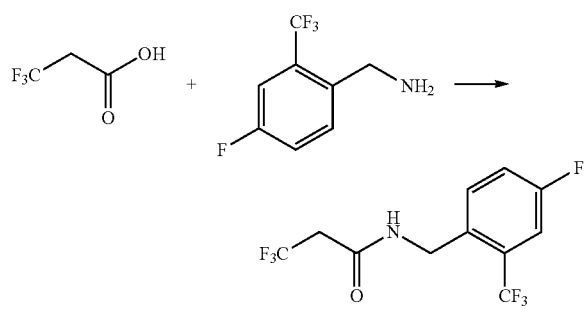

The title compound was prepared from 3,3,3-trifluoropropanoic acid and (4-fluoro-2-(trifluoromethyl)phenyl)methanamine by the general procedure used for the synthesis of Example 651A. MS(ES): m/z=304.32 [M+H]+.

502B. 3,3,3-Trifluoro-N-(4-fluoro-2-(trifluoromethyl)benzyl)propan-1-amine

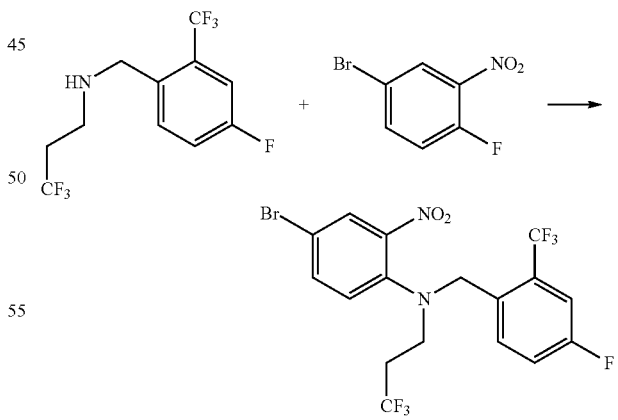

The title compound was prepared from 3,3,3-trifluoro-N-(4-fluoro-2-(trifluoromethyl)benzyl)propanamide by the general procedure used for the synthesis of Example 651B. MS(ES): m/z=290 [M+H]+.

502C. 4-Bromo-N-(4-fluoro-2-(trifluoromethyl)benzyl)-2-nitro-N-(3,3,3-trifluoropropyl)aniline To a solution of 3,3,3-trifluoro-N-(4-fluoro-2-(trifluoromethyl)benzyl)propan-1-amine (631 mg, 2.182 mmol) in tetrahydrofuran (4 mL) was added LiHMDS (5.45 mL, 5.45 mmol, 1 M) at −78° C. The mixture stirred for 10 min, then 4-bromo-1-fluoro-2-nitrobenzene was added (400 mg, 1.818 mmol). After 3 h TLC suggested the complete consumption of starting material. The reaction mixture was poured into cooled saturated ammonium chloride solution and extracted with ethyl acetate. The organic layer was washed with brine, dried over sodium sulfate, filtered and concentrated. The crude material was purified by silica gel (230-400 mesh) column chromatography using ethyl acetate and hexane. The solvent was evaporated to get 4-bromo-N-(4-fluoro-2-(trifluoromethyl)benzyl)-2-nitro-N-(3,3,3-trifluoropropyl)aniline (550 mg, 47.0% yield) as a yellow liquid. MS(ES): m/z=489 [M+1-1]+.

502D. 4-Bromo-N1-(4-fluoro-2-(trifluoromethyl)benzyl)-N1-(3,3,3-trifluoropropyl)benzene-1,2-diamine g
The title compound was prepared from 4-bromo-N-(4-fluoro-2-(trifluoromethyl)benzyl)-2-nitro-N-(3,3,3-trifluoropropyl)aniline at 0° C. by the general procedure used for the conversion of 1A to 1B. MS(ES): m/z=461.14 [M+H]+.

502E. N4-(4-Fluoro-2-(trifluoromethyl)benzyl)-2'-(1H-tetrazol-5-yl)-N4-(3,3,3-trifluoropropyl)-[1,1'-biphenyl]-3,4-diamine

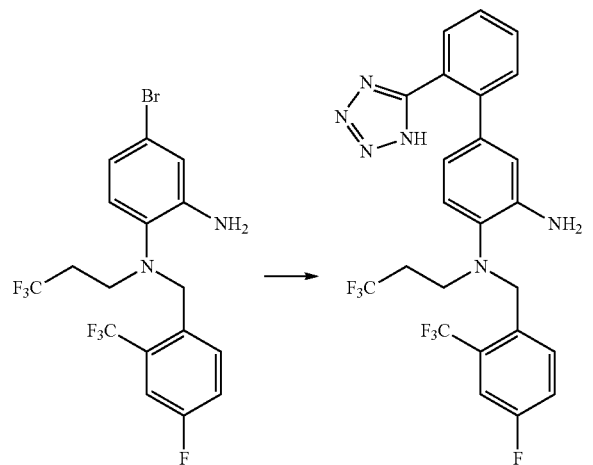 [SMILES: Nc1cc(Br)ccc1N(CCC(F)(F)F)Cc1ccc(F)cc1C(F)(F)F ; Nc1cc(-c2ccccc2-c2nnn[nH]2)ccc1N(CCC(F)(F)F)Cc1ccc(F)cc1C(F)(F)F]

The title compound was prepared from 4-bromo-N1-(4-fluoro-2-(trifluoromethyl)benzyl)-N1-(3,3,3-trifluoropropyl)benzene-1,2-diamine by the general procedure used for the synthesis of Example 651 MS(ES): m/z=525 [M+1-1]+.

502. 1-(4-((4-Fluoro-2-(trifluoromethyl)benzyl)(3,3,3-trifluoropropyl)amino)-2'-(1H-tetrazol-5-yl)-[1,1'-biphenyl]-3-yl)-3-(p-tolyl)urea

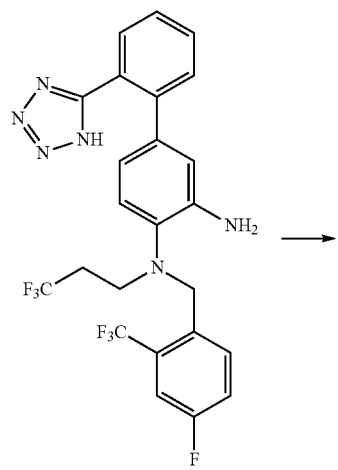

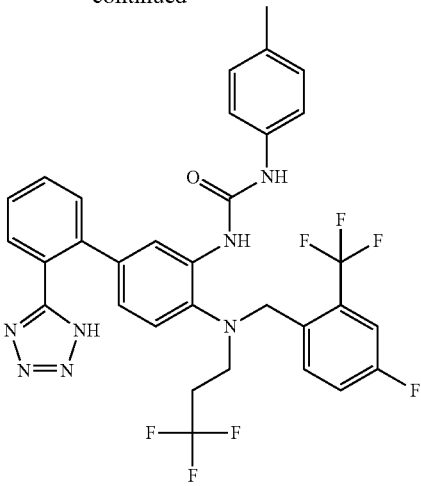

To the stirred solution of N4-(4-fluoro-2-(trifluoromethyl)benzyl)-2'-(1H-tetrazol-5-yl)-N4-(3,3,3-trifluoropropyl)-[1,1'-biphenyl]-3,4-diamine (20 mg, 0.038 mmol) in methylene chloride (200 µL) was added 1-isocyanato-4-methylbenzene (5.08 mg, 0.038 mmol). The reaction was stirred overnight. The solvent was evaporated and the crude sample was purified by RP-HPLC (acetonitrile-water gradient+TFA). The product containing fraction was partially evaporated to remove the acetonitrile and then lyophilized to give the product (15 mg). MS(ES): m/z=656 [M+H]+ HPLC T$_r$: 22.46$^u$.

Example 503

1-(2'-(1H-Tetrazol-5-yl)-4-((4-(trifluoromethoxy)benzyl)(3,3,3-trifluoropropyl)amino)-[1,1'-biphenyl]-3-yl)-3-(4-(trifluoromethoxy)phenyl)urea

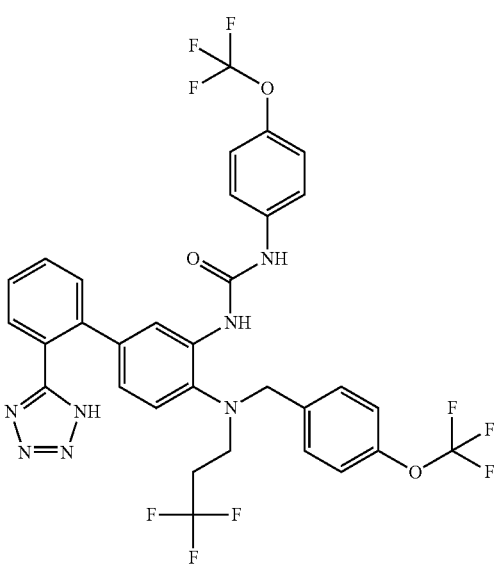 [SMILES: O=C(Nc1ccc(OC(F)(F)F)cc1)Nc1cc(-c2ccccc2-c2nnn[nH]2)ccc1N(CCC(F)(F)F)Cc1ccc(OC(F)(F)F)cc1]

Example 503 was prepared using the procedures used to make Example 503. MS(ES): m/z=724 [M+H]+, HPLC T$_r$: 23.63$^u$.

Example 504

1-(2'-(1H-Tetrazol-5-yl)-4-((4-(trifluoromethoxy)benzyl)(3,3,3-trifluoropropyl)amino)-[1,1'-biphenyl]-3-yl)-3-(2,4-difluorophenyl)urea

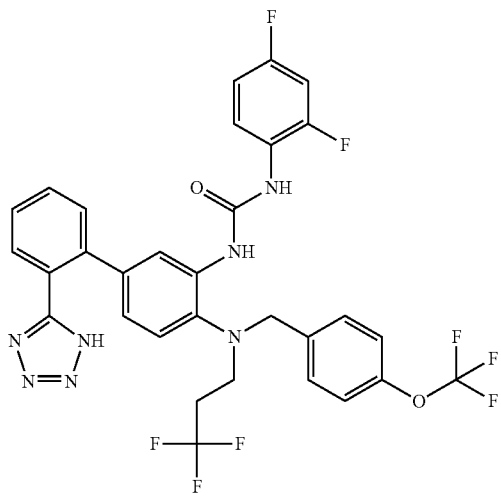 [SMILES: O=C(Nc1ccc(F)cc1F)Nc1cc(-c2ccccc2-c2nnn[nH]2)ccc1N(CCC(F)(F)F)Cc1ccc(OC(F)(F)F)cc1]

Example 504 was prepared using the procedures used to make Example 503. MS(ES): m/z=676 [M+H]⁺, HPLC T$_r$: 22.63"

Example 505

1-(4-((2,4-Dichlorobenzyl)(3,3,3-trifluoropropyl)amino)-2'-(1H-tetrazol-5-yl)-[1,1'-biphenyl]-3-yl)-3-(p-tolyl)urea

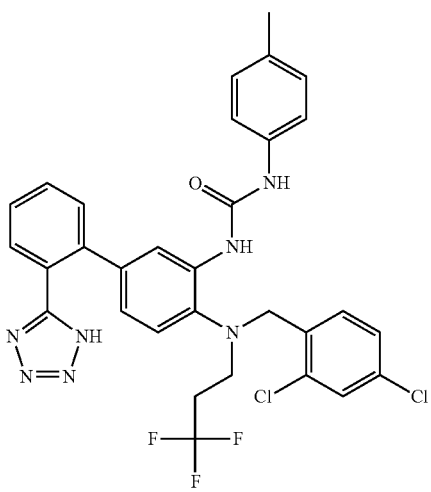 [SMILES: Cc1ccc(NC(=O)Nc2cc(-c3ccccc3-c3nnn[nH]3)ccc2N(CCC(F)(F)F)Cc2ccc(Cl)cc2Cl)cc1]

505A. N-(2,4-Dichlorobenzyl)-3,3,3-trifluoropropanamide

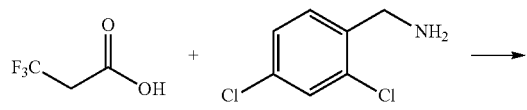

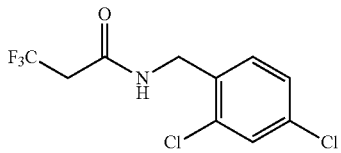

To a stirred solution of (2,4-dichlorophenyl)methanamine (2.0 g, 11.36 mmol), 3,3,3-trifluoropropanoic acid (1.74 g, 13.63 mmol) and pyridine (1.79 g, 22.72 mmol), in methylene chloride was added phosphorus oxychloride (1.27 mL, 13.63 mmol) at 0° C. The reaction mixture was brought to room temperature and stirred for 1 h. The reaction mixture was diluted with methylene chloride and washed with water then brine solution. The organic layer was dried over sodium sulfate, filtered and concentrated to provided N-(2,4-dichlorobenzyl)-3,3,3-trifluoropropanamide (2.93 g). ¹H NMR (400 MHz, CDCl₃) δ ppm 7.40 (d, 1H, J=2.0 Hz), 7.32 (d, 1H, J=14.4 Hz), 7.24 (dd, 1H, J=8.4, 2.0 Hz), 6.17 (brs, 1H), 4.53 (d, 2H, J=6.0 Hz), 3.06-3.14 (q, 2H).

505B. N-(2,4-Dichlorobenzyl)-3,3,3-trifluoropropan-1-amine

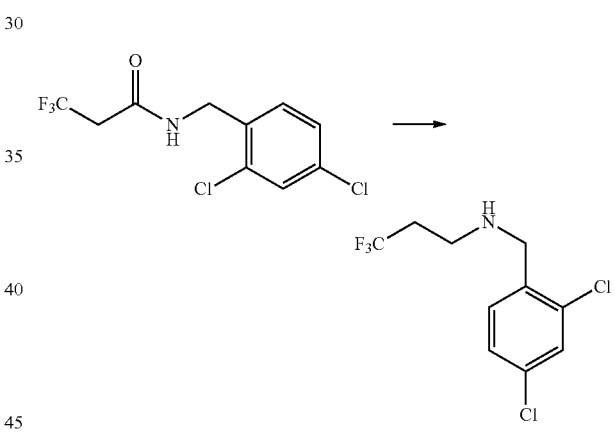

To a stirred solution of N-(2,4-dichlorobenzyl)-3,3,3-trifluoropropanamide (2.9 g, 10.14 mmol) in tetrahydrofuran (150 mL) was added borane-methyl sulfide complex (4.81 mL, 50.7 mmol) at 0° C. The reaction mixture was stirred at room temperature for 30 minutes. The reaction mixture was refluxed for 2 hours. The reaction mixture was cooled to 0° C., quenched with methanol slowly (effervescence observed), then excess solvent was removed completely under reduced pressor. Methanol was added at 0° C. and the mixture refluxed overnight. The methanol was removed and 1.5 N hydrochloric acid was added. The mixture was extracted with methylene chloride. The organic layer was dried over sodium sulfate, filtered and concentrated to provide N-(2,4-dichlorobenzyl)-3,3,3-trifluoropropan-1-amine (2.25 g, 8.27 mmol). ¹H NMR (400 MHz, CDCl₃) δ ppm 7.78 (d, 1H, J=8.4 Hz), 7.32 (d, 1H, J=14.4 Hz), 7.24 (dd, 1H, J=8.4, 2.0 Hz), 4.22 (d, 2H, J=8.4 Hz), 3.08-3.11 (q, 2H), 2.78-2.84 (q, 2H).

505C. 4-Bromo-N-(2,4-dichlorobenzyl)-2-nitro-N-(3,3,3-trifluoropropyl)aniline

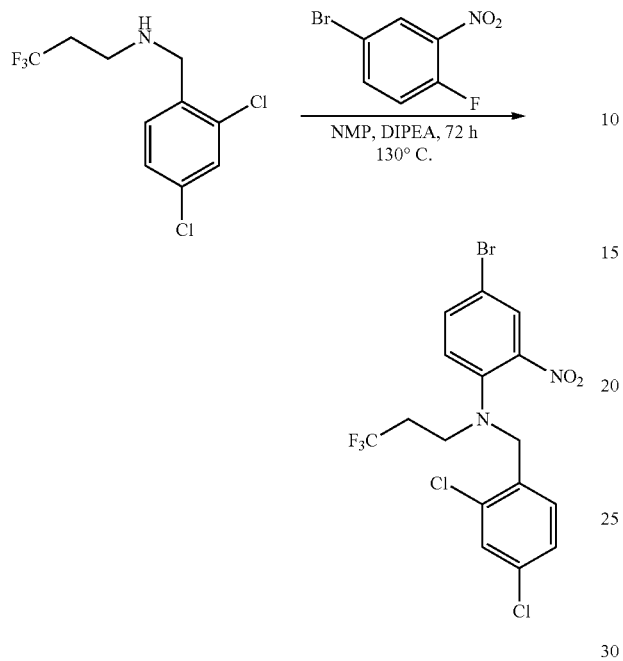

A pressure tube was charged with 4-bromo-1-fluoro-2-nitrobenzene (1.5 g, 6.82 mmol), N-(2,4-dichlorobenzyl)-3,3,3-trifluoropropan-1-amine (2.22 g, 8.18 mmol), DIPEA (2.38 mL, 13.64 mmol), in NMP (10.5 mL) solvent. The reaction mixture was heated at 130° C. for 72 hours. The reaction mixture was cooled to room temperature, diluted with MTBE, washed with water (3×), brine (1×). The organic layer was dried over sodium sulfate, filtered and concentrated in vacuo to give a crude dark brown solid. Purification using flash column chromatography (0% to 5% ethyl acetate/hexane gradient) provided 4-bromo-N-(2,4-dichlorobenzyl)-2-nitro-N-(3,3,3-trifluoropropyl)aniline (0.750 g).

505D. 4-Bromo-N1-(2,4-dichlorobenzyl)-N1-(3,3,3-trifluoropropyl)benzene-1,2-diamine

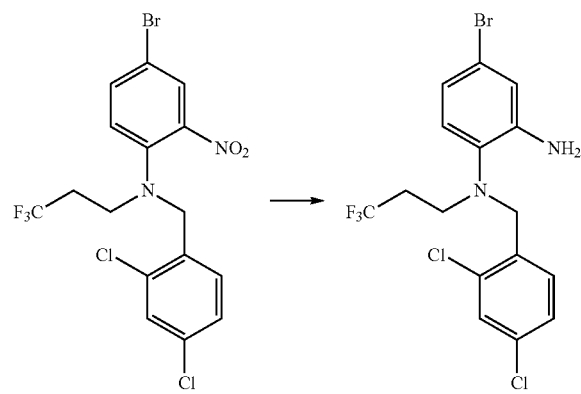 [SMILES: O=[N+]([O-])c1cc(Br)ccc1N(CCC(F)(F)F)Cc1ccc(Cl)cc1Cl ; Nc1cc(Br)ccc1N(CCC(F)(F)F)Cc1ccc(Cl)cc1Cl]

The title compound was prepared from 4-bromo-N-(2,4-dichlorobenzyl)-2-nitro-N-(3,3,3-trifluoropropyl)aniline by the general procedure used for forming 1B. MS(ES): m/z=443.0 [M+H]$^+$.

505E. N4-(2,4-Dichlorobenzyl)-2'-(1H-tetrazol-5-yl)-N4-(3,3,3-trifluoropropyl)biphenyl-3,4-diamine

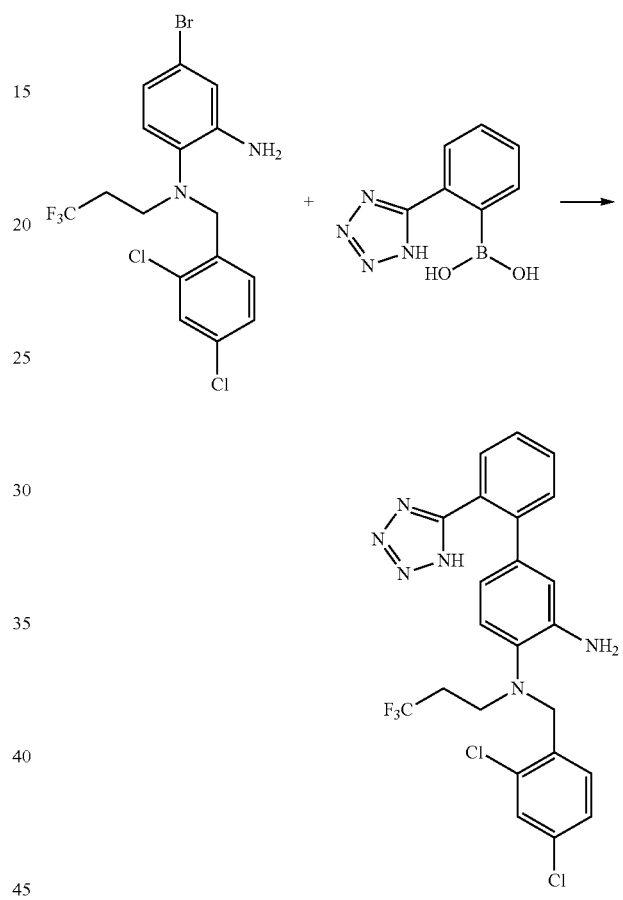

To a stirred solution of 4-bromo-N1-(2,4-dichlorobenzyl)-N1-(3,3,3-trifluoropropyl)benzene-1,2-diamine (140 mg, 0.317 mmol), potassium carbonate 2M solution (3.33 mL, 6.65 mmol), in dioxane ethanol mixture was added (2-(1H-tetrazol-5-yl)phenyl)boronic acid (60 mg, 0.317 mmol). The reaction mixture was degassed for 30 minutes. Pd(Ph$_3$P)$_4$ (18 mg, 0.016 mmol) was added and the reaction was again degassed for 5 minutes then heated at 85° C. for 3 hours. The reaction mixture was concentrated in vacuo. The resulting residue was dissolved in ethyl acetate and washed with water, dried over sodium sulfate, filtered and concentrated to give the crude product. Purification using flash chromatography provided (80 mg). $^1$H NMR (400 MHz, CDCl$_3$) δ ppm 7.63-7.67 (m, 2H), 7.51-7.56 (m, 2H), 7.44 (d, 1H, J=2.0 Hz), 7.27 (dd, 1H, J=8.0, 2.0 Hz), 7.17 (d, 1H, J=8.4 Hz), 7.01 (d, 1H, J=8.0 Hz), 6.61 (d, 1H, J=2.0 Hz), 6.34 (dd, 1H, J=8.0, 2.0 Hz), 4.20 (s, 2H), 3.24 (t, 2H), 2.31-2.38 (m, 2H). MS(ES): m/z=507 [M+H]$^+$.

505. 1-(4-((2,4-Dichlorobenzyl)(3,3,3-trifluoropropyl)amino)-2'-(1H-tetrazol-5-yl)-[1,1'-biphenyl]-3-yl)-3-(p-tolyl)urea

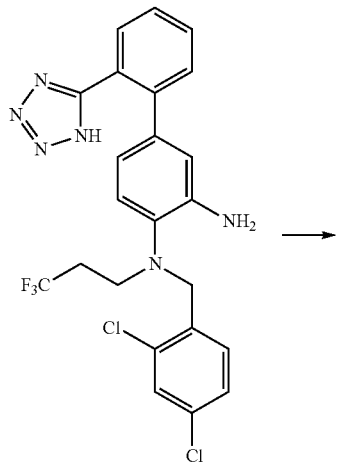

→

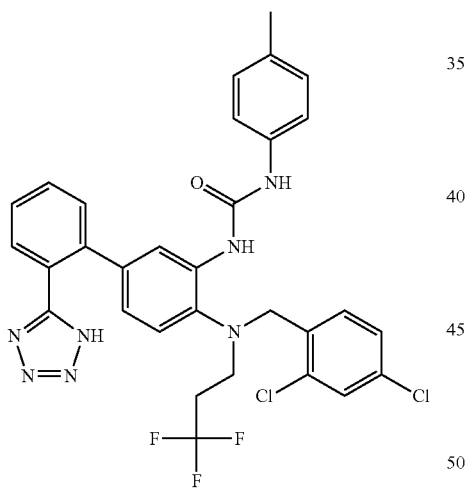

To the stirred solution of N4-(4-fluoro-2-(trifluoromethyl)benzyl)-2'-(1H-tetrazol-5-yl)-N4-(3,3,3-trifluoropropyl)-[1,1'-biphenyl]-3,4-diamine (20 mg, 0.038 mmol) in methylene chloride (200 μL) was added 1-isocyanato-4-methylbenzene (5.08 mg, 0.038 mmol). The reaction was stirred overnight. The solvent was evaporated and the crude sample was purified by RP-HPLC (acetonitrile-water gradient+TFA). The product containing fraction was partially evaporated to remove the acetonitrile and then lyophilized to give the product (20 mg). MS(ES): m/z=640 [M+H]$^+$ HPLC T$_r$: 23.54$^u$.

Example 506

1-(4-((pyridin-2-ylmethyl)(3,3,3-trifluoropropyl)amino)-2'-(1H-tetrazol-5-yl)-[1,1'-biphenyl]-3-yl)-3-(p-tolyl)urea

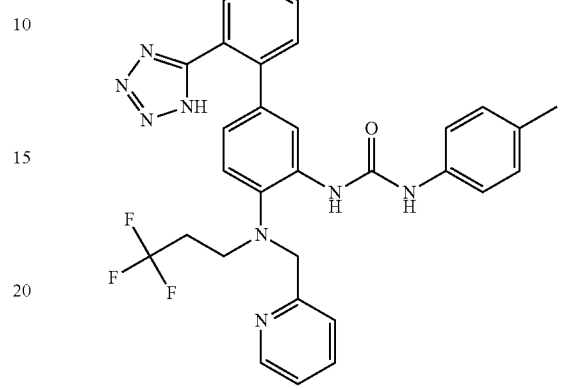

Example 506 was prepared using the procedures described for Example 505. MS(ES): m/z=573 [M+H]$^+$, HPLC T$_r$: 14.4$^u$.

Example 507

4'-(Cyclohexyl(isobutyl)amino)-3'-(3-(3,5-dibromo-4-methylphenyl)ureido)-5-fluoro-[1,1'-biphenyl]-2-carboxylic acid

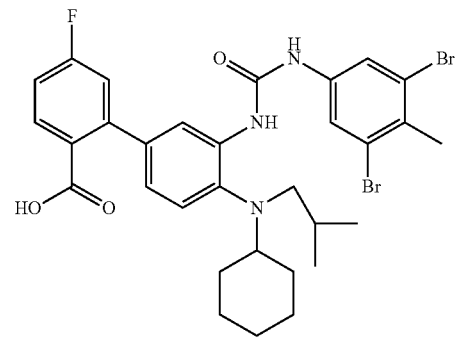 [SMILES: Cc1c(Br)cc(NC(=O)Nc2cc(-c3cc(F)ccc3C(=O)O)ccc2N(CC(C)C)C2CCCCC2)cc1Br]

507A. Methyl 3'-amino-4'-(cyclohexyl(isobutyl)amino)-5-fluoro-[1,1'-biphenyl]-2-carboxylate

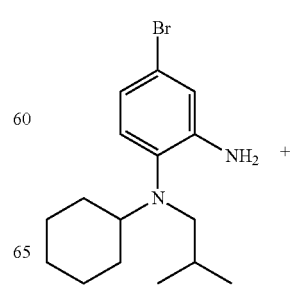

+

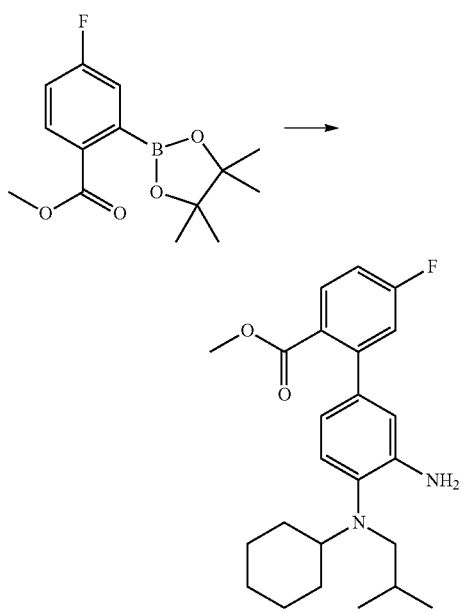

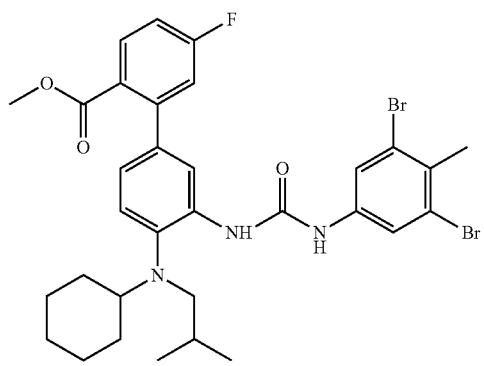

To a stirred solution of 4-bromo-N1-cyclohexyl-N1-isobutylbenzene-1,2-diamine (200 mg, 0.615 mmol)(Intermediate iiiz in Table 1A) in dry dioxane (4.0 ml) added methyl 4-fluoro-2-(4,4,5,5-tetramethyl-1,3,2-dioxaborolan-2-yl)benzoate (207 mg, 0.738 mmol), followed by potassium phosphate (0.153 ml, 1.845 mmol). The reaction was purged with argon for 15 minutes and $PdCl_2(dppf)$ (90 mg, 0.123 mmol) was added. The reaction was again purged with argon for 5 minutes. The reaction was then sealed and heated to 80° C. overnight. The reaction was diluted with ethyl acetate (10 ml) and washed sequentially with water (10 ml) and brine (10 ml). The organic phase was dried over sodium sulfate, filtered and concentrated to give the crude product. The crude product was purified by flash column using 60-120 mesh silica gel using 0-20% ethyl acetate/petroleum ether as eluent. Evaporation of the appropriate fractions provided the product as a semi-solid.

507B. Methyl 4'-(cyclohexyl(isobutyl)amino)-3'-(3-(3,5-dibromo-4-methylphenyl)ureido)-5-fluoro-[1,1'-biphenyl]-2-carboxylate To a stirred solution of 3,5-dibromo-4-methylaniline (0.020 g, 0.075 mmol) in dry methylene chloride (2.0 mL) under nitrogen was added sodium carbonate (0.040 g, 0.377 mmol). The reaction was cooled to 0° C. and phosgene (0.037 g, 0.075 mmol) solution was added. The reaction was stirred at room temperature for 1.5 hour. The reaction was filtered through celite, washed with dry methylene chloride (2 ml) and concentrated under reduced pressure. After pumping down under high vacuum the product 1,3-dibromo-5-isocyanato-2-methylbenzene (20 mg, 0.069 mmol, 91% yield) was obtained. This intermediate 1,3-dibromo-5-isocyanato-2-methylbenzene (0.02 g, 0.069 mmol) was dissolved in dry methylene chloride (1.0 ml) and methyl 3'-amino-4'-(cyclohexyl(isobutyl)amino)-5-fluoro-[1,1'-biphenyl]-2-carboxylate (0.027 g, 0.069 mmol)(dissolved in methylene chloride (2 ml)) was added. The reaction was stirred for 30 minutes when the mixture was concentrated to give the crude product. The crude product was purified by preparative TLC using 10% ethyl acetate in petroleum ether as eluent. The pure product band was extracted with methylene chloride and filtered through a celite bed. Evaporation then gave the pure product (22 mg).

507. 4'-(Cyclohexyl(isobutyl)amino)-3'-(3-(3,5-dibromo-4-methylphenyl)ureido)-5-fluoro-[1,1'-biphenyl]-2-carboxylic acid

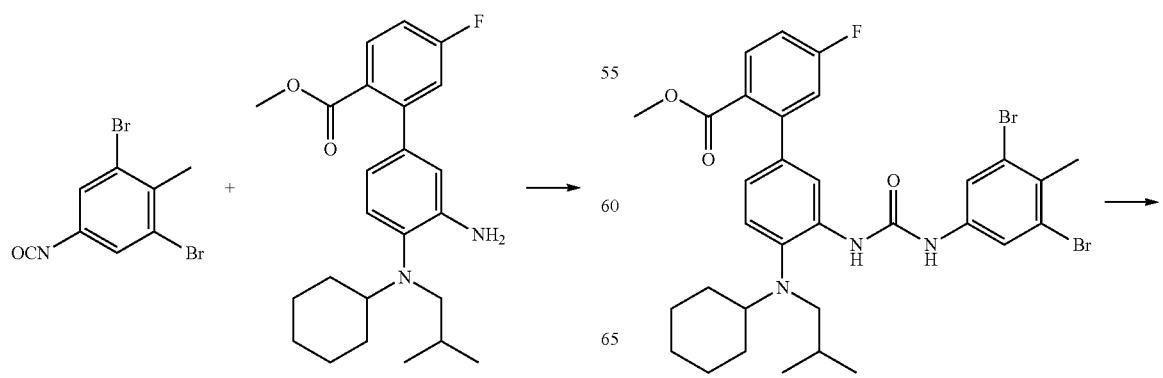

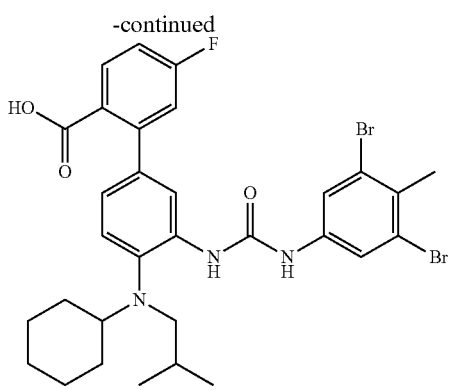

To a stirred solution of methyl 4'-(cyclohexyl(isobutyl)amino)-3'-(3-(3,5-dibromo-4-methylphenyl)ureido)-5-fluoro-[1,1'-biphenyl]-2-carboxylate (0.02 g, 0.029 mmol), in a mixture of dry tetrahydrofuran (1.0 mL), methanol (1.0 mL), and water (0.200 mL) cooled to 0° C. was added lithium hydroxide monohydrate (6.09 mg, 0.145 mmol). The reaction was stirred at room temperature for 36 hours. Reaction mixture was concentrated to give an off white solid, The reaction was diluted with MTBE and washed with water. Aqueous layer was extracted with MTBE (2×10 ml). The combined organic layers were dried over sodium sulfate, filtered and concentrated to give an off white solid. The crude product was purified by preparative HPLC to give the final product (10 mg). MS(ES): m/z=676 [M+H]$^+$ HPLC T$_r$: 27.32$^a$.

Example 509

1-(4-(Dicyclopropylamino)-2'-(1H-tetrazol-5-yl)-[1,1'-biphenyl]-3-yl)-3-(5-methylisoxazol-3-yl)urea

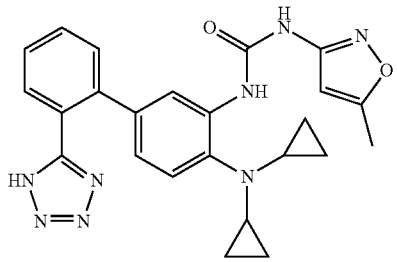 [SMILES: Cc1cc(NC(=O)Nc2cc(-c3ccccc3-c3nnn[nH]3)ccc2N(C2CC2)C2CC2)no1]

509A. 4-Bromo-N,N-dicyclopropyl-2-nitroaniline

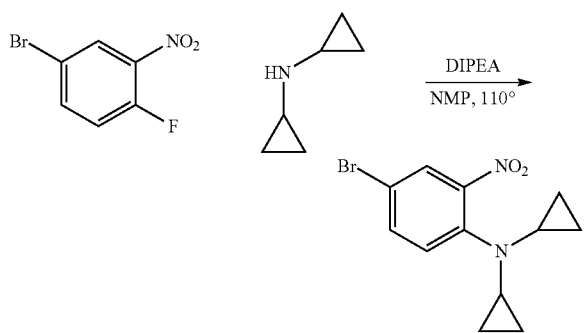

To a homogeneous mixture of 4-bromo-1-fluoro-2-nitrobenzene (700 mg, 3.18 mmol) in N-methylpyrrolidinone (3.2 mL) in a sealable tube, was added DIPEA (2.2 mL, 12.60 mmol) followed by dicyclopropylamine hydrochloride (510 mg, 3.82 mmol). The tube was sealed and the mixture was heated to 110° C. The reaction was heated for 3 hours when it was cooled. The reaction was quenched with water then extracted with three portions of ethyl acetate. The combined organic layers were washed with brine then dried with anhydrous sodium sulfate, filtered and concentrated in vacuo to afford a blood red oil (1.3035 g). The crude product was purified on an Isco CombiFlash System using a 40 g silica gel column. The compound was eluted with 0-50% ethyl acetate in hexanes. As the separation was not good, the chromatography was repeated; however, adequate separation did not occur on this attempt either. Evaporation of the product containing fractions in vacuo afforded an amber oil (609.8 mg). This material still contains significant impurities but, as purification is problematic, the compound is carried forward into the next reaction.

509B.
4-Bromo-N1,N1-dicyclopropylbenzene-1,2-diamine

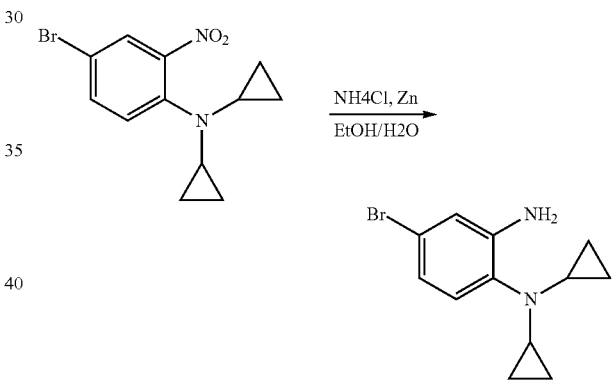

To a solution of 4-bromo-N,N-dicyclopropyl-2-nitroaniline (609.8 mg, 2.052 mmol) in ethanol (15 mL) and water (3.00 mL), under nitrogen, was added ammonium chloride (2195 mg, 41.0 mmol). The reaction was stirred for 5 minutes before adding zinc (2683 mg, 41.0 mmol). The mixture was stirred at room temperature for ca. 6 hours. The reaction mixture was filtered through a pad of Celite which was then thoroughly rinsed with chloroform. The combined organic filtrates were concentrated in vacuo to afford a dark brown residue which was redissolved in chloroform. The crude product was purified on Isco CombiFlash System using a 40 g silica flash column. The compound was eluted with a gradient of 0-100% ethyl acetate in hexanes. Evaporation of the appropriate fractions gave the desired product as a golden oil (180 mg). $^1$H NMR (400 MHz, DMSO-d$_6$) δ 7.09 (d, J=8.4 Hz, 1H), 6.77 (d, J=2.2 Hz, 1H), 6.64 (dd, J=8.3, 2.3 Hz, 1H), 4.93 (s, 2H), 0.48-0.34 (m, 8H) (cyclopropyl methines are obscured by DMSO).

509C. N4,N4-Dicyclopropyl-2'-(1H-tetrazol-5-yl)-[1,1'-biphenyl]-3,4-diamine

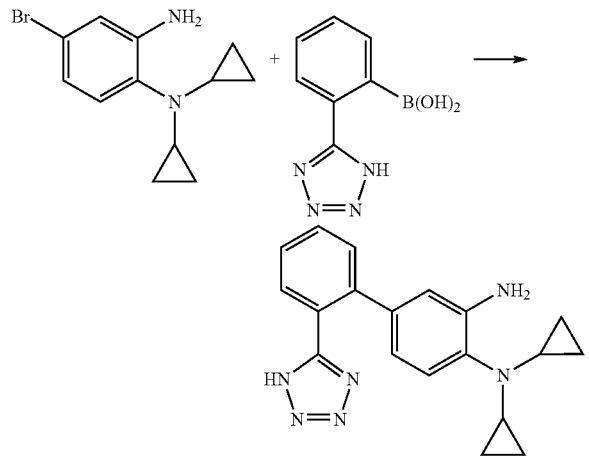

To a stirred solution of 4-bromo-N1,N1-dicyclopropyl-benzene-1,2-diamine (45 mg, 0.168 mmol) in argon-purged dimethylformamide (1 mL) was added 2-(tetrazol-5-yl)phenylboronic acid (64.0 mg, 0.337 mmol), followed by cesium carbonate (0.561 mL, 0.842 mmol, 1.5 M aqueous). The reaction was purged with argon for 15 minutes then Pd(Ph$_3$P)4 (19.46 mg, 0.017 mmol) was added. The reaction was purged with argon for another 5 minutes when the vial was capped and heated to 100° C. The reaction was heated for 4.5 hours and then allowed to cool to room temperature overnight. The crude product was purified on an Isco CombiFlash System using a RediSep normal phase silica flash column (12 g). The compound was eluted with a 0-100% ethyl acetate in hexanes gradient. Evaporation of the product containing fractions gave the desired product as a gold residue (15.5 mg). MS(ES): m/z=333 [M+H]$^+$.

509. 1-(4-(Dicyclopropylamino)-2'-(1H-tetrazol-5-yl)-[1,1'-biphenyl]-3-yl)-3-(5-methylisoxazol-3-yl)urea

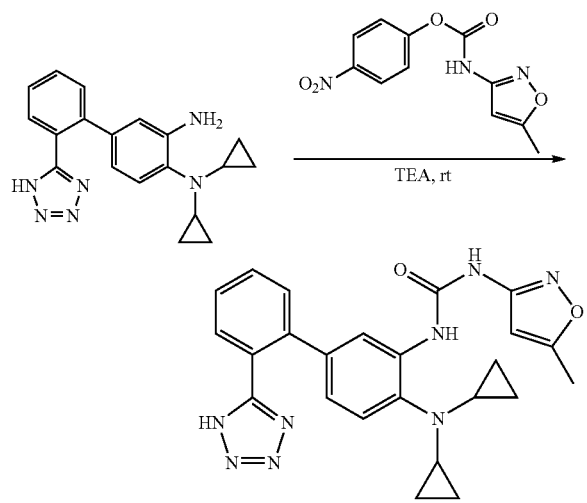

To a solution of 5-methylisoxazol-3-amine (11 mg, 0.112 mmol) in anhydrous tetrahydrofuran (1 mL), at room temperature in a sealable vial, was added 4-nitrophenyl chloroformate (27.1 mg, 0.135 mmol). The mixture was stirred for 0.5 hour when LCMS indicated the presence of the desired carbamate intermediate. The reaction was divided in half by volume and one portion was used in this preparation. This material was added to a solution of N4,N4-dicyclopropyl-2'-(1H-tetrazol-5-yl)-[1,1'-biphenyl]-3,4-diamine (15.5 mg, 0.047 mmol) in methylene chloride (2 mL) in a sealable vial. Triethylamine (0.01 mL, 0.072 mmol) was then added and the reaction stirred for 10 days. The reaction was concentrated to dryness then redissolved in 1.5 mL dimethylformamide. The reaction was filtered through an Acrodisc (13 mm syringe filter with 0.45 μm Nylon membrane) syringe filter. The crude material was purified via preparative LCMS with the following conditions: Column: Waters XBridge C18, 19×100 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 20-100% B over 10 minutes, then a 5-minute hold at 100% B; Flow: 20 mL/min. Fractions containing the desired product were combined and dried via centrifugal evaporation to give 0.6 mg. MS(ES): m/z=457 [M+H]$^+$, HPLC T$_r$: 1.85$^k$.

Example 510

4'-((4,4-Difluorocyclohexyl)(isobutyl)amino)-3'-(3-(2-fluorophenyl)ureido)-[1,1'-biphenyl]-2-carboxylic acid

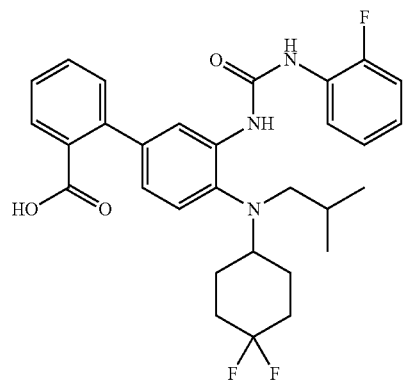 [SMILES: CC(C)CN(c1ccc(-c2ccccc2C(=O)O)cc1NC(=O)Nc1ccccc1F)C1CCC(F)(F)CC1]

Example 510 was prepared using the procedures used to make Example 532. $^1$H NMR (500 MHz, METHANOL-d$_4$) δ 8.06 (d, J=2.0 Hz, 1H), 7.89-7.82 (m, 1H), 7.74 (d, J=7.4 Hz, 1H), 7.53-7.44 (m, 2H), 7.38 (td, J=7.4, 1.5 Hz, 1H), 7.19 (d, J=8.4 Hz, 1H), 7.16-7.07 (m, 3H), 7.06 (dd, J=7.9, 2.0 Hz, 1H), 2.82 (br. s., 3H), 2.12-2.02 (m, 2H), 1.88 (br. s., 2H), 1.79-1.60 (m, 4H), 1.51 (dquin, J=13.3, 6.7 Hz, 1H), 0.86 (d, J=6.9 Hz, 6H). MS(ES): m/z=539 [M+H]$^+$, HPLC T$_r$: 2.18$^k$.

Example 511

4'-((4,4-Difluorocyclohexyl)(isobutyl)amino)-3'-(3-(4-(trifluoromethoxy)phenyl)ureido)-[1,1'-biphenyl]-2-carboxylic acid

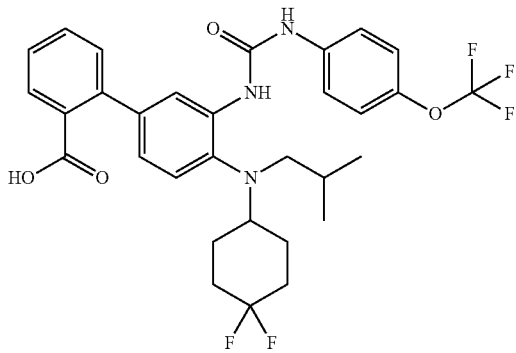 [SMILES: CC(C)CN(c1ccc(-c2ccccc2C(=O)O)cc1NC(=O)Nc1ccc(OC(F)(F)F)cc1)C1CCC(F)(F)CC1]

Example 511 was prepared using the procedures used to make Example 532. MS(ES): m/z=606 [M+H]$^+$ HPLC T$_r$: 2.39$^k$, $^1$H NMR (500 MHz, METHANOL-d$_4$) δ 8.13 (d, J=2.0 Hz, 1H), 7.52 (d, J=9.4 Hz, 2H), 7.45 (d, J=4.0 Hz, 3H), 7.36 (dq, J=8.2, 4.0 Hz, 1H), 7.20 (d, J=8.4 Hz, 1H), 7.17 (d, J=8.4 Hz, 2H), 7.11 (dd, J=8.4, 2.0 Hz, 1H), 2.83 (br. s., 3H), 2.05 (d, J=6.4 Hz, 2H), 1.98-1.89 (m, 2H), 1.79-1.58 (m, 4H), 1.50 (dquin, J=13.3, 6.7 Hz, 1H), 0.87 (d, J=6.4 Hz, 6H).

Example 512

4'-((4,4-Difluorocyclohexyl)(isobutyl)amino)-3'-(3-(p-tolyl)ureido)-[1,1'-biphenyl]-2-carboxylic acid

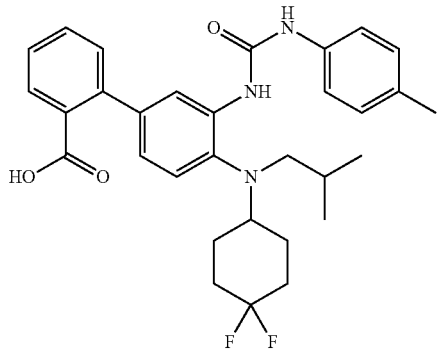 [SMILES: Cc1ccc(NC(=O)Nc2cc(-c3ccccc3C(=O)O)ccc2N(CC(C)C)C2CCC(F)(F)CC2)cc1]

Example 512 was prepared using the procedures used to make Example 532. MS(ES): m/z=536 [M+H]$^+$ HPLC T$_r$: 2.25$^k$, $^1$H NMR (500 MHz, METHANOL-d$_4$) δ 8.16 (d, J=2.0 Hz, 1H), 7.80-7.76 (m, 1H), 7.54-7.49 (m, 1H), 7.48-7.44 (m, 1H), 7.38 (td, J=7.6, 1.2 Hz, 1H), 7.28 (d, J=8.4 Hz, 2H), 7.19-7.10 (m, 3H), 6.99 (dd, J=7.9, 2.0 Hz, 1H), 2.82-2.68 (m, 3H), 2.32 (s, 3H), 2.08-1.98 (m, 2H), 1.83-1.53 (m, 6H), 1.51-1.42 (m, 1H), 0.82 (d, J=6.4 Hz, 6H).

Example 513

4'-(4,4-Difluorocyclohexyl)(isobutyl)amino)-3'-(3-(4-(trifluoromethyl)phenyl)ureido)-[1,1'-biphenyl]-2-carboxylic acid

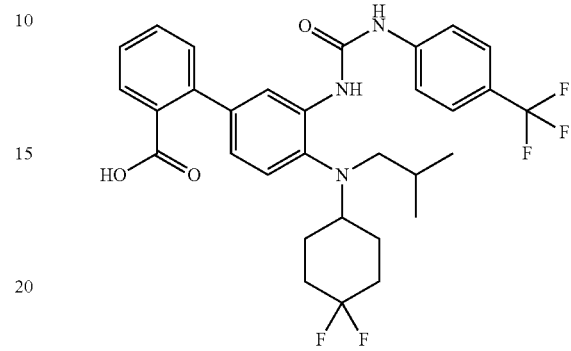

Example 513 was prepared using the procedures used to make Example 532. MS(ES): m/z=590 [M+H]$^+$ HPLC T$_r$: 2.38$^k$. $^1$H NMR (500 MHz, METHANOL-d$_4$) δ 8.12 (d, J=2.0 Hz, 1H), 7.67 (d, J=7.4 Hz, 1H), 7.65-7.61 (m, 2H), 7.54 (d, J=8.9 Hz, 2H), 7.44 (d, J=4.0 Hz, 2H), 7.38-7.30 (m, 1H), 7.22-7.17 (m, 1H), 7.13 (dd, J=8.4, 2.0 Hz, 1H), 2.84 (br. s., 3H), 2.13-2.02 (m, 2H), 1.96 (d, J=8.9 Hz, 2H), 1.78-1.60 (m, 4H), 1.51 (dquin, J=13.3, 6.6 Hz, 1H), 0.88 (d, J=6.9 Hz, 6H).

Example 514

1-(4((4,4-Difluorocyclohexyl)(isobutyl)amino)-2'-(1H-tetrazol-5-yl)-[1,1'-biphenyl]-3-yl)-3-(4-(trifluoromethoxy)phenyl)urea

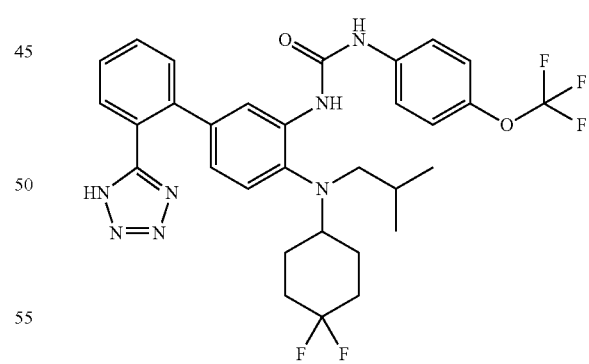

Example 514 was prepared using the procedures used to make Example 531. MS(ES): m/z=630 [M+H]$^+$ HPLC T$_r$: 2.35$^k$. $^1$H NMR (500 MHz, METHANOL-d$_4$) δ 7.95 (d, J=2.0 Hz, 1H), 7.66 (d, J=7.4 Hz, 1H), 7.57 (d, J=4.0 Hz, 2H), 7.52 (d, J=8.9 Hz, 2H), 7.50-7.45 (m, 1H), 7.17 (d, J=8.9 Hz, 2H), 6.99 (d, J=7.9 Hz, 1H), 6.55 (dd, J=7.9, 2.0 Hz, 1H), 2.77 (d, J=6.9 Hz, 3H), 2.05 (br. s., 2H), 1.86 (br. s., 2H), 1.77-1.57 (m, 4H), 1.43 (dquin, J=13.3, 6.6 Hz, 1H), 0.84 (d, J=6.9 Hz, 6H).

Example 515

4'-(Cyclohexyl(isobutyl)amino)-2',5-difluoro-5'-(3-(1-methyl-1H-pyrazol-3-yl)ureido)-[1,1'-biphenyl]-2-carboxylic acid

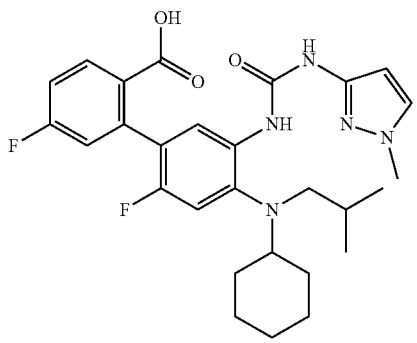 [SMILES: CC(C)CN(c1cc(F)c(-c2cc(F)ccc2C(=O)O)cc1NC(=O)Nc1ccn(C)n1)C1CCCCC1]

Example 515 was prepared using the methology described for Example 522. MS(ES): m/z=526 [M+H]$^+$ HPLC T$_r$: 1.79$^k$. $^1$H NMR (500 MHz, DMSO-d$_6$) δ 13.86-11.94 (m, 1H), 9.65 (br. s., 1H), 8.08 (d, J=8.4 Hz, 1H), 7.91 (dd, J=8.9, 5.9 Hz, 1H), 7.55 (d, J=2.0 Hz, 1H), 7.34 (td, J=8.4, 2.5 Hz, 1H), 7.26 (dd, J=9.7, 2.7 Hz, 1H), 7.07 (d, J=11.9 Hz, 1H), 6.02 (br. s., 1H), 3.74 (s, 3H), 2.82 (br. s., 2H), 2.69-2.58 (m, 1H), 1.88 (d, J=11.4 Hz, 2H), 1.69 (d, J=11.9 Hz, 2H), 1.53 (d, J=10.9 Hz, 1H), 1.41 (dquin, J=13.3, 6.7 Hz, 1H), 1.35-1.20 (m, 2H), 1.16-0.97 (m, 3H), 0.87 (d, J=6.4 Hz, 6H).

Example 516

4'-(Cyclohexyl(isobutyl)amino)-2',5-difluoro-5'-(3-(m-tolyl)ureido)-[1,1'-biphenyl]-2-carboxylic acid

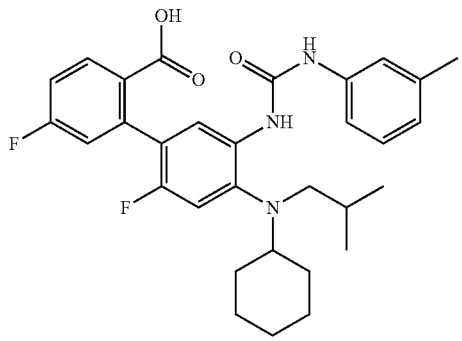 [SMILES: Cc1cccc(NC(=O)Nc2cc(-c3cc(F)ccc3C(=O)O)c(F)cc2N(CC(C)C)C2CCCCC2)c1]

Example 516 was prepared using the methology described for Example 522. MS(ES): m/z=536 [M+H]$^+$ HPLC T$_r$: 2.06$^k$. $^1$H NMR (500 MHz, METHANOL-d$_4$) δ 8.02-7.96 (m, 2H), 7.26 (s, 1H), 7.21-7.16 (m, 3H), 7.12 (td, J=8.2, 2.5 Hz, 1H), 6.92 (d, J=5.9 Hz, 1H), 6.86 (d, J=11.4 Hz, 1H), 2.76 (d, J=6.9 Hz, 2H), 2.60 (t, J=11.6 Hz, 1H), 2.33 (s, 3H), 1.73 (d, J=9.9 Hz, 4H), 1.58 (d, J=11.9 Hz, 1H), 1.51 (dquin, J=13.3, 6.7 Hz, 1H), 1.35-1.21 (m, 2H), 1.21-0.99 (m, 3H), 0.84 (d, J=6.4 Hz, 6H).

Example 517

4'-(Cyclohexyl(isobutyl)amino)-2',5-difluoro-5'-(3-(6-(trifluoromethyl)pyridin-3-yl)ureido)-[1,1'-biphenyl]-2-carboxylic acid

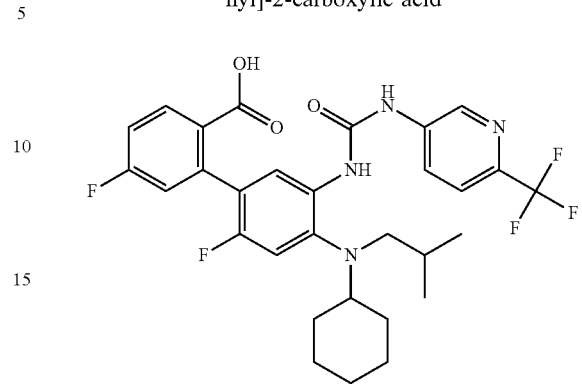

Example 517 was prepared using the methology described for Example 522. MS(ES): m/z=591 [M+H]$^+$ HPLC T$_r$: 2.06$^k$. $^1$H NMR (500 MHz, METHANOL-d$_4$) δ 8.64 (d, J=2.5 Hz, 1H), 8.34 (dd, J=8.7, 2.2 Hz, 1H), 8.03-7.95 (m, 2H), 7.67 (d, J=8.4 Hz, 1H), 7.18 (dd, J=9.4, 3.0 Hz, 1H), 7.13 (td, J=8.3, 2.7 Hz, 1H), 6.92 (d, J=11.4 Hz, 1H), 2.84 (d, J=6.9 Hz, 2H), 2.75-2.65 (m, 1H), 1.93 (d, J=11.4 Hz, 2H), 1.78 (d, J=12.9 Hz, 2H), 1.60 (d, J=11.9 Hz, 1H), 1.58-1.49 (m, 1H), 1.44-1.33 (m, 2H), 1.28-1.04 (m, 4H), 0.90 (d, J=6.4 Hz, 6H).

Example 518

4'-((4,4-Difluorocyclohexyl)(isobutyl)amino)-2',5-difluoro-5'-(3-(5-methylisoxazol-3-yl)ureido)-[1,1'-biphenyl]-2-carboxylic acid

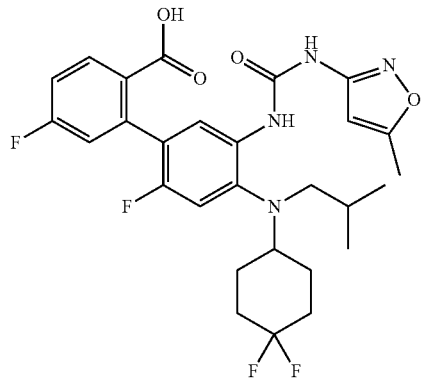 [SMILES: Cc1cc(NC(=O)Nc2cc(-c3cc(F)ccc3C(=O)O)c(F)cc2N(CC(C)C)C2CCC(F)(F)CC2)no1]

518A. N-(4,4-difluorocyclohexyl)isobutyramide

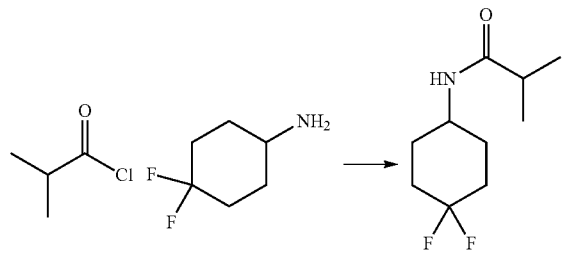

A solution of 4,4-difluorocyclohexanamine hydrochloride (426.3 mg, 2.484 mmol) in anhydrous methylene chloride (15 mL) was cooled to 0° C. under nitrogen. Triethylamine (0.74 mL, 5.31 mmol) was then added. The mixture was stirred at 0° C. for 15 minutes when isobutyryl chloride (0.25 mL, 2.386 mmol) was added dropwise via syringe. The mixture was stirred and allowed to warm slowly to room temperature overnight. The reaction was quenched with saturated aqueous sodium bicarbonate solution then extracted with four portions of methylene chloride. The combined organic extracts were washed with 1N hydrochloric acid and brine. This organic phase was dried over sodium sulfate. LCMS of acidic aqueous layer suggests presence of product. Extract with three portions of 5% MeOH/CHCl3. HPLC of the aqueous layer showed no further product and was discarded. The methanol-chloroform extract was washed with brine and the organic layer was added to the original methylene chloride extract. The combined extracts were dried over sodium sulfate, filtered and evaporated to afford a white solid (513.9 mg). $^1$H NMR (400 MHz, CHLOROFORM-d) δ 5.46-5.23 (m, 1H), 4.03-3.78 (m, 1H), 2.43-2.26 (m, 1H), 2.22-1.98 (m, 4H), 1.98-1.73 (m, 2H), 1.59-1.45 (m, 2H), 1.18 (d, J=7.0 Hz, 6H).

518B. 4,4-Difluoro-N-isobutylcyclohexanamine

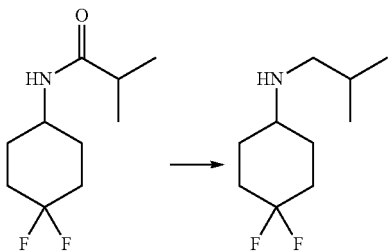

To a solution of N-(4,4-difluorocyclohexyl)isobutyramide (510 mg, 2.485 mmol) in anhydrous THF (15 mL), at room temperature under nitrogen, was added borane-THF complex (6 mL, 6.00 mmol, 1M solution in THF) via syringe. Stirring was continued overnight. The reaction carefully quenched with methanol before being concentrated in vacuo to afford an off-white residue (491.9 mg). This material was used in the subsequent transformation without purification.

518C. 4-Bromo-N-(4,4-difluorocyclohexyl)-5-fluoro-N-isobutyl-2-nitro aniline

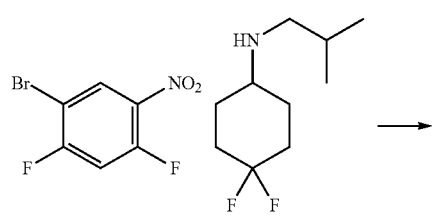

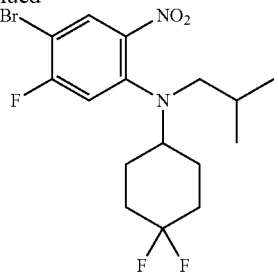

To a solution of 5-bromo-2,4-difluoronitrobenzene (537 mg, 2.258 mmol) in anhydrous. NMP (1 mL), under nitrogen, was added DIPEA (1.183 mL, 6.77 mmol) followed by 4,4-difluoro-N-isobutylcyclohexanamine (475 mg, 2.484 mmol) in NMP (2 mL). The mixture was warmed to 110° C. and stirred for three days. The reaction was cooled to room temperature and diluted with ether. The diluted reaction was washed twice with 1N hydrochloric acid. The organic layer was then washed twice with a saturated solution of sodium bicarbonate and then brine. The organic phase was dried over sodium sulfate, filtered and concentrated in vacuo to afford a dark brown residue (925.2 mg). The crude product was purified on an Isco CombiFlash System using a 24 g silica column. The product was eluted with a gradient of 0-100% ethyl acetate in hexanes. Evaporation of the appropriate fractions gave the desired product as a red-orange solid (682 mg). $^1$H NMR (400 MHz, CHLOROFORM-d) δ 8.04 (d, J=7.3 Hz, 1H), 6.95 (d, J=10.8 Hz, 1H), 3.13-2.95 (m, 1H), 2.87 (d, J=7.3 Hz, 2H), 2.16 (dd, J=11.0, 3.3 Hz, 2H), 1.99-1.75 (m, 5H), 1.75-1.63 (m, 2H), 0.92 (d, J=6.6 Hz, 6H). MS(ES): m/z=409 [M+H]$^+$.

518D. 4-Bromo-N1-(4,4-difluorocyclohexyl)-5-fluoro-N1-isobutylbenzene-1,2-diamine

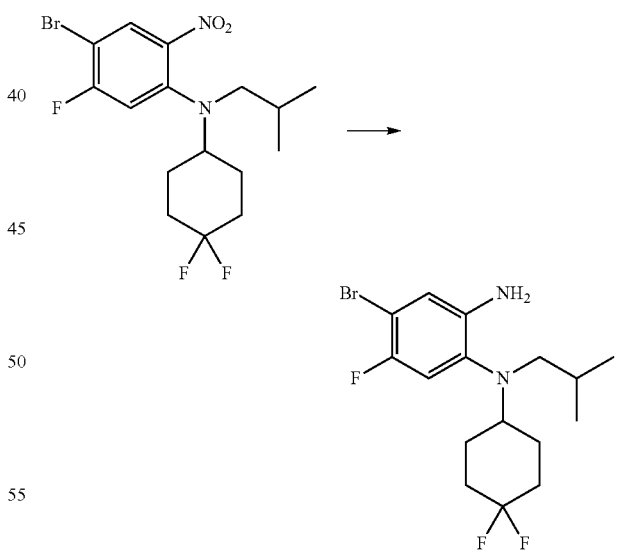

A solution of 4-bromo-N-(4,4-difluorocyclohexyl)-5-fluoro-N-isobutyl-2-nitroaniline (680 mg, 1.662 mmol) in ethanol (6 mL) and water (1.200 mL) was cooled to 0° C. under nitrogen. The reaction was treated with zinc (652 mg, 9.97 mmol) and ammonium chloride (533 mg, 9.97 mmol). The reaction was then stirred overnight. The reaction mixture was then filtered through a pad of Celite which was then thoroughly rinsed with chloroform. The combined organic filtrates were concentrated in vacuo to afford a dark residue which was partitioned between ethyl acetate and water. The layers were separated and the organic layer was concentrated in vacuo to afford a dark purple oily residue (722.0 mg). The crude product was purified on an Isco CombiFlash System using a 40 g silica gel column. The product was eluted with a gradient of 0-100% ethyl acetate in hexanes. Evaporation of the appropriate fractions gave the desired product as a purple oil (308 mg). $^1$H NMR (400 MHz, DMSO-$d_6$) δ 7.06 (d, J=10.6 Hz, 1H), 6.93 (d, J=7.5 Hz, 1H), 4.89 (s, 2H), 2.95-2.64 (m, 3H), 1.91-1.68 (m, 4H), 1.58 (d, J=11.4 Hz, 2H), 1.36 (dquin, J=13.4, 6.7 Hz, 1H), 0.81 (d, J=6.6 Hz, 6H). MS(ES): m/z=379 [M+H]$^+$.

518E. Methyl 5'-amino-4'-((4,4-difluorocyclohexyl)(isobutyl)amino)-2',5-difluoro-[1,1'-biphenyl]-2-carboxylate

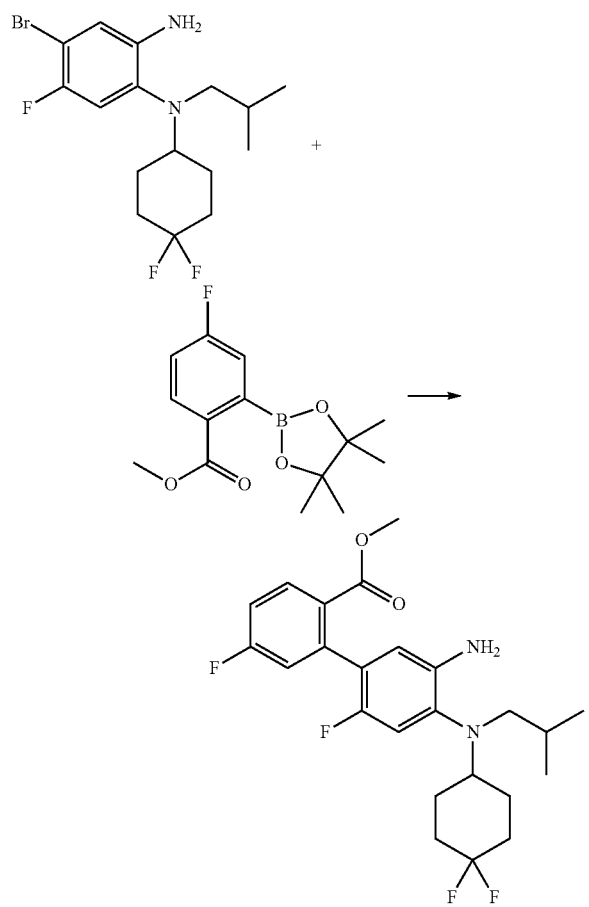

To a stirred solution of 4-bromo-N1-(4,4-difluorocyclohexyl)-5-fluoro-N1-isobutylbenzene-1,2-diamine (305 mg, 0.804 mmol) in dry dioxane (5 mL) was added methyl 4-fluoro-2-(4,4,5,5-tetramethyl-1,3,2-dioxaborolan-2-yl)benzoate (270 mg, 0.965 mmol) and potassium phosphate (512 mg, 2.413 mmol). The reaction was purged with argon for 15 minutes and then PdCl$_2$(dppf) (118 mg, 0.161 mmol) was added. The reaction was purged with argon for another 5 minutes. The reaction was sealed and heated to 80° C. overnight. The cooled reaction mixture was concentrated in vacuo to remove volatiles before being redissolved in ethyl acetate. The mixture was washed sequentially with water, then brine, before being dried over sodium sulfate, filtered and evaporated to afford a dark brown oil (928.9 mg). The crude product was purified on an Isco CombiFlash System using a 40 g silica gel column. The product was eluted with a gradient of 0-50% ethyl acetate in hexanes. Evaporation of the appropriate fractions gave the desired product as an oil (224.3 mg). MS(ES): m/z=453 [M+H]$^+$.

518. 4'-((4,4-Difluorocyclohexyl)(isobutyl)amino)-2',5-difluoro-5'-(3-(5-methylisoxazol-3-yl)ureido)-[1,1'-biphenyl]-2-carboxylic acid

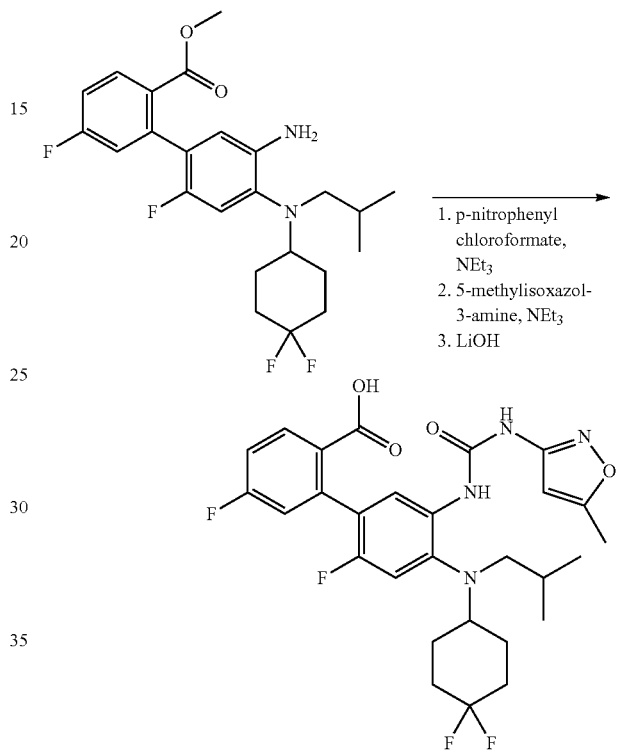

A reaction vial was charged with methyl 5'-amino-4'-((4,4-difluorocyclohexyl)(isobutyl)amino)-2',5-difluoro-[1,1'-biphenyl]-2-carboxylate (37 mg, 0.082 mmol) in anhydrous tetrahydrofuran (2 mL). 4-Nitrophenyl chloroformate (18.13 mg, 0.090 mmol) was added followed by triethylamine (0.23 mL, 1.650 mmol). After 40 minutes, 5-methylisoxazol-3-amine (64.2 mg, 0.654 mmol) was added and the reaction warmed to 50° C. The reaction was stirred overnight. LCMS suggests partial conversion to product. The reaction was quenched with water and then extracted twice with ethyl acetate. The combined organic extracts were washed with brine and then concentrated in vacuo to afford a gold-yellow residue. This material was resubjected to the reaction conditions. The cooled reaction was quenched with water and extracted twice with ethyl acetate. The combined organic layers were washed with brine and concentrated in vacuo to afford a yellow residue (49 mg). LCMS is consistent with the presence of the expected product. To a homogeneous mixture of methyl 4'-((4,4-difluorocyclohexyl)(isobutyl)amino)-2',5-difluoro-5'-(3-(5-methylisoxazol-3-yl)ureido)-[1,1'-biphenyl]-2-carboxylate (47.1 mg, 0.082 mmol) in anhydrous tetrahydrofuran (2 mL), methanol (2 mL) and water (1 mL) was added lithium hydroxide (19.56 mg, 0.817 mmol). The mixture was stirred for 21 hours. The reaction was concentrated in vacuo to remove volatiles then treated with 2 mL of water. 1 N hydrochloric acid was then added until the pH was ca. 4. The resulting mixture was extracted twice with ethyl acetate and the combined organic extracts were washed with brine then concentrated in vacuo to afford the crude product. The residue was redissolved in 1.5 mL DMF and passed through a syringe filter. The crude material was purified via preparative LCMS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation. The yield of the product was 17.6 mg, MS(ES): m/z=563 [M+H]$^+$ HPLC T$_r$: 1.88$^k$. $^1$H NMR (500 MHz, DMSO-d$_6$) δ 10.44 (br. s., 1H), 8.84 (br. s., 1H), 8.24-8.07 (m, 1H), 7.94-7.73 (m, 1H), 7.33 (t, J=8.2 Hz, 1H), 7.24 (d, J=9.4 Hz, 1H), 7.20 (d, J=11.4 Hz, 1H), 6.38 (br. s., 1H), 2.88-2.76 (m, 2H), 2.35 (d, J=3.0 Hz, 3H), 2.09-1.91 (m, 4H), 1.87-1.69 (m, 2H), 1.58 (q, J=12.2 Hz, 2H), 1.44-1.31 (m, 1H), 0.89-0.82 (m, 6H).

Example 519

4'-((4,4-Difluorocyclohexyl)(isobutyl)amino)-2',5-difluoro-5'-(3-(p-tolyl)ureido)-[1,1'-biphenyl]-2-carboxylic acid

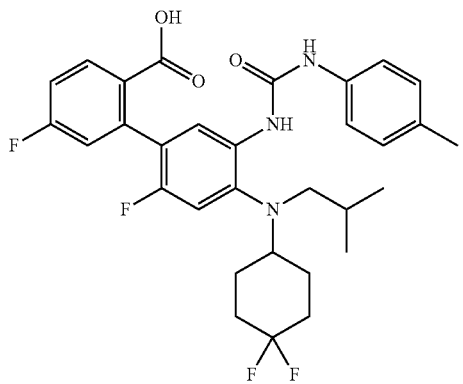 [SMILES: Cc1ccc(NC(=O)Nc2cc(-c3cc(F)ccc3C(=O)O)c(F)cc2N(CC(C)C)C2CCC(F)(F)CC2)cc1]

519A. Methyl 5'-amino-4'-((4,4-difluorocyclohexyl)(isobutyl)amino)-2',5-difluoro-[1,1'-biphenyl]-2-carboxylate

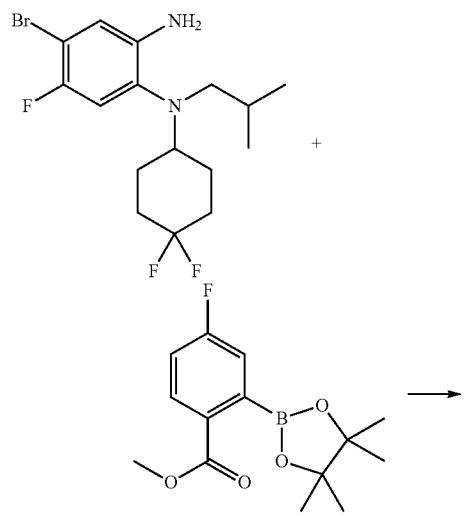

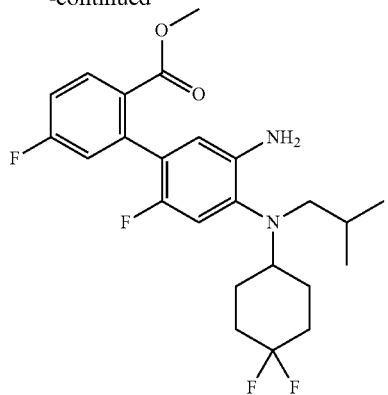

To a stirred solution of 4-bromo-N1-(4,4-difluorocyclohexyl)-5-fluoro-N1-isobutylbenzene-1,2-diamine (150 mg, 0.396 mmol) in dry dioxane (3 mL) was added methyl 4-fluoro-2-(4,4,5,5-tetramethyl-1,3,2-dioxaborolan-2-yl)benzoate (133 mg, 0.475 mmol), followed by potassium phosphate (252 mg, 1.187 mmol). The reaction mixture was purged with argon for 15 minutes before adding PdCl$_2$(dppf) (57.9 mg, 0.079 mmol). The reaction mixture was again purged with argon for another 5 minutes before the reaction was equipped with a Vigreaux column and heated to 80° C. under an argon atmosphere. After heating for 5 hour, LCMS suggests partial conversion to product. Reaction was again purged with argon for 15 min before 62.5 mg of the boronate reagent and 49 mg of the Pd catalyst were added. Argon was bubbled through the reaction mixture for 5 minutes before heating again at 80° C. The reaction was stirred overnight. Reaction was cooled to room temperature and diluted with ethyl acetate. The mixture was washed sequentially with water then brine. The organic phase was dried over sodium sulfate, filtered and concentrated in vacuo to afford a dark brown oil (528.3 mg). The crude product was purified on an Isco CombiFlash System using a 24 g silica gel column. The product was eluted with a gradient of 0-50% ethyl acetate in hexanes. Evaporation of the appropriate fractions gave the desired product (53 mg). MS(ES): m/z=453 [M+H]$^+$.

519B. Methyl 4'-((4,4-difluorocyclohexyl)(isobutyl)amino)-2',5-difluoro-5'-(3-(p-tolyl)ureido)-[1,1'-biphenyl]-2-carboxylate

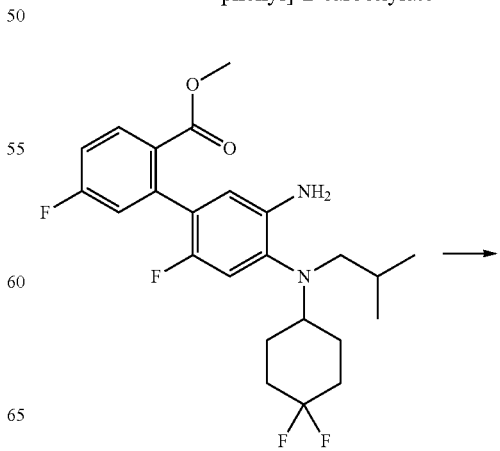

-continued

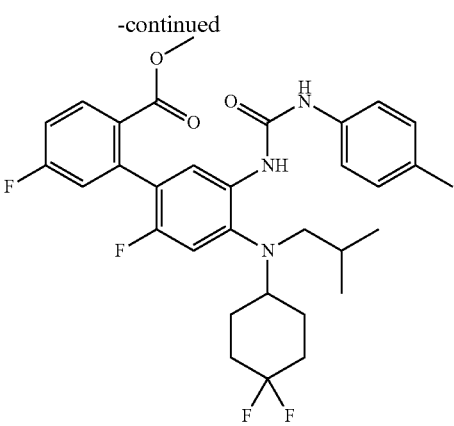

To a solution of methyl 5'-amino-4'-((4,4-difluorocyclohexyl)(isobutyl)amino)-2',5-difluoro-[1,1'-biphenyl]-2-carboxylate (52.8 mg, 0.117 mmol) in anhydrous tetrahydrofuran (2 mL) was added 1-isocyanato-4-methylbenzene (21.75 mg, 0.163 mmol). The mixture was warmed to 50° C. under nitrogen atmosphere. After 2 hours, heating was stopped and the reaction allowed to stir at room temperature overnight. The reaction was partitioned between water and ethyl acetate. The layers were separated and the aqueous layer was extracted twice more with ethyl acetate. The combined organic extracts were washed once each with water and brine. The organic layer was dried over sodium sulfate, filtered and evaporated to afford a dark brown residue (106.6 mg). The crude product was purified on Isco CombiFlash System using a 12 g silica gel column. The product was eluted with a gradient of 0-100% ethyl acetate in hexanes. Evaporation of the appropriate fractions gave the desired product as a colorless glass (56 mg). MS(ES): m/z=586 [M+H]$^+$.

519. 4'-((4,4-Difluorocyclohexyl)(isobutyl)amino)-2',5-difluoro-5'-(3-(p-tolyl)ureido)-[1,1'-biphenyl]-2-carboxylic acid

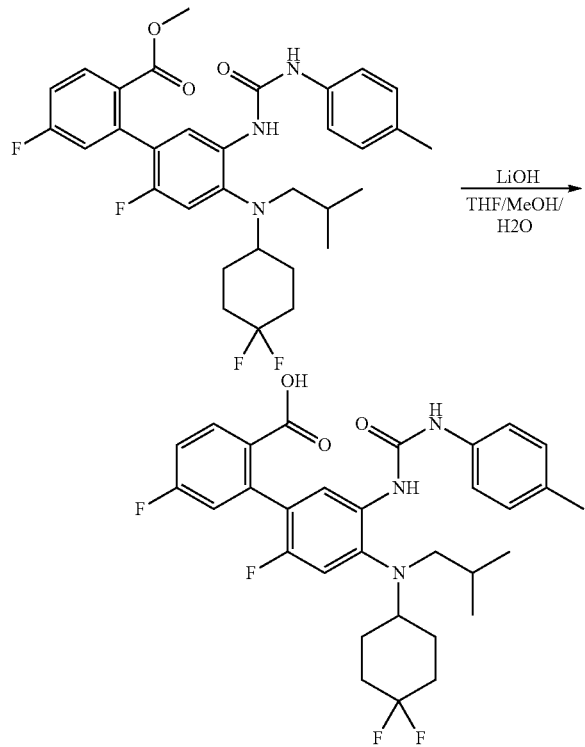

To a homogeneous mixture of methyl 4'-((4,4-difluorocyclohexyl)(isobutyl)amino)-2',5-difluoro-5'-(3-(p-tolyl)ureido)-[1,1'-biphenyl]-2-carboxylate (56.0 mg, 0.096 mmol) in anhydrous tetrahydrofuran (1 mL), methanol (1 mL) and water (0.5 mL), at room temperature under nitrogen, was added lithium hydroxide (22.90 mg, 0.956 mmol). The reaction was stirred overnight. The reaction was concentrated in vacuo to remove volatiles then treated with 2 mL of water. Hydrochloric acid (1N) was then added until ca. pH 4. The resulting mixture was extracted twice with ethyl acetate and the combined organic extracts were washed with brine. Evaporation then afforded a glassy residue. The crude product was purified on an Isco CombiFlash System using a 12 g silica gel column. The product was eluted with a gradient of 0-100% ethyl acetate in hexanes. Appropriate fractions containing expected product peak were combined and concentrated to remove volatiles then lyophilized to afford a white solid (21.1 mg). MS(ES): m/z=572 [M+H]$^+$, HPLC T$_r$: 12.97 g. $^1$H NMR (400 MHz, DMSO-d$_6$) δ 12.79 (br. s., 1H), 9.45 (s, 1H), 8.10 (d, J=8.4 Hz, 1H), 8.00-7.87 (m, 2H), 7.46-7.32 (m, 3H), 7.25 (dd, J=9.6, 2.5 Hz, 1H), 7.16 (d, J=11.4 Hz, 1H), 7.10 (d, J=8.4 Hz, 2H), 2.96-2.78 (m, 3H), 2.26 (s, 3H), 2.14-1.93 (m, 4H), 1.93-1.68 (m, 2H), 1.65-1.50 (m, 2H), 1.42 (dquin, J=13.2, 6.7 Hz, 1H), 0.88 (d, J=6.6 Hz, 6H).

Example 520

4'-((4,4-Difluorocyclohexyl)(isobutyl)amino)-2',5-difluoro-5'-(3-(1-(2,2,2-trifluoroethyl)-1H-pyrazol-4-yl)ureido)-[1,1'-biphenyl]-2-carboxylic acid

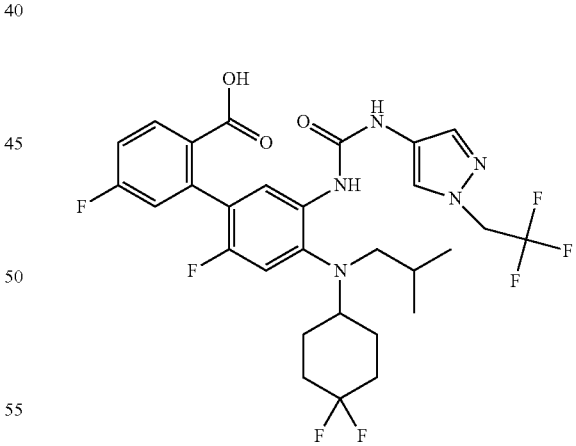

Example 520 was prepared using the chemistry described for Example 518. MS(ES): m/z=630 [M+H]$^+$, HPLC T$_r$: 2.13$^k$. $^1$H NMR (500 MHz, DMSO-d$_6$) δ 9.54 (br. s., 1H), 8.17 (s, 1H), 8.01-7.88 (m, 4H), 7.53 (s, 1H), 7.35 (td, J=8.5, 2.7 Hz, 1H), 7.26 (dd, J=9.4, 2.5 Hz, 1H), 7.18 (d, J=11.4 Hz, 1H), 5.06 (q, J=9.2 Hz, 2H), 2.88-2.78 (m, 3H), 2.14-1.92 (m, 4H), 1.91-1.71 (m, 2H), 1.62-1.47 (m, 2H), 1.38 (dquin, J=13.3, 6.6 Hz, 1H), 0.86 (d, J=6.9 Hz, 6H).

Example 521

4'-((4,4-Difluorocyclohexyl)(isobutyl)amino)-2',5-difluoro-5'-(3-(3-methylisoxazol-5-yl)ureido)-[1,1'-biphenyl]-2-carboxylic acid

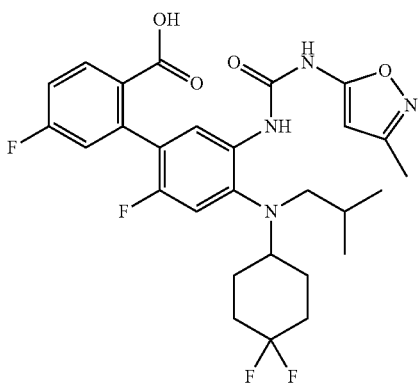 [SMILES: Cc1cc(NC(=O)Nc2cc(-c3cc(F)ccc3C(=O)O)c(F)cc2N(CC(C)C)C2CCC(F)(F)CC2)on1]

Example 521 was prepared using the chemistry described for Example 518. MS(ES): m/z=675 [M+H]⁺, HPLC T,: 2.12ᵏ. ¹H NMR (500 MHz, DMSO-d₆) δ 11.29 (br. s., 1H), 8.28 (br. s., 1H), 8.09 (dd, J=8.2, 3.2 Hz, 1H), 7.99-7.90 (m, 2H), 7.40-7.32 (m, 1H), 7.27 (d, J=8.9 Hz, 1H), 7.22 (d, J=11.4 Hz, 1H), 2.82 (br. s., 3H), 2.16 (d, J=3.5 Hz, 3H), 2.09-1.94 (m, 4H), 1.90-1.71 (m, 2H), 1.61-1.47 (m, 2H), 1.43-1.30 (m, 1H), 0.91-0.80 (m, 6H)

Example 522

4'-(Cyclohexyl(isobutyl)amino)-2',5-difluoro-5'-(3-(6-methylpyridazin-3-yl)ureido)-[1,1'-biphenyl]-2-carboxylic acid

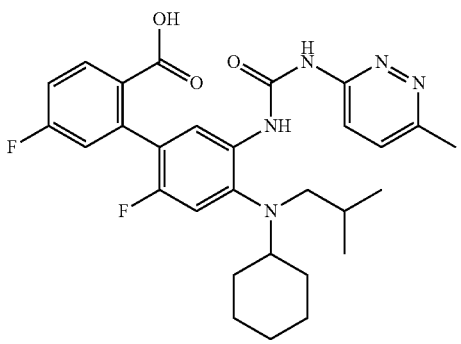 [SMILES: Cc1ccc(NC(=O)Nc2cc(-c3cc(F)ccc3C(=O)O)c(F)cc2N(CC(C)C)C2CCCCC2)nn1]

522A. N-Cyclohexylisobutyramide

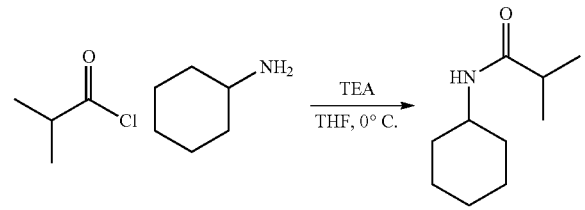

A solution of cyclohexanamine (3.65 g, 36.8 mmol) in anhydrous tetrahydrofuran (30 mL) was cooled to 0° C. under nitrogen. Triethylamine (5.60 mL, 40.1 mmol) was added. The mixture was stirred at 0° C. for 10 minutes before isobutyryl chloride (3.51 mL, 33.5 mmol) was added dropwise via syringe. The mixture was allowed to warm slowly to room temperature. After three days, the reaction was quenched with saturated sodium bicarbonate solution then extracted with four portions of methylene chloride. The combined organic extracts were washed with 1N hydrochloric acid and brine. The aqueous layer was further extracted with three portions of 5% MeOH/CHCl3. No product is apparent in aqueous layer, which was then discarded. The organic extracts were combined with the original organic layer and concentrated in vacuo to afford an off-white solid (5.43 g). The crude product was purified on an Isco CombiFlash System using a 120 g silica gel column. The product was eluted with a gradient of 0-100% ethyl acetate in hexanes. Evaporation of the appropriate fractions gave the desired product as a colorless solid (5.05 g). ¹H NMR (400 MHz, CHLOROFORM-d) δ 5.28 (br. s., 1H), 3.92-3.60 (m, 1H), 2.32 (spt, J=6.9 Hz, 1H), 2.01-1.86 (m, 2H), 1.81-1.69 (m, 2H), 1.51-1.33 (m, 2H), 1.17 (d, J=6.8 Hz, 6H) (some resonances are obscured by the methyls of the isobutyl group).

522B. N-Isobutylcyclohexanamine

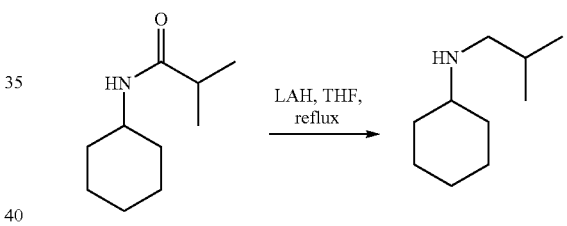

Lithium aluminum hydride (48 mL, 48.0 mmol, 1M in tetrahydrofuran) was slowly added to a solution of N-cyclohexylisobutyramide (4 g, 23.63 mmol) in anhydrous tetrahydroduran (100 mL) under nitrogen. The resulting solution was heated at 70° C. for 20 hours. The reaction mixture was cooled to room temperature then diluted with ether and cooled in an ice bath to 0° C. Water (2 mL) was slowly added to the reaction mixture followed by 15% aqueous sodium hydroxide (2 mL). Water (6 mL) was then added and the reaction mixture was removed from the ice bath and allowed to warm to room temperature. The mixture was stirred for 15 minutes at room temperature before magnesium sulfate was added and the mixture stirred for another 15 minutes. The mixture was filtered through a fritted glass funnel to remove salts. The filtrate was transferred to a separatory funnel where the layers were separated. The aqueous layer was extracted twice more with ethyl acetate. The combined organic extracts were washed with water then brine. The organic phase was dried over magnesium sulfate, filtered and concentrated in vacuo to afford an oil (2.9573 g). This material was used without purification. ¹H NMR (400 MHz, DMSO-d₆) δ 2.52 (dt, J=3.6, 1.9 Hz, 1H), 2.33 (d, J=6.8 Hz, 2H), 1.88-1.75 (m, 2H), 1.73-1.63 (m, 2H), 1.62-1.48 (m, 2H), 1.27-1.09 (m, 4H), 1.06-0.93 (m, 2H), 0.87 (d, J=6.6 Hz, 6H).

522C. 4-Bromo-N-cyclohexyl-5-fluoro-N-isobutyl-2-nitroaniline

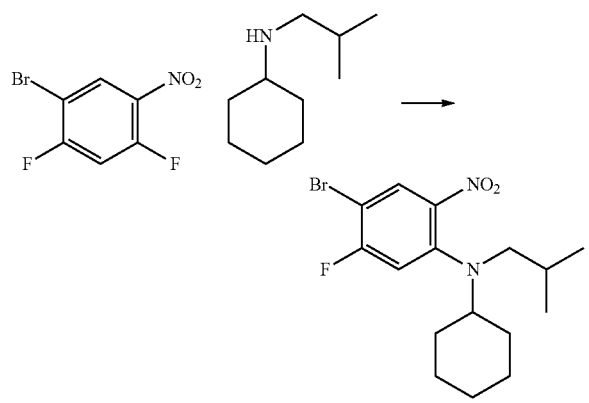

To a solution of 5-bromo-2,4-difluoronitrobenzene (1.806 g, 7.59 mmol) in anhydrous NMP (3 mL) was added diisopropylethylamine (3.98 mL, 22.77 mmol) followed by N-isobutylcyclohexanamine (1.2964 g, 8.35 mmol) in NMP (6 mL). The mixture was heated at 110° C. under nitrogen. After stirring for 19 hours, the reaction was allowed to cool to room temperature before being diluted with ether. The ether solution was washed twice with 1N hydrochloric acid. The organic layer was then washed twice with each saturated sodium bicarbonate solution then brine. The organic layer was dried over sodium sulfate, filtered and concentrated in vacuo to afford a dark residue (3.06 g). The crude product was purified on an Isco CombiFlash System using a 80 g silica gel column. The product was eluted with a gradient of 0-100% ethyl acetate in hexanes. Evaporation of the appropriate fractions gave the desired product as a red-orange solid (2.30 g). $^1$H NMR (400 MHz, CHLOROFORM-d) δ 7.99 (d, J=7.3 Hz, 1H), 6.89 (d, J=11.0 Hz, 1H), 2.97-2.90 (m, 1H), 2.89 (d, J=7.3 Hz, 2H), 1.91-1.77 (m, 4H), 1.71 (dt, J=13.5, 6.8 Hz, 1H), 1.67-1.58 (m, 1H), 1.50-1.38 (m, 2H), 1.34-1.18 (m, 2H), 1.16-1.02 (m, 1H), 0.92 (d, J=6.6 Hz, 6H). MS(ES): m/z=373 [M+H]$^+$.

522D. 4-Bromo-N1-cyclohexyl-5-fluoro-N1-isobutylbenzene-1,2-diamine

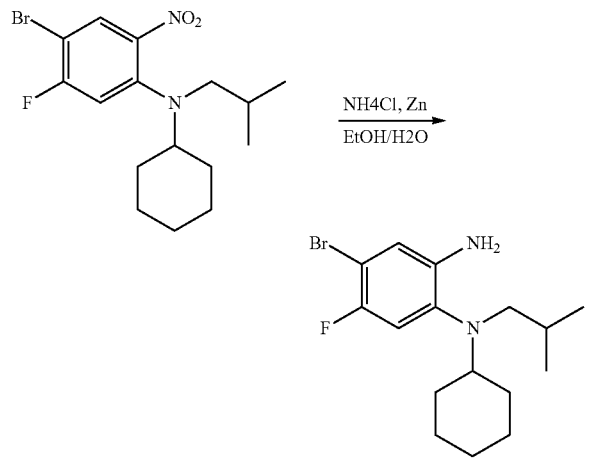

A solution of 4-bromo-N-cyclohexyl-5-fluoro-N-isobutyl-2-nitroaniline (1.116 g, 2.99 mmol) in ethanol (20 mL) and water (4.00 mL) was cooled to 0° C. under nitrogen. Zinc (3.91 g, 59.8 mmol) and ammonium chloride (3.20 g, 59.8 mmol) were then added. The mixture was stirred at room temperature for an hour. The reaction mixture was filtered through a pad of Celite which was then thoroughly rinsed with chloroform. The combined organic filtrates were concentrated in vacuo to afford a waxy, gold residue (1.1283 g). The sample was suspended in chloroform. The sample was filtered and the filtrate applied to a 40 g Isco silica gel column. The product was eluted with 0-100% ethyl acetate in hexanes. Only partial purification was achieved. Concentrate product containing fractions. The partially purified product was purified on Isco CombiFlash System using a 40 g silica gel column. The product was eluted with a gradient of 0-50% ethyl acetate in hexanes. Evaporation of the appropriate fractions gave the desired product as a gold oil (246 mg). $^1$H NMR (400 MHz, DMSO-d$_6$) δ 7.00 (d, J=10.8 Hz, 1H), 7.11-6.96 (m, 1H), 6.91 (d, J=7.3 Hz, 1H), 4.80 (s, 2H), 2.89-2.67 (m, 2H), 2.60 (tt, J=11.7, 3.2 Hz, 1H), 1.73 (br. s., 4H), 1.55 (d, J=9.9 Hz, 1H), 1.44-1.28 (m, 3H), 1.16-0.95 (m, 3H), 0.80 (d, J=6.6 Hz, 6H). MS(ES): m/z=343 [M+H]$^+$.

522E. Methyl 5'-amino-4'-(cyclohexyl(isobutyl)amino)-2',5-difluoro-[1,1'-biphenyl]-2-carboxylate

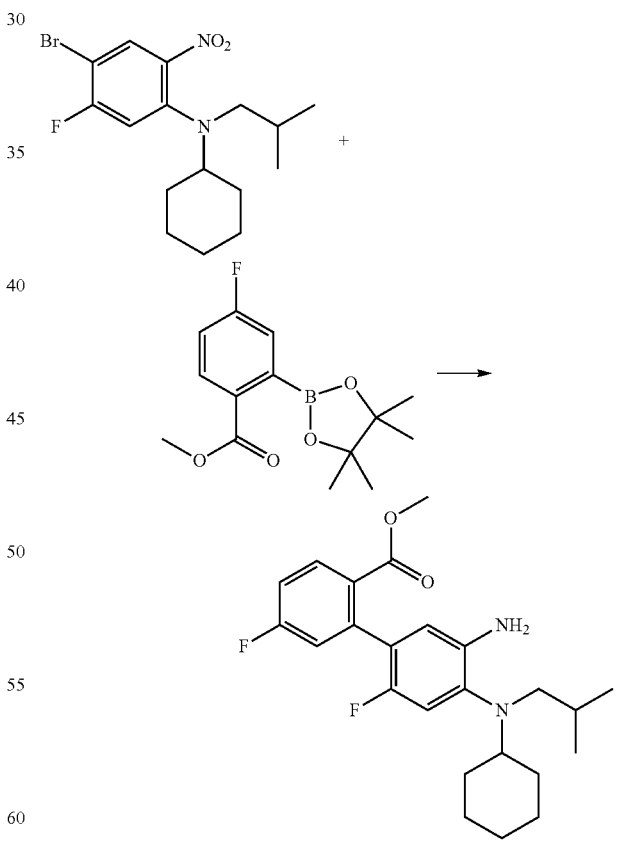

To a stirred solution of 4-bromo-N1-cyclohexyl-5-fluoro-N1-isobutylbenzene-1,2-diamine (246 mg, 0.717 mmol) in dry dioxane (5 mL) was added methyl 4-fluoro-2-(4,4,5,5-tetramethyl-1,3,2-dioxaborolan-2-yl)benzoate (241 mg, 0.860 mmol), followed by potassium phosphate (456 mg, 2.150 mmol). The reaction was purged with argon for 15 minutes. PdCl$_2$(dppf) (105 mg, 0.143 mmol) was added and purging with argon continued for 5 minutes. The reaction was then heated to 80° C. The reaction was heated for ca. 24 hours. The cooled reaction was evaporated then resuspended in ethyl acetate. The mixture was washed sequentially with water and then brine, The organic layer was dried over sodium sulfate, filtered and concentrated in vacuo to afford a dark brown residue (953.5 mg). Purification was attempted on a CombiFlash System using a 40 g Isco silica gel column. The column was eluted with a gradient of 0-100% ethyl acetate in hexanes. As only partial purification was achieved the material was purified a second time on the Isco CombiFlash System using a 24 g silica gel column. The product was eluted with a 0-50% ethyl acetate in hexanes gradient. Evaporation of the appropriate fractions gave the desired product as an oil (144.7 mg). $^1$H NMR (400 MHz, DMSO-d$_6$) δ 7.88 (dd, J=8.7, 6.1 Hz, 1H), 7.34 (td, J=8.5, 2.6 Hz, 1H), 7.28 (dd, J=9.9, 2.6 Hz, 1H), 6.87 (d, J=12.1 Hz, 1H), 6.67 (d, J=7.9 Hz, 1H), 4.65 (s, 2H), 3.60 (s, 3H), 2.78 (br. s., 2H), 2.75-2.64 (m, 1H), 1.77 (t, J=11.1 Hz, 4H), 1.58 (d, J=10.6 Hz, 1H), 1.49-1.35 (m, 3H), 1.19-1.00 (m, 3H), 0.84 (d, J=6.6 Hz, 6H)

522. 4'-(Cyclohexyl(isobutyl)amino)-2',5-difluoro-5'-(3-(6-methylpyridazin-3-yl)ureido)-[1,1'-biphenyl]-2-carboxylic acid The rest of the preparation was accomplished as in Example 518. MS(ES): m/z=538 [M+H]$^+$, HPLC T$_r$: 1.82$^j$. $^1$H NMR (500 MHz, DMSO-d$_6$) δ 10.32 (br. s., 1H), 8.09 (d, J=8.4 Hz, 1H), 7.91 (dd, J=8.7, 6.2 Hz, 1H), 7.63 (br. s., 1H), 7.51 (d, J=9.4 Hz, 1H), 7.33 (td, J=8.4, 2.5 Hz, 1H), 7.26 (dd, J=9.7, 2.2 Hz, 1H), 7.11 (d, J=11.9 Hz, 1H), 2.84 (d, J=6.4 Hz, 2H), 2.69 (t, J=11.6 Hz, 1H), 2.53 (s, 3H), 2.00-1.87 (m, 2H), 1.67 (d, J=9.4 Hz, 2H), 1.52 (br. s., 1H), 1.44 (dt, J=13.4, 6.7 Hz, 1H), 1.40-1.27 (m, 2H), 1.14-0.97 (m, 3H), 0.86 (d, J=6.4 Hz, 6H).

Example 523

4'-(Cyclohexyl(isobutyl)amino)-5'-(3-(4-cyclohexylphenyl)ureido)-2',5-difluoro-[1,1'-biphenyl]-2-carboxylic acid

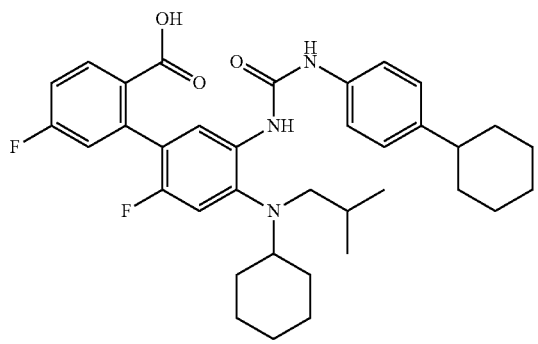 [SMILES: CC(C)CN(c1cc(F)c(-c2cc(F)ccc2C(=O)O)cc1NC(=O)Nc1ccc(C2CCCCC2)cc1)C1CCCCC1]

Example 523 was prepared using the chemistry described for Example 522. MS(ES): m/z=604 [M+H]$^+$, HPLC T$_r$: 2.78$^k$. $^1$H NMR (500 MHz, DMSO-d$_6$) δ 9.41 (s, 1H), 7.97 (d, J=8.4 Hz, 1H), 7.91 (dd, J=8.7, 6.2 Hz, 1H), 7.80 (s, 1H), 7.36 (d, J=8.9 Hz, 2H), 7.34-7.29 (m, 1H)(partially obscured), 7.25 (dd, J=9.4, 2.5 Hz, 1H), 7.13 (d, J=8.4 Hz, 2H), 7.07 (d, J=11.4 Hz, 1H), 2.81 (d, J=5.9 Hz, 2H), 2.66-2.57 (m, 1H), 2.47-2.39 (m, 1H), 1.87 (d, J=10.9 Hz, 2H), 1.81-1.66 (m, 7H), 1.53 (d, J=11.4 Hz, 1H), 1.46-1.17 (m, 8H), 1.16-0.95 (m, 3H).

Example 524

4'-(Cyclohexyl(isobutyl)amino)-2',5-difluoro-5'-(3-(4-morpholinophenyl)ureido)-[1,1'-biphenyl]-2-carboxylic acid

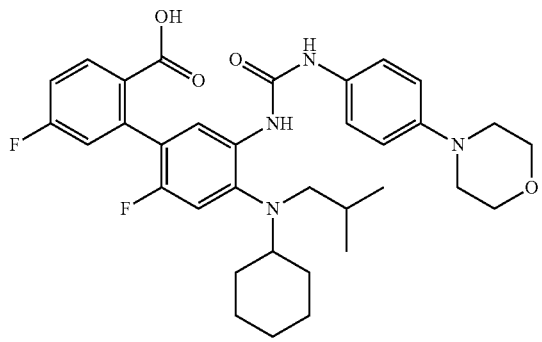 [SMILES: CC(C)CN(c1cc(F)c(-c2cc(F)ccc2C(=O)O)cc1NC(=O)Nc1ccc(N2CCOCC2)cc1)C1CCCCC1]

Example 524 was prepared using the chemistry described for Example 522. MS(ES): m/z=607 [M+H]$^+$, HPLC T$_r$: 2.04$^k$. $^1$H NMR (500 MHz, DMSO-d$_6$) δ 9.23 (br. s., 1H), 8.00 (d, J=8.4 Hz, 1H), 7.91 (dd, J=8.9, 5.9 Hz, 1H), 7.74 (s, 1H), 7.39-7.33 (m, 1H), 7.31 (d, J=8.9 Hz, 2H), 7.25 (dd, J=9.7, 2.7 Hz, 1H), 7.07 (d, J=11.4 Hz, 1H), 6.90 (d, J=8.9 Hz, 2H), 3.79-3.69 (m, 4H), 3.08-3.00 (m, 4H), 2.79 (d, J=5.0 Hz, 2H), 2.59 (t, J=11.4 Hz, 1H), 1.84 (d, J=9.9 Hz, 2H), 1.71 (d, J=12.4 Hz, 2H), 1.53 (d, J=11.4 Hz, 1H), 1.39 (dquin, J=13.3, 6.6 Hz, 1H), 1.32-1.19 (m, 2H), 1.16-0.95 (m, 3H), 0.85 (d, J=6.4 Hz, 6H).

Example 525

4'-(Cyclohexyl(isobutyl)amino)-2',5-difluoro-5'-(3-(5-methylpyrazin-2-yl)ureido)-[1,1'-biphenyl]-2-carboxylic acid

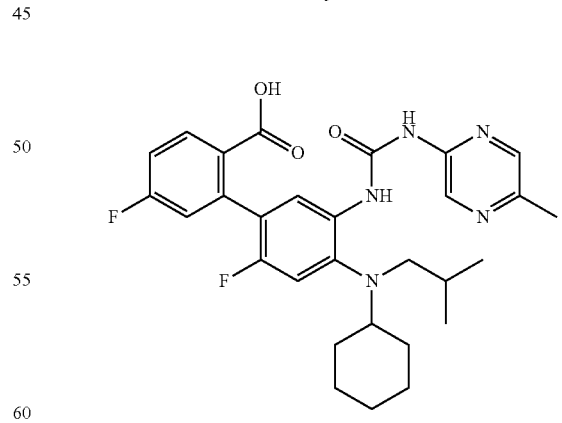

Example 525 was prepared using the chemistry described for Example 522. MS(ES): m/z=538 [M+H]$^+$, HPLC T$_r$: 2.28$^k$. $^1$H NMR (500 MHz, DMSO-d$_6$) δ 10.24 (s, 1H), 8.59 (br. s., 1H), 8.16-8.08 (m, 2H), 7.98-7.88 (m, 2H), 7.35 (td, J=8.4, 2.5 Hz, 1H), 7.29 (dd, J=9.7, 2.7 Hz, 1H), 7.13 (d, J=11.4 Hz, 1H), 2.86 (d, J=5.4 Hz, 2H), 2.71-2.61 (m, 1H), 2.43 (s, 3H), 1.87 (d, J=10.9 Hz, 2H), 1.67 (d, J=12.4 Hz, 2H), 1.52 (d, J=10.9 Hz, 1H), 1.43 (dquin, J=13.4, 6.7 Hz, 1H), 1.37-1.25 (m, 2H), 1.13-0.96 (m, 3H), 0.87 (d, J=6.4 Hz, 6H).

Example 526

4'-(Diisobutylamino)-3'-(3-(2-fluorophenyl)ureido)-5-methyl-[1,1'-biphenyl]-2-carboxylic acid

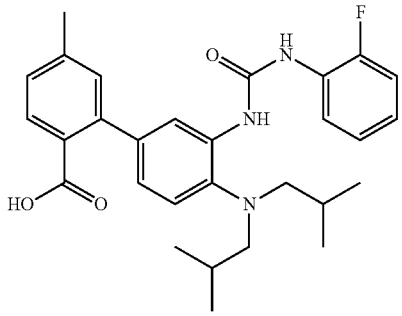 [SMILES: Cc1ccc(C(=O)O)c(-c2ccc(N(CC(C)C)CC(C)C)c(NC(=O)Nc3ccccc3F)c2)c1]

526A. 4-(5,5-Dimethyl-1,3,2-dioxaborinan-2-yl)-N,N-diisobutyl-2-nitroaniline

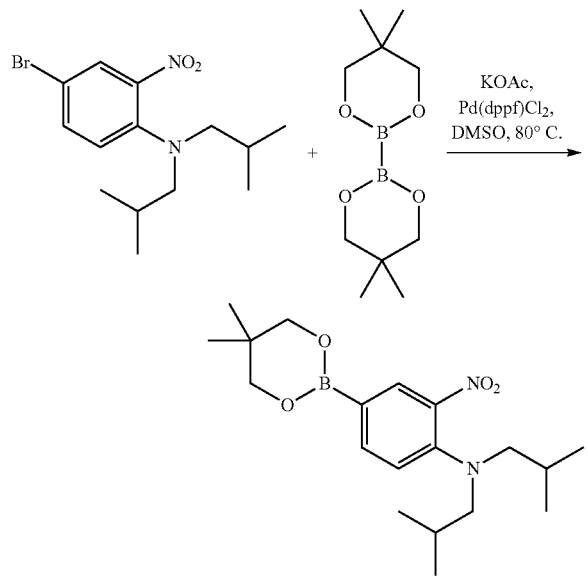

4-bromo-N,N-diisobutyl-2-nitroaniline (20 g, 60.7 mmol) (1A), 5,5,5',5'-tetramethyl-2,2'-bi(1,3,2-dioxaborinane) (15.09 g, 66.8 mmol), PdCl₂(dppf)-CH2Cl2 adduct (1.111 g, 1.519 mmol) and potassium acetate (17.89 g, 182 mmol) were combined in a round bottom flask. Dimethylsulfoxide (200 mL) was added and the flask evacuated and back-filled with nitrogen 3 times. The reaction was then heated at 80° C. for 8 h. The reaction was cooled to room temperature, divided in half, and passed through a two short silica gel plugs. The silica gel was rinsed with hexane/ethyl acetate (4:1) (3×100 mL). After removal of the solvent, the crude product was purified on a 750 g RediSep silica gel column using a 0-10% ethyl acetate in hexanes gradient. 4-(5,5-Dimethyl-1,3,2-dioxaborinan-2-yl)-N,N-diisobutyl-2-nitroaniline (22.17 g) was obtained as a yellow/orange oil. $^1$H NMR (400 MHz, CHLOROFORM-d) δ 8.15 (d, J=1.5 Hz, 1H), 7.75 (dd, J=8.4, 1.5 Hz, 1H), 7.06 (d, J=8.6 Hz, 1H), 3.76 (s, 4H), 3.09-2.89 (m, 4H), 1.95 (dquin, J=13.5, 6.8 Hz, 2H), 1.03 (s, 6H), 0.85 (d, J=6.6 Hz, 12H).

526B. Methyl 4'-(diisobutylamino)-5-methyl-3'-nitro-[1,1'-biphenyl]-2-carboxylate

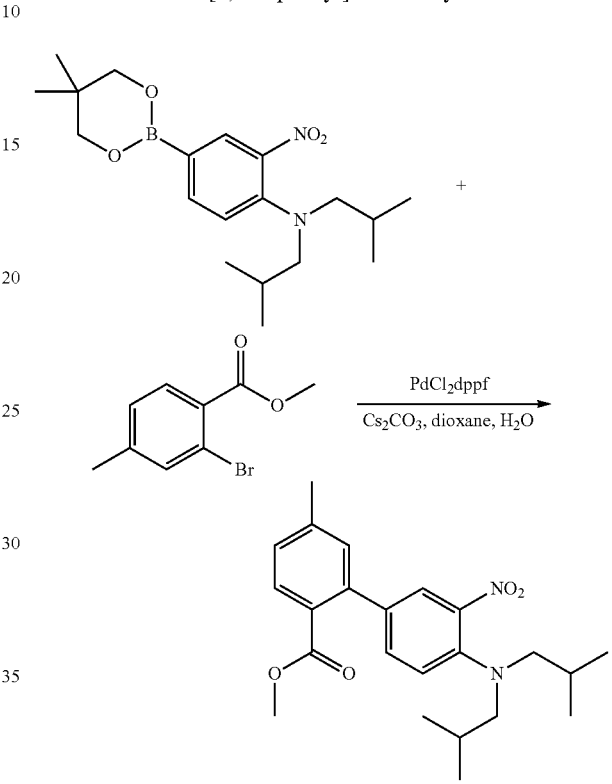

A 20 mL vial was charged with 4-(5,5-dimethyl-1,3,2-dioxaborinan-2-yl)-N,N-diisobutyl-2-nitroaniline (300 mg, 0.828 mmol), methyl 2-bromo-4-methylbenzoate (158 mg, 0.690 mmol) and cesium carbonate (675 mg, 2.070 mmol). The vial was sealed, evacuated, and back-filled with argon (×3). Dioxane-water (3:1, 3.0 mL) was then added and the mixture purged again with argon. PdCl₂(dppf)-CH₂Cl₂ adduct (56.4 mg, 0.069 mmol) was added and the reaction vial then sealed and heated at 100° C. The reaction was heated for ca. 5 hours. The cooled reaction was transferred to a separatory funnel and diluted with ethyl acetate. The organic layer was washed with water. The layers were separated and the aqueous layer was extracted twice more with ethyl acetate. The combined organic extracts were washed with water then brine. The organic layer was dried over sodium sulfate, filtered and concentrated in vacuo to afford a dark brown residue (637 mg). The crude product was purified on Isco CombiFlash System using a 12 g silica gel column. The product was eluted with a gradient of 0-100% ethyl acetate in hexanes. Evaporation of the appropriate fractions gave the desired product as a viscous orange red oil (292.5 mg).

$^1$H NMR (400 MHz, CHLOROFORM-d) δ 7.82 (d, J=7.9 Hz, 1H), 7.73 (d, J=2.2 Hz, 1H), 7.33 (dd, J=8.6, 2.2 Hz, 1H), 7.28-7.23 (m, 1H), 7.22-7.19 (m, 1H), 7.15 (d, J=8.8 Hz, 1H), 3.69 (s, 3H), 3.00 (d, J=7.0 Hz, 4H), 2.45 (s, 3H), 2.05-1.92 (m, 2H), 0.90 (d, J=6.6 Hz, 12H).

526C. Methyl 3'-amino-4'-(diisobutylamino)-5-methyl-[1,1'-biphenyl]-2-carboxylate

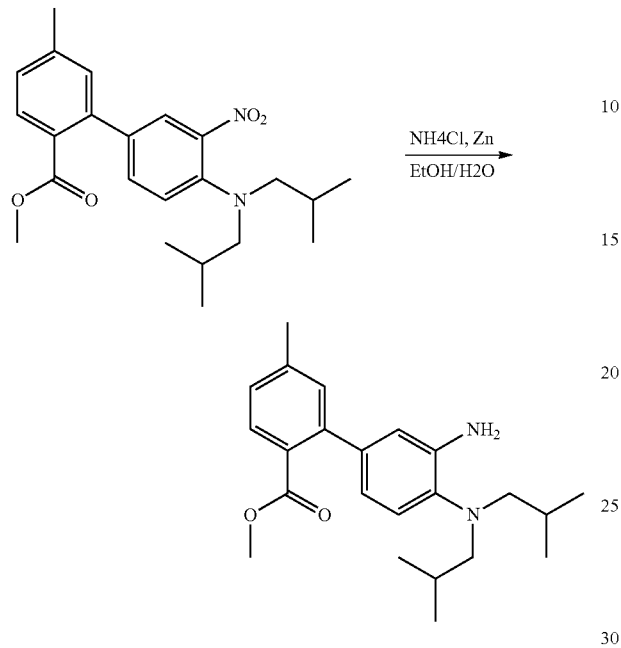

To a solution of methyl 4'-(diisobutylamino)-5-methyl-3'-nitro-[1,1'-biphenyl]-2-carboxylate (275 mg, 0.690 mmol) in ethanol (3.5 mL) and water (0.5 mL), at 0° C. under nitrogen, was added zinc (271 mg, 4.14 mmol) and ammonium chloride (221 mg, 4.14 mmol). The mixture was stirred at room temperature for 4 hours then placed in refrigerator overnight. The reaction was filtered through a pad of Celite which was then thoroughly rinsed with chloroform. The filtrate was concentrated in vacuo to afford an oily residue (313.3 mg). The crude product was purified on Isco CombiFlash System using a 12 g silica gel column. The product was eluted with a gradient of 0-100% ethyl acetate in hexanes. Evaporation of the appropriate fractions gave the desired product as an amber oil (150.1 mg). $^1$H NMR (400 MHz, CHLOROFORM-d) δ 7.69 (d, J=7.7 Hz, 1H), 7.23 (d, J=1.1 Hz, 1H), 7.21-7.15 (m, 1H), 7.08 (d, J=7.9 Hz, 1H), 6.72 (d, J=2.0 Hz, 1H), 6.65 (dd, J=8.0, 2.1 Hz, 1H), 4.24-4.16 (m, 2H), 3.62 (s, 3H), 2.68 (d, J=7.3 Hz, 4H), 2.43 (s, 3H), 1.82 (dquin, J=13.5, 6.8 Hz, 2H), 0.96 (d, J=6.6 Hz, 12H).

526. 4'-(Diisobutylamino)-3'-(3-(2-fluorophenyl)ureido)-5-methyl-[1,1'-biphenyl]-2-carboxylic acid The rest of the preparation was accomplished as in Example 519. MS(ES): m/z=492 [M+H]$^+$, HPLC T$_r$: 2.11$^k$. $^1$H NMR (500 MHz, DMSO-d$_6$) δ 9.38 (br. s., 1H), 8.16 (d, J=4.0 Hz, 1H), 8.05-7.94 (m, 1H), 7.90 (d, J=2.0 Hz, 1H), 7.58 (dd, J=7.4, 4.5 Hz, 1H), 7.30-7.09 (m, 5H), 7.08-6.99 (m, 1H), 6.97-6.87 (m, 1H), 2.73 (d, J=2.0 Hz, 4H), 2.38 (d, J=3.5 Hz, 3H), 1.79-1.64 (m, 2H), 0.96-0.81 (m, 12H).

Example 527

3'-(3-(4-Chloro-2-fluorophenyl)ureido)-4'-(diisobutylamino)-5-methyl-[1,1'-biphenyl]-2-carboxylic acid

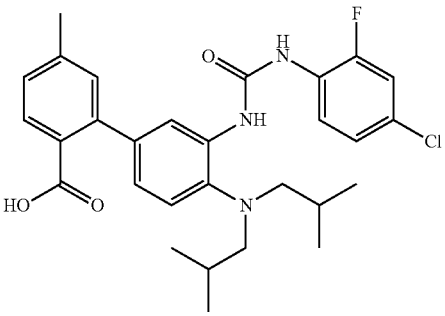 [SMILES: Cc1ccc(C(=O)O)c(-c2ccc(N(CC(C)C)CC(C)C)c(NC(=O)Nc3ccc(Cl)cc3F)c2)c1]

Example 527 was prepared using the procedures described for Example 526. MS(ES): m/z=526 [M+H]$^+$, HPLC T$_r$: 2.20$^k$.

Example 528

3'-(3-(2,4-Difluorophenyl)ureido)-4'-(diisobutylamino)-5-methyl-[1,1'-biphenyl]-2-carboxylic acid

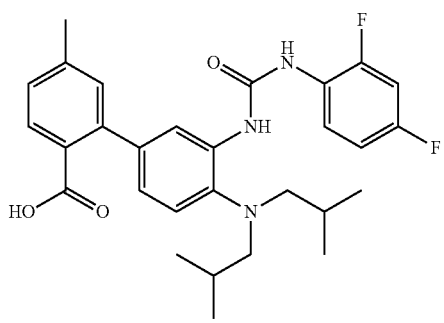 [SMILES: Cc1ccc(C(=O)O)c(-c2ccc(N(CC(C)C)CC(C)C)c(NC(=O)Nc3ccc(F)cc3F)c2)c1]

Example 528 was prepared using the procedures described for Example 526. MS(ES): m/z=510 [M+H]$^+$ HPLC T$_r$: 2.16$^k$. $^1$H NMR (500 MHz, METHANOL-d$_4$) δ 7.94 (d, J=2.0 Hz, 1H), 7.78 (td, J=8.9, 5.9 Hz, 1H), 7.66 (d, J=7.9 Hz, 1H), 7.60 (s, 1H), 7.20-7.13 (m, 2H), 7.02 (dd, J=8.4, 2.0 Hz, 1H), 6.95-6.79 (m, 2H), 2.70 (d, J=7.4 Hz, 4H), 2.40 (s, 3H), 1.78 (dquin, J=13.4, 6.7 Hz, 2H), 0.91 (d, J=6.4 Hz, 12H).

Example 529

4'-(Diisobutylamino)-3'-(3-(4-ethoxyphenyl)ureido)-5-methyl-[1,1'-biphenyl]-2-carboxylic acid

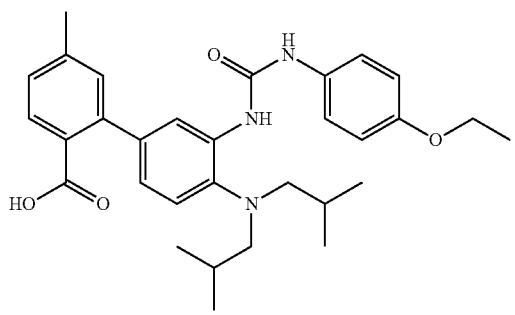 [SMILES: CCOc1ccc(NC(=O)Nc2cc(-c3cc(C)ccc3C(=O)O)ccc2N(CC(C)C)CC(C)C)cc1]

Example 529 was prepared using the procedures described for Example 526. MS(ES): m/z=518 [M+H]+, HPLC T$_r$: 2.14$^k$. $^1$H NMR (500 MHz, METHANOL-d$_4$) δ 8.02 (d, J=2.0 Hz, 1H), 7.68 (d, J=7.9 Hz, 1H), 7.60 (s, 1H), 7.29 (d, J=8.9 Hz, 2H), 7.25 (s, 1H), 7.18 (d, J=7.9 Hz, 1H), 7.15 (d, J=8.4 Hz, 1H), 6.98 (dd, J=8.4, 2.0 Hz, 1H), 6.89-6.80 (m, 2H), 4.02 (q, J=6.9 Hz, 2H), 2.64 (d, J=6.9 Hz, 4H), 2.40 (s, 3H), 1.72 (dquin, J=13.5, 6.7 Hz, 2H), 1.40 (t, J=6.9 Hz, 3H), 0.86 (d, J=6.4 Hz, 12H).

Example 530

4'-(Diisobutylamino)-5-methyl-3'-(3-(p-tolyl)ureido)-[1,1'-biphenyl]-2-carboxylic acid

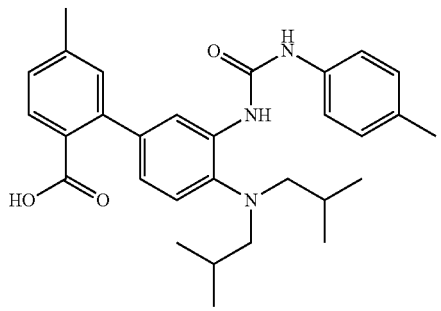 [SMILES: Cc1ccc(NC(=O)Nc2cc(-c3cc(C)ccc3C(=O)O)ccc2N(CC(C)C)CC(C)C)cc1]

Example 530 was prepared using the procedures described for Example 526. MS(ES): m/z=488 [M+H]+, HPLC T$_r$: 2.16$^k$, $^1$H NMR (500 MHz, DMSO-d$_6$) δ 9.39 (s, 1H), 8.00 (d, J=2.0 Hz, 1H), 7.90 (s, 1H), 7.58 (d, J=7.4 Hz, 1H), 7.36 (d, J=8.4 Hz, 2H), 7.22 (dd, J=7.7, 3.7 Hz, 2H), 7.18 (s, 1H), 7.09 (d, J=8.4 Hz, 2H), 6.90 (dd, J=7.9, 2.0 Hz, 1H), 2.71 (d, J=6.9 Hz, 4H), 2.38 (s, 3H), 2.25 (s, 3H), 1.70 (dquin, J=13.3, 6.6 Hz, 2H), 0.88 (d, J=6.4 Hz, 12H).

Example 531

5'-(3-(Benzo[d][1,3]dioxol-5-yl)ureido)-4'-((4,4-difluorocyclohexyl)(isobutyl)amino)-2',5-difluoro-[1,1'-biphenyl]-2-carboxylic acid

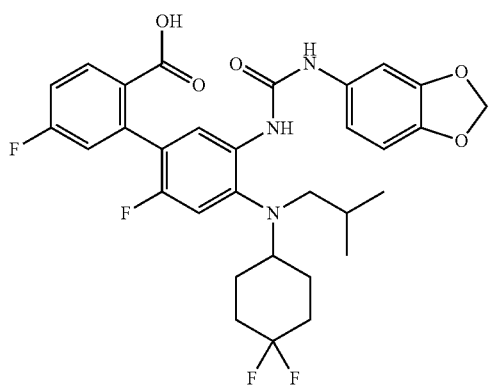 [SMILES: CC(C)CN(c1cc(F)c(-c2cc(F)ccc2C(=O)O)cc1NC(=O)Nc1ccc2c(c1)OCO2)C1CCC(F)(F)CC1]

531A. 1-(Benzo[d][1,3]dioxol-5-yl)-3-(5-bromo-2-((4,4-difluorocyclohexyl) (isobutyl)amino)-4-fluorophenyl)urea

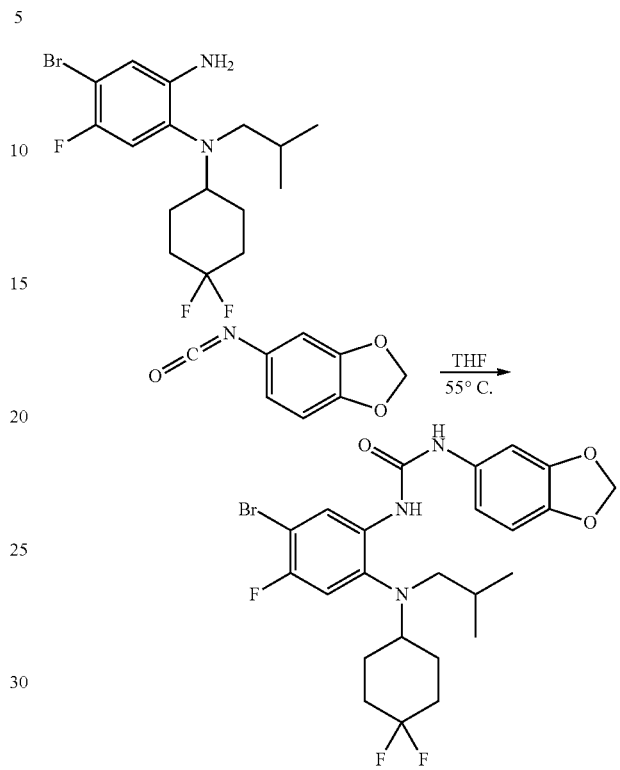

To a solution of 4-bromo-N1-(4,4-difluorocyclohexyl)-5-fluoro-N1-isobutylbenzene-1,2-diamine (60 mg, 0.158 mmol)(Intermediate 518D) in anhydrous tetrahydrofuran (1 mL) was added 3,4-(methylenedioxy)phenyl isocyanate (43.9 mg, 0.269 mmol). The tube was sealed and the resulting mixture was heated at 50° C. for 0.5 hour and then allowed to stir at room temperature overnight. The crude product was purified on an Isco CombiFlash System using a 24 g silica gel column. The product was eluted with a gradient of 0-50% ethyl acetate in hexanes. Evaporation of the appropriate fractions gave the desired product as a glass (71.2 mg). MS(ES): m/z=542 [M+H]+.

531. 5'-(3-(Benzo[d][1,3]dioxol-5-yl)ureido)-4'-(4,4-difluorocyclohexyl)(isobutyl)amino)-2',5-difluoro-[1,1'-biphenyl]-2-carboxylic acid

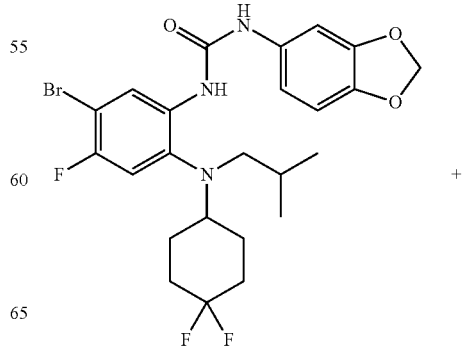

+

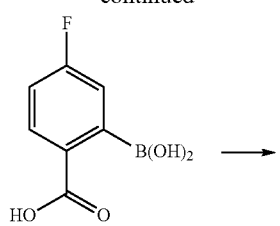

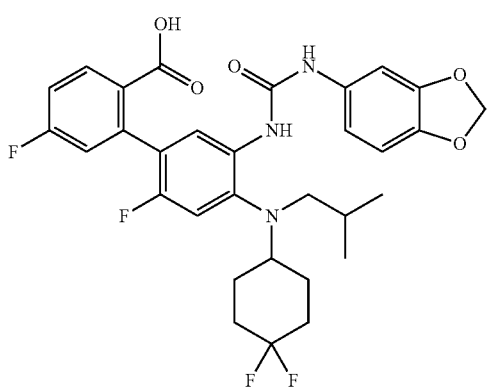

To a stirred solution of 1-(benzo[d][1,3]dioxol-5-yl)-3-(5-bromo-2-(4,4-difluorocyclohexyl)(isobutyl)amino)-4-fluorophenyl)urea (35.6 mg, 0.066 mmol) in argon-purged dimethylformamide (1 mL) was added 2-borono-4-fluorobenzoic acid (24.14 mg, 0.131 mmol), followed by potassium carbonate (0.219 mL, 0.328 mmol, 1.5 M aqueous). The reaction was purged with argon for 15 minutes and then Pd(Ph$_3$P)4 (7.58 mg, 6.56 μmol) was added. Purging with argon was continued for another 5 minutes. The vial was then capped vial and heated to 100° C. The reaction was heated for 2.25 hours then allowed to cool to room temperature. The reaction was treated with dropwise addition of glacial acetic acid until ca. pH 4, then diluted with 1.5 mL dimethylformamide. The reaction was filtered through an Acrodisc (13 mm syringe filter with 0.45 μm Nylon membrane) syringe filter. The crude material was purified via preparative LCMS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 15 minutes, then a 5-minute hold at 100% B; Flow: 20 mL/min. Fractions containing the desired product were combined and dried via centrifugal evaporation to give the final product (7.2 mg). MS(ES): m/z=602 [M+H]$^+$, HPLC T$_r$: 2.18$^k$, $^1$H NMR (500 MHz, METHANOL-d$_4$) δ 8.05 (d, J=7.9 Hz, 1H), 8.00-7.94 (m, 1H), 7.19-7.06 (m, 2H), 7.00 (s, 1H), 6.89 (d, J=11.4 Hz, 1H), 6.79-6.74 (m, 2H), 5.95 (s, 2H), 2.75 (d, J=6.4 Hz, 3H), 2.04 (br. s., 2H), 1.82-1.58 (m, 6H), 1.55-1.43 (m, 1H), 0.84 (d, J=6.4 Hz, 6H).

Example 532

1-(Benzo[d][1,3]dioxol-5-yl)-3-(4-((4,4-difluorocyclohexyl)(isobutyl)amino)-6-fluoro-2'-(1H-tetrazol-5-yl)-[1,1'-biphenyl]-3-yl)urea

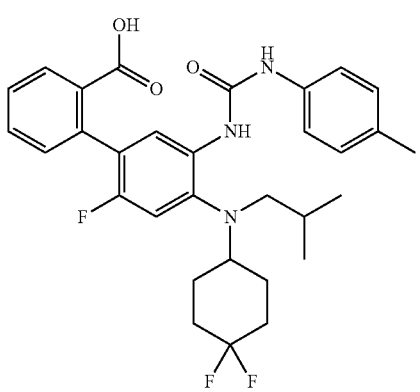 [SMILES: Cc1ccc(NC(=O)Nc2cc(-c3ccccc3C(=O)O)c(F)cc2N(CC(C)C)C2CCC(F)(F)CC2)cc1]

Example 532 was prepared using the methodology shown for Example 531. MS(ES): m/z=608 [M+H]$^+$, HPLC T$_r$: 2.07$^k$.

Example 533

4'-((4,4-Difluorocyclohexyl)(isobutyl)amino)-2'-fluoro-5'-(3-(p-tolyl)ureido)-[1,1'-biphenyl]-2-carboxylic acid Example 533 was prepared using the methodology shown for Example 531. MS(ES): m/z=554 [M+H]$^+$, HPLC T$_r$: 2.26$^k$, $^1$H NMR (500 MHz, METHANOL-d$_4$) δ 8.08-8.02 (m, 1H), 7.93 (d, J=7.9 Hz, 1H), 7.58-7.53 (m, 1H), 7.48-7.40 (m, 2H), 7.28 (d, J=8.4 Hz, 2H), 7.14 (d, J=8.4 Hz, 2H), 6.88 (d, J=10.9 Hz, 1H), 2.75 (d, J=5.9 Hz, 3H), 2.32 (s, 3H), 2.09-1.99 (m, 2H), 1.81-1.56 (m, 6H), 1.50 (dquin, J=13.4, 6.7 Hz, 1H), 0.85 (d, J=6.4 Hz, 6H).

Example 534

1-(4-((4,4-Difluorocyclohexyl)(isobutyl)amino)-6-fluoro-2'-(1H-tetrazol-5-yl)-[1,1'-biphenyl]-3-yl)-3-(p-tolyl)urea

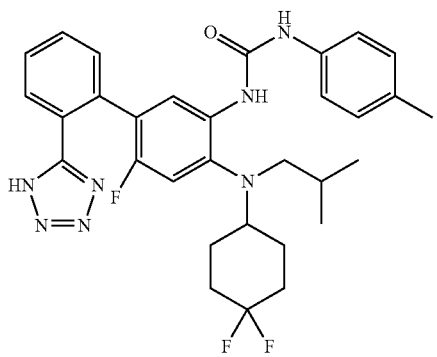 [SMILES: Cc1ccc(NC(=O)Nc2cc(-c3ccccc3-c3nnn[nH]3)c(F)cc2N(CC(C)C)C2CCC(F)(F)CC2)cc1]

Example 534 was prepared using the methodology shown for Example 531. MS(ES): m/z=578 [M+H]$^+$, HPLC T$_r$: 2.23$^k$, $^1$H NMR (500 MHz, METHANOL-d$_4$) δ 7.86 (d, J=7.9 Hz, 1H), 7.79 (d, J=7.4 Hz, 1H), 7.68-7.62 (m, 1H), 7.60-7.56 (m, 1H), 7.55-7.49 (m, 1H), 7.30 (d, J=7.9 Hz, 2H), 7.14 (d, J=8.4 Hz, 2H), 6.74 (d, J=11.4 Hz, 1H), 2.83-2.68 (m, 3H), 2.32 (s, 3H), 2.11-2.01 (m, 2H), 1.81-1.57 (m, 6H), 1.46 (dquin, J=13.4, 6.7 Hz, 1H), 0.84 (d, J=6.4 Hz, 6H).

Example 535

4'-(Diisobutylamino)-3-methyl-3'-(3-(3-methylisoxazol-5-yl)ureido)-[1,1'-biphenyl]-2-carboxylic acid

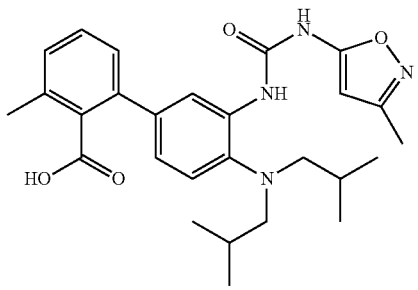 [SMILES: Cc1cc(NC(=O)Nc2cc(-c3cccc(C)c3C(=O)O)ccc2N(CC(C)C)CC(C)C)on1]

535A. Methyl 4'-(diisobutylamino)-3-methyl-3'-nitro-[1,1'-biphenyl]-2-carboxylate

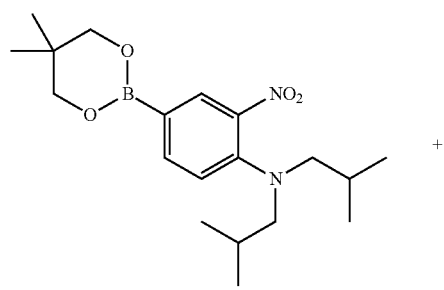

+

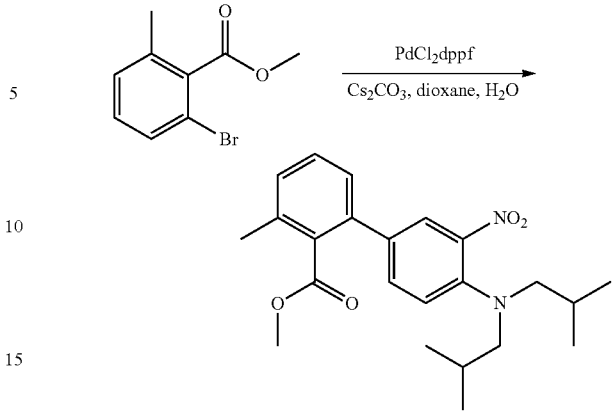

A scintillation vial was charged with 4-(5,5-dimethyl-1,3,2-dioxaborinan-2-yl)-N,N-diisobutyl-2-nitroaniline (300 mg, 0.828 mmol) (intermediate 526A) and methyl 2-bromo-6-methylbenzoate (158 mg, 0.690 mmol). Dioxane (3.00 mL) and water (1 mL) were then added. To this mixture was added cesium carbonate (675 mg, 2.070 mmol) and the resulting mixture was purged with argon for 15-20 min. To the reaction mixture was then added PdCl$_2$(dppf)-CH2Cl2 adduct (56.4 mg, 0.069 mmol). The reaction mixture was purged with argon for 5 minutes more when the vial was sealed and warmed to 100° C. After stirring overnight, the cooled reaction mixture was partitioned between ethyl acetate and water. The layers were separated and the aqueous layer was extracted twice more with ethyl acetate. The combined organic extracts were washed with water and then brine. The organic layer was dried over sodium sulfate filtered and concentrated in vacuo to afford a dark brown oil (428.0 mg). The crude product was purified on Isco CombiFlash System using a 24 g silica gel column. The product was eluted with a gradient of 0-100% ethyl acetate in hexanes. Evaporation of the appropriate fractions gave the desired product as an orange oil (244.2 mg). $^1$H NMR (400 MHz, CHLOROFORM-d) δ 7.78 (d, J=2.4 Hz, 1H), 7.46-7.34 (m, 2H), 7.24 (dd, J=7.4, 5.0 Hz, 2H), 7.15 (d, J=8.6 Hz, 1H), 3.69 (s, 3H), 2.99 (d, J=7.3 Hz, 4H), 2.42 (s, 3H), 1.97 (dquin, J=13.5, 6.8 Hz, 2H), 0.89 (d, J=6.6 Hz, 12H).

535B. Methyl 3'-amino-4'-(diisobutylamino)-3-methyl-[1,1'-biphenyl]-2-carboxylate

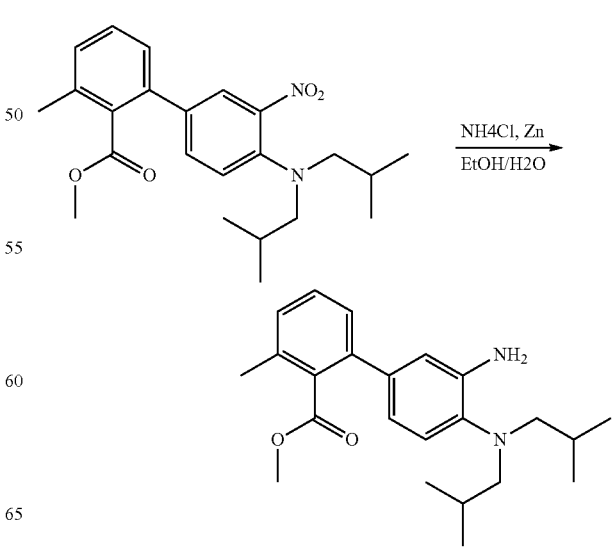

To a solution of methyl 4'-(diisobutylamino)-3-methyl-3'-nitro-[1,1'-biphenyl]-2-carboxylate (230.9 mg, 0.579 mmol) in ethanol (4.90 mL) and water (0.7 mL) under nitrogen, was added ammonium chloride (310 mg, 5.79 mmol). The mixture was stirred at room temperature for 10 min before zinc (379 mg, 5.79 mmol) was added. The reaction was stirred for 2 hours. The reaction was diluted with methylene chloride and filtered through a pad of Celite. The filtrate was concentrated in vacuo to afford an oily residue (206.7 mg). MS(ES): m/z=369 [M+H]+.

535C. Methyl 4'-(diisobutylamino)-3-methyl-3'-(3-(3-methylisoxazol-5-yl)ureido)-[1,1'-biphenyl]-2-carboxylate

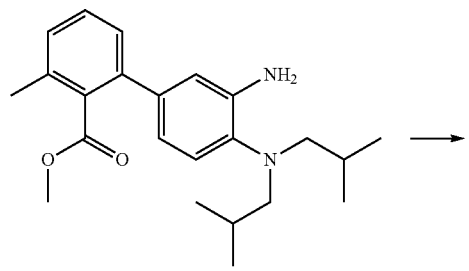

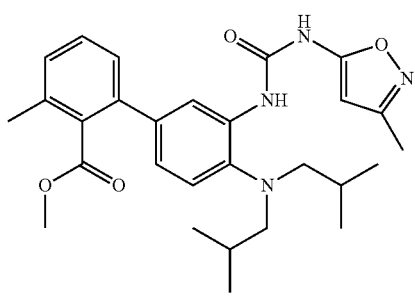

To a solution of methyl 3'-amino-4'-(diisobutylamino)-3-methyl-[1,1'-biphenyl]-2-carboxylate (34.4 mg, 0.093 mmol) in anhydrous tetrahydrofuran (2 mL) was treated with 4-nitrophenyl chloroformate (20.70 mg, 0.103 mmol). The mixture was stirred for ca. 2 hours. 5-Amino-3-methylisoxazole (73.3 mg, 0.747 mmol) and triethylamine (0.23 mL, 1.650 mmol) were added and the reaction warmed to 50° C. After stirring overnight, the reaction was partitioned between water and ethyl acetate. The layers were separated and the aqueous layer was then extracted twice with ethyl acetate. These combined organic extracts were washed with brine. The organic layer was then concentrated in vacuo. The crude product was purified on an Isco CombiFlash System using a 12 g silica gel column. The product was eluted with a gradient of 0-100% ethyl acetate in hexanes. Evaporation of the appropriate fractions gave the desired product as a yellow solid (14.8 mg). MS(ES): m/z=493 [M+H]+.

535. 4'-(Diisobutylamino)-3-methyl-3'-(3-(3-methylisoxazol-5-yl)ureido)-[1,1'-biphenyl]-2-carboxylic acid

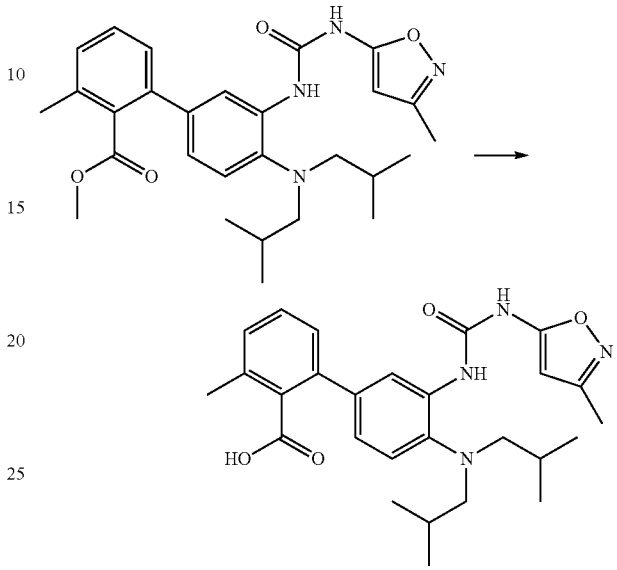

To a homogeneous mixture of methyl 4'-(diisobutylamino)-3-methyl-3'-(3-(3-methylisoxazol-5-yl)ureido)-[1,1'-biphenyl]-2-carboxylate (14.8 mg, 0.030 mmol) in tetrahydrofuran (1 mL) methanol (1 mL) and water (0.5 mL) was added lithium hydroxide (7.20 mg, 0.300 mmol). The mixture was stirred at room temperature for a day. More lithium hydroxide (7.20 mg, 0.300 mmol) and water (0.5 mL) were added. The reaction was stirred for 3 days when the temperature was raised to 40° C. After ca. 5 hours, sodium hydroxide solution (0.060 mL, 0.300 mmol, 5 M) was added and the reaction heated at 50° C. After 4 hours, the reaction was allowed to cool to room temperature. The next morning the reaction was warmed to 70° C. and stirred for 5 days. The reaction was allowed to stand for 16 days when LCMS analysis suggested the presence of some of the desired product. The reaction mixture was treated with glacial acetic acid until ca. pH 4. The acidified reaction mixture was diluted with 1.5 mL dimethylformamide before being filtered through an Acrodisc (13 mm syringe filter with 0.45 µm Nylon membrane) syringe filter. The crude material was purified via preparative LCMS with the following conditions: Column: Waters XBridge C18, 19×150 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 15 minutes, then a 5-minute hold at 100% B; Flow: 20 mL/min. Fractions containing the desired product were combined and dried via centrifugal evaporation to give 0.8 mg of the desired product. MS(ES): m/z=479 [M+H]+, HPLC $T_r$: 1.74$^k$.

Example 536

4'-(Diisobutylamino)-3-methyl-3'-(3-(p-tolyl)ureido)-[1,1'-biphenyl]-2-carboxylic acid

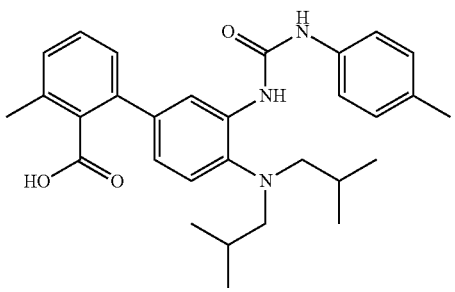

To a solution of 4-(5,5-dimethyl-1,3,2-dioxaborinan-2-yl)-N1,N1-diisobutylbenzene-1,2-diamine (80 mg, 0.241 mmol) (Intermediate 4B) in anhydrous tetrahydrofuran (2.5 mL) was added 1-isocyanato-4-methylbenzene (54.5 mg, 0.409 mmol). The tube was sealed and the resulting mixture was stirred at 50° C. The reaction was heated overnight. The reaction was then cooled and the crude product was purified on an Isco CombiFlash System using a 12 g silica gel column. The product was eluted with a gradient of 0-100% ethyl acetate in hexanes. Evaporation of the appropriate fractions gave the desired product which was dried under vacuum overnight (107.4 mg). LCMS suggests presence of boronic acid (MS(ES): m/z=479 [M+H]$^+$). A portion of this material 1-(2-(diisobutylamino)-5-(5,5-dimethyl-1,3,2-dioxaborinan-2-yl)phenyl)-3-(p-tolyl)urea (26.8 mg, 0.058 mmol) was dissolved in argon-purged dimethylformamide (1 mL). 2-Bromo-6-methylbenzoic acid (24.76 mg, 0.115 mmol) was added followed by potassium carbonate (0.192 mL, 0.288 mmol, 1.5 M aqueous). Purging with argon was continued for 15 minutes when Pd(Ph$_3$P)4 (6.65 mg, 5.76 μmol) was added. The reaction was purged with argon for 5 minutes, capped, and heated to 100° C. The reaction was heated for 4 hours and then allowed to cool to room temperature. The reaction was treated with a dropwise addition of glacial acetic acid until ca. pH 4, then diluted with dimethylformamide (1.5 mL). The reaction was passed through an Acrodisc (13 mm syringe filter with 0.45 μm Nylon membrane) syringe filter. The crude material was purified via preparative LCMS with the following conditions: Column: Waters XBridge C18, 19×250 mm, 5 μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation to give 0.8 mg of the desired product. MS(ES): m/z=488 [M+H]$^+$, HPLC T$_r$: 2.13$^k$, $^1$H NMR (500 MHz, METHANOL-d$_4$) δ 8.04 (s, 1H), 7.33-7.25 (m, 4H), 7.22-7.15 (m, 2H), 7.14-7.05 (m, 3H), 2.65 (d, J=7.4 Hz, 4H), 2.42 (s, 3H), 2.30 (s, 3H), 1.73 (dquin, J=13.4, 6.7 Hz, 2H), 0.87 (d, J=6.4 Hz, 12H).

Example 537

1-(4-((4,4-Difluorocyclohexyl)(isobutyl)amino)-6-fluoro-2'-(1H-tetrazol-5-yl)-[1,1'-biphenyl]-3-yl)-3-(2-fluorophenyl)urea

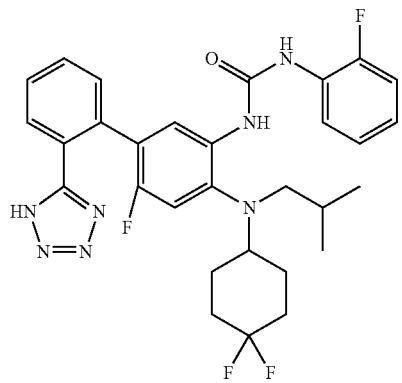 [SMILES: CC(C)CN(c1cc(F)c(-c2ccccc2-c2nnn[nH]2)cc1NC(=O)Nc1ccccc1F)C1CCC(F)(F)CC1]

Example 537 was prepared using the procedures described for Example 531. MS(ES): m/z=582 [M+H]$^+$, HPLC T$_r$: 2.18$^k$.

Example 538

4'-((4,4-Difluorocyclohexyl)(isobutyl)amino)-2',5-difluoro-5'-(3-(2-fluorophenyl)ureido)-[1,1'-biphenyl]-2-carboxylic acid

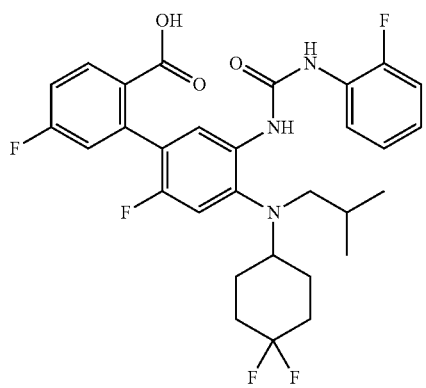 [SMILES: CC(C)CN(c1cc(F)c(-c2cc(F)ccc2C(=O)O)cc1NC(=O)Nc1ccccc1F)C1CCC(F)(F)CC1]

Example 538 was prepared using the procedures described for Example 531. MS(ES): m/z=576 [M+H]$^+$, HPLC T$_r$: 1.93$^k$.

Example 539

1-(4-((4,4-Difluorocyclohexyl)(isobutyl)amino)-6-fluoro-2'-(1H-tetrazol-5-yl)-[1,1'-biphenyl]-3-yl)-3-(4-ethoxyphenyl)urea

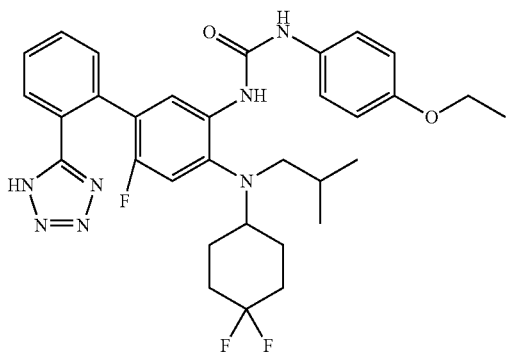 [SMILES: CCOc1ccc(NC(=O)Nc2cc(-c3ccccc3-c3nnn[nH]3)c(F)cc2N(CC(C)C)C2CCC(F)(F)CC2)cc1]

Example 539 was prepared using the procedures described for Example 531. MS(ES): m/z=608 [M+H]+, HPLC T$_r$: 1.88$^k$.

Example 540

4'-(4,4-Difluorocyclohexyl)(isobutyl)amino)-5'-(3-(4-ethoxyphenyl)ureido)-2',5-difluoro-[1,1'-biphenyl]-2-carboxylic acid

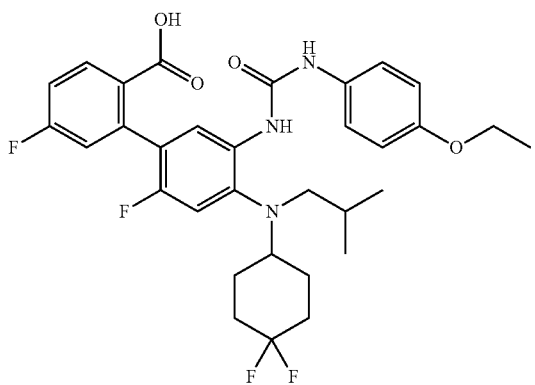 [SMILES: CCOc1ccc(NC(=O)Nc2cc(-c3cc(F)ccc3C(=O)O)c(F)cc2N(CC(C)C)C2CCC(F)(F)CC2)cc1]

Example 540 was prepared using the procedures described for Example 531. MS(ES): m/z=602 [M+H]+, HPLC T$_r$: 1.96$^k$.

Example 541

4'-(Dicyclopropylamino)-5-fluoro-3'-(3-(p-tolyl)ureido)-[1,1'-biphenyl]-2-carboxylic acid

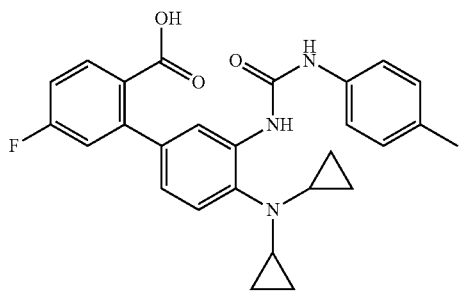 [SMILES: Cc1ccc(NC(=O)Nc2cc(-c3cc(F)ccc3C(=O)O)ccc2N(C2CC2)C2CC2)cc1]

541A. 1-(5-Bromo-2-(dicyclopropylamino)phenyl)-3-(p-tolyl)urea

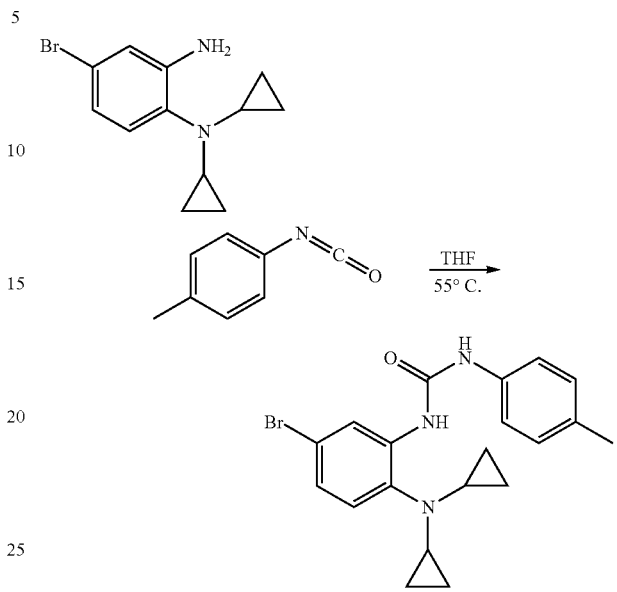

To a solution of 4-bromo-N1,N1-dicyclopropylbenzene-1,2-diamine (30 mg, 0.112 mmol) (Intermediate 509B) in anhydrous tetrahydrofuran (1 mL), in a sealable tube, was added 1-isocyanato-4-methylbenzene (0.024 mL, 0.191 mmol). The tube was sealed and the resulting mixture was heated at 50° C. The reaction was heated for ca. 1.5 hour. The reaction was quenched with water then partitioned between ethyl acetate and brine. The layers were separated and the aqueous layer extracted twice more with ethyl acetate. The organic extracts were combined and concentrated in vacuo to afford a tan solid (60.8 mg). LCMS suggests the presence of the desired product and N,N'-ditoluylurea. Use this material directly in the next transformation.

541. 4'-(Dicyclopropylamino)-5-fluoro-3'-(3-(p-tolyl)ureido)-[1,1'-biphenyl]-2-carboxylic acid

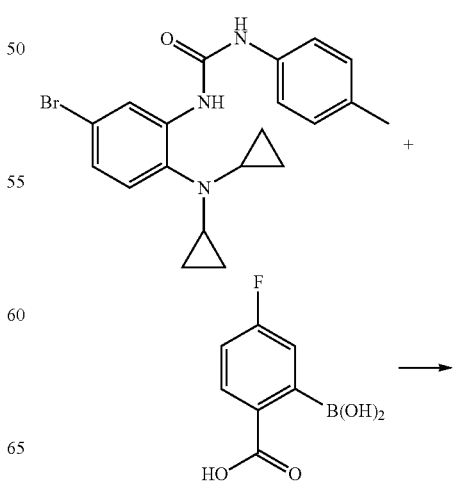

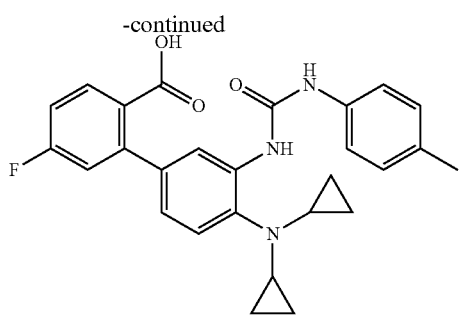

To a stirred solution of 1-(5-bromo-2-(dicyclopropylamino)phenyl)-3-(p-tolyl)urea (22.5 mg, 0.056 mmol) in argon-purged dimethylformamide (1 mL) was added 2-borono-4-fluorobenzoic acid (20.68 mg, 0.112 mmol), followed by an aqueous solution of potassium carbonate (0.187 mL, 0.281 mmol, 1.5 M). The reaction was purged with argon for 15 minutes then Pd(Ph₃P)4 (6.49 mg, 5.62 µmol) was added. Purging with argon was continued for another 5 minutes when the vial was capped and heated to 100° C. Heating was continued for 6 hours when the reaction was allowed to cool to room temperature. After 3 days, the reaction was treated with the dropwise addition of glacial acetic acid until ca. pH 4. The reaction was then diluted with 1.5 mL dimethylformamide and filtered through an Acrodisc (13 mm syringe filter with 0.45 µm Nylon membrane) syringe filter. The crude material was purified via preparative LCMS with the following conditions: Column: Waters XBridge C18, 19×250 mm, 5 µm particles; Guard Column: Waters XBridge C18, 19×10 mm, 5 µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of the product was 3.3 mg. MS(ES): m/z=460 [M+H]⁺, HPLC T$_r$: 2.17$^k$, ¹H NMR (500 MHz, METHANOL-d₄) δ 8.11 (d, J=2.0 Hz, 1H), 7.80 (dd, J=8.4, 5.9 Hz, 1H), 7.27 (dd, J=7.9, 3.0 Hz, 3H), 7.16 (dd, J=9.9, 2.5 Hz, 1H), 7.13 (d, J=8.4 Hz, 2H), 7.07 (td, J=8.4, 2.5 Hz, 1H), 7.01 (dd, J=8.4, 2.0 Hz, 1H), 2.62-2.53 (m, 2H), 2.32 (s, 3H), 0.49 (d, J=5.9 Hz, 4H), 0.39 (br. s., 4H).

Using the methods described herein, the following additional compounds of the invention were prepared.

| Example No. | Compound | HPLC T$_r$ | (M + H)⁺ |
|---|---|---|---|
| 542 | 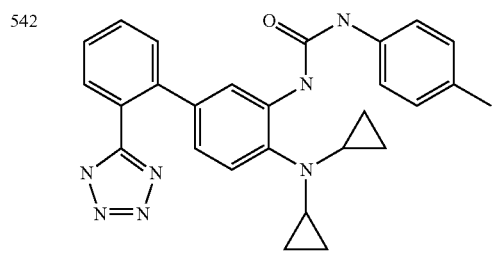 | | |
| 543 | 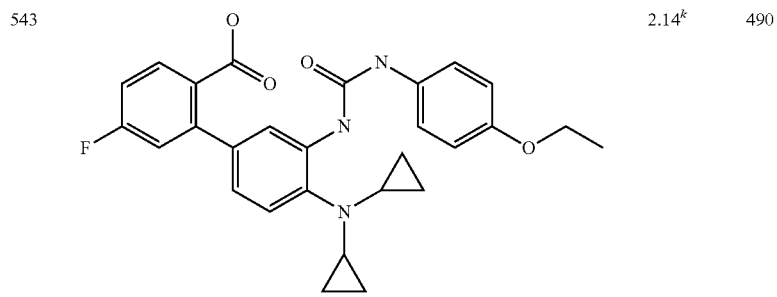 | 2.14$^k$ | 490 |
| 544 | 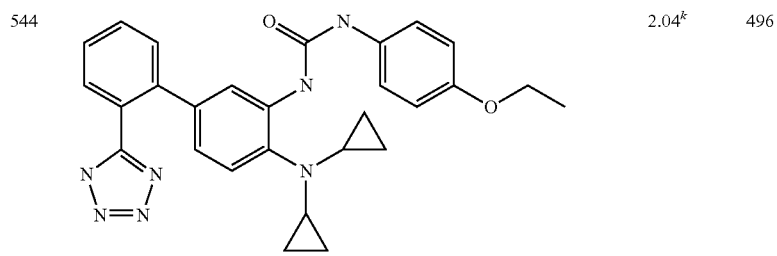 | 2.04$^k$ | 496 |

-continued

| Example No. | Compound | HPLC T$_r$ | (M + H)$^+$ |
|---|---|---|---|
| 545 | [structure] | 2.15$^k$ | 518 |

EVALUATION OF BIOLOGICAL ACTIVITY

Exemplary compounds were tested for inhibition of IDO activity. Experimental procedures and results are provided below.

IDO Kynurenine Assay with Human IDO1/HEK293 Cells

Human IDO1/HEK293 cells were seeded at 10,000 cells per 50 uL per well with RPMI/phenol red free media contains 10% FBS in a 384-well black wall clear bottom tissue culture plate (Matrix Technologies LLC) 125 nL of certain concentration of compound was then added to each well using ECHO liquid handling systems. The cells were incubated for 20 hours in 37° C. incubator with 5% $CO_2$.

The compound treatments were stopped by adding Trichloroacetic Acid (Sigma-Aldrich) to a final concentration at 0.2%. The cell plate was further incubated at 50° C. for 30 minute. The equal volume supernatant (20 uL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound $IC_{50}$ values were calculated using the counts of 500 nM of a reference standard treatment as one hundred percent inhibition, and counts of no compound but DMSO treatment as zero percent inhibition.

Reagents:
Hela cells (ATCC, CCL-2)
IFNg (R&D, 28-IF-100)—resuspend at 10 ug/mL in PBS with 0.1% BSA 30% TCA
Ehrlich reagent (2% w/v p-dimethylaminobenzaldehyde in glacial acetic acid)
Cell Titer 96 Aqueous Non-Radioactive Cell Proliferation Assay, MTS (Promega, Cat # G5430)
Cell Lines and Culture Conditions Hela cancer cell lines were acquired from the American Type Culture Collection. Cells were maintained in phenol red free-RPMI1640 medium containing high glucose and L-glutamine (Invitrogen) supplemented with 10% fetal bovine serum (FBS; Invitrogen). Cell cultures were incubated at 37° C., 5% $CO_2$, and 100% humidity.

Cell Treatment and Kynurenine Assay

Hela cells were seeded on 96-well plates (40,000 cells per well) and allowed to adhere for 5-6 hours. Cells were then treated with vehicle (DMSO) or with IDO inhibitor at a top dose of 30 μM (3-fold dilution all the way down to 1.5 nM). A final concentration of 100 ng/mL of human recombinant IFN-γ (R&D, 28-IF-100) was immediately added to the cells to stimulate IDO expression. Treated cells were then incubated for 20 hours at 37° C. At the end of the 20 h incubation, reactions were terminated by the addition of 30% TCA to each well. Plates were incubated for 30 minutes at 50° C. to hydrolyze N-formylkynurenine to kynurenine. Cells were centrifuged 10 minutes at 2400 rpm. 100 ul of supernatants were transferred to new 96 flat well plates and mixed with 100 ul Ehrlich reagent. The resulting solution was incubated 10 minutes at RT. Absorbance at 490 nM was read using Spectra Max 384 (Molecular Devices).

Results of the IDO assays are shown in the table below.

| Ex. No. | HEK human IDO-1 (IC50, uM) | Hela Kyurenine (IC50, uM) | LLE_IDO_ABS_DR (IC50, uM) |
|---|---|---|---|
| 1 | 3.31E−03 | 1.37E−03 | 3.45E−03 |
| 2 | | 0.02 | 0.09 |
| 3 | | 0.01 | 0.06 |
| 4 | | | 0.08 |
| 5 | | | 4.05E−03 |
| 6 | | | 6.47E−03 |
| 7 | | | 0.02 |
| 8 | | | 0.18 |
| 9 | | | 0.35 |
| 10 | | | 0.10 |
| 11 | | | 0.25 |
| 12 | | | 0.22 |
| 13 | 0.06 | | 0.03 |
| 14 | 0.10 | | 0.08 |
| 15 | | | 0.09 |
| 16 | 0.02 | | 0.01 |
| 17 | | | 0.27 |
| 18 | | | 0.63 |
| 19 | 0.04 | | 0.02 |
| 20 | | | 0.13 |
| 21 | | | 0.15 |
| 22 | | | 0.03 |
| 23 | | | 0.45 |
| 24 | | | 0.01 |
| 25 | | | 0.03 |
| 26 | | | 0.37 |
| 27 | | | 2.55E−03 |
| 28 | | | 0.01 |
| 29 | | | 4.76E−03 |
| 30 | | | 5.19E−03 |
| 31 | | | 5.18E−03 |
| 32 | | | 2.54E−03 |
| 33 | | | 4.99E−03 |
| 34 | | | 4.01E−03 |
| 35 | | | 0.01 |
| 36 | | | 5.90E−03 |
| 37 | | 0.01 | 0.04 |
| 38 | 1.78E−03 | | 1.84E−03 |
| 39 | 2.37E−03 | | 1.00E−03 |
| 40 | 0.01 | | 3.79E−03 |
| 41 | 6.31E−03 | | 1.78E−03 |
| 42 | | 1.17 | |
| 43 | | 1.43 | |

| Ex. No. | HEK human IDO-1 (IC50, uM) | Hela Kyurenine (IC50, uM) | LLE_IDO_ABS_DR (IC50, uM) |
|---|---|---|---|
| 44 | | 1.72E−03 | 7.93E−03 |
| 45 | | 0.01 | 0.06 |
| 46 | | 0.09 | 0.13 |
| 47 | | 0.01 | 0.04 |
| 48 | | 0.85 | 0.50 |
| 49 | | 0.18 | 0.16 |
| 50 | | 0.06 | 0.31 |
| 51 | | 2.13 | |
| 52 | | 5.57E−03 | 0.01 |
| 53 | | 7.72E−04 | 3.45E−03 |
| 54 | | 0.08 | 0.30 |
| 55 | | 0.11 | 0.23 |
| 56 | | 3.12 | 3.59 |
| 57 | | 0.22 | 0.27 |
| 58 | | 0.06 | 0.10 |
| 59 | | 0.01 | 0.02 |
| 60 | | 0.14 | 0.14 |
| 61 | | 0.70 | 0.51 |
| 62 | | 2.28 | 4.12 |
| 63 | | | 0.12 |
| 64 | | | 0.29 |
| 65 | | | 3.70 |
| 66 | | | 0.03 |
| 67 | | | 0.35 |
| 68 | | | 0.56 |
| 69 | | | 0.89 |
| 70 | | | 0.11 |
| 71 | | | 1.74 |
| 72 | | | 0.85 |
| 73 | | | 0.15 |
| 74 | | | 5.77 |
| 75 | | | 3.24E−03 |
| 76 | | | 0.02 |
| 77 | | | 3.26 |
| 78 | | | 1.92 |
| 79 | | | 1.81E−03 |
| 80 | | | 8.75E−03 |
| 81 | | | 0.27 |
| 82 | | | 0.0038 |
| 83 | | | 0.02 |
| 84 | | | 2.11 |
| 85 | | | 1.65E−03 |
| 86 | | | 4.16E−03 |
| 87 | | | 3.68E−03 |
| 88 | | | 9.82E−03 |
| 89 | | | 0.05 |
| 90 | | | 0.01 |
| 91 | | | 0.06 |
| 92 | | | 0.02 |
| 93 | | | 0.08 |
| 94 | | | 9.24E−03 |
| 95 | | | 0.20 |
| 96 | | | 1.18 |
| 97 | | | 4.64 |
| 98 | | | 0.03 |
| 99 | | | 0.09 |
| 100 | | | 0.09 |
| 101 | | | 0.01 |
| 102 | | | 0.21 |
| 103 | | | 1.76 |
| 104 | | | 0.10 |
| 105 | | | 0.19 |
| 106 | | | 8.81E−03 |
| 107 | | | 1.86 |
| 108 | | | 0.25 |
| 109 | | | 0.41 |
| 110 | | | 0.04 |
| 111 | | | 0.21 |
| 112 | | | 0.03 |
| 113 | | | 0.40 |
| 114 | | | 0.16 |
| 115 | | | 0.35 |
| 116 | | | 2.34 |
| 117 | | | 0.01 |
| 118 | | | 4.76E−03 |
| 119 | | | 5.19E−03 |
| 120 | | | 0.03 |
| 121 | | | 2.59E−03 |
| 122 | | | 3.47E−03 |
| 123 | | | 0.02 |
| 124 | | | 5.18E−03 |
| 125 | | | 5.92E−03 |
| 126 | 0.01 | | 0.02 |
| 127 | 0.08 | | 0.13 |
| 128 | | | 0.39 |
| 129 | | | 9.53E−03 |
| 130 | | | 0.04 |
| 131 | | | 0.05 |
| 132 | | | 0.05 |
| 133 | | | 6.45E−03 |
| 134 | | | 0.03 |
| 135 | | | 0.02 |
| 136 | | | 0.07 |
| 137 | | | 5.24E−03 |
| 138 | | | 6.24E−03 |
| 139 | | | 1.98 |
| 140 | | | 2.96 |
| 141 | | | 0.43 |
| 142 | | | 0.95 |
| 143 | | | 0.15 |
| 144 | | | 0.01 |
| 145 | | | 0.08 |
| 146 | | | 0.01 |
| 147 | | | 0.01 |
| 148 | | | 0.04 |
| 149 | | | 0.06 |
| 150 | 0.06 | | 0.04 |
| 151 | | | 4.62 |
| 152 | | | 0.77 |
| 153 | | | 5.16E−03 |
| 154 | | | 0.03 |
| 155 | | | 0.04 |
| 156 | | | 7.45E−03 |
| 157 | | | 0.02 |
| 158 | | | 0.03 |
| 159 | | | 0.98 |
| 160 | | | 0.19 |
| 161 | | | 0.24 |
| 162 | | | 1.27 |
| 163 | | | 1.03 |
| 164 | | | 5.40E−03 |
| 165 | | | 0.01 |
| 166 | | | 0.02 |
| 167 | | | 0.04 |
| 168 | | | 0.03 |
| 169 | | | 4.55E−03 |
| 170 | | | 5.68E−03 |
| 171 | | | 0.02 |
| 172 | | | 0.01 |
| 173 | | | 0.01 |
| 174 | | | 9.92E−03 |
| 175 | | | 4.36E−03 |
| 176 | | | 7.86E−03 |
| 177 | | | 9.59E−03 |
| 178 | | | 5.49E−03 |
| 179 | | | 0.05 |
| 180 | | | 0.23 |
| 181 | | | 0.27 |
| 182 | | | 0.05 |
| 183 | | | 0.02 |
| 184 | | | 0.01 |
| 185 | | | 2.63E−03 |
| 186 | | | 0.03 |
| 187 | | | 0.02 |
| 188 | | | 0.29 |
| 189 | | | 0.48 |
| 190 | | | 0.08 |
| 191 | | | 5.79E−03 |
| 192 | | | 7.82E−03 |
| 193 | 0.07 | | 0.03 |
| 194 | | | 4.74E−03 |
| 195 | | | 4.79E−03 |

-continued

| Ex. No. | HEK human IDO-1 (IC50, uM) | Hela Kyurenine (IC50, uM) | LLE_IDO_ABS_DR (IC50, uM) |
|---|---|---|---|
| 196 | | | 0.02 |
| 197 | | | 0.01 |
| 198 | | | 0.21 |
| 199 | | | 0.06 |
| 200 | | | 0.11 |
| 201 | | | 4.46E-03 |
| 202 | | | 0.01 |
| 203 | | | 7.31E-03 |
| 204 | | | 5.26E-03 |
| 205 | | | 0.02 |
| 206 | | | 0.60 |
| 207 | | | 0.13 |
| 208 | | | 0.05 |
| 209 | | | 0.56 |
| 210 | | | 0.21 |
| 211 | | 0.11 | 0.49 |
| 212 | | 0.20 | 1.27 |
| 213 | | 6.56E-03 | 0.01 |
| 214 | | 1.07E-03 | 2.36E-03 |
| 215 | | 0.12 | 1.28 |
| 216 | | 8.31E-04 | 8.35E-04 |
| 217 | | 0.01 | 0.06 |
| 218 | | 0.09 | 0.49 |
| 219 | | 0.01 | 0.08 |
| 220 | | 0.44 | 1.47 |
| 221 | | 6.56E-03 | 9.05E-03 |
| 222 | | 2.63E-03 | 0.01 |
| 223 | | 0.16 | 0.42 |
| 224 | | 0.44 | 0.64 |
| 225 | | | 2.52E-03 |
| 226 | | | 2.67E-03 |
| 227 | | | 2.91E-03 |
| 228 | | | 1.74E-03 |
| 229 | | | 2.56E-03 |
| 230 | | | 2.14E-03 |
| 231 | 2.13E-03 | | 2.73E-03 |
| 232 | | | 0.66 |
| 233 | | | 0.81 |
| 234 | | | 9.37 |
| 235 | | | 0.79 |
| 236 | | | 2.14 |
| 237 | | | 1.29 |
| 238 | | | 0.75 |
| 239 | | | 3.86 |
| 240 | | | 2.23 |
| 241 | | | 0.02 |
| 242 | | | 4.72E-03 |
| 243 | | | 7.60E-04 |
| 244 | | | 9.30E-03 |
| 245 | | | 0.18 |
| 246 | | | 1.22 |
| 247 | | | 2.76 |
| 248 | | | 5.07 |
| 249 | | | 0.14 |
| 250 | | | 0.93 |
| 251 | | | 0.09 |
| 252 | | | 1.23 |
| 253 | | | 2.49 |
| 254 | | | 6.07 |
| 255 | | | 0.03 |
| 256 | | | 4.18 |
| 257 | | | 2.73E-03 |
| 258 | | | 0.09 |
| 259 | | | 2.44E-03 |
| 260 | | | 6.48E-03 |
| 261 | | | 4.31 |
| 262 | | | 0.19 |
| 263 | | | 7.97E-03 |
| 264 | | | 2.61E-03 |
| 266 | | | 4.49 |
| 267 | | | 1.46 |
| 268 | | | 0.83 |
| 269 | | | 0.25 |
| 270 | | | 1.83 |
| 271 | | | 1.01 |
| 272 | | | 2.72 |

-continued

| Ex. No. | HEK human IDO-1 (IC50, uM) | Hela Kyurenine (IC50, uM) | LLE_IDO_ABS_DR (IC50, uM) |
|---|---|---|---|
| 273 | | | 0.18 |
| 274 | | | 0.46 |
| 275 | | | 0.50 |
| 276 | | | 0.78 |
| 277 | | | 0.16 |
| 278 | | | 1.31E-03 |
| 279 | | | 5.05 |
| 280 | | | 2.39 |
| 281 | | | 1.45 |
| 282 | | | 8.20E-03 |
| 283 | | | 0.01 |
| 284 | | | 2.09 |
| 285 | | | 2.28E-03 |
| 286 | | | 0.11 |
| 287 | | | 4.47E-03 |
| 288 | | | 9.12 |
| 289 | | | 1.21 |
| 290 | 0.05 | | 0.03 |
| 291 | 1.83 | | 0.09 |
| 292 | | | 4.03E-03 |
| 295 | | | 0.30 |
| 296 | | | 0.18 |
| 297 | | | 0.01 |
| 298 | | | 0.08 |
| 299 | 0.05 | | 0.02 |
| 300 | | | 0.18 |
| 301 | 7.87E-03 | | 2.85E-03 |
| 302 | 5.53E-03 | | 3.26E-03 |
| 303 | 0.28 | | 0.05 |
| 304 | | | 0.07 |
| 305 | 0.006 | | |
| 306 | 0.04 | | |
| 307 | 0.04 | | |
| 308 | 0.27 | | |
| 309 | 0.004 | | |
| 315 | | | 7.77 |
| 316 | | | 7.72 |
| 317 | 0.05 | | 0.03 |
| 318 | | | 0.12 |
| 319 | 0.02 | | 0.02 |
| 320 | | | 4.85E-03 |
| 321 | | | 0.61 |
| 322 | 0.22 | | 0.06 |
| 323 | | | 0.54 |
| 324 | | | 0.16 |
| 325 | | | 0.09 |
| 326 | | | 1.33 |
| 327 | | | 0.26 |
| 328 | | | 0.39 |
| 329 | | | 4.03E-03 |
| 330 | | | 0.02 |
| 331 | | | 0.16 |
| 332 | 0.11 | | 0.08 |
| 333 | | | 0.30 |
| 334 | | | 0.02 |
| 335 | | | 1.08 |
| 336 | | | 0.34 |
| 337 | | | 0.41 |
| 338 | | | 0.49 |
| 339 | | | 0.16 |
| 340 | 0.04 | | 0.03 |
| 341 | 8.45E-04 | | 1.73E-03 |
| 342 | | | 0.17 |
| 343 | | | 0.23 |
| 344 | 0.05 | | 0.03 |
| 345 | | | 0.82 |
| 346 | | | 0.09 |
| 347 | | | 5.26 |
| 348 | 0.01 | | 0.01 |
| 349 | 0.13 | | 7.49E-03 |
| 350 | | | 0.25 |
| 351 | | | 0.35 |
| 352 | 0.22 | | 0.09 |
| 353 | 2.37E-03 | | 5.10E-03 |
| 354 | | | 0.12 |
| 355 | 3.29E-03 | | 2.37E-03 |

| Ex. No. | HEK human IDO-1 (IC50, uM) | Hela Kyurenine (IC50, uM) | LLE_IDO_ABS_DR (IC50, uM) |
|---|---|---|---|
| 356 | 4.06E-03 | | |
| 357 | 0.32 | | 0.04 |
| 358 | 0.35 | | 0.02 |
| 359 | 0.55 | | |
| 360 | 0.02 | | |
| 361 | 0.22 | | 0.11 |
| 362 | | | 5.49 |
| 363 | | | 0.90 |
| 364 | | | 4.67 |
| 365 | | | 5.06 |
| 366 | | | 5.01 |
| 367 | 0.01 | | 0.02 |
| 368 | | | 2.50 |
| 369 | | | 0.52 |
| 370 | 0.07 | | 0.05 |
| 371 | | | 3.74 |
| 372 | | | 1.94 |
| 373 | 4.00 | | 3.34 |
| 374 | | | 6.84 |
| 375 | | | 4.74 |
| 376 | 2.15E-03 | | |
| 377 | 1.68E-03 | | |
| 378 | 0.07 | | 0.06 |
| 379 | 0.03 | | 0.02 |
| 380 | 0.07 | | 0.05 |
| 381 | | | 0.11 |
| 382 | 0.35 | | 0.50 |
| 383 | 0.13 | | 0.07 |
| 384 | 1.89 | | 1.64 |
| 385 | 0.20 | | |
| 386 | | | 0.04 |
| 387 | | | 2.23 |
| 388 | | | 10.00 |
| 389 | | | 0.62 |
| 390 | | | 1.59 |
| 391 | 0.28 | | |
| 392 | 0.01 | | |
| 393 | 2.07E-03 | | |
| 394 | 7.90E-03 | | |
| 395 | 0.07 | | |
| 396 | 6.07E-03 | | |
| 397 | 0.01 | | |
| 398 | 9.69E-03 | | |
| 399 | 0.02 | | |
| 400 | 5.35E-03 | | |
| 401 | 1.18 | | |
| 402 | 4.83 | | |
| 403 | 2.32E-03 | | |
| 404 | 2.56 | | |
| 405 | 1.23 | | |
| 406 | 7.59E-03 | | |
| 407 | 3.11 | | |
| 408 | 0.01 | | |
| 409 | 0.11 | | |
| 410 | 0.05 | | |
| 411 | 0.05 | | |
| 412 | 0.06 | | |
| 413 | 1.96 | | |
| 414 | 8.45E-04 | | 1.73E-03 |
| 415 | 0.13 | | |
| 416 | 0.10 | | |
| 417 | 1.89E-03 | | |
| 418 | 4.63E-03 | | |
| 419 | 5.08E-03 | | |
| 420 | 5.25 | | |
| 421 | 3.30 | | |
| 422 | 1.48 | | |
| 423 | 0.02 | | |
| 424 | 5.27E-03 | | |
| 425 | 0.01 | | |
| 426 | 8.85E-03 | | |
| 427 | 1.61E-03 | | |
| 428 | 1.84E-03 | | |
| 429 | 5.55E-03 | | |
| 430 | 6.06E-04 | | |
| 431 | 3.76E-03 | | |
| 432 | 1.82E-03 | | |
| 433 | 1.97E-03 | | |
| 434 | 3.70E-03 | | |
| 435 | 3.00E-03 | | |
| 436 | 1.16E-03 | | |
| 437 | 3.13E-03 | | |
| 438 | 1.67E-03 | | |
| 439 | 0.01 | | |
| 440 | 1.55E-03 | | |
| 441 | 1.14E-03 | | |
| 442 | 2.23E-03 | | |
| 443 | 0.01 | | |
| 444 | 3.21E-03 | | |
| 445 | 0.05 | | |
| 446 | 2.45E-03 | | |
| 447 | 0.06 | | |
| 448 | 1.56E-03 | | |
| 449 | 1.41E-03 | | |
| 450 | 5.47E-03 | | |
| 451 | 1.74E-03 | | |
| 452 | 6.61E-04 | | |
| 453 | 9.90E-03 | | |
| 454 | 2.35E-03 | | |
| 455 | 0.51 | | |
| 456 | 8.63E-04 | | |
| 457 | 0.37 | | |
| 458 | 0.14 | | |
| 459 | 7.09E-03 | | |
| 460 | 2.40E-03 | | |
| 461 | 4.24E-03 | | |
| 462 | 1.11E-03 | | |
| 463 | 0.02 | | |
| 464 | 0.79 | | |
| 465 | 0.20 | | |
| 466 | 1.74 | | |
| 467 | 0.01 | | |
| 468 | | | 0.08 |
| 469 | | | 0.72 |
| 470 | | | 0.19 |
| 471 | | | 0.04 |
| 472 | 9.13E-03 | | 0.01 |
| 473 | 0.06 | | 0.07 |
| 474 | | | 0.09 |
| 475 | | | 0.05 |
| 476 | | | 0.14 |
| 477 | 7.65E-03 | | |
| 478 | 0.01 | | |
| 479 | | | 3.80 |
| 480 | | | 1.84 |
| 481 | | | 1.84 |
| 482 | 0.04 | | 0.02 |
| 483 | 7.33E-03 | | 6.12E-03 |
| 484 | 0.01 | | 2.50E-03 |
| 485 | 5.75E-03 | | |
| 486 | 0.03 | | |
| 487 | 1.05 | | |
| 488 | 3.46E-03 | | |
| 489 | 0.22 | | |
| 491 | 0.13 | | |
| 492 | 0.16 | | |
| 493 | 0.12 | | |
| 494 | 0.03 | | |
| 495 | 0.05 | | |
| 496 | 0.01 | | |
| 497 | 0.23 | | |
| 498 | 0.59 | | |
| 499 | 1.26 | | |
| 500 | 0.02 | | |
| 501 | 0.32 | | |
| 502 | 0.02 | | 5.01E-03 |
| 503 | 0.01 | | 2.24E-03 |
| 504 | 5.14E-03 | | 4.00E-04 |
| 505 | | | 0.04 |
| 506 | | | 0.04 |
| 507 | 2.87 | | |
| 509 | 6.63 | | |

-continued

| Ex. No. | HEK human IDO-1 (IC50, uM) | Hela Kyurenine (IC50, uM) | LLE_IDO_ABS_DR (IC50, uM) |
|---|---|---|---|
| 510 | | | 1.38E−03 |
| 511 | | | 8.10E−03 |
| 512 | | 0.05 | 2.88E−03 |
| 513 | | | 0.01 |
| 514 | | 0.02 | 0.01 |
| 515 | 4.22 | | |
| 516 | | 0.05 | |
| 517 | | 0.07 | |
| 518 | | 0.02 | |
| 519 | 6.91E−03 | | |
| 520 | 4.87 | | |
| 521 | 8.44E−03 | | |
| 522 | 1.22 | | |
| 523 | 5.52 | | |
| 524 | 2.72 | | |
| 525 | | 0.09 | |
| 526 | | 0.24 | |
| 527 | | 0.04 | |
| 528 | | 0.16 | |
| 529 | | 0.39 | |
| 530 | | 0.30 | |
| 531 | | 0.02 | |
| 532 | 4.82E−03 | | |
| 533 | 8.02E−03 | | |
| 534 | 3.05E−03 | | |
| 535 | | 0.14 | |
| 536 | | 0.07 | |
| 537 | 6.08E−03 | | |
| 538 | | 0.01 | |
| 539 | 0.0033 | | |
| 540 | | 0.01 | |
| 541 | 3.43 | | |
| 542 | 0.76 | | |
| 543 | 7.24 | | |
| 544 | 1.74 | | |
| 545 | | 0.06 | |

What is claimed is:

1. A compound of Formula (I)

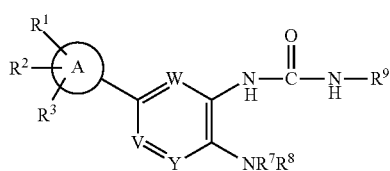

wherein:

W is $CR^4$,

V is $CR^5$, and

Y is $CR^6$;

is optionally substituted aryl or optionally substituted 5- to 7-membered monocyclic heteroaryl;

$R^1$ is COOH, optionally substituted heterocyclyl, —$NHSO_2R^{20}$,

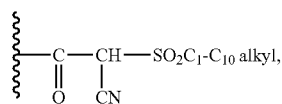

—$CONHSO_2R^{21}$, —$CONHCOOR^{22}$ or —$SO_2NHCOR^{23}$;

$R^2$ and $R^3$ are independently H, halogen, optionally substituted $C_1$-$C_6$ alkyl, optionally substituted $C_1$-$C_6$ alkoxy or optionally substituted $N(C_1$-$C_6$ alkyl$)_2$;

$R^4$, $R^5$ and $R^6$ are independently H, halogen, CN, OH, optionally substituted $C_1$-$C_6$ alkyl or optionally substituted $C_1$-$C_6$ alkoxy;

$R^7$ and $R^8$ are independently H, optionally substituted $C_1$-$C_6$ alkyl, optionally substituted aryl, optionally substituted $C_1$-$C_6$ alkoxy, optionally substituted $C_3$-$C_8$ cycloalkyl, optionally substituted di-deutero-$C_1$-$C_{10}$-alkyl, optionally substituted $C_2$-$C_{10}$ alkynyl, optionally substituted 5- to 7-membered monocyclic heteroaryl, optionally substituted 8- to 10-membered bicyclic heteroaryl, optionally substituted aryl $C_1$-$C_6$ alkyl, arylsulfonyl, optionally substituted $C_2$-$C_6$ alkenyl, or optionally substituted $C_5$-$C_8$ cycloalkenyl, provided that only one of $R^7$ and $R^8$ is H, or $R^7$ and $R^8$ are taken together with the nitrogen to which they are attached to form an optionally substituted 4- to 10-membered monocyclic or bicyclic heterocyclic ring, or an optionally substituted 5- to 7-membered monocyclic heteroaryl ring;

$R^9$ is optionally substituted aryl; optionally substituted $C_3$-$C_8$ cycloalkyl, optionally substituted $C_1$-$C_6$ alkyl, optionally substituted 5- to 7-membered monocyclic heterocyclo, optionally substituted 7- to 10-membered bicyclic heterocyclo, optionally substituted 5- to 7-membered monocyclic heteroaryl, optionally substituted 8- to 10-membered bicyclic heteroaryl, optionally substituted $C_1$-$C_6$ alkanoyloxy 5- to 7-membered monocyclic heteroaryl, $R^{24}CO$—, optionally substituted $C_1$-$C_6$ alkoxy, optionally substituted aryloxy, optionally substituted $C_2$-$C_6$ alkenyl, optionally substituted $C_2$-$C_6$ alkynyl, or optionally substituted $C_5$-$C_8$ cycloalkenyl;

$R^{20}$ is optionally substituted $C_1$-$C_6$ alkyl, $CH_2CF_3$, $CF_3$ or $CF_2CF_3$;

$R^{21}$ is optionally substituted $C_1$-$C_6$ alkyl or optionally substituted $C_3$-$C_8$ cycloalkyl;

$R^{22}$ is optionally substituted $C_1$-$C_6$ alkyl, optionally substituted $C_3$-$C_8$ cycloalkyl, optionally substituted $C_2$-$C_6$ alkenyl, or optionally substituted $C_2$-$C_6$ alkynyl;

$R^{23}$ is optionally substituted $C_1$-$C_6$ alkyl, optionally substituted $C_3$-$C_8$ cycloalkyl, optionally substituted $C_2$-$C_6$ alkenyl, or optionally substituted $C_2$-$C_6$ alkynyl;

$R^{24}$ is optionally substituted aryl-$C_1$-$C_6$-alkyl, optionally substituted $C_1$-$C_6$ alkylaryl, aryl-$C_1$-$C_6$-alkyl(hydroxy), or optionally substituted $C_1$-$C_6$ alkyl;

and/or a stereoisomer, a tautomer or a pharmaceutically acceptable salt thereof.

2. The compound as defined in claim 1 wherein:

W is $CR^4$;

V is $CR^5$;

Y is $CR^6$;

$R^4$ is H or halo;

$R^5$ is H or halo; and $R^6$ is H or halo;

and/or a stereoisomer, a tautomer or a pharmaceutically acceptable salt thereof.

3. The compound as defined in claim 1 wherein (A)

is phenyl or a 5- to 6-membered monocyclic heteroaryl.

4. The compound as defined in claim 3 wherein (A)

is:

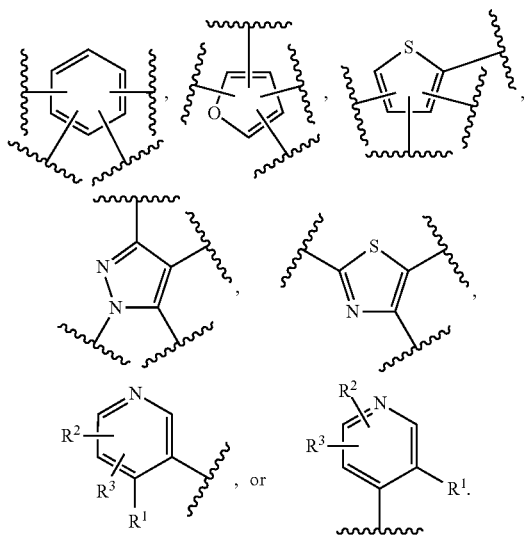

5. The compound as defined in claim 1 wherein:
$R^1$ is COOH, optionally substituted heterocyclyl, —NHSO$_2$R$^{20}$,

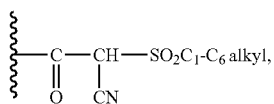

—CONHSO$_2$R$^{21}$ or —CONHCOOR$^{22}$;
$R^2$ is H, halogen, optionally substituted $C_1$-$C_6$ alkyl or optionally substituted $C_1$-$C_6$ alkoxy; and
$R^3$ is H or $C_1$-$C_6$ alkyl.

6. The compound as defined in claim 5 wherein:
$R^1$ is COOH, optionally substituted heterocyclyl, —NHSO$_2$CH$_3$,

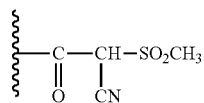

or —CONHSO$_2$R$^{21}$;
where $R^{21}$ is $C_1$-$C_6$ alkyl, $C_3$-$C_8$ cycloalkyl or CF$_3$;
$R^2$ is H, CH$_3$, C$_2$H$_5$, CH$_3$O, CF$_3$O, F, or Cl; and
$R^3$ is H, CH$_3$, or C$_2$H$_5$;
and/or a stereoisomer, a tautomer or a pharmaceutically acceptable salt thereof.

7. The compound as defined in claim 1 wherein:
$R^7$ and $R^8$ are independently optionally substituted $C_1$-$C_6$ alkyl, optionally substituted aryl, optionally substituted $C_1$-$C_6$ alkoxy, optionally substituted $C_3$-$C_8$ cycloalkyl, optionally substituted di-deutero-$C_1$-$C_6$-alkyl, optionally substituted $C_1$-$C_6$-alkylphenyl-$C_1$-$C_6$-alkyl, optionally substituted $C_2$-$C_6$ alkynyl, optionally substituted $C_3$-$C_8$-cycloalkyl-$C_1$-$C_6$-alkyl, optionally substituted $C_1$-$C_6$-alkoxy-$C_1$-$C_6$-alkyl, optionally substituted 5- to 6-membered monocyclic heteroaryl, optionally substituted 7- to 10-membered bicyclic heteroaryl, optionally substituted aryl $C_1$-$C_6$ alkyl, phenylsulfonyl, optionally substituted $C_2$-$C_6$ alkenyl, or 5- to 6-membered monocyclic heteroaryl-$C_1$-$C_6$-alkyl,
or $R^7$ and $R^8$ are taken together with the nitrogen to which they are attached to form
(a) a 7- to 10-membered bicyclic heterocyclic ring which is optionally substituted with a phenyl-$C_1$-$C_6$-alkyl group, or
(b) a 5- to 7-membered monocyclic heterocyclic ring which is optionally substituted with 1 or 2 $C_1$-$C_6$ alkyl groups, phenyl, a $C_1$-$C_6$-alkyl-substituted 5- to 7-membered monocyclic heteroaryl, and/or 1 or 2 halo groups; or
(c) a 5- to 7-membered monocyclic heteroaryl which is optionally substituted with a $C_1$-$C_6$ alkyl;
$R^9$ is optionally substituted aryl; optionally substituted $C_3$-$C_8$ cycloalkyl, optionally substituted $C_1$-$C_6$ alkyl, optionally substituted $C_1$-$C_6$ alkoxy, optionally substituted $C_1$-$C_6$ alkylaryl, optionally substituted $C_1$-$C_6$ alkoxyaryl, optionally substituted $C_3$-$C_8$ cycloalkyl $C_1$-$C_6$ alkyl, optionally substituted 5- to 7-membered monocyclic heterocyclo, optionally substituted 7- to 10-membered bicyclic heterocyclo, optionally substituted 5- to 6-membered monocyclic heteroaryl, optionally substituted 8- to 10-membered bicyclic heteroaryl, optionally substituted $C_1$-$C_6$ alkanoyloxy 5- to 7-membered monocyclic heteroaryl, optionally substituted aryloxy, optionally substituted $C_2$-$C_6$ alkenyl, optionally substituted $C_2$-$C_6$ alkynyl, or optionally substituted $C_5$-$C_8$ cycloalkenyl, $C_2$-$C_6$ alkynylaryl, $C_2$-$C_6$ alkynyloxyaryl, 5- to 6-membered heteroarylaryl, 5- or 6-membered heterocycloaryl, $C_3$-$C_8$ cycloalkylaryl or $C_1$-$C_6$ alkanoyl.

8. A compound of Formula (II)

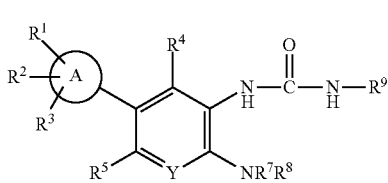

wherein:
Y is CR$^6$;

(A)

is phenyl substituted with $R^1$, and optionally substituted with $R^2$ and/or $R^3$
or

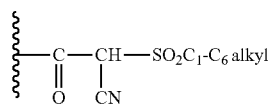

is a 5- to 7-membered monocyclic heteroaryl substituted with $R^1$, and optionally substituted with $R^2$ and/or $R^3$;

$R^1$ is COOH, optional substituted tetrazol-5-yl, —NHSO$_2$R$^{20}$ $$\begin{array}{c}\xi\!\!-\!\!\underset{\underset{O}{\|}}{C}\!\!-\!\!\underset{\underset{CN}{|}}{CH}\!\!-\!\!SO_2C_1\text{-}C_6\,\text{alkyl}\end{array}$$

or —CONHSO$_2$R$^{21}$;

$R^{20}$ is $C_1$-$C_6$ alkyl or $CF_3$;

$R^{21}$ is $C_1$-$C_6$ alkyl, $C_3$-$C_8$ cycloalkyl or $CF_3$;

$R^2$ is H, $C_1$-$C_6$ alkyl, halo, optionally substituted $C_1$-$C_6$-alkoxy or $N(C_1$-$C_6$ alkyl)$_2$, $R^3$ is H, $C_1$-$C_6$ alkyl, $C_1$-$C_6$ alkoxy, or halo;

$R^4$ is H, halo or $C_1$-$C_6$ alkyl;

$R^5$ is H, halo or $C_1$-$C_6$ alkyl;

$R^6$ is H or halo;

$R^7$ and $R^8$ are independently H, optionally substituted $C_1$-$C_6$ alkyl, optionally substituted aryl, optionally substituted $C_3$-$C_8$ cycloalkyl, phenyl sulfonyl, dideutero-$C_1$-$C_6$-alkyl, optionally substituted $C_3$-$C_8$-cycloalkyl-$C_1$-$C_6$-alkyl, optionally substituted aryl-$C_1$-$C_6$-alkyl, optionally substituted $C_2$-$C_6$ alkynyl, optionally substituted 5- to 7-membered monocyclic heterocyclo, optionally substituted 7- to 10-membered bicyclic heterocyclo, optionally substituted $C_1$-$C_6$-alkoxy-$C_1$-$C_6$-alkyl, 5- to 7-membered monocyclic heteroaryl-$C_1$-$C_6$-alkyl, $C_2$-$C_6$ alkenyl, or $C_5$-$C_8$ cycloalkenyl, provided that only one of $R^7$ and $R^8$ is H, and wherein the optional substituents on $R^7$ and $R^8$, where possible, are 1 or 2 groups independently selected from hydroxy, optionally substituted $C_1$-$C_6$ alkyl, optionally substituted $C_1$-$C_6$ alkoxy, halo, optionally substituted aryl, optionally substituted $C_3$-$C_8$ cycloalkyl, 5- to 7-membered monocyclic heteroaryl or 5- to 7-membered monocyclic heterocyclic;

or $R^7$ and $R^8$ are taken together with the nitrogen to which they are attached to form an optionally substituted 5- to 7-membered monocyclic heterocyclo ring, an optionally substituted 7- to 10-membered bicyclic heterocyclo ring, an optionally substituted 5- to 7-membered monocyclic heteroaryl ring, an optionally substituted 5- to 7-membered monocyclic heteroaryl-substituted 5- to 7-membered monocyclic heterocyclo ring, or a $C_3$-$C_8$-cycloalkyl-$C_1$-$C_6$-alkyl-substituted 7- to 10-membered bicyclic heterocyclo ring;

$R^9$ is H, $C_1$-$C_{10}$ alkyl, aryl, optionally substituted phenyl, $C_1$-$C_6$ alkylphenyl, optionally substituted $C_1$-$C_6$ alkoxyphenyl, di-$C_1$-$C_6$-alkylphenyl, dihalo($C_1$-$C_6$-alkyl)phenyl, $C_2$-$C_6$ alkynylphenyl, optionally substituted 5- to 7-membered monocyclic heteroaryl, 7- to 10-membered bicyclic heteroaryl, $C_3$-$C_8$ cycloalkyl, $C_3$-$C_8$-cycloalkyl-$C_1$-$C_6$-alkyl, $C_2$-$C_6$ alkynyloxyphenyl, $C_2$-$C_6$-alkynyl-$C_1$-$C_6$-alkoxyphenyl, 5- to 7-membered monocyclic heteroarylphenyl, di-$C_1$-$C_6$-alkylaminophenyl, $C_1$-$C_6$ alkyl sulfonylaminophenyl, 5- to 7-membered monocyclic heterocyclophenyl, $C_3$-$C_8$ cycloalkyl optionally substituted phenyl, optionally substituted phenyl-$C_1$-$C_6$-alkylcarbonyl, phenyl-$C_1$-$C_6$-alkyl or $C_1$-$C_6$ alkylcarbonyl;

and/or a pharmaceutically acceptable salt thereof, a tautomer thereof or stereoisomer thereof.

9. The compound according to claim 1 wherein the IC$_{50}$ in the HEK Human IDO-1 assay is <10 nM.

10. A pharmaceutical composition comprising one or more compounds according to claim 1 and a pharmaceutically acceptable carrier or diluent.

11. A method of inhibiting activity of indoleamine 2,3-dioxygenase comprising contacting said indoleamine 2,3-dioxygenase with a compound according to claim 1 or a pharmaceutically acceptable salt thereof.

* * * * *